US008088820B2

(12) United States Patent
Draper et al.

(10) Patent No.: US 8,088,820 B2
(45) Date of Patent: *Jan. 3, 2012

(54) SUBSTITUTED TETRACYCLINE COMPOUNDS FOR THE TREATMENT OF MALARIA

(75) Inventors: Michael Draper, Plaistow, NH (US); Mark L. Nelson, Norfolk, MA (US)

(73) Assignee: Paratek Pharmaceuticals, Inc., Boston, MA (US)

(*) Notice: Subject to any disclaimer, the term of this patent is extended or adjusted under 35 U.S.C. 154(b) by 426 days.

This patent is subject to a terminal disclaimer.

(21) Appl. No.: 10/692,563

(22) Filed: Oct. 24, 2003

(65) Prior Publication Data

US 2004/0242548 A1  Dec. 2, 2004

Related U.S. Application Data

(63) Continuation-in-part of application No. 10/128,990, filed on Apr. 24, 2002, now abandoned.

(60) Provisional application No. 60/421,259, filed on Oct. 24, 2002, provisional application No. 60/286,193, filed on Apr. 24, 2001.

(51) Int. Cl.
*A61K 31/36* (2006.01)
*C07D 317/50* (2006.01)
*C07D 317/54* (2006.01)
*C07D 317/58* (2006.01)

(52) U.S. Cl. ........ 514/464; 514/441; 514/452; 514/466; 549/443; 549/444; 549/446

(58) Field of Classification Search .................. 552/203, 552/205; 514/152, 441, 452, 464, 466; 549/443, 549/444, 446
See application file for complete search history.

(56) References Cited

U.S. PATENT DOCUMENTS

| 2,980,584 | A | 4/1961 | Hammer |
| 2,990,331 | A | 6/1961 | Neumann et al. |
| 3,062,717 | A | 11/1962 | Hammer |
| 3,165,531 | A | 1/1965 | Blackwood et al. |
| 3,454,697 | A | 7/1969 | Joyner et al. |
| 3,557,280 | A | 1/1971 | Weber et al. |
| 3,674,859 | A | 7/1972 | Beutel et al. |
| 3,957,980 | A | 5/1976 | Noseworthy |
| 4,018,889 | A | 4/1977 | Armstrong |
| 4,024,272 | A | 5/1977 | Rogalski et al. |
| 4,126,680 | A | 11/1978 | Armstrong |
| 5,523,297 | A | 6/1996 | Pruzanski et al. |
| 5,532,227 | A | 7/1996 | Golub et al. |
| 5,589,470 | A | 12/1996 | Levy .............................. 514/154 |
| 5,639,742 | A | 6/1997 | Lee et al. |
| 5,789,395 | A | 8/1998 | Amin et al. |
| 5,811,412 | A | 9/1998 | Levy .............................. 514/154 |
| 5,834,450 | A | 11/1998 | Su |
| 5,919,395 | A | 7/1999 | Bastin et al. |
| 5,919,775 | A | 7/1999 | Amin et al. |
| 6,043,231 | A | 3/2000 | Pruzanski et al. |
| 6,319,910 | B1 | 11/2001 | Amin et al. |
| 6,326,023 | B1 | 12/2001 | Dutta et al. |
| 6,500,812 | B2 | 12/2002 | Nelson et al. |
| 6,617,318 | B1 | 9/2003 | Nelson et al. |
| 6,624,168 | B2 * | 9/2003 | Nelson et al. .............. 514/252.1 |
| 6,642,041 | B2 | 11/2003 | Nelson et al. |
| 6,642,270 | B2 * | 11/2003 | Nelson et al. .................. 514/464 |
| 6,683,068 | B2 | 1/2004 | Nelson et al. |
| 6,756,365 | B2 | 6/2004 | Levy .............................. 541/154 |
| 6,818,634 | B2 | 11/2004 | Nelson et al. |
| 6,818,635 | B2 | 11/2004 | Nelson et al. |
| 6,833,365 | B2 | 12/2004 | Levy et al. |
| 6,841,546 | B2 | 1/2005 | Draper et al. |
| 6,846,939 | B2 | 1/2005 | Nelson et al. |
| 6,849,615 | B2 | 2/2005 | Nelson et al. |
| 7,001,918 | B2 | 2/2006 | Huss et al. |
| 7,045,507 | B2 | 5/2006 | Draper et al. |
| 7,056,902 | B2 * | 6/2006 | Nelson et al. ................. 514/152 |
| 7,326,696 | B2 * | 2/2008 | Nelson et al. ................. 514/152 |
| 7,361,674 | B2 | 4/2008 | Nelson et al. ................. 514/357 |
| 7,414,041 | B2 | 8/2008 | Levy .............................. 541/154 |
| 2002/0045602 | A1 | 4/2002 | Nelson et al. |
| 2002/0103171 | A1 | 8/2002 | Nelson et al. |
| 2002/0111335 | A1 | 8/2002 | Nelson et al. |
| 2002/0115644 | A1 | 8/2002 | Levy et al. |

(Continued)

FOREIGN PATENT DOCUMENTS

DE  2814974  10/1978

(Continued)

OTHER PUBLICATIONS

Dorwald F. A. Side Reactions in Organic Synthesis, 2005, Wiley: VCH, Weinheim p. IX of Preface.*
Clyde, A.F. "Treatment of drug-resistant malaria in man," *Bull. World Health Organ.* 1974;50(3-4):243-9.
Colwell, E.J. et al. "Tetracycline treatment of chloroquine-resistant falciparum malaria in Thailand," *JAMA* May 1, 1972;220(5):684-6.
Colwell, E.J. et al. "Minocycline and tetracycline treatment of acute falciparum malaria in Thailand," *Am. J. Trop. Med. Hyg.* Mar. 1972;21(2):144-9.

(Continued)

*Primary Examiner* — Sabiha Qazi
(74) *Attorney, Agent, or Firm* — Mintz Levin Cohn Ferris Glovsky and Popeo, P.C.; Ivor R. Elrifi; Heidi A. Erlacher

(57) ABSTRACT

This invention provides a method for treating or preventing malaria in a subject. The method includes administering to the subject an effective amount of a substituted tetracycline compound, such that malaria is treated or prevented. In one aspect, the invention relates to pharmaceutical compositions which include an effective amount of a tetracycline compound to treat malaria in a subject and a pharmaceutically acceptable carrier. The substituted tetracycline compounds of the invention can be used to in combination with one or more anti-malarial compounds or can be used to treat or prevent malaria which is resistant to one or more other anti-malarial compounds.

45 Claims, No Drawings

U.S. PATENT DOCUMENTS

| | | |
|---|---|---|
| 2002/0123637 A1 | 9/2002 | Levy et al. |
| 2002/0128237 A1 | 9/2002 | Nelson et al. |
| 2002/0128238 A1 | 9/2002 | Nelson et al. |
| 2002/0132798 A1 | 9/2002 | Nelson et al. |
| 2002/0147182 A1 | 10/2002 | Nelson et al. |
| 2002/0193354 A1 | 12/2002 | Nelson et al. |
| 2003/0055025 A1 | 3/2003 | Nelson et al. |
| 2003/0100017 A1 | 5/2003 | Draper et al. |
| 2003/0125348 A1 | 7/2003 | Nelson et al. |
| 2003/0166585 A1 | 9/2003 | Draper et al. |
| 2003/0166952 A1 | 9/2003 | Nelson et al. |
| 2004/0033996 A1 | 2/2004 | Nelson et al. |
| 2004/0048835 A1 | 3/2004 | Nelson et al. |
| 2004/0063674 A1 | 4/2004 | Levy et al. |
| 2004/0092490 A1 | 5/2004 | Draper et al. |
| 2004/0138183 A1 | 7/2004 | Nelson et al. |
| 2004/0157806 A1 | 8/2004 | Nelson et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0224928 A1 | 11/2004 | Nelson et al. ............... 514/154 |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0148551 A1 | 7/2005 | Nelson et al. |
| 2005/0187198 A1 | 8/2005 | Nelson et al. |
| 2005/0215532 A1 | 9/2005 | Levy et al. |
| 2005/0288262 A1 | 12/2005 | Bandarage et al. |
| 2006/0003971 A1 | 1/2006 | Nelson |
| 2006/0084634 A1 | 4/2006 | Huss et al. |
| 2006/0089336 A1 | 4/2006 | Nelson et al. |
| 2006/0148765 A1 | 7/2006 | Nelson et al. ............... 514/152 |
| 2006/0166945 A1 | 7/2006 | Abato et al. ............... 514/152 |
| 2006/0166946 A1 | 7/2006 | Nelson et al. ............... 514/152 |
| 2006/0194773 A1 | 8/2006 | Levy et al. ............... 514/152 |
| 2006/0281717 A1 | 12/2006 | Berniac et al. ............... 514/152 |
| 2007/0167415 A1 | 7/2007 | Levy et al. ............... 514/152 |
| 2008/0070873 A1 | 3/2008 | Alekshun et al. ............... 514/153 |
| 2008/0118979 A1 | 5/2008 | Draper et al. ............... 435/375 |
| 2008/0167273 A1 | 7/2008 | Nelson et al. ............... 514/152 |
| 2008/0287401 A1 | 11/2008 | Johnson et al. ............... 514/152 |
| 2008/0300424 A1 | 12/2008 | Nelson et al. ............... 564/167 |
| 2008/0312193 A1 | 12/2008 | Assefa et al. ............... 514/152 |
| 2009/0118269 A1 | 5/2009 | Berniac et al. ............... 514/231.5 |
| 2009/0131696 A1 | 5/2009 | Levy ............... 552/203 |

FOREIGN PATENT DOCUMENTS

| | | |
|---|---|---|
| DE | 2820983 | 10/1979 |
| WO | WO-9634852 A1 | 11/1996 |
| WO | WO-99/30720 A1 | 6/1999 |
| WO | WO 00/28983 | 5/2000 |
| WO | WO-00/64479 A1 | 11/2000 |
| WO | WO-01/19784 A1 | 3/2001 |
| WO | WO-0174761 A1 | 10/2001 |
| WO | WO-0187824 A2 | 11/2001 |
| WO | WO 02/00208 A2 | 1/2002 |
| WO | WO 02/04406 A2 | 1/2002 |
| WO | WO 02/04407 A2 | 1/2002 |
| WO | WO 02/072022 A2 | 9/2002 |
| WO | WO-02/072031 A2 | 9/2002 |
| WO | WO 02/072532 A1 | 9/2002 |
| WO | WO 02/085303 A2 | 10/2002 |
| WO | WO 03/005971 A2 | 1/2003 |
| WO | WO 03/079984 A2 | 10/2003 |
| WO | WO 2008/045507 A2 | 4/2008 |
| WO | WO 2008/079339 A2 | 7/2008 |

OTHER PUBLICATIONS

Committee to Advise on Tropical Medicine and Travel. New Drugs for the Prevention and Treatment of Malaria. Canada Communicable Disease Report (CCDR), vol. 26S2, Mar. 200. pp. 1-6.

Lin, Q. et al. "Inhibition of mitochondrial and plastid activity of Plasmodium falciparum by minocycline," *FEBS Lett.* Mar. 27, 2002;515(1-3):71-4.

Ponnampalam, J.T. "Doxycycline in the treatment of falciparum malaria among aborigine children in West Malaysia," *Trans. R. Soc. Pop. Med. Hyg.* 1981;75(3):372-373.

Pradines, B. et al. "Antibiotics for prophylaxis of Plasmodium falciparum infections: in vitro activity of doxycycline against Senegalese isolates," *Am. J. Trop. Med. Hyg.* Jan. 2000;62(1):82-5.

Pradines, B. et al. "In vitro activities of antibiotics against Plasmodium falciparum are inhibited by iron," *Antimicrob. Agents Chemother.* Jun. 2001;45(6):1746-50.

Ralph, S.A. et al. "The apicoplast as an antimalarial drug target," *Drug Resist. Updat.* Jun. 2001;4(3):145-51.

Sponer, U. et al. "Pharmacodynamic interaction of doxycycline and artemisinin in Plasmodium falciparum," *Antimicrob. Agents Chemother.* Jan. 2002;46(1):262-4.

White, N. "Tetracycline for chloroquine-resistant malaria," *Lancet.* Jun. 4, 1983;1(8336):1271.

Willerson, D. et al. "Effects of minocycline against chloroquine-resistant falciparum malaria," *Am. J. Trop. Med. Hyg.* Nov. 1972;21(6):857-62.

"Tetracyclines for malaria," *Br. Med. J.* Aug. 26, 1972;3(825):487.

Bunnag, D. et al, "Quinine-tetracycline for multidrug resistant fulciparum malaria," *Southeast Asian J. Trop. Med. Public Health*, vol. 27(1):15-18 (1996).

Draper, M.P. et al, "Novel Tetracycline Derivatives as Antimalarial Agents," 41st *ICAAC Abstracts*, Poster Session 115, P-1140, Sep. 22-25, 2001.

Geary, Timothy G. et al, "Stage Specific Actions of Antimalarial Drugs on *Plasmodium falciparum* in Culture," *Am. J. Trop. Med. Hyg.*, vol. 40(3):240-244 (1989).

Karbwang, Juntra et al, "Plasma Quinine Levels in Patients with Fulciparum Malaria when Given Alone or in Combination with Tetracycline With or Without Primaquine," *Southeast Asian Journal of Tropical Medicine and Public Health*, vol. 22(1):72-76 (1991).

Patenotte, A. et al, "Antibiotiques et paludisme. Revue de la littérature," *Méd. Mal. Infect.*, vol. 25:970-975 (1995).

European Search Report for Application No. 02723955.7-2103 PCT/US02/12935, dated Feb. 6, 2006.

Toama, M.A., "In vitro synergism between tetracyclines and antimalarials", *Chemotherapy*, 26:191-195 (1980).

McColm et al., "Evaluation of a range of antimicrobial agents against the parasitic protozoa, Plasmodium falciparum, Babesia rodhaini and Theileria parva in vitro", *Ann. of Trop. Med. and Par.*, 78:4:345-554 (1984).

Kumar et al., "Antimalarial activity of demeclocycline against Plasmodium cynomolgi bastianellii in rhesus monkeys", *Ann. of Trop. Med. and Par*, 83:3:199-206 (1989).

Koza, D. J., "Synthesis of 7-Substituted Tetracycline Derivatives", *Organic Letters, American Chemical Society*, US, 2(6), 815-817 (2000), XP000926764, ISSN: 1523-7060.

Koza, D. J. et al., "Synthesis and Biological Evaluation of 9-Substituted Tetracycline Derivatives", *Bioorganic & Medicinal Chemistry Letters, Pergamon, Elsevier Science*, GB, vol. 12, 2163-2165 (2002), XP002964855, ISSN: 0960-894X.

* cited by examiner

SUBSTITUTED TETRACYCLINE COMPOUNDS FOR THE TREATMENT OF MALARIA

RELATED APPLICATIONS

This application claims the benefit of U.S. Provisional Patent Application No. 60/421,259, filed Oct. 24, 2002. This patent application is a continuation-in-part of U.S. patent application Ser. No. 10/128,990, filed Apr. 24, 2002 now abandoned, which claims priority to U.S. Provisional Patent Application No. 60/286,193, filed Apr. 24, 2001. The entire contents of each of the aforementioned applications are hereby incorporated by reference in their entirety.

BACKGROUND OF THE INVENTION

Every year there are about 300-500 million clinical cases of malaria. About 40% of the world's population is at risk of acquiring the disease. (Croft (2000) *BMJ* 321:154-160.) Malaria is characterized by headache, malaise, anemia, splenomegaly, and paroxysms with cold, hot, and wet the stages. (Winstanley (1998) *Journal of the Royal College of Physicians of London* 32(3):203-207.) Hemolysis and ischemia cause the majority of the symptoms seen with acute malaria. Malaria is caused by protozoa of the genus *Plasmodium*. There are over 100 species of which 22 infect nonhuman primates and 82 are pathogenic for reptiles and birds. The four species that commonly infect man are: *P. falciparum, P. malariae, P. vivax*, and *P. ovale*. Malaria may be transmitted by a bite of the *Anopheles* mosquito, infected blood transfusions, transplacentally, and in laboratory inoculation accidents.

Plasmodia have a complex life cycle where the sexual phase occurs in the *Anopheles* mosquito and the asexual phase takes place in the veterbrate host (i.e. a human). (Randall, et al. (1985) *Pediatric Clinics of North America* 32(4): 893-916.) The process of sexual reproduction in the mosquito is called Sporogony and includes the period from gametocyte maturation to sporozoite development. When a female *Anopheles* mosquito feeds, it takes up gametocytes present in the blood of an infected host. The gametocytes taken up by the mosquito pass to the mosquito's gut. A zygote is formed by the fusion of the microgamete and macrogamete. After 12 to 24 hours, the zygotes elongates and becomes motile and is called an ookinete. The ookinete later penetrates the mosquito's stomach to form an oocyst which divides into thousands of spindle-shaped sporozoites which are released throughout the mosquito's body.

When a blood meal is taken by an infected *Anopheles* mosquito, sporozoites from the salivary glands of the mosquito are inoculated into the bloodstream of the veterbrate host (i.e. human) and are carried to the liver. At the end of the hepatic phase of development, thousands of merozoites are released into the circulation where they bind to and enter red blood cells. The erythrocyte phase of asexual reproduction is termed Schizogeny. When the infected erythrocytes rupture, they release merozoites which can invade more red blood cells. Other released merozoites become gametophytes capable of infecting feeding mosquitoes and restarting the life cycle of the Plasmodia.

SUMMARY OF THE INVENTION

This invention pertains, at least in part, to a method for treating or preventing malaria in a subject by administering an effective amount of a substituted tetracycline compound. The method includes administering to a subject an effective amount of a substituted tetracycline compound of formula I:

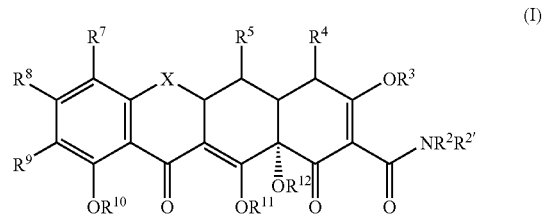

wherein:
X is CHC($R^{13}$Y'Y), C$R^{6'}R^6$, S, N$R^6$, or 0;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is N$R^{4'}$ is N$R^4R^{4''}$, alkyl, alkenyl, alkynyl, hydroxyl, halogen, or hydrogen;
$R^3$, $R^{11}$ and $R^{12}$ are each hydrogen or a pro-drug moiety;
$R^{10}$ is hydrogen, a prodrug moiety, or linked to $R^9$ to form a ring;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ is hydrogen, alkylamino, dialkylamino, or a malaria interacting moiety;
$R^9$ is hydrogen, or a malaria interacting moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; with the proviso that the compound of formula I is not oxytetracycline, demeclocycline, doxycycline, chlorotetracycline, minocycline, or tetracycline; and pharmaceutically acceptable salts thereof.

This invention also relates, at least in part, to the use of a substituted tetracycline compound of formula I in the preparation of a medicament to treat or prevent malaria in a subject, e.g., a mammal.

This invention pertains, at least in part, to a method for treating or preventing malaria which is resistant to one or more anti-malarial compounds such as, for example, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, and pyronaridine.

In another aspect, this invention also pertains to pharmaceutical compositions which include an effective amount of one of the above-described substituted tetracycline compounds and a pharmaceutically acceptable carrier This invention also features a packaged malarial treatment, including one or more of the substituted tetracycline compounds of the invention packaged with instructions for using the compound to treat malaria.

DETAILED DESCRIPTION OF THE INVENTION

In one aspect, this invention pertains to methods of treating or preventing malaria in a subject, by administering an effective amount of a substituted tetracycline compound.

The term "malaria" includes the art recognized condition known as "malaria" e.g., disorders which are caused by a protozoan of the genus *Plasmodium*. Malaria is generally characterized by symptoms such as headache, malaise, anemia, splenomegaly, and paroxyms with cold, hot, and wet stages and is transmitted by mosquitoes. (Winstanley (1998) *Journal of the Royal College of Physicians of London* 32(3): 203-207.) In a further embodiment, the protozoan is selected from the group consisting of: *P. falciparum, P. vivax, P. ovale*, and *P. malariae*.

The term "treated," "treating" or "treatment" includes the diminishment or alleviation of at least one symptom associated or caused by malaria, e.g., headache, malaise, anemia, splenomegaly, and paroxyms with cold, hot, and wet stages. For example, treatment can be diminishment of one or several symptoms of malaria or complete eradication of malaria.

The term "prevented," or "preventing" includes administration of a substituted tetracycline compound of the invention to a subject who is not currently suffering from malaria, such that the subject does not contract malaria for a period of time after the administration and after exposure to malaria.

The term "tetracycline compounds" includes tetracycline family members such as methacycline, sancycline, apicycline, clomocycline, guamecycline, meglucycline, mepylcycline, penimepicycline, pipacycline, etamocycline, penimocycline, etc. as well as other tetracycline compounds having the characteristic naphthacene A-B-C-D ring structure. Additional tetracycline compounds can be found, for example, in U.S. patent application Ser. No. 09/234,847, and U.S. Pat. Nos. 5,834,450; 5,532,227; 5,789,395; 5,639,742 and German patents DE 28 14 974 and DE 28 20 983. The entire contents of the aforementioned applications and patents are hereby expressly incorporated herein by reference.

Recent research efforts have focused on developing new tetracycline antibiotic compositions effective under varying therapeutic conditions and routes of administration; and for developing new tetracycline analogues which might prove to be equal or more effective than the originally introduced tetracycline families beginning in 1948. Representative of such developments include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These issued patents are merely representative of the range of diversity of investigations seeking tetracycline and tetracycline analogue compositions which are pharmacologically active, and the contents of each are expressly incorporated by reference.

Historically, soon after their initial development and introduction, the tetracyclines, regardless of specific formulation or chemical structure, were found to be highly effective pharmacologically against rickettsiae, a number of gram-positive and gram-negative bacteria, and the agents responsible for lymphogranuloma venereum, including conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and *Salmonella*). The rise of tetracycline-resistant organisms has resulted in a general decline in use of tetracyclines and tetracycline analogue compositions as antibiotics of choice.

The terms "substituted tetracycline" and "substituted tetracycline compounds" include tetracycline compounds of formula I. In an embodiment, the term "substituted tetracycline compounds" does not include oxytetracycline, demeclocycline, doxycycline, chlorotetracycline, minocycline, and tetracycline. In a further embodiment, "substituted tetracycline compounds" does not include methacycline and sancycline. In another further embodiment, the substituted tetracycline compounds of the invention do not include, for example, compounds described in U.S. Pat. Nos. 6,043,231, 5,919,775, and 5,789,395, which are each incorporated in their entirety herein by reference. The substituted tetracycline compounds of the invention may be substituted such that certain biological or physical properties are enhanced, e.g., such that the substituted tetracycline compound is able to perform its intended function, e.g., treat or prevent malaria.

In one embodiment, the substituted tetracycline compound of the invention may have anti-microbial gram positive activity, as measured by assays known in the art or the assay described in Example 6. In an embodiment, the anti-microbial gram positive activity of the substituted tetracycline compound is greater than about 0.0001 µg/ml, greater than about 0.05 µg/ml, greater than about 0.5 µg/ml, greater than about 1.0 µg/ml, or greater than about 5.0 µg/ml. Values and ranges included and/or intermediate of the values set forth herein are also intended to be within the scope of the present invention.

In another embodiment, the substituted tetracycline compounds of the invention are not antibacterial. In certain embodiments, the substituted tetracycline compounds of the invention have antibacterial activity against gram+ and/or gram–bacteria. In certain embodiments, the tetracycline compounds of the invention do not have antibacterial activity against gram+ and/or gram–bacteria. In other embodiments, compounds with MIC of greater than about 2 µg/ml, greater than about 3 µg/ml, greater than about 4 µg/ml, greater than about 5 µg/ml, greater than about 6 µg/ml, greater than about 8 µg/ml, greater than about 9 µg/ml, greater than about 10 µg/ml, greater than about 11 µg/ml, greater than about 12 µg/ml, greater than about 13 µg/ml, greater than about 14 µg/ml, greater than about 15 µg/ml, greater than about 16 µg/ml, greater than about 17 µg/ml, greater than about 18 µg/ml, greater than about 19 µg/ml, greater than about 20 µg/ml, greater than about 25 µg/ml, greater than about 30 µg/ml, greater than about 40 µg/ml, or greater than about 50 µg/ml for gram+ and/or gram–bacteria are considered not to have anti-bacterial activity.

In another embodiment, the substituted tetracycline compound of the invention has a cytotoxicity which allows the compound to be administered in an effective amount to the subject with out causing prohibitive cytotoxic side effects. In an embodiment, the cytotoxicity of the substituted tetracycline compound of the invention is greater than about 10 µg/ml, about 15 µg/ml, about 20 µg/ml, or about 25 µg/ml as measured by cytoxicity assays known in the art such as the assay described in Example 5.

In another embodiment, the substituted tetracycline compound of the invention has a MIC which allows it to perform its intended function, e.g., treat or prevent malaria in a subject. The MIC is a measure of the concentration of the compound necessary to inhibit the malaria parasite. The MIC can be tested using methods known in the art as well as the in vitro method described in Example 3 or the in vivo method described in Example 4. In an embodiment, the MIC of a substituted tetracycline compound as measured in vitro is about 1000 nM or less, about 900 nM or less, about 800 nM or less, about 700 nM or less, about 600 nM or less, about 500 nM or less, about 450 nM or less, about 400 nM or less, about 350 nM or less, about 300 nM or less, about 250 nM or less, about 200 nM or less, about 190 nM or less, about 180 nM or less, about 170 nM or less, about 160 nM or less, about 150 nM or less, about 140 nM or less, about 130 nM or less, about 120 nM or less, about 110 nM or less, about 100 nM or less, about 90 nM or less, about 80 nM or less, about 70 nM or less, about 60 nM or less, about 50 nM or less, about 45 nM or less, about 40 nM or less, about 35 nM or less, about 30 nM or less, about 25 nM or less, about 20 nM or less, about 15 nM or less, about 12.5 nM or less, about 10 nM or less, about 9 nM or less, about 8 nM or less, about 7 nM or less, about 6 nM or less, about 5 nM or less, about 4.5 nM or less, about 4.0 nM or less, about 3.5 nM or less, about 3.0 nM or less, about 2.5 nM or less, about 2.0 nM or less, about 1.5 nM or less, about 1.0 nM or less, about 0.5 nM or less, about 0.4 nM or less, about 0.3 nM or less, about 0.2 nM or less, or about 0.1 nM or less.

In another embodiment, the MIC of a substituted tetracycline compound as measured in vivo is about 500 mg/kg or less, about 250 mg/kg or less, about 200 mg/kg or less, about 190 mg/kg or less, about 180 mg/kg or less, about 170 mg/kg or less, about 160 mg/kg or less, about 150 mg/kg or less, about 140 mg/kg or less, about 130 mg/kg or less, about 120 mg/kg or less, about 110 mg/kg or less, about 100 mg/kg or less, about 95 mg/kg or less, about 90 mg/kg or less, about 85 mg/kg or less, about 80 mg/kg or less, about 75 mg/kg or less, about 70 mg/kg or less, about 65 mg/kg or less, about 60 mg/kg or less, about 55 mg/kg or less, about 50 mg/kg or less, about 45 mg/kg or less, about 40 mg/kg or less, about 35 mg/kg or less, about 30 mg/kg or less, about 29 mg/kg or less, about 28 mg/kg or less, about 27 mg/kg or less, about 26 mg/kg or less, about 25 mg/kg or less, about 24 mg/kg or less, about 23 mg/kg or less, about 22 mg/kg or less, about 21 mg/kg or less, about 20 mg/kg or less, about 19 mg/kg or less, about 18 mg/kg or less, about 17 mg/kg or less, about 16 mg/kg or less, about 15 mg/kg or less, 14 mg/kg or less, 13 mg/kg or less, 12 mg/kg or less, 11 mg/kg or less, 10 mg/kg or less, about 9 mg/kg or less, about 8 mg/kg or less, about 7 mg/kg or less, about 6 mg/kg or less, about 5 mg/kg or less, about 4.5 mg/kg or less, about 4 mg/kg or less, about 3.5 mg/kg or less, about 3 mg/kg or less, about 2.5 mg/kg or less, about 2 mg/kg or less, about 1.5 mg/kg or less, about 1 mg/kg or less, about 0.8 mg/kg or less, about 0.6 mg/kg or less, about 0.4 mg/kg or less, about 0.2 mg/kg or less, about 0.1 mg/kg or less, about 0.05 mg/kg or less, or about 0.01 mg/kg or less.

This invention provides a method for treating or preventing malaria in a subject by administering to the subject an effective amount of a substituted tetracycline compound, such that malaria is treated or prevented in said subject. The substituted tetracycline compound is of formula I:

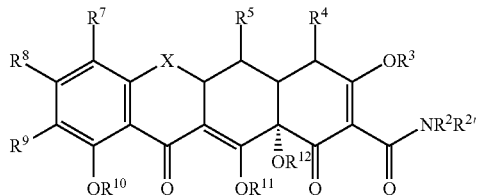

(I)

wherein:
X is $CHC(R^{13}Y'Y)$, $CR^{6'}R^6$, S, $NR^6$, or O;
$R^2$, $R^{2'}$, $R^{4'}$, and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is $NR^{4'}R^{4''}$, alkyl, alkenyl, alkynyl, hydroxyl, halogen, or hydrogen;
$R^3$, $R^{11}$ and $R^{12}$ are each hydrogen, or a pro-drug moiety;
$R^{10}$ is hydrogen, a prodrug moiety, or linked to $R^9$ to form a ring;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^7$ is hydrogen, alkylamino, dialkylamino, or a malaria interacting moiety;
$R^9$ is hydrogen, or a malaria interacting moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl; with the proviso that the compound of formula I is not oxytetracycline, demeclocycline, doxycycline, chlorotetracycline, minocycline, or tetracycline; and pharmaceutically acceptable salts thereof.

Examples of compounds of formula I which can be used in the methods of the invention include substituted tetracycline compounds wherein $R^{2'}$, $R^3$, $R^8$, $R^{10}$, $R^{11}$, and $R^{12}$ are hydrogen; $R^4$ is NR'R" and $R^{4'}$ and $R^{4''}$ are alkyl (e.g., methyl); and X is $CR^6R^{6'}$. The substituted tetracycline compounds of the invention may also include substituted minocycline derivatives, e.g., wherein $R^5$, $R^6$, and $R^{6'}$ are hydrogen, and $R^7$ is dialkylamino. The invention also includes methods which use substituted doxycycline derivatives, e.g., substituted tetracycline compounds of the invention wherein $R^6$ is alkyl, $R^{6'}$ is hydrogen, and $R^7$ is hydrogen. $R^5$ may be hydroxyl or a prodrug moiety. The invention also includes substituted sancycline compounds wherein $R^5$, $R^6$, and $R^{6'}$ are hydrogen. In certain embodiments, the substituted sancycline compounds include compounds wherein at least one of W and $R^9$ is a malaria interacting moiety. In another embodiment, $R^4$ is hydrogen.

In one embodiment, the substituted tetracycline compound of the invention is substituted at least at the 7 or 9 position by a substituent other than hydrogen (at either the 9 or 7 position) or dimethyl amino at the 7 position.

In another embodiment, the substituted tetracycline compound of the invention is substituted at the 7 or 9 position with a malaria interacting moiety. The term "malaria interacting moiety" is a moiety which allows the substituted tetracycline compound of the invention to perform its intended function, e.g., treat or prevent malaria. It may interact with the malaria parasite or allow other portions of the tetracycline molecule to interact with the parasite. It also may allow the molecule to treat malaria by affecting the way the tetracycline compound interacts with the malaria parasite, the subject, or other microbes. For example, the malaria interacting moiety may alter the tetracycline compounds' properties such that the resulting compound is, for example, non-antibacterial.

Not to be limited, but in an embodiment, the malaria interacting moiety is a moiety which comprises from about 2 to 40, from about 3 to 30, from about 3 to 20 carbon, nitrogen, oxygen and sulfur atoms. The malaria interacting moiety may further be substituted with hydrogen and other substituents (e.g., halogens) which are not counted amongst the 2 to 40, from about 3 to 30, from about 3 to 20 atoms. In a further embodiment, the malaria interacting moiety comprises an aryl or heteroaryl moiety. Furthermore, the aryl or heteroaryl moiety can be substituted with any substituent which allows it to perform its intended function. The malaria interacting moiety also may comprise alkenyl, alkynyl, alkyl, nitroso, oximyl, or other moieties, which may also be substituted. In another embodiment, the malaria interacting moiety comprises about 4 to 16 carbon, sulfur, nitrogen, and oxygen atoms or from about 5 to about 15 carbon, sulfur, nitrogen and oxygen atoms. Examples of malaria interacting moieties include, but are not limited, to substituted and unsubstituted aryl (e.g., substituted and unsubstituted phenyl), alkyl, alkenyl, alkynyl, arylalkynyl, etc. In another embodiment, the malaria interacting moiety is substituted aminoalkyl, e.g., alkylaminoalkyl, dialkylaminoalkyl, alkenylaminoalkyl, alkynylaminoalkyl, aralkylaminoalkyl, arylaminoalkyl, etc.

In one embodiment, when $R^7$ is a malaria interacting moiety, the malaria interacting moiety may be hydroxyl, halogen, thiol, alkyl, alkenyl, alkynyl, aryl, alkoxy, alkylthio, oximyl, alkylsulfinyl, alkylsulfonyl, arylalkyl, amino(e.g., unsubstituted amino, alkylamino, dialkyl amino, alkoxycarbonylalkylamino, etc.), substituted carbonyl, arylalkenyl, heterocyclic, arylalkynyl, alkoxycarbonylalkylamino, or —$(CH_2)_{0-3}$NR$^{7c}$C(=W')WR$^{7a}$; wherein W is CR$^{7d}$R$^{7e}$, NR$^{7b}$, S, or O; W' is O or S; and R$^{7a}$, R$^{7b}$, R$^{7c}$, R$^{7d}$, and R$^{7e}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety.

In one embodiment, when $R^9$ is a malaria interacting moiety, the malaria interacting moiety may be hydroxyl, heterocyclic, halogen, thiol, alkyl, alkenyl, alkynyl, aryl, alkoxy, alkylthio, oximyl, alkylsulfinyl, alkylsulfonyl, arylalkyl, amino (e.g., unsubstituted amino, alkylamino, dialkyl amino, alkoxycarbonylalkylamino, etc.), substituted carbonyl, arylalkenyl, arylalkynyl, or —$(CH_2)_{0-3}$NR$^{9c}$C(=Z')ZR$^{9a}$, wherein Z is CR$^{9d}$R$^{9e}$, NR$^{9b}$ or O; Z' is O or S; and R$^{9a}$, R$^{9b}$, R$^{9c}$, R$^{9d}$, and R$^{9e}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety. In embodiment, Z is N and Z' is O, and R$^{9a}$ is optionally aryl. In another embodiment, Z and Z' are O, and R$^{9a}$ is, for example, alkyl. Further examples of R$^9$ include —NR$^{9c}$C(=Z')ZR$^{9a}$, wherein Z is CR$^{9d}$R$^{9e}$, NR$^{9b}$ or O; Z' is O or S; and R$^{9a}$, R$^{9b}$, R$^{9c}$, R$^{9d}$, and R$^{9e}$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety. In another embodiment, the malaria interacting moiety is substituted aminoalkyl, e.g., alkylaminoalkyl, dialkylaminoalkyl, aralkylaminoalkyl, alkenylaminoalkyl, alkynylaminoalkyl, arylaminoalkyl, aminomethyl, etc.

Examples of malaria interacting moieties include aryl groups such as phenyl and heteroaryl groups (e.g., furanyl, imidazolyl, benzothiophenyl, benzofuranyl, quinolinyl, isoquinolinyl, pyridinyl, pyrazolyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, and deazapurinyl). The aryl group may be substituted or unsubstituted. Examples of substituents include, but are not limited, alkyl, alkenyl, alkynyl, aralkyl, alkoxyalkyl, aminoalkyl, amino, nitro, cyano, halogen (e.g., fluorine, chlorine, bromine, iodine, etc.), hydroxy, thiol, formyl, acetyl, acyl, alkoxy (e.g., methylene dioxy, methoxy, ethoxy, propoxy, etc.) and heterocyclic (e.g., morpholino, piperazine, etc.). The substituents may be further substituted as appropriate.

Other examples of malaria interacting moieties include substituted and unsubstituted alkynyl groups. Examples of substituted alkynyls include aryl alkynyls (e.g., a methoxy substituted aryl alkynyl, cycloalkenyl substituted alkynyls, amino substituted alkynyls, etc.). Other examples of malaria interacting groups include substituted and unsubstituted alkenyl groups, such as, for example, arylalkenyl groups. Furthermore, $R^9$ groups can also be substituted or unsubstituted alkyl groups (e.g., lower alkyl groups, such as, for example, methyl, ethyl, propyl, butyl, t-butyl, etc.). $R^9$ may also be heterocyclic (e.g. thiazole, amino thiazole, etc.), or substituted amino alkyl, amino alkenyl.

The malaria interacting moiety may be substituted with one or more substituents which allow it to performs its intended function, e.g., treat or prevent malaria. Examples of substituents include, but are not limited to, alkyl, alkenyl, alkynyl, halogen, hydroxyl, alkoxy, alkylcarbonyloxy, alkyloxycarbonyl, carboxy, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the phenyl is substituted with at least one alkyl, amino, heterocycle, alkoxy, halogen, nitro, alkoxycarbonyl, dialkylamino, or alkylamino.

In a further embodiment, the malaria interacting moiety comprises one or more ionizable nitrogen atom. In a further embodiment, the pKa of the malaria interacting moiety is greater than about 7, greater than about 8, greater than about 9, greater than about 9.5, or greater than about 10. In a further embodiment, the pKa of the malaria interacting moiety is between about 7 and about 12, between about 7.5 and about 11.5, between about 8.0 and about 11.0, between about 9.0 and about 11.0, between about 9.0 and about 10.5, between about 9.0 and about 10.0. The pKa of the malaria interacting moiety can be determined by methods known in the art. For example, the pKa can be determined using computational methods such as ACD software (Advanced Chemistry Development, Inc., 90 Adelaide Street West, Toronto, Ontario, Canada).

In a further embodiment, the malaria interacting moiety is selected from the group consisting of:

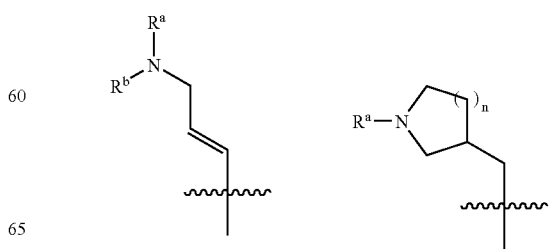

-continued

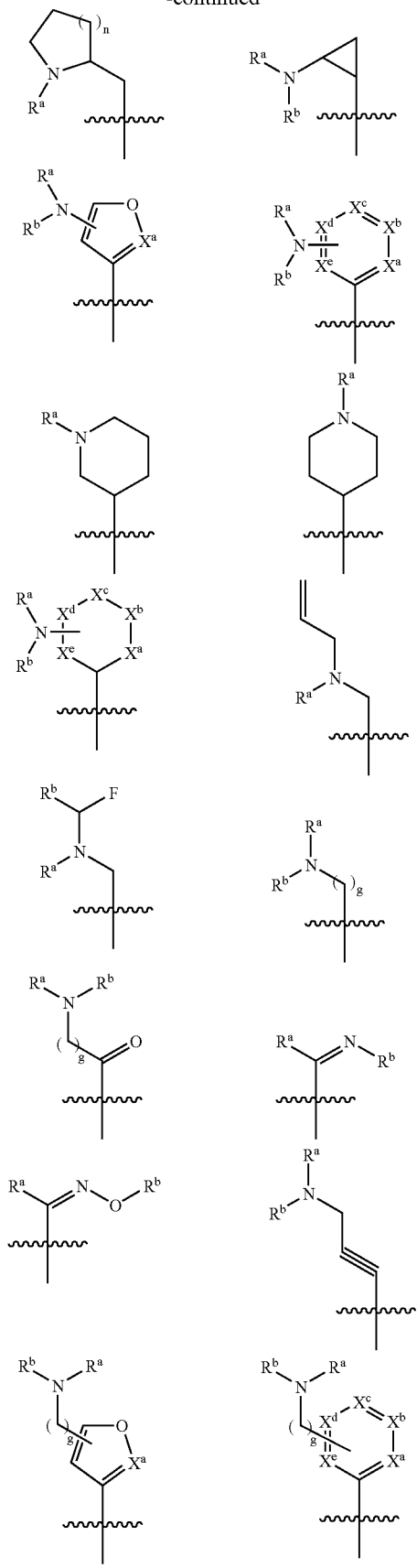

wherein:

$R^a$ and $R^b$ are each independently hydrogen, halogen, alkyl, alkenyl, alkynyl, aryl, aralkyl, alkoxy, or heterocyclic ($R^a$ and $R^b$ may optionally be linked to form a ring);

g is 1, 2, 3, 4, 5, 6, 7, 8, 9, 10, 11, 12, 13, 14, 15, 16, 17, 18, 19, or 20;

n is 0, 1, 2, or 3; and $X^a$, $X^b$, $X^c$ $X^d$, and $X^e$ are each independently optionally substituted carbon, oxygen, nitrogen, or sulfur. Furthermore, each carbon atom of the malaria interacting moieties shown above may be further substituted with substituents which allow the tetracycline compound to perform its intended function. Examples of such substituents include, but are not limited to, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aromatic, and heteroaromatic moieties.

In another further embodiment, the malaria interacting moiety is at the 7-position of the tetracycline compound.

The methods of the invention also include the use of substituted tetracycline compounds which are sancycline derivatives, e.g., wherein $R^5$, $R^6$, and $R^{6'}$ are hydrogen. Examples of sancycline derivatives include tetracycline compounds wherein $R^7$ is a malaria interacting moiety. Examples of malaria interacting moieties which may be used for substituted sancycline compounds of the invention include those described above. Furthermore, other examples of malaria interacting moieties include, but are not limited to, aryl group such as substituted or unsubstituted phenyl or a heteroaryl moieties. Examples of substituents include halogens (e.g., fluorine, chlorine, bromine, iodine), alkoxy (e.g. methoxy, ethoxy, propoxy, methylene dioxy, etc.), amino, and alkyl (e.g. methyl, ethyl, propyl, butyl, t-butyl, etc.). In other embodiments, the substituted sancycline compounds of the invention include compounds wherein $R^7$ is alkyl (e.g. methyl, ethyl, propyl, butyl, etc.), alkynyl (e.g. aryl substituted, e.g., amino substituted arylalkynyl, etc.), halogen (e.g., fluorine, chlorine, bromine, iodine), substituted or unsubstituted methyl amido. Other substituted sancycline compounds include compounds wherein $R^9$ is hydrogen or a malaria interacting moiety.

The methods of the invention also include methods which use substituted doxycycline compounds as the substituted tetracycline compound. Examples of substituted doxycycline compounds include compounds wherein $R^5$ is hydroxy or an ester groups, such as alkyl esters (i.e., alkyl carbonyloxy groups, cyclohexane esters, cycloheptane esters, pentyl esters, and ethyl esters).

Examples of the substituted tetracycline compounds of the invention include the compounds shown in Tables 1 and 2. Certain of the substituted tetracycline compounds of the invention are shown below:

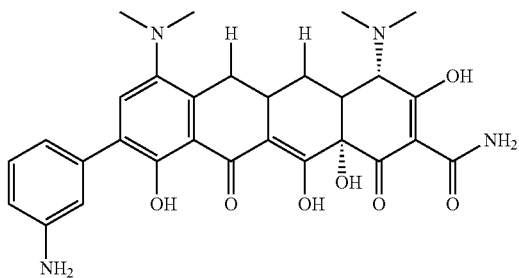
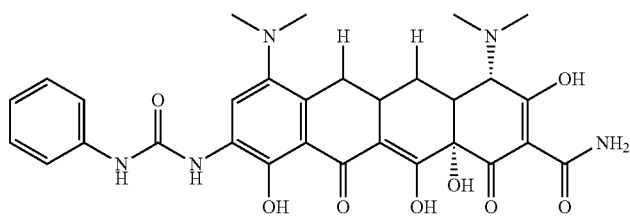
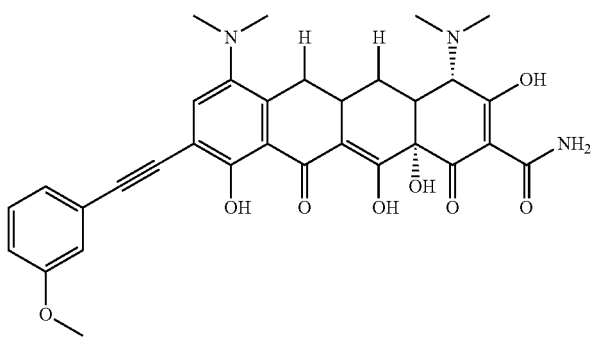
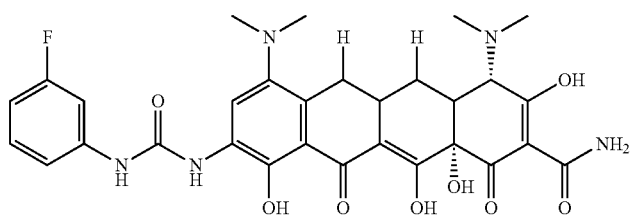
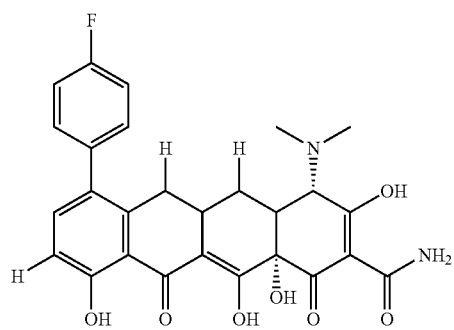

-continued
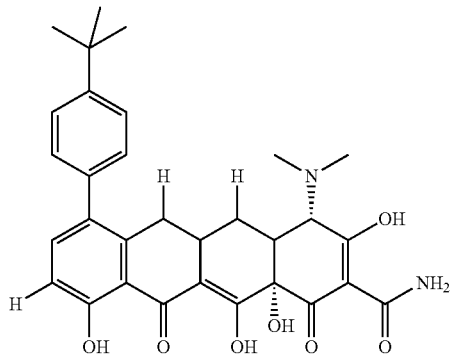
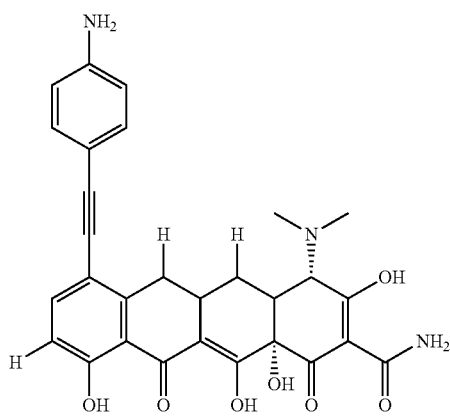
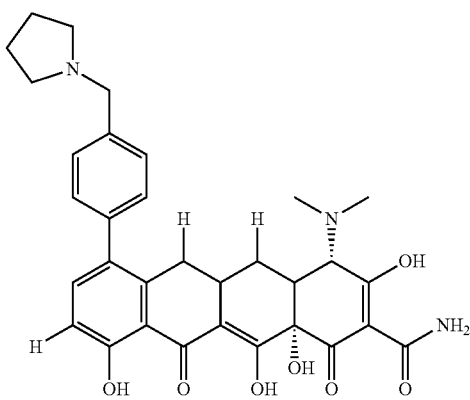
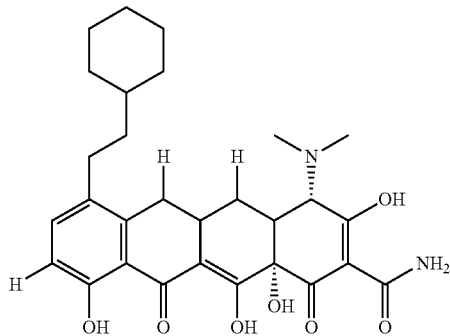

-continued
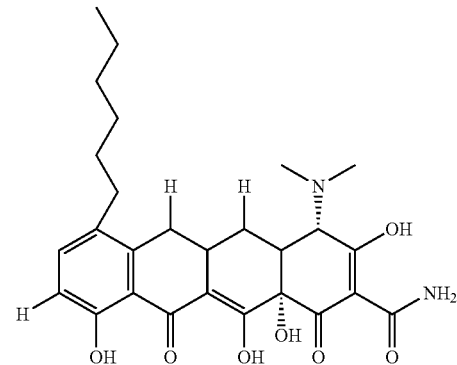
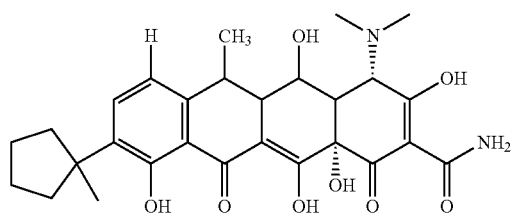
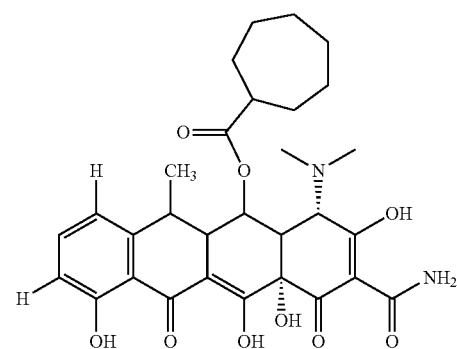
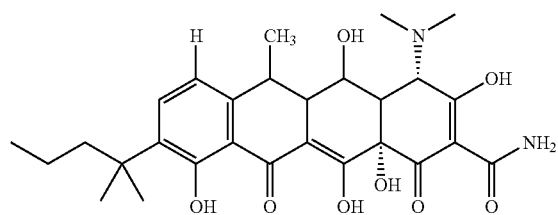
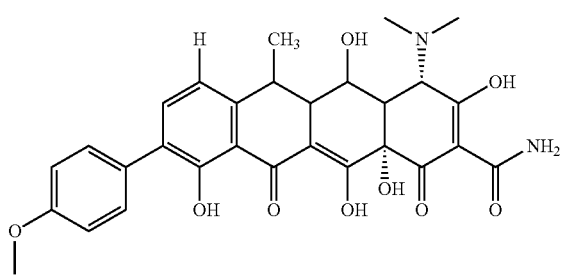

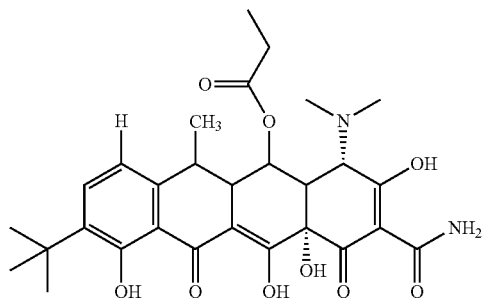
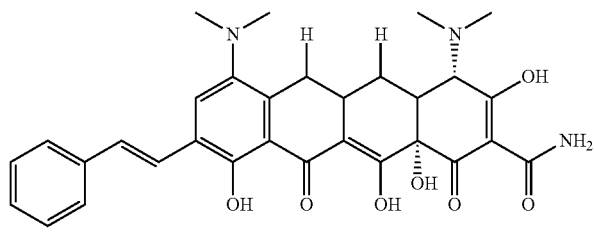
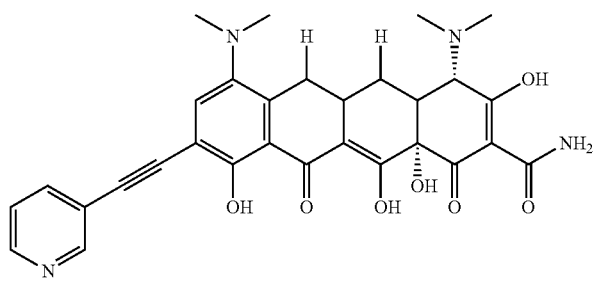
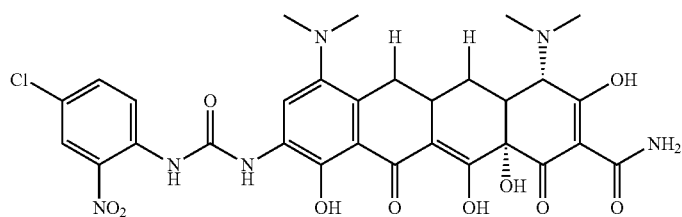
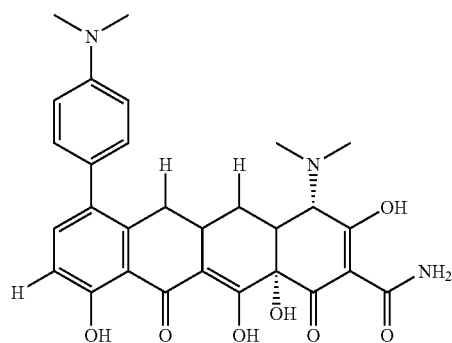

-continued
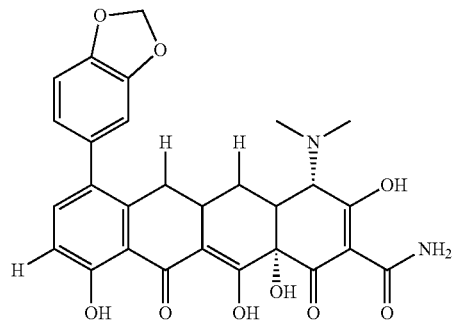
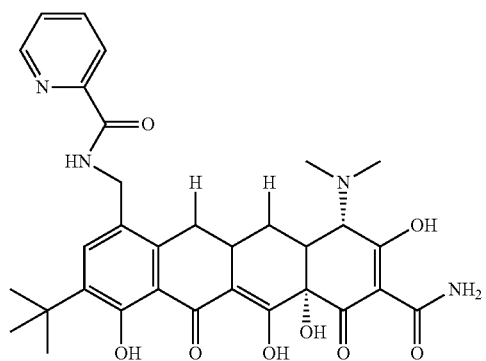
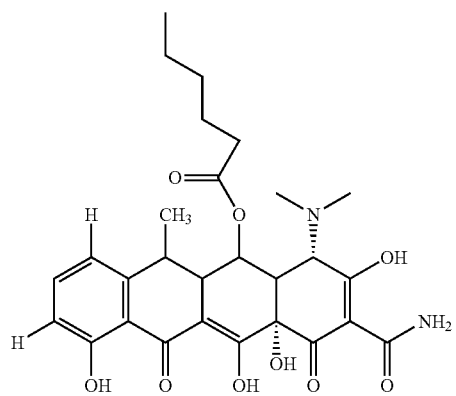
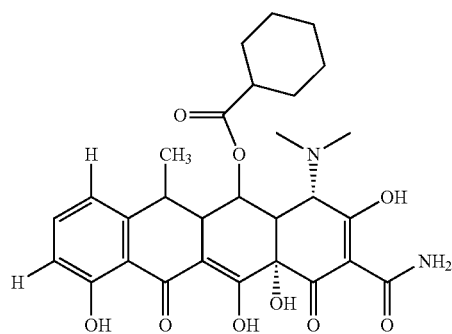

-continued
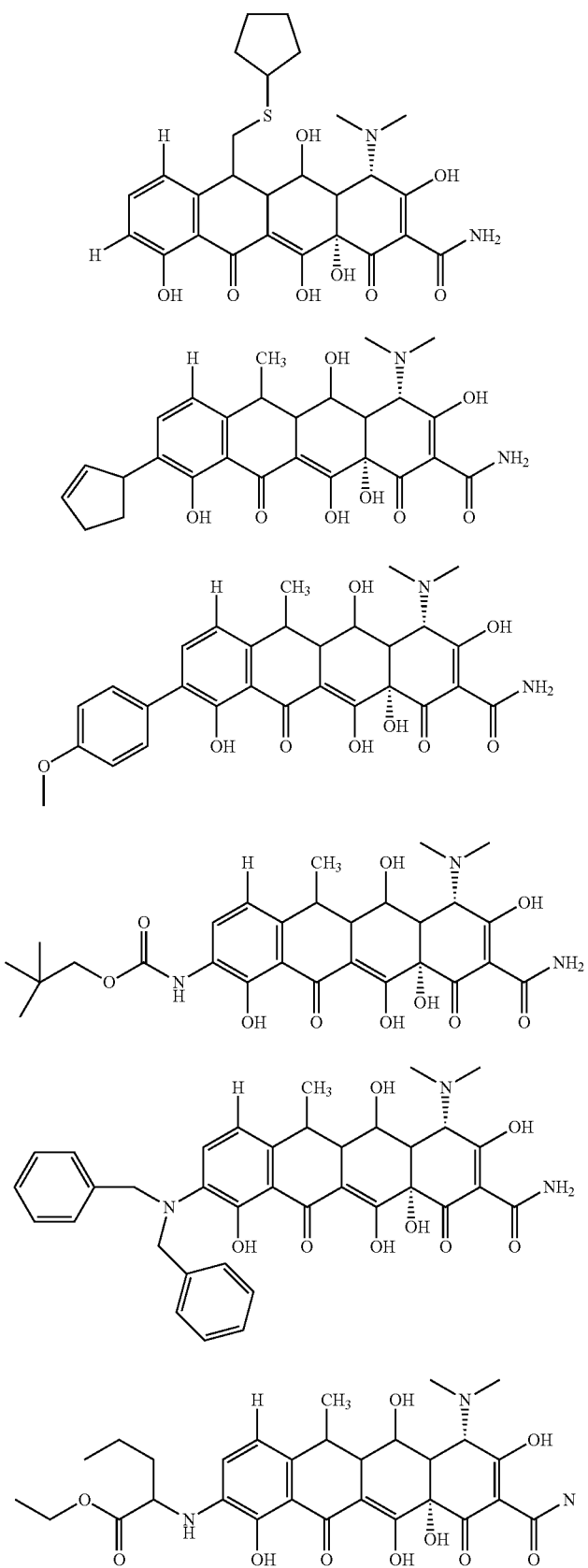

-continued
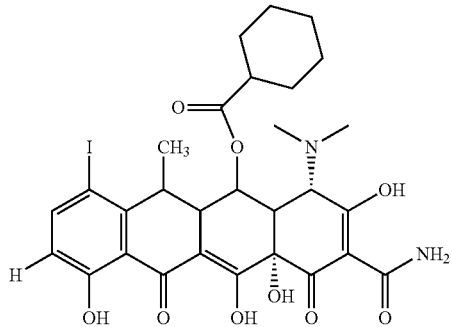
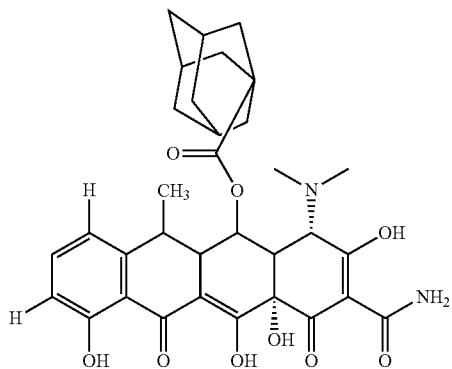
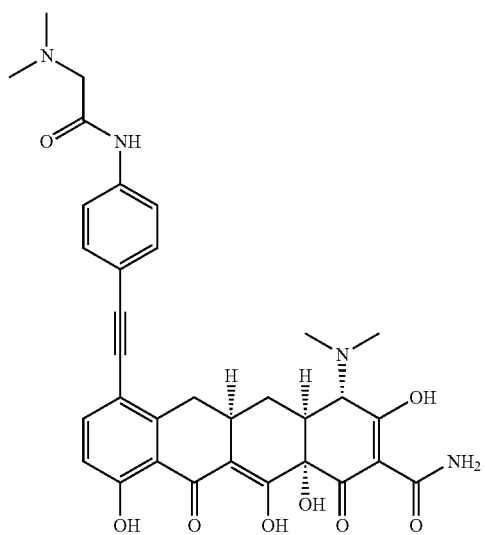
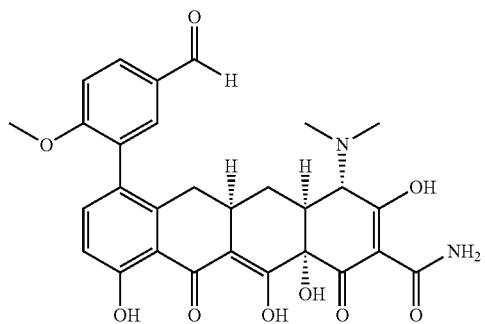

-continued
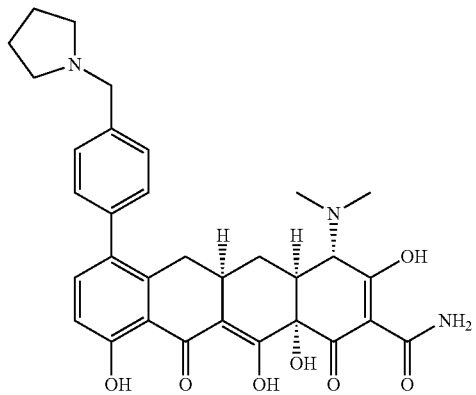
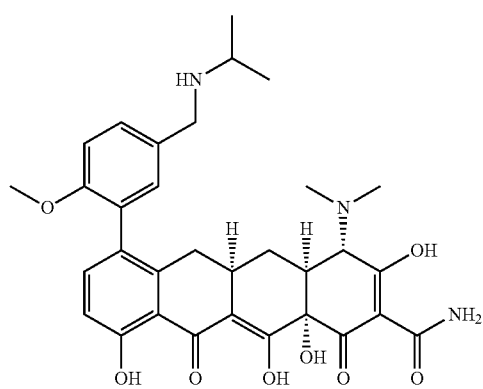
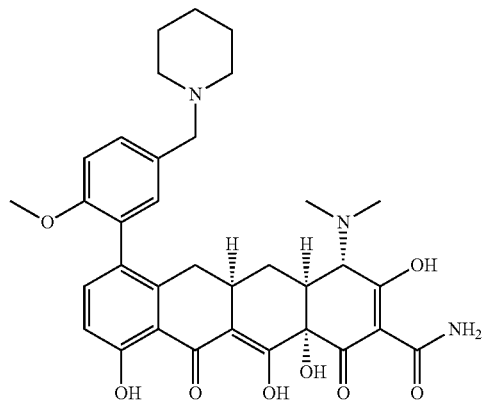
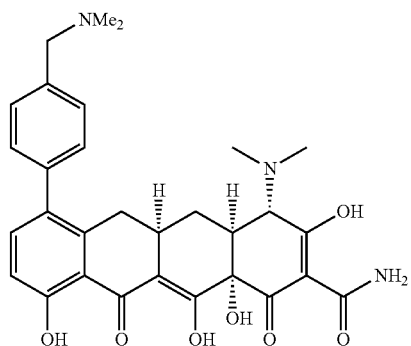

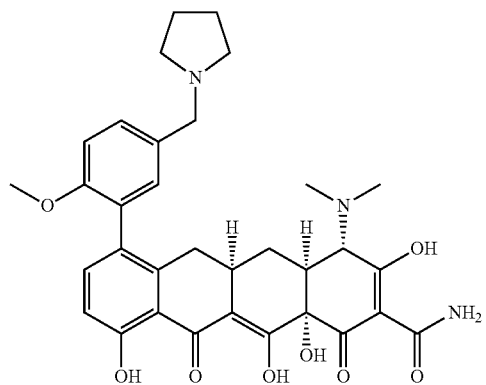
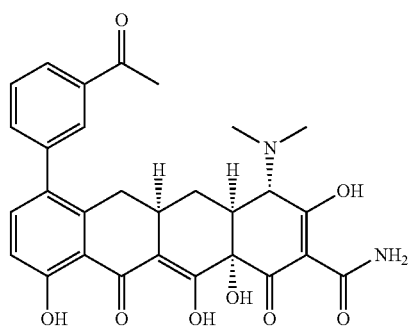
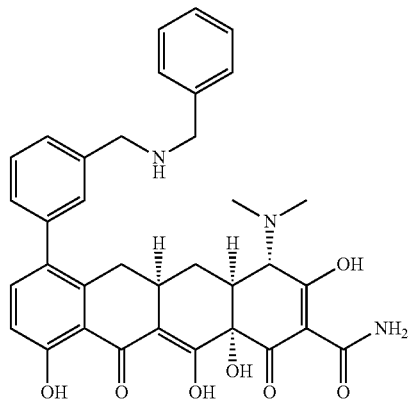
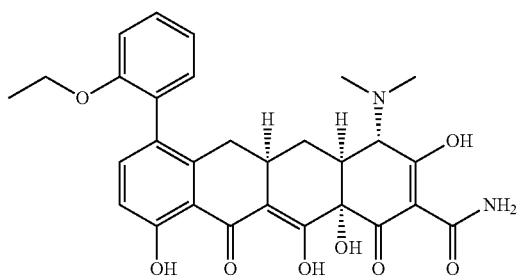

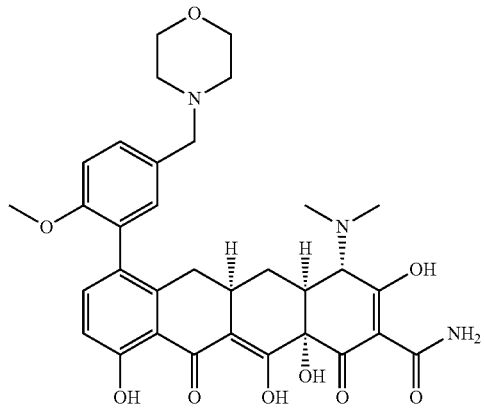
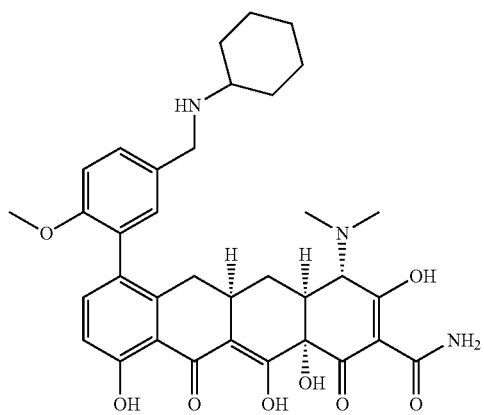
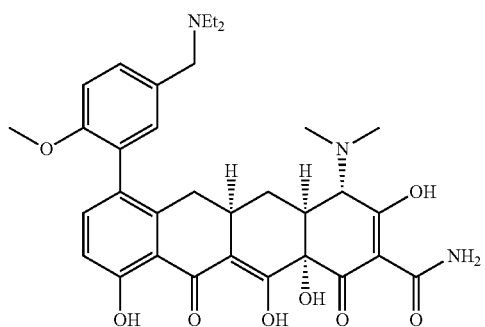
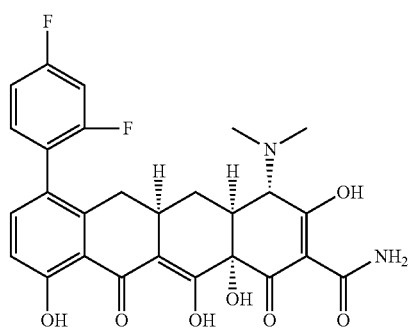

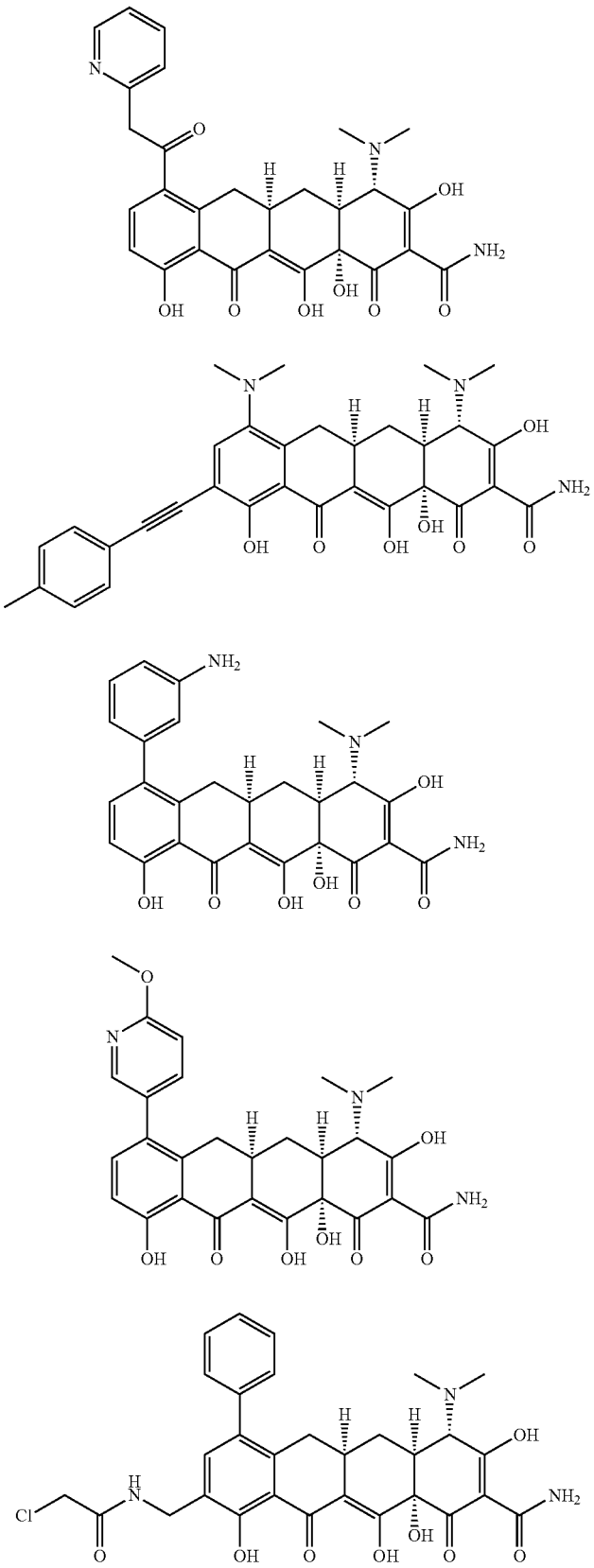

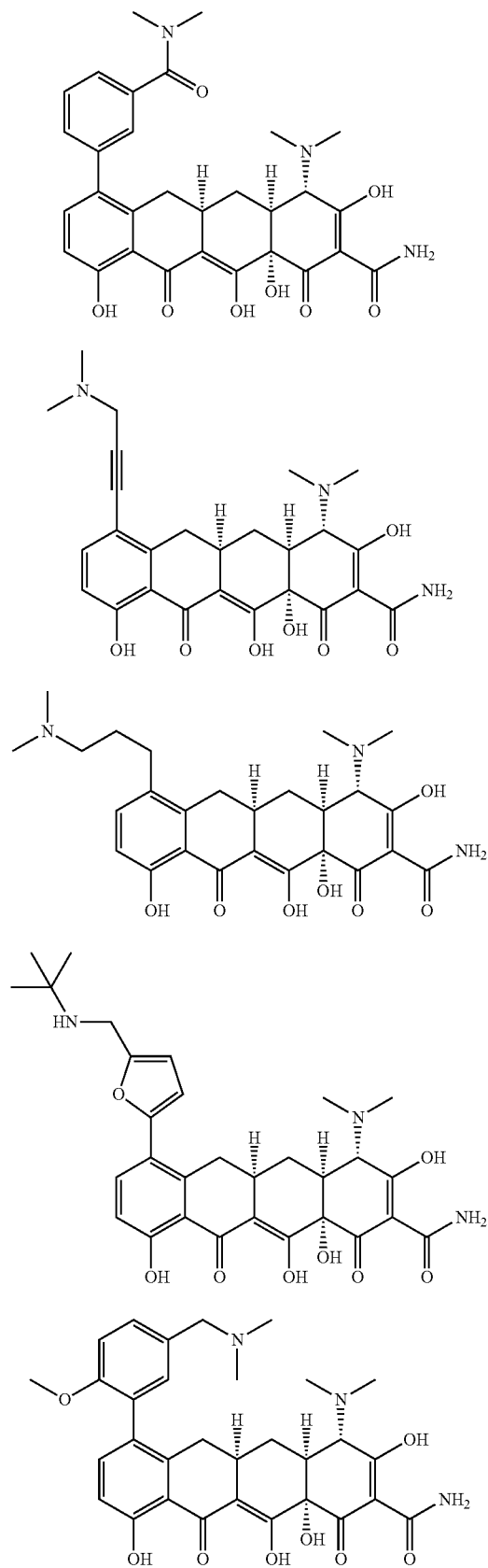

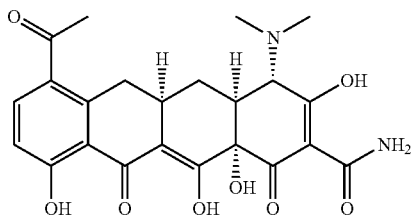
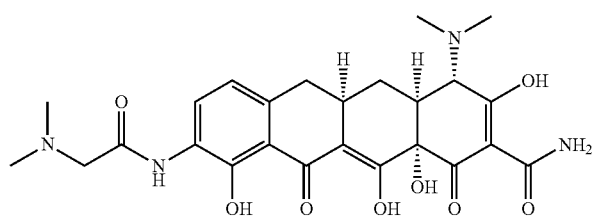
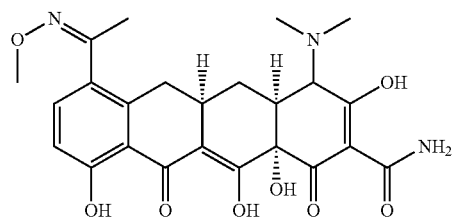
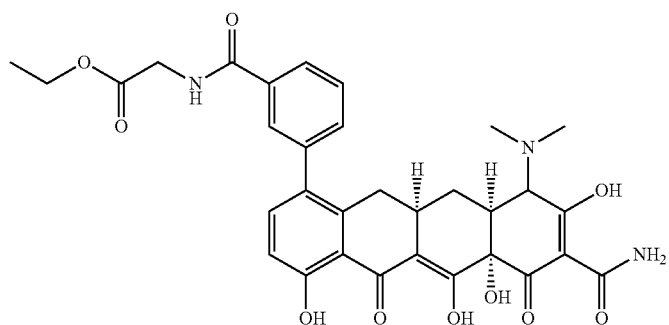
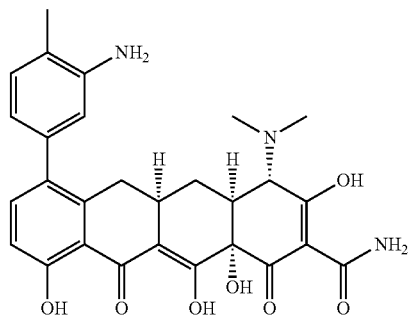

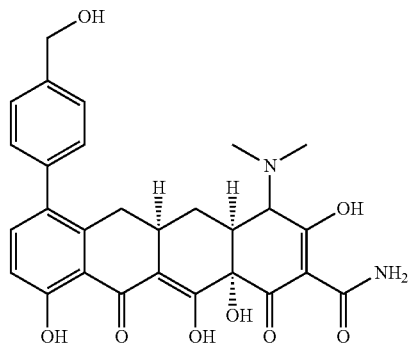
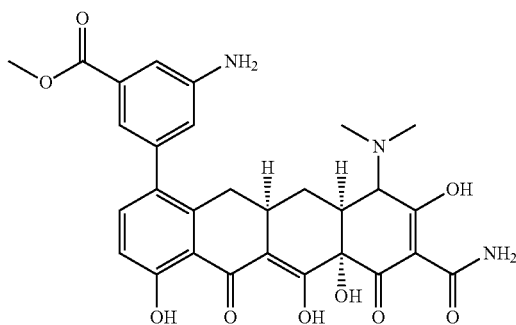
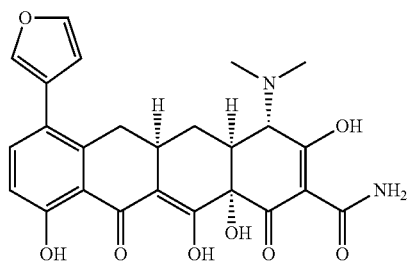
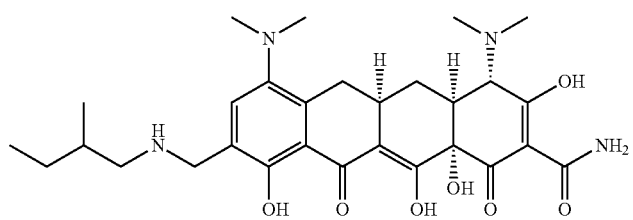
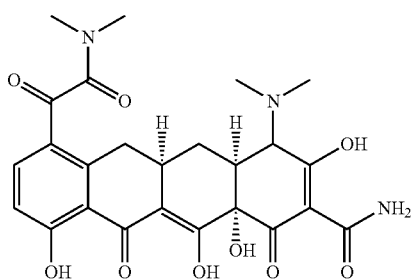

-continued
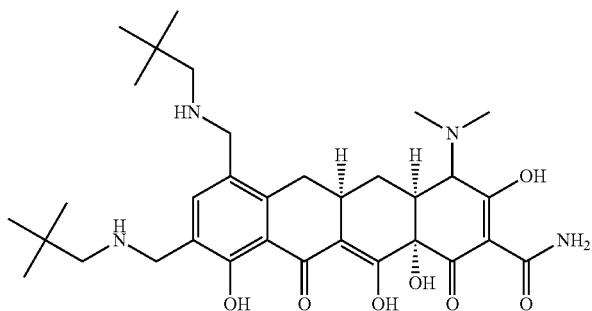
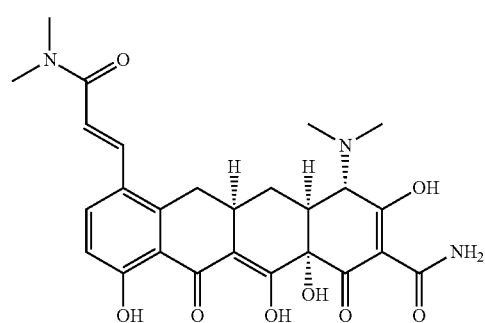
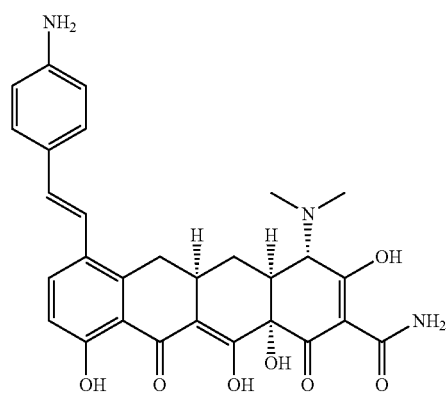
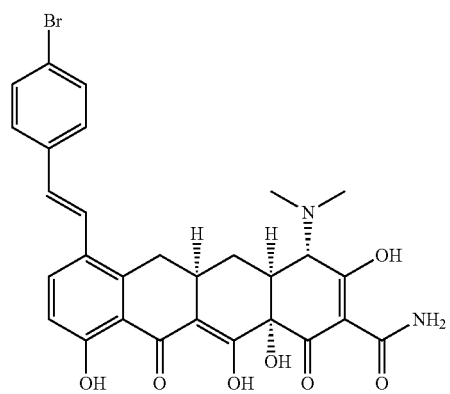

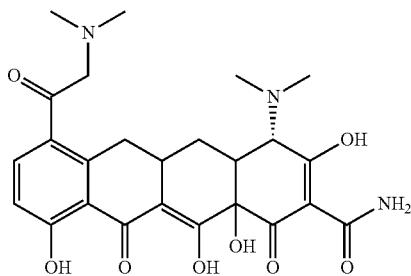

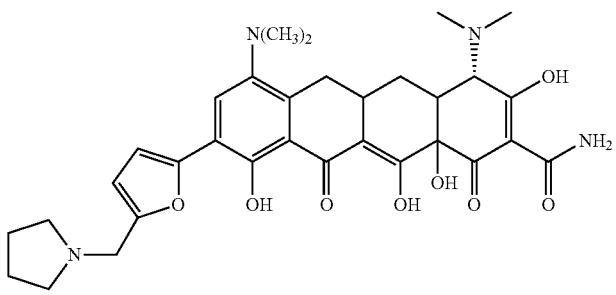

In certain embodiments, the substituted tetracycline compound has a molecular weight of less than 800, less than 600, less than 550, less than 500, or less than 400 grams/mole.

Other substituted tetracycline compounds which may be used in the methods of the invention include, but are not limited to, the compounds described in U.S. Ser. Nos. 60/346,930; 60/346,929; 60/347,065; 60/346,956; 60/367,048; 60/366,915; 60/367,045; 09/823,884; 09/852,908; 09/882,505; 09/882,273; 09/894,805; 09/883,137; 09/895,797; 09/895,857; 09/895,812; 10/097,095 and 10/097,135; the contents of each of the aforementioned applications are incorporated herein by reference in their entirety. Additional tetracycline compounds of the invention are shown in Table 1, below.

TABLE 1

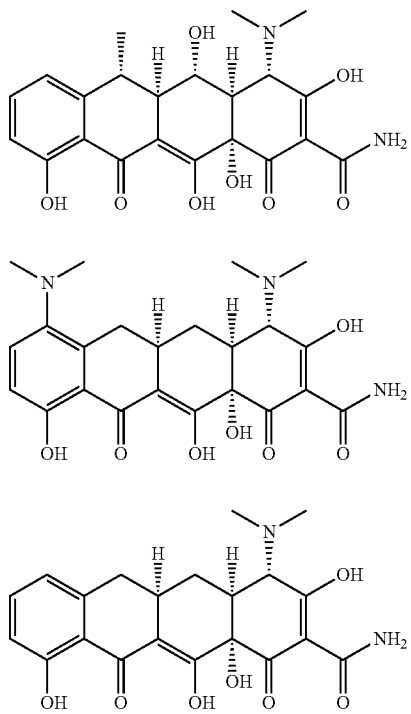

TABLE 1-continued
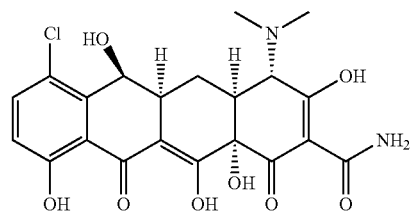
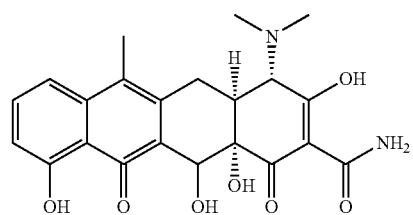
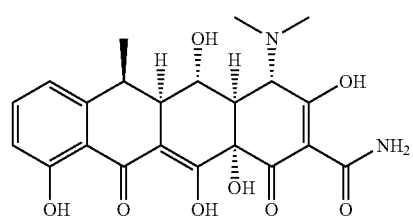
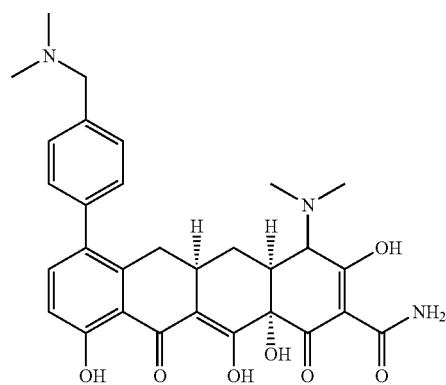
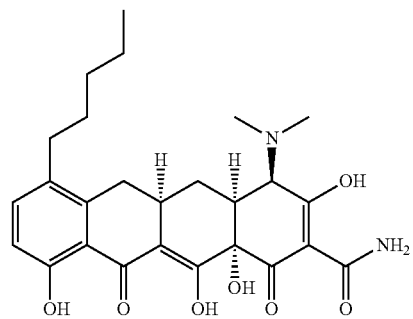

TABLE 1-continued
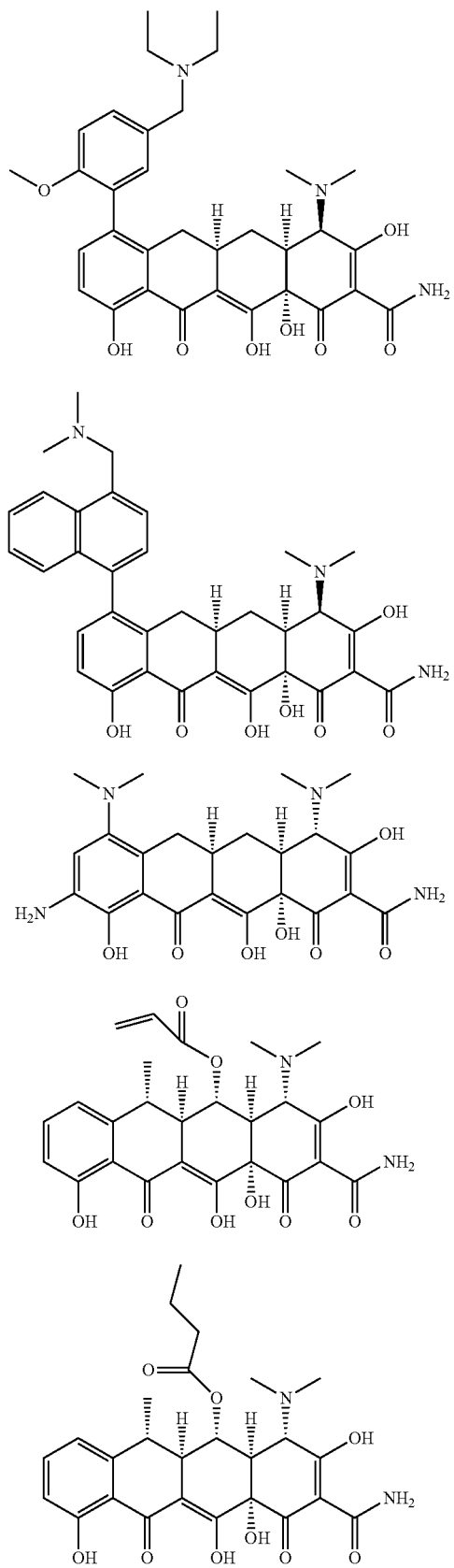

TABLE 1-continued
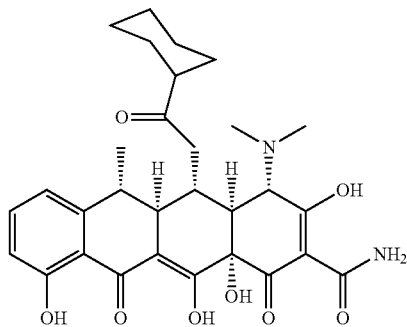
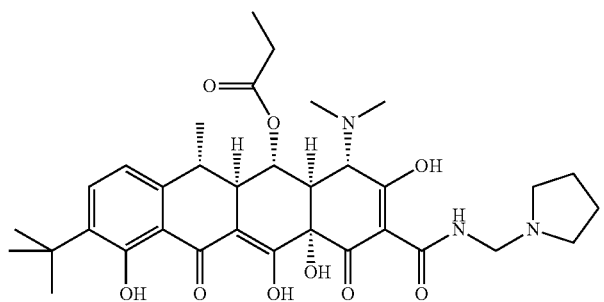
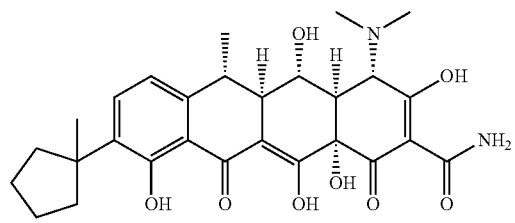
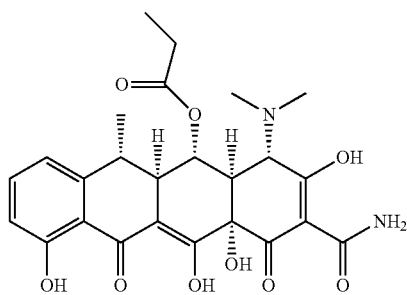
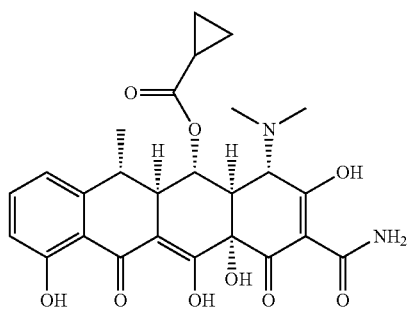

TABLE 1-continued
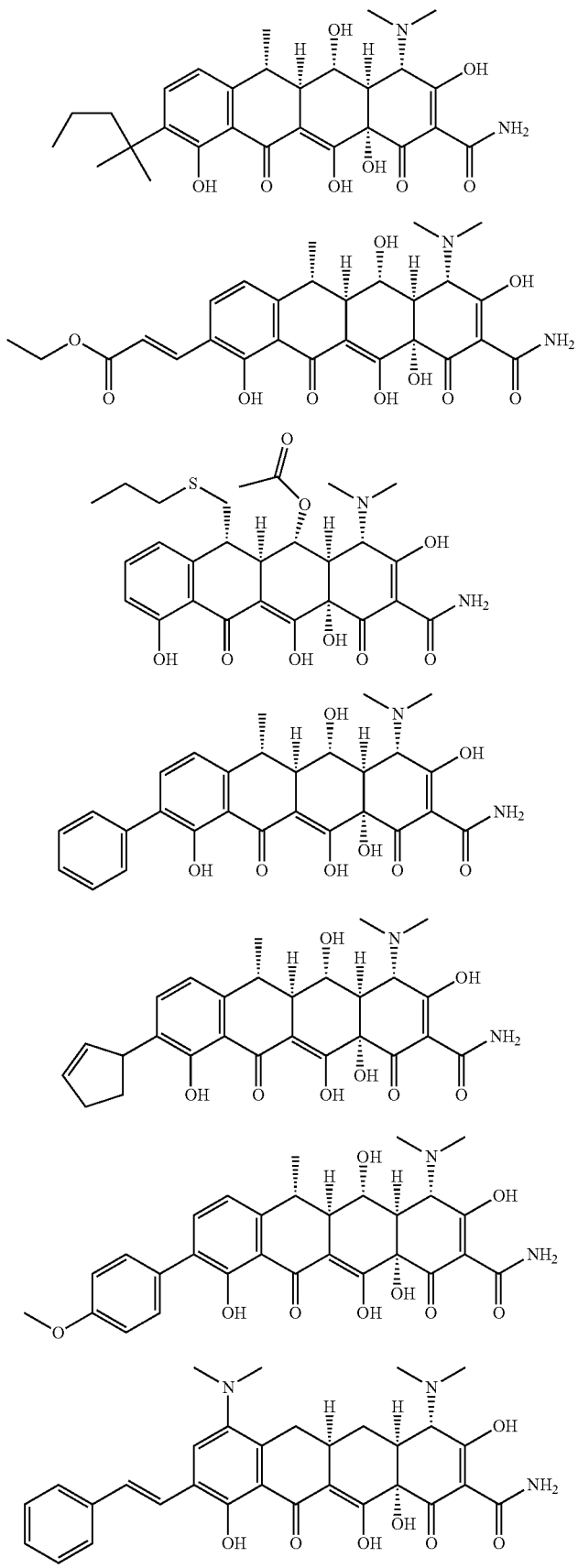

TABLE 1-continued
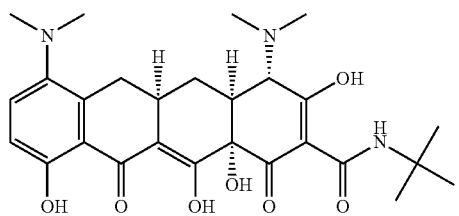
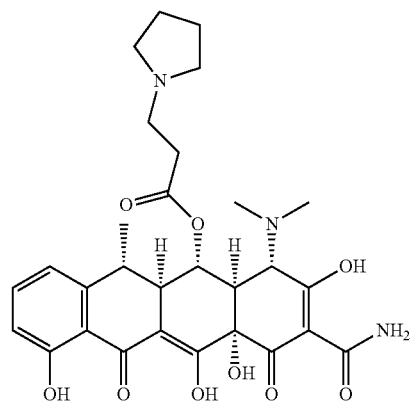
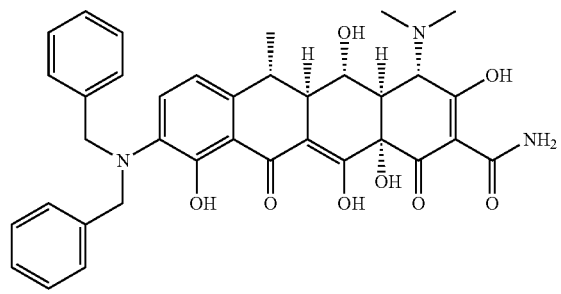
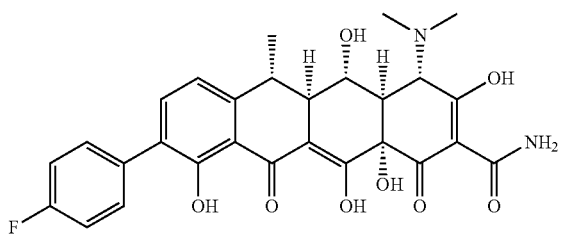
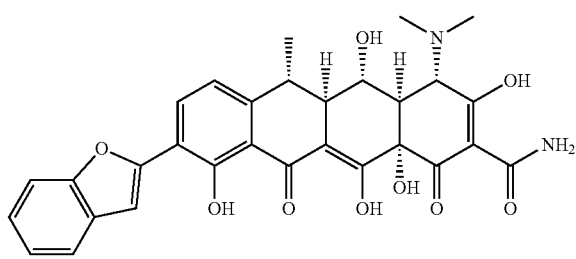

TABLE 1-continued
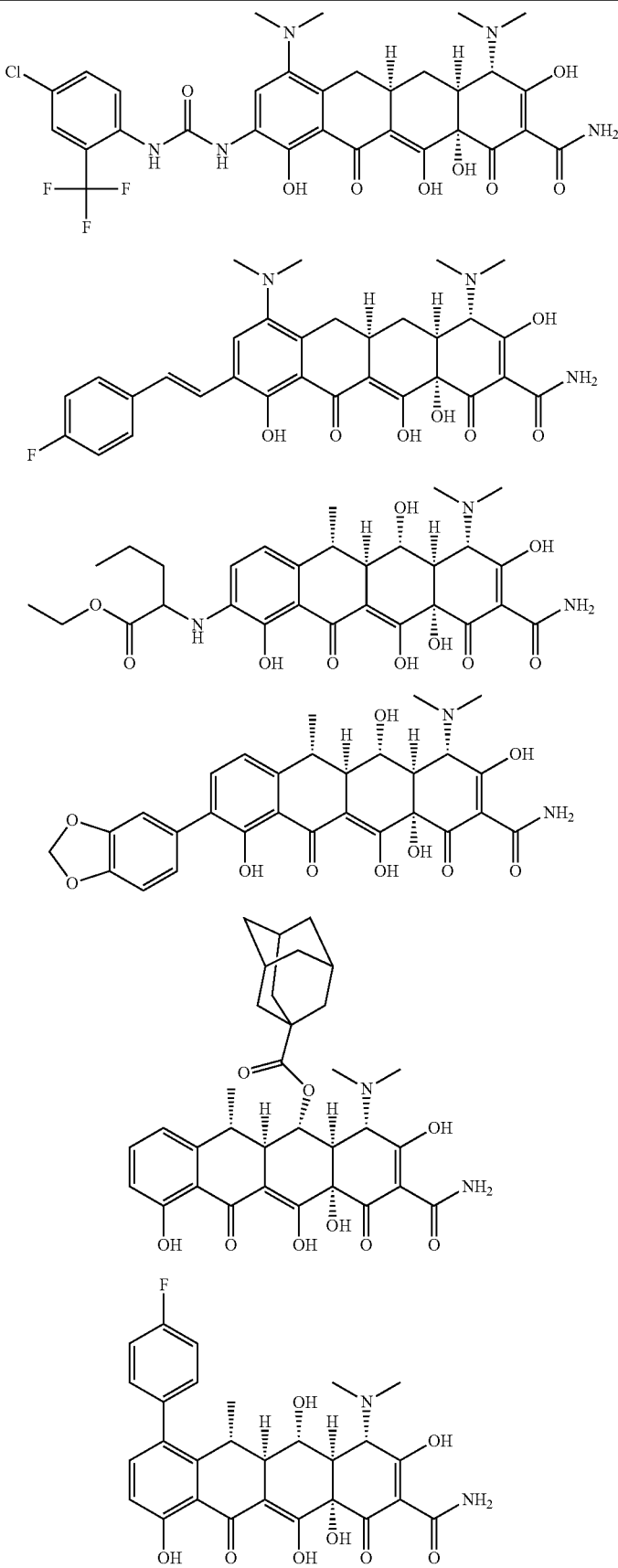

TABLE 1-continued
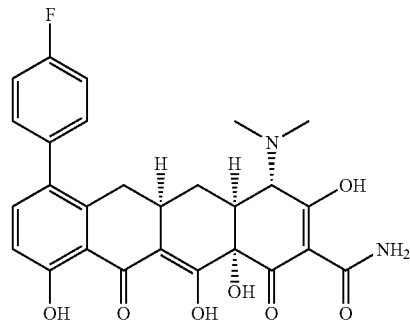
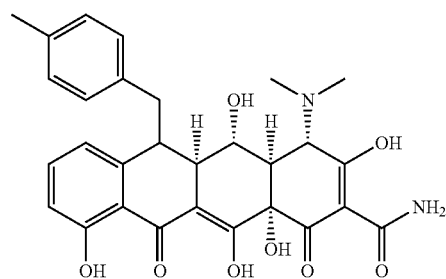
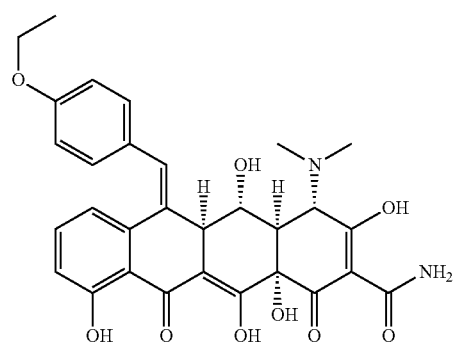
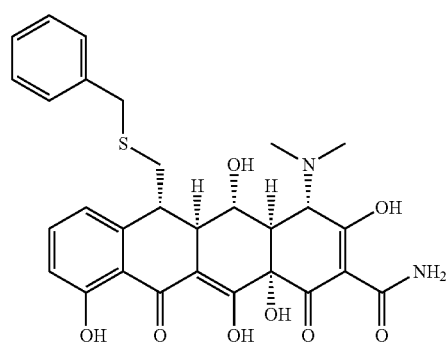

TABLE 1-continued
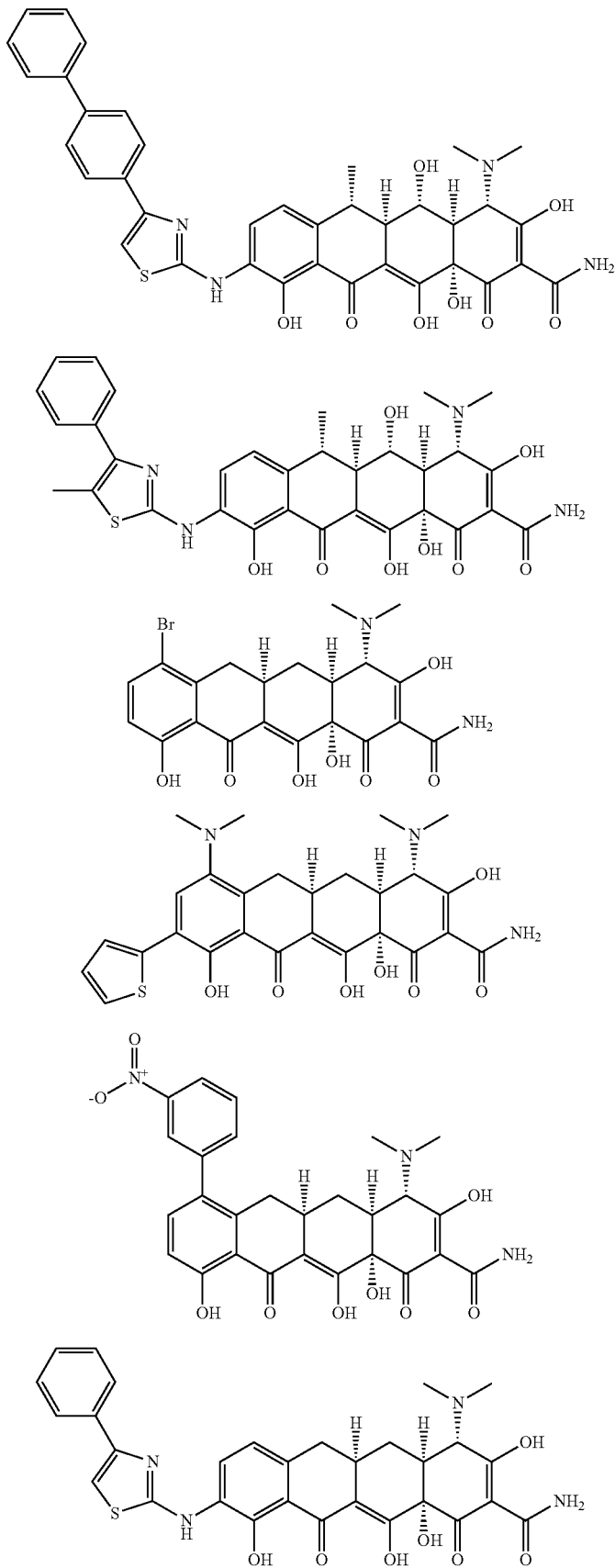

TABLE 1-continued
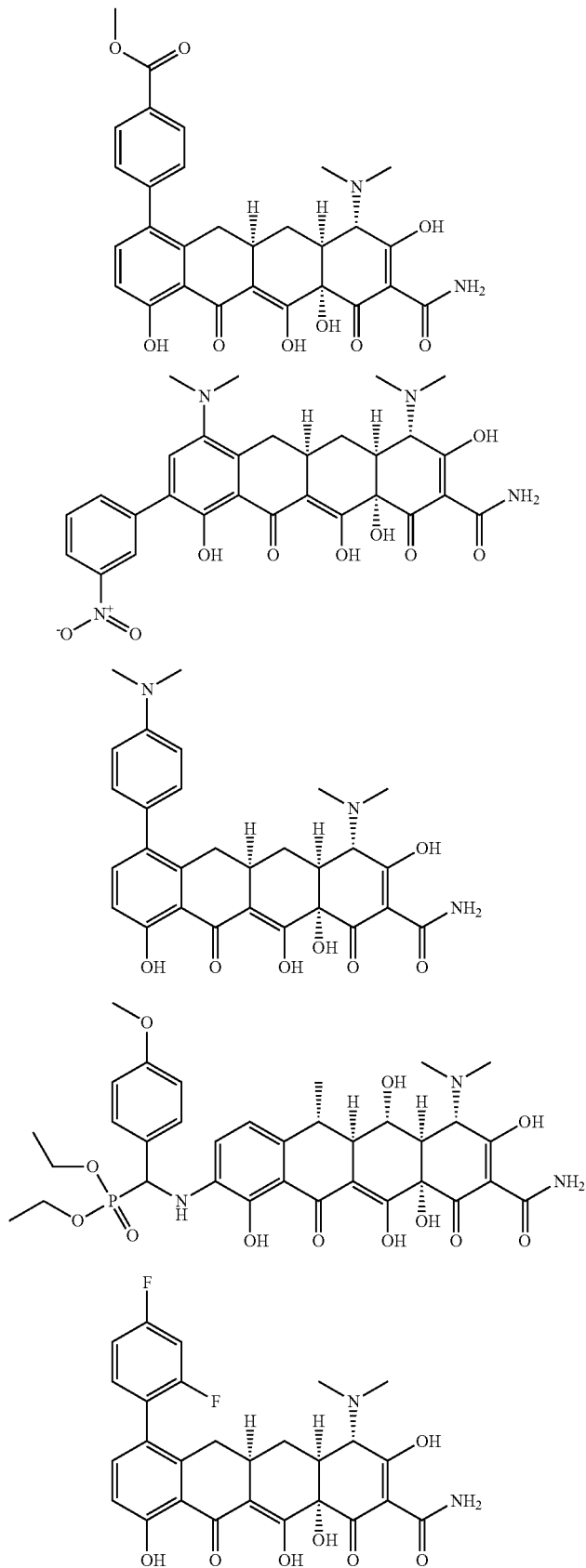

TABLE 1-continued
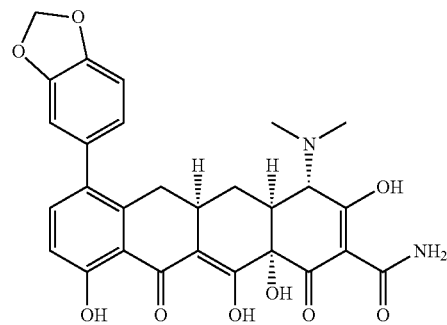
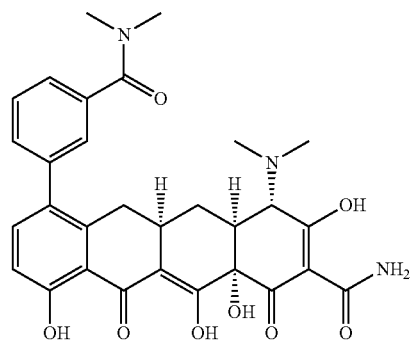
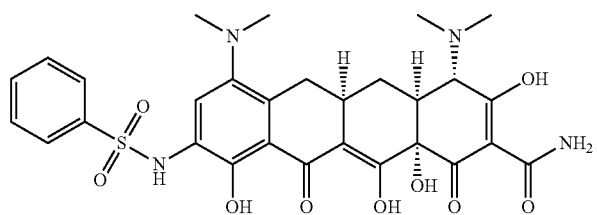
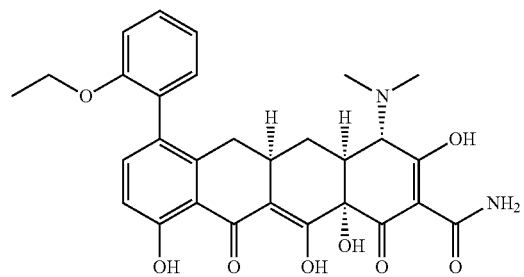
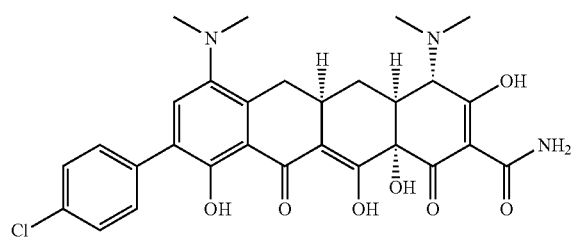

TABLE 1-continued
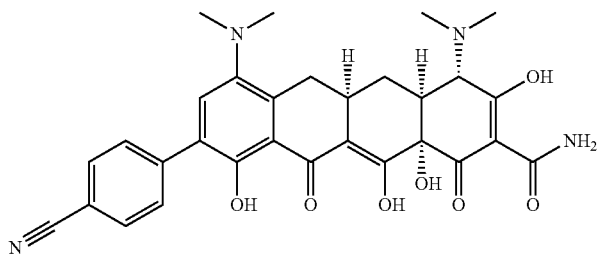
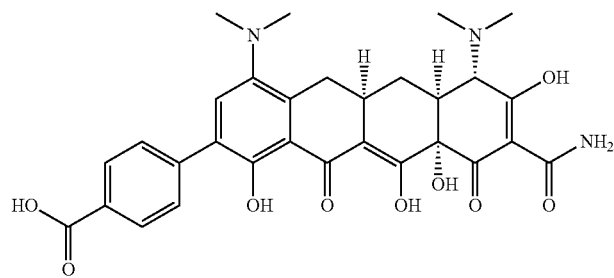
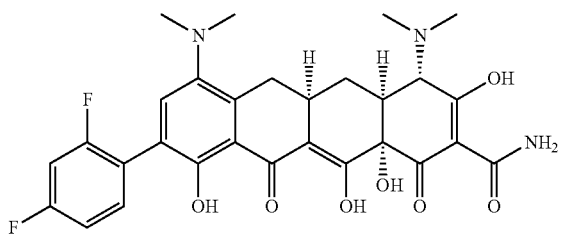
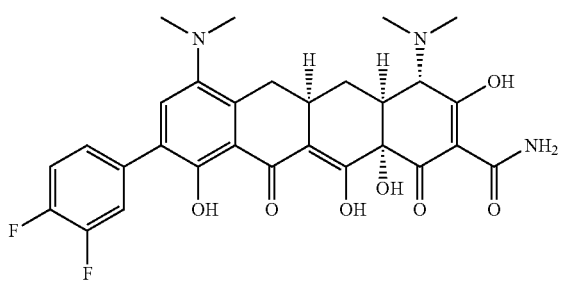
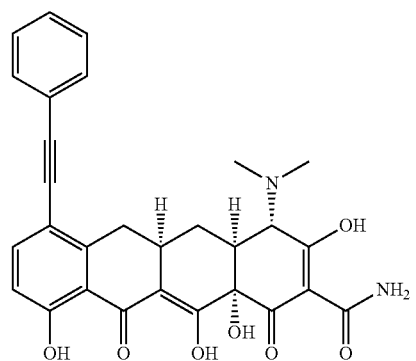

TABLE 1-continued
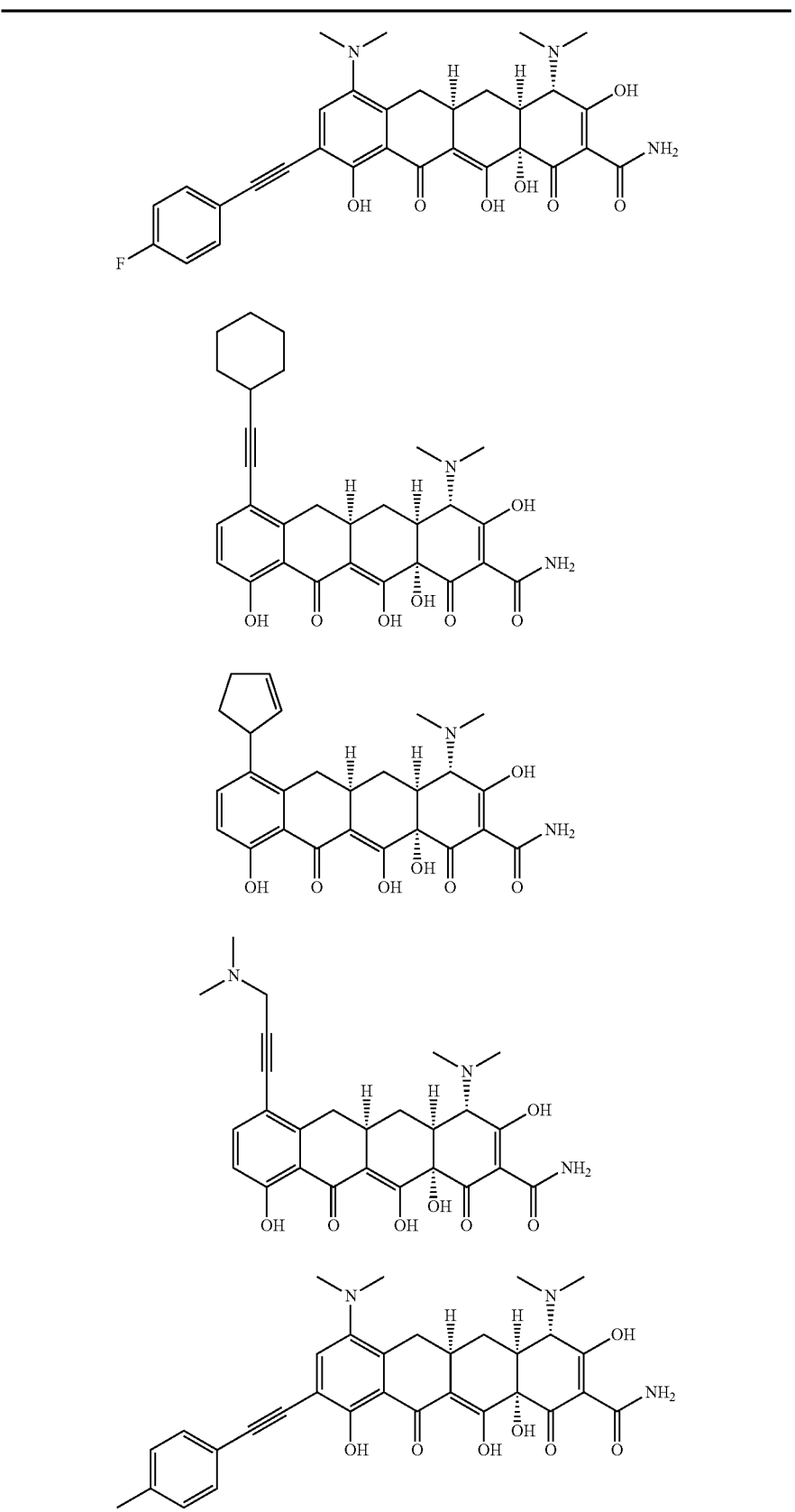

TABLE 1-continued
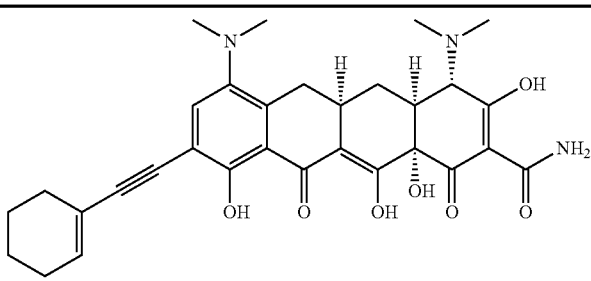
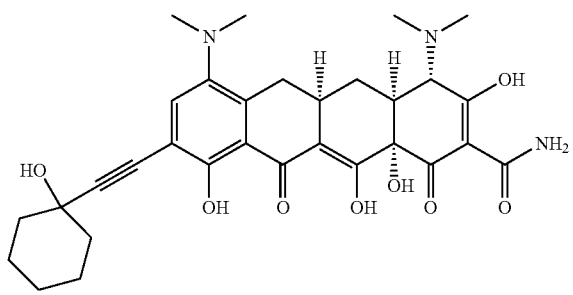
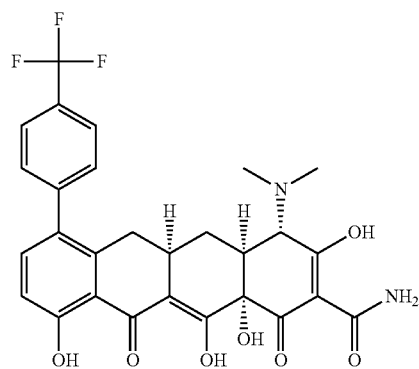
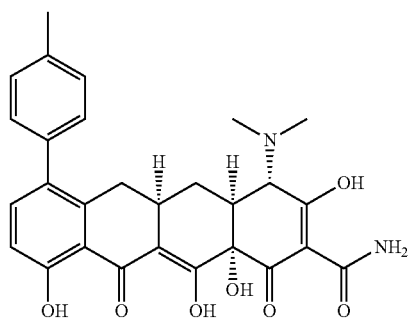
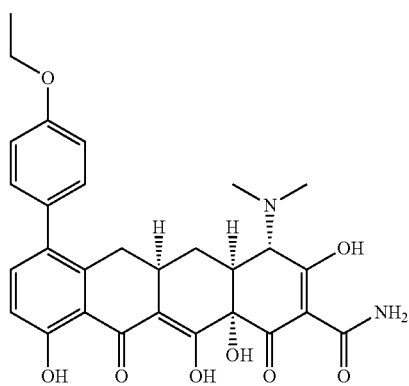

TABLE 1-continued
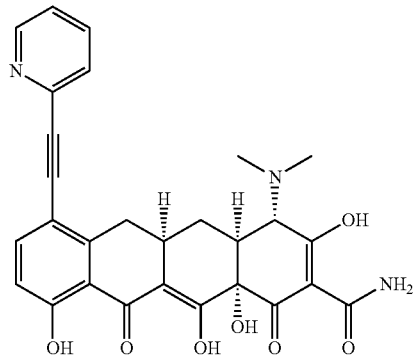
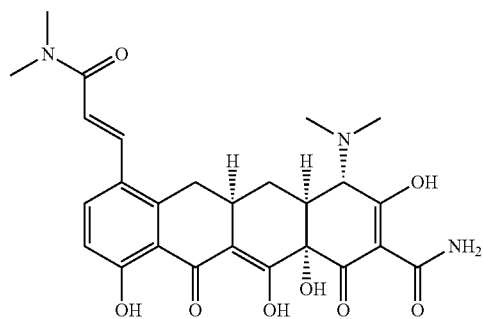
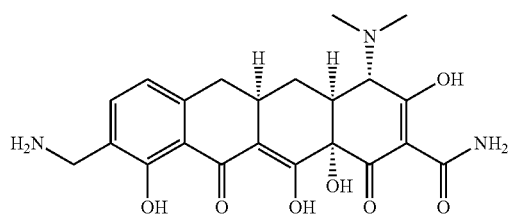
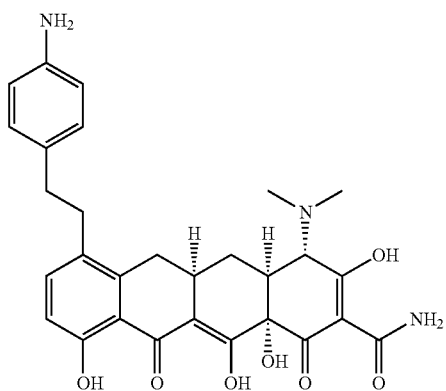
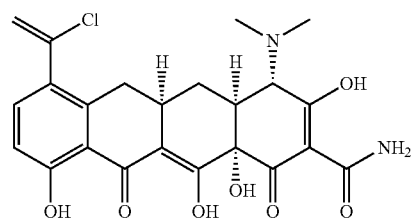

TABLE 1-continued
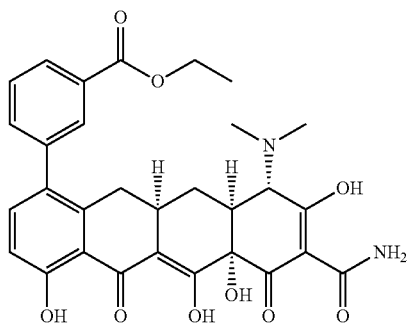
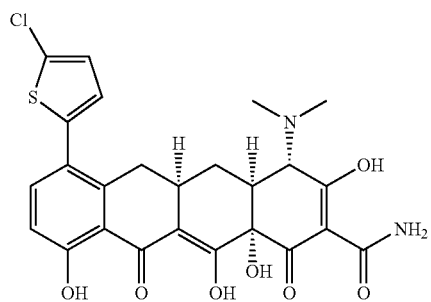
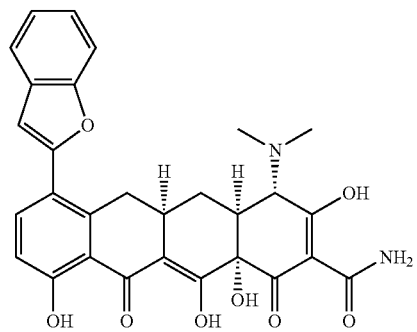
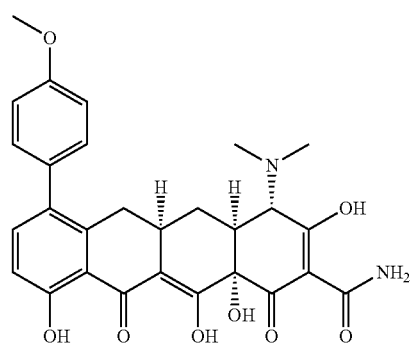

TABLE 1-continued
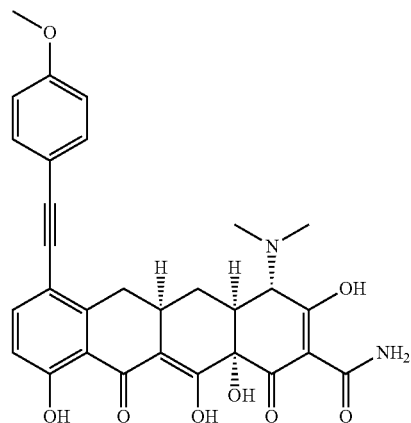
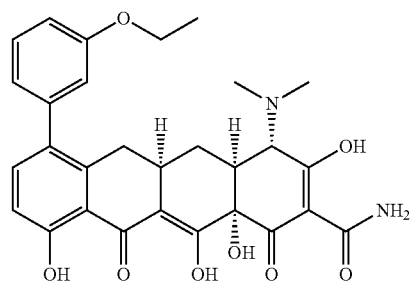
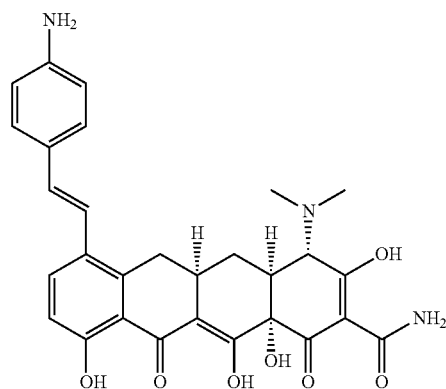
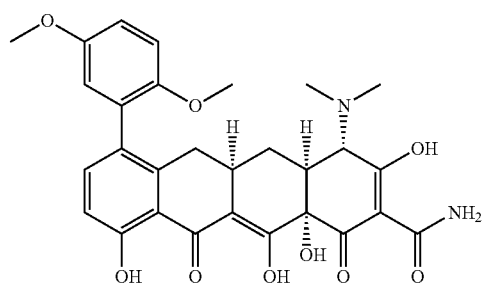

TABLE 1-continued
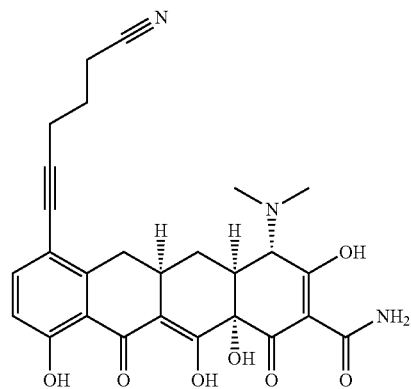
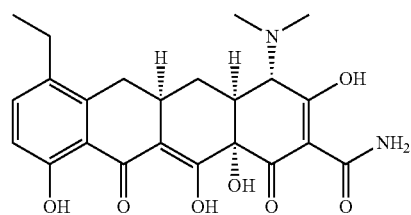
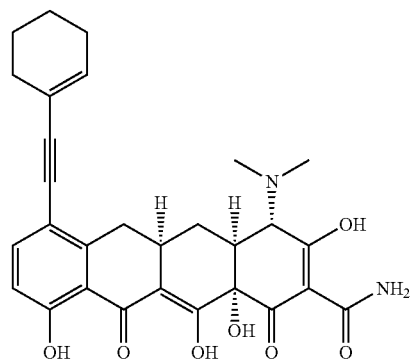
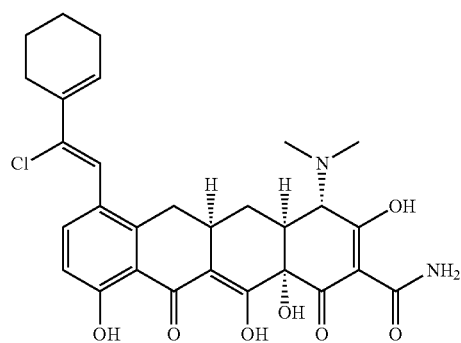

TABLE 1-continued
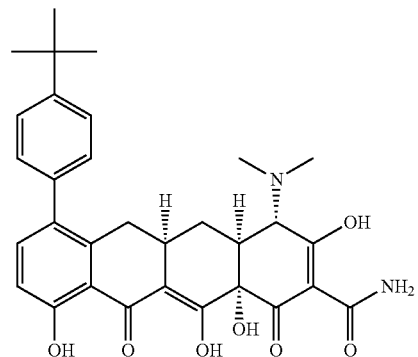
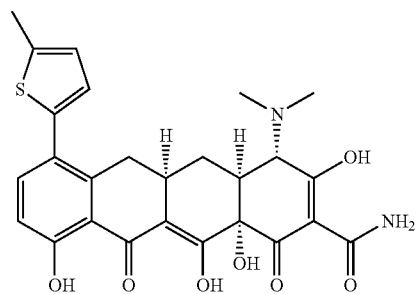
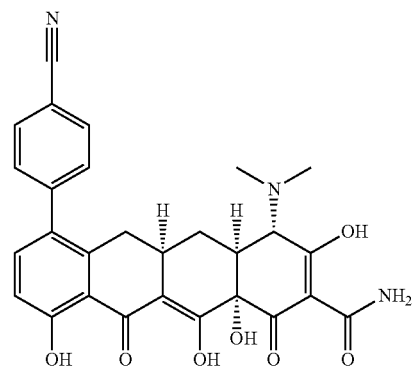
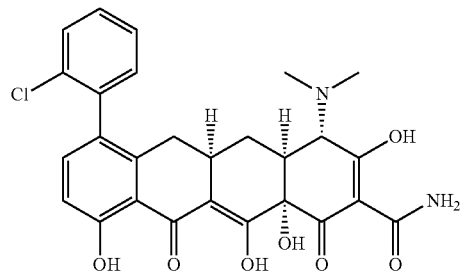
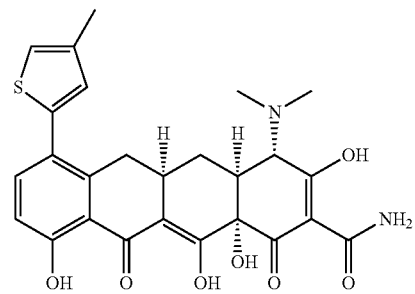

TABLE 1-continued
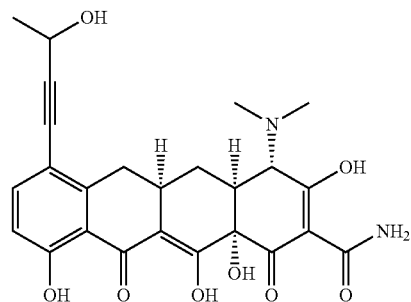
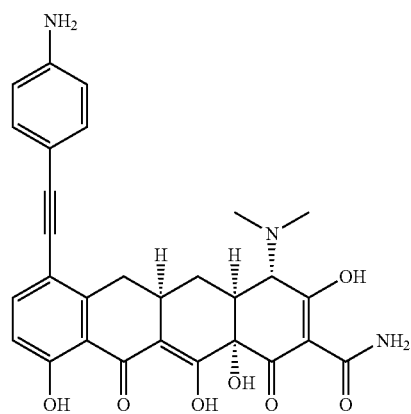
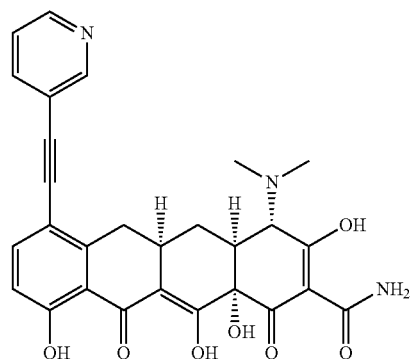
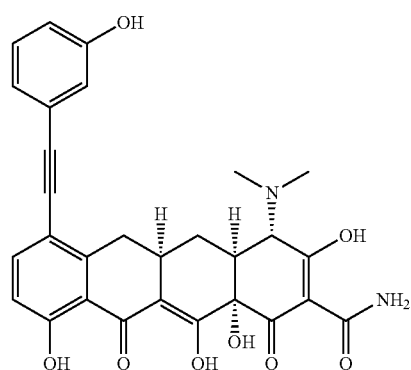

TABLE 1-continued
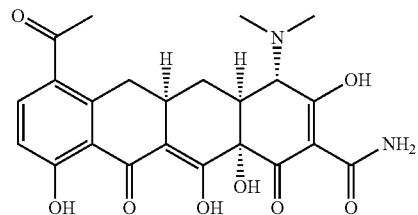
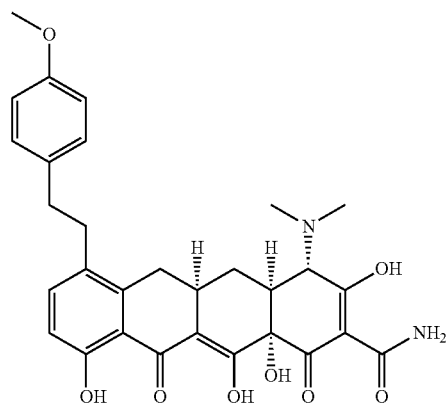
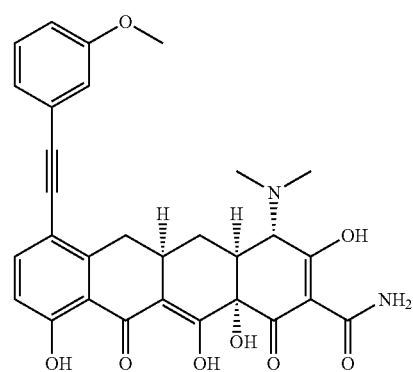
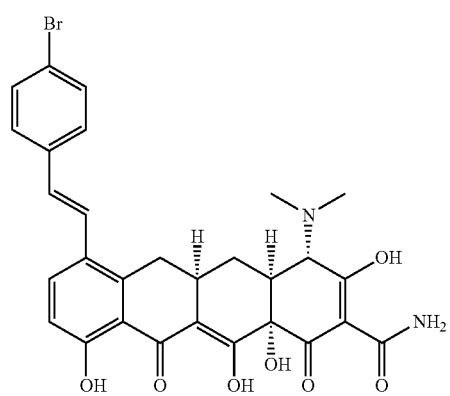

TABLE 1-continued
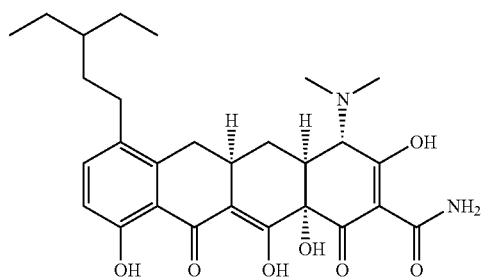
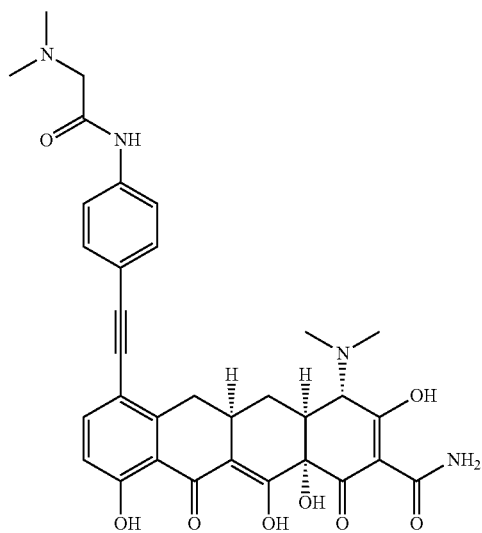
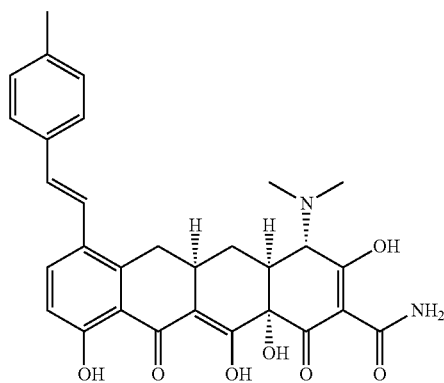
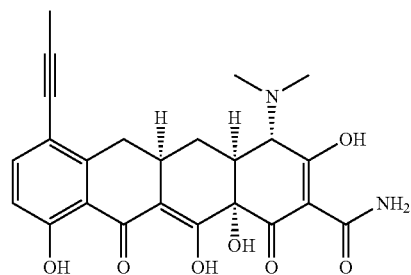

TABLE 1-continued
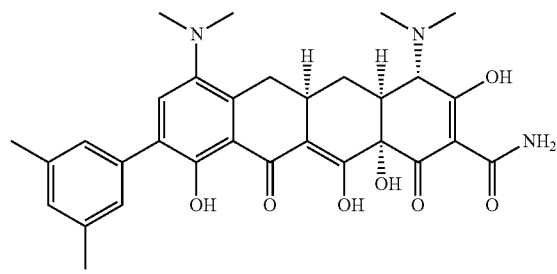
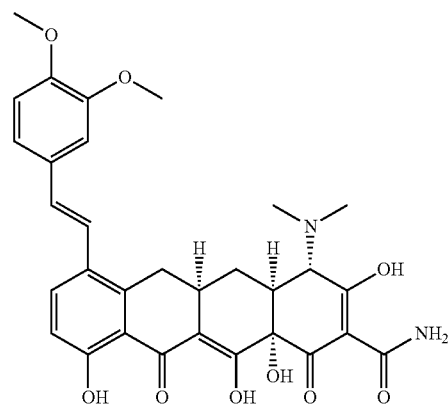
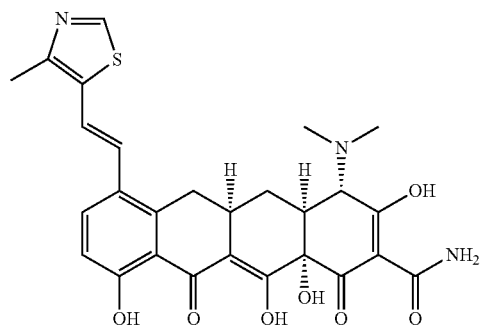
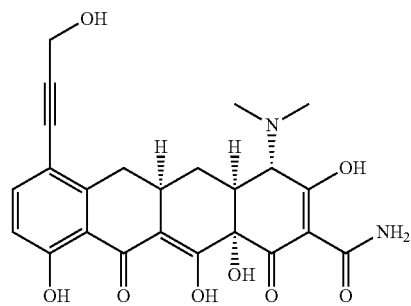
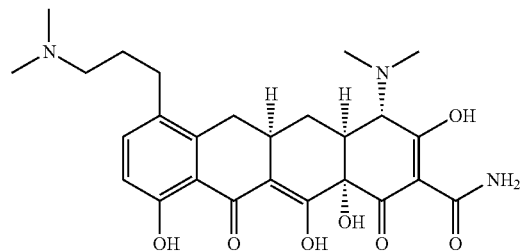

TABLE 1-continued
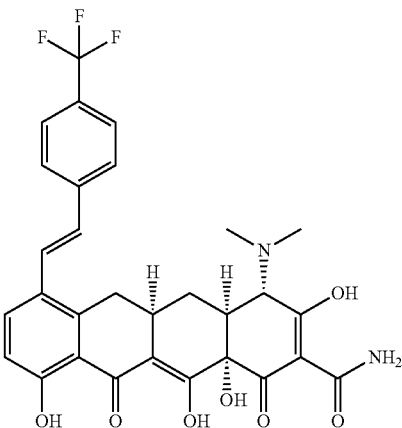
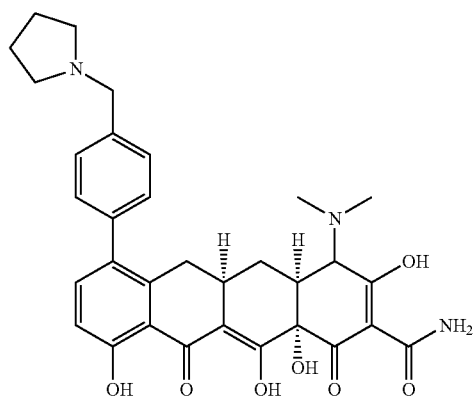
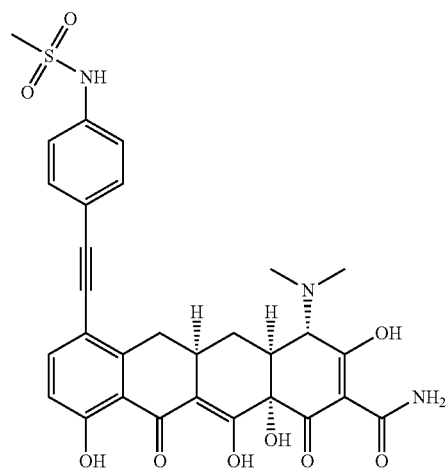

TABLE 1-continued
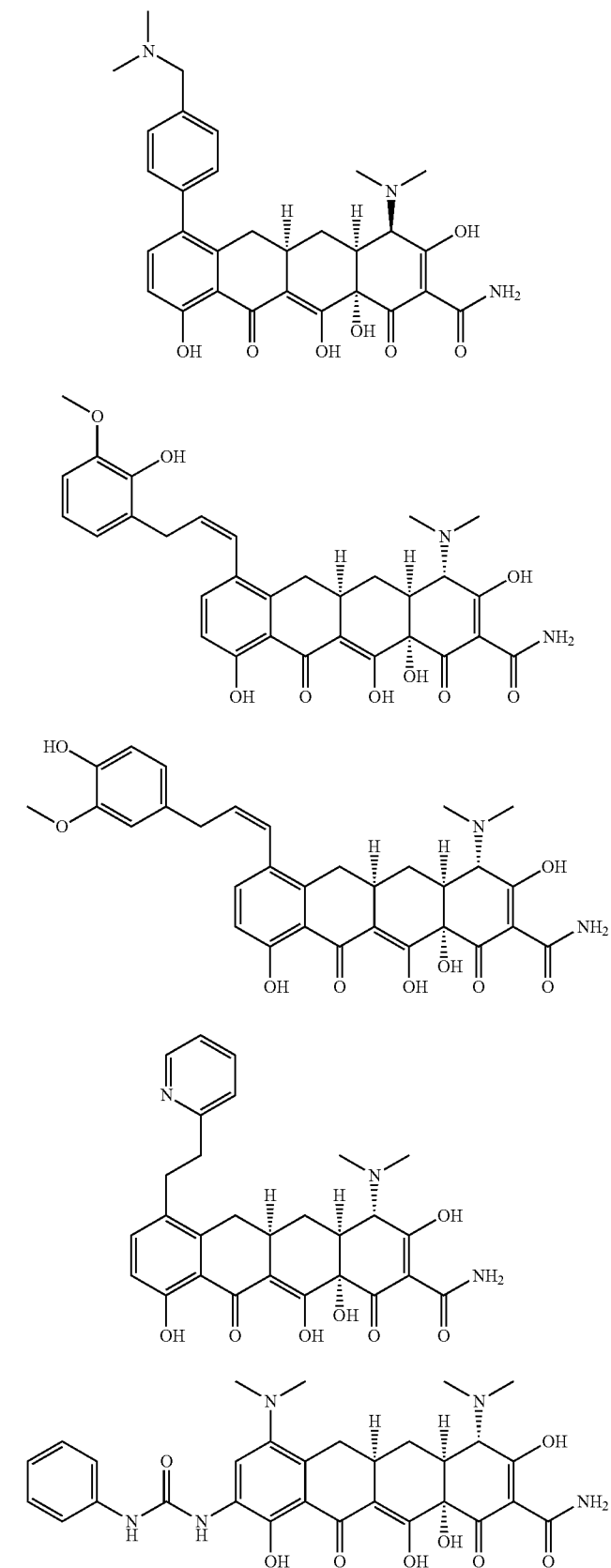

TABLE 1-continued
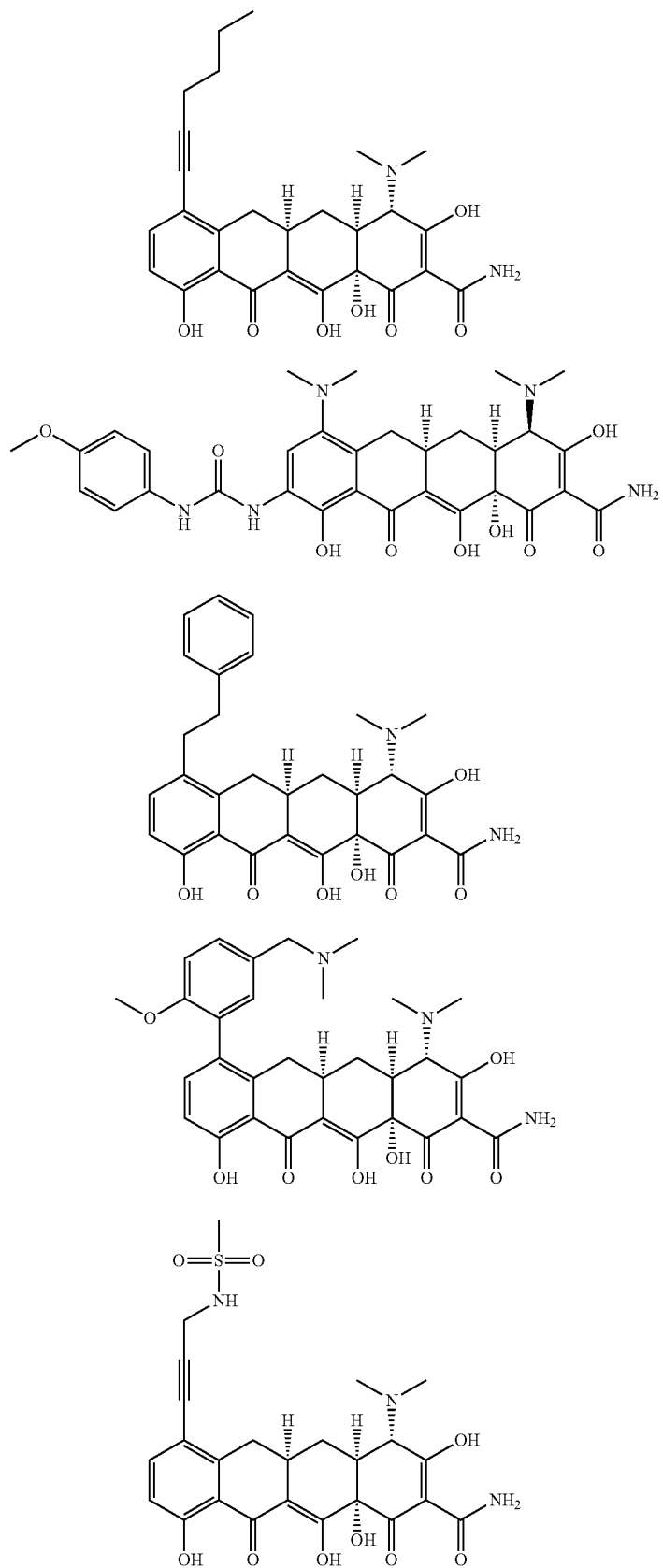

TABLE 1-continued
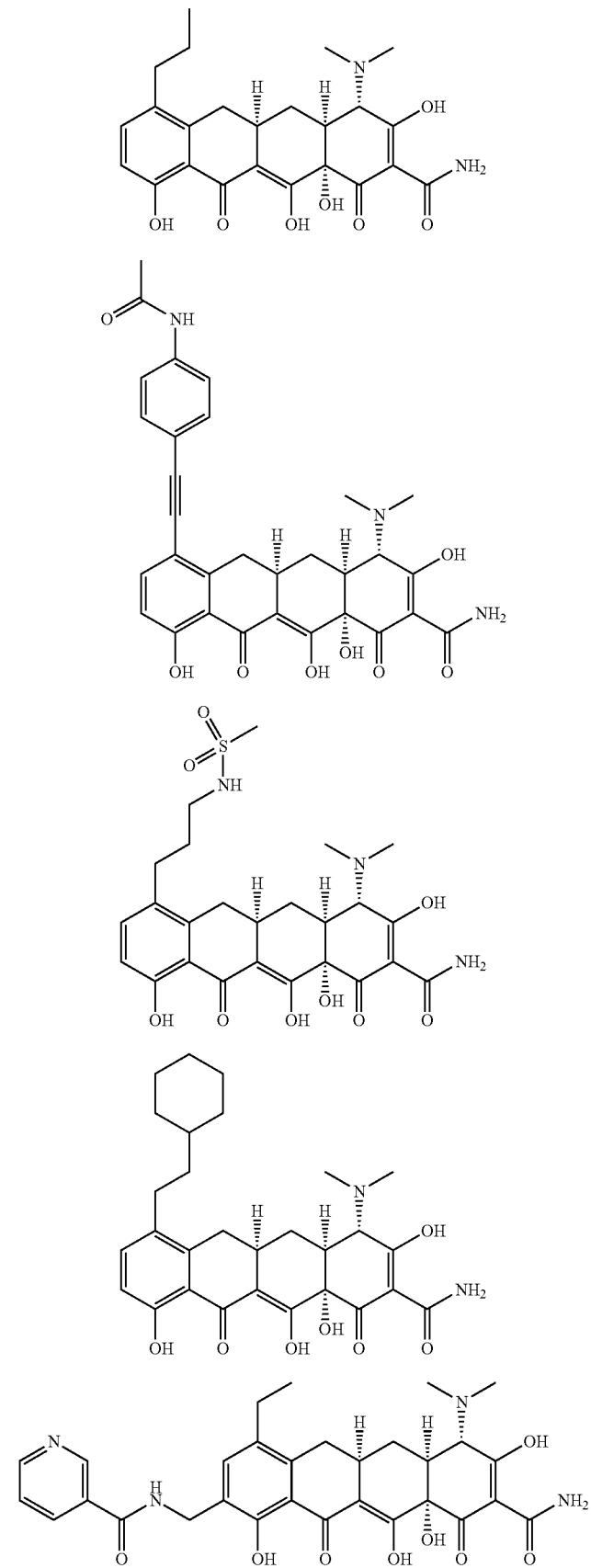

TABLE 1-continued
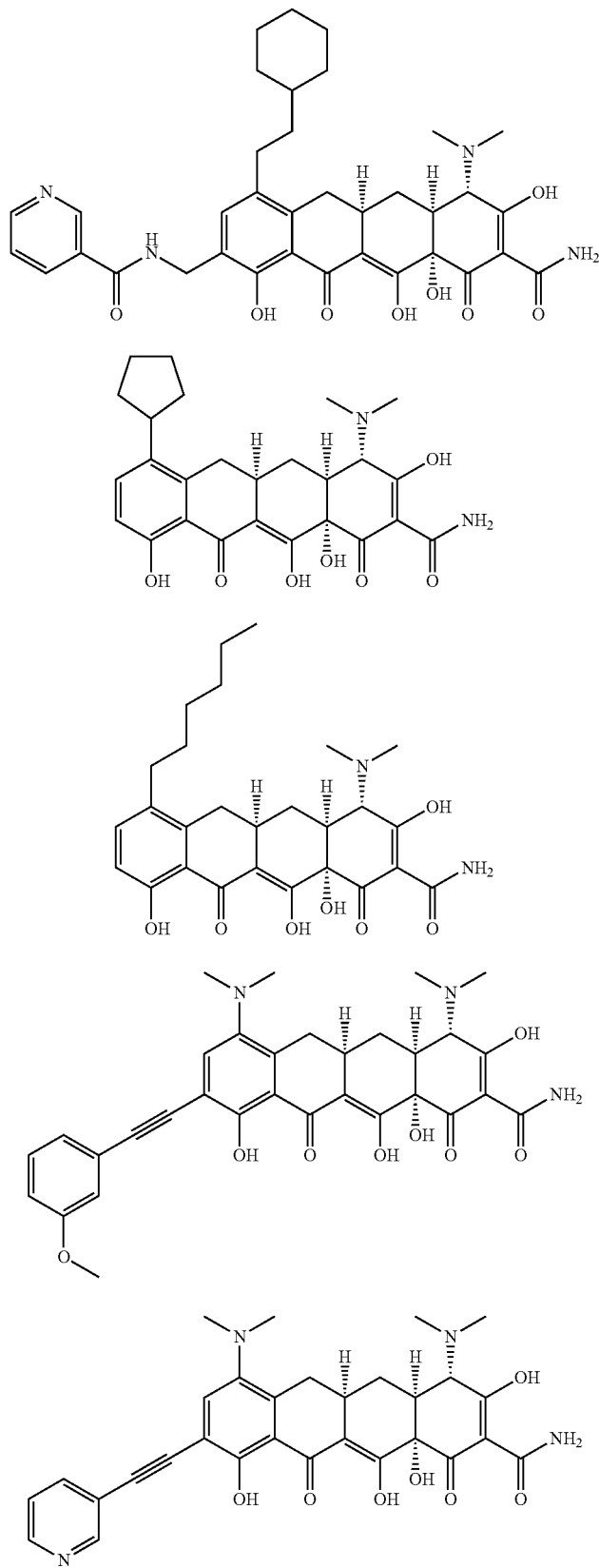

TABLE 1-continued
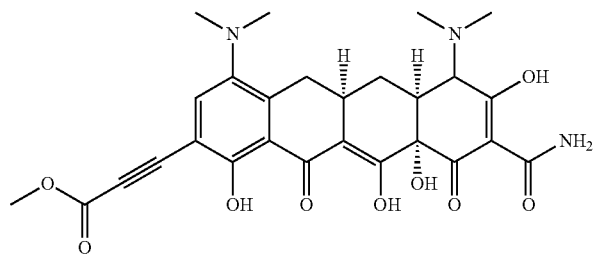
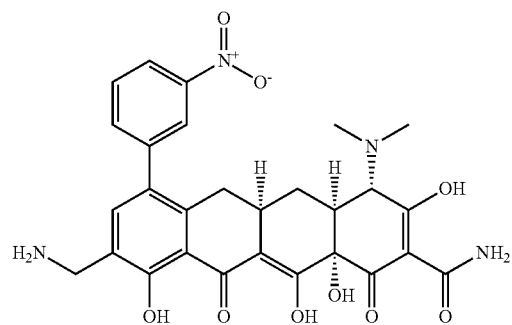
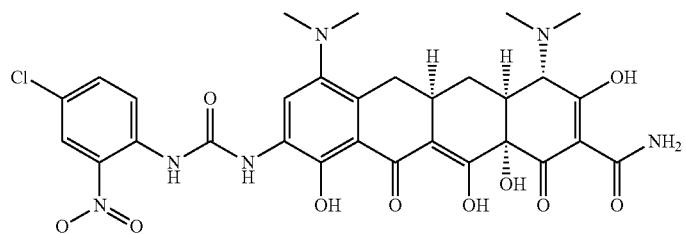
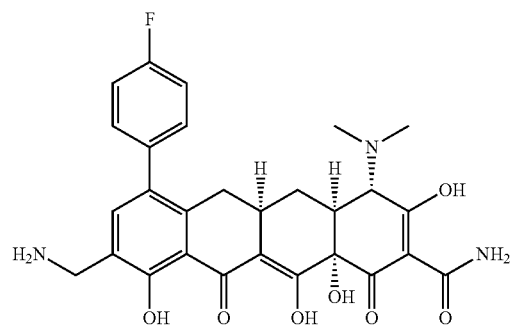
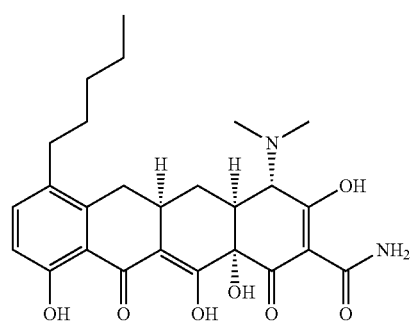

TABLE 1-continued
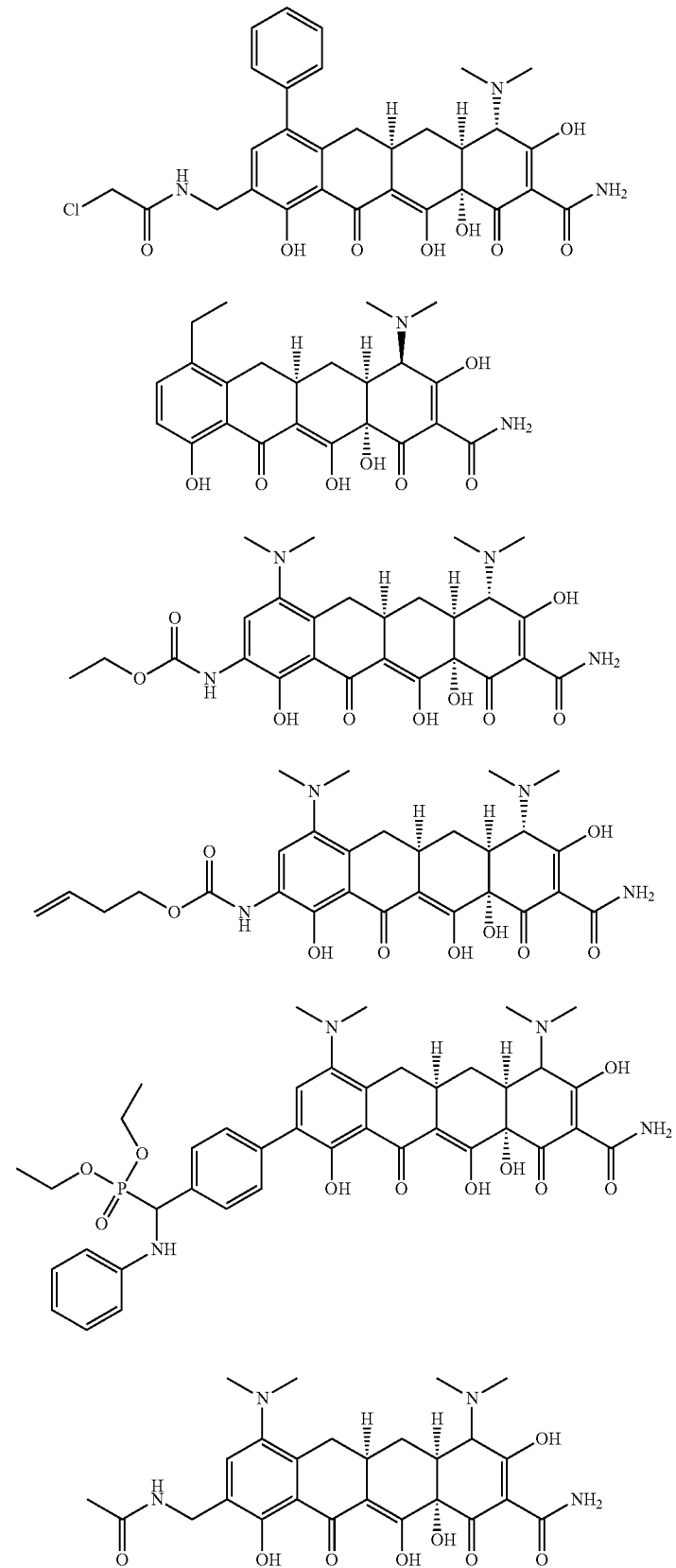

TABLE 1-continued
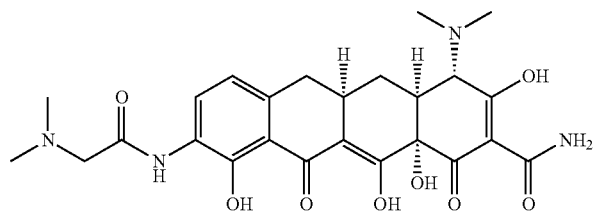
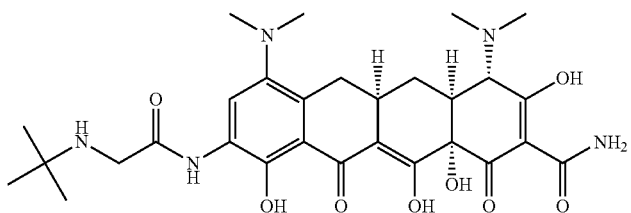
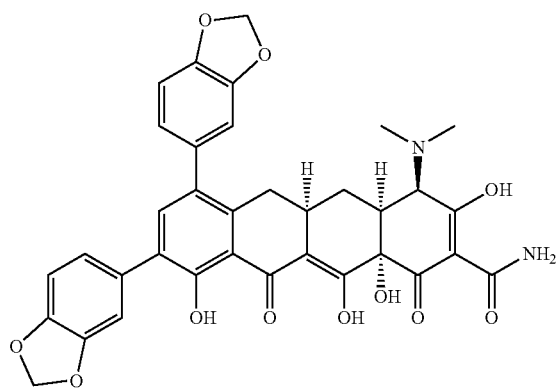
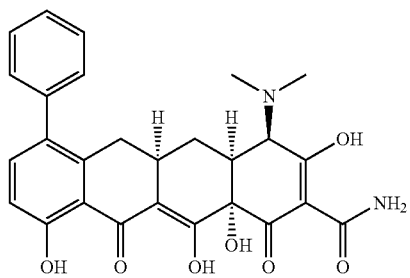
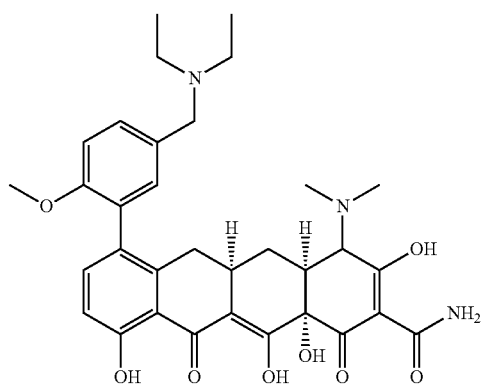

TABLE 1-continued
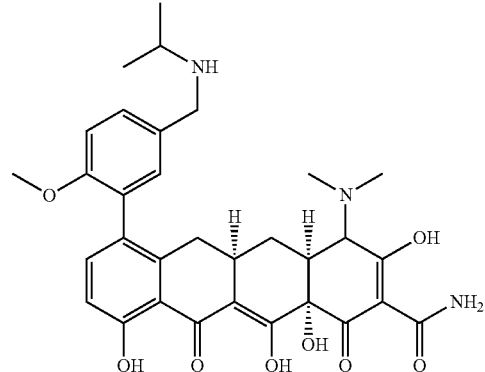
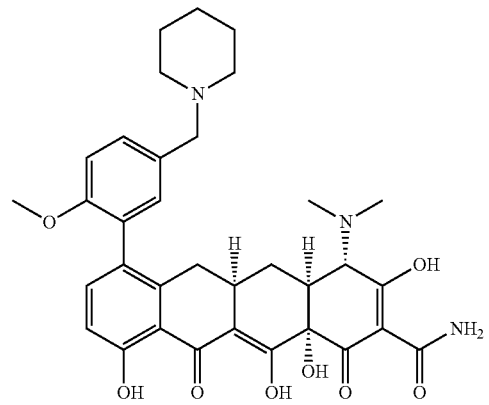
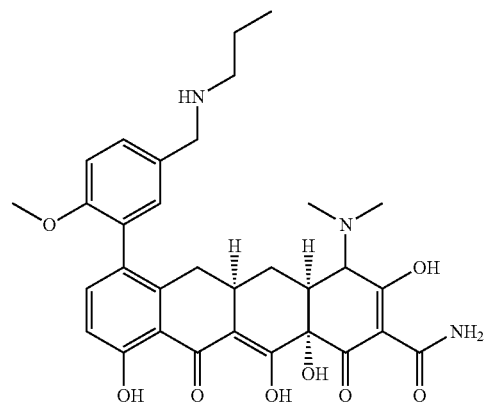
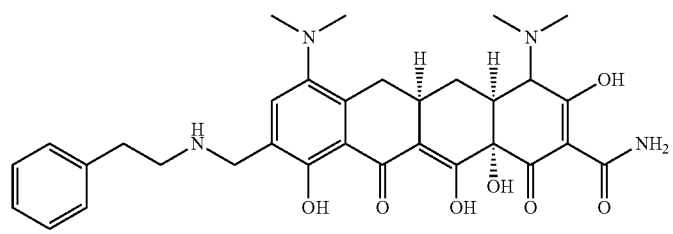
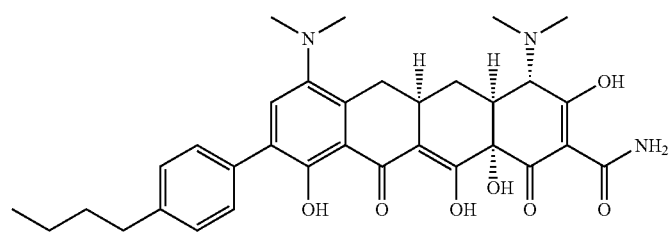

TABLE 1-continued
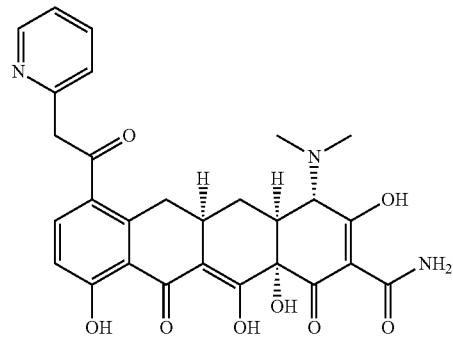
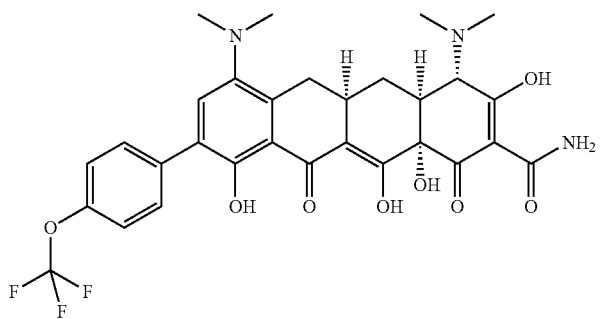
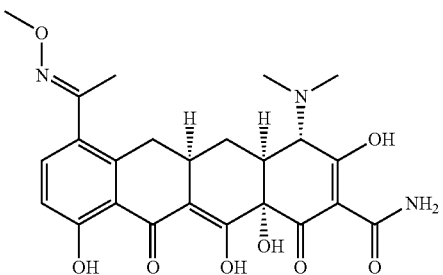
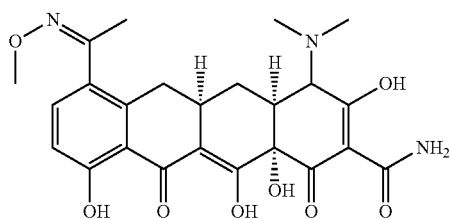
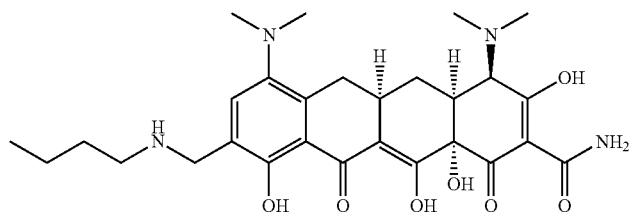
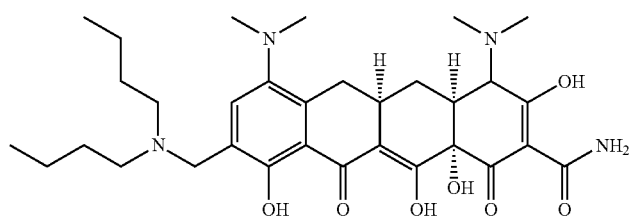

TABLE 1-continued
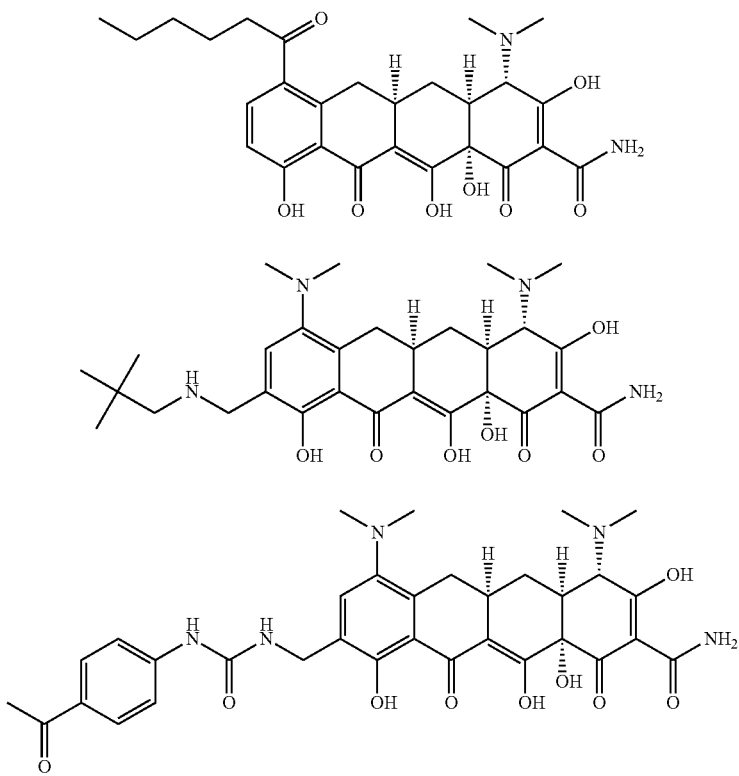
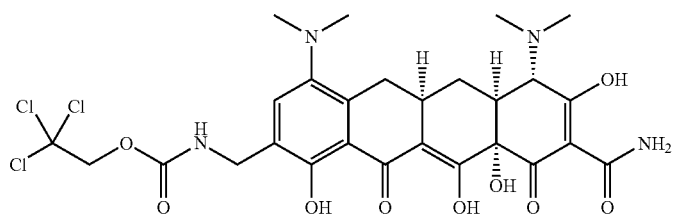
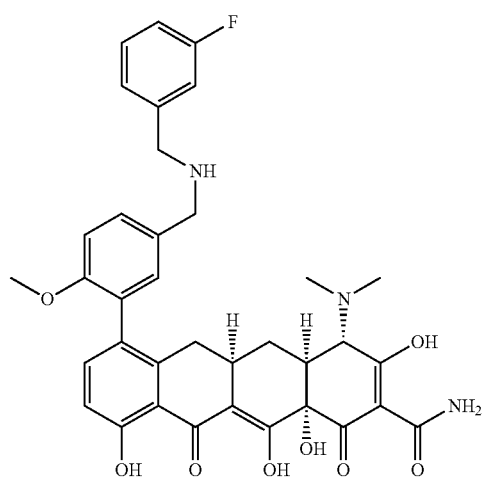

TABLE 1-continued
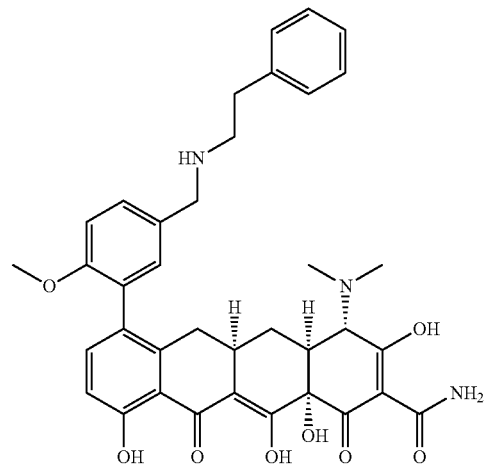
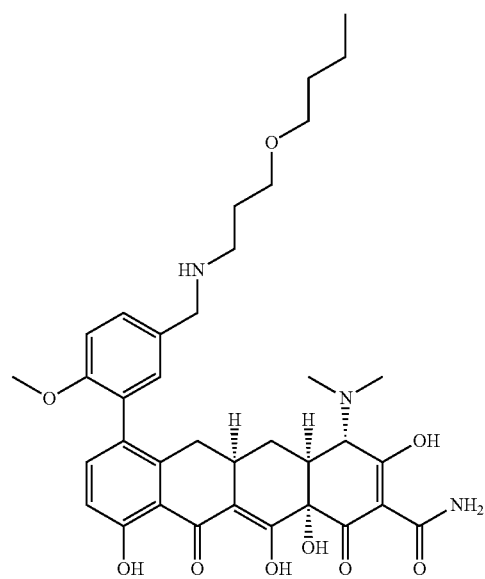
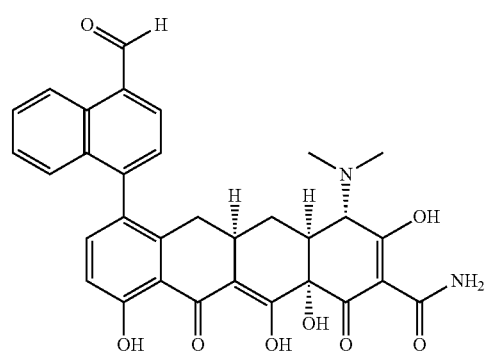

TABLE 1-continued
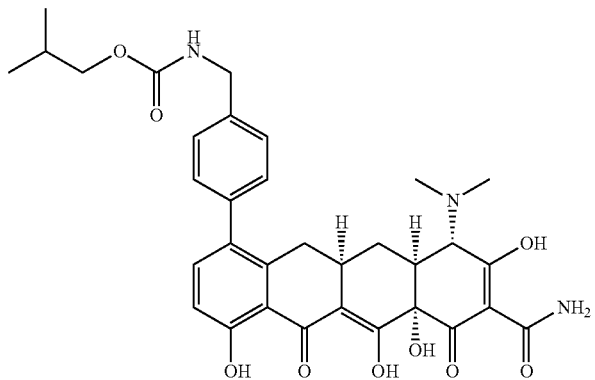
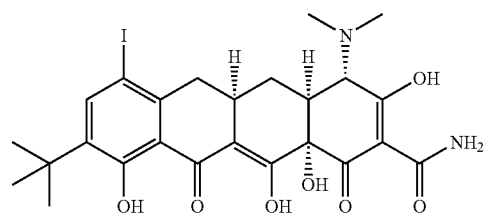
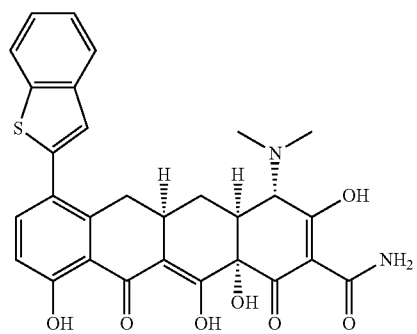
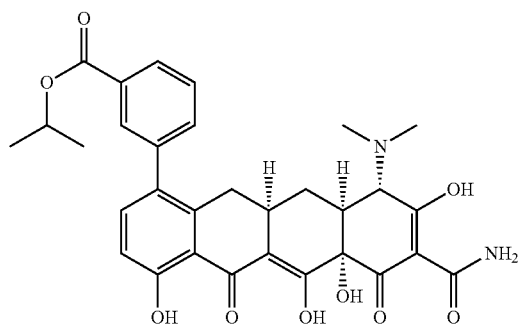

TABLE 1-continued
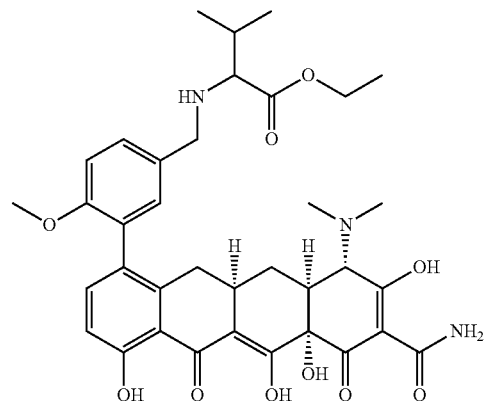
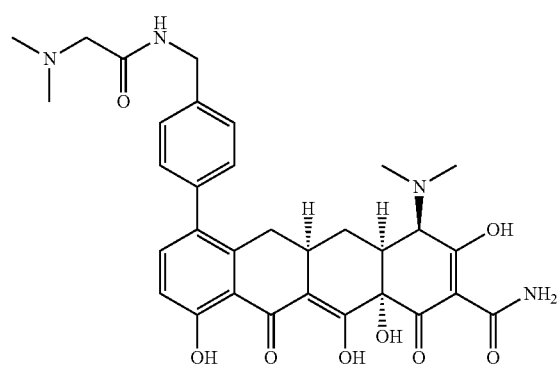
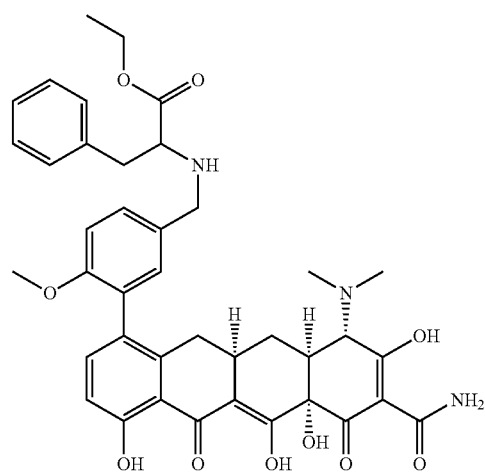

TABLE 1-continued
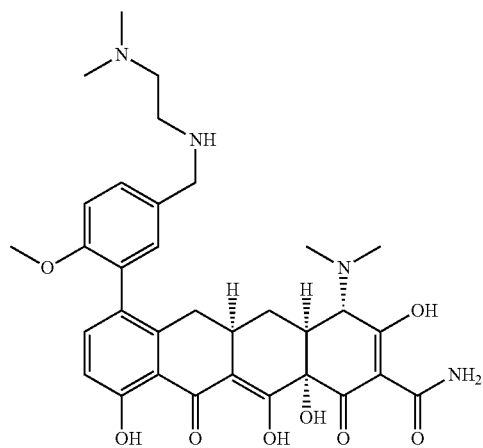
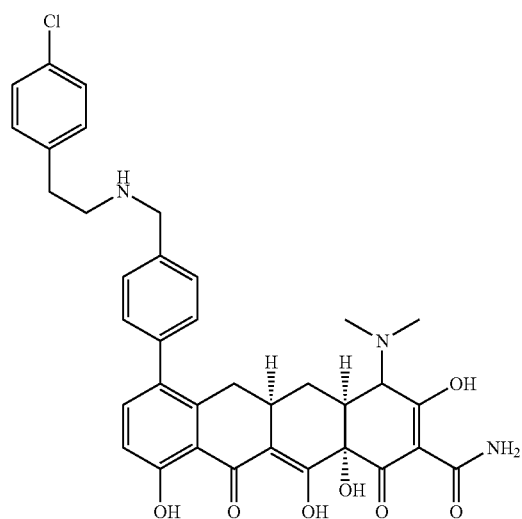
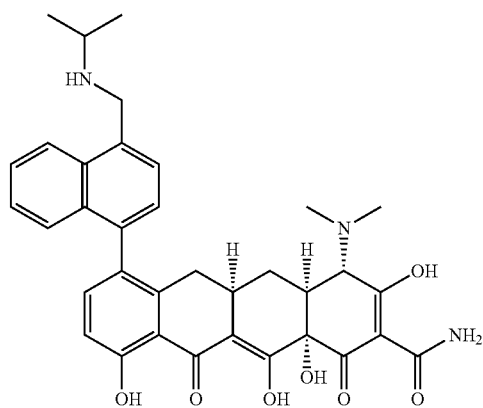

TABLE 1-continued
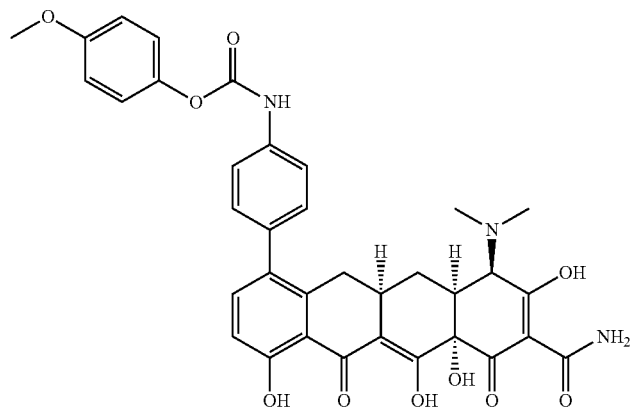
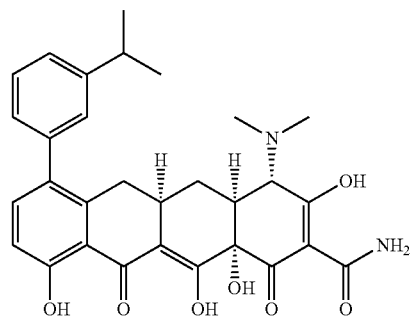
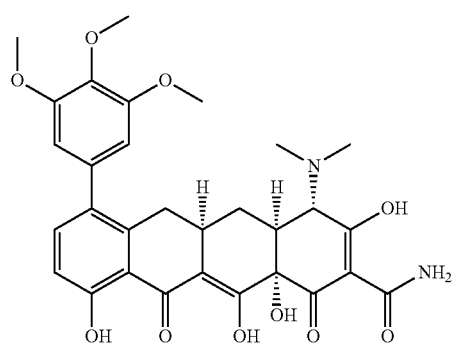
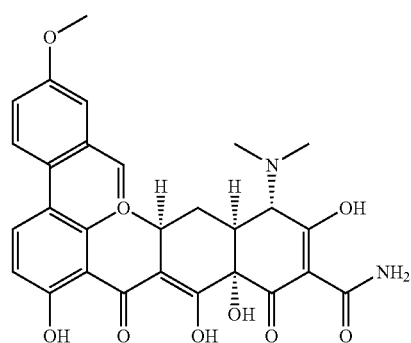

TABLE 1-continued
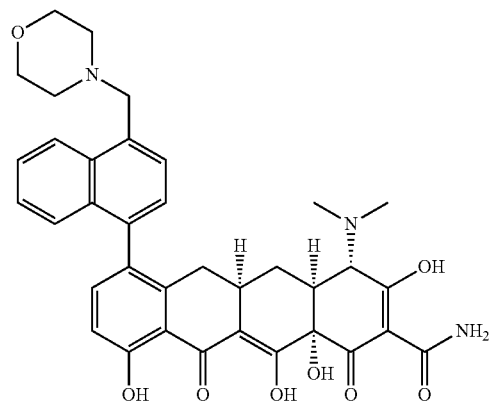
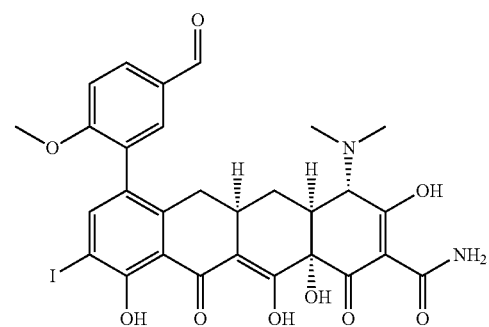
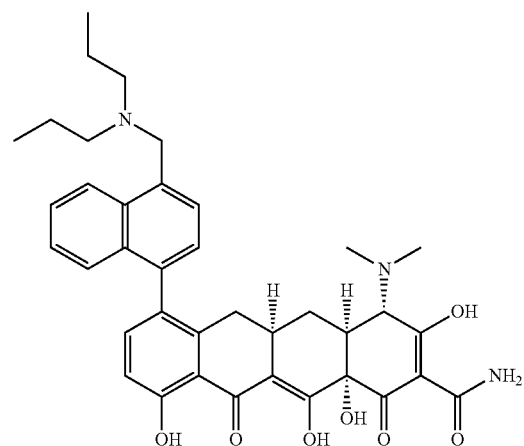
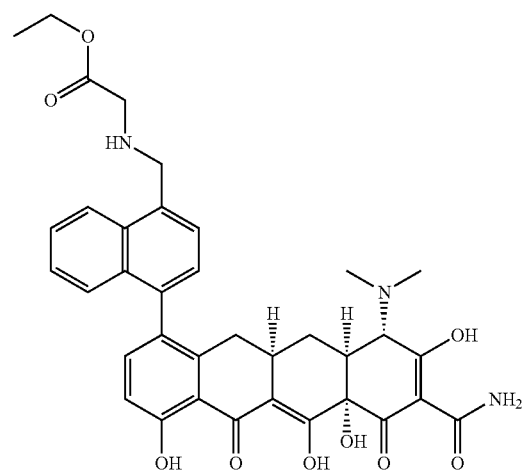

TABLE 1-continued
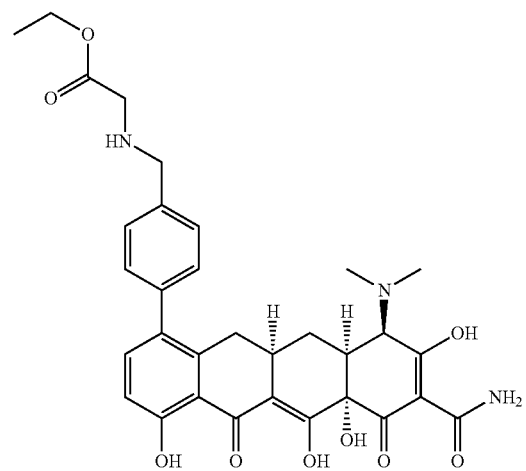
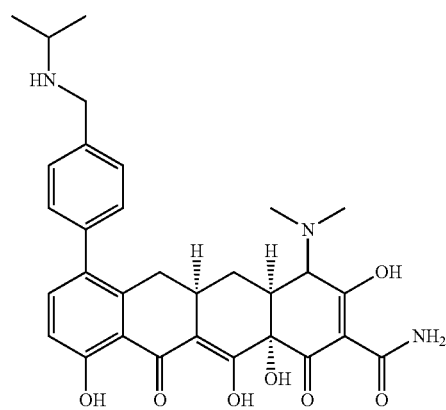
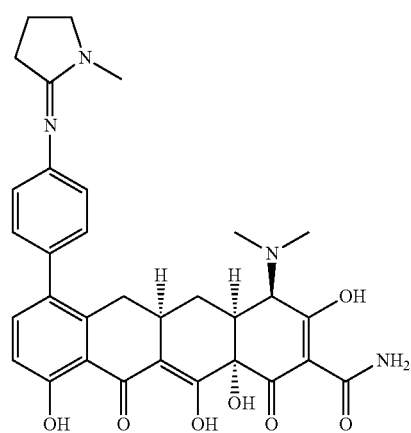

TABLE 1-continued
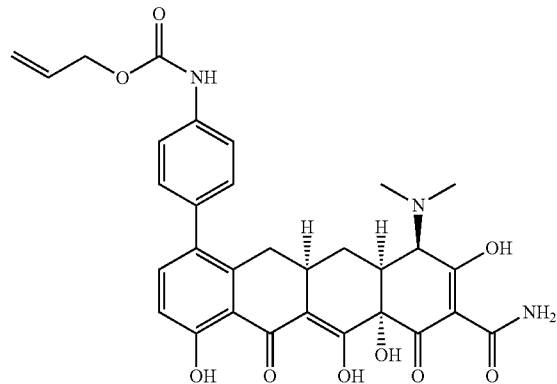
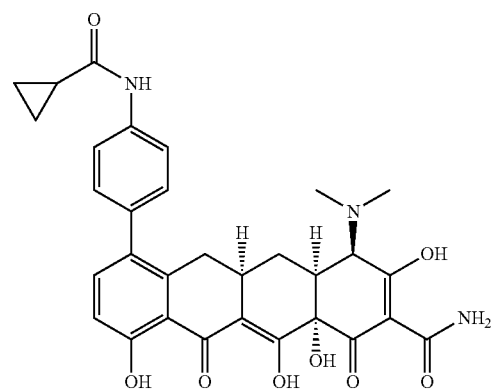
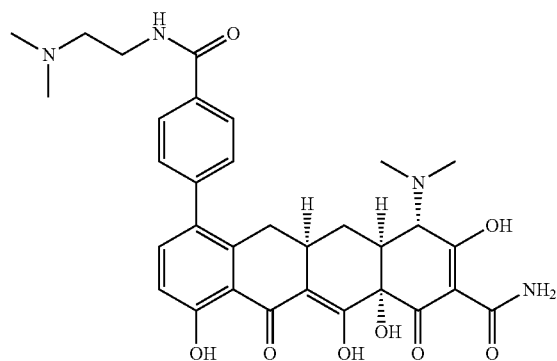
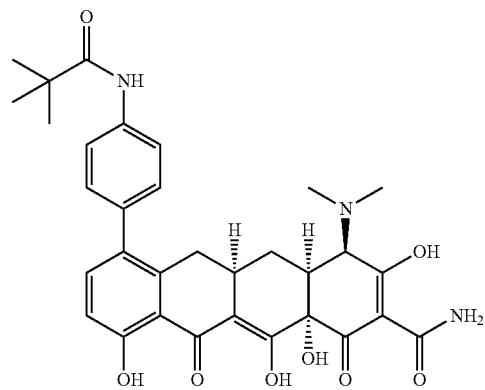

TABLE 1-continued
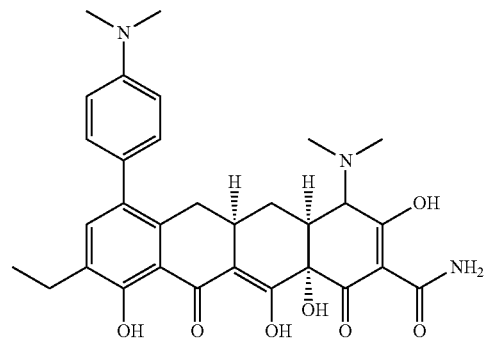
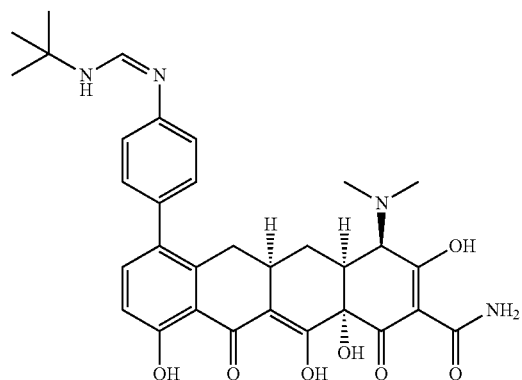
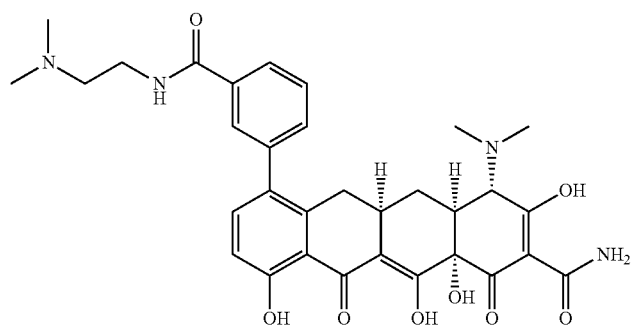
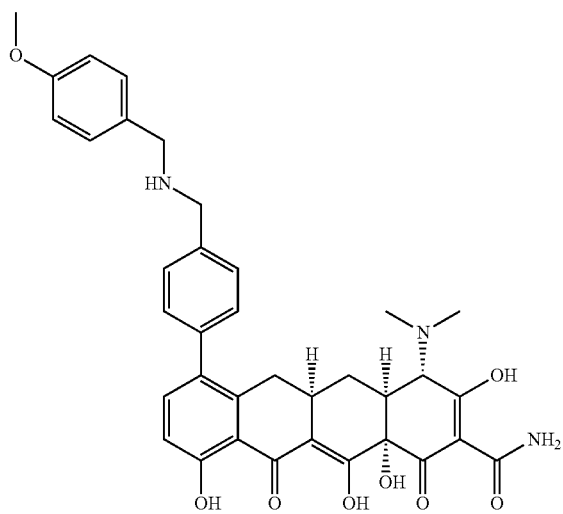

TABLE 1-continued
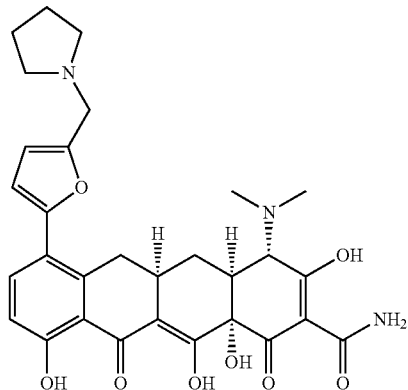
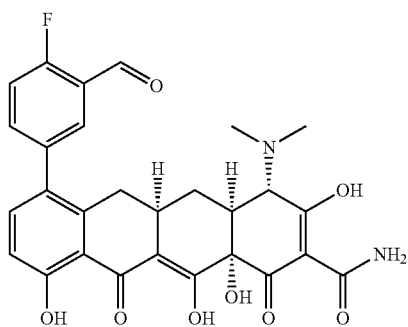
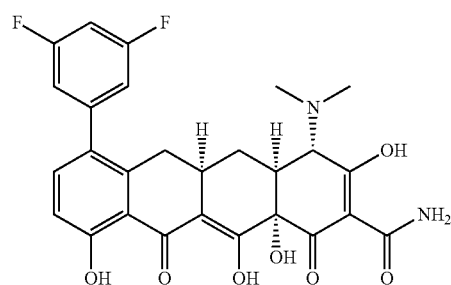
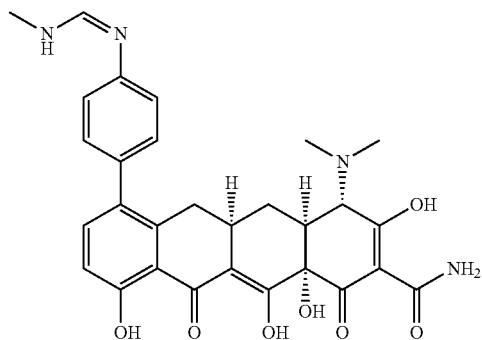

TABLE 1-continued
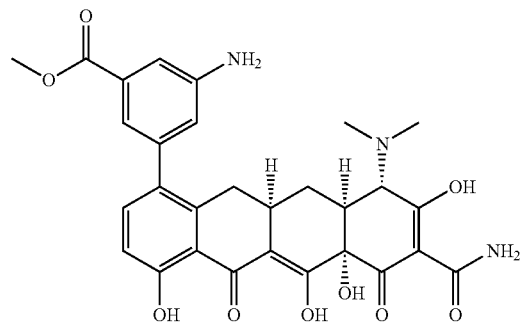
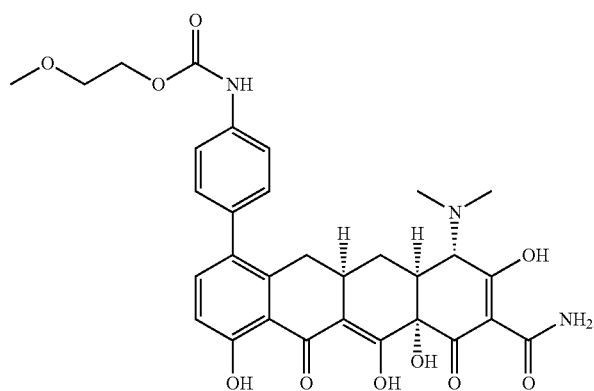
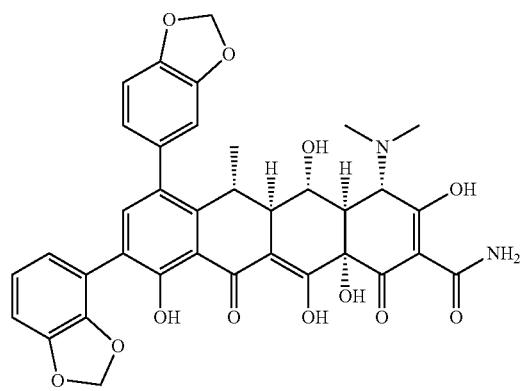
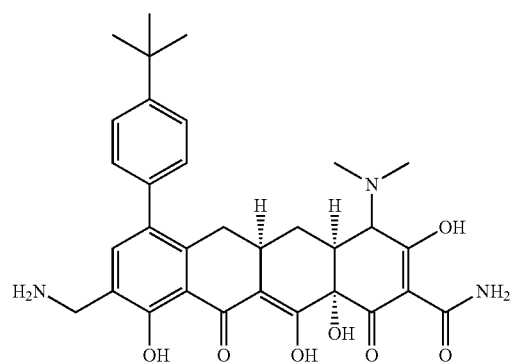

TABLE 1-continued
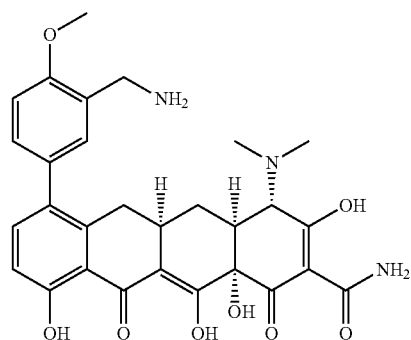
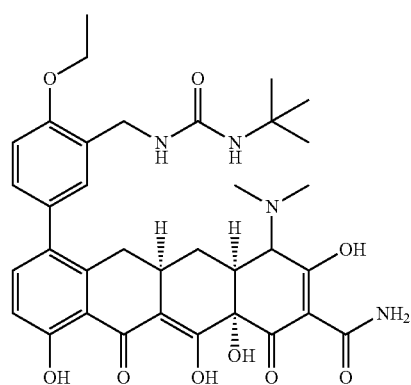
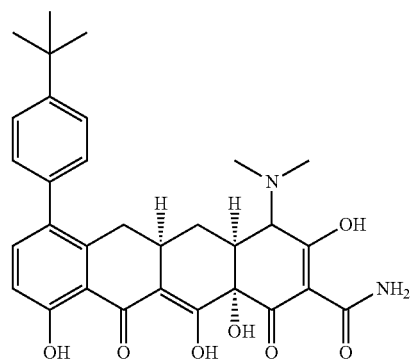
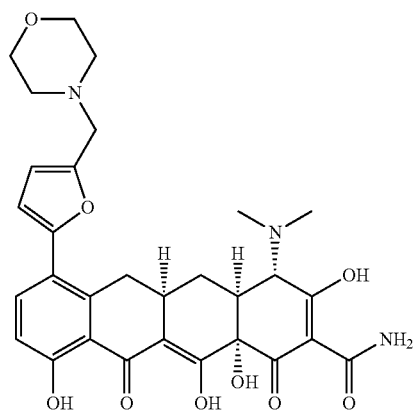

TABLE 1-continued
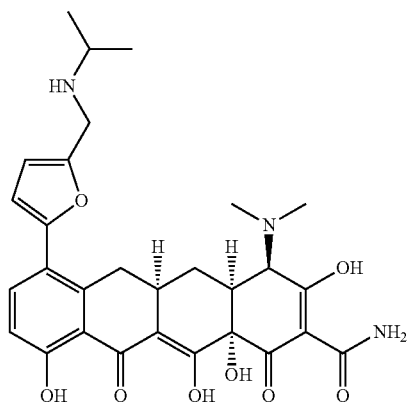
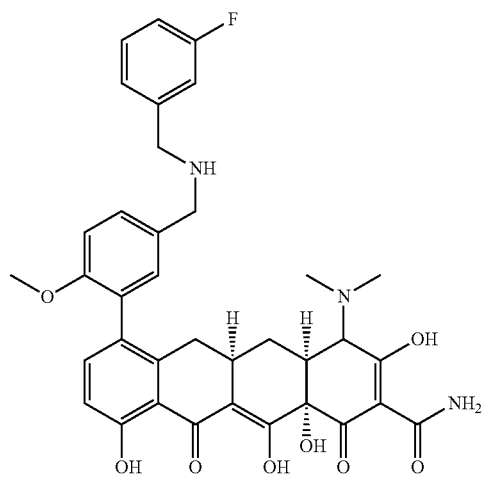
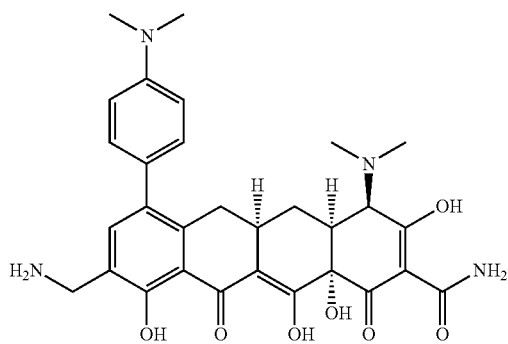
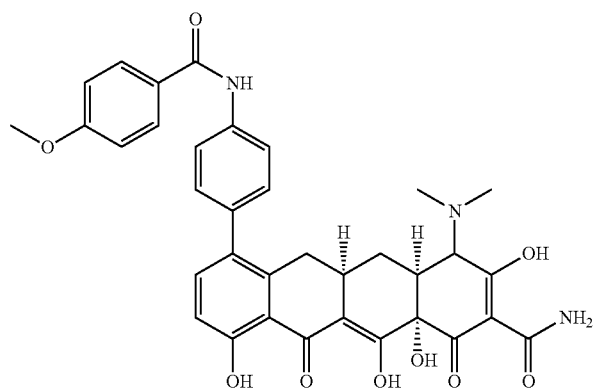

TABLE 1-continued
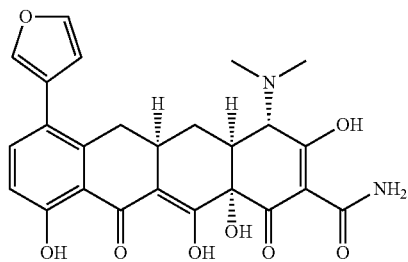
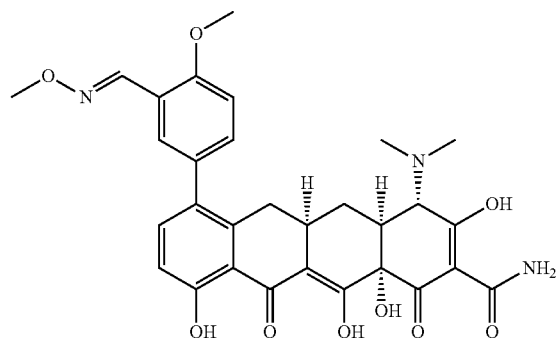
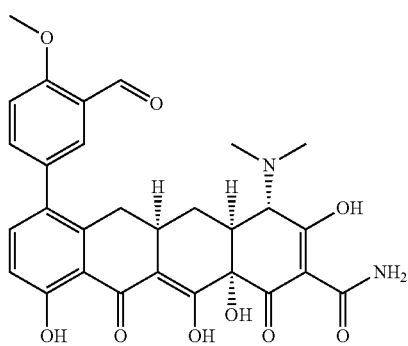
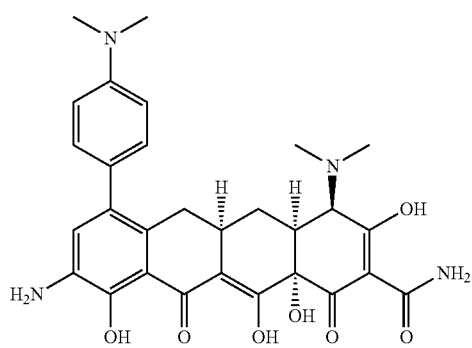
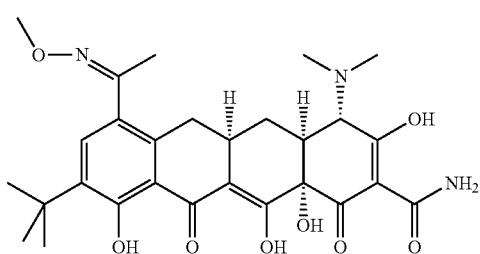

TABLE 1-continued
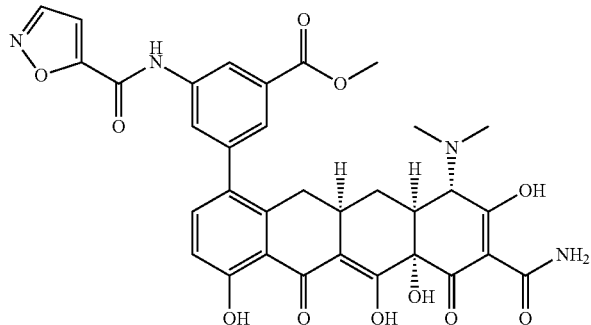
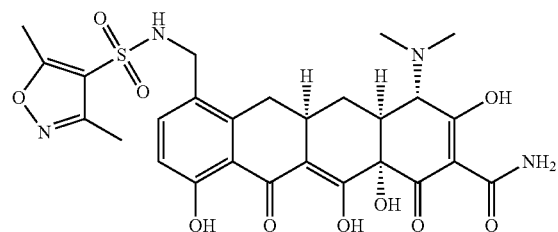
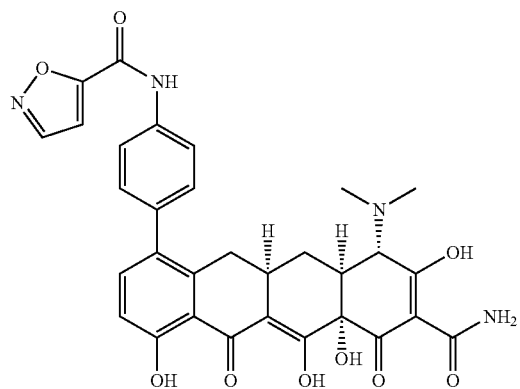
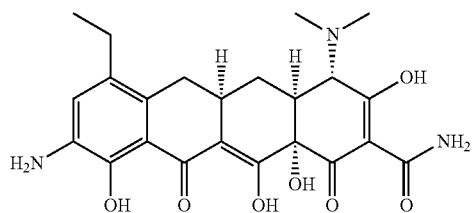
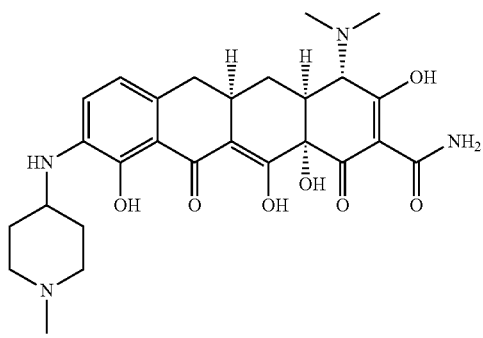

TABLE 1-continued
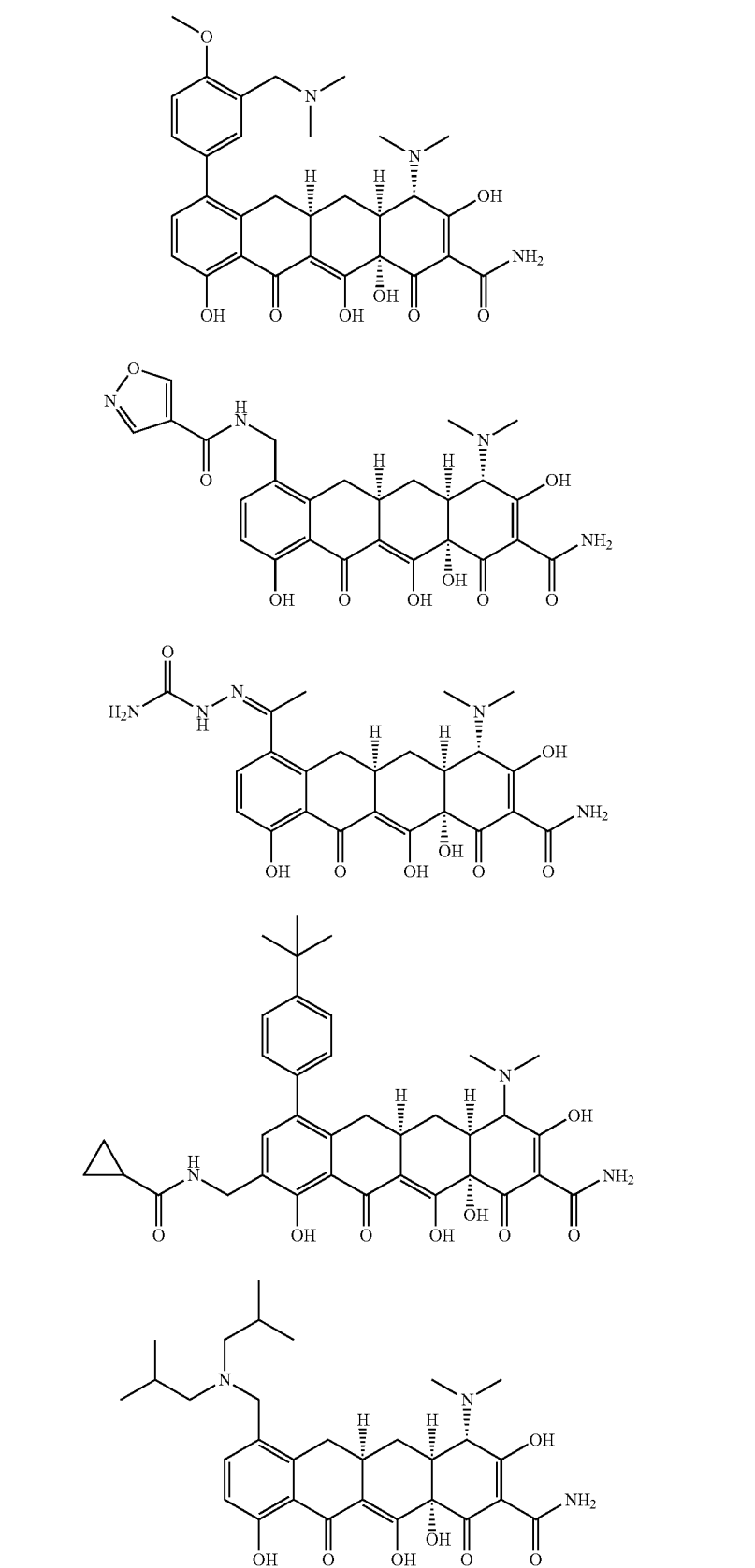

TABLE 1-continued
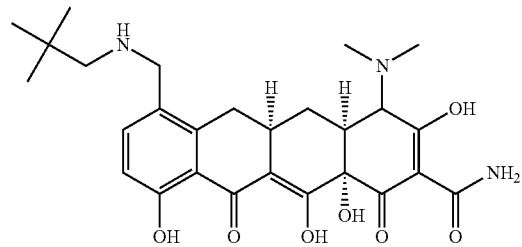
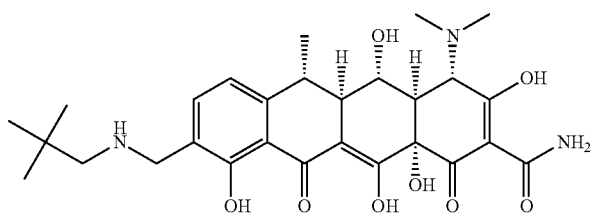
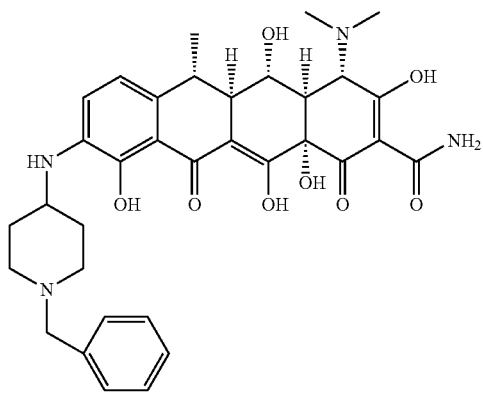
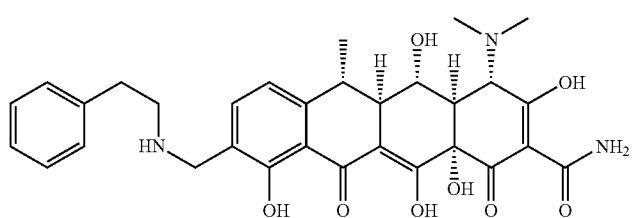
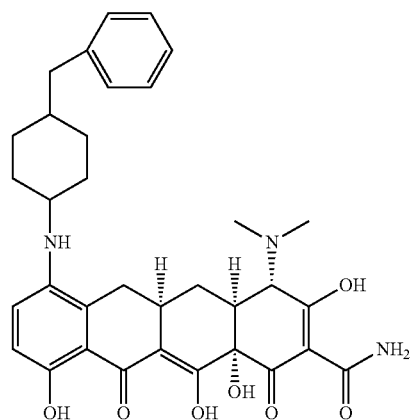

TABLE 1-continued
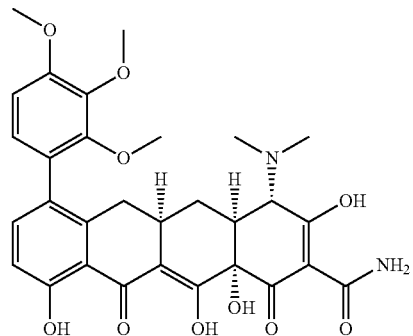
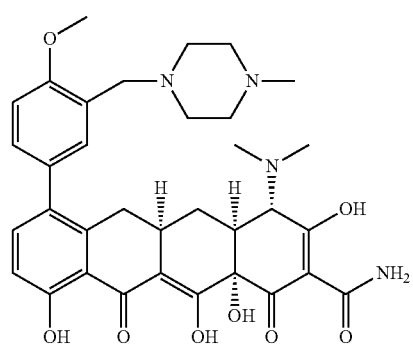
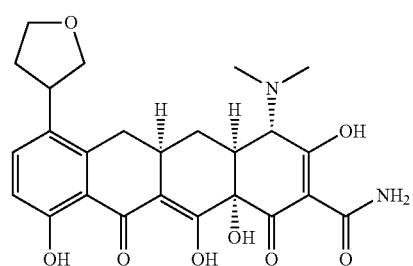
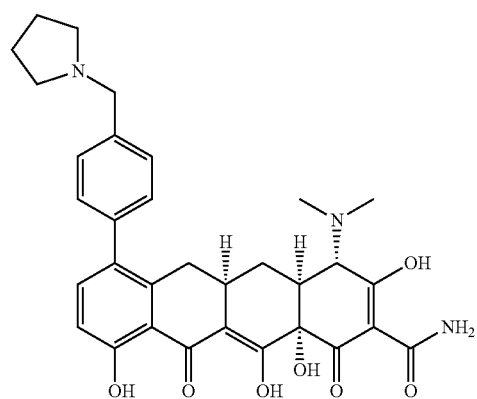

TABLE 1-continued
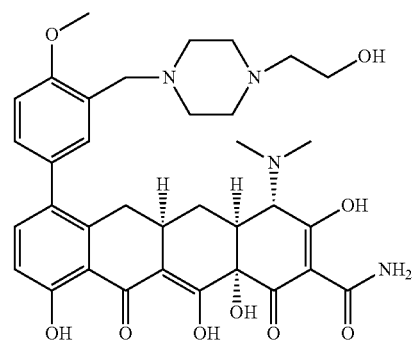
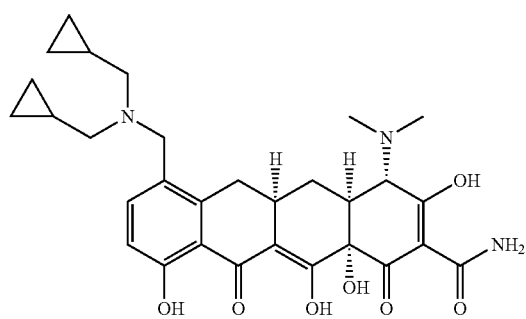
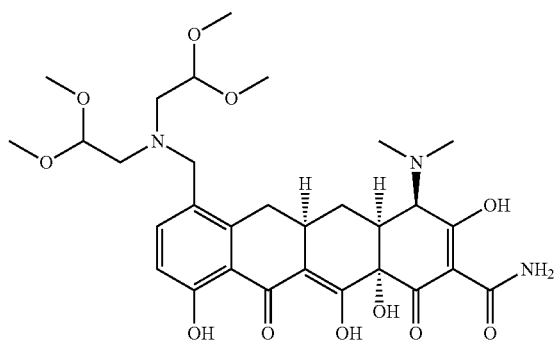
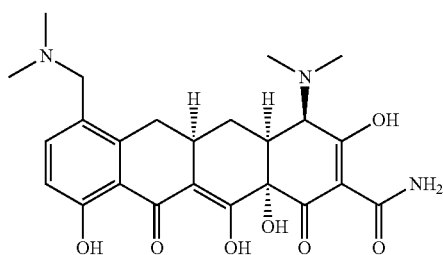
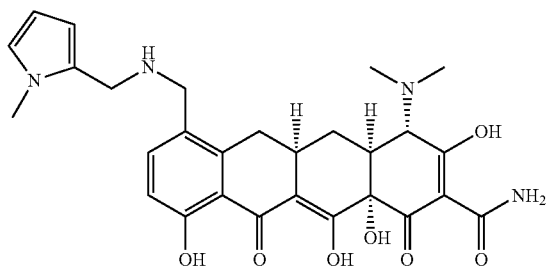

TABLE 1-continued
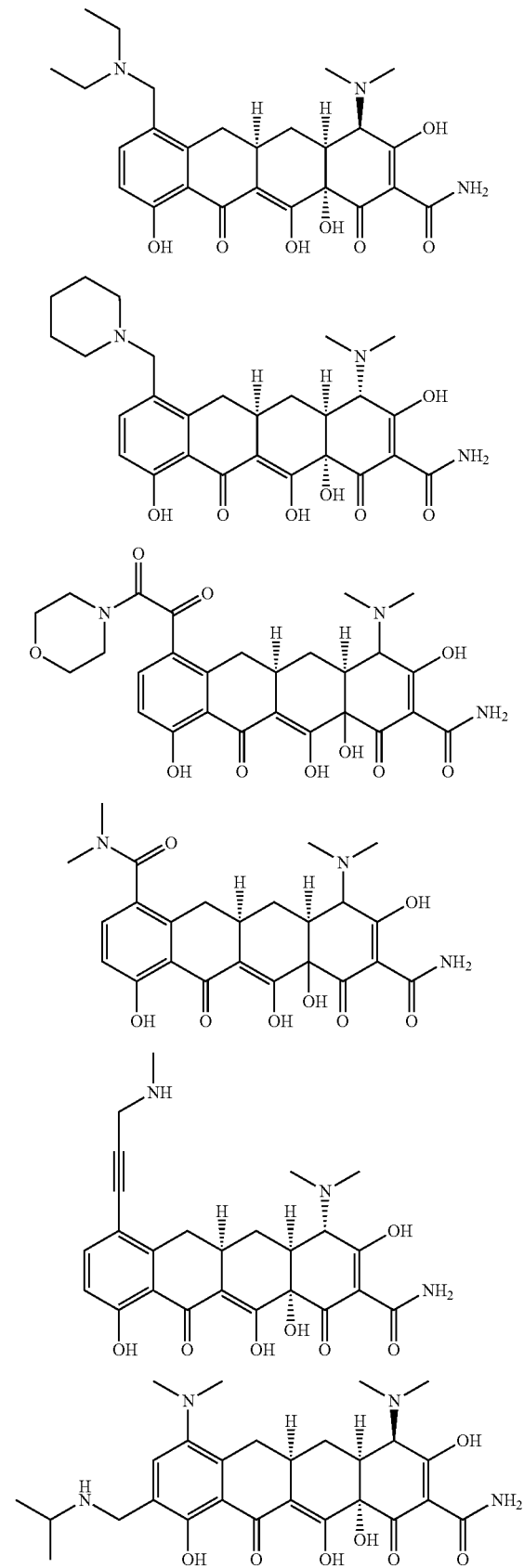

TABLE 1-continued
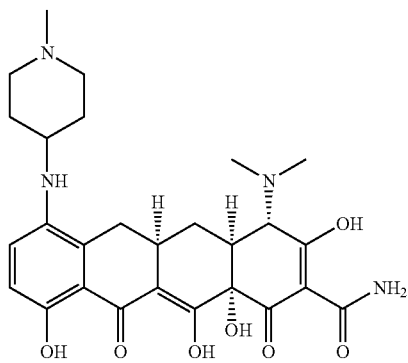
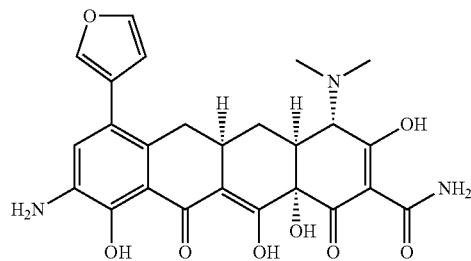
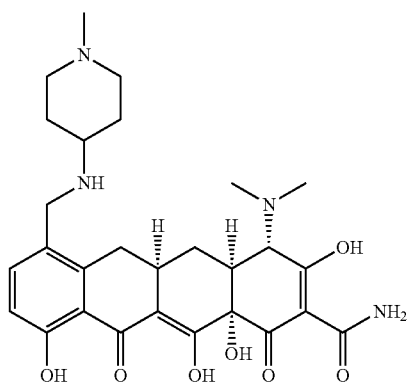
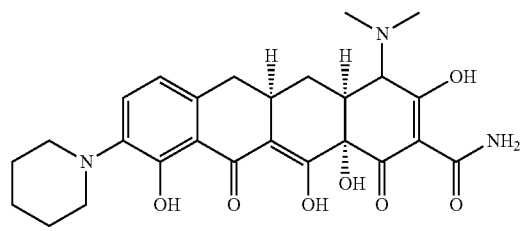
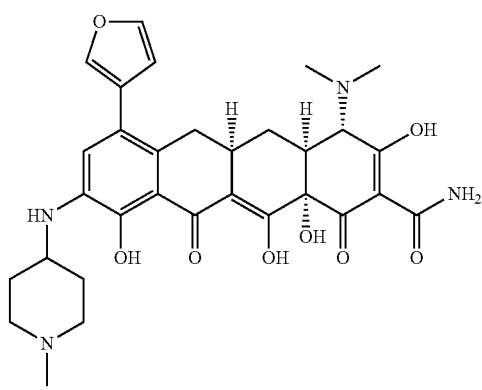

TABLE 1-continued
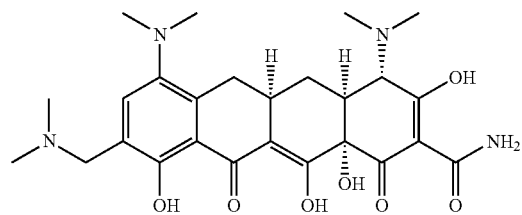
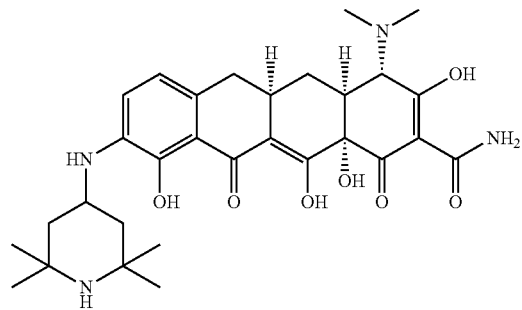
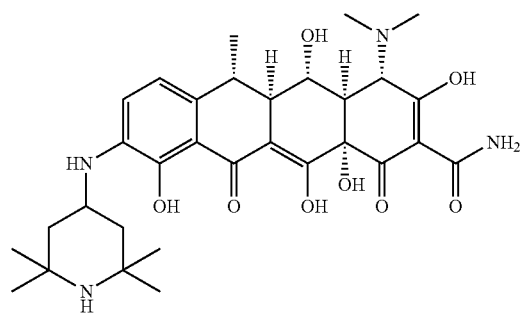
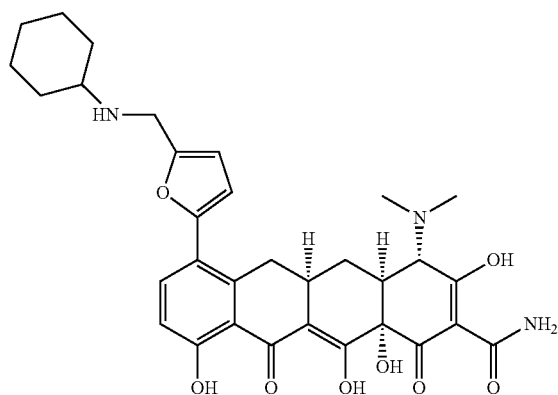
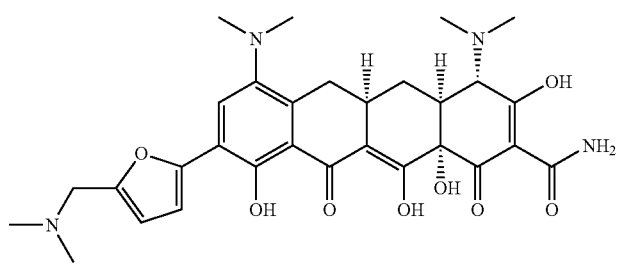

TABLE 1-continued
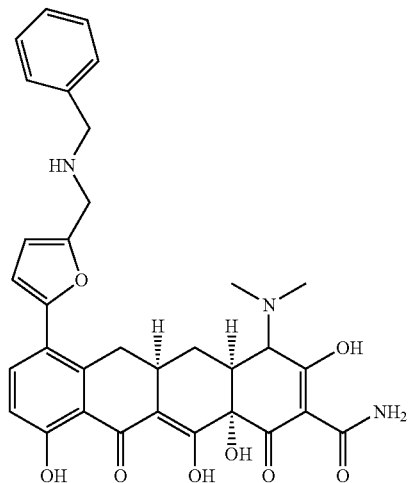
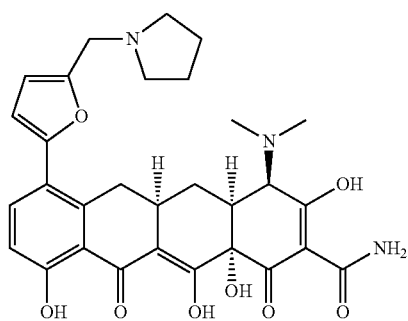
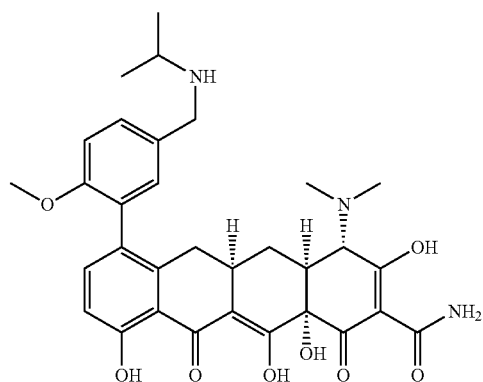
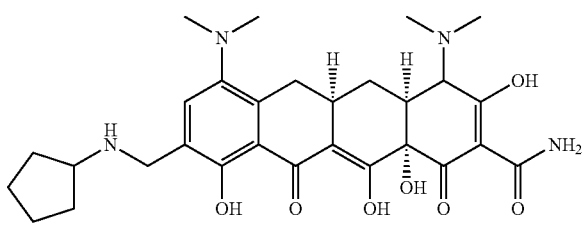
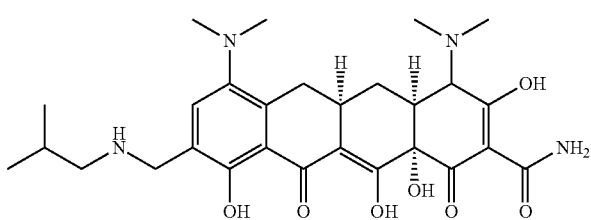

TABLE 1-continued
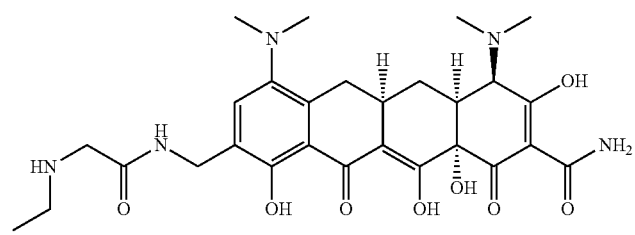
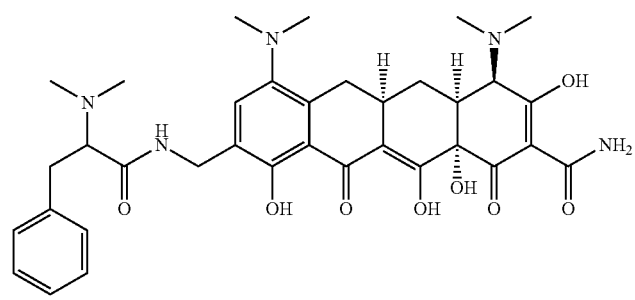
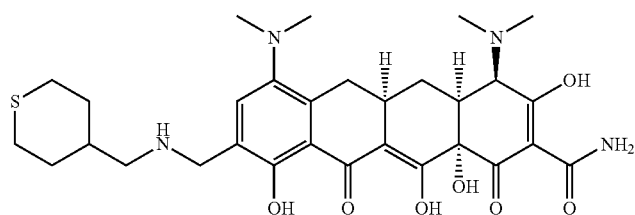
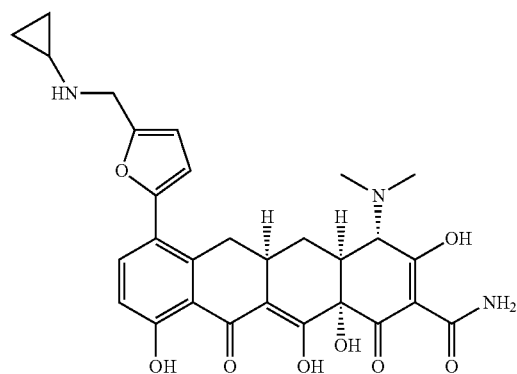
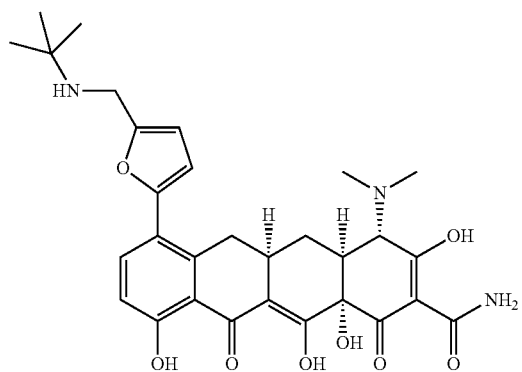

TABLE 1-continued
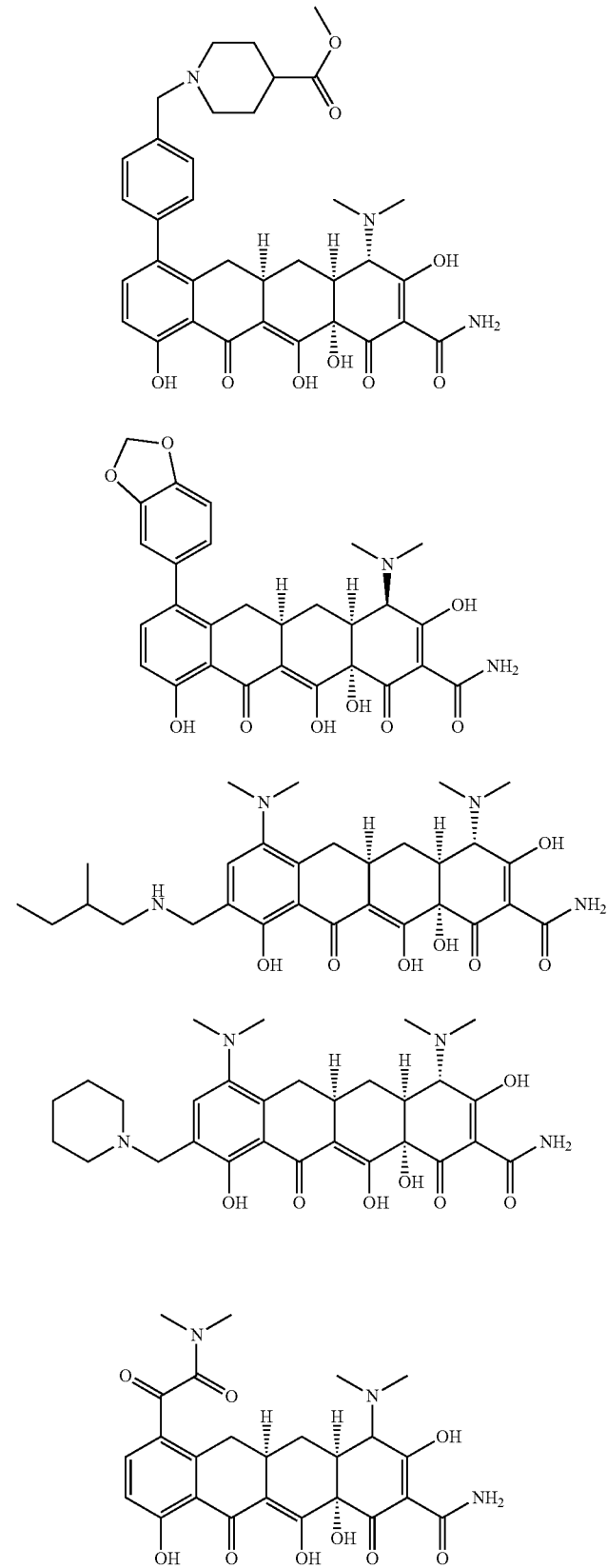

TABLE 1-continued
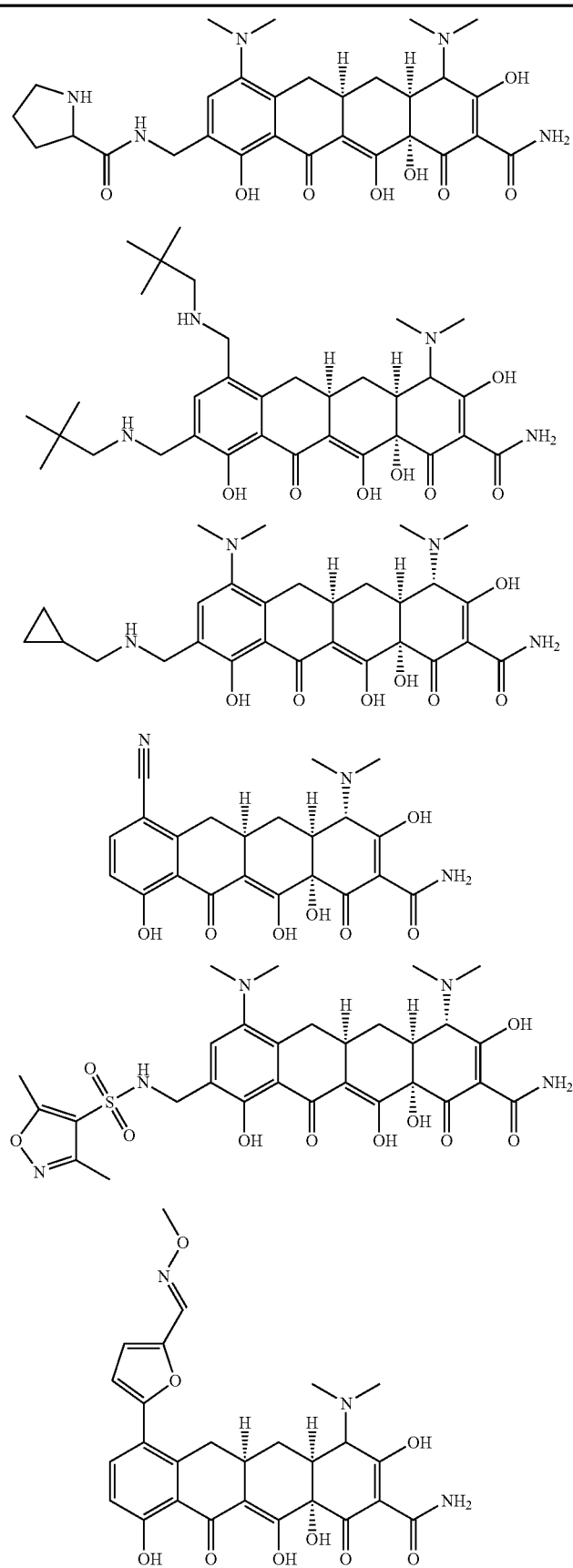

TABLE 1-continued
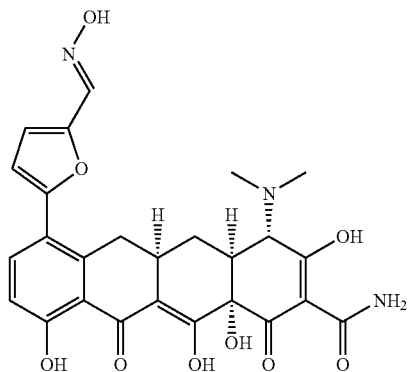
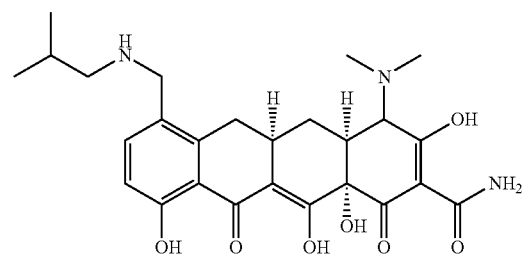
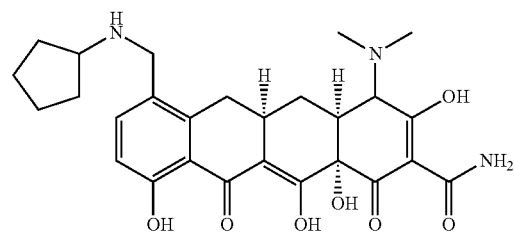
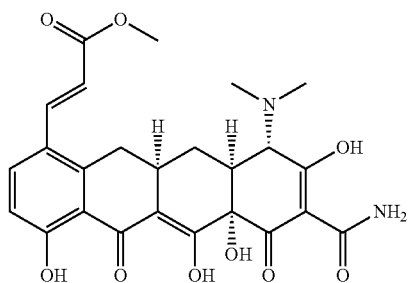
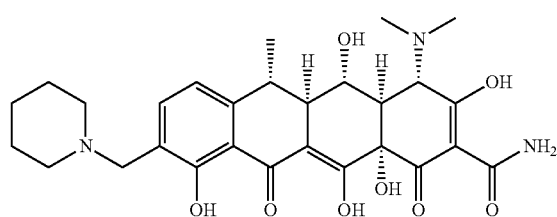

TABLE 1-continued
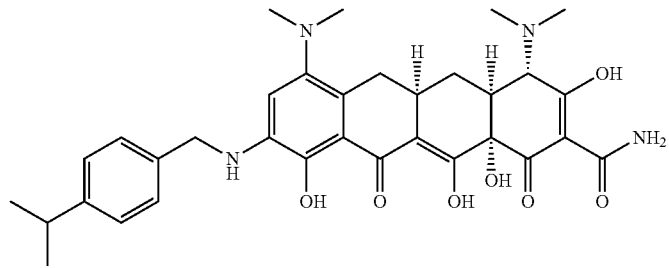
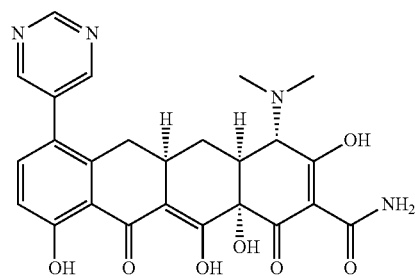
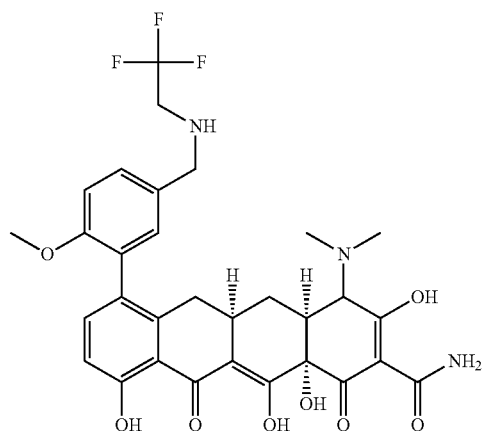
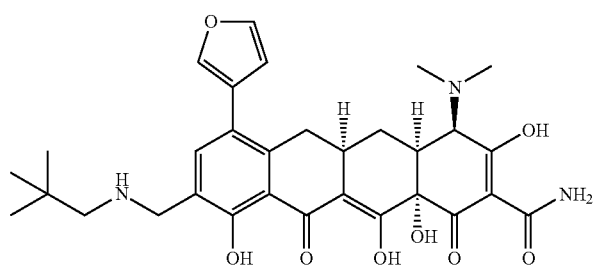

TABLE 1-continued
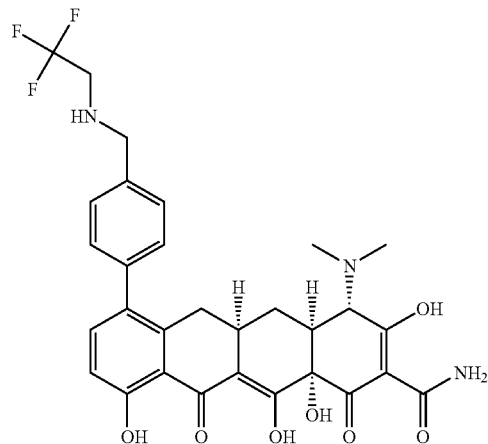
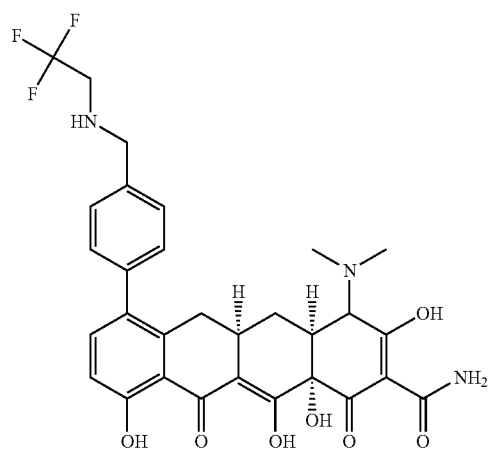
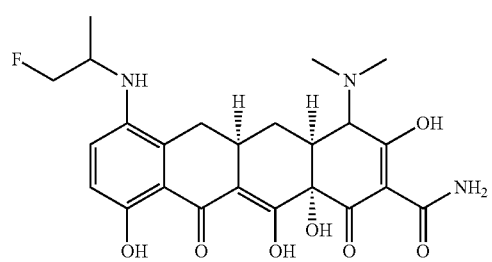
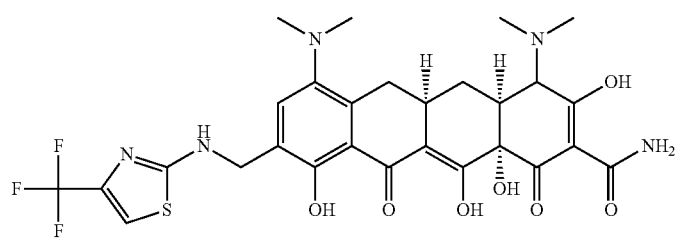

TABLE 1-continued
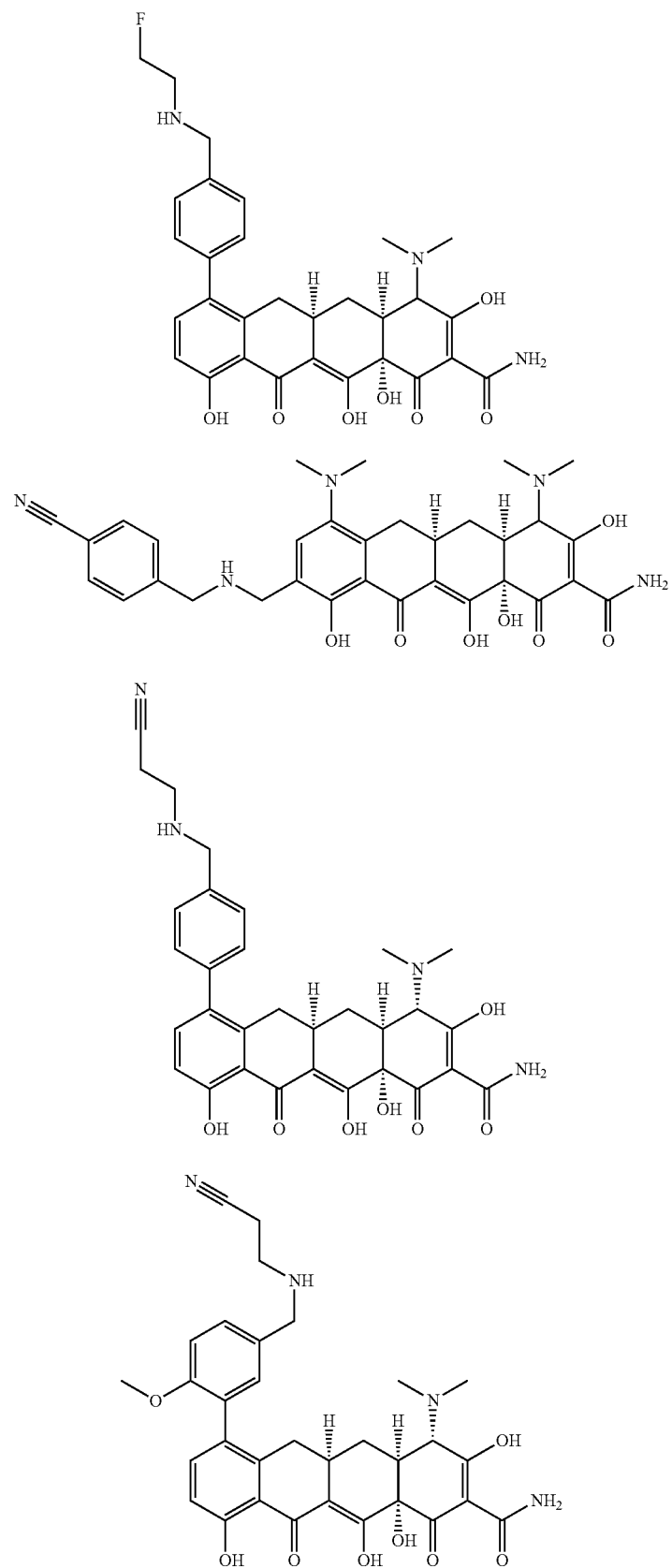

TABLE 1-continued
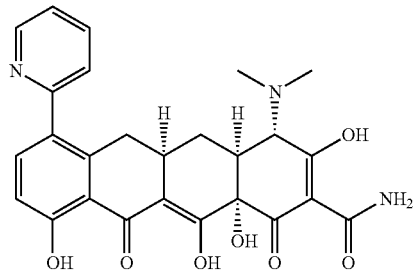
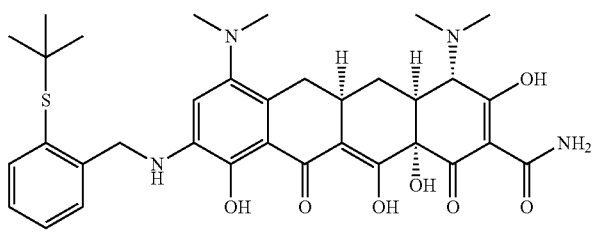
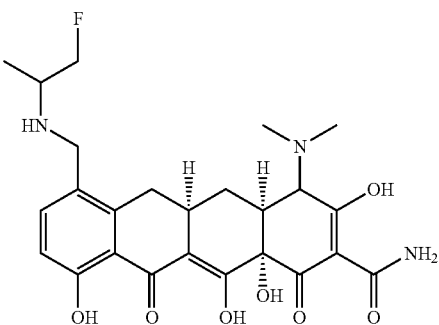
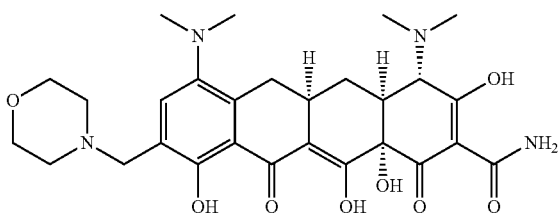
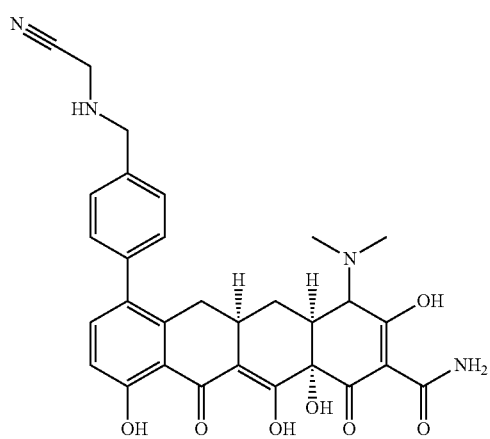

TABLE 1-continued
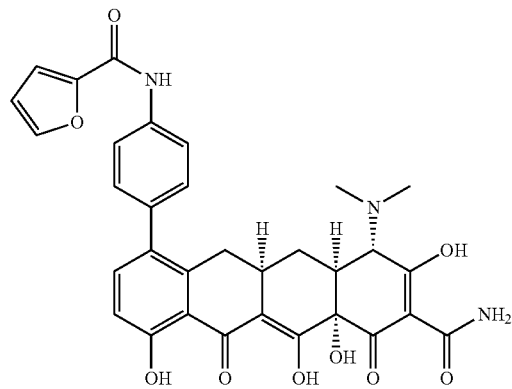
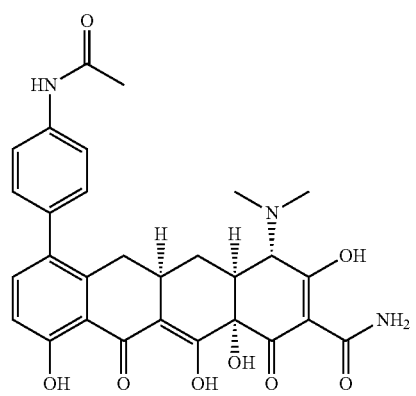
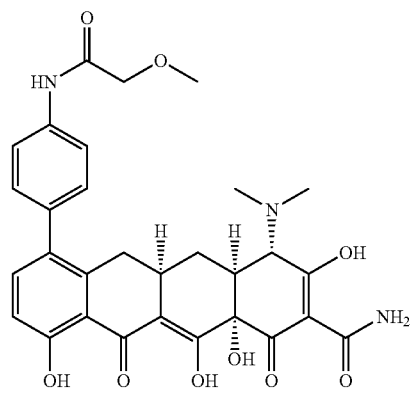
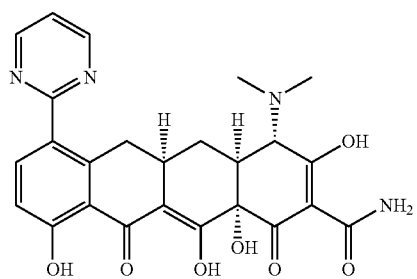

TABLE 1-continued
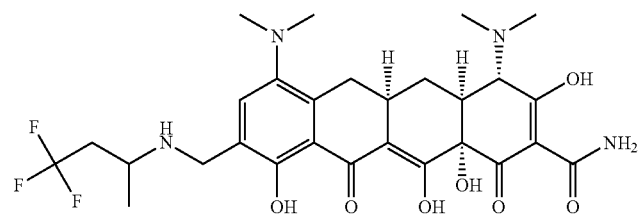
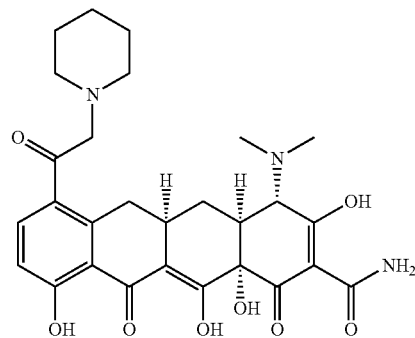
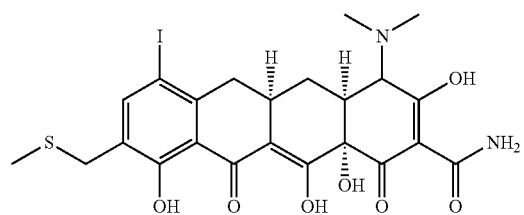
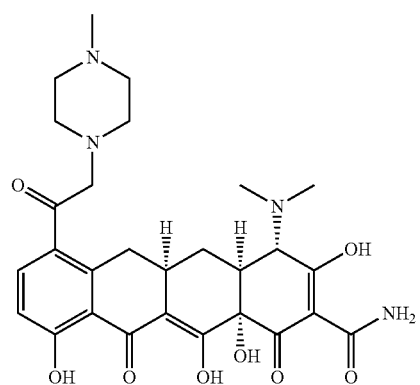
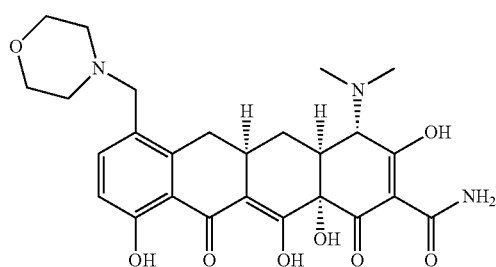

TABLE 1-continued
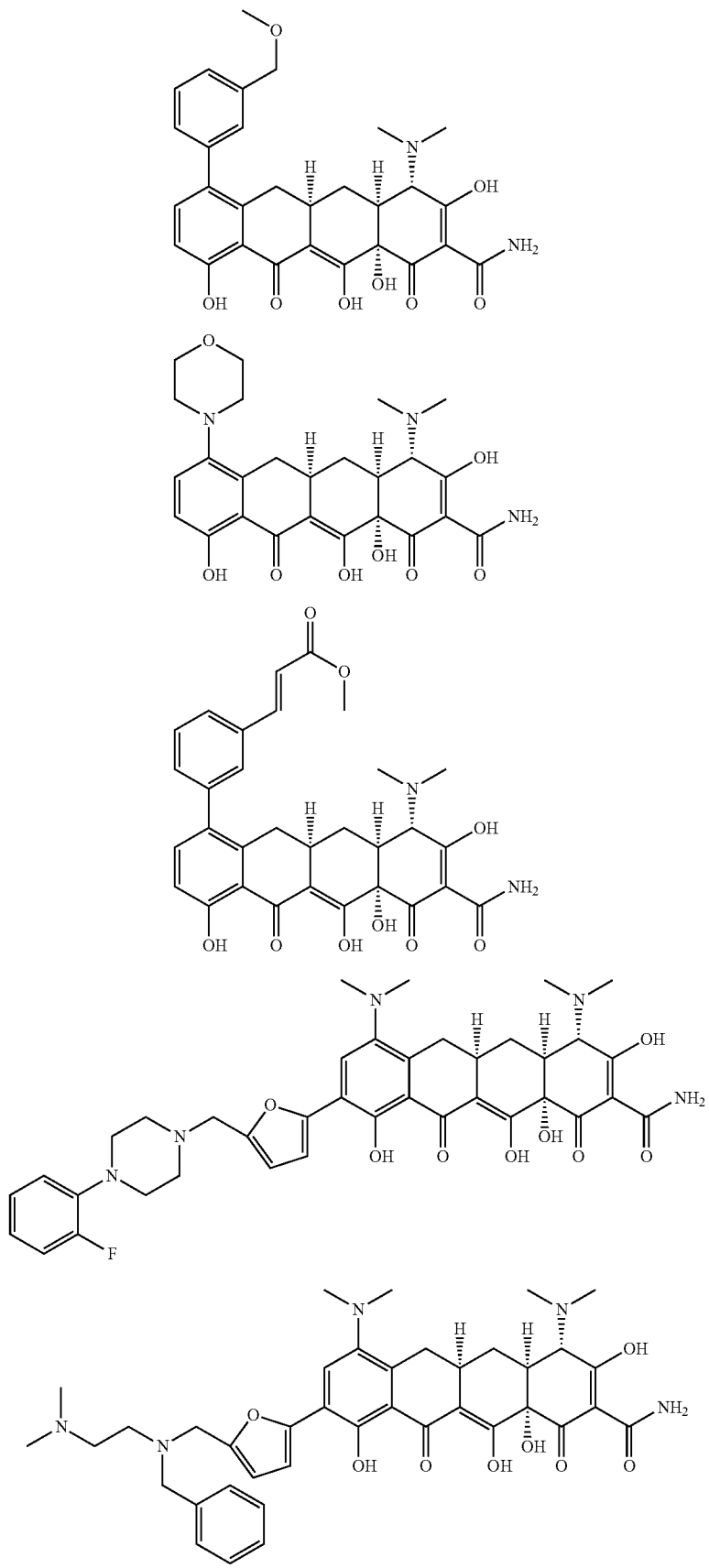

TABLE 1-continued
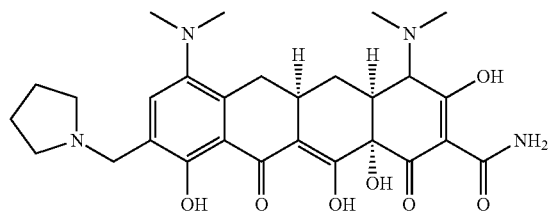
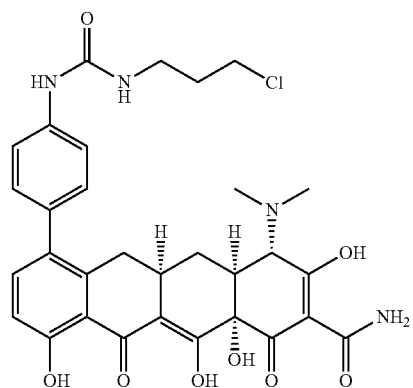
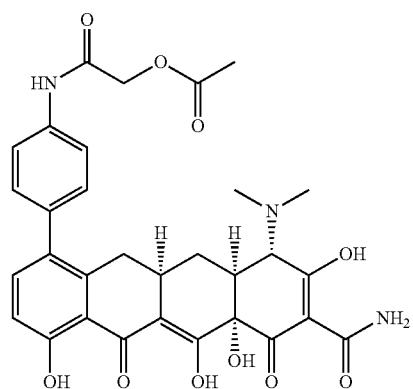
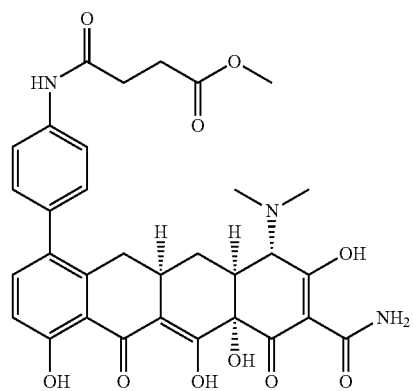

TABLE 1-continued
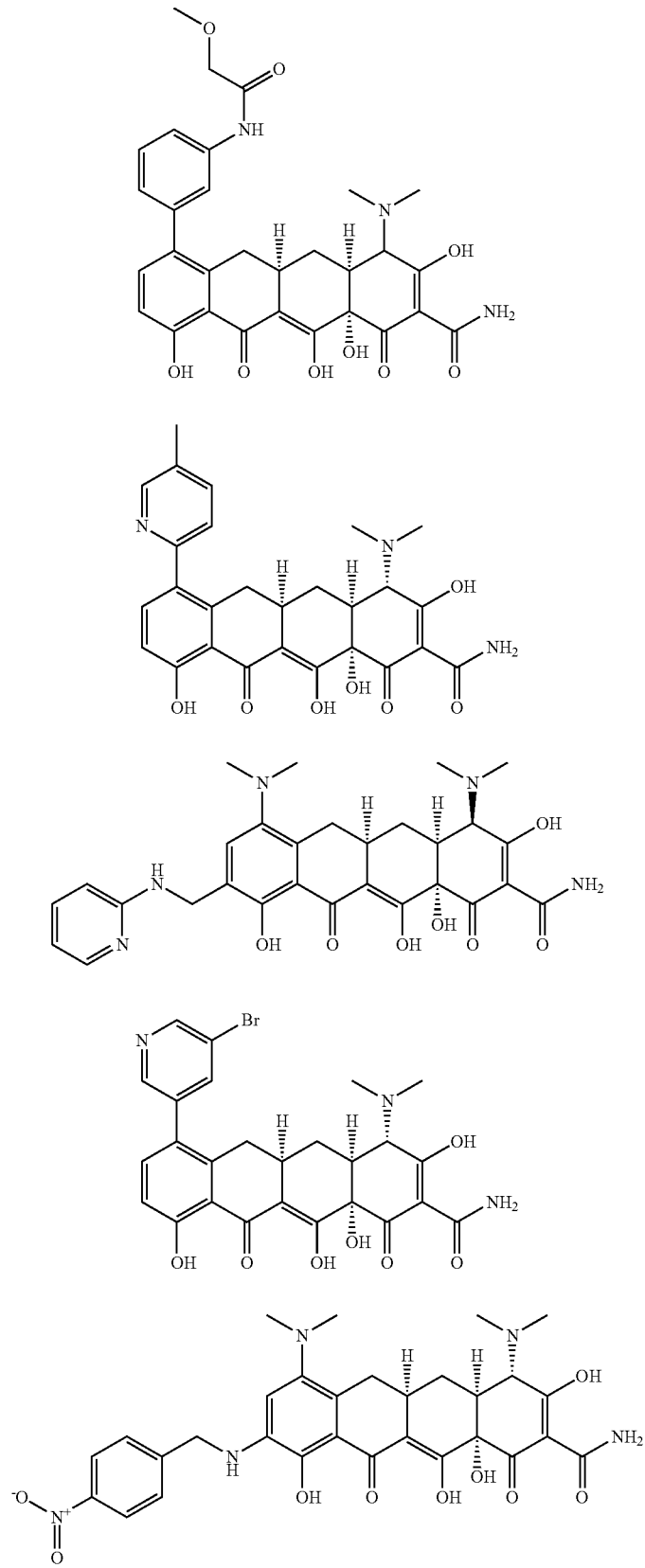

TABLE 1-continued
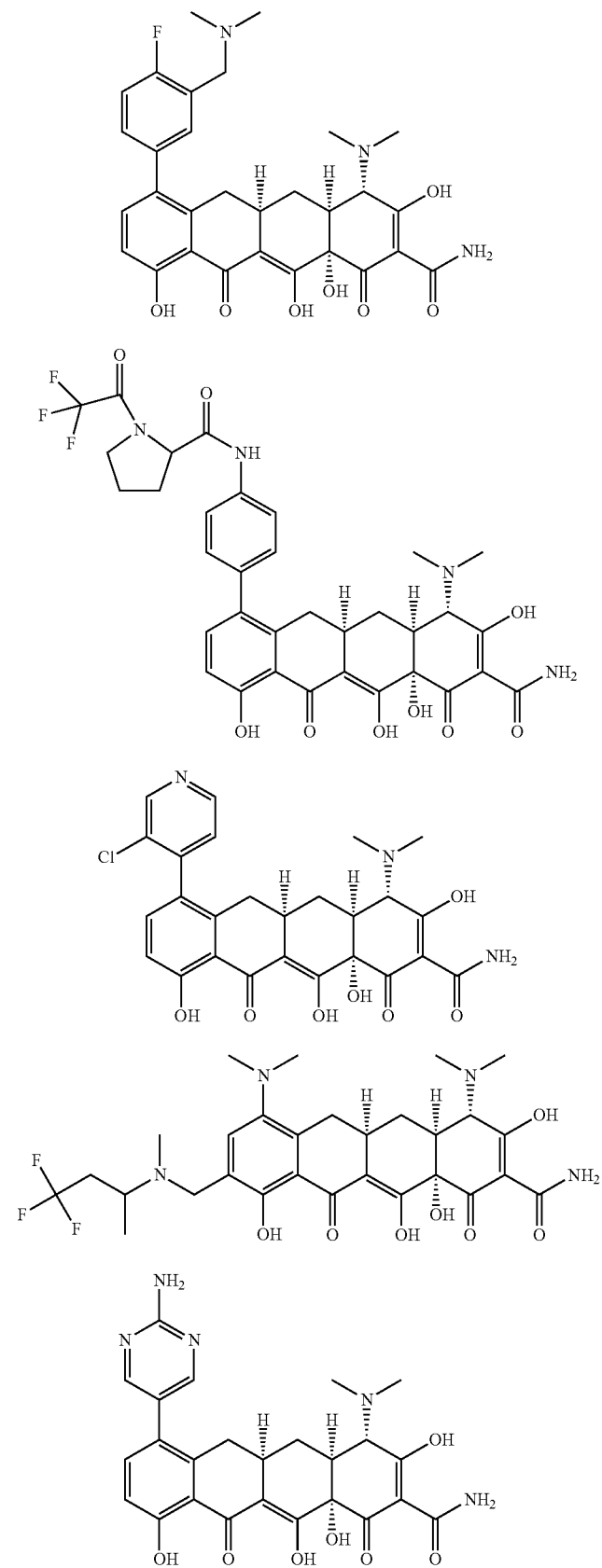

TABLE 1-continued
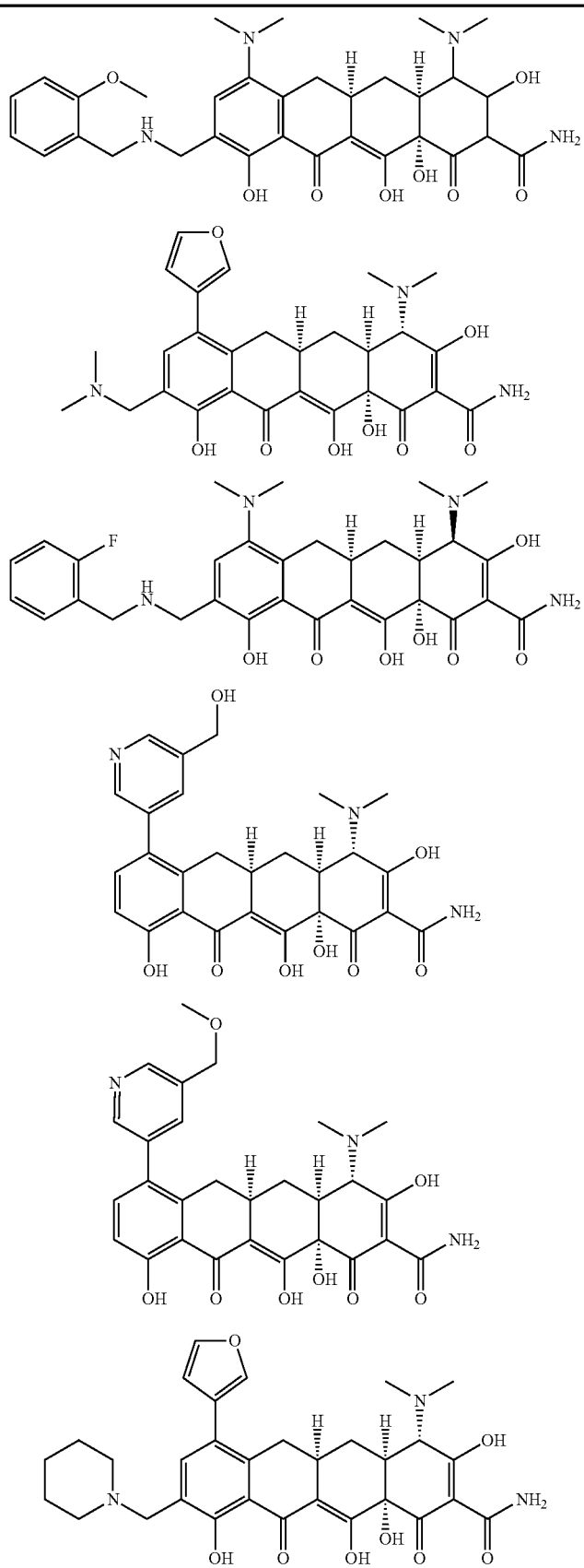

TABLE 1-continued
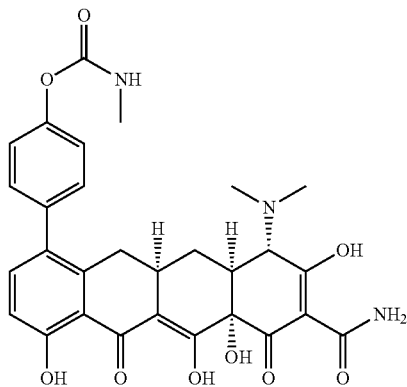
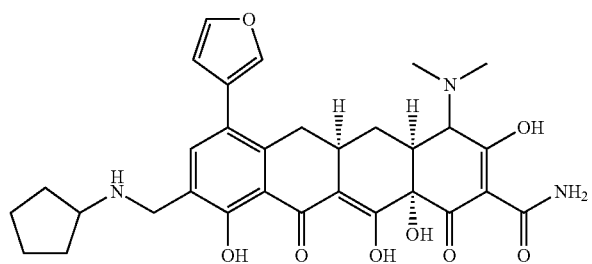
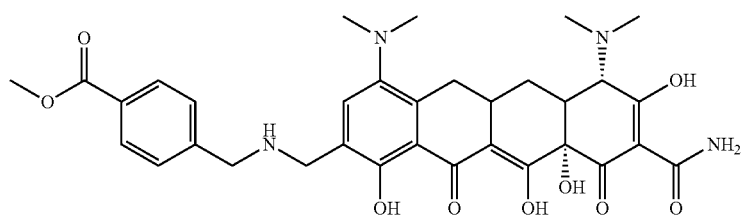
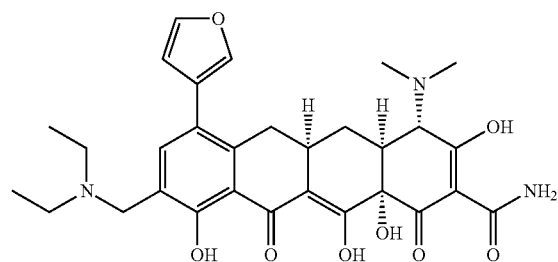
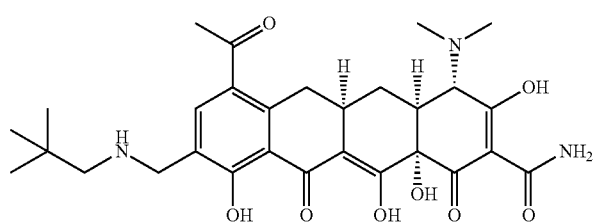

TABLE 1-continued
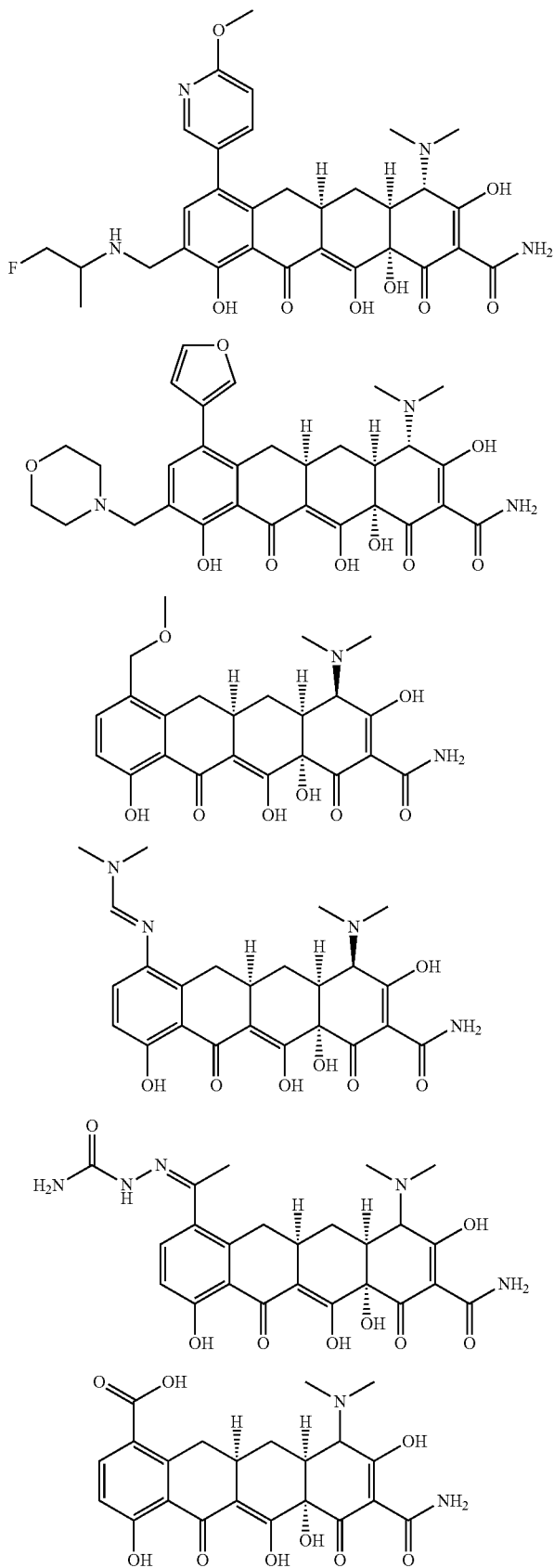

TABLE 1-continued
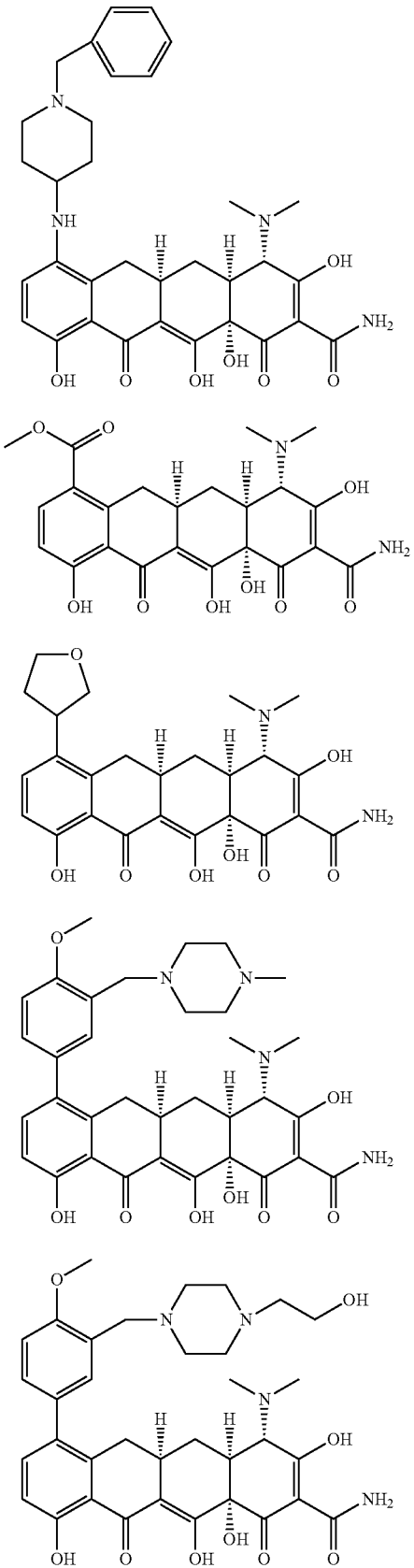

TABLE 1-continued
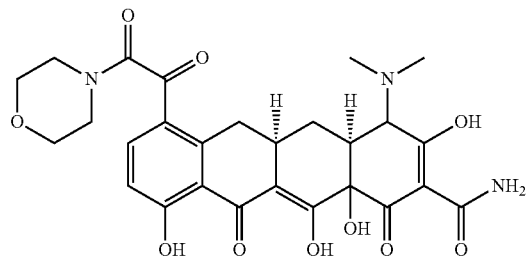
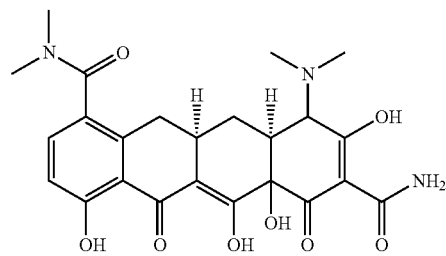
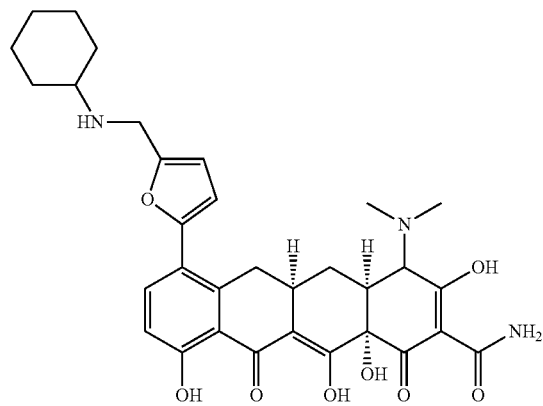
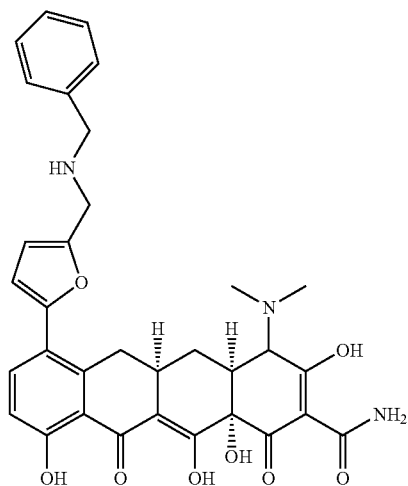

TABLE 1-continued
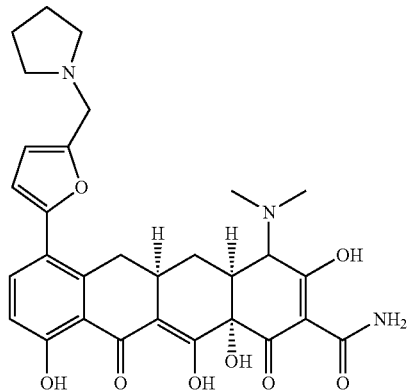
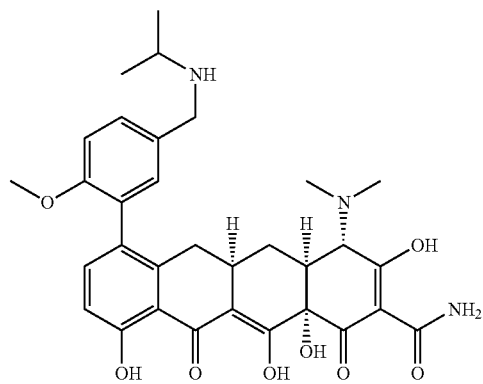
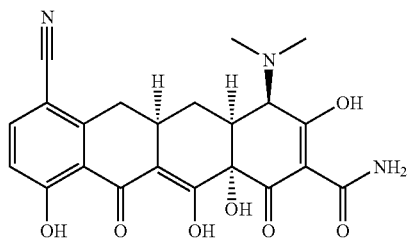
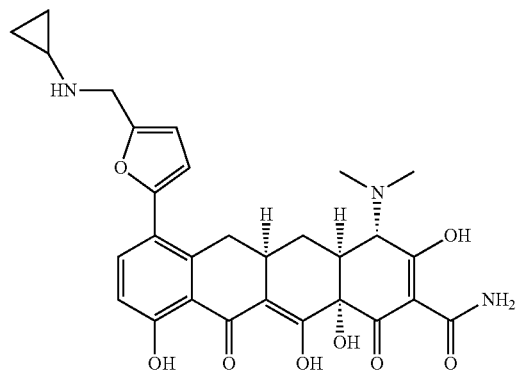

TABLE 1-continued
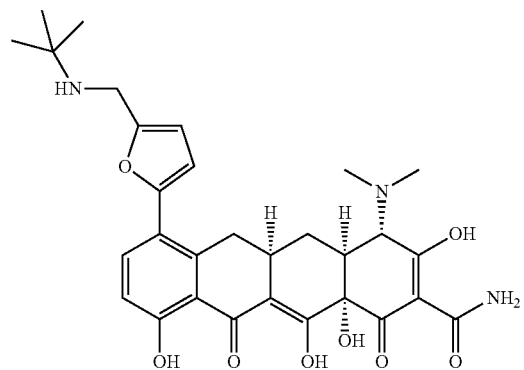
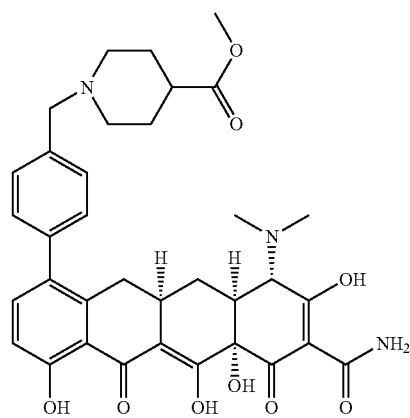
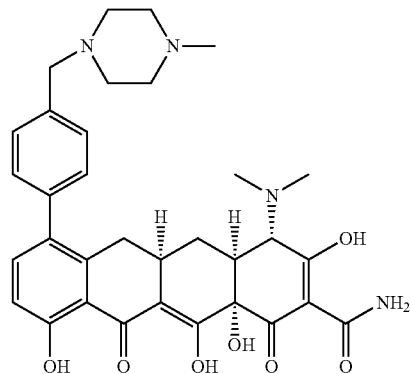
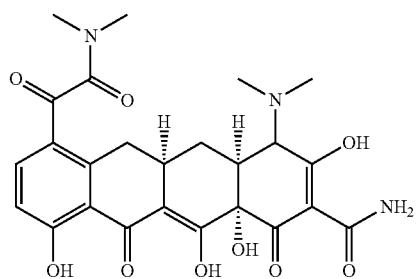

TABLE 1-continued
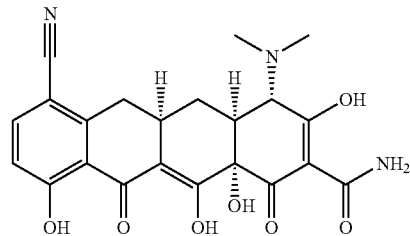
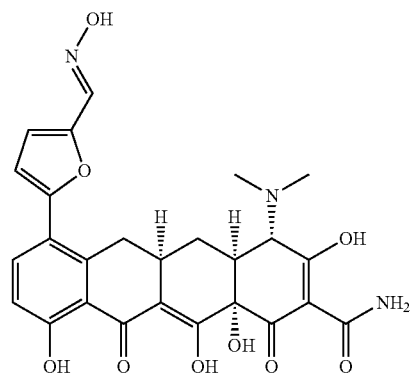
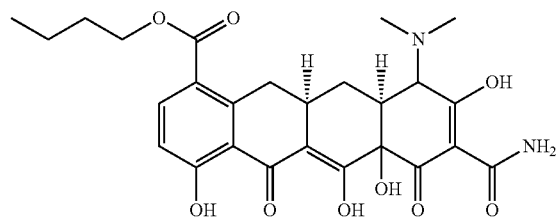
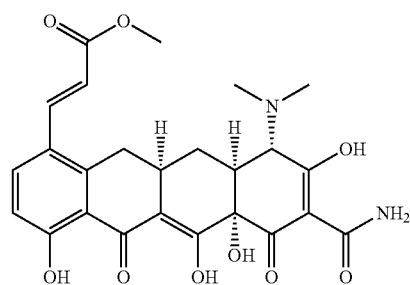
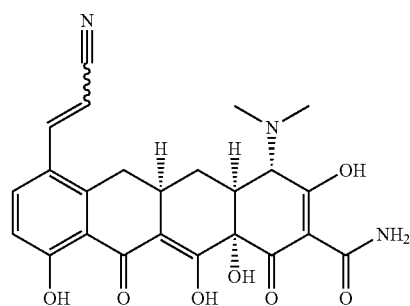

TABLE 1-continued
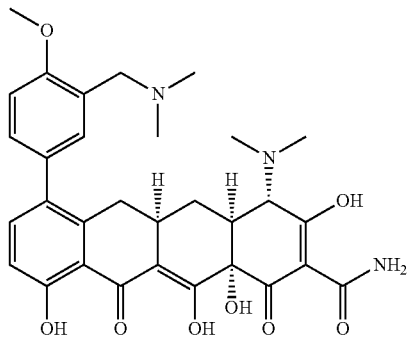
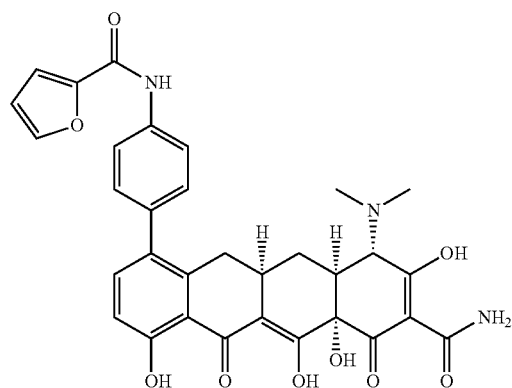
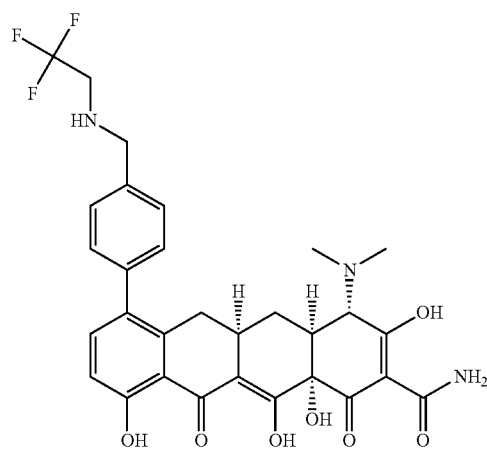
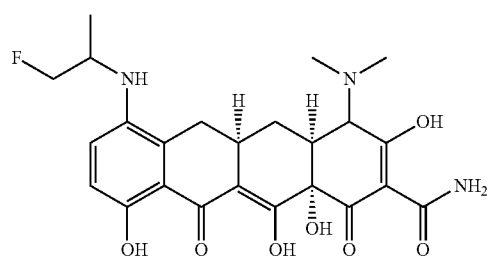

TABLE 1-continued
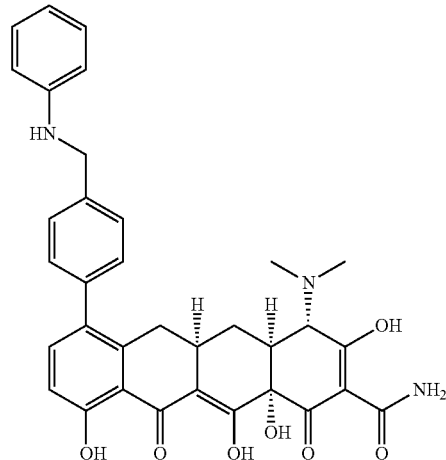
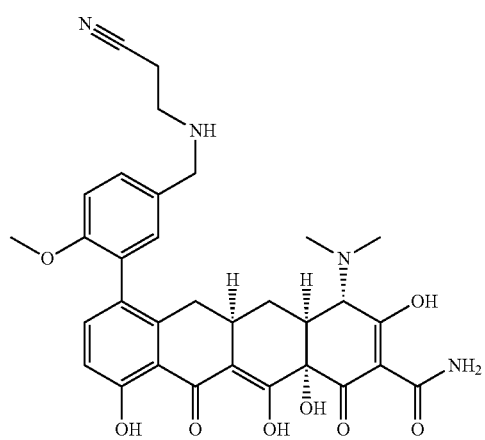
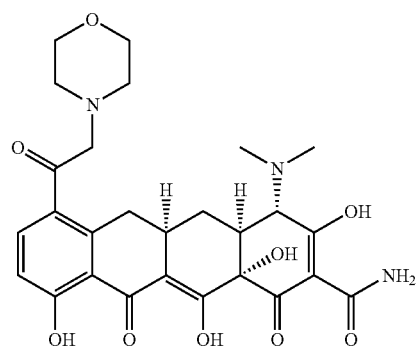
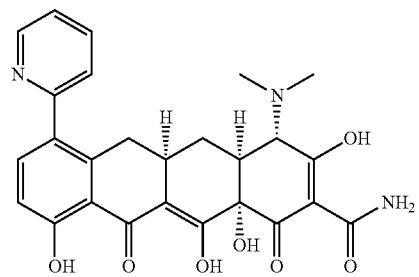

TABLE 1-continued
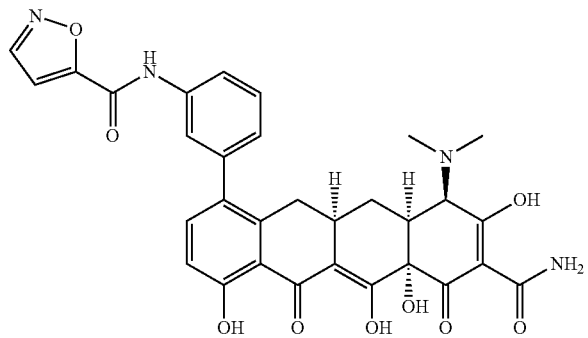
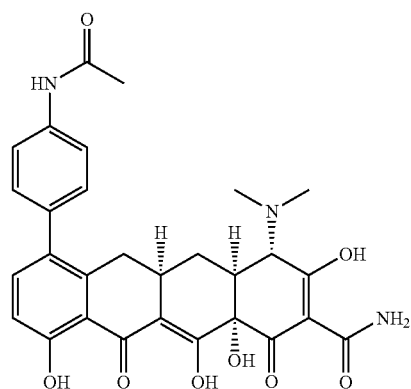
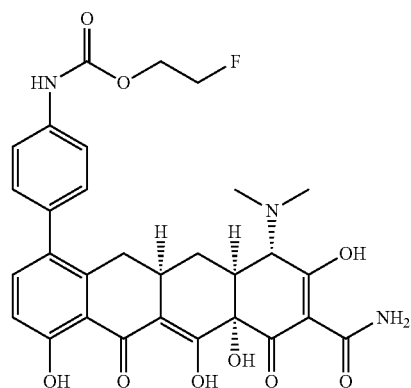
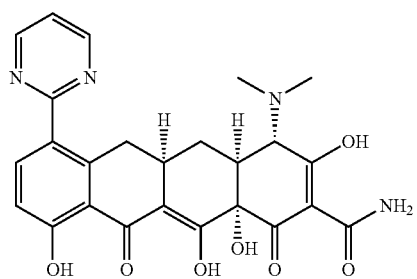

TABLE 1-continued
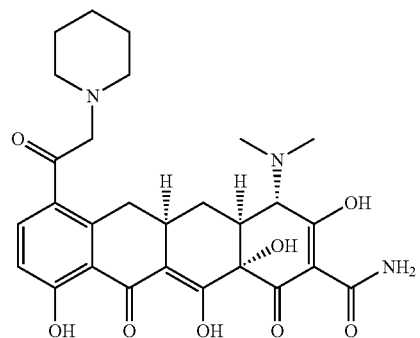
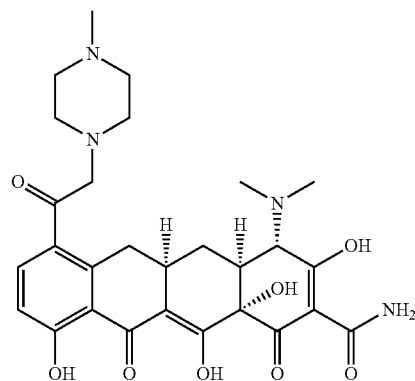
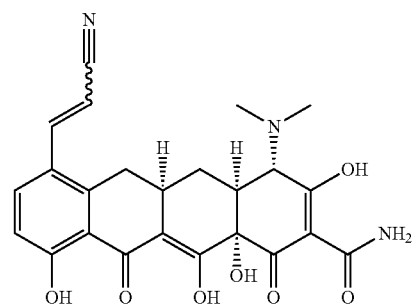
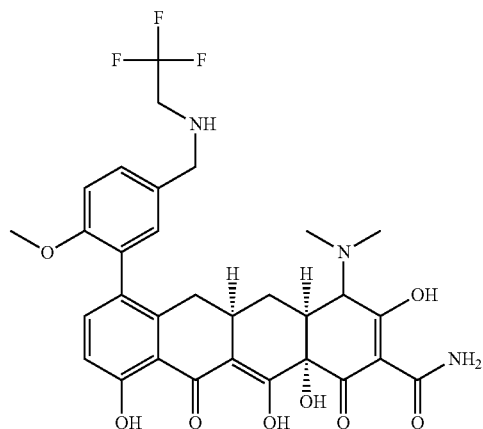

TABLE 1-continued
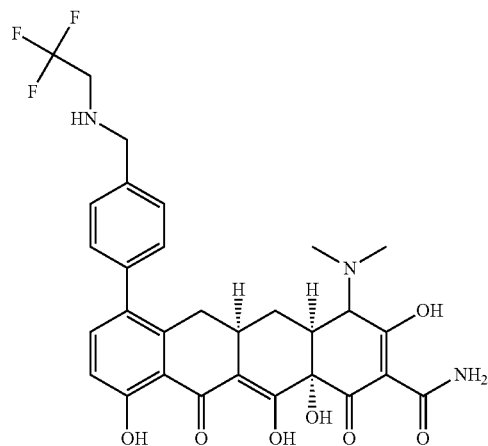
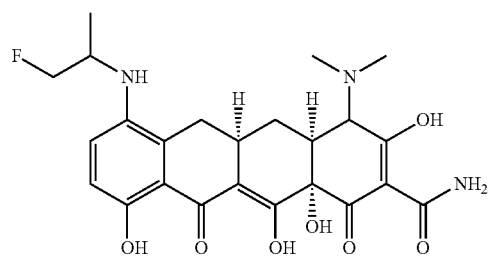
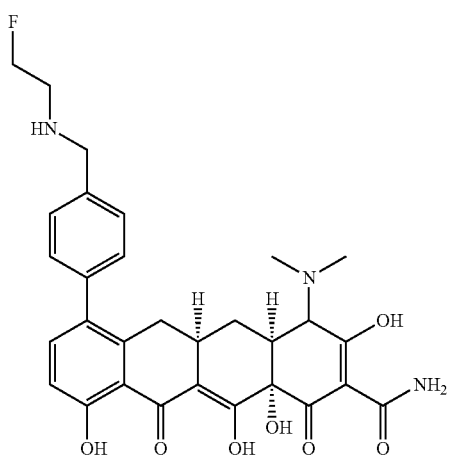
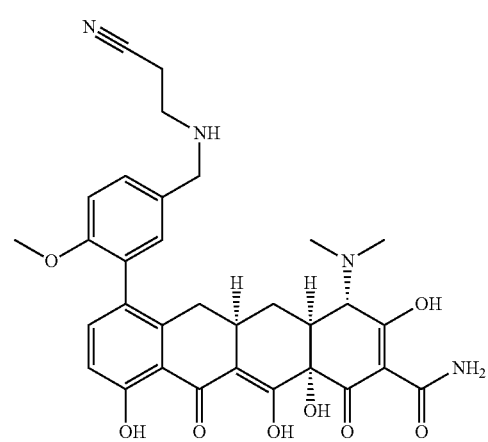

TABLE 1-continued
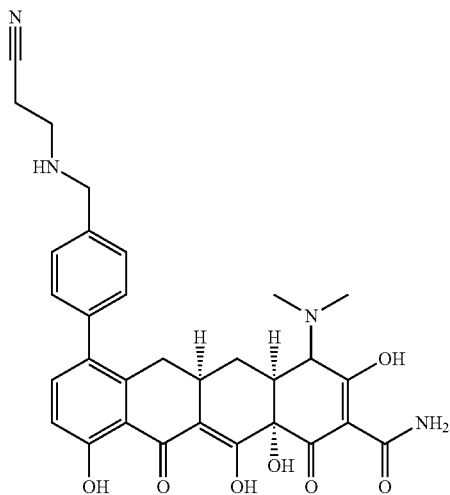
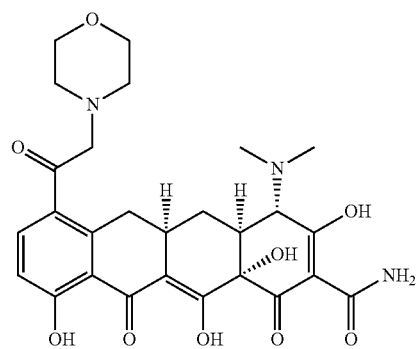
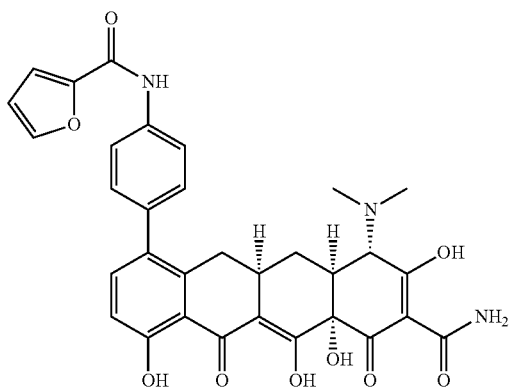
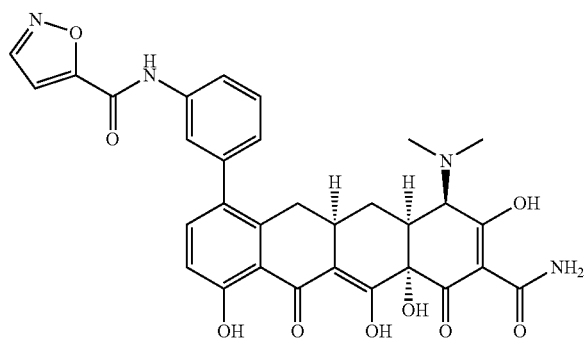

TABLE 1-continued
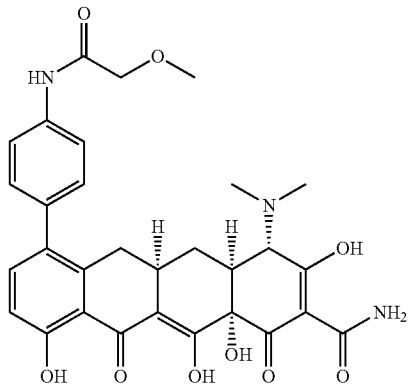
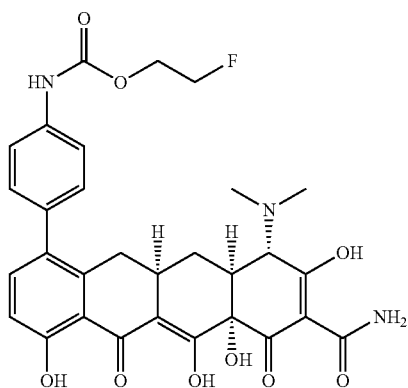
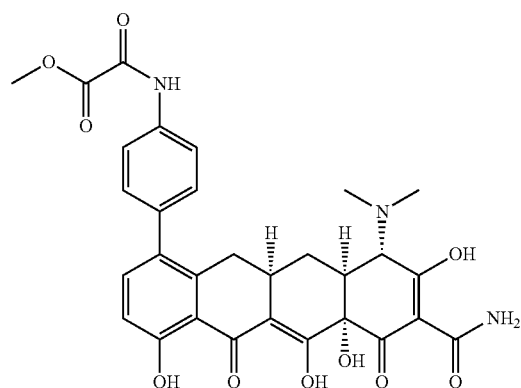
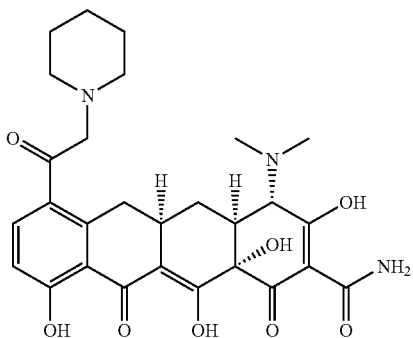

TABLE 1-continued
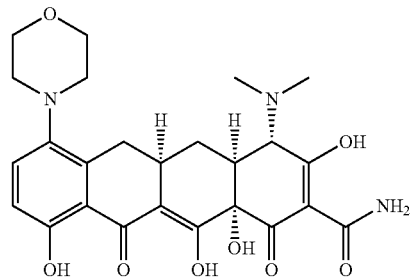
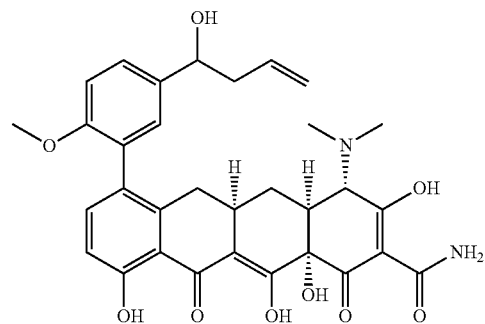
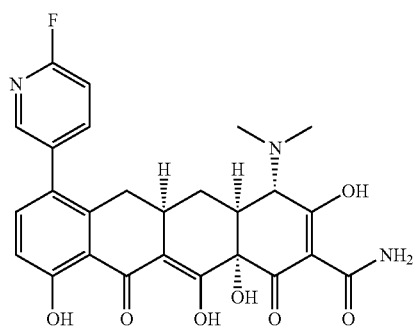
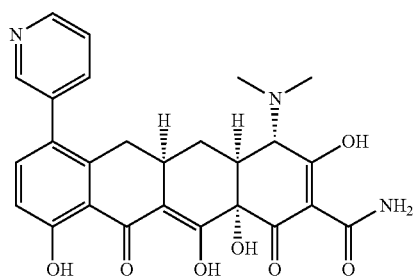

TABLE 1-continued
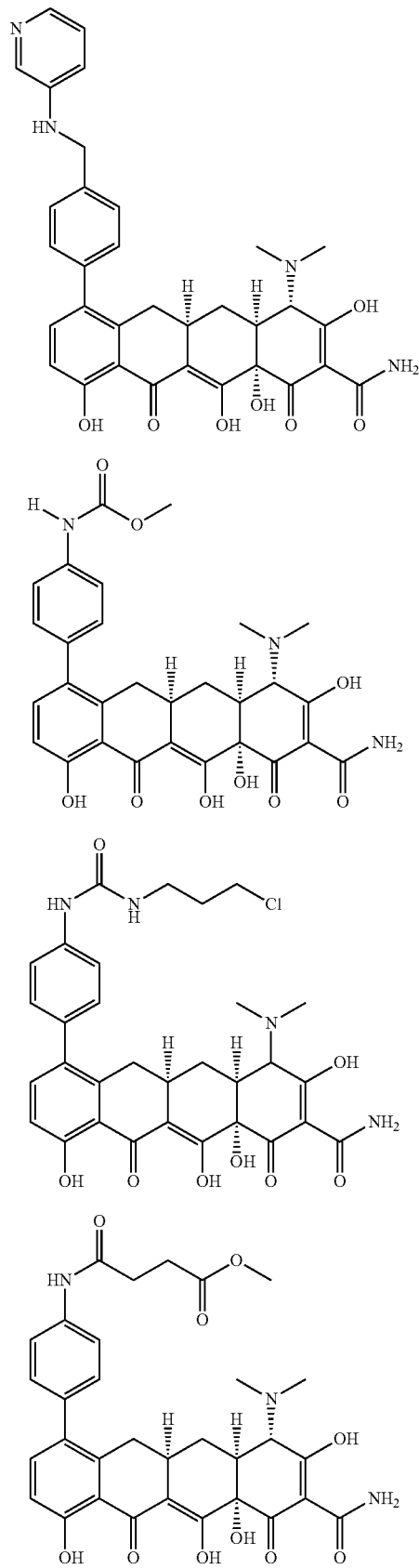

TABLE 1-continued
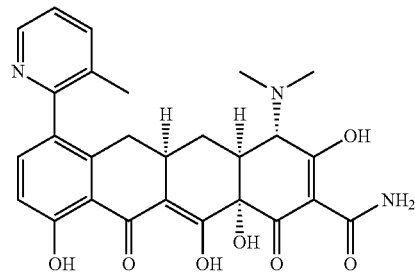
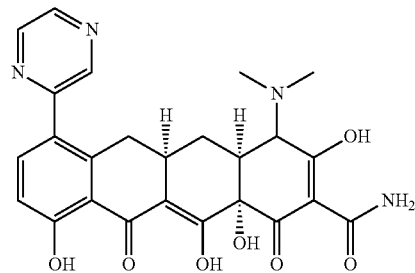
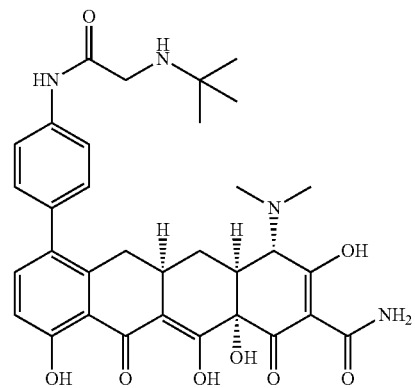
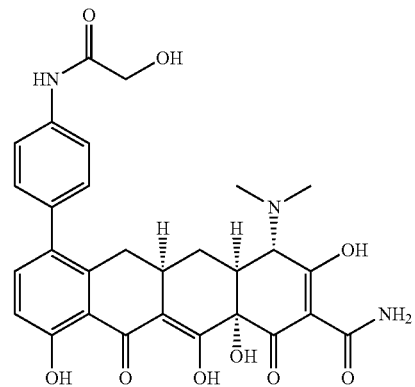
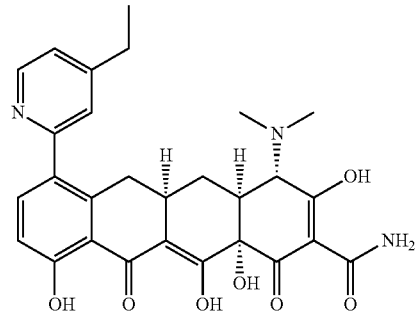

TABLE 1-continued
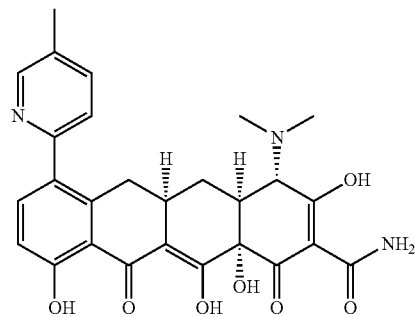
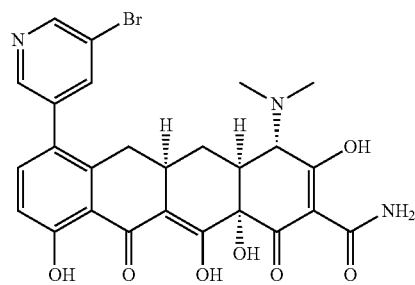
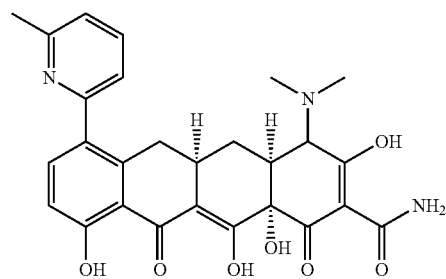
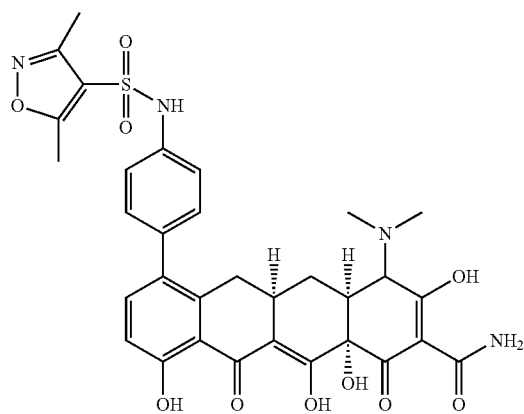

TABLE 1-continued
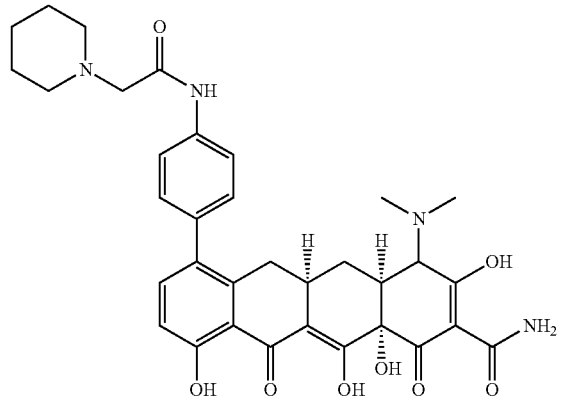
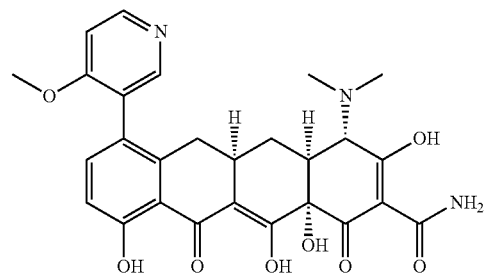
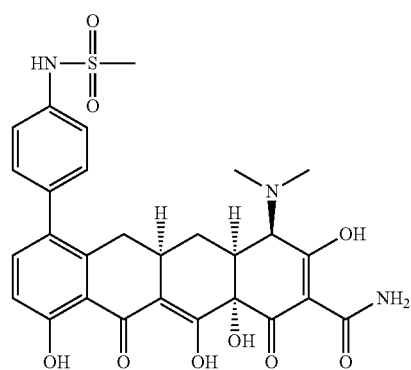
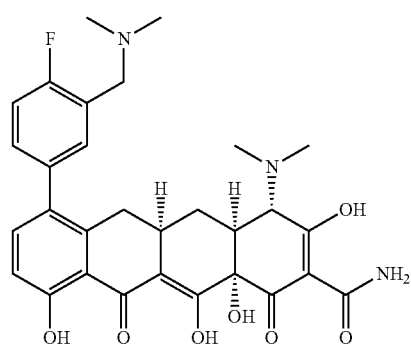

TABLE 1-continued
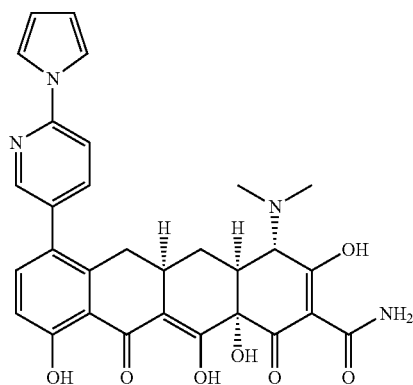
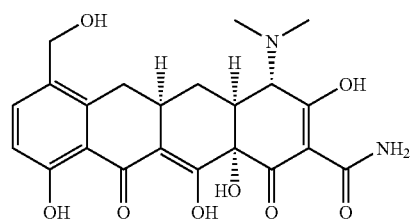
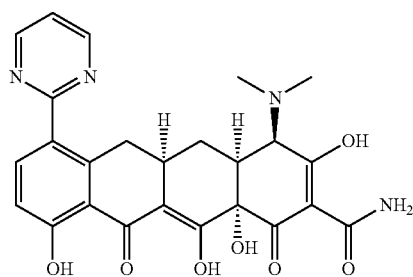
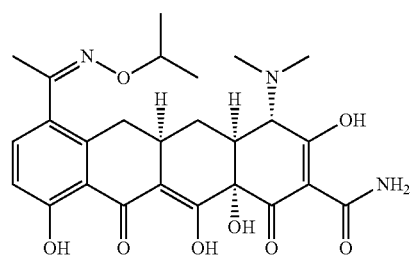
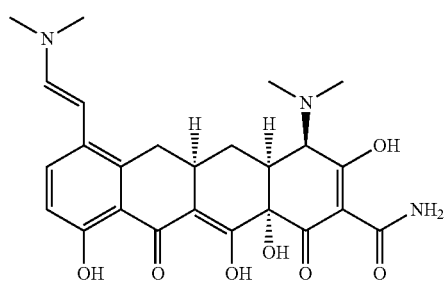

TABLE 1-continued
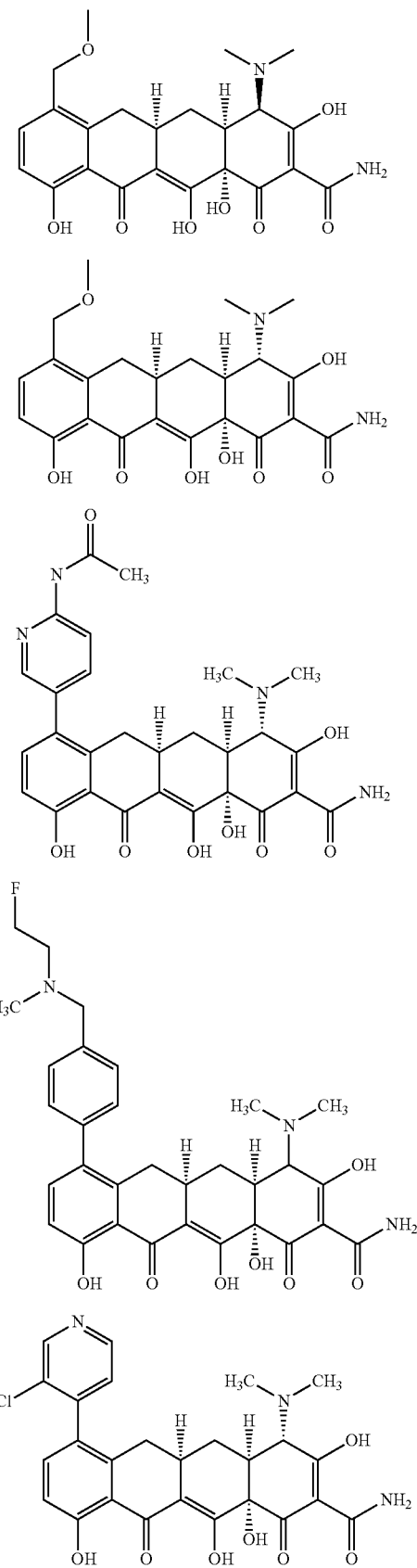

TABLE 1-continued
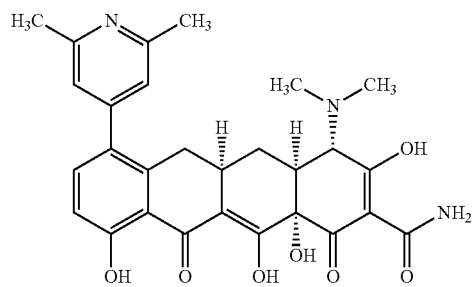
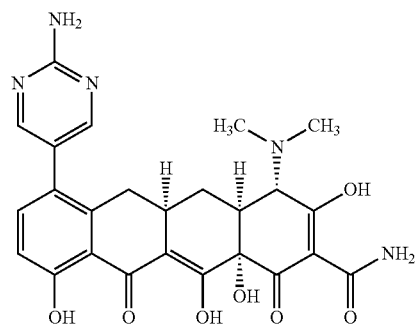
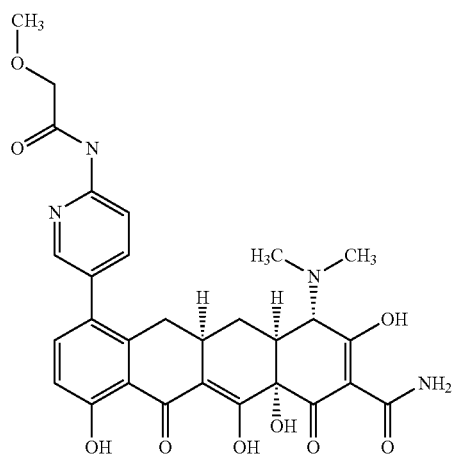
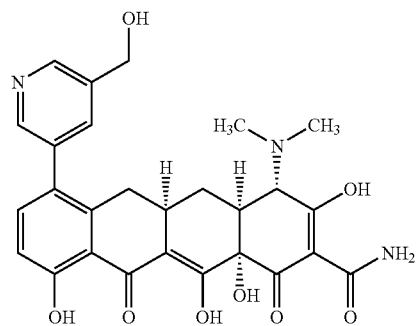

TABLE 1-continued
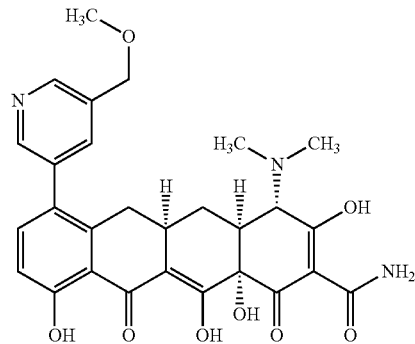
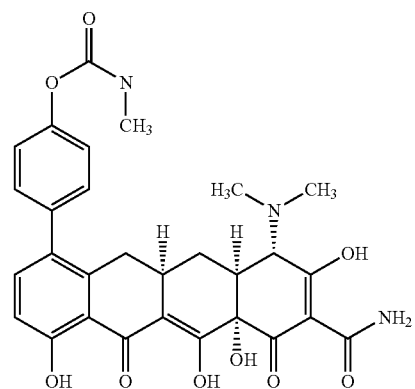
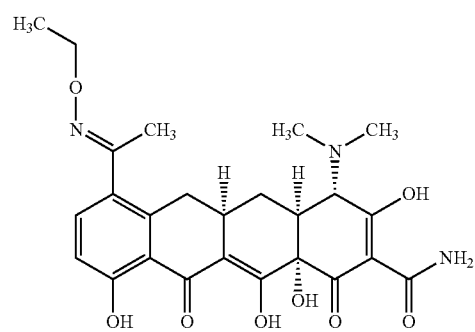
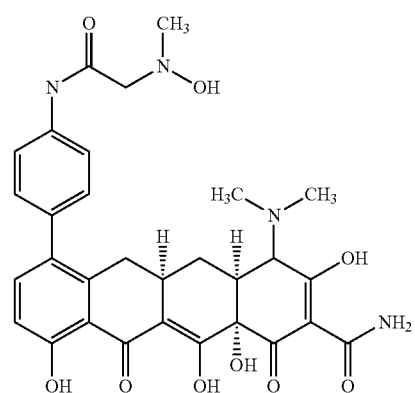

TABLE 1-continued
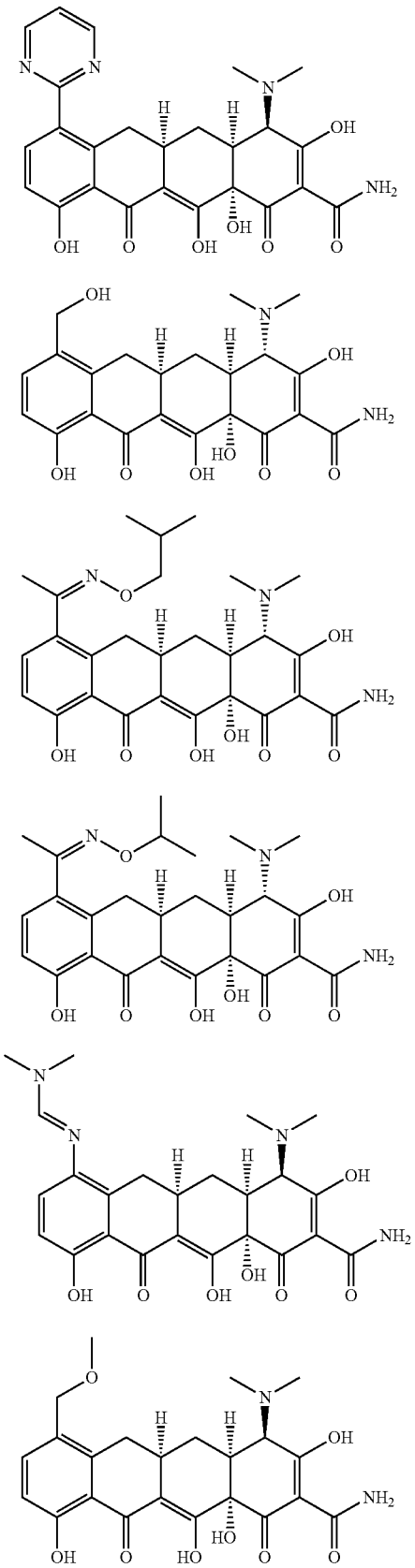

TABLE 1-continued
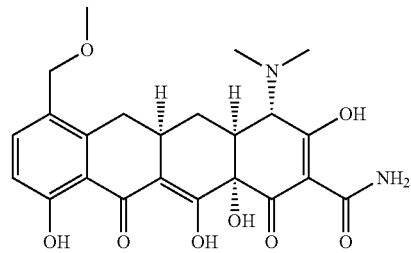
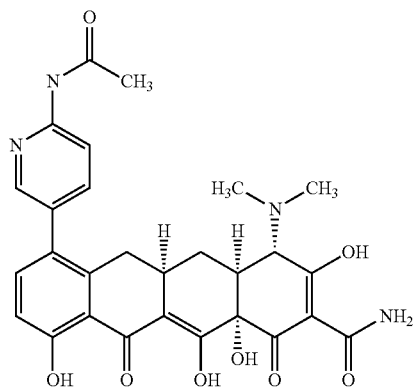
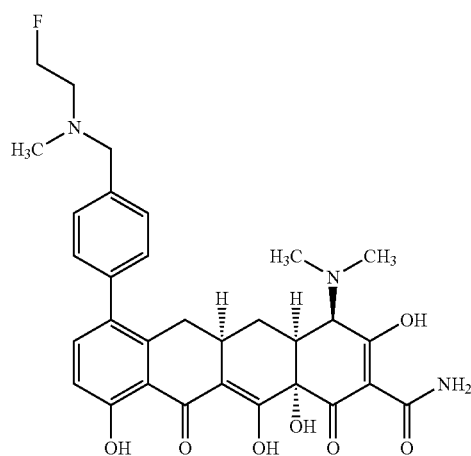
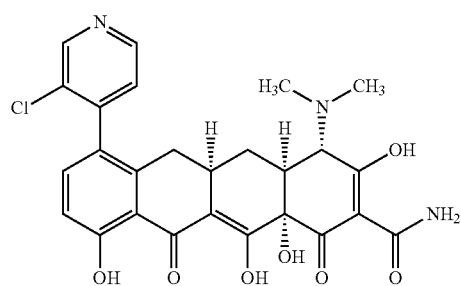

TABLE 1-continued
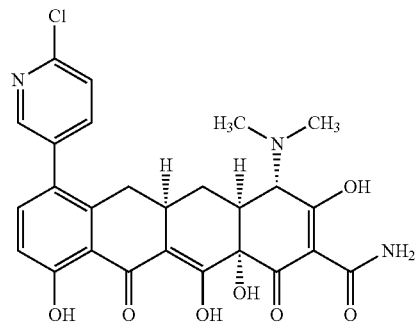
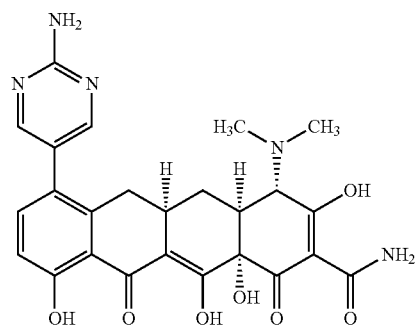
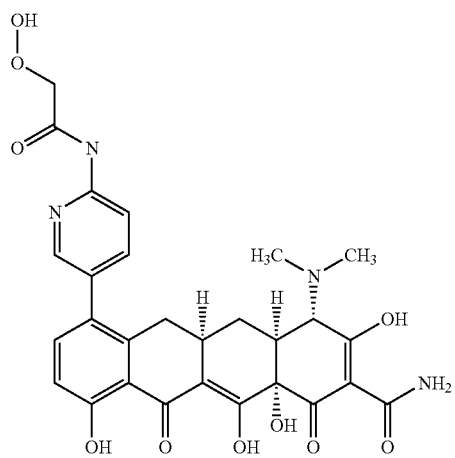
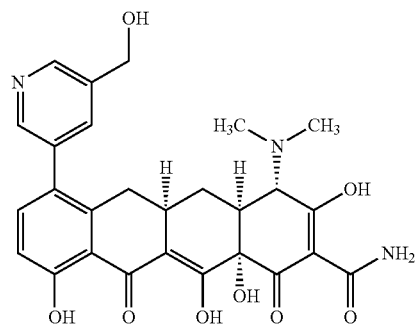

TABLE 1-continued
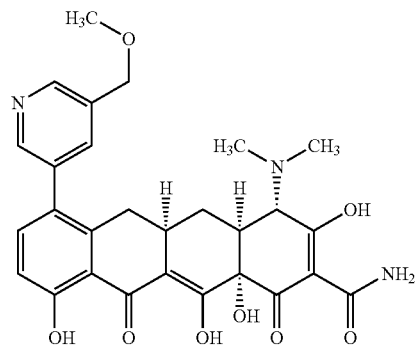
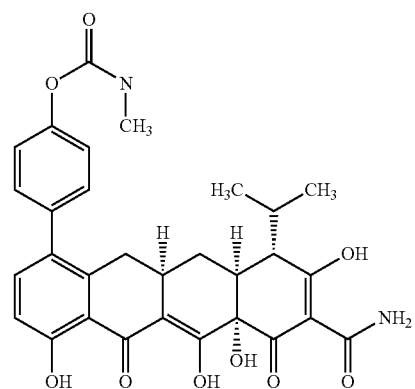
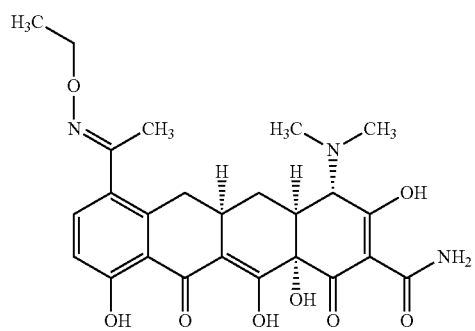
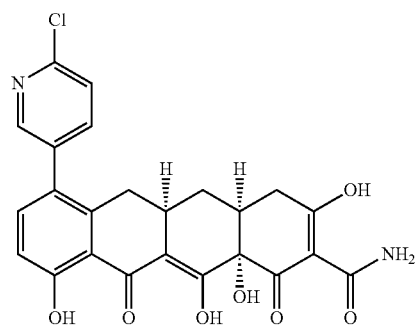

TABLE 1-continued
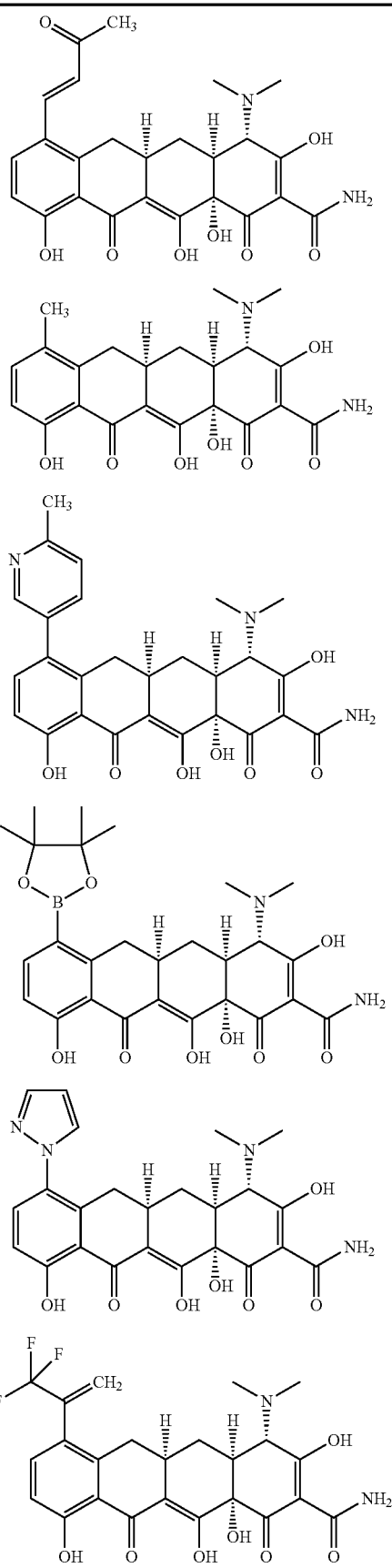

TABLE 1-continued
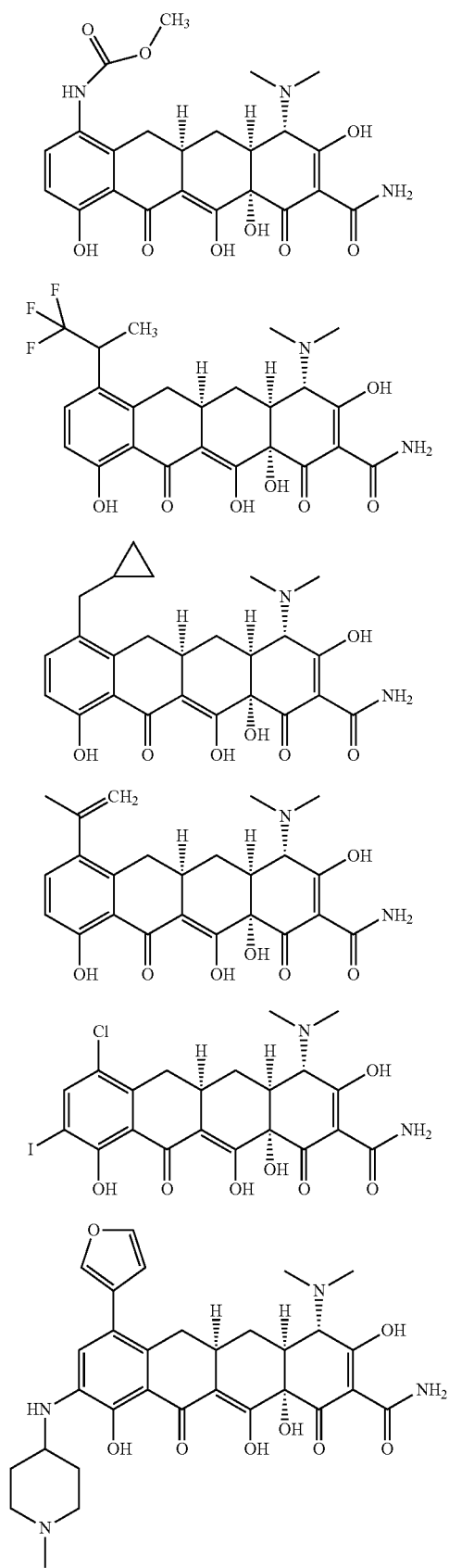

TABLE 1-continued
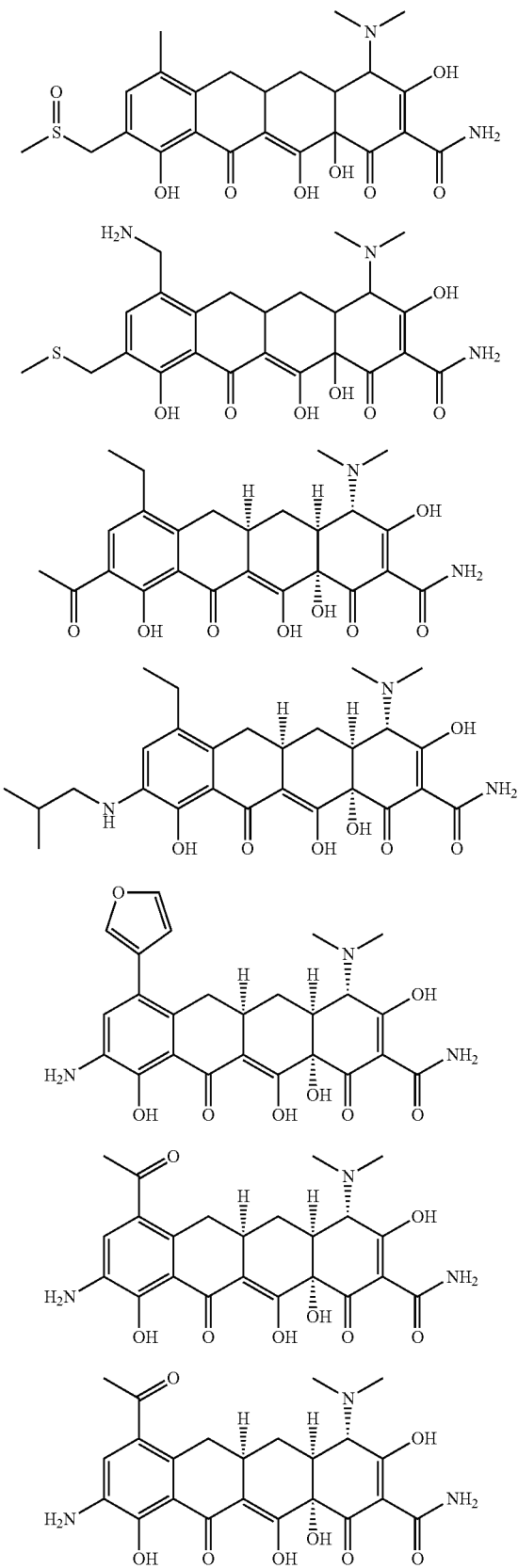

TABLE 1-continued
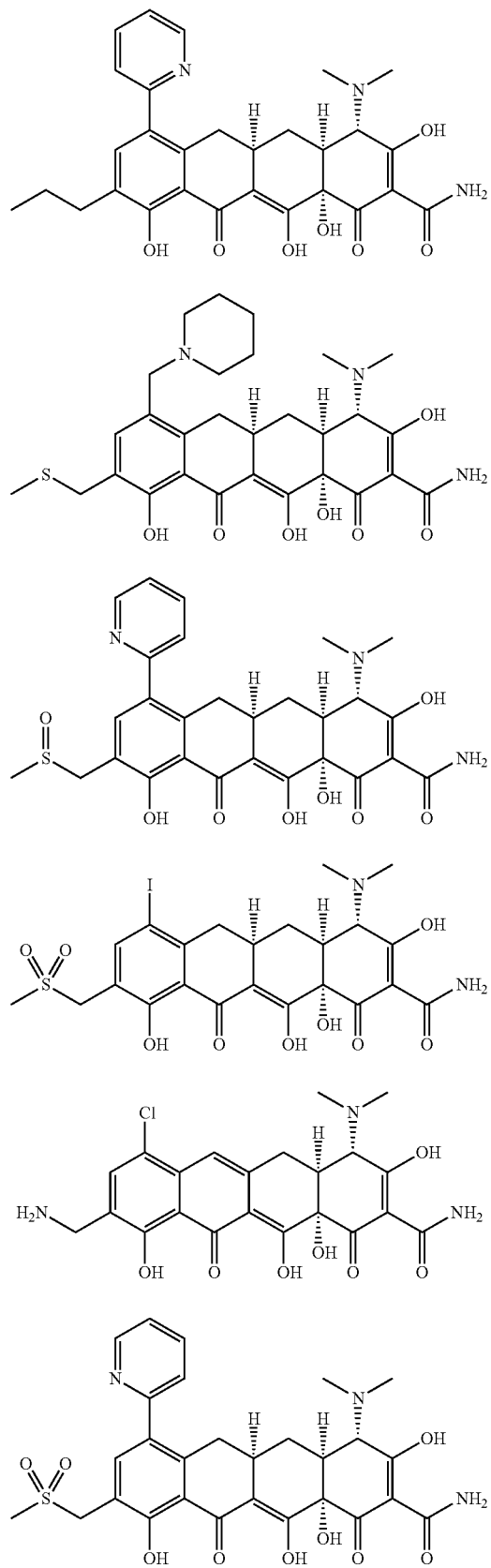

TABLE 1-continued
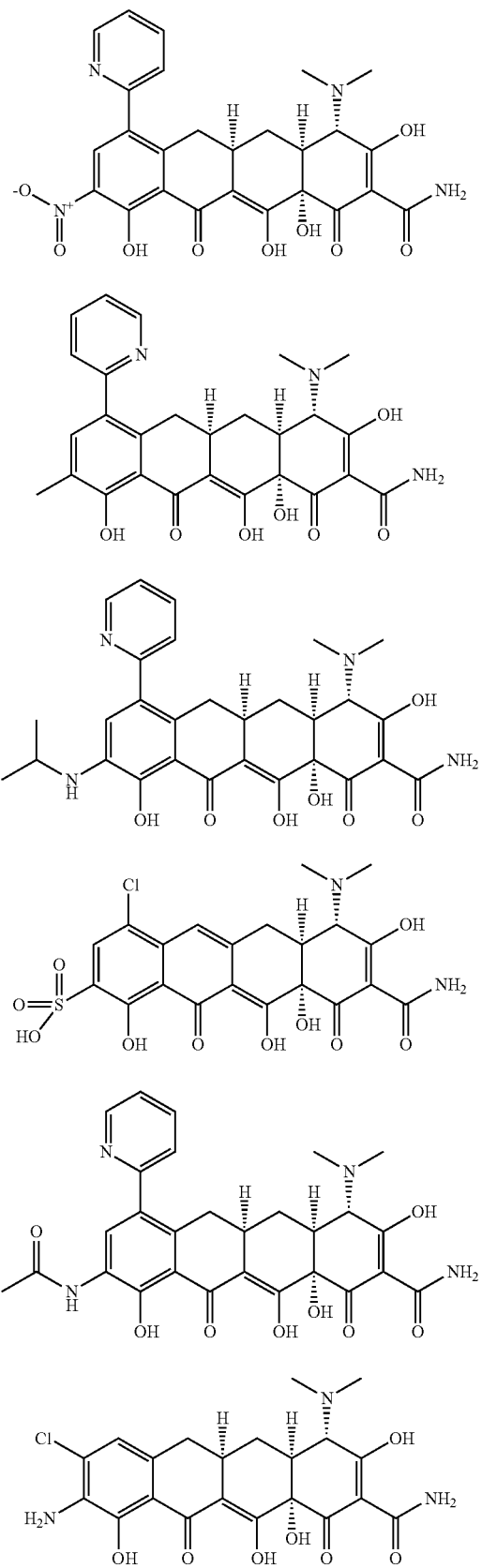

TABLE 1-continued
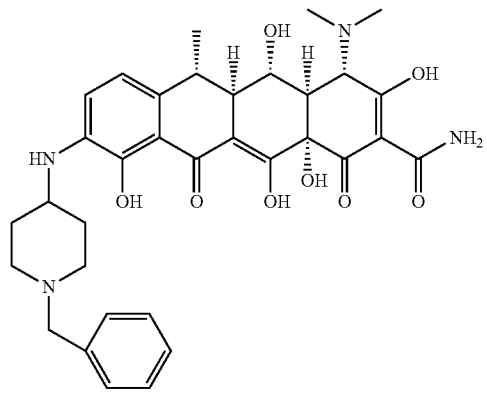
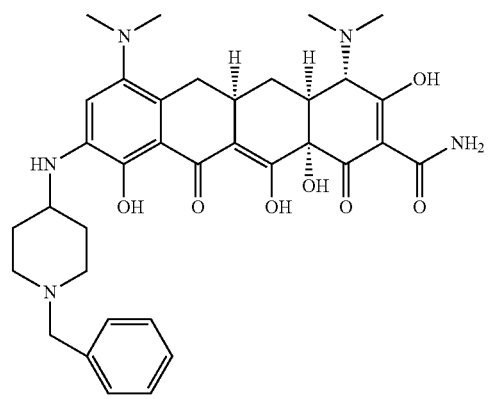
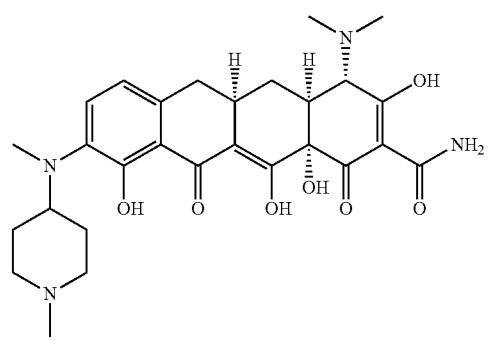
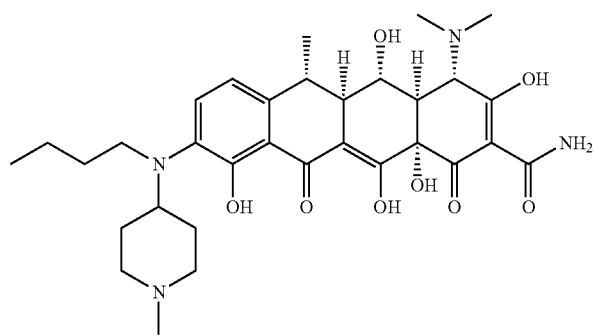

TABLE 1-continued
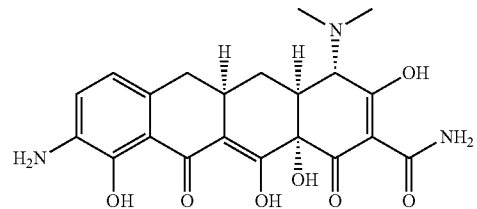
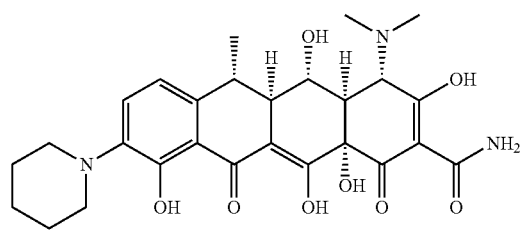
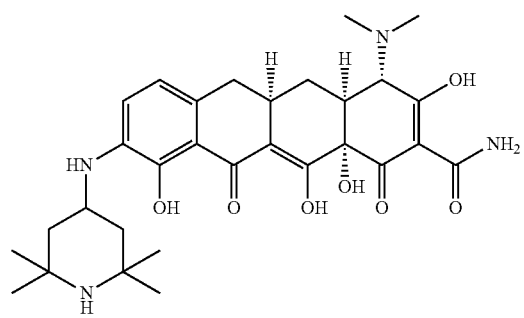
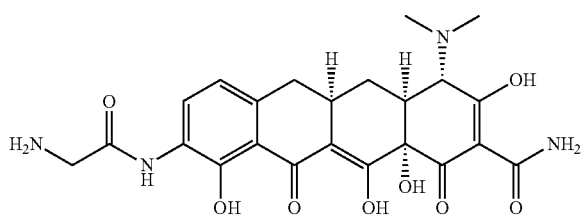
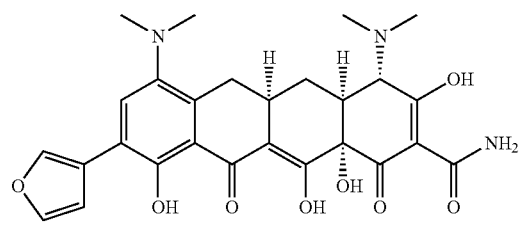
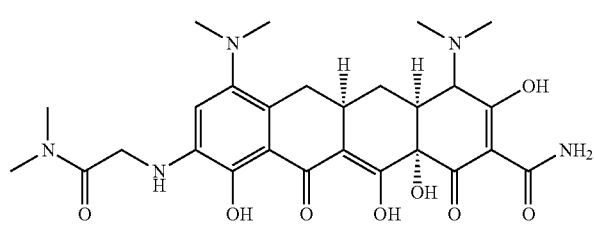

TABLE 1-continued
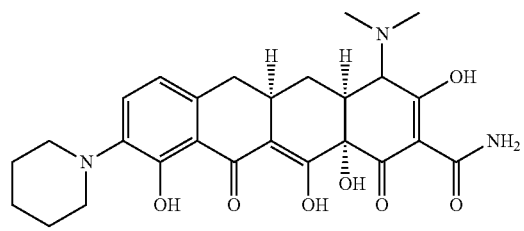
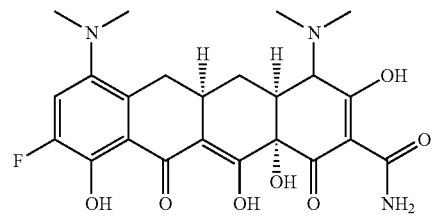
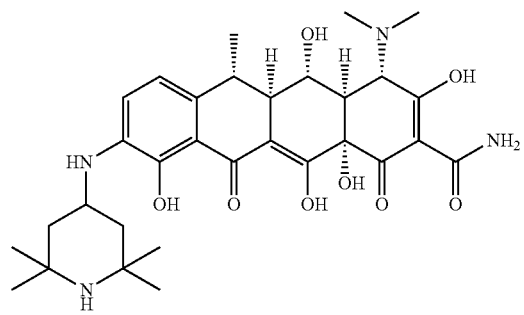
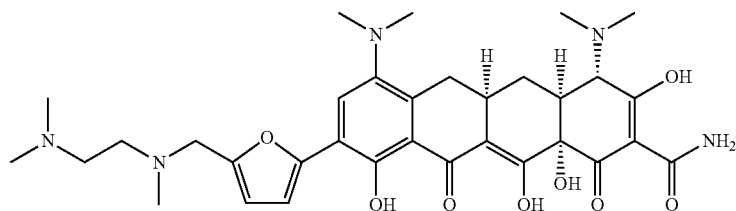
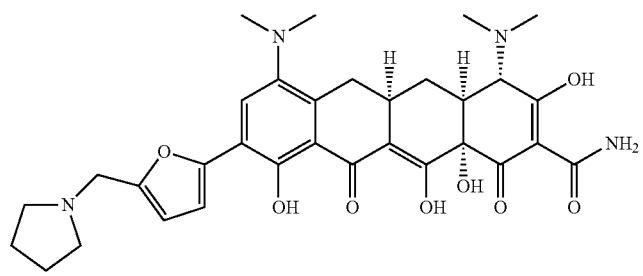
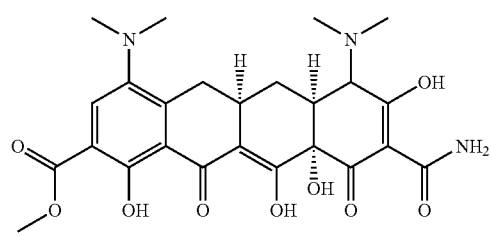

TABLE 1-continued
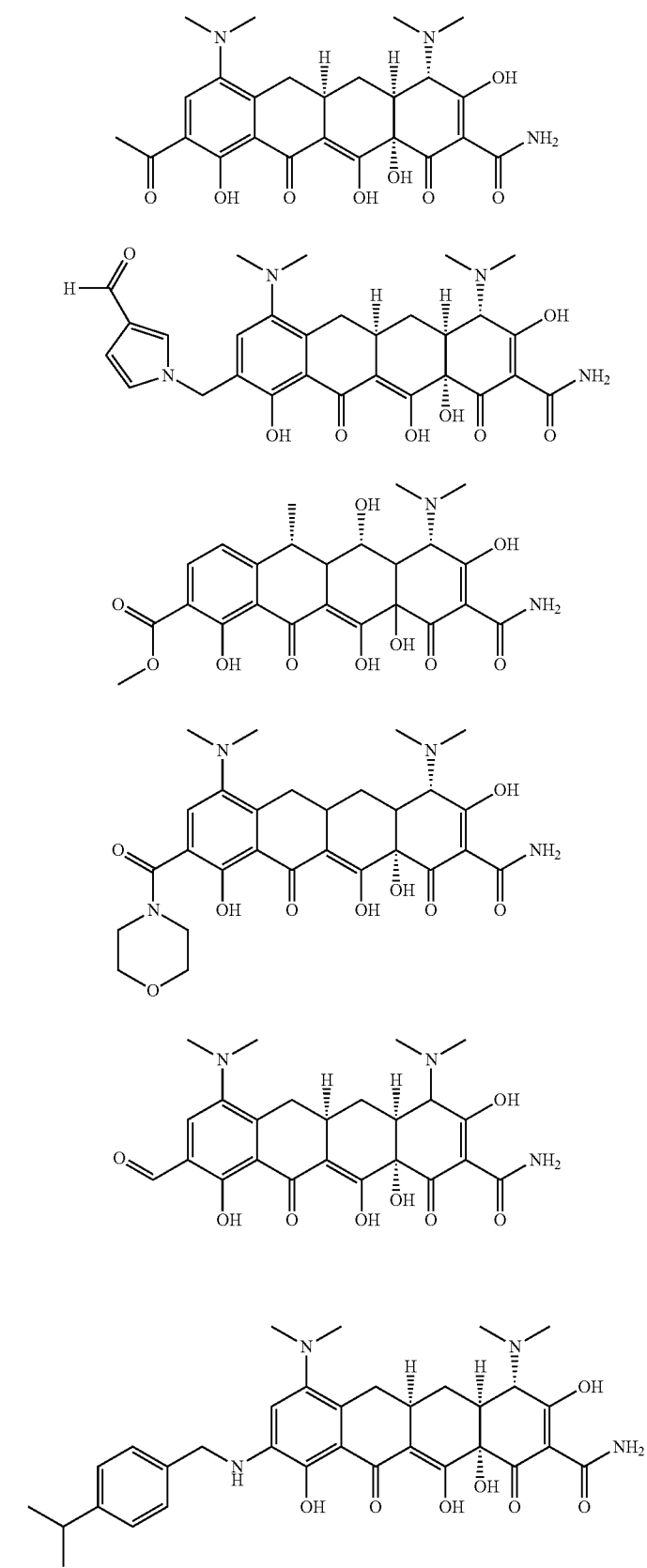

TABLE 1-continued
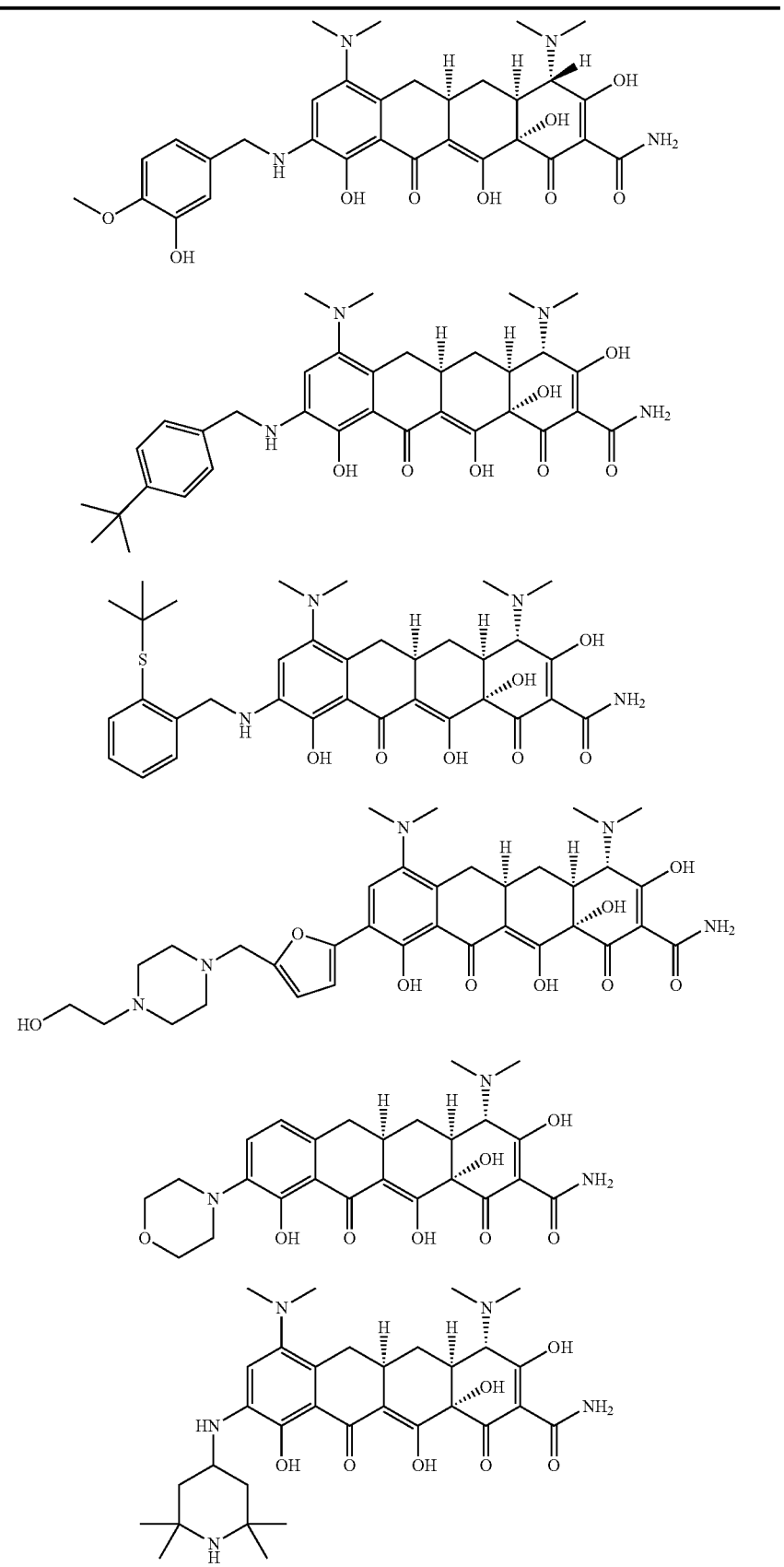

TABLE 1-continued
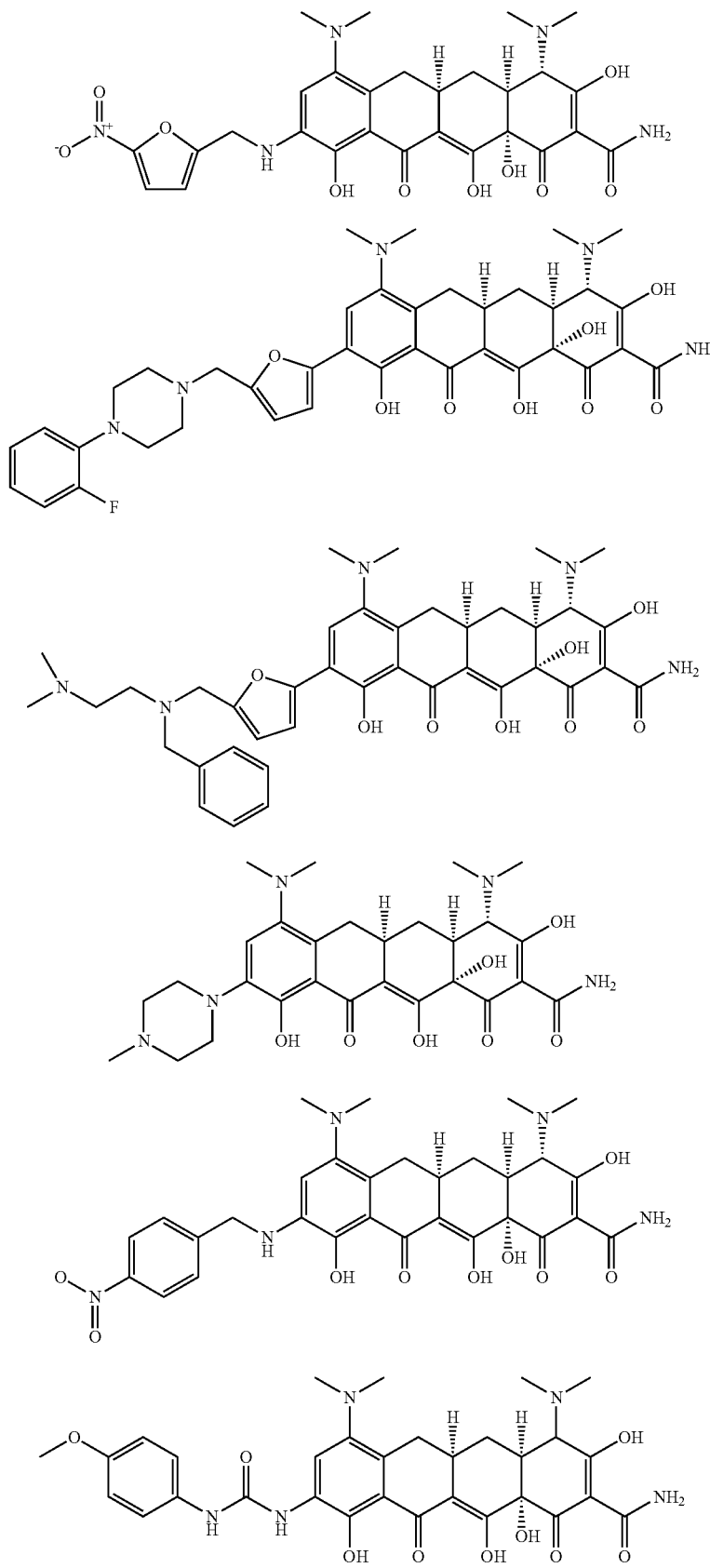

TABLE 1-continued
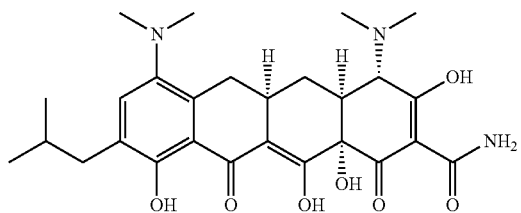
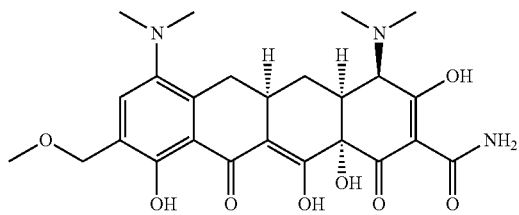
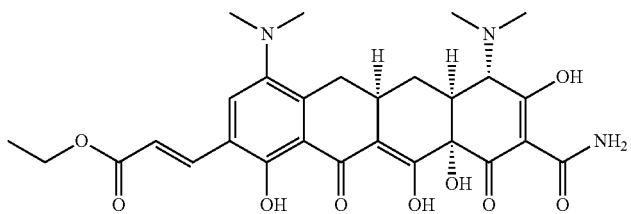
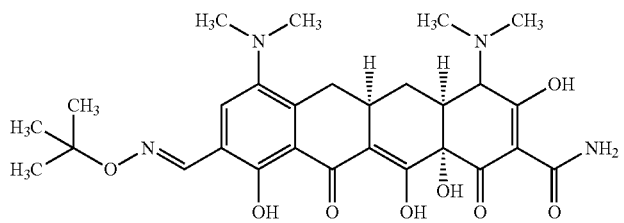
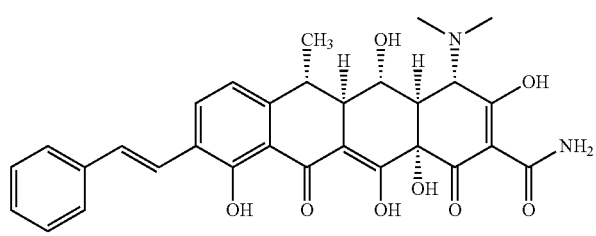
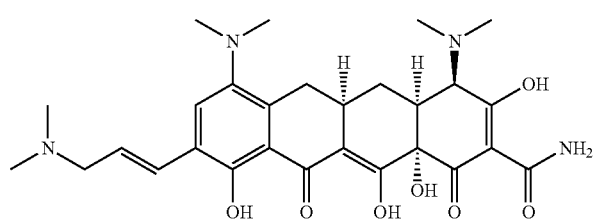
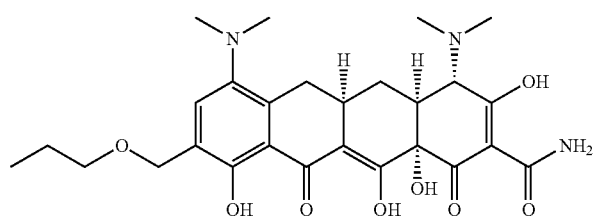

TABLE 1-continued
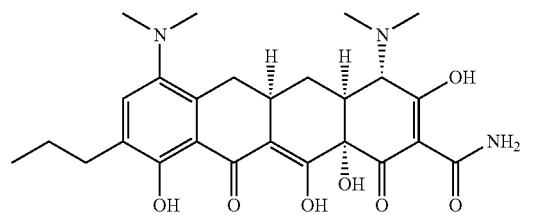
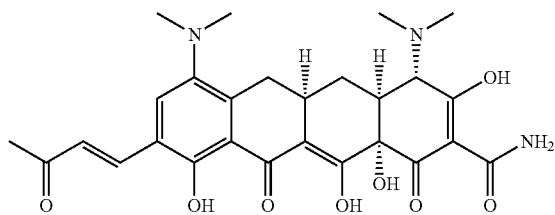
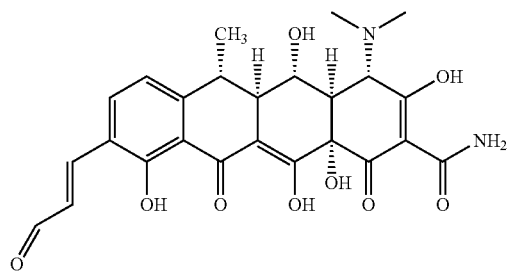
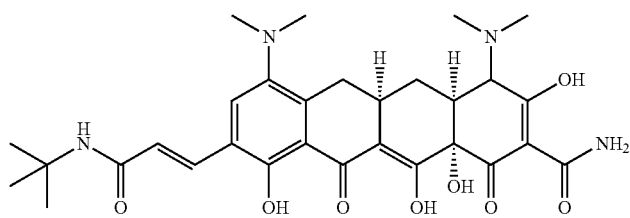
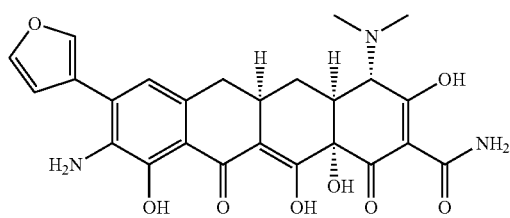
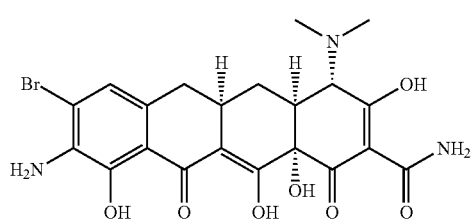
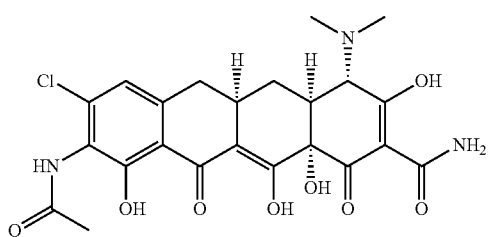

TABLE 1-continued
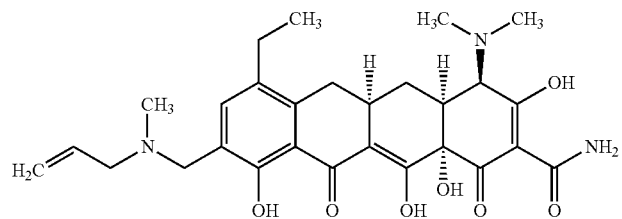
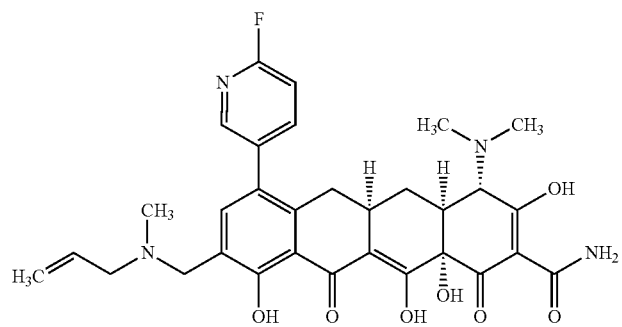
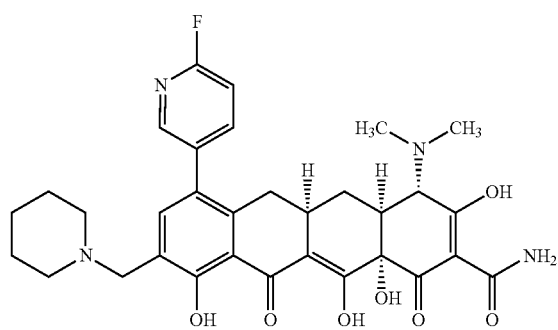
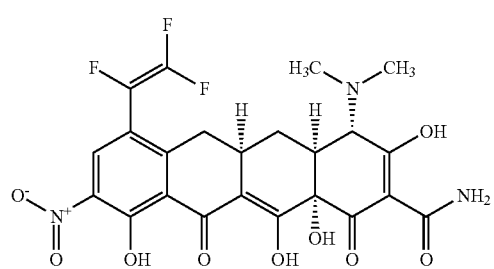
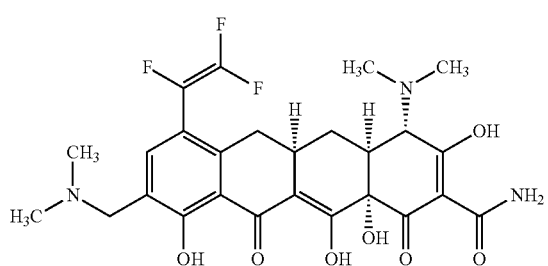

TABLE 1-continued
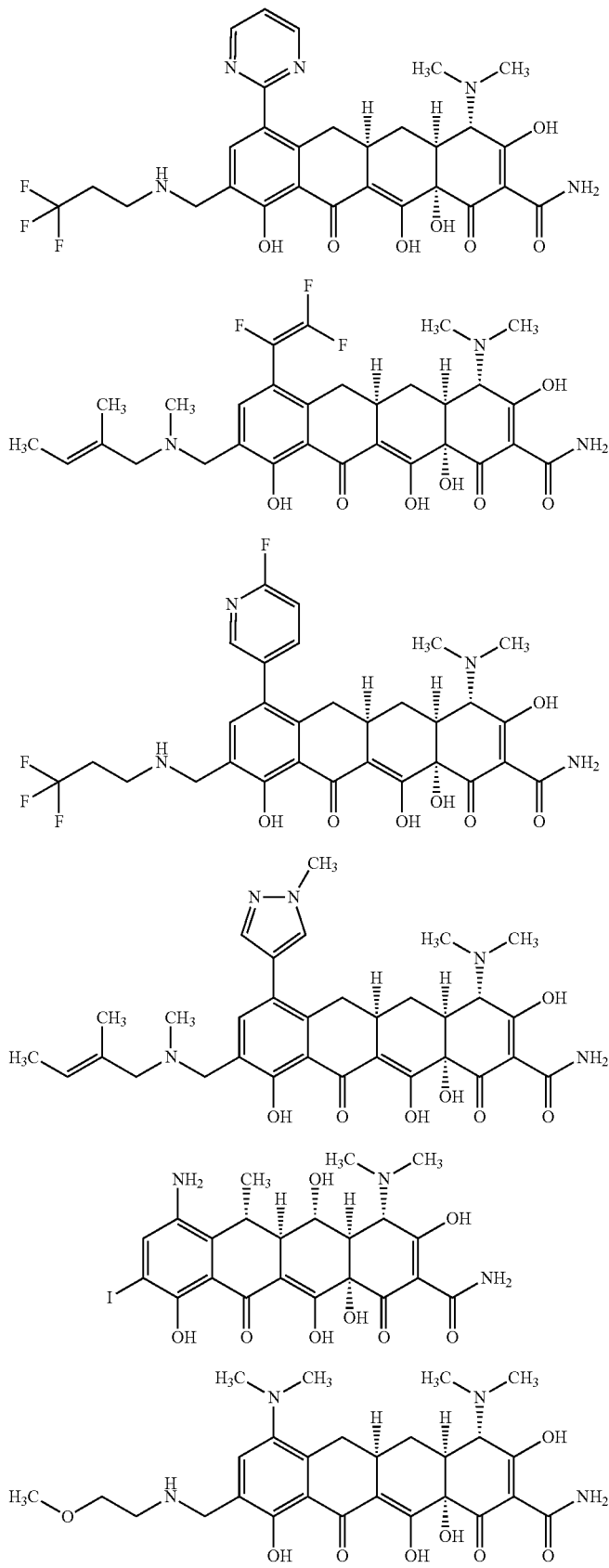

TABLE 1-continued
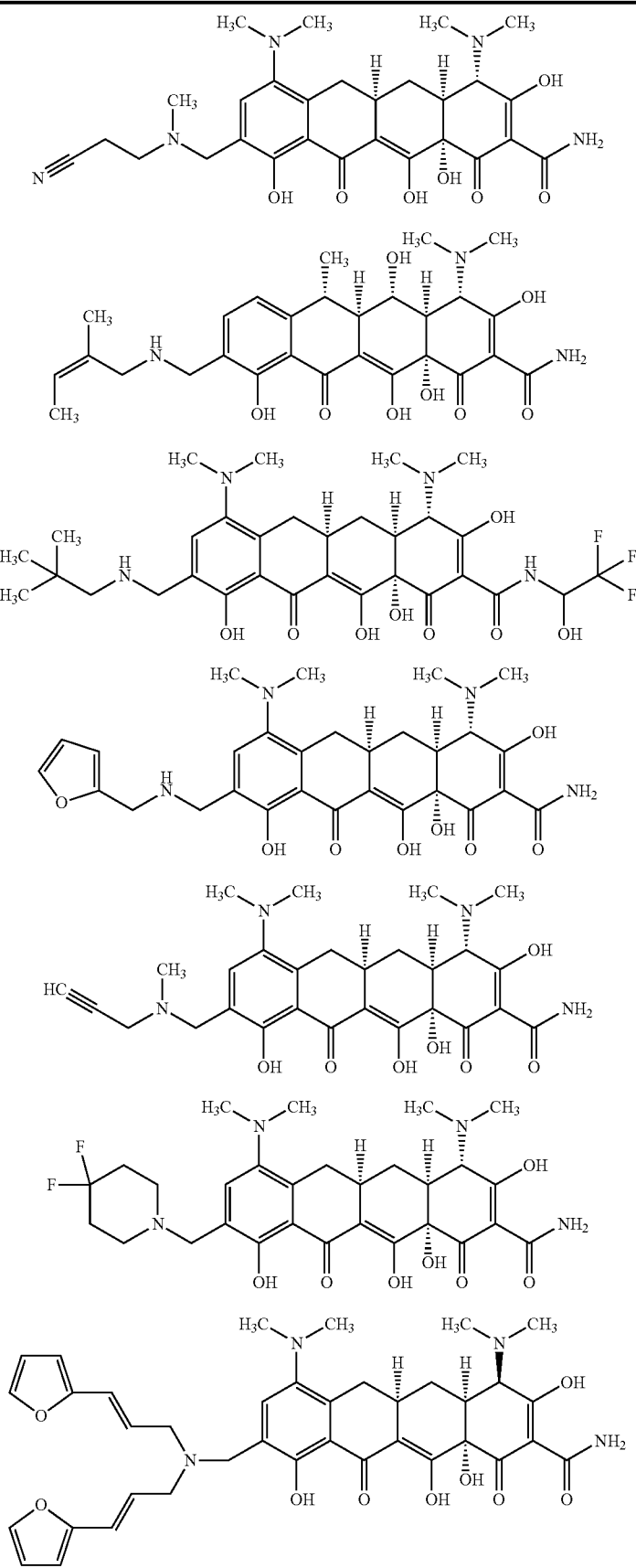

TABLE 1-continued
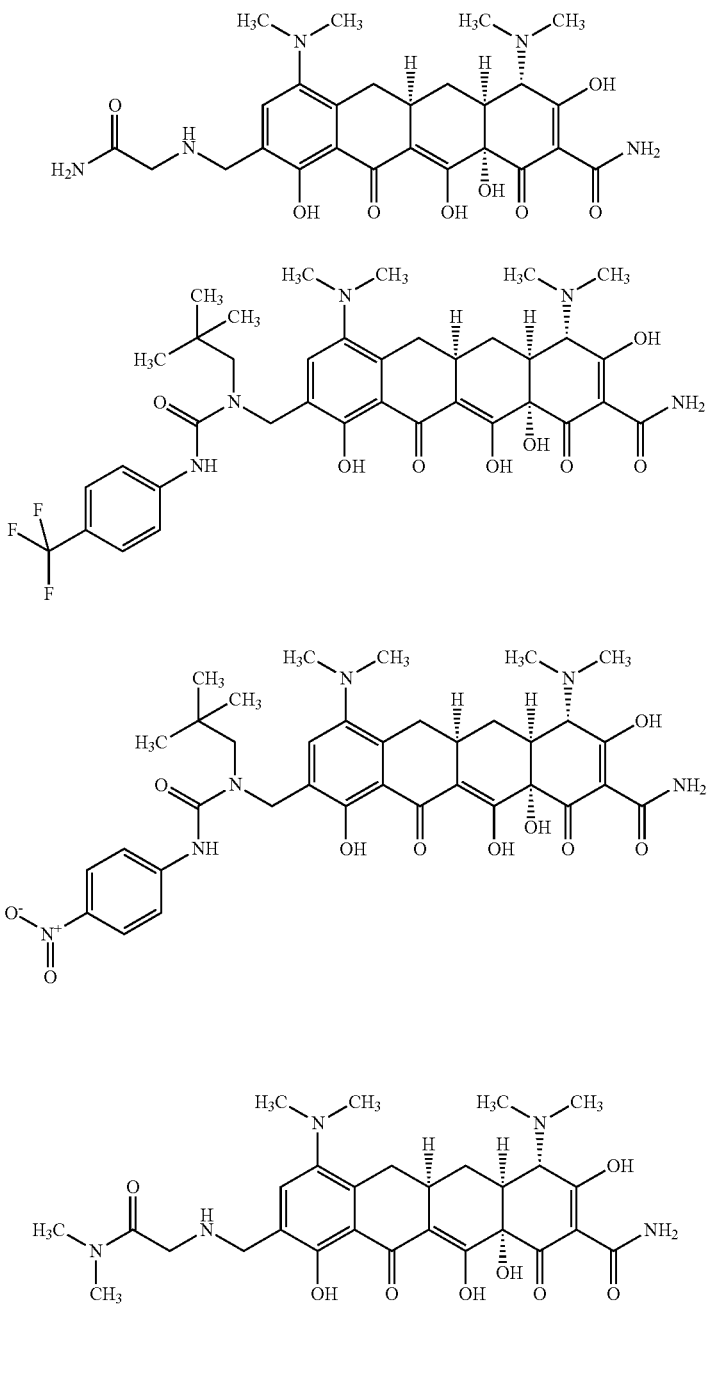
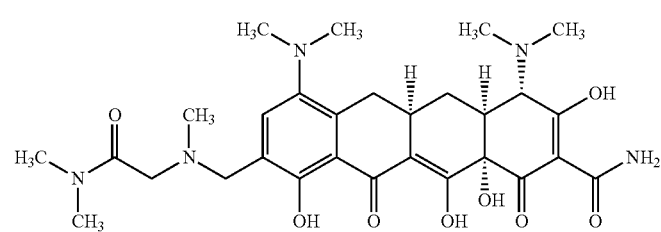

TABLE 1-continued
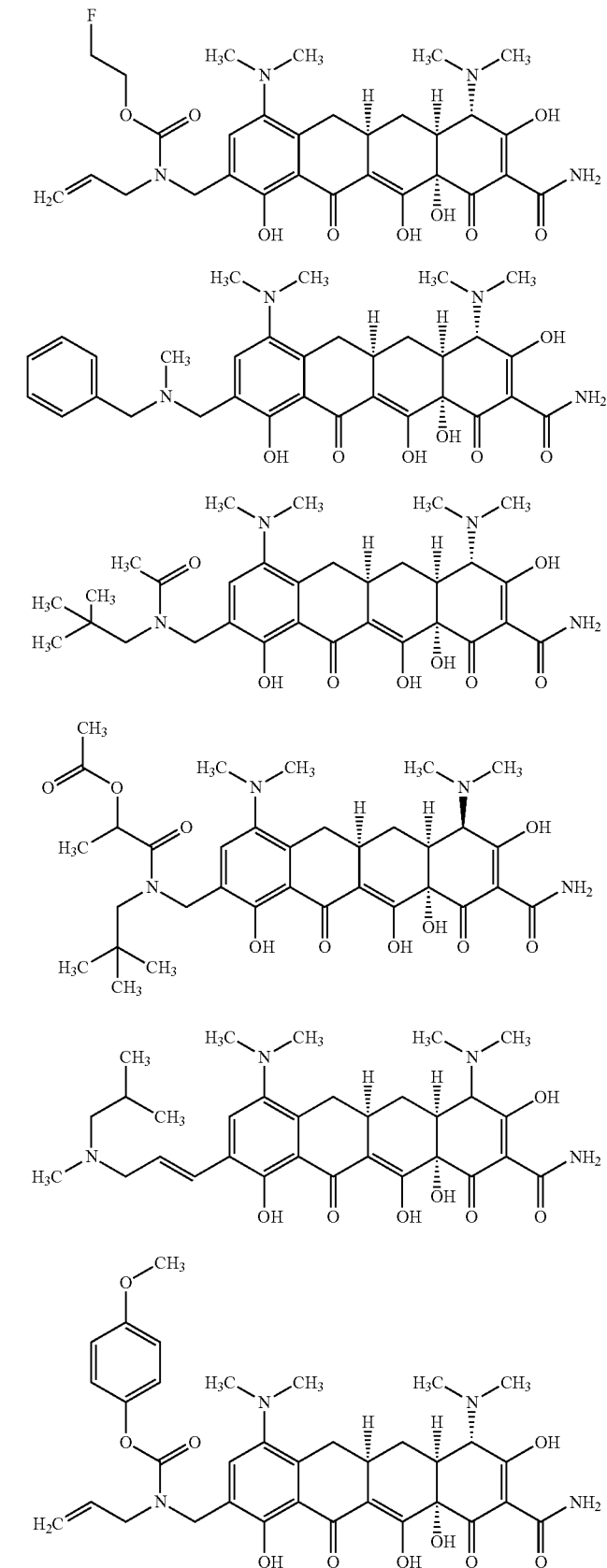

TABLE 1-continued
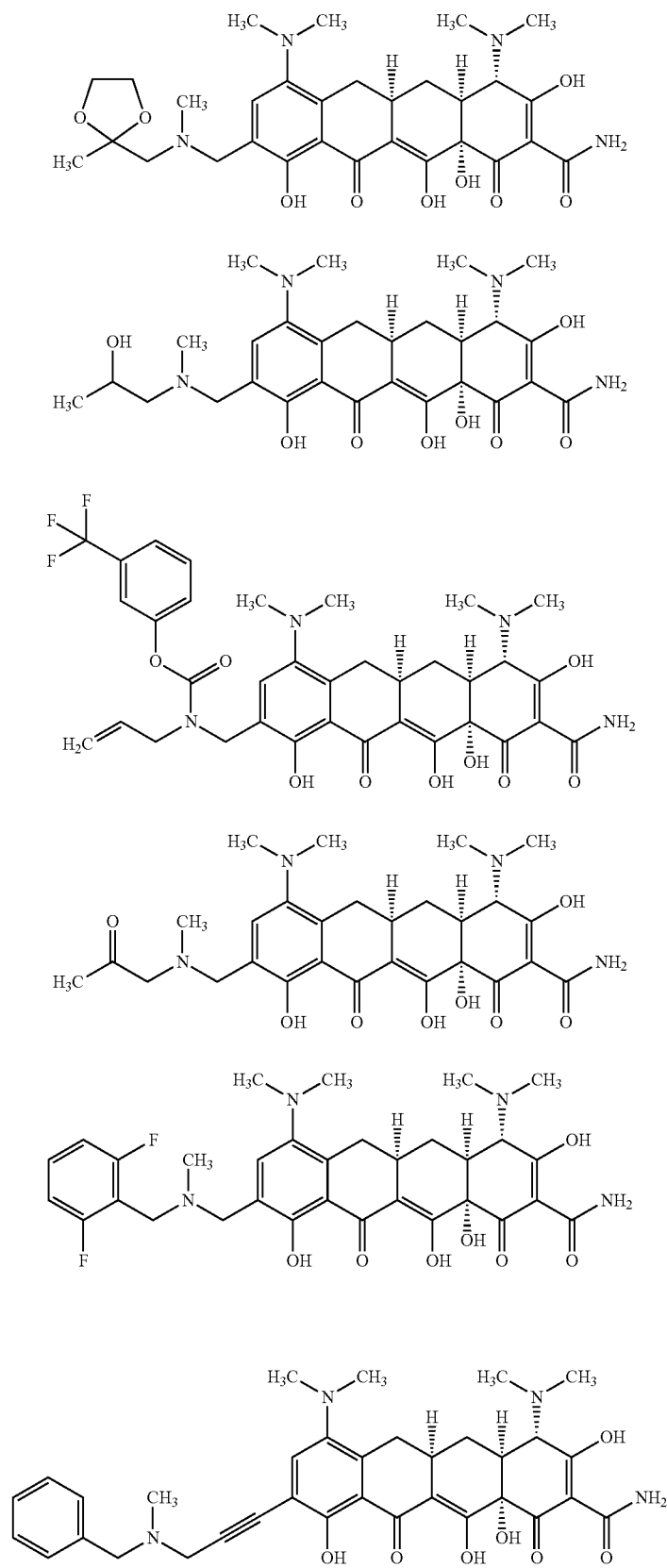

TABLE 1-continued
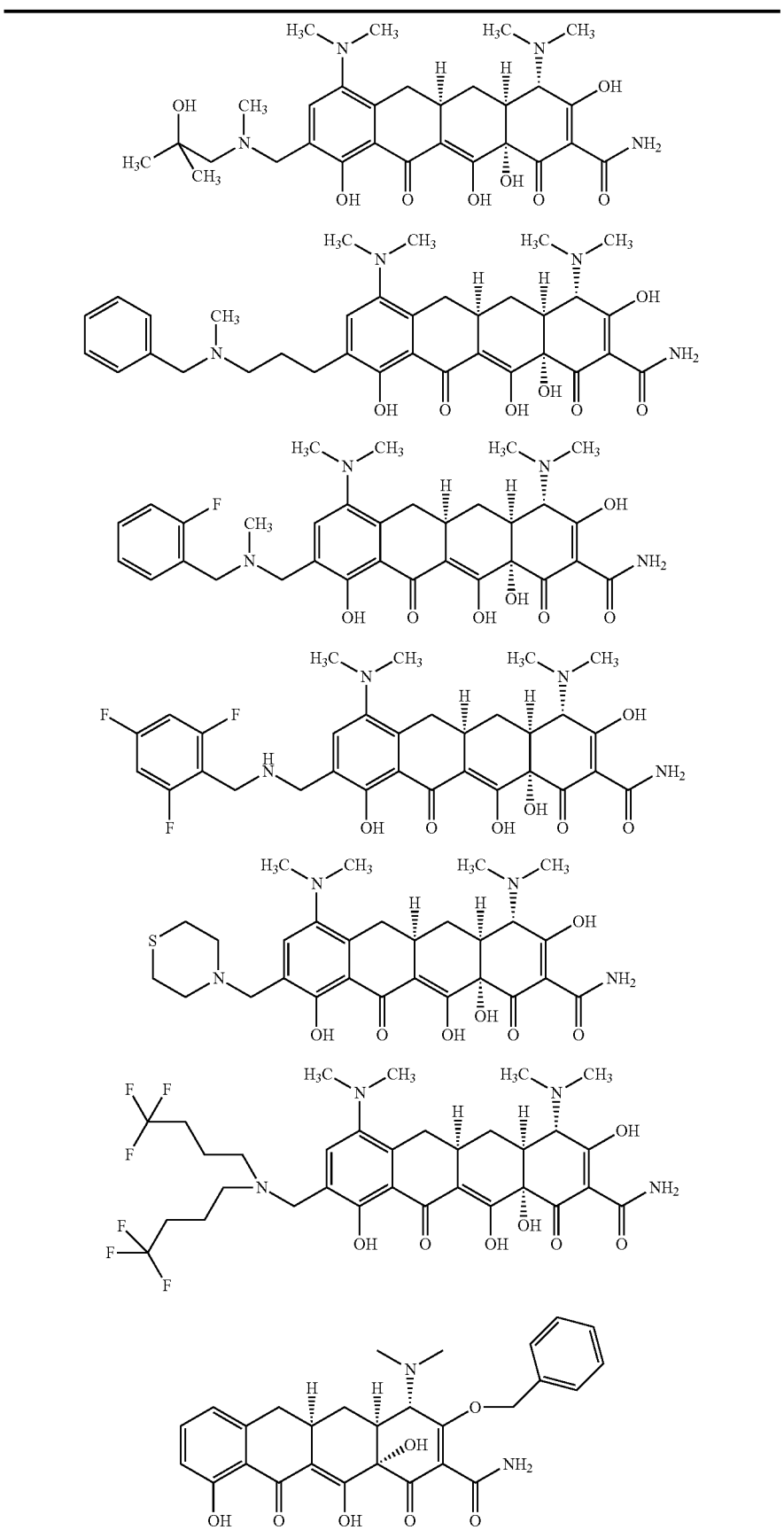

TABLE 1-continued
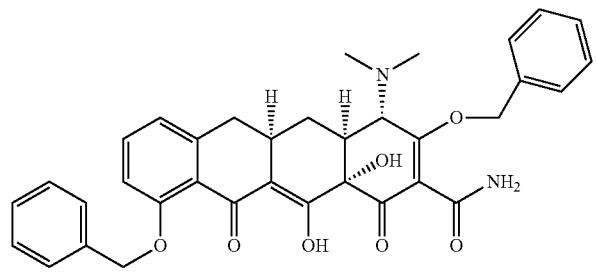
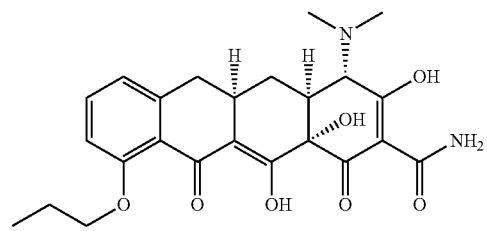
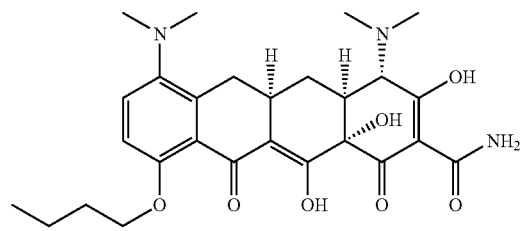
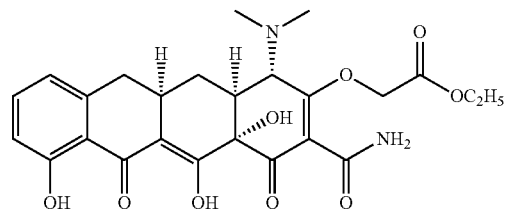
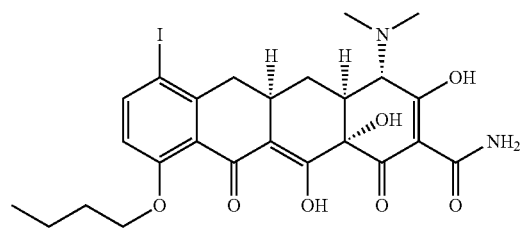
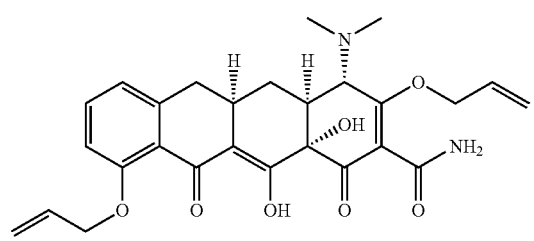

TABLE 1-continued
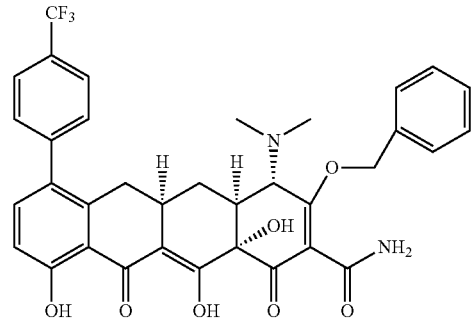
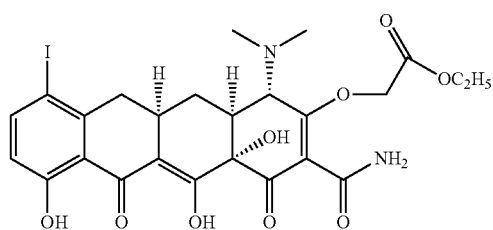
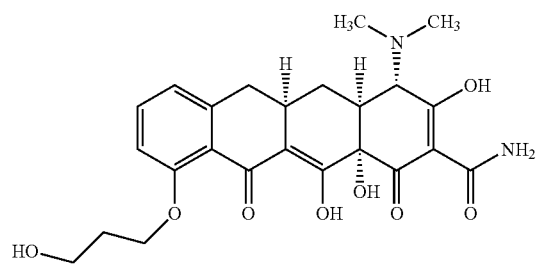
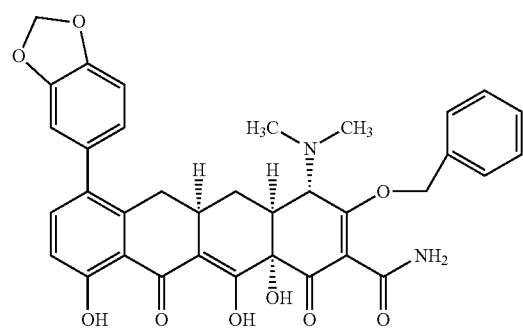
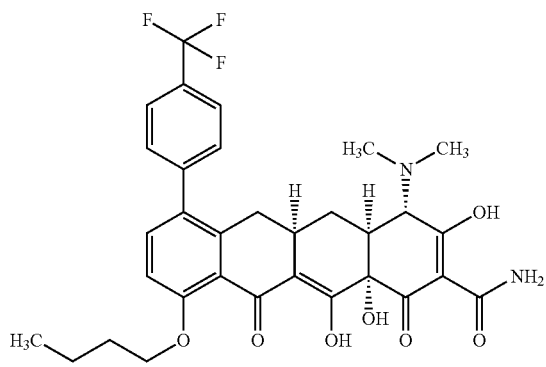

TABLE 1-continued
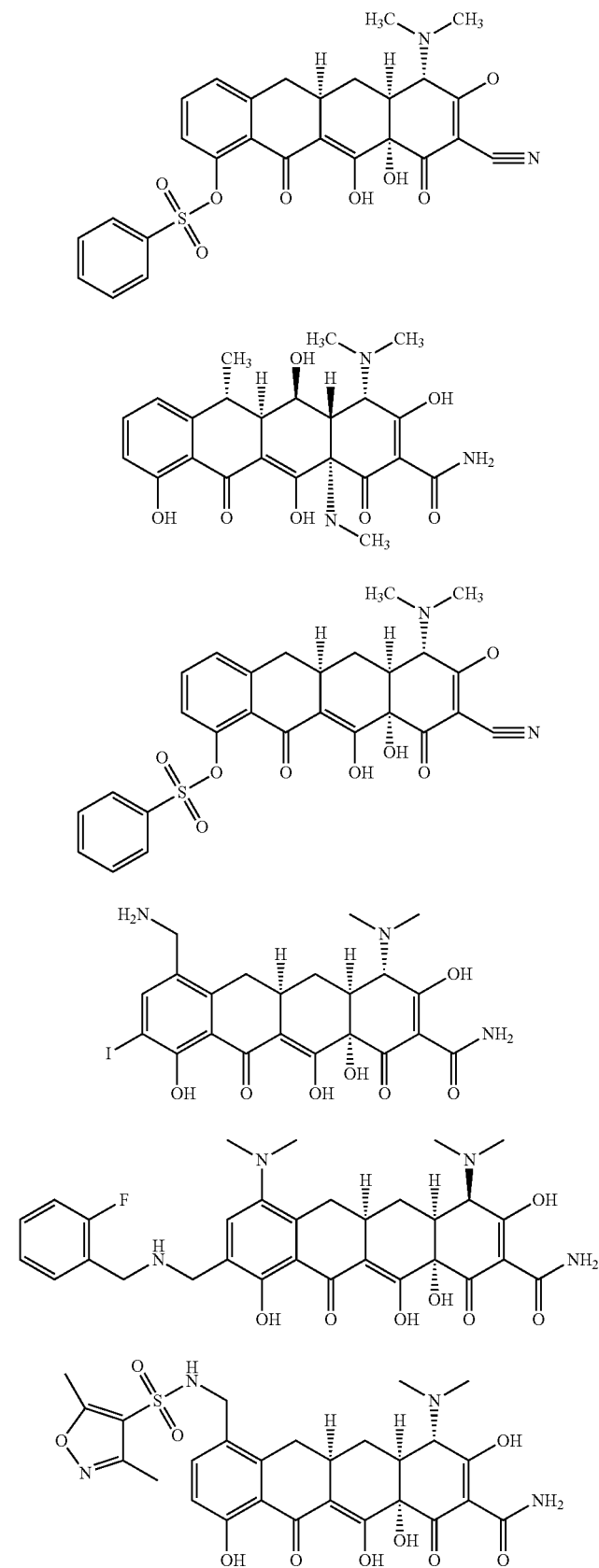

TABLE 1-continued
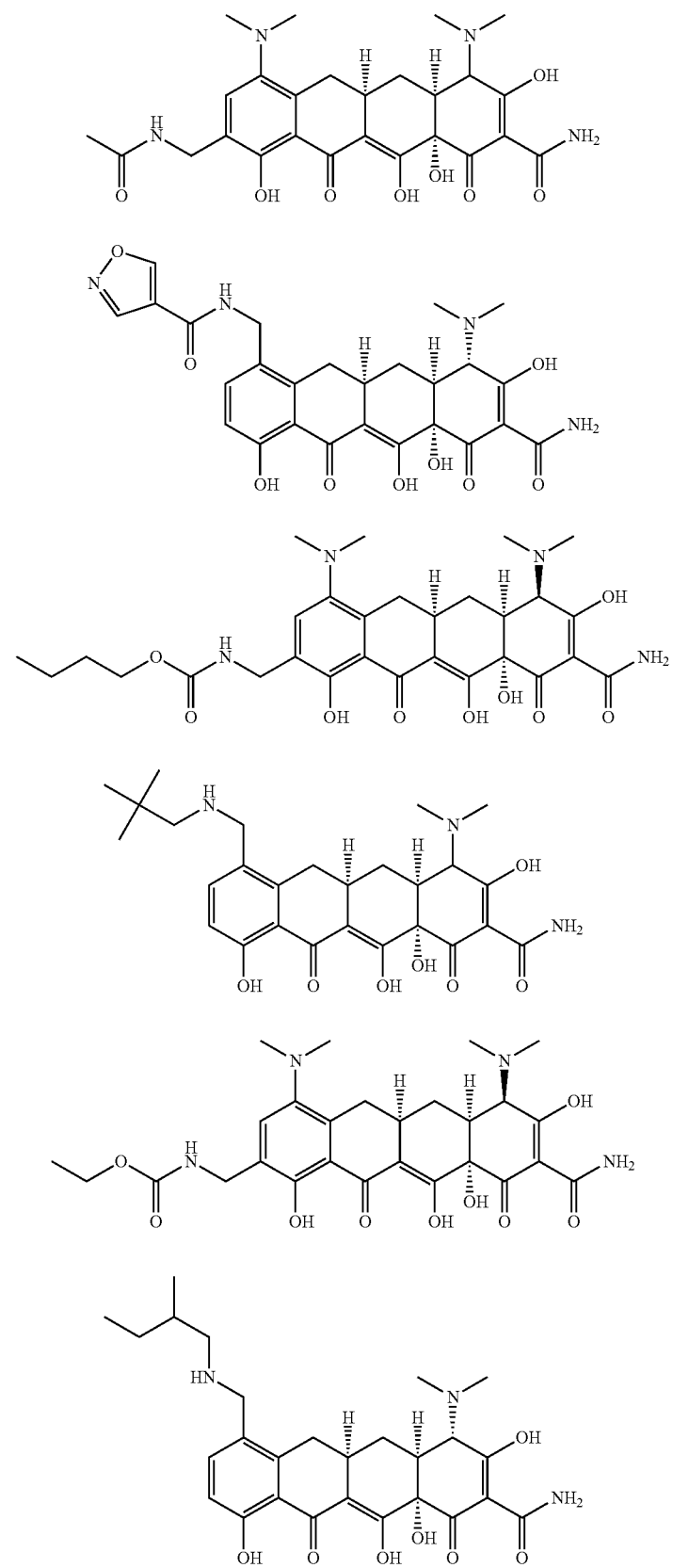

TABLE 1-continued
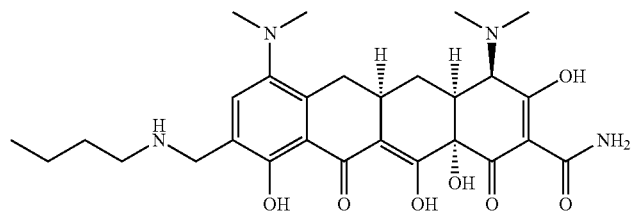
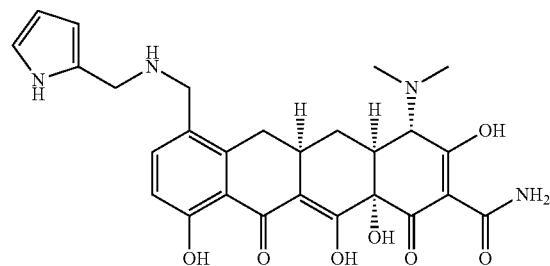
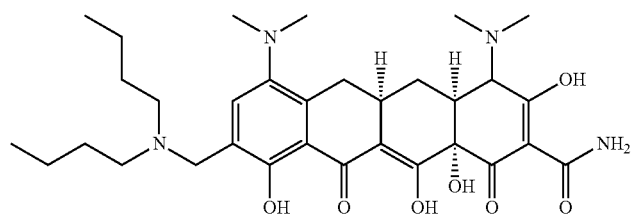
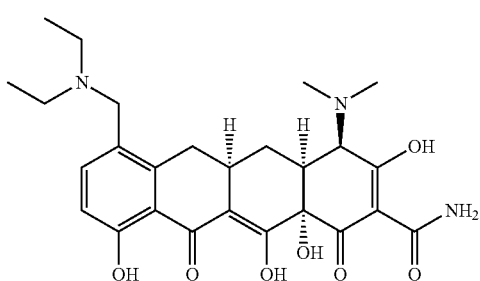
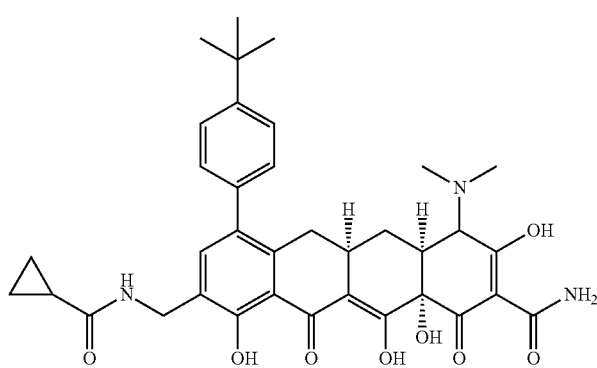

TABLE 1-continued
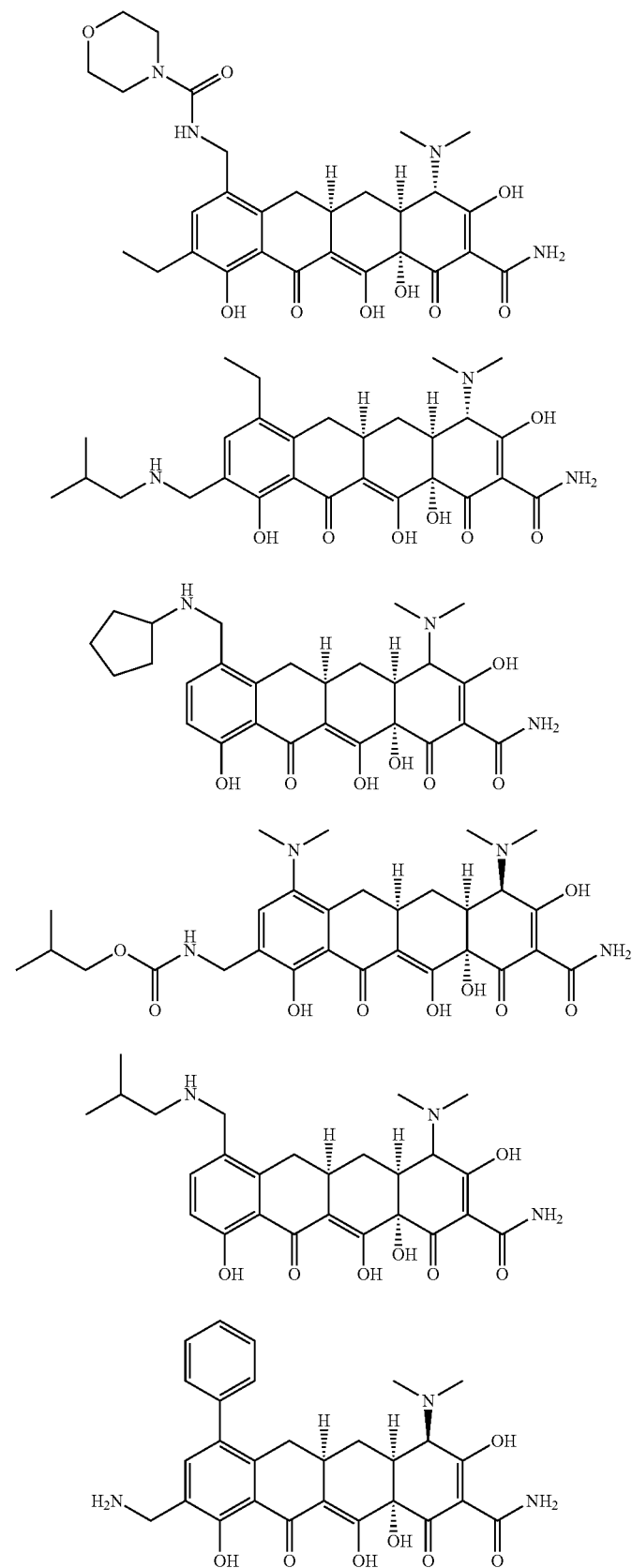

TABLE 1-continued
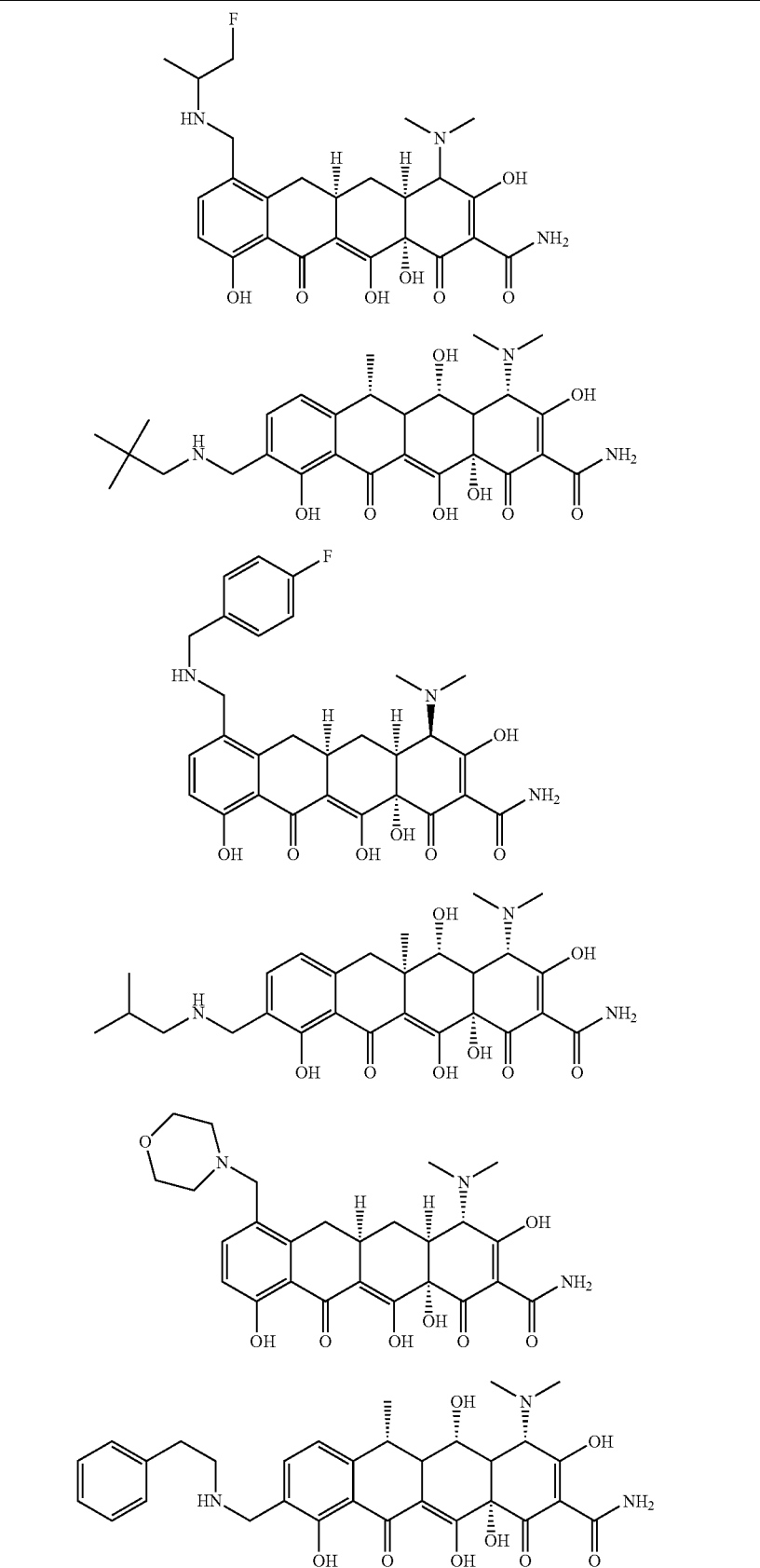

TABLE 1-continued
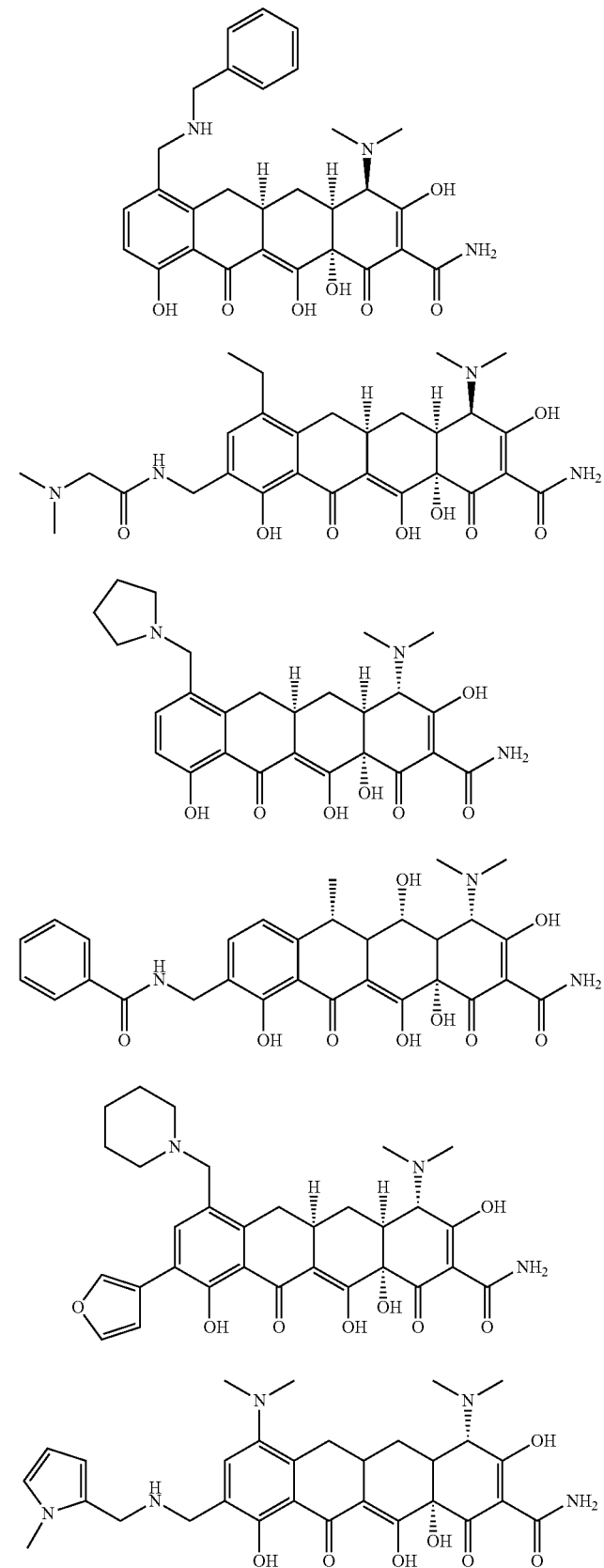

TABLE 1-continued
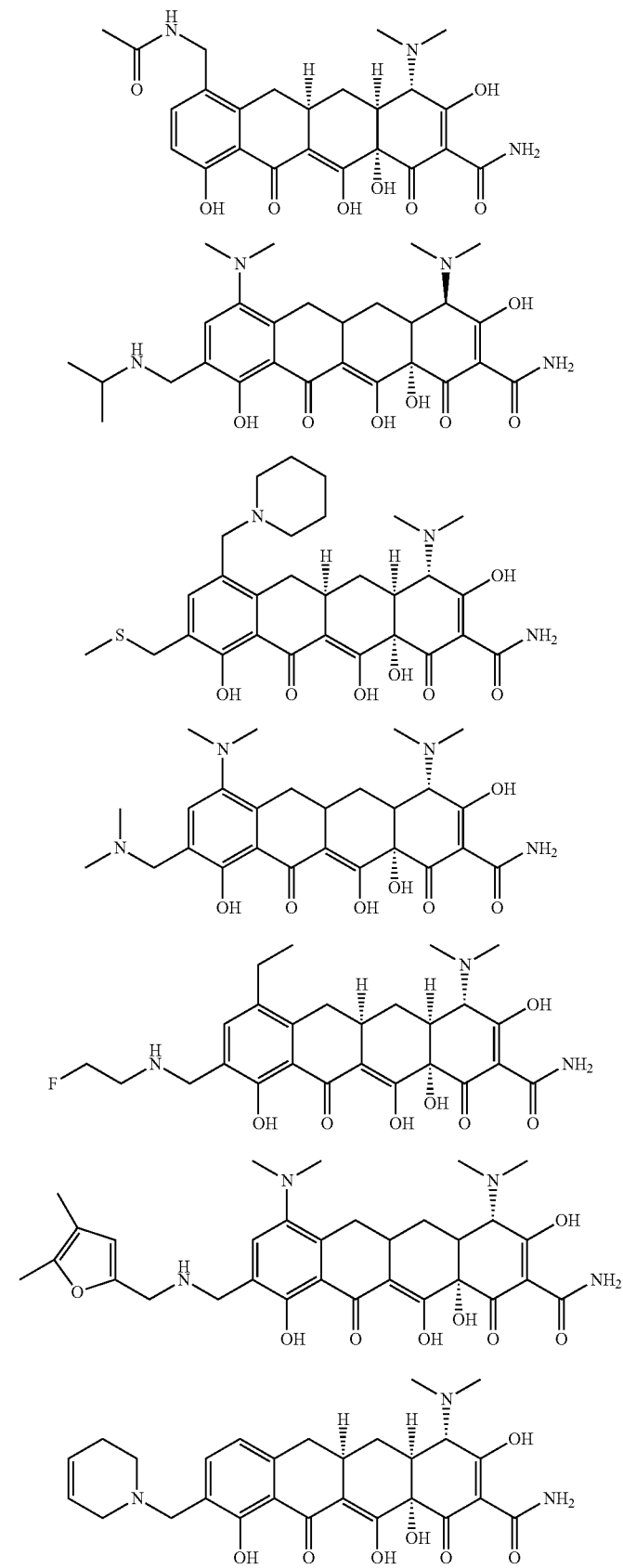

TABLE 1-continued
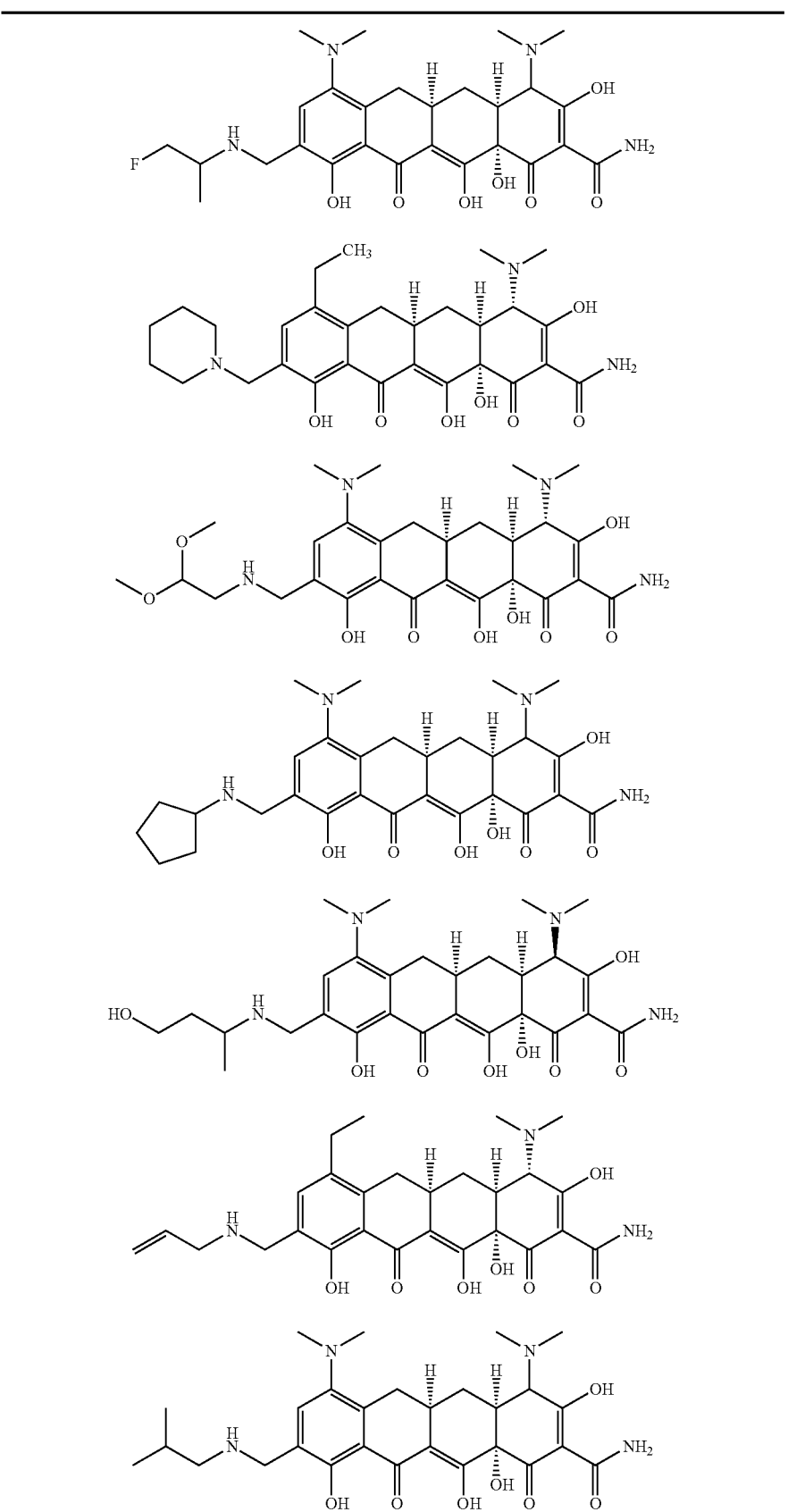

TABLE 1-continued
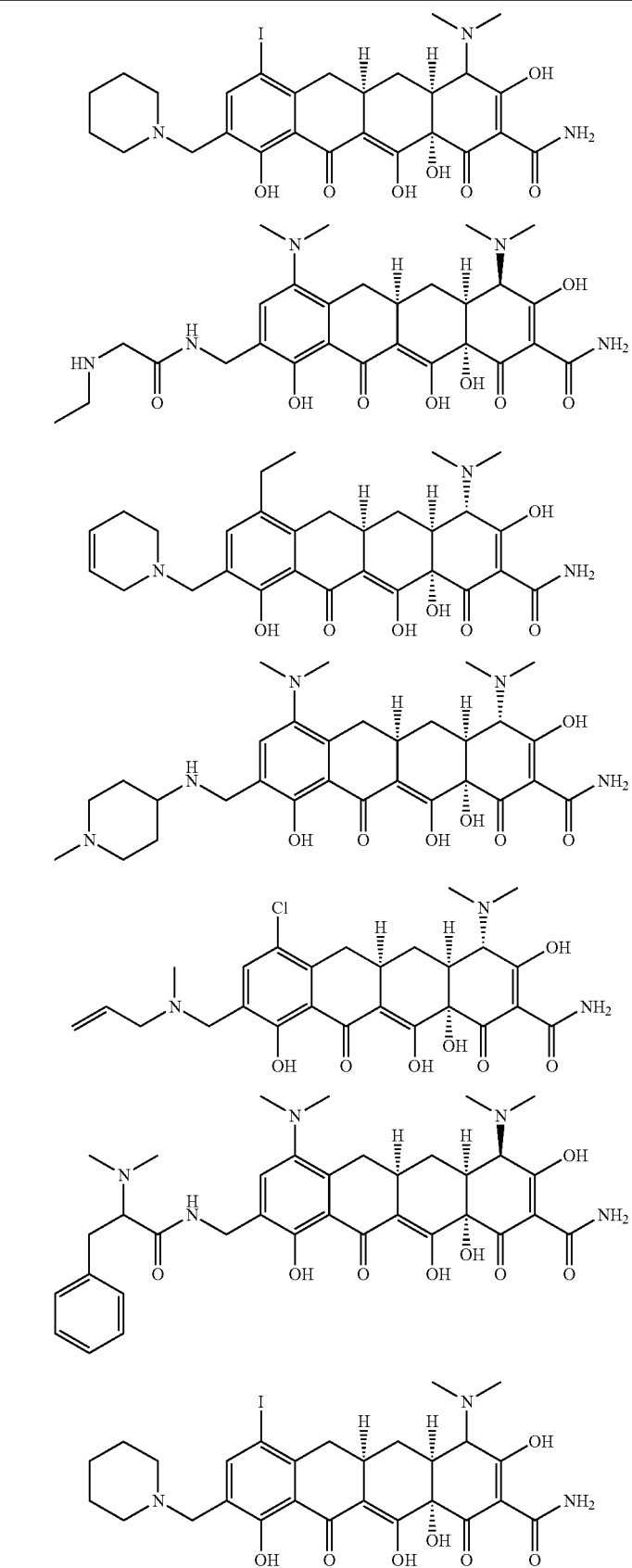

TABLE 1-continued
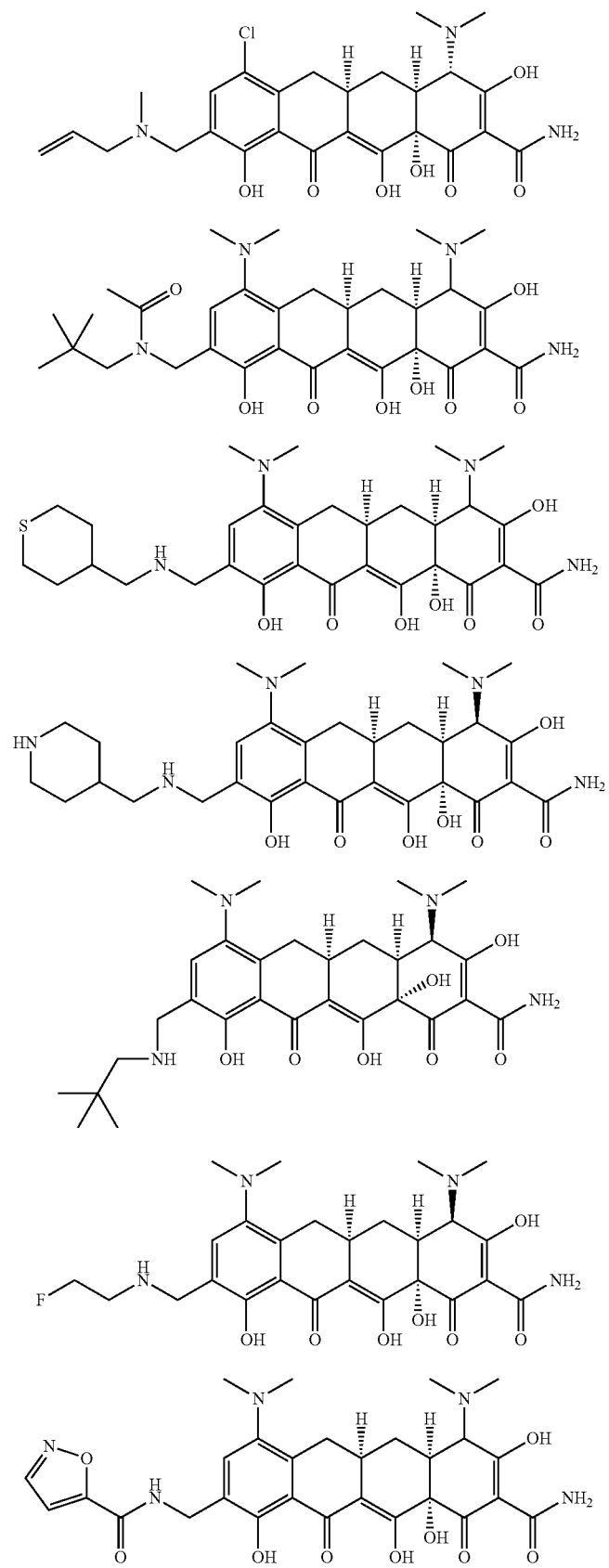

TABLE 1-continued
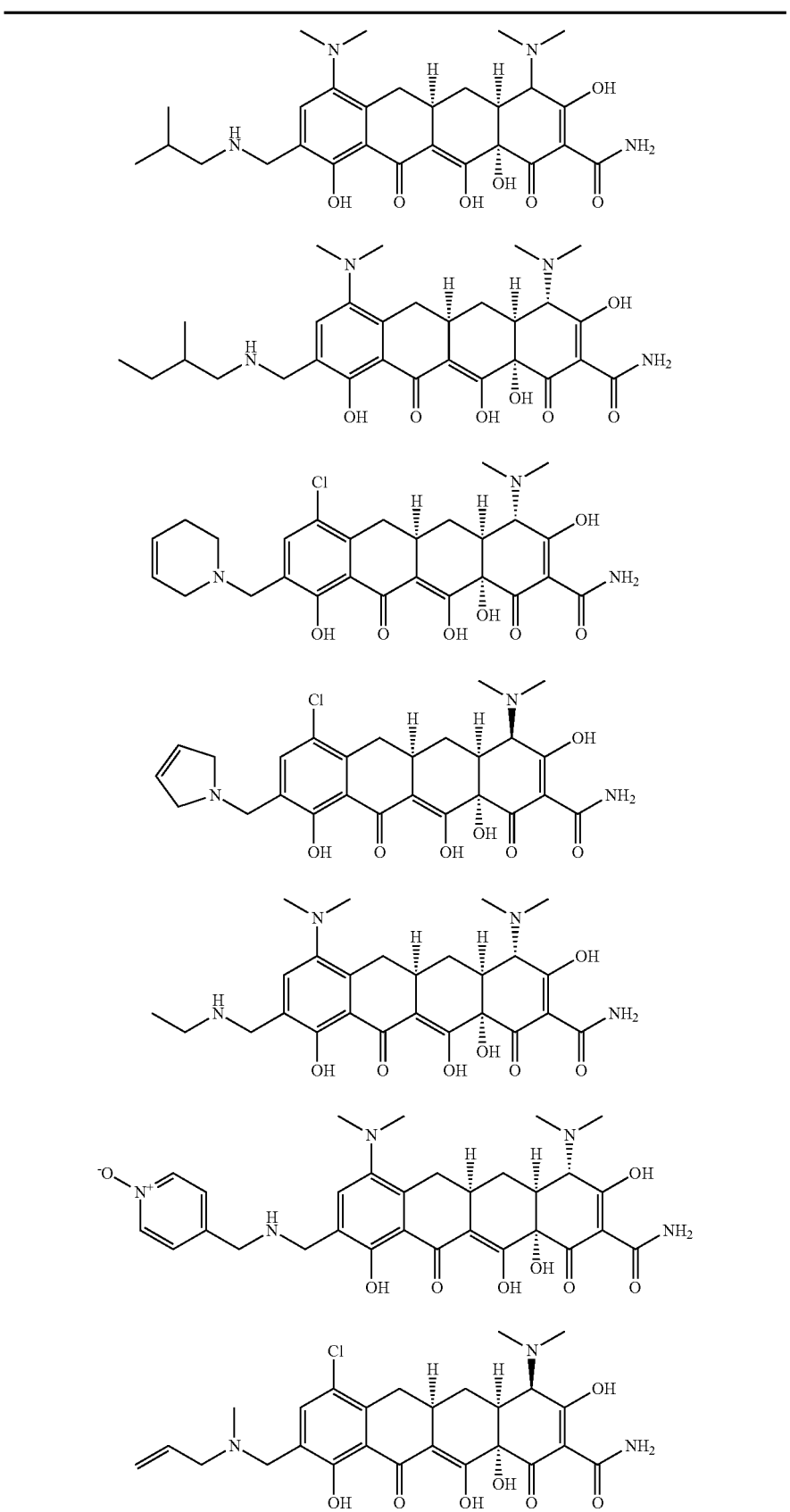

TABLE 1-continued
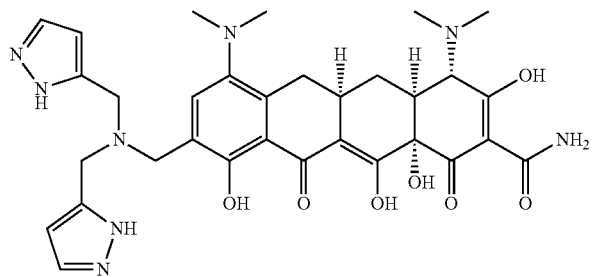
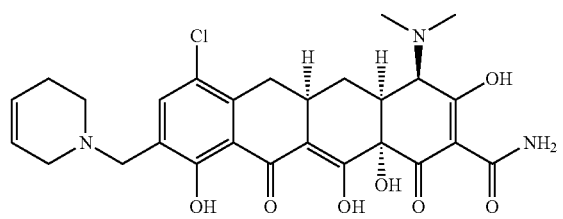
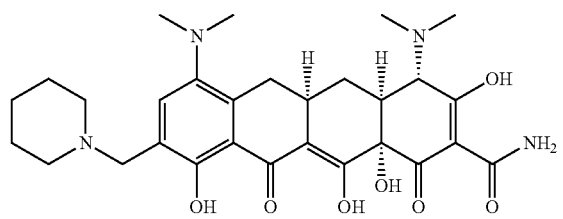
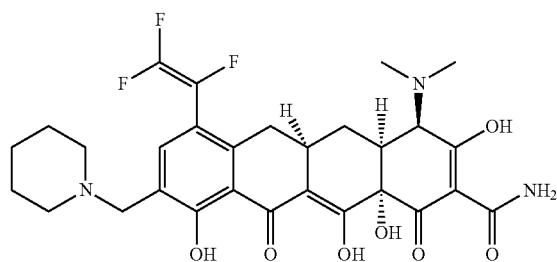
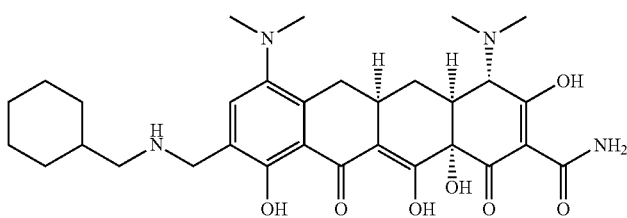
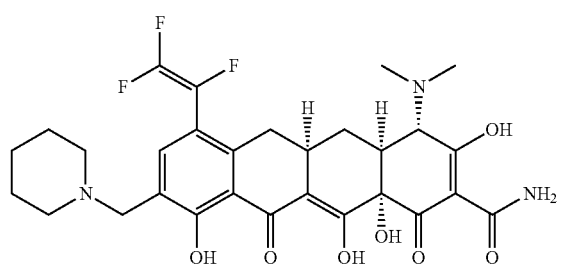

TABLE 1-continued
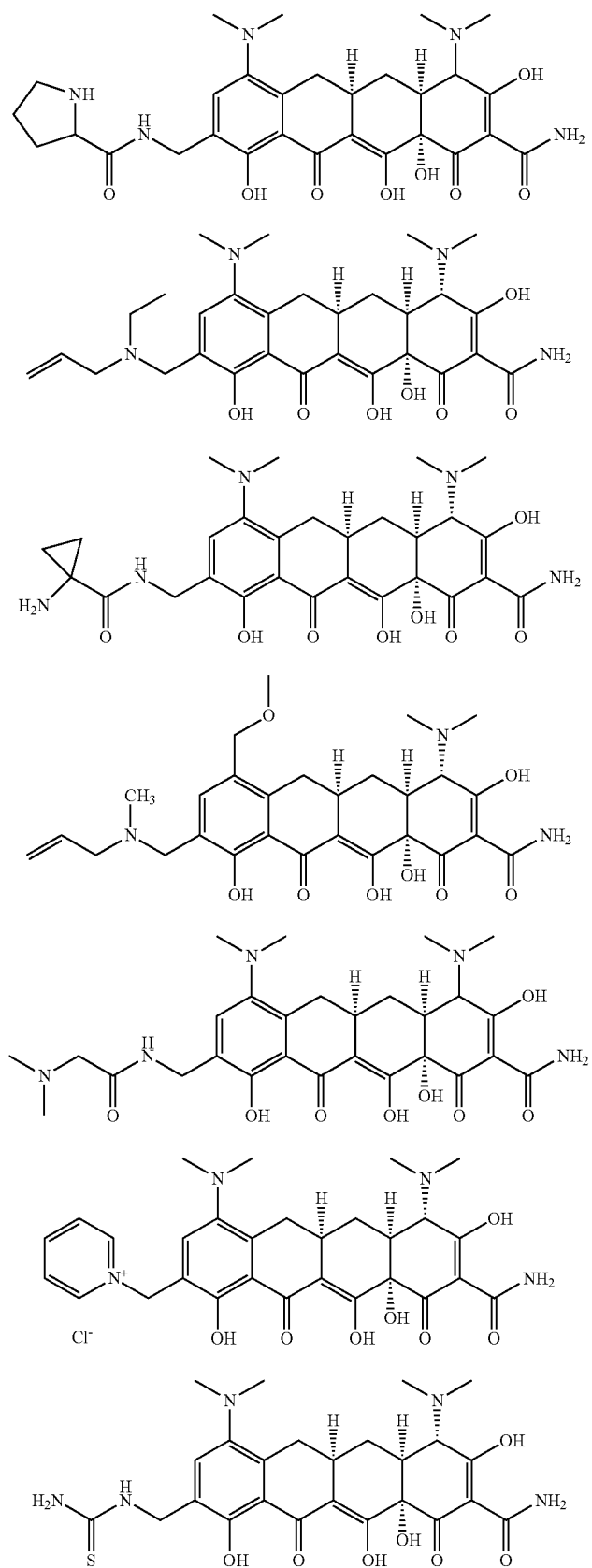

TABLE 1-continued
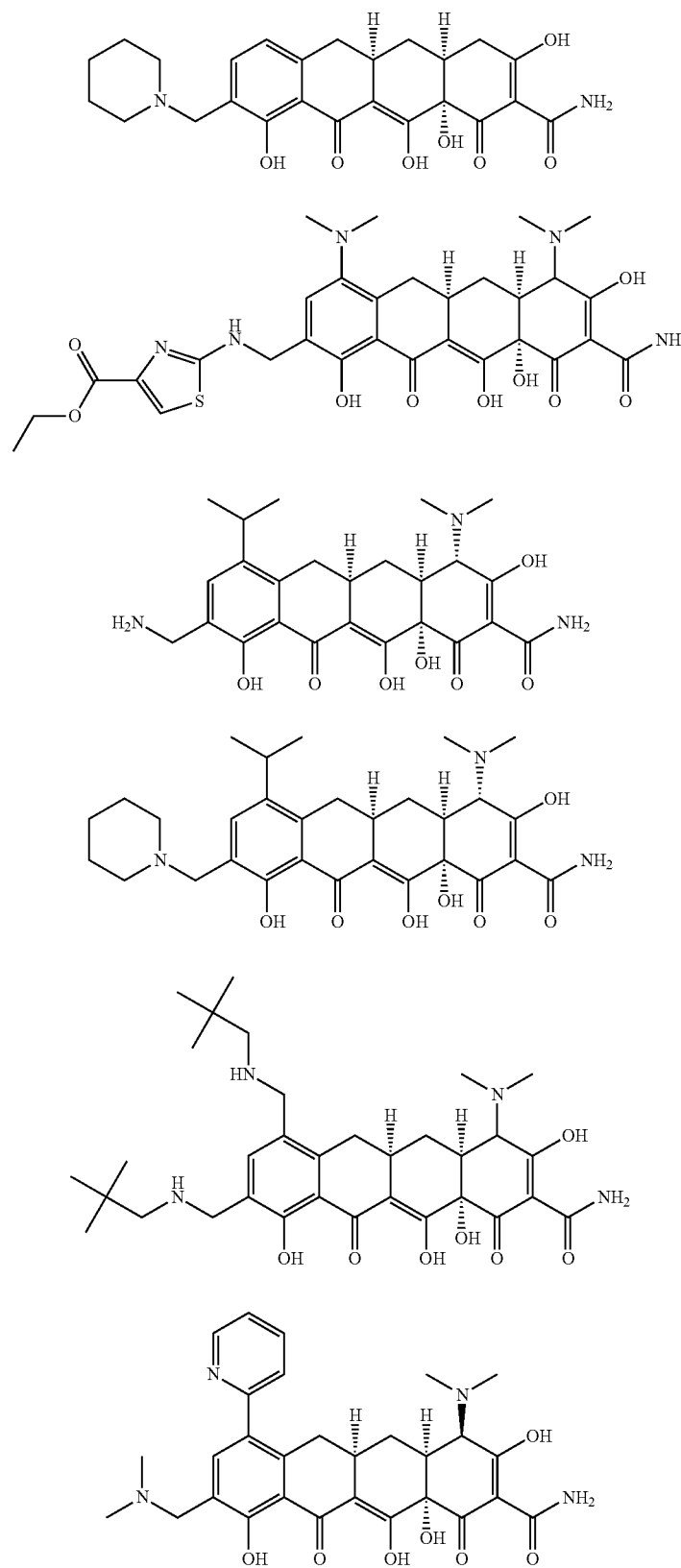

TABLE 1-continued
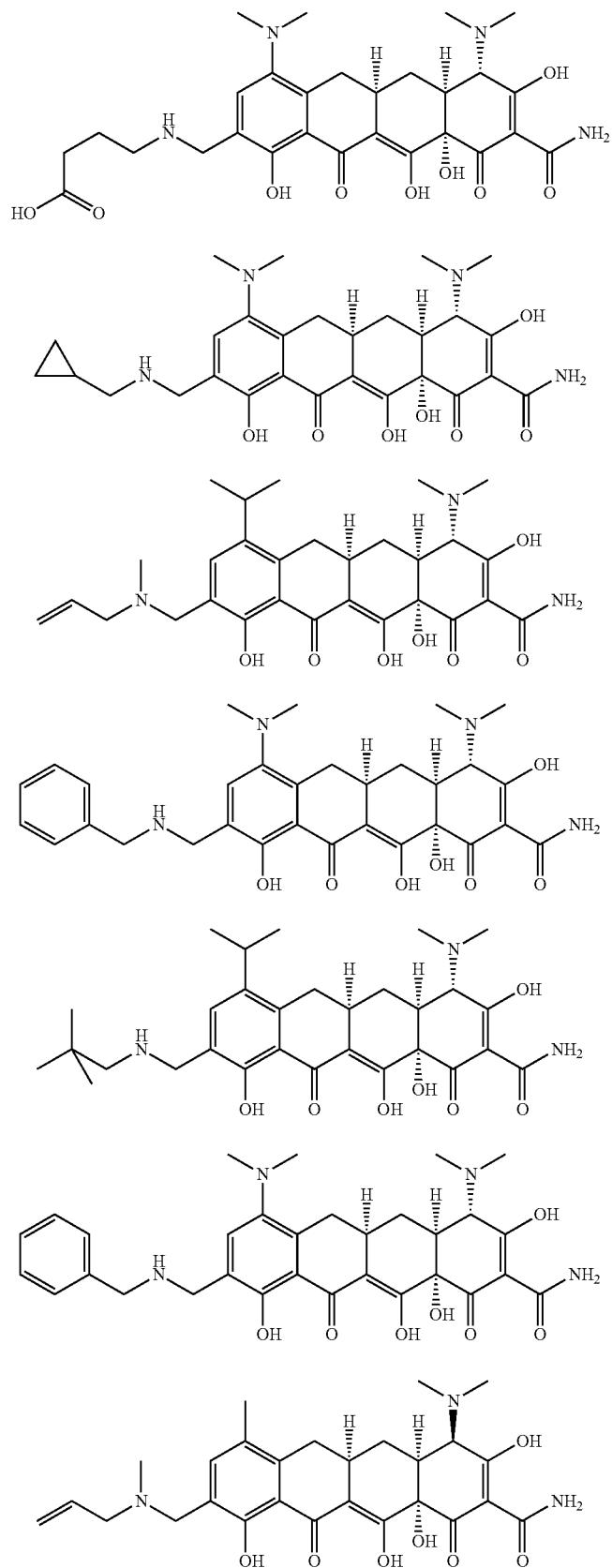

TABLE 1-continued
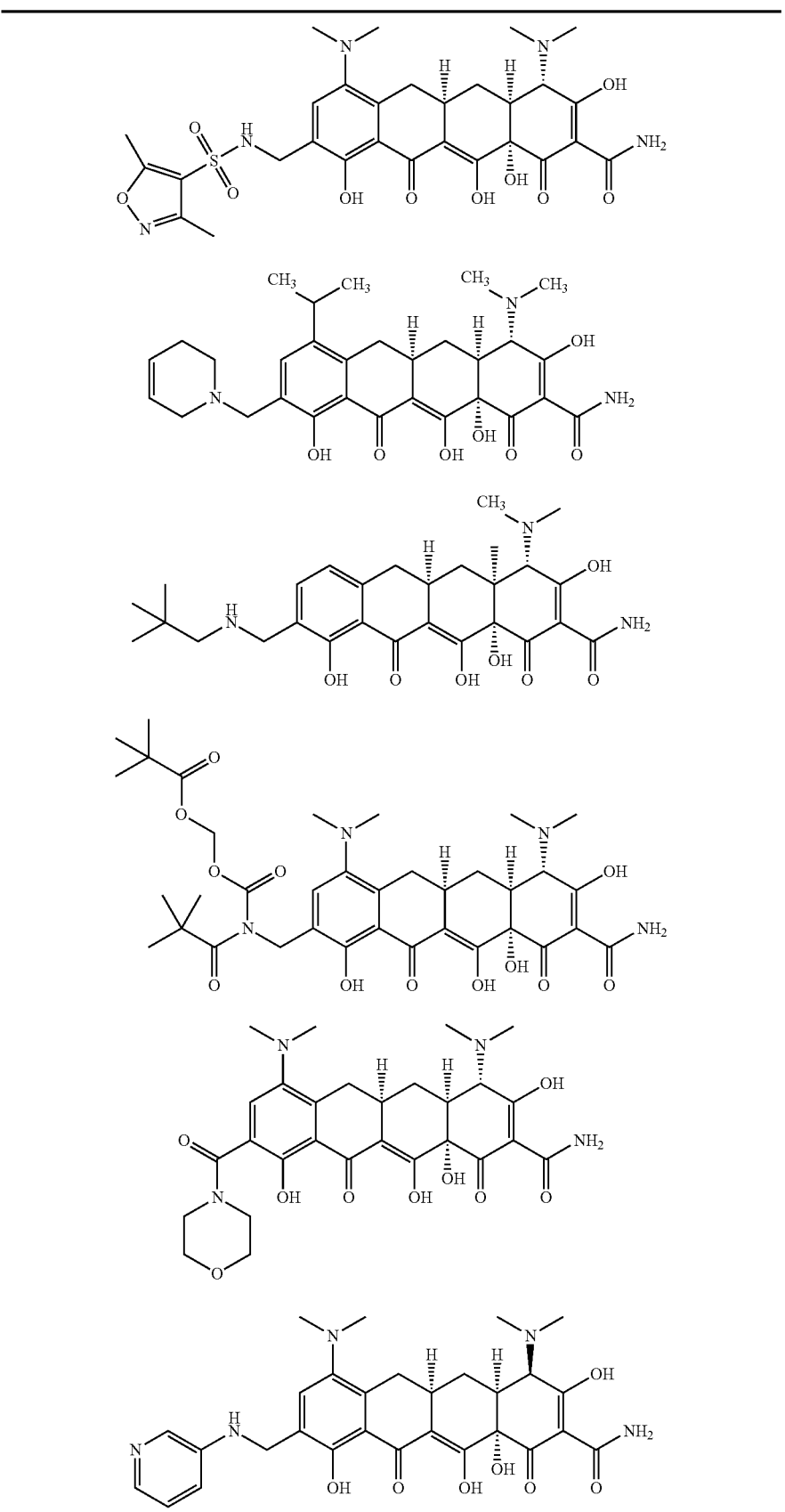

TABLE 1-continued
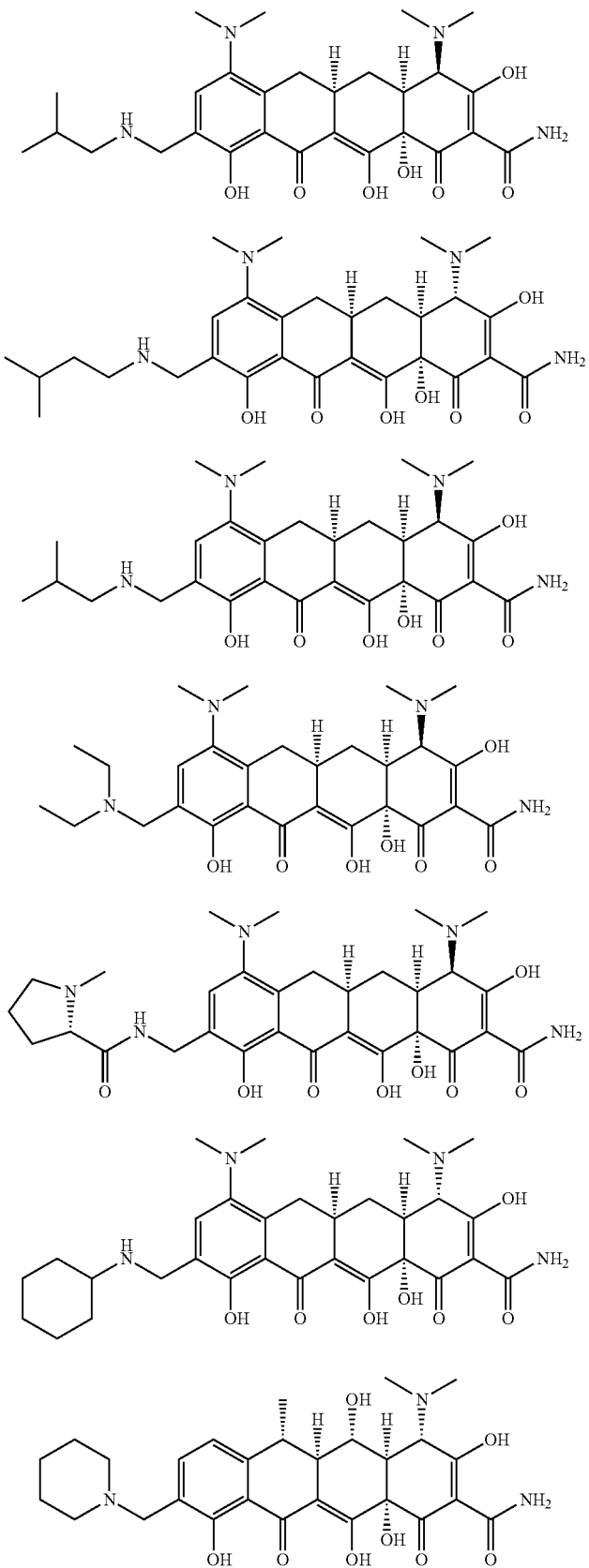

TABLE 1-continued
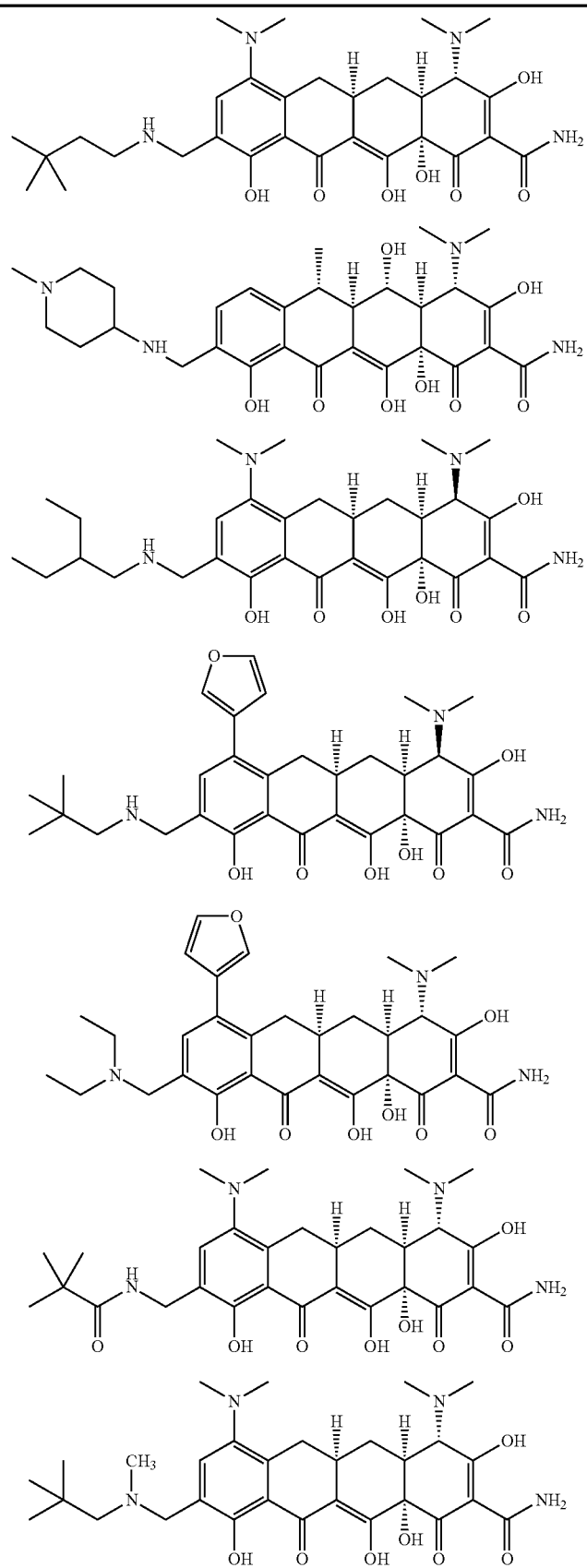

TABLE 1-continued
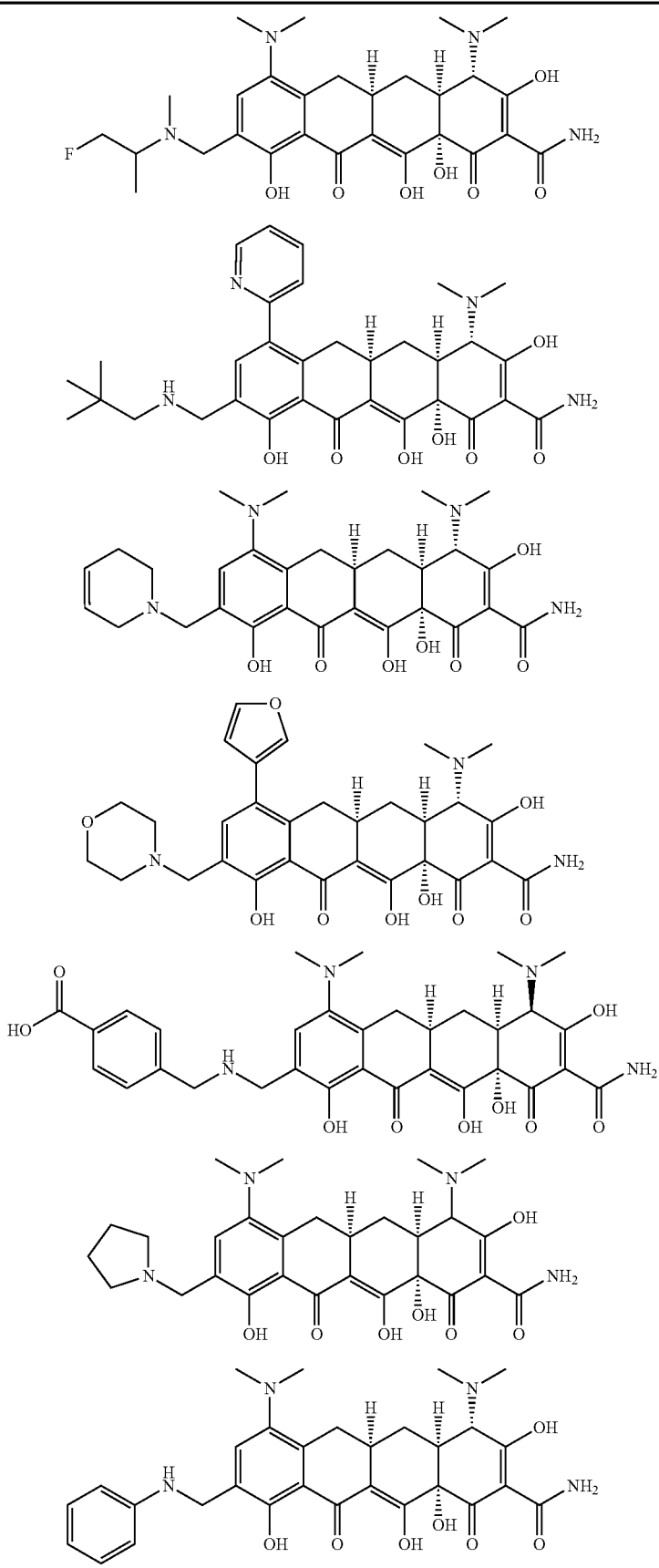

TABLE 1-continued
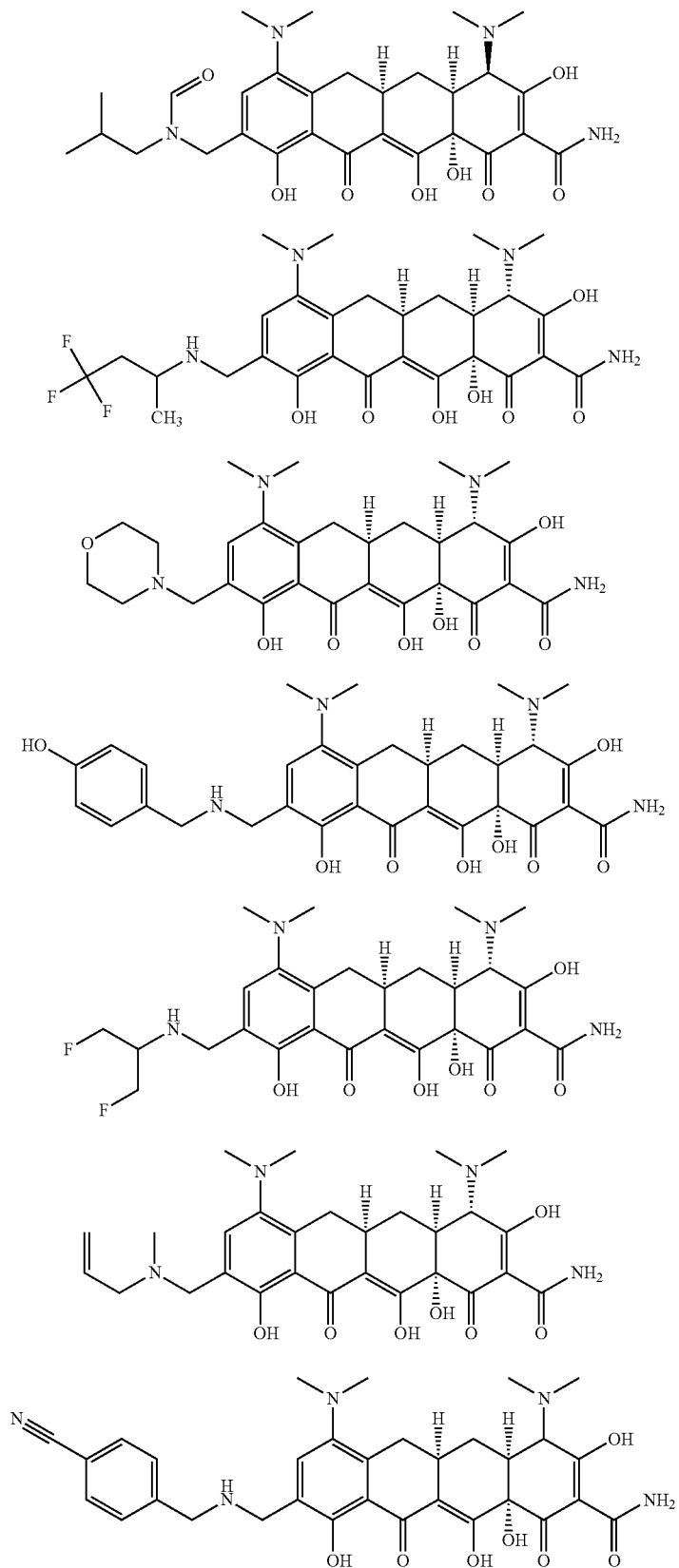

TABLE 1-continued
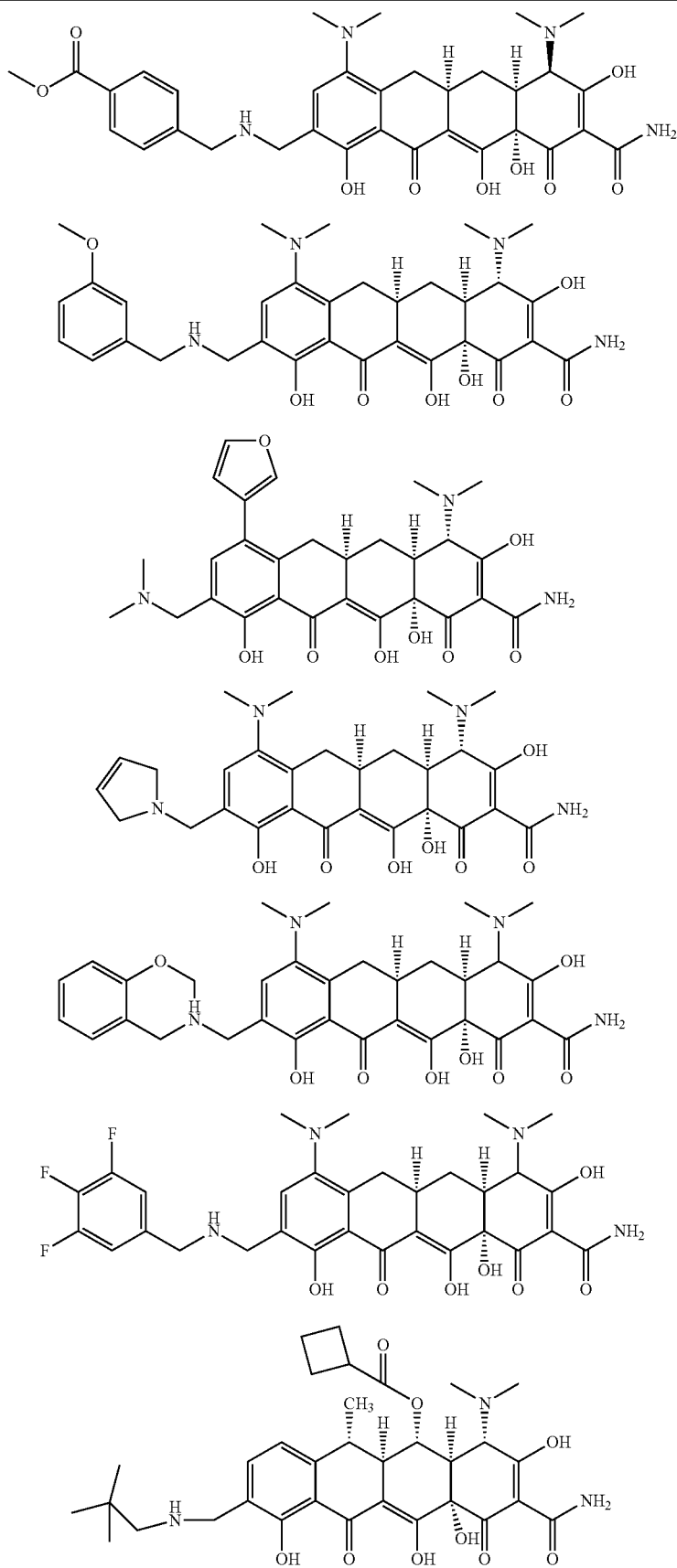

TABLE 1-continued
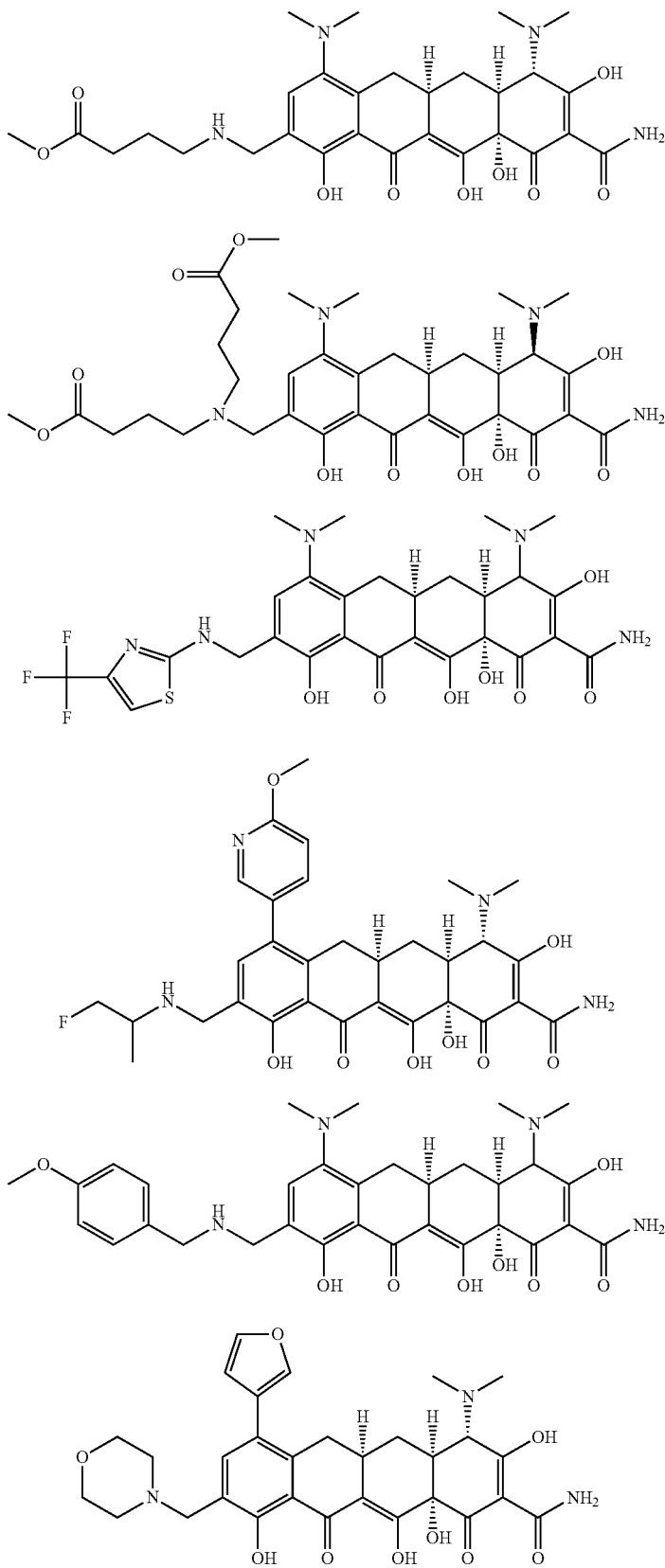

TABLE 1-continued
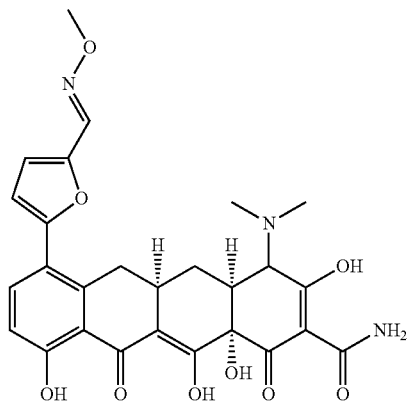
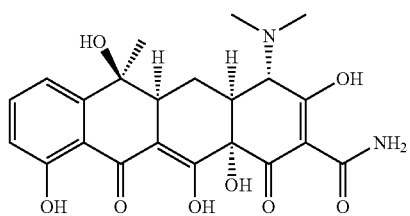
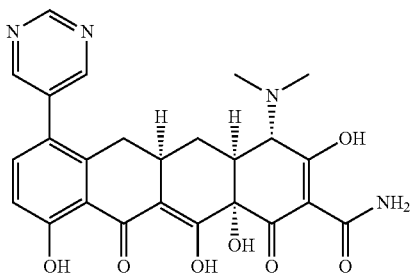
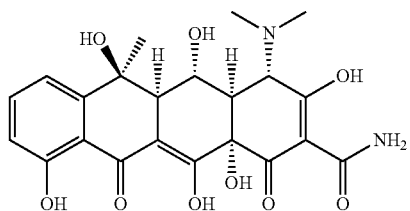
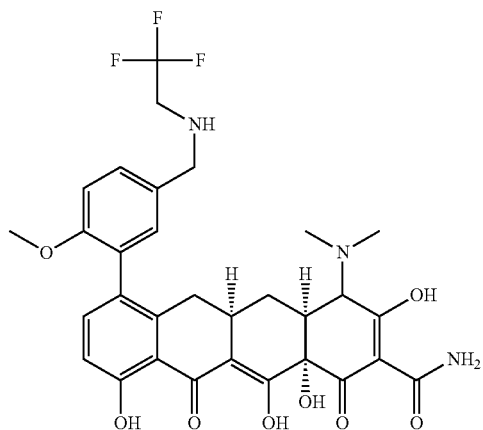

TABLE 1-continued
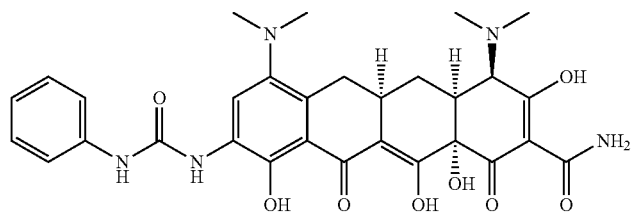
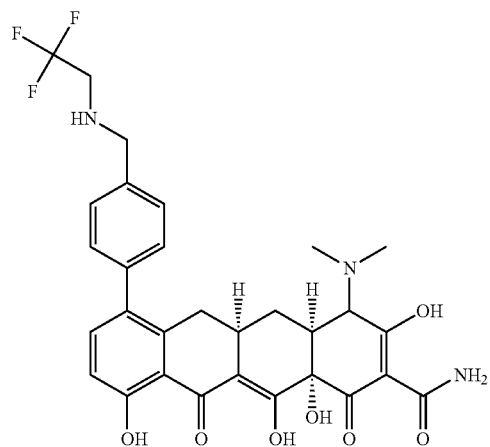
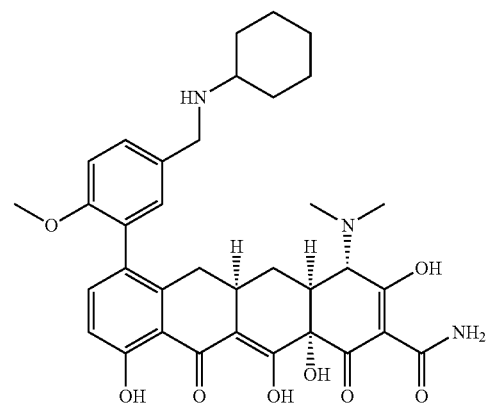
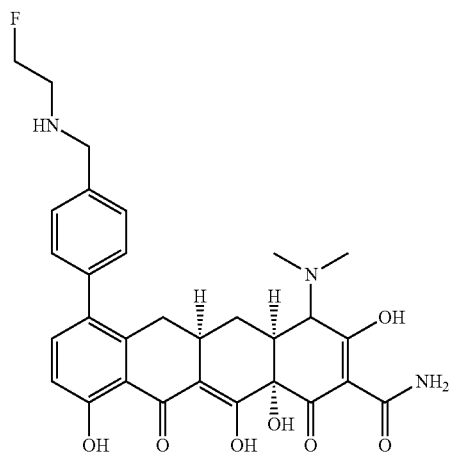

TABLE 1-continued
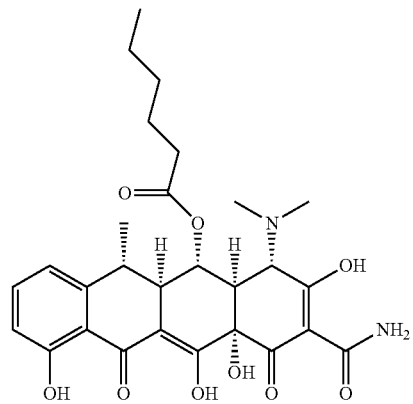
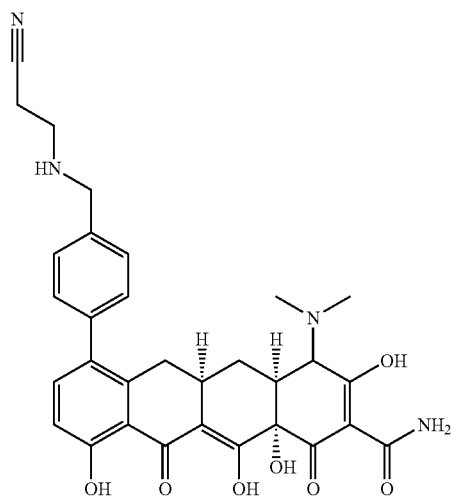
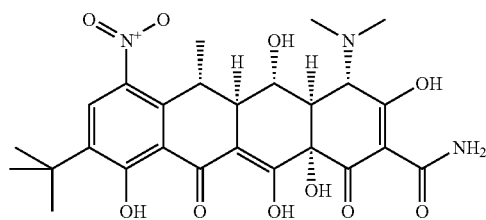
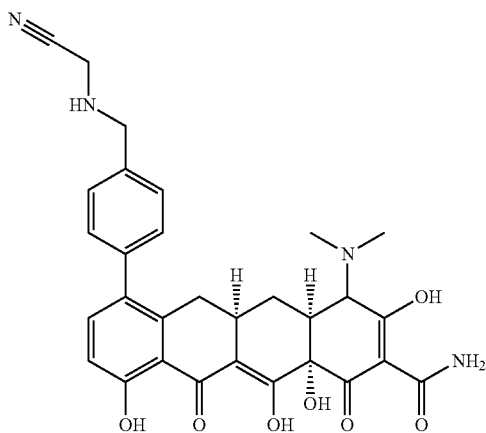

TABLE 1-continued
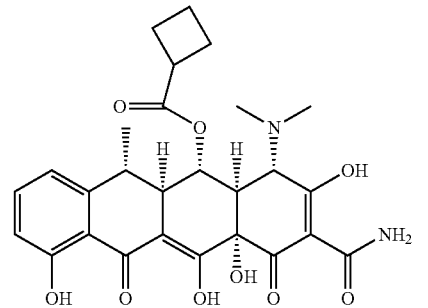
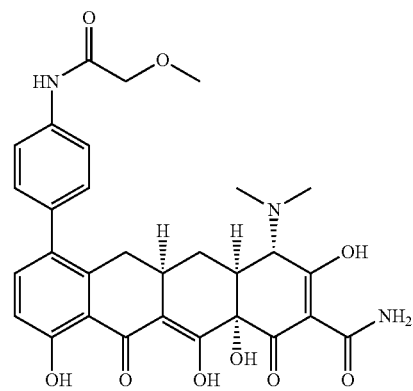
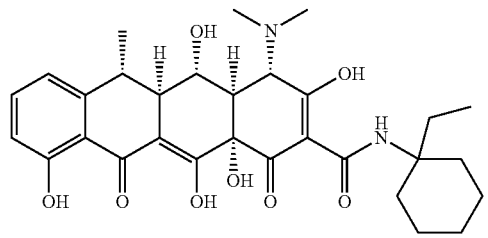
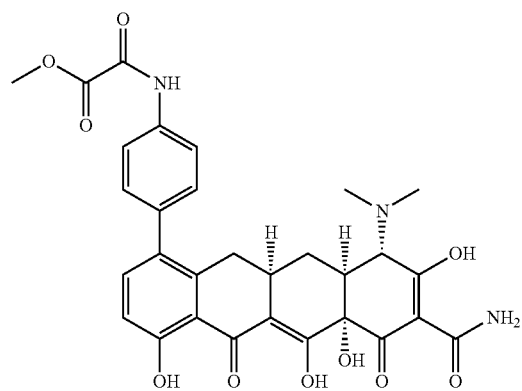
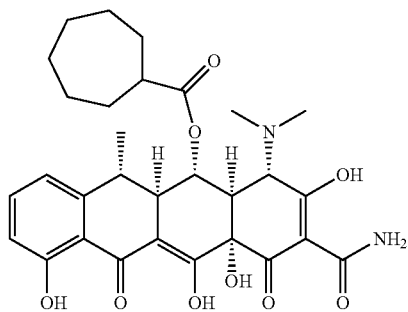

TABLE 1-continued
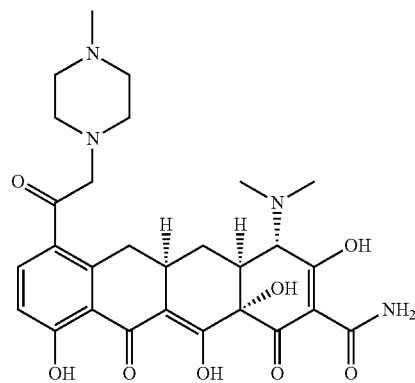
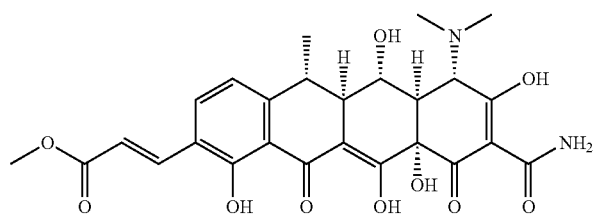
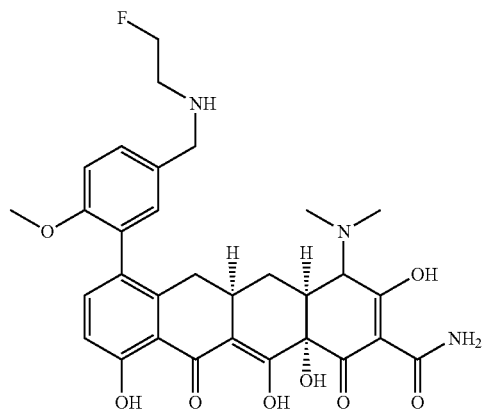
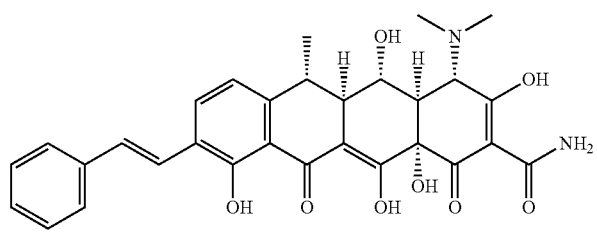

TABLE 1-continued
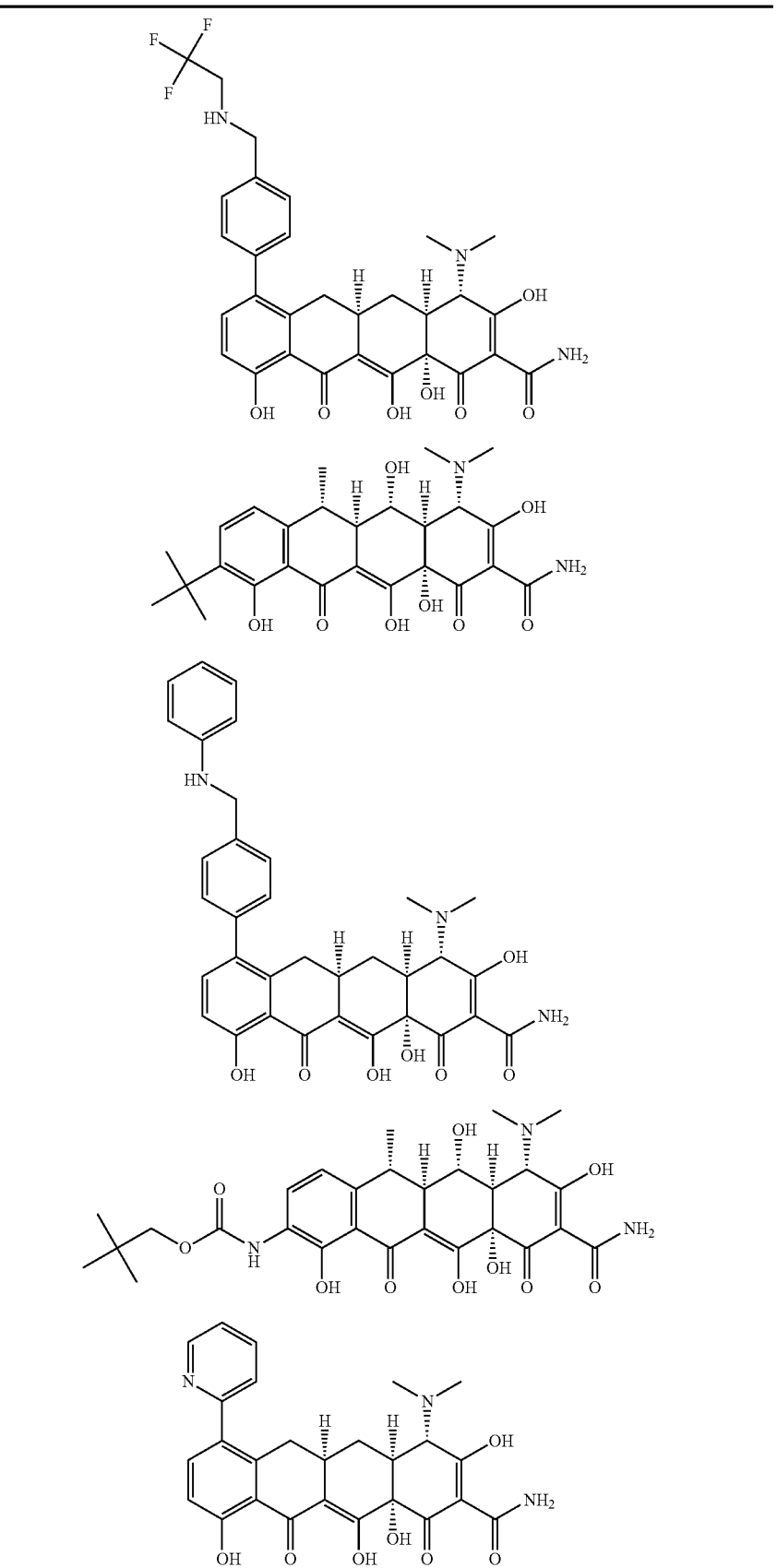

TABLE 1-continued
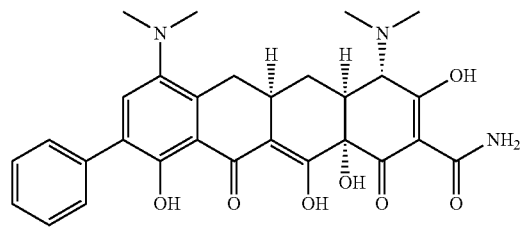
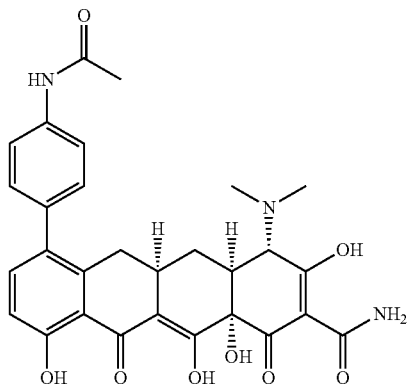
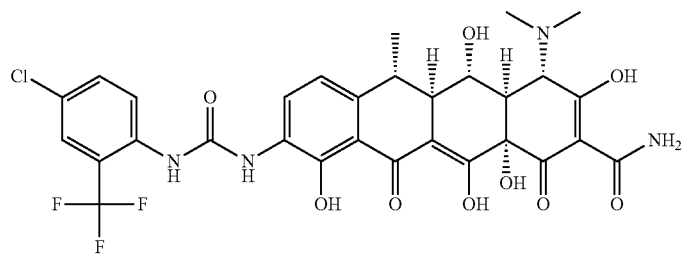
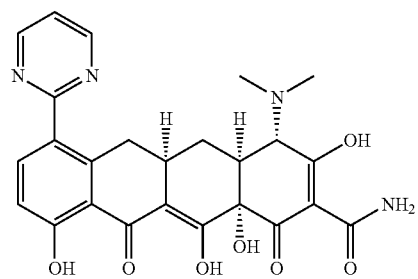
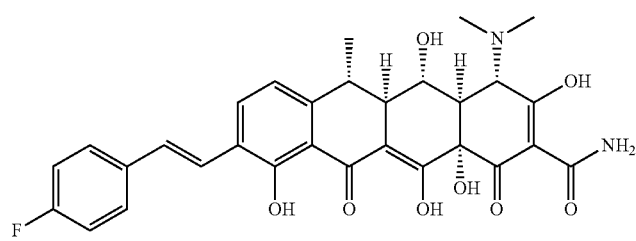

TABLE 1-continued
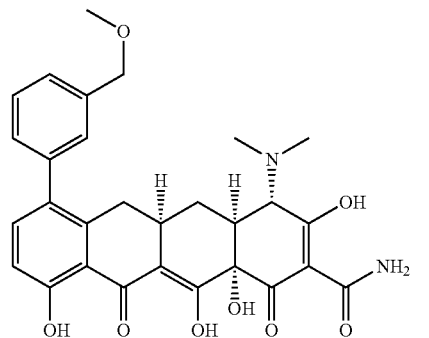
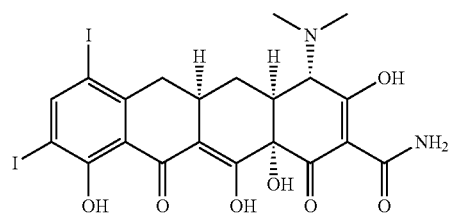
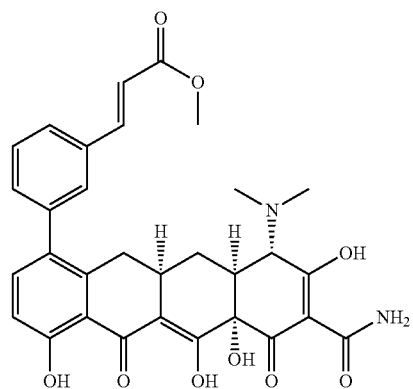
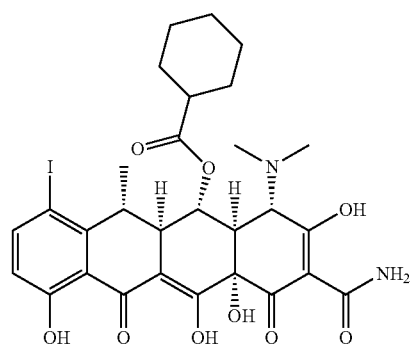
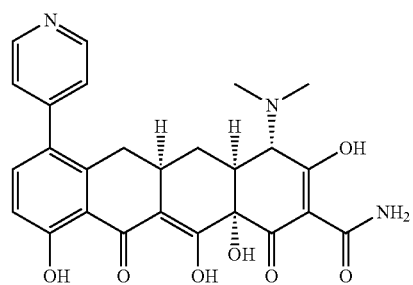

TABLE 1-continued
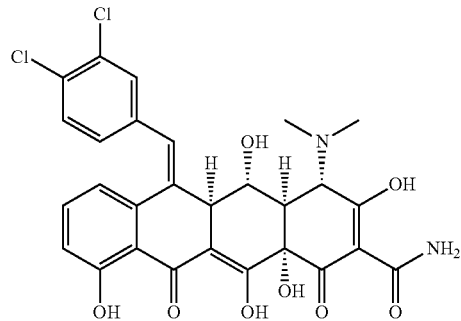
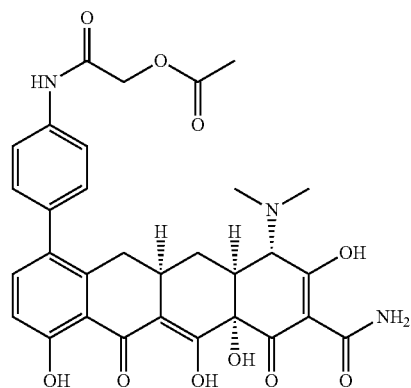
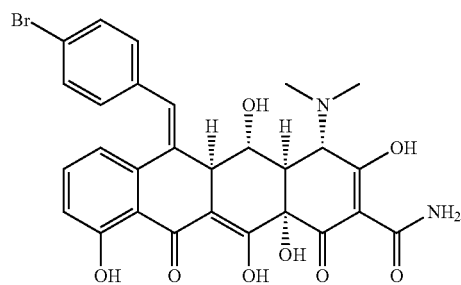
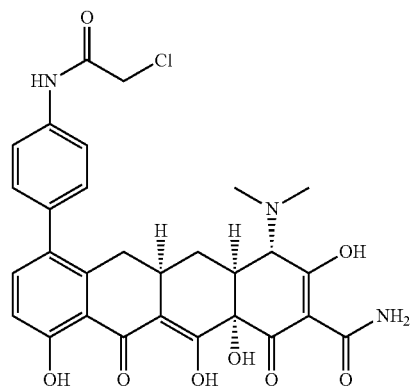

TABLE 1-continued
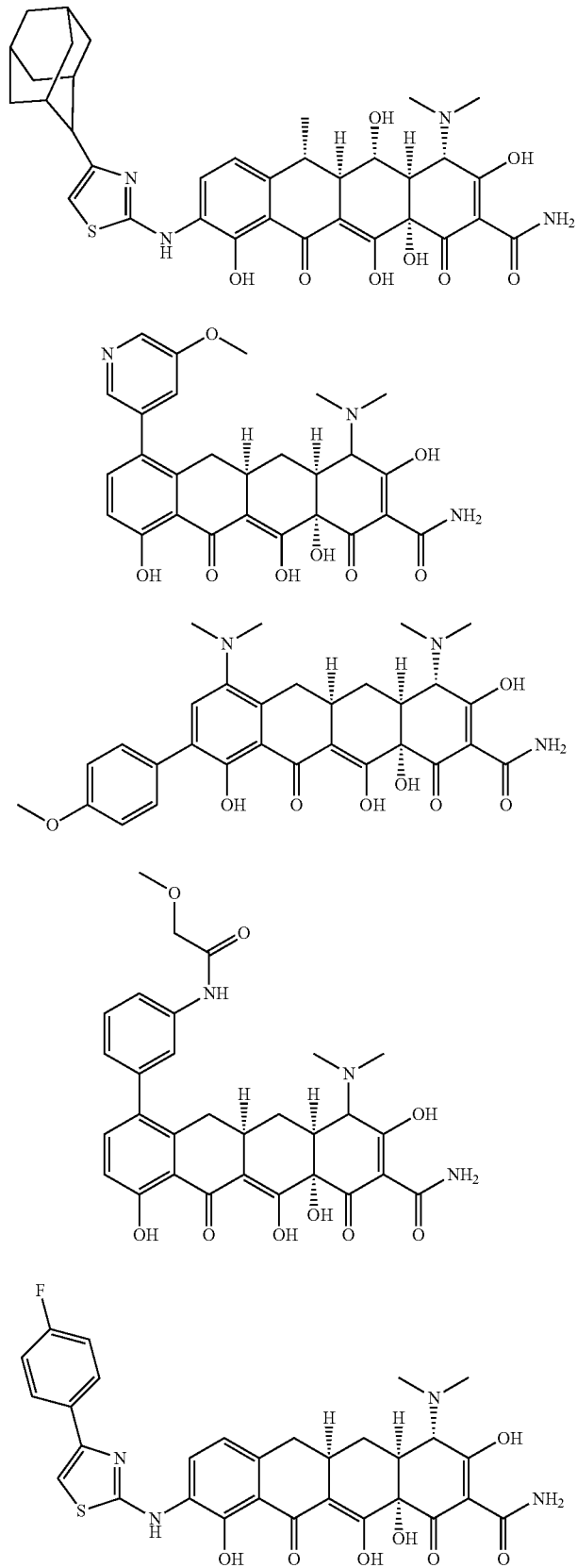

TABLE 1-continued
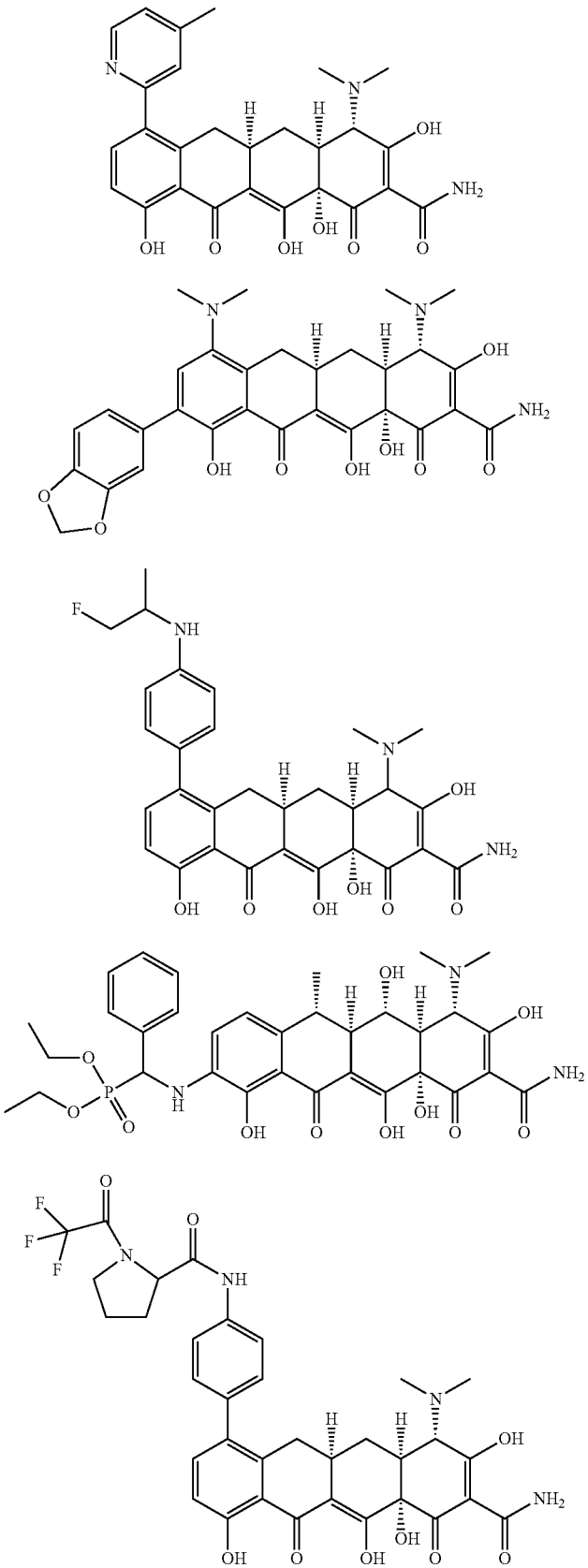

TABLE 1-continued
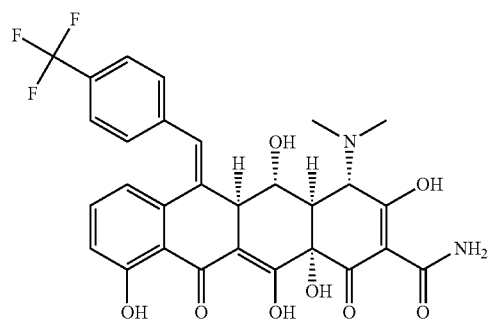
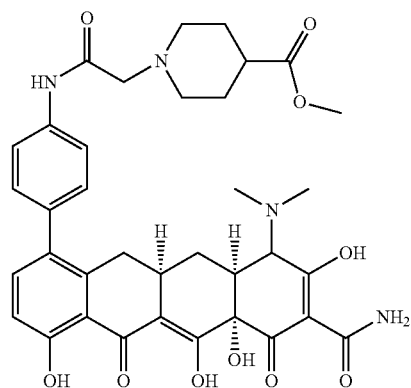
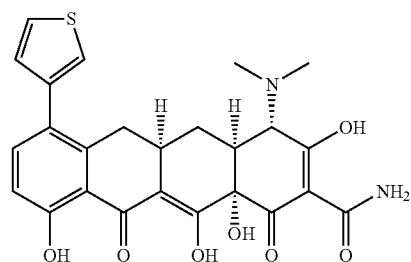
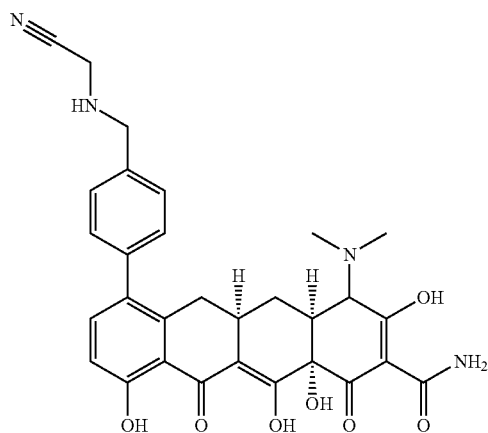

TABLE 1-continued
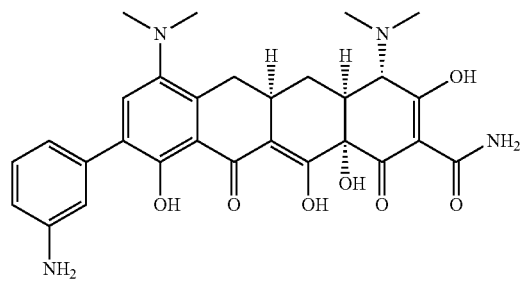
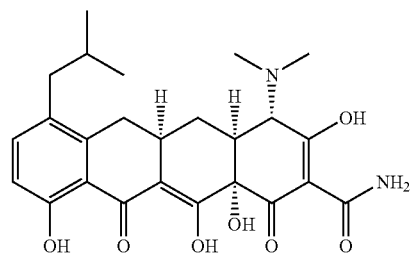
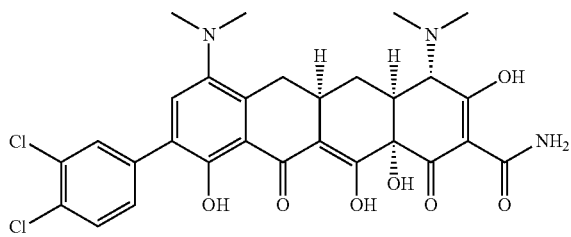
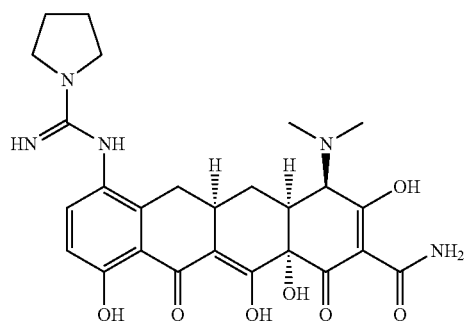
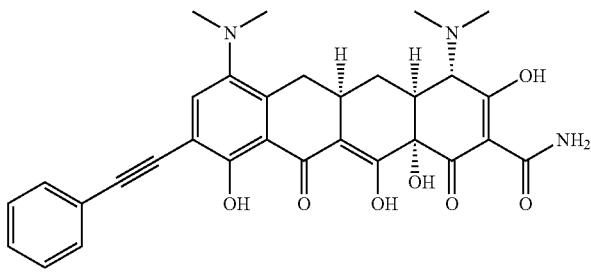
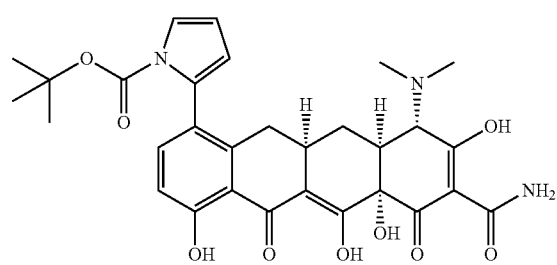

TABLE 1-continued
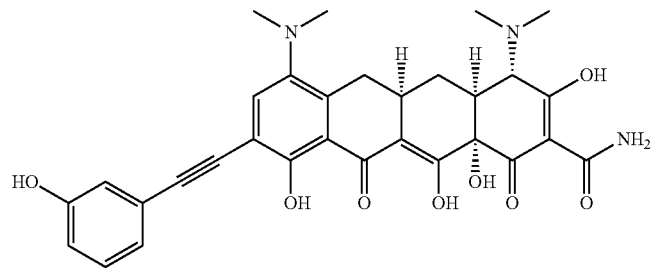
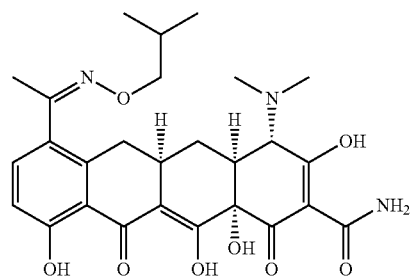
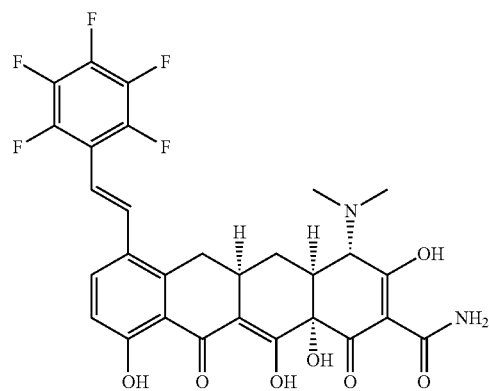
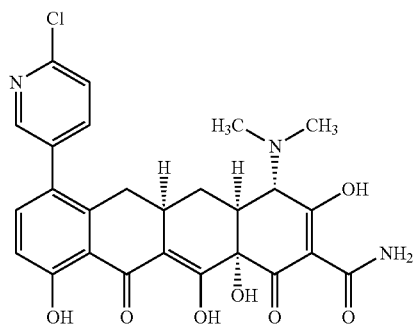
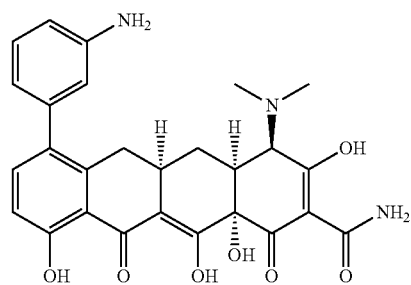

TABLE 1-continued
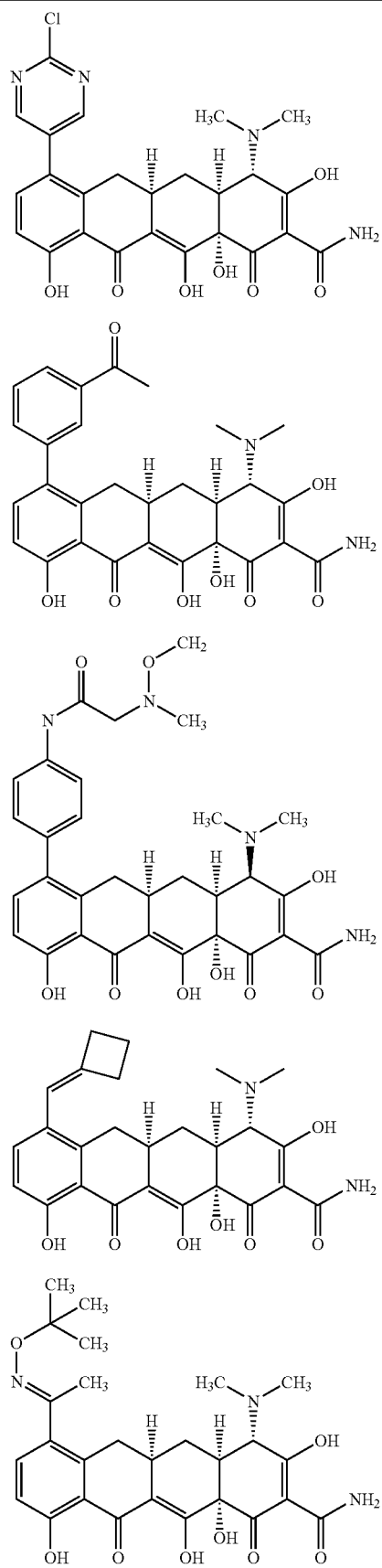

TABLE 1-continued
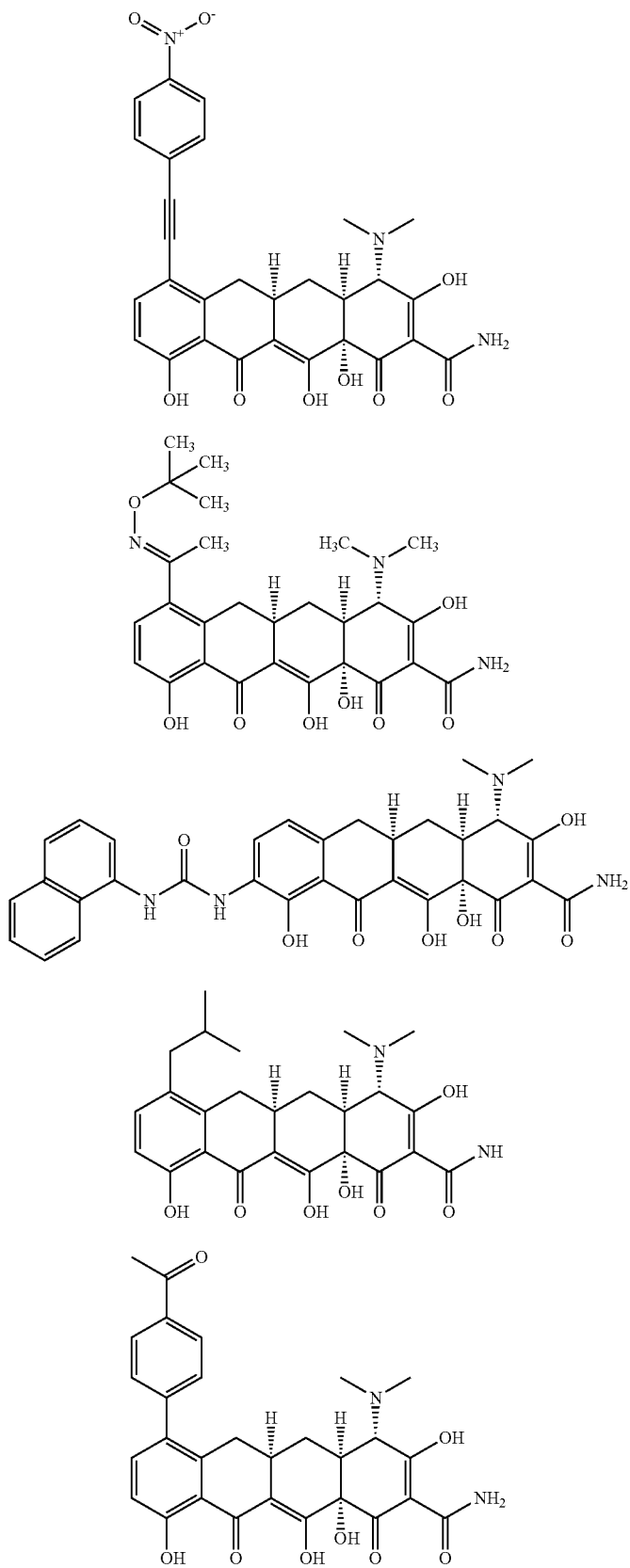

TABLE 1-continued
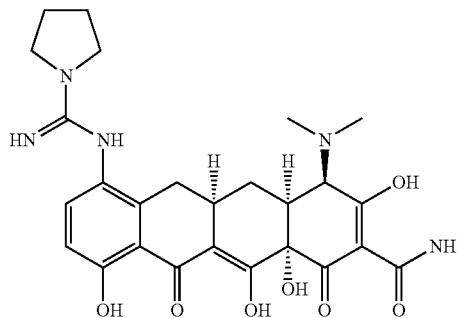
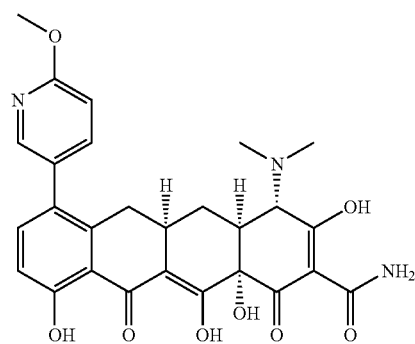
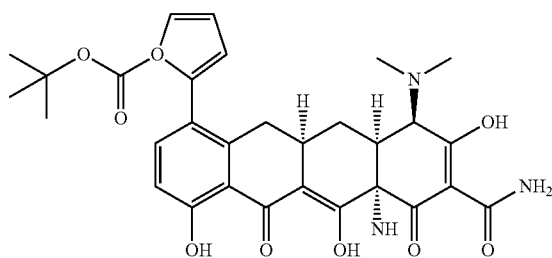
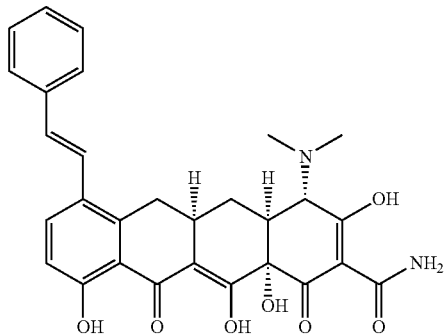
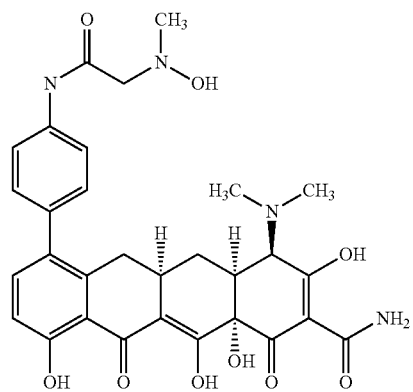

TABLE 1-continued
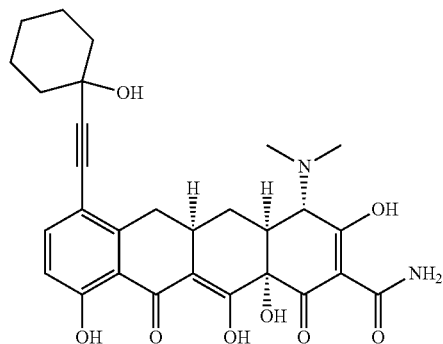
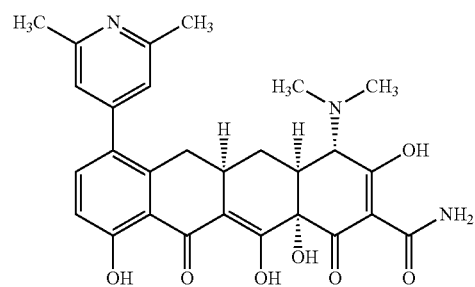
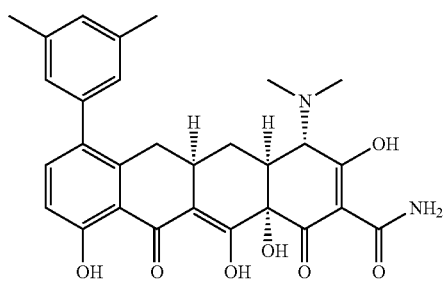
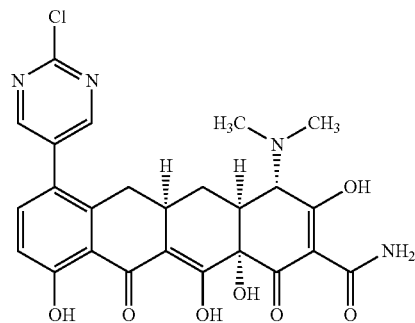
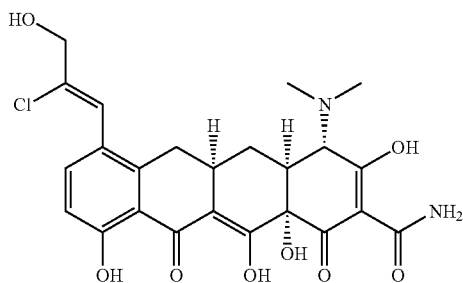

TABLE 1-continued
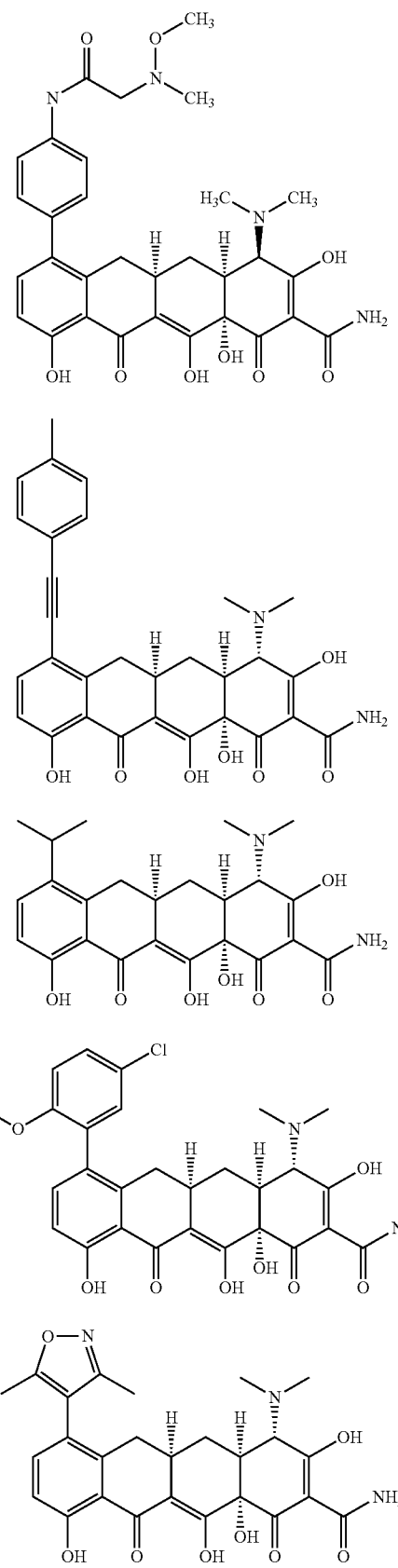

TABLE 1-continued
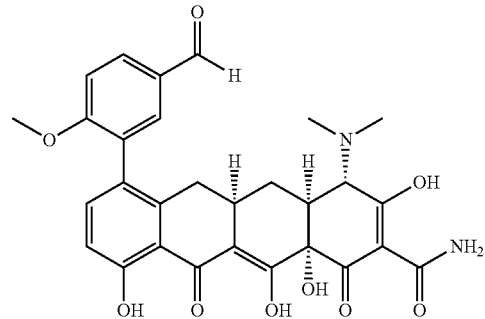
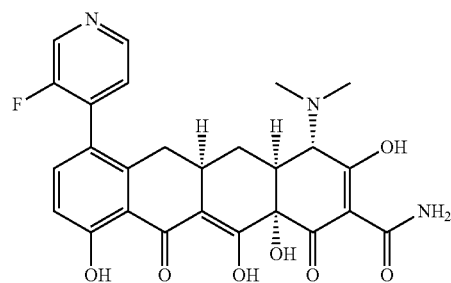
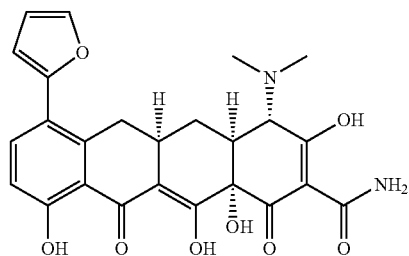
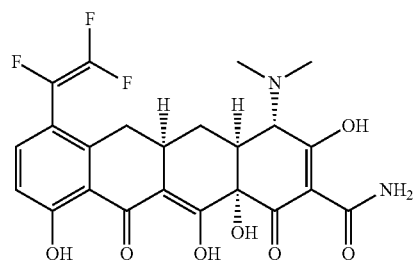
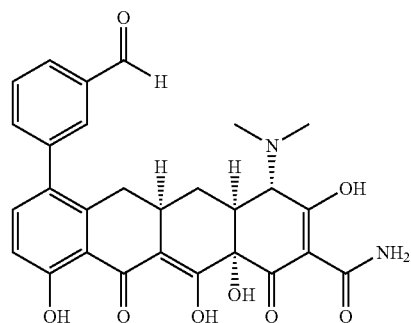

TABLE 1-continued
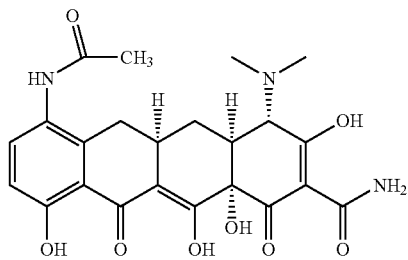
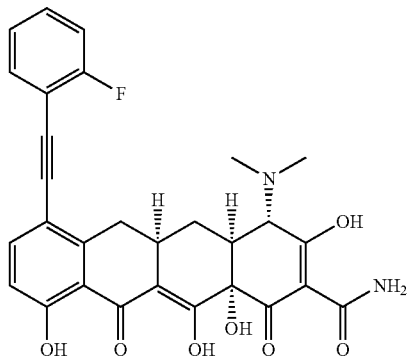
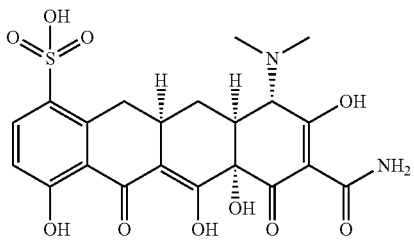
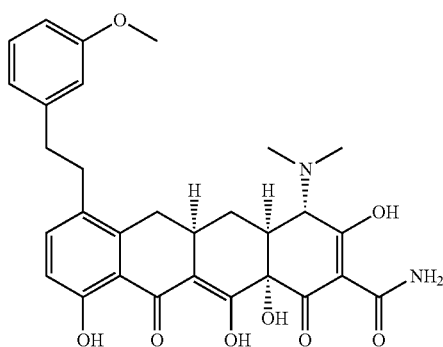
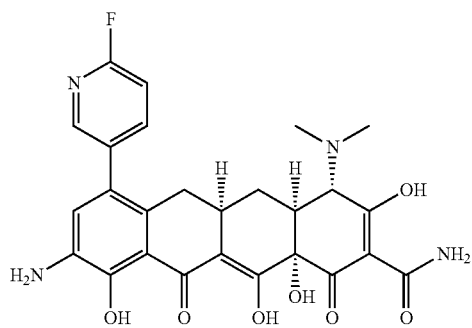

TABLE 1-continued
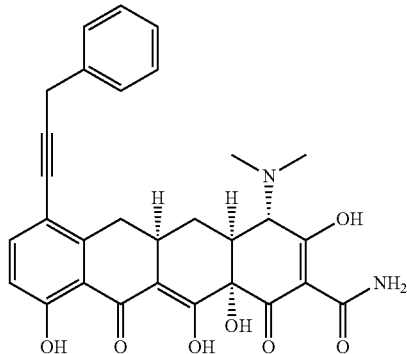
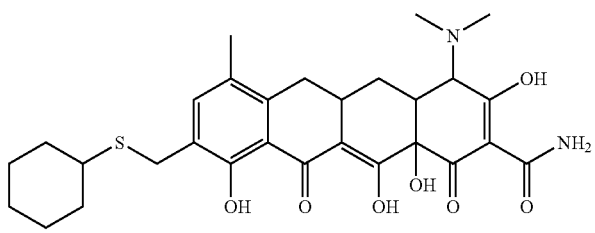
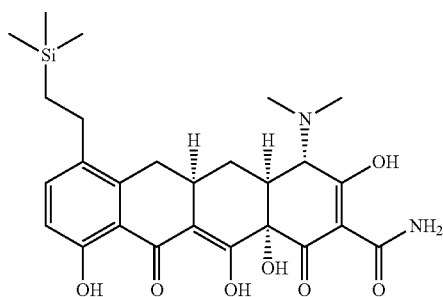
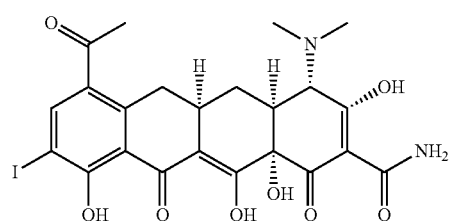
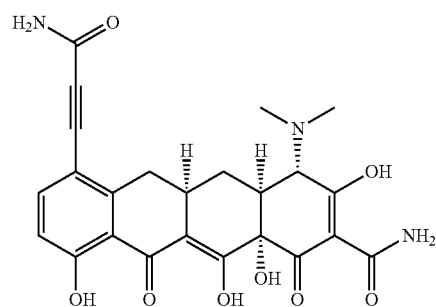

TABLE 1-continued
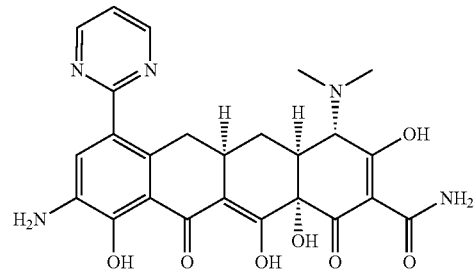
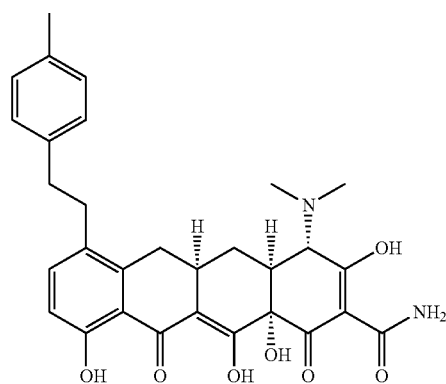
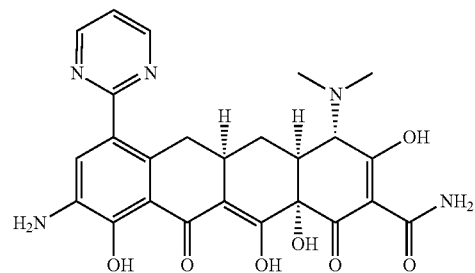
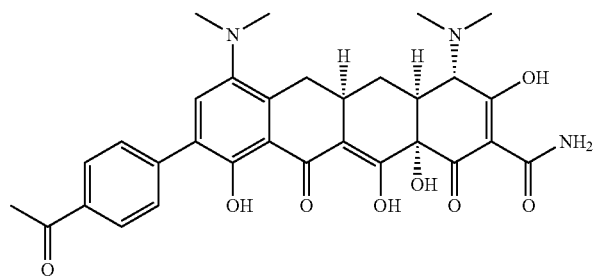
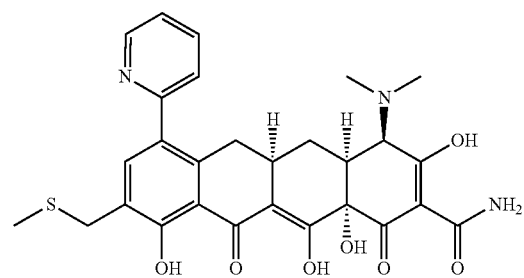

TABLE 1-continued
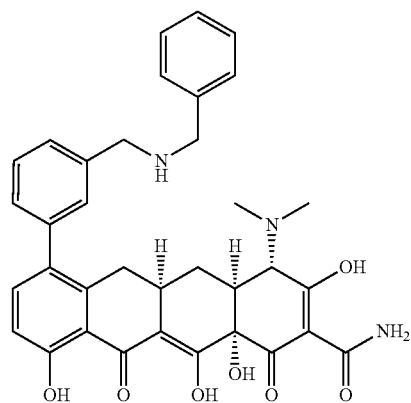
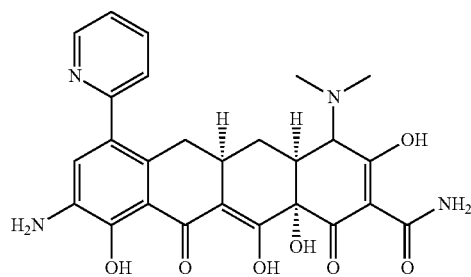
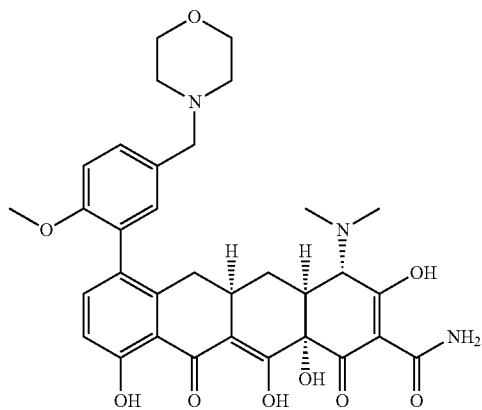
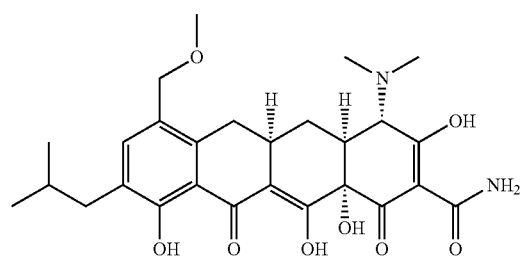

TABLE 1-continued
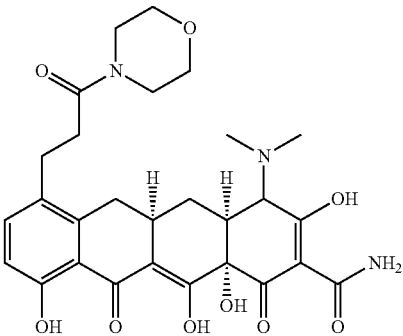
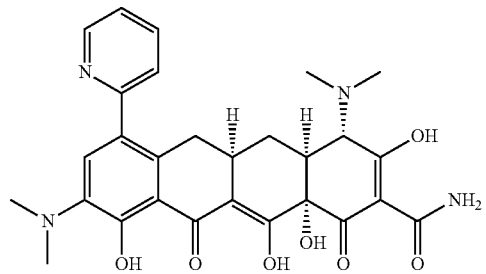
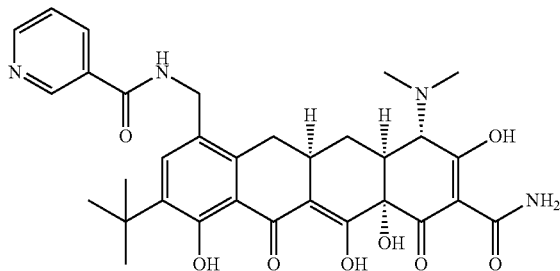
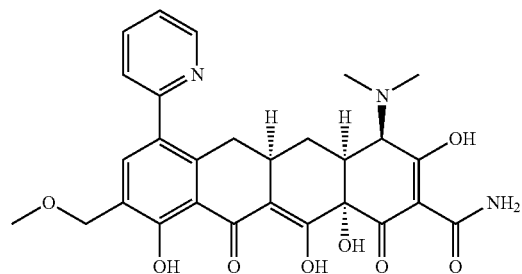
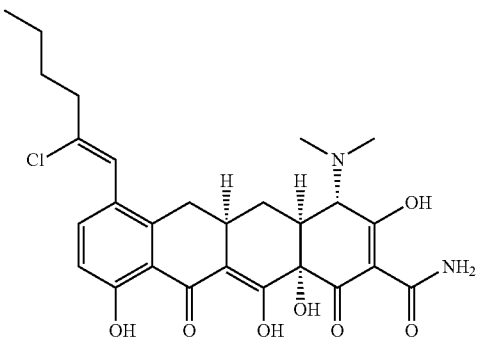

TABLE 1-continued
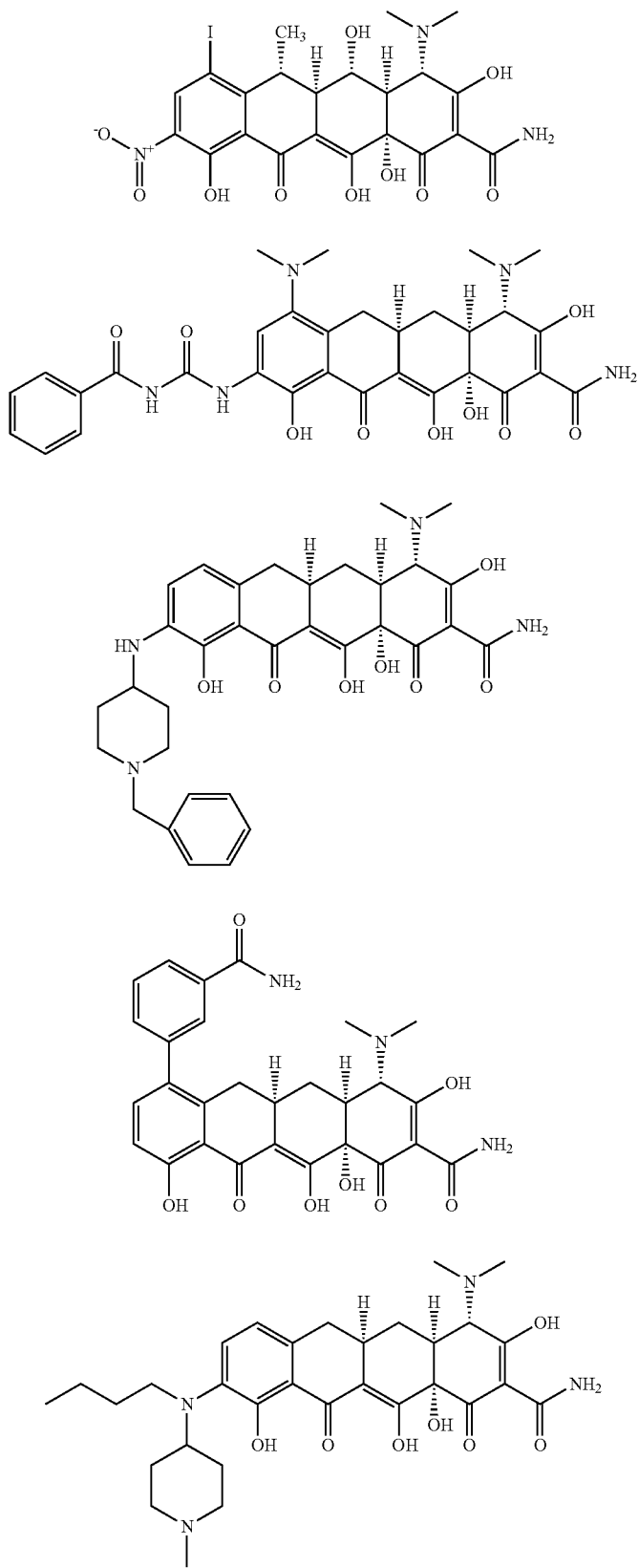

TABLE 1-continued
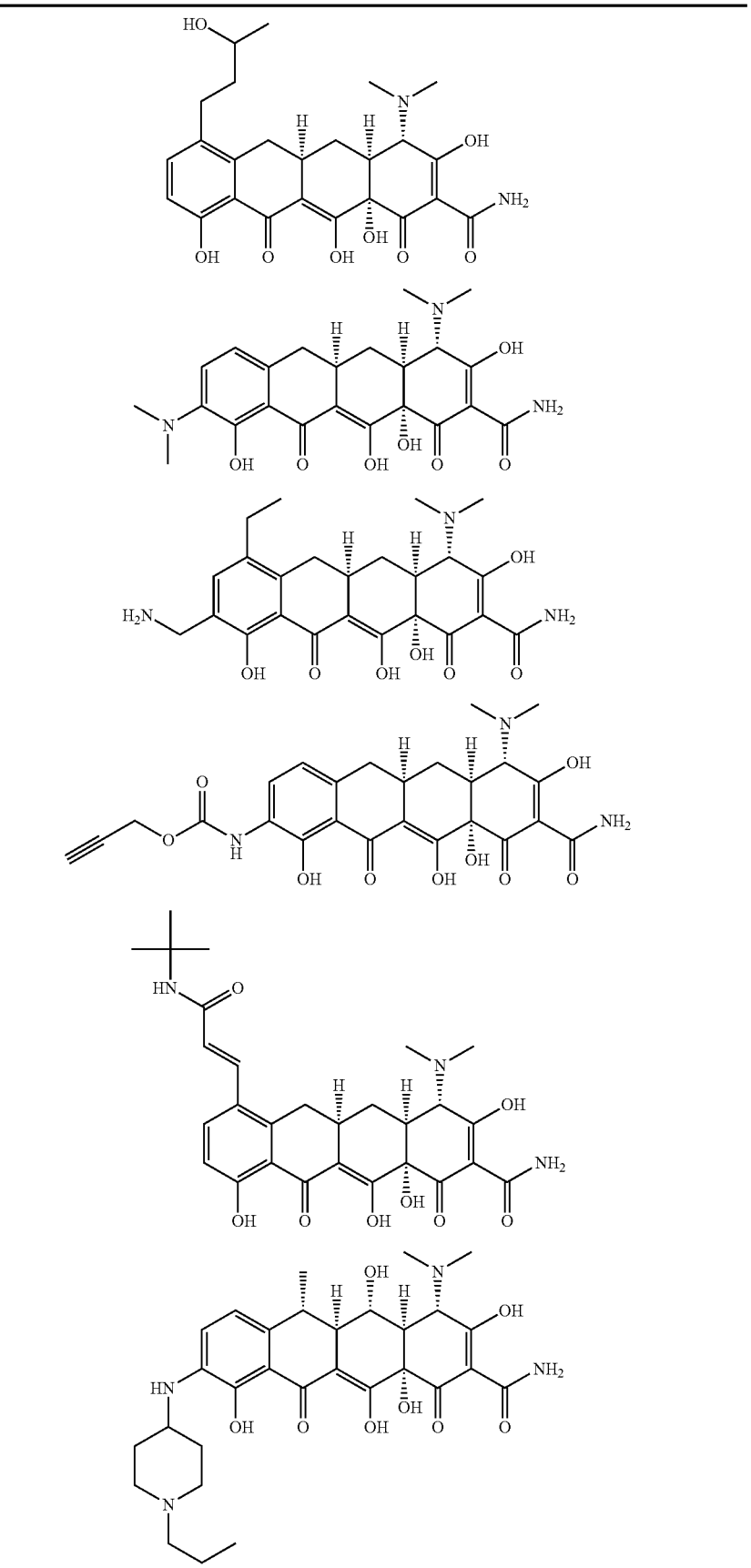

TABLE 1-continued
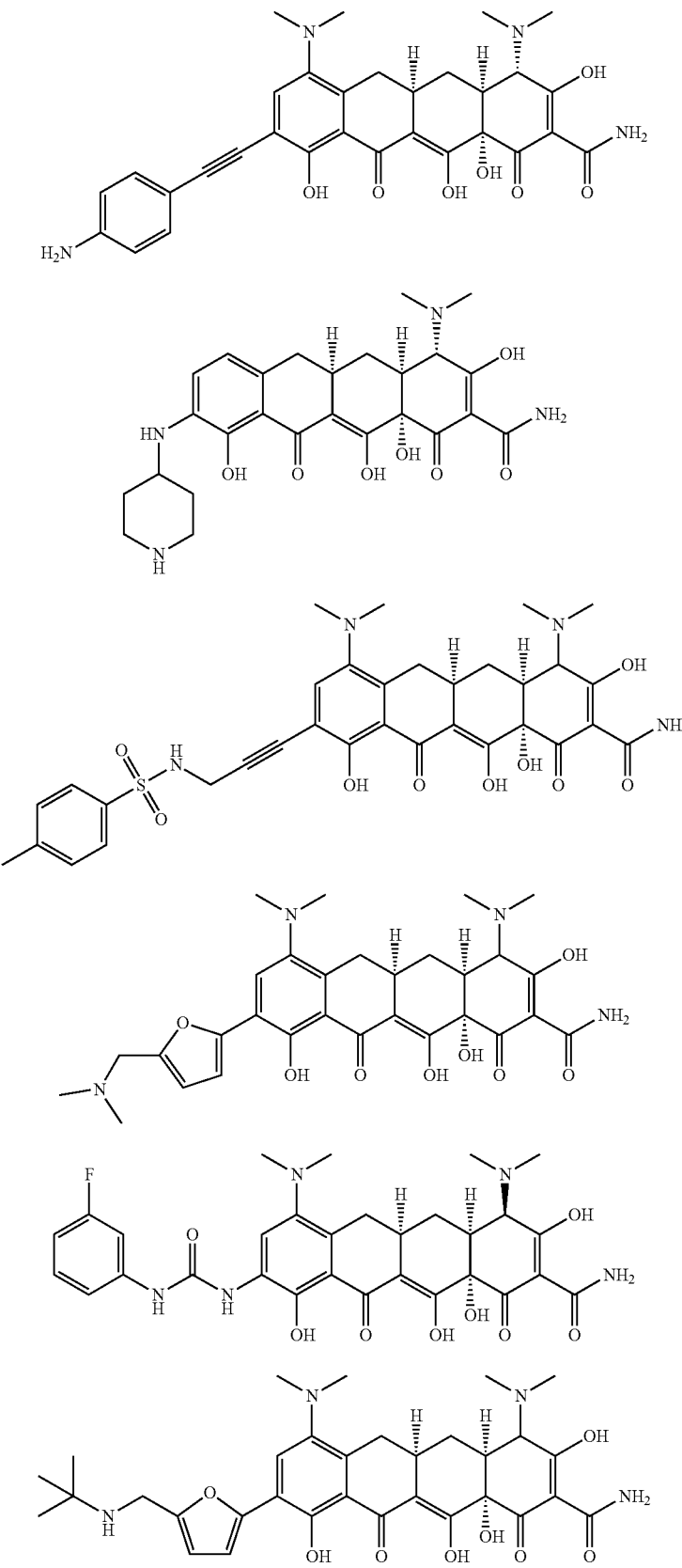

TABLE 1-continued
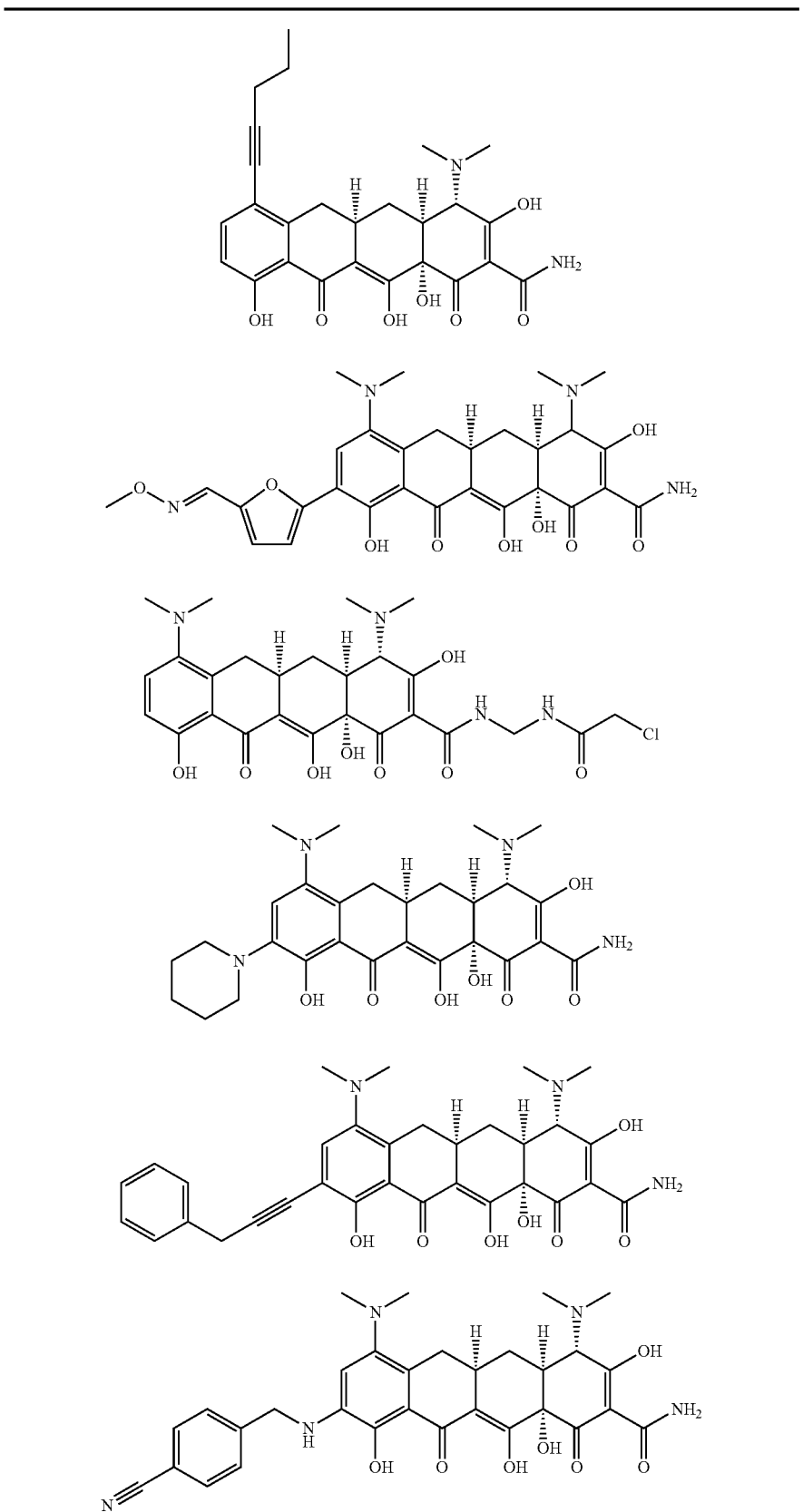

TABLE 1-continued
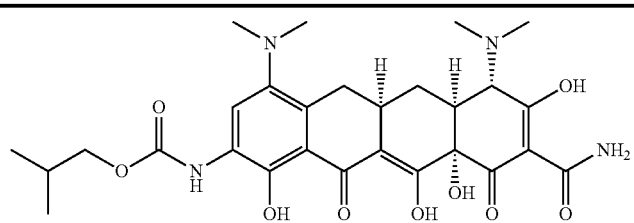
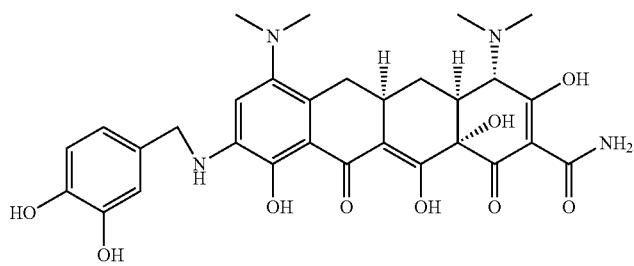
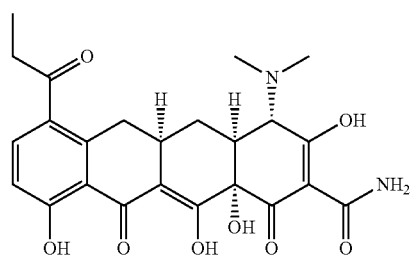
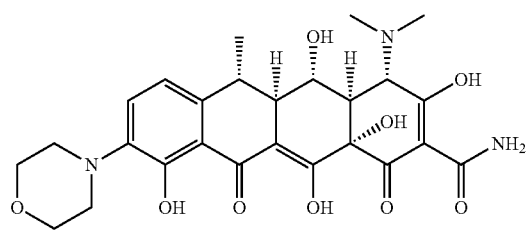
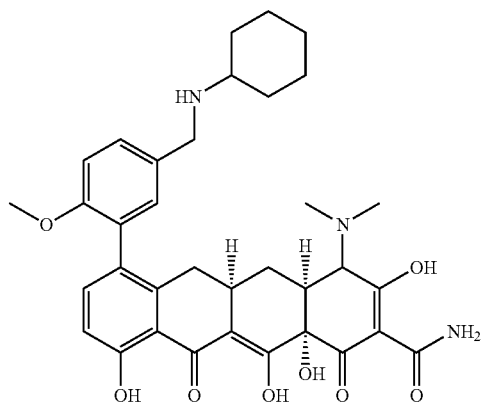
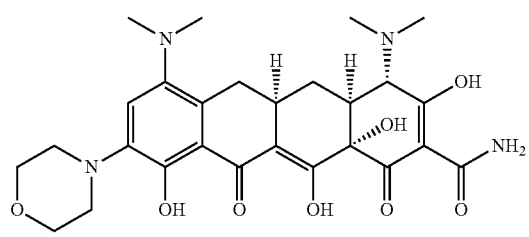

TABLE 1-continued
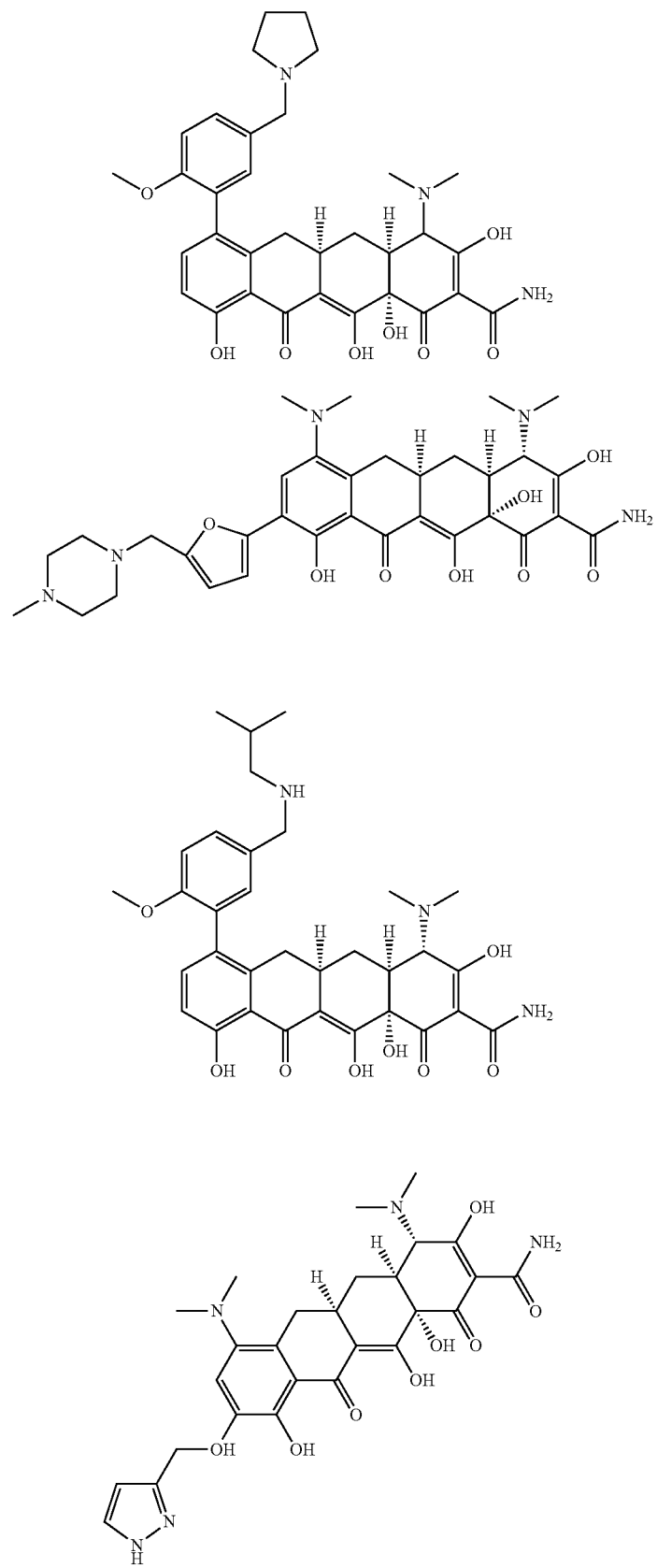

TABLE 1-continued
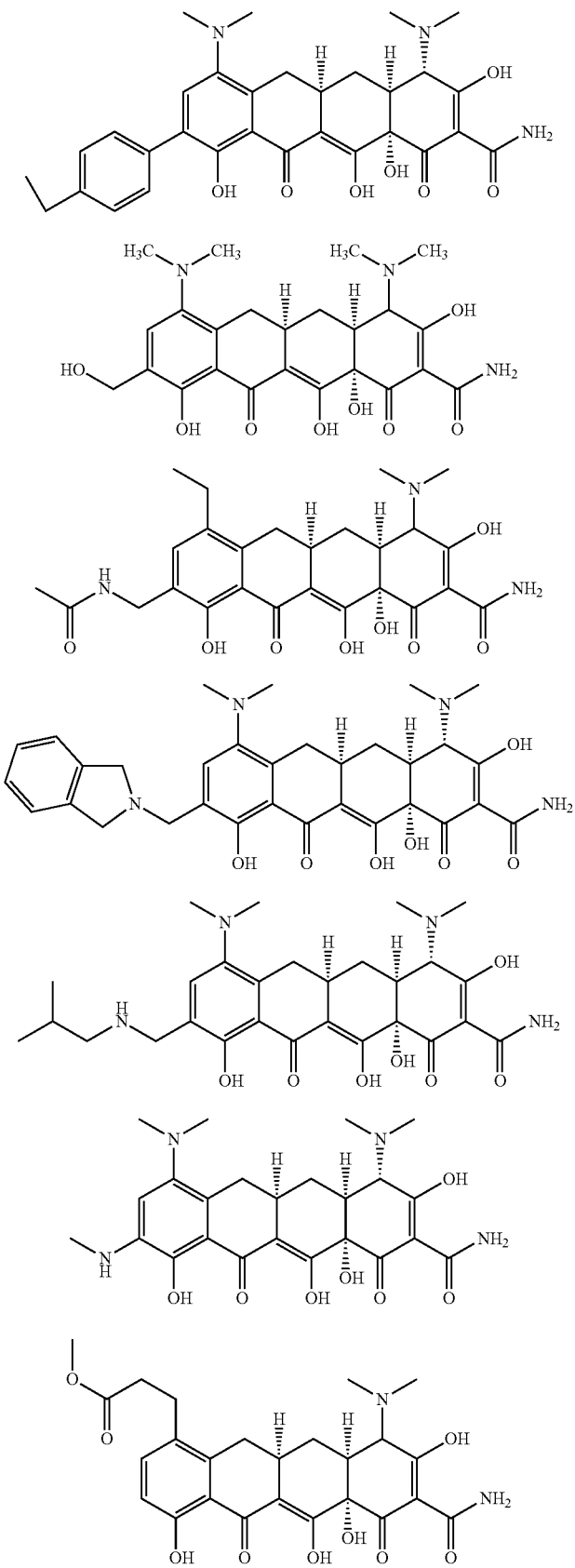

TABLE 1-continued
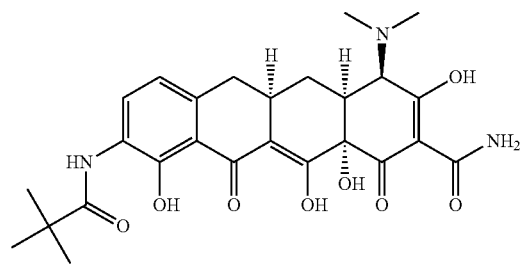
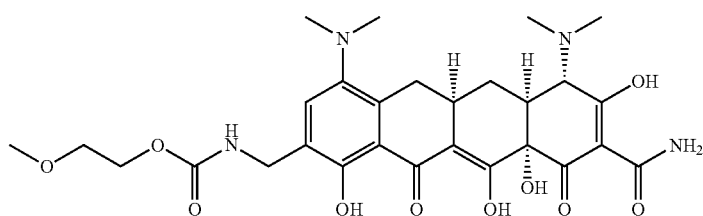
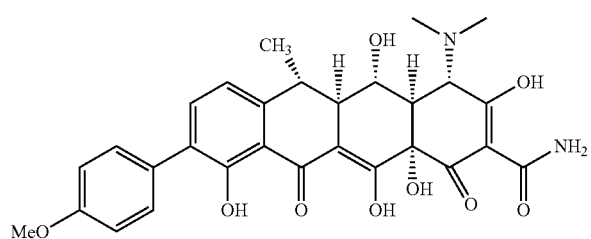
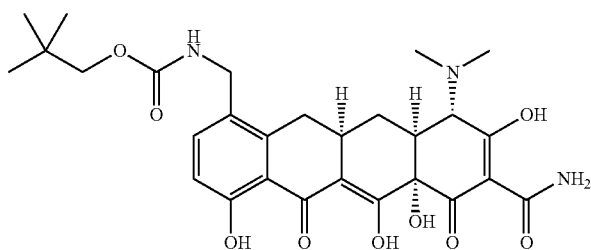
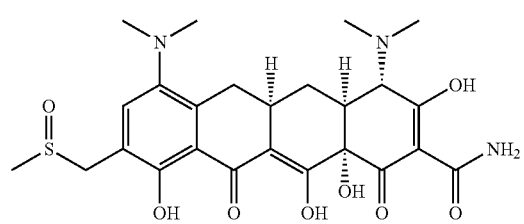

TABLE 1-continued
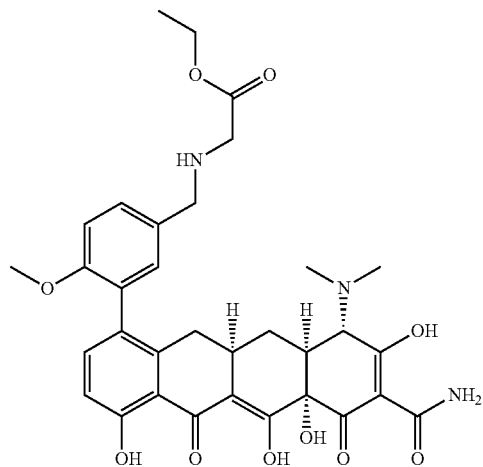
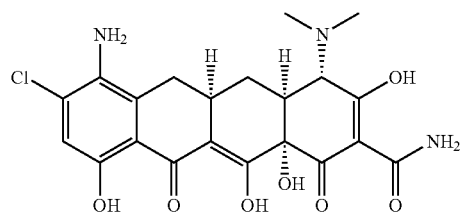
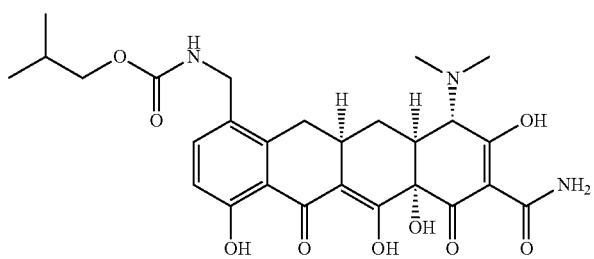
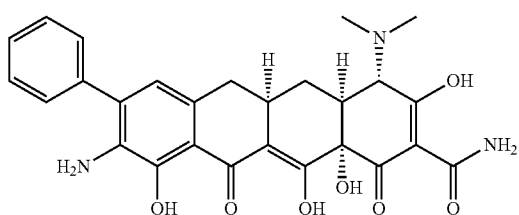
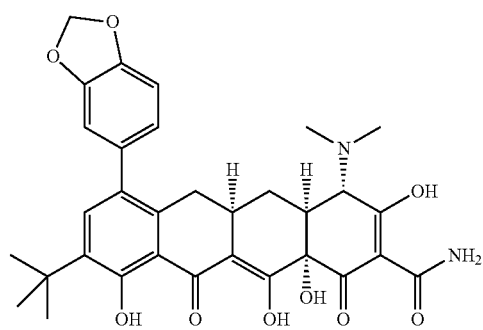

TABLE 1-continued
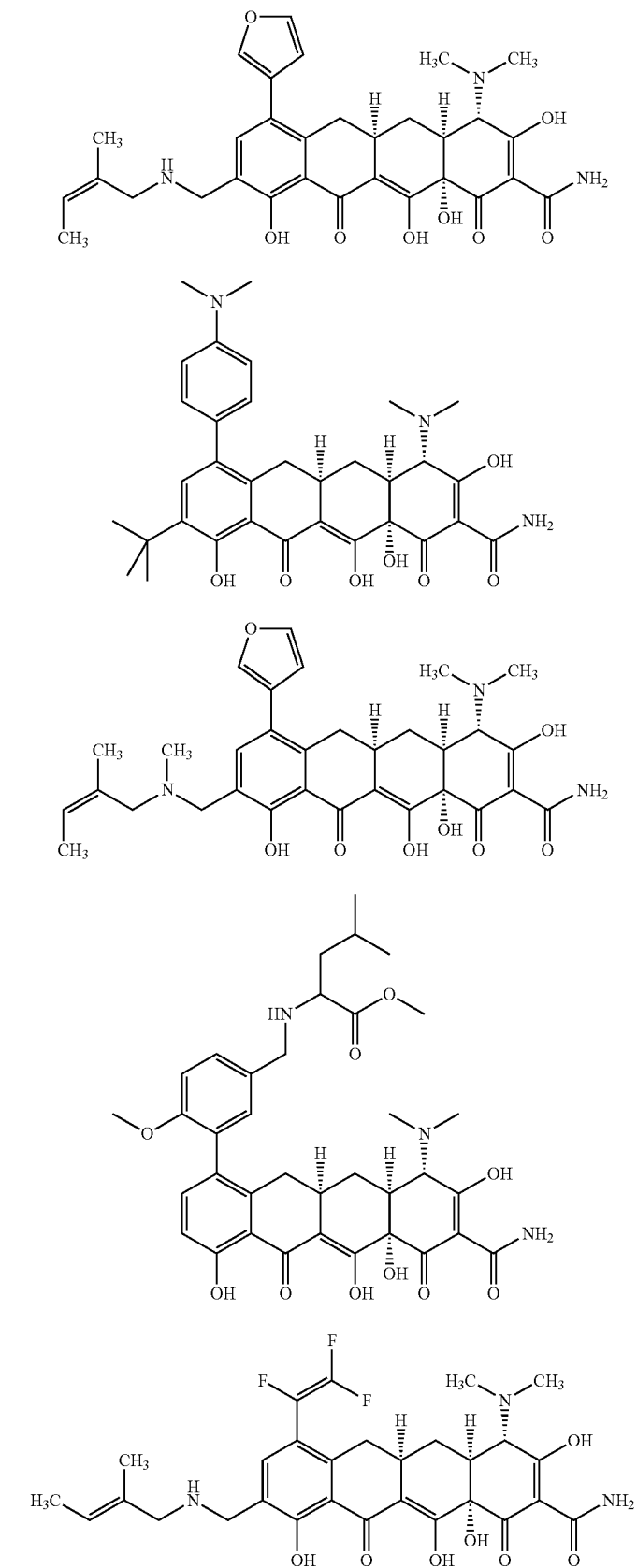

TABLE 1-continued
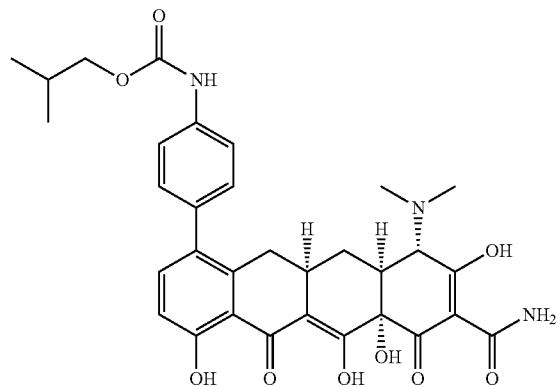
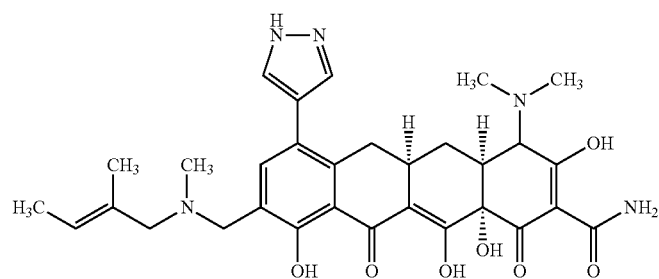
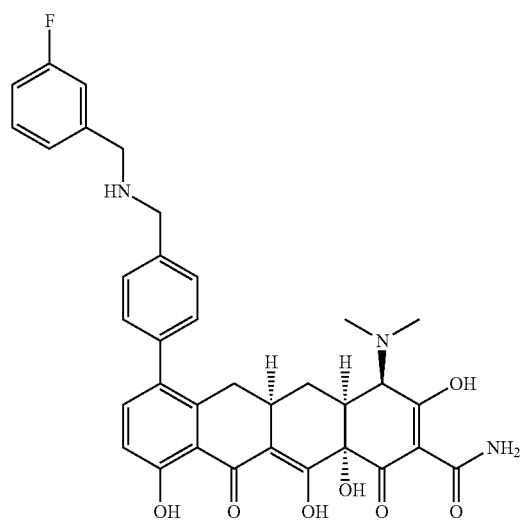
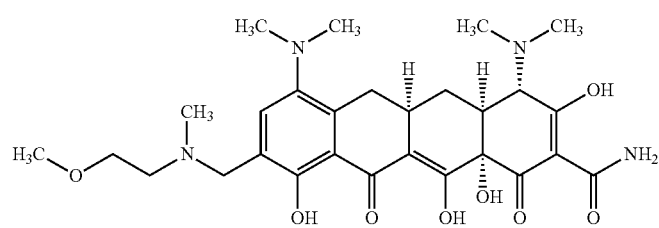

TABLE 1-continued
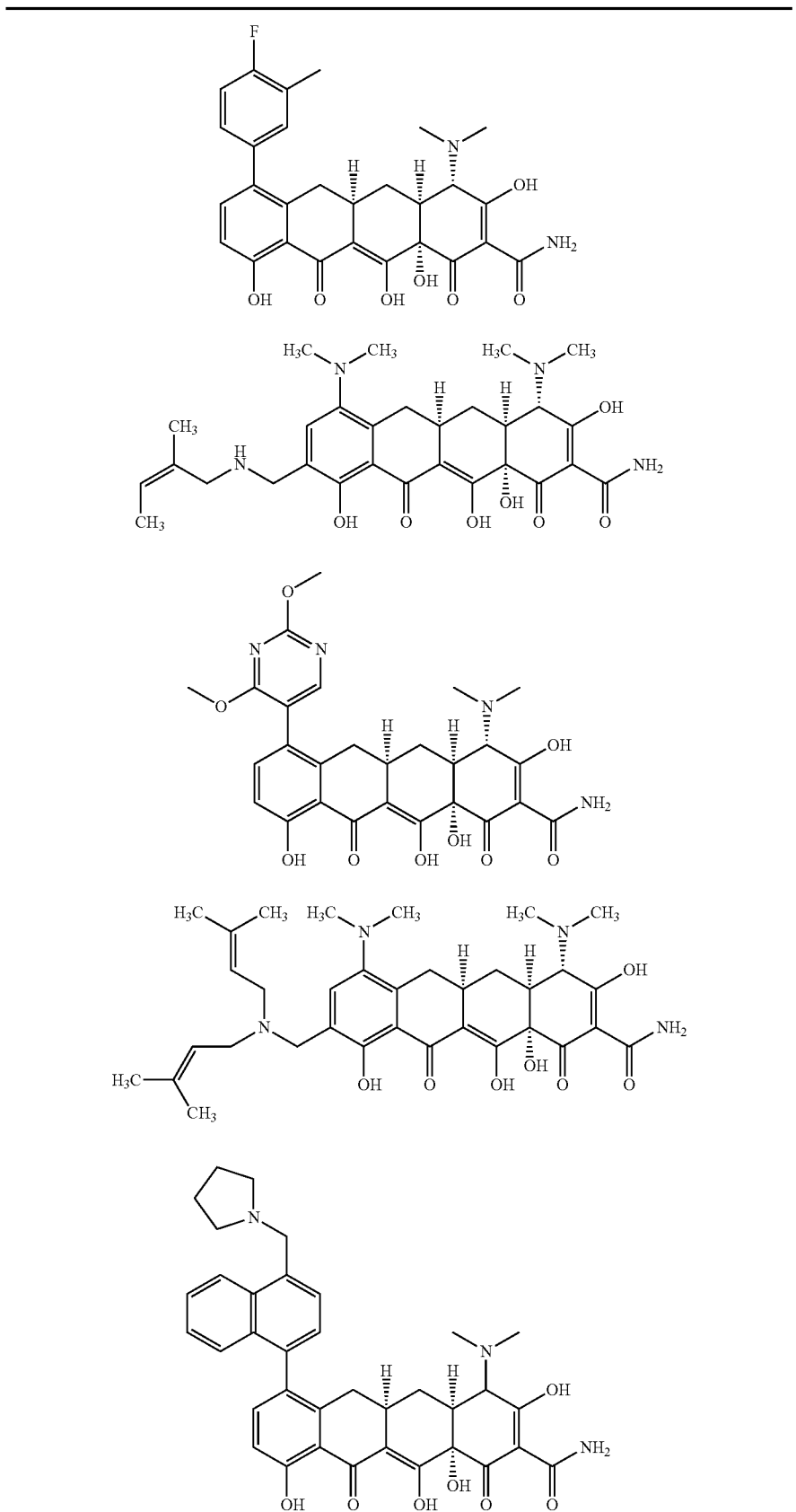

TABLE 1-continued
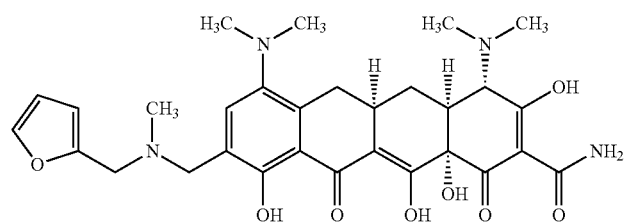
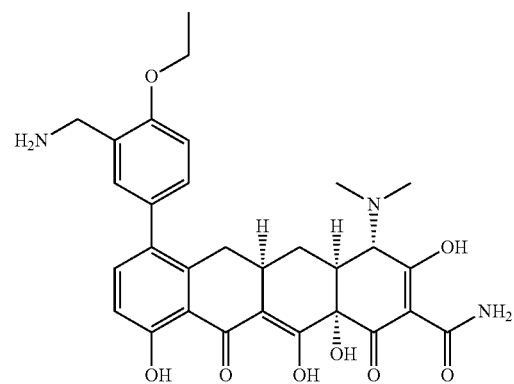
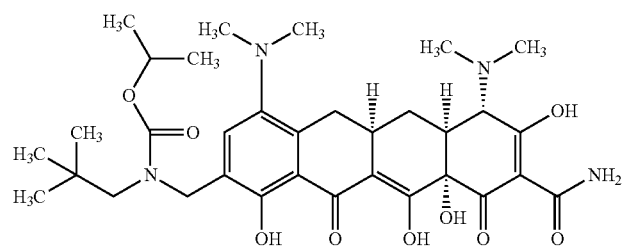
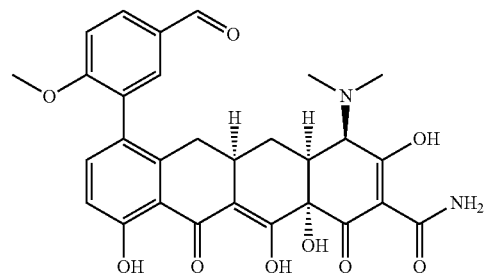
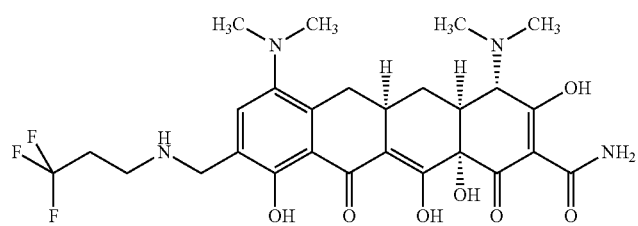

TABLE 1-continued
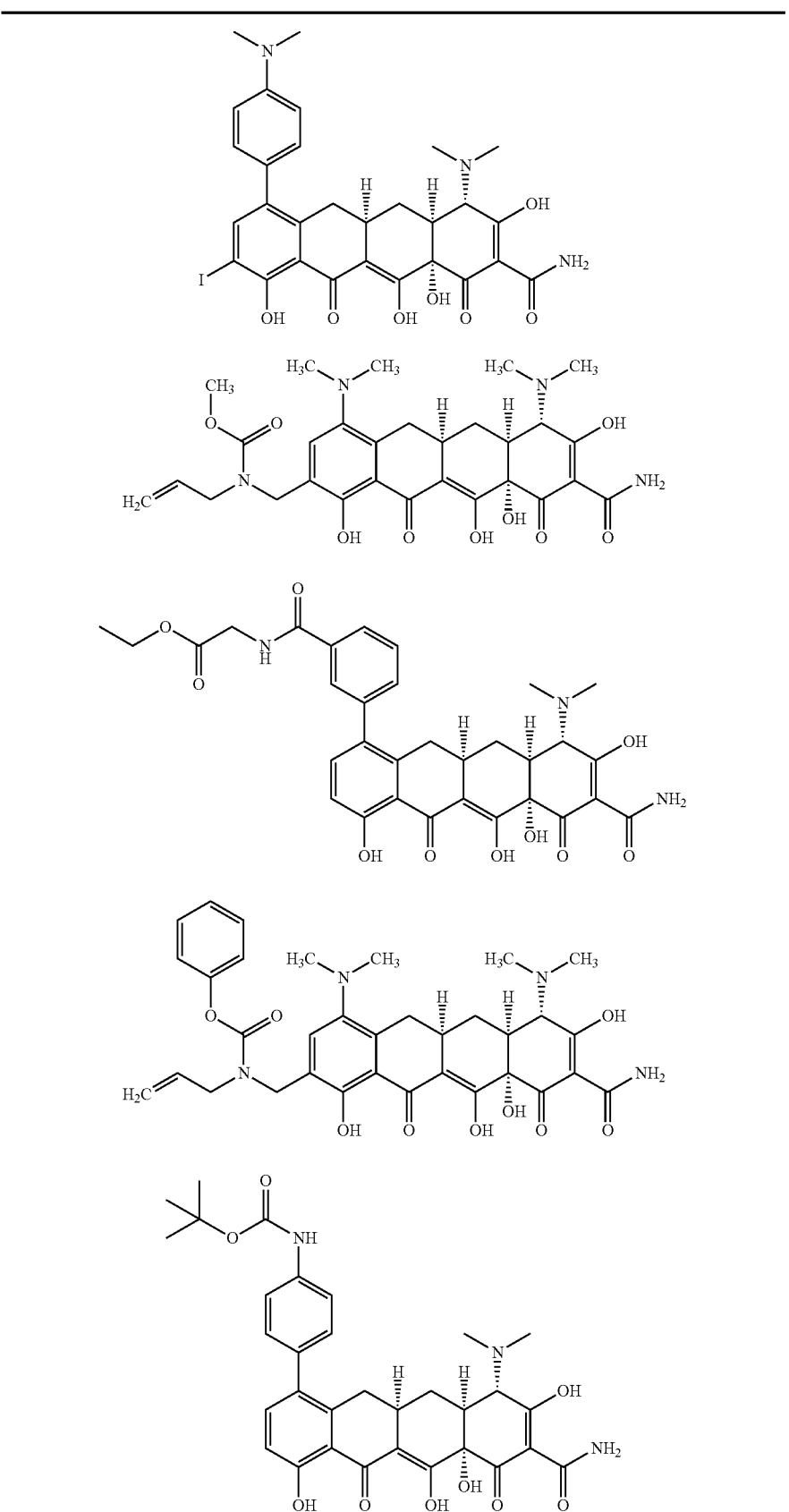

TABLE 1-continued
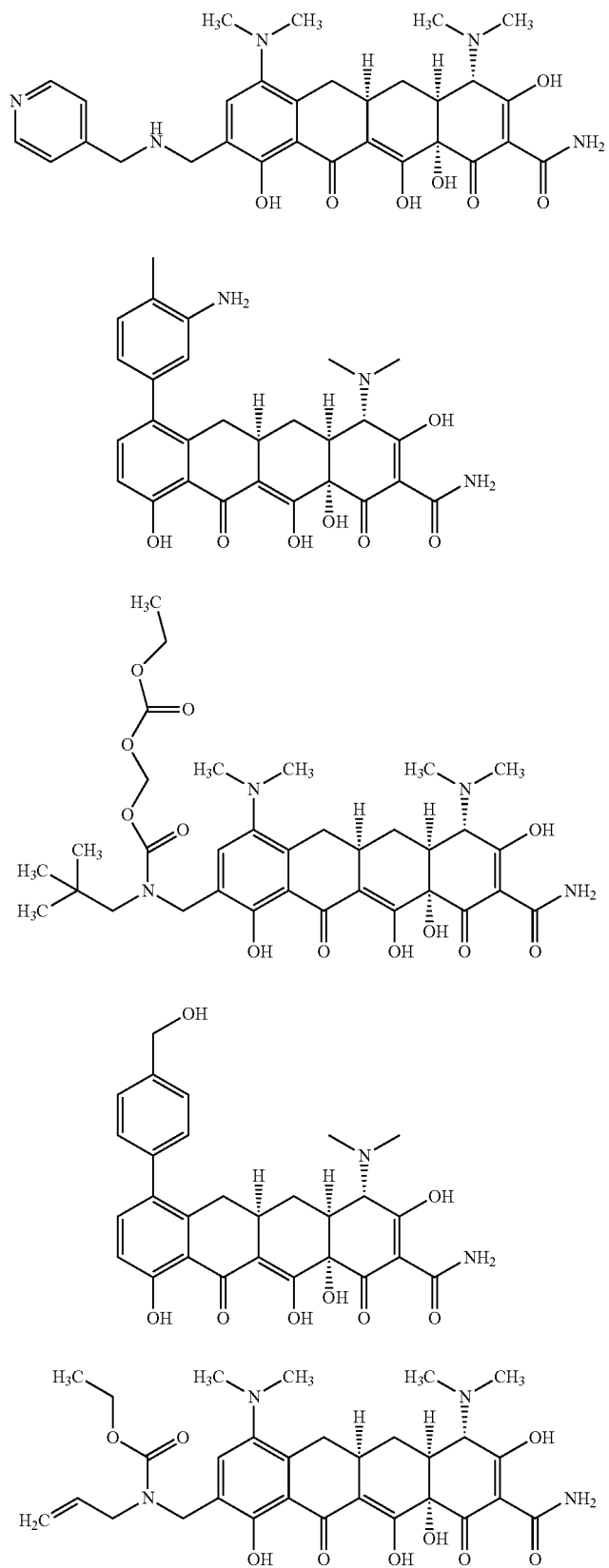

TABLE 1-continued
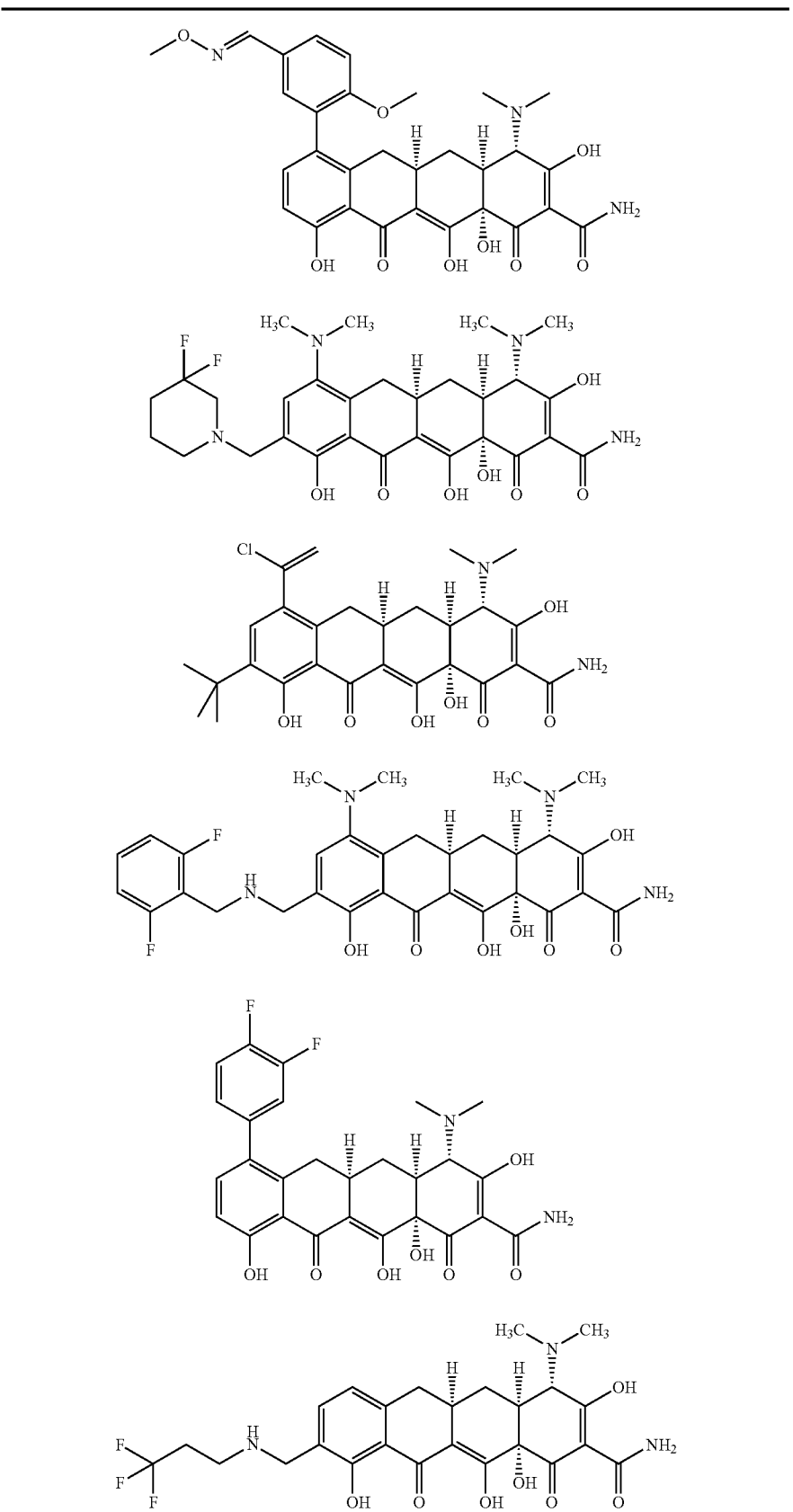

TABLE 1-continued
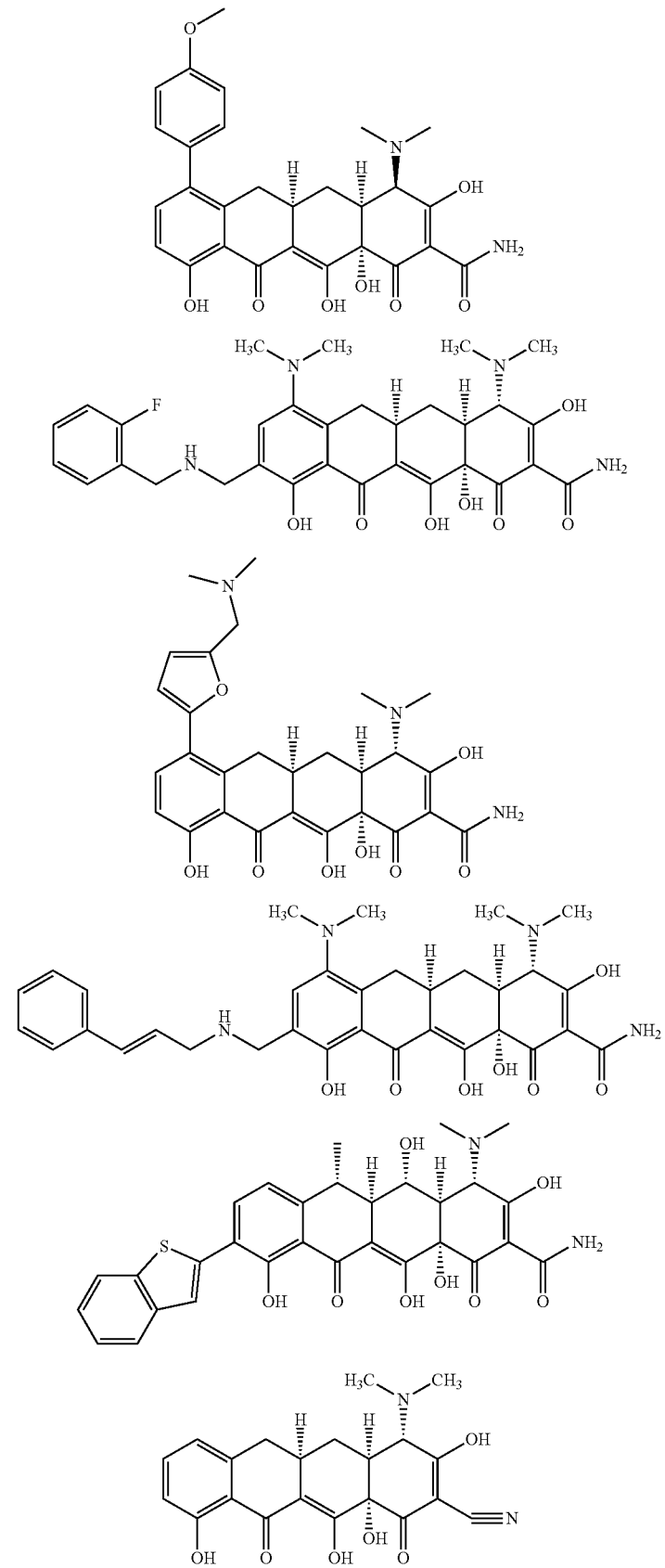

TABLE 1-continued
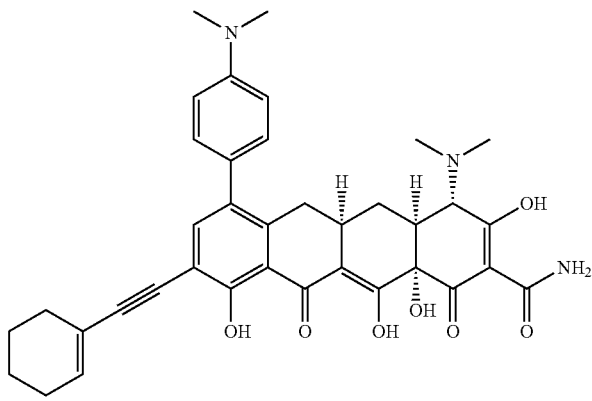
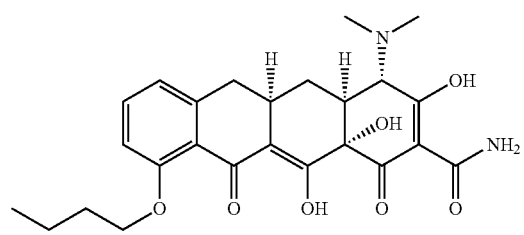
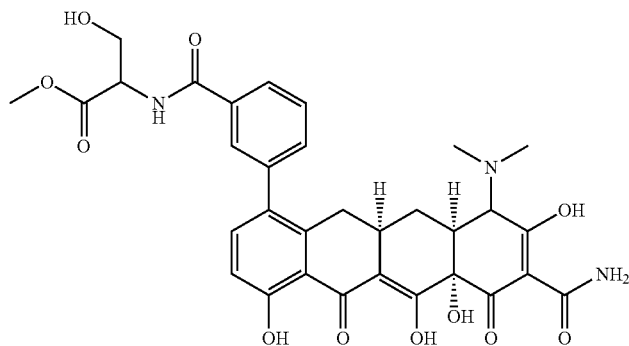
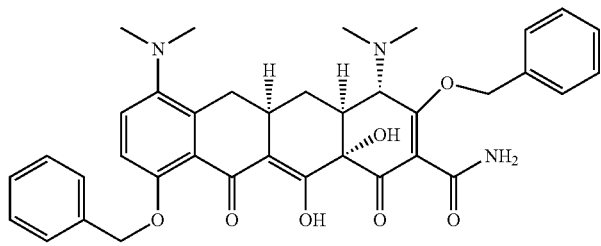
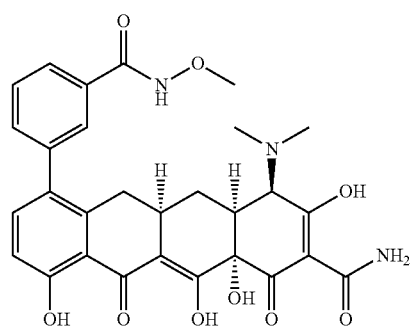

TABLE 1-continued
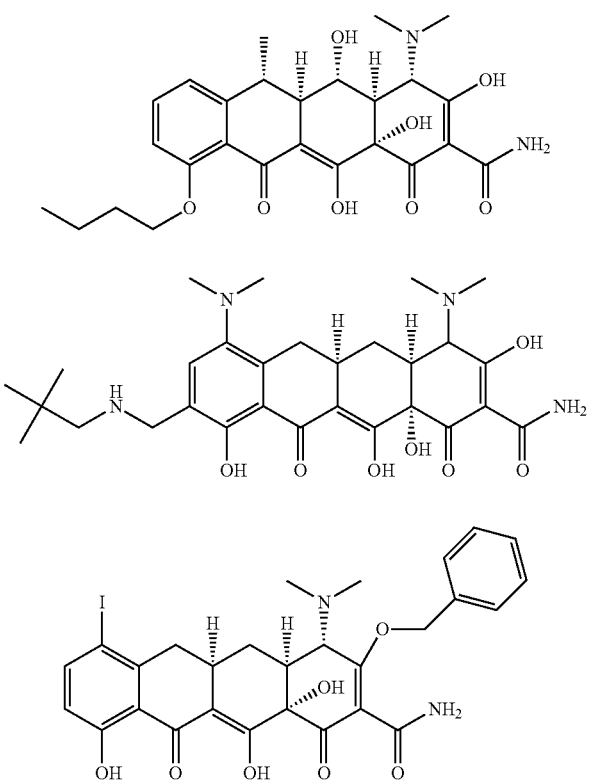
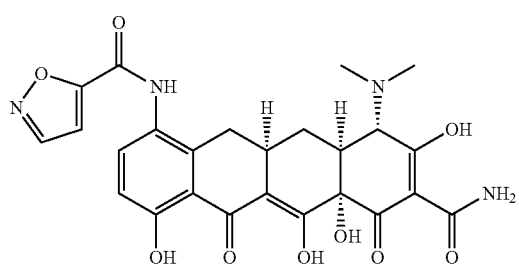
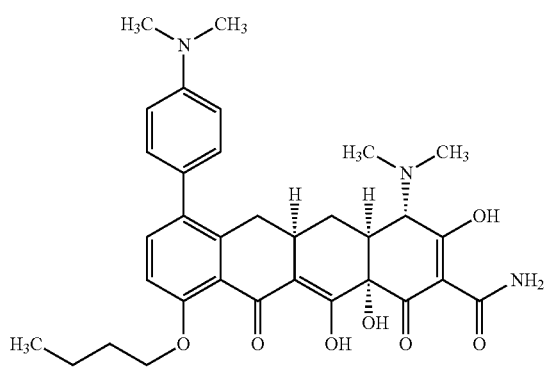

TABLE 1-continued
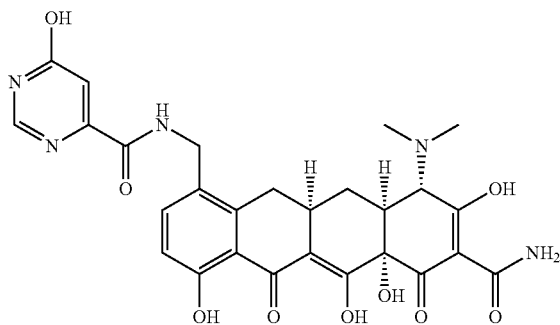
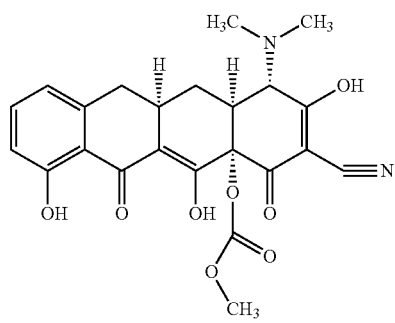
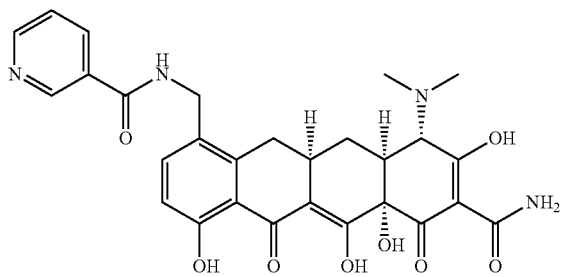
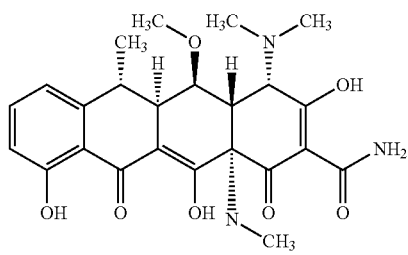
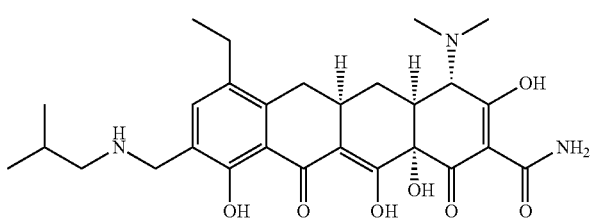

TABLE 1-continued
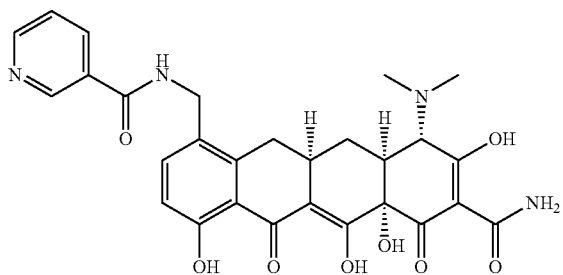
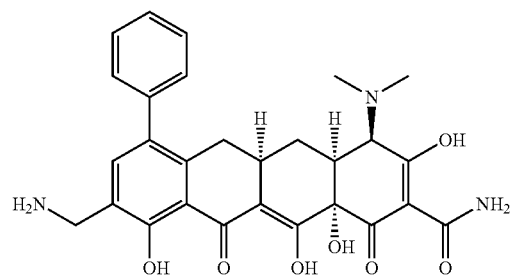
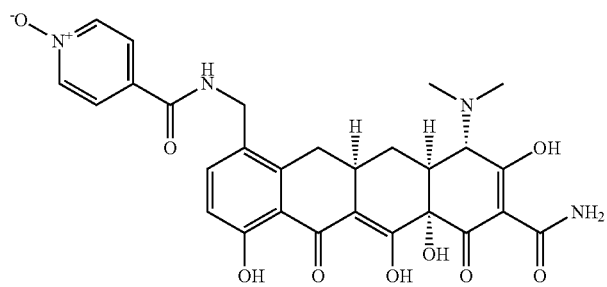
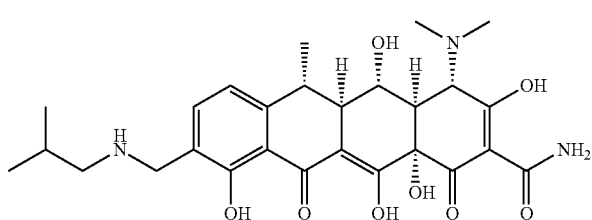
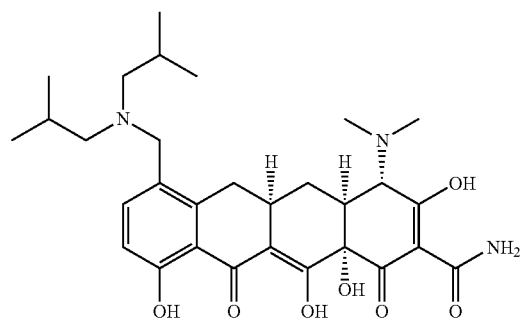

TABLE 1-continued
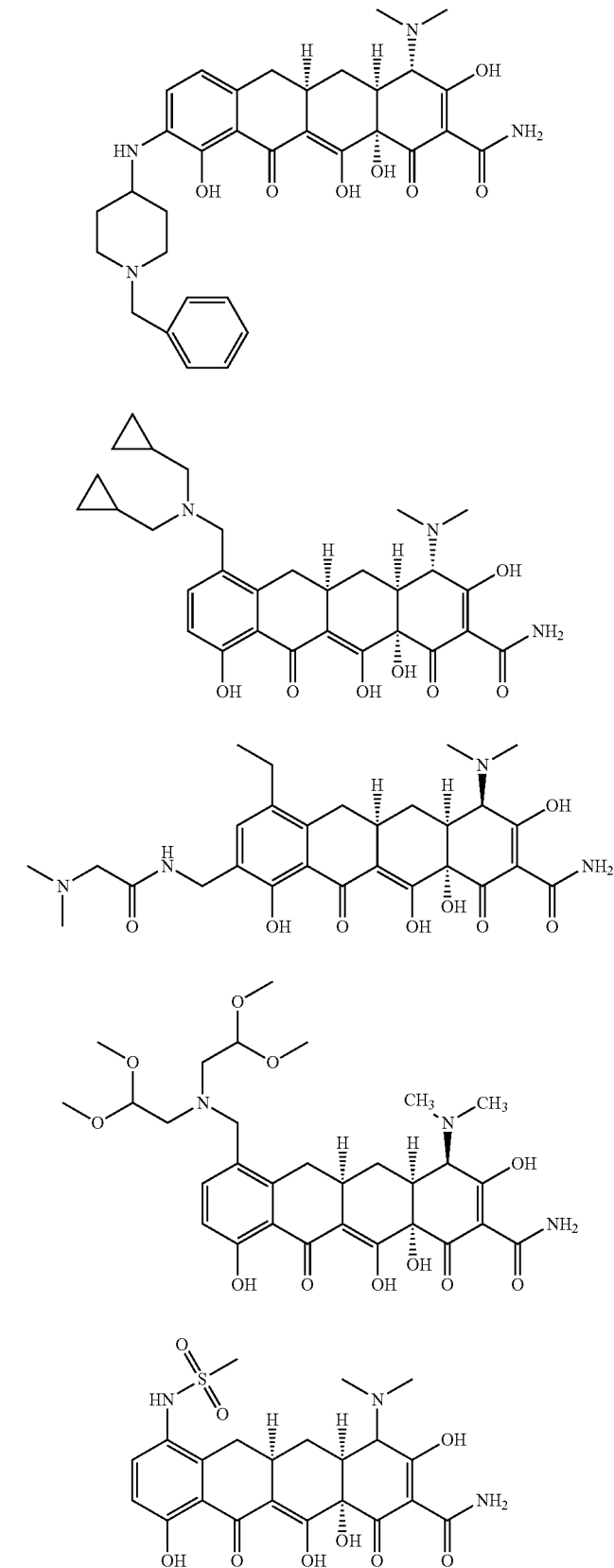

TABLE 1-continued
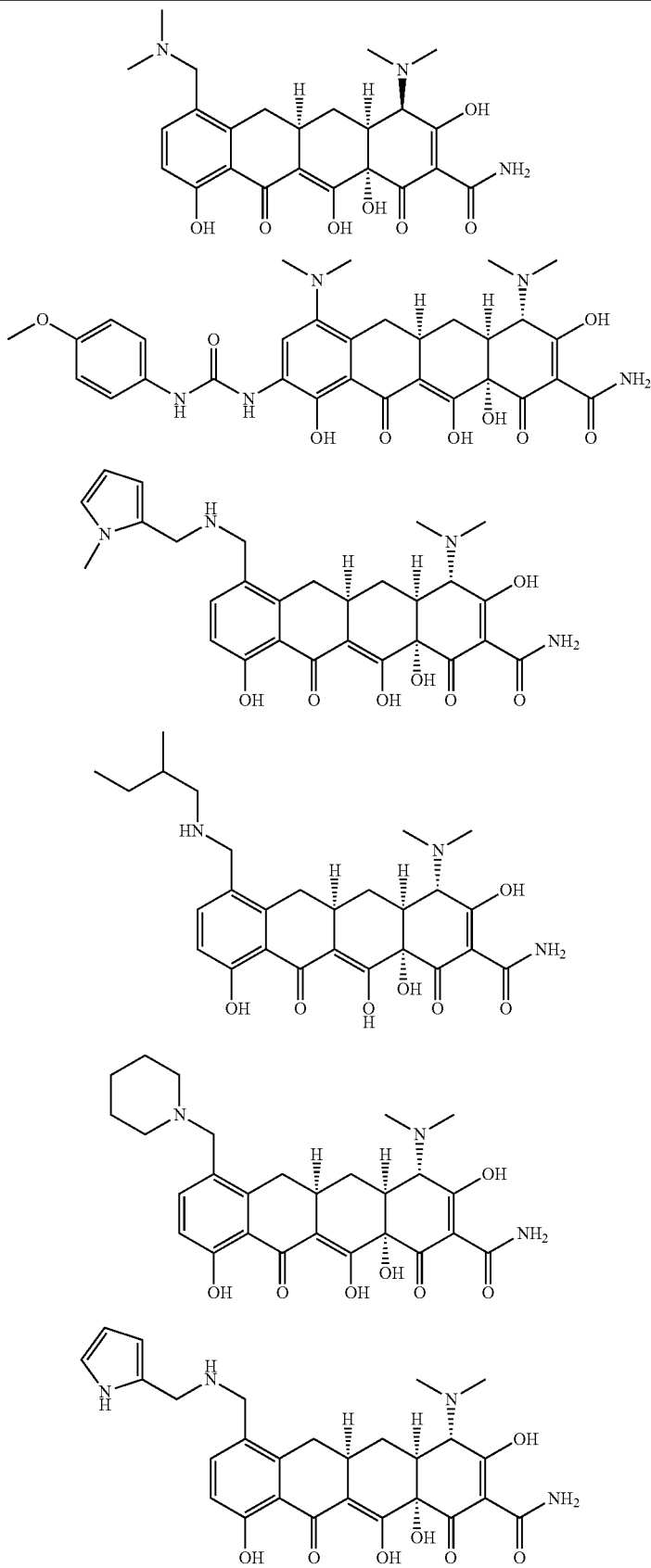

TABLE 1-continued
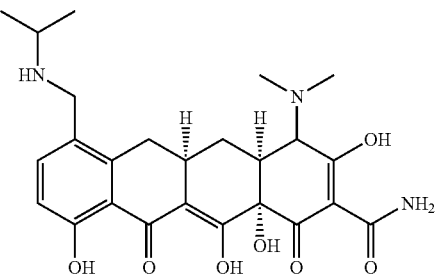
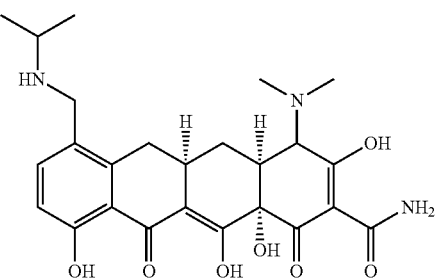
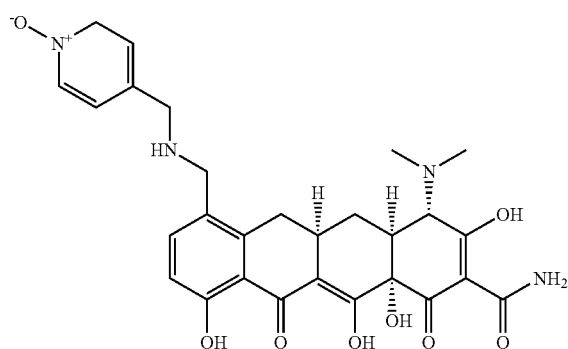
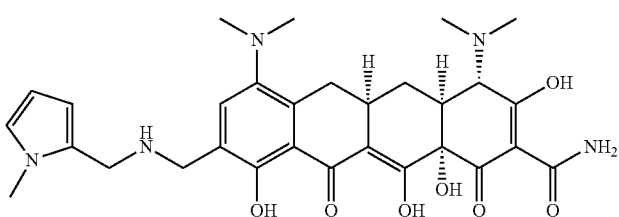
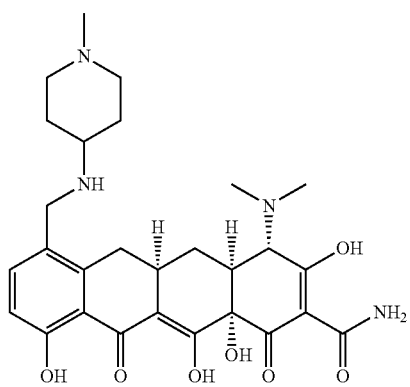

TABLE 1-continued
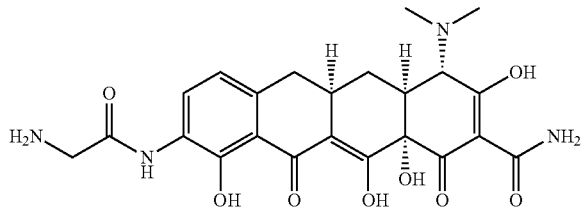
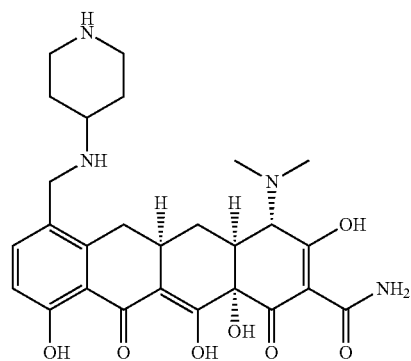
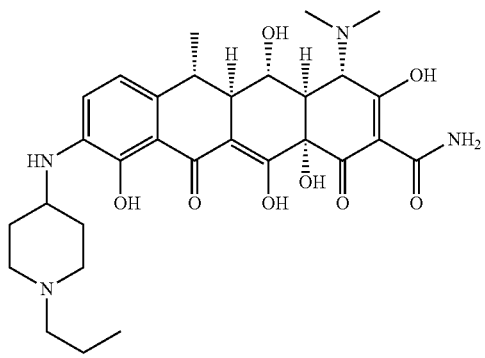
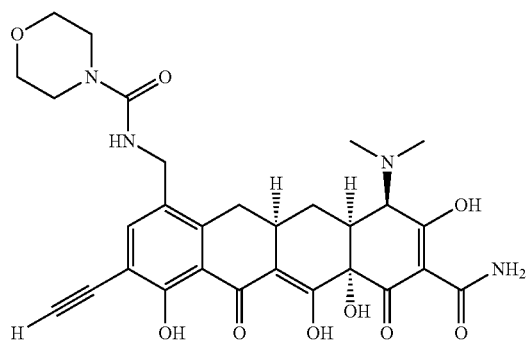
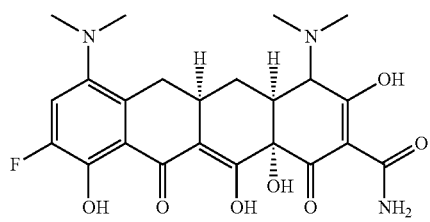

TABLE 1-continued
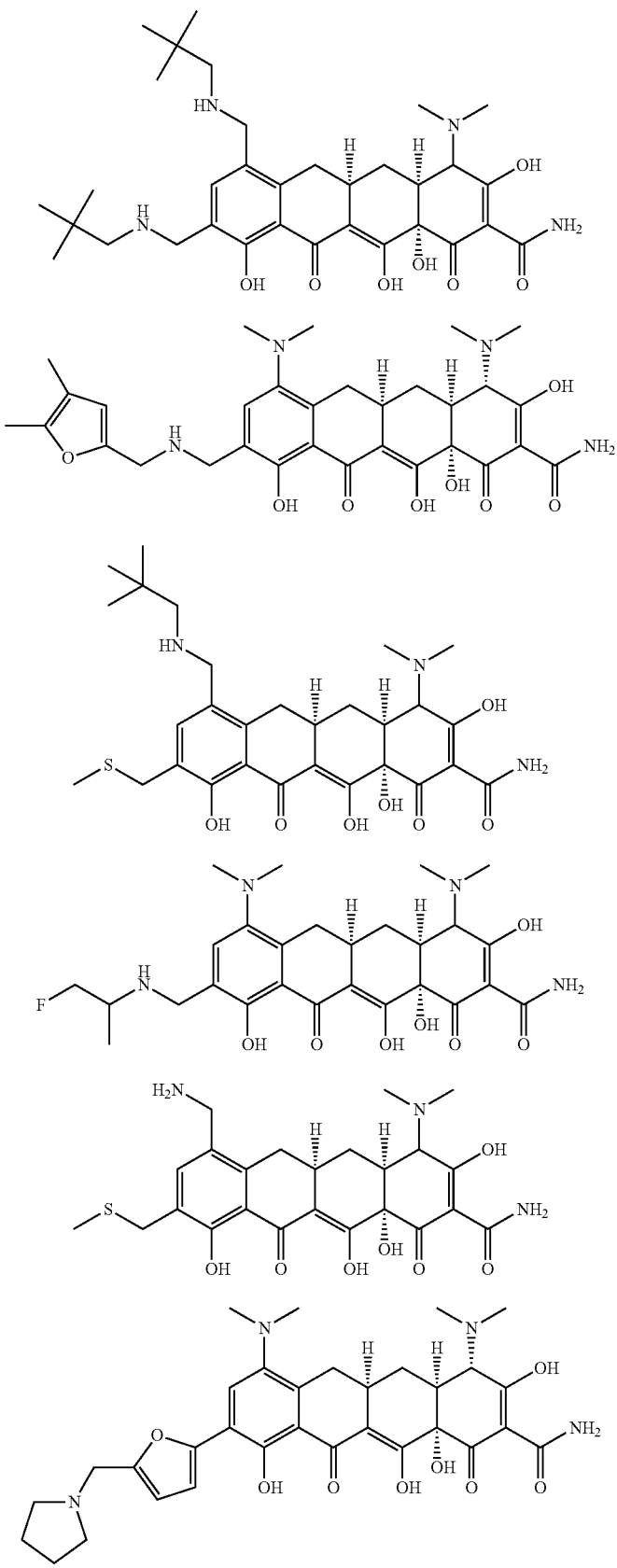

TABLE 1-continued
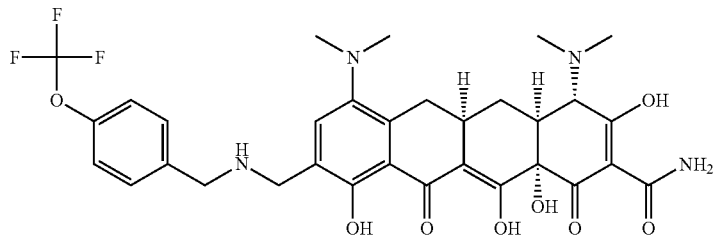
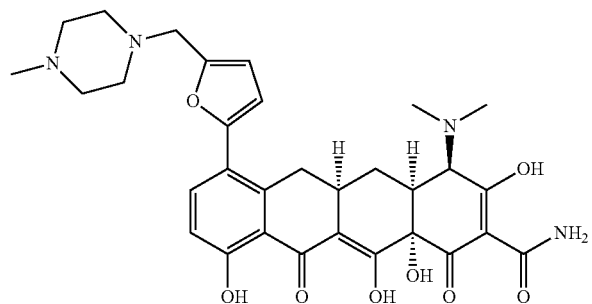
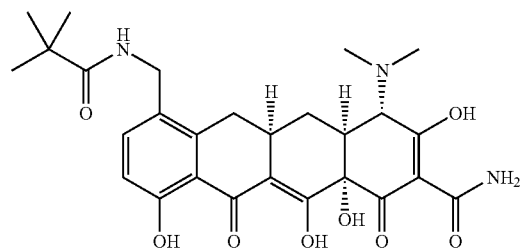
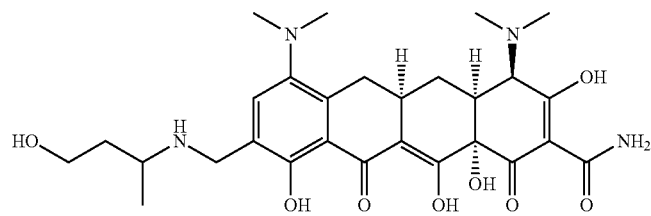
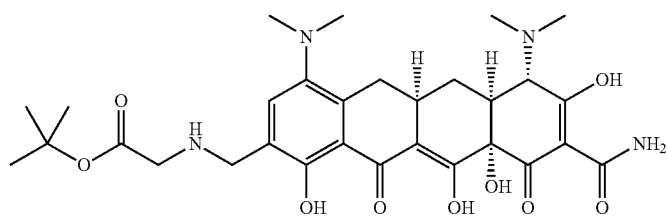
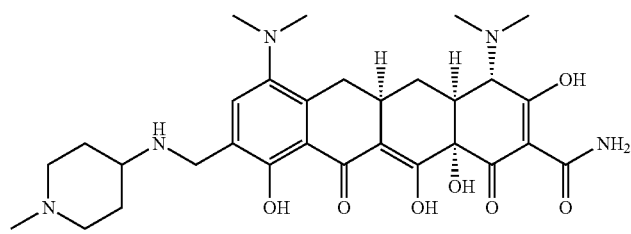

TABLE 1-continued
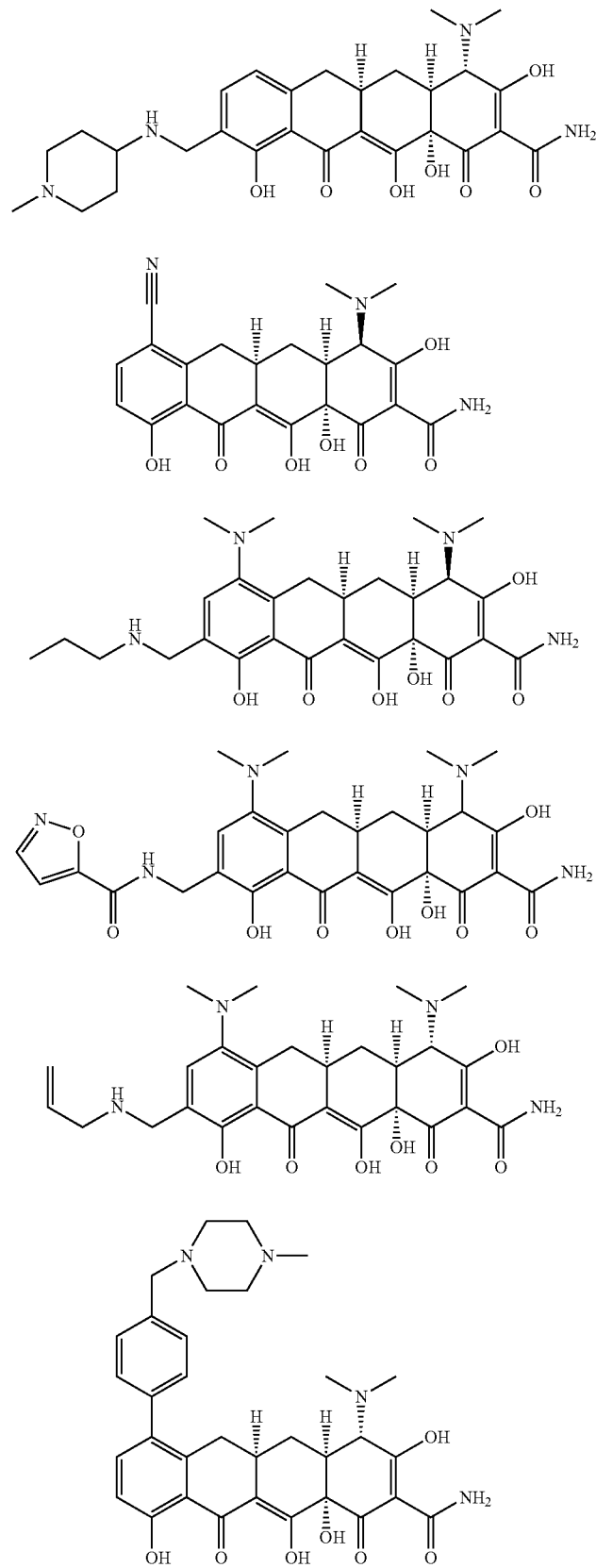

TABLE 1-continued
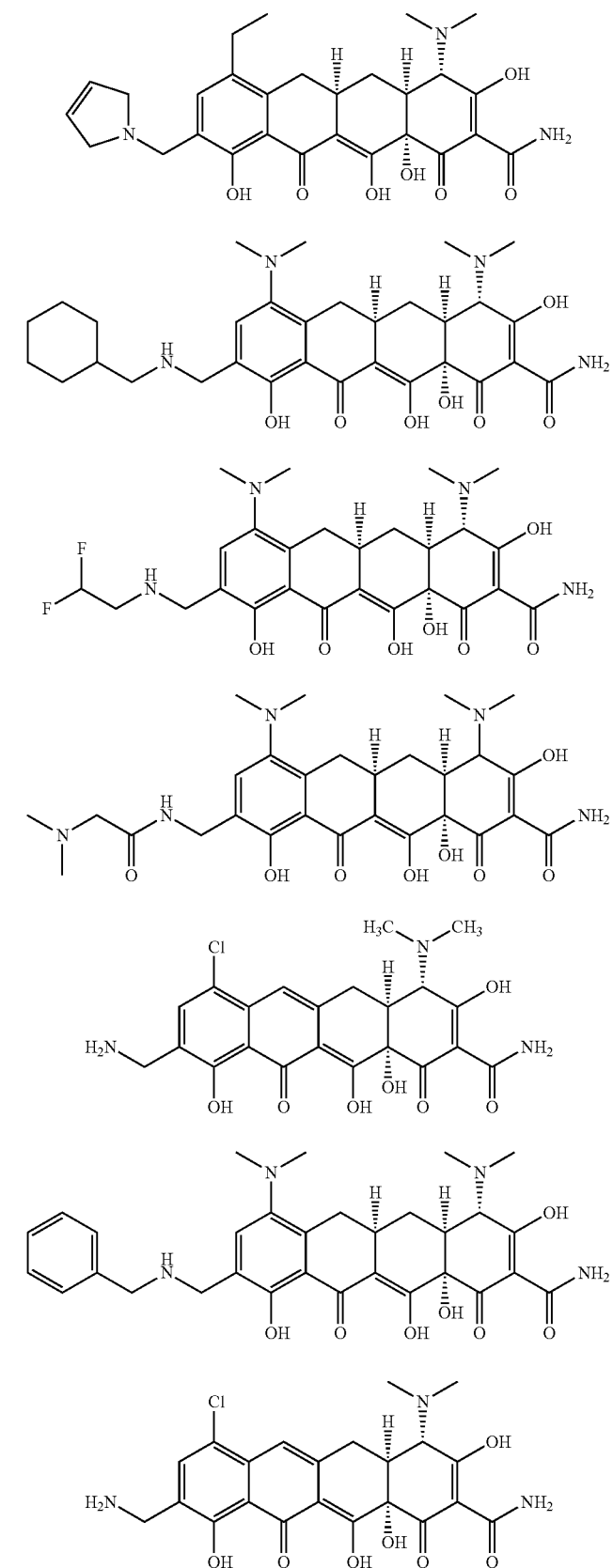

TABLE 1-continued
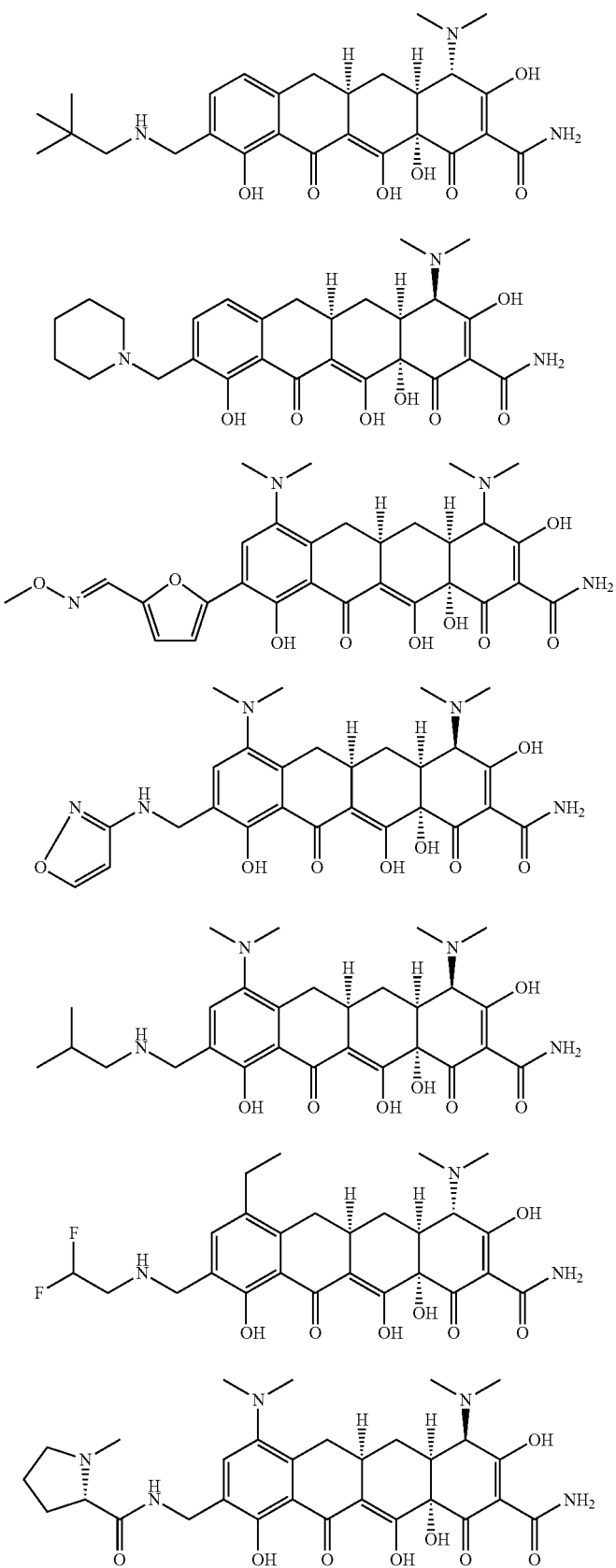

TABLE 1-continued
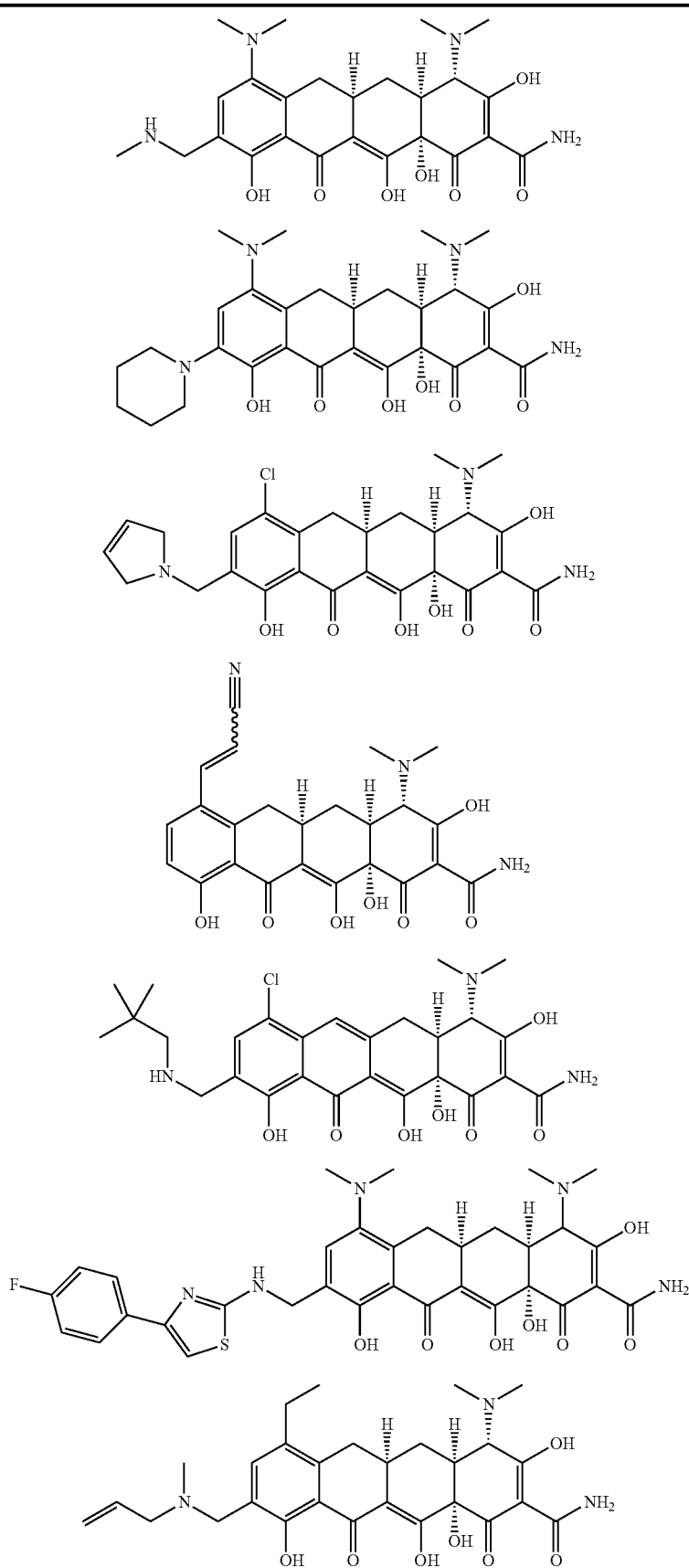

TABLE 1-continued
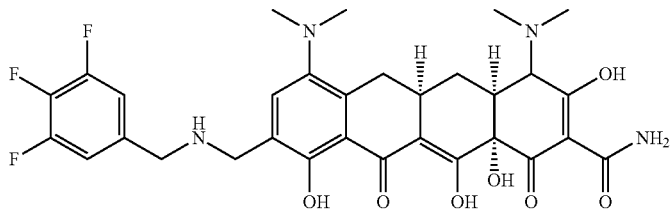
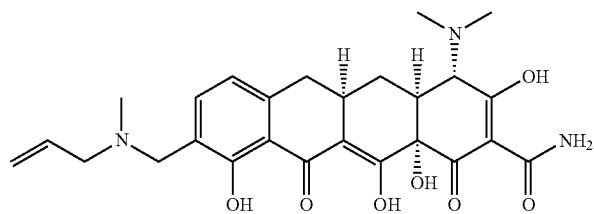
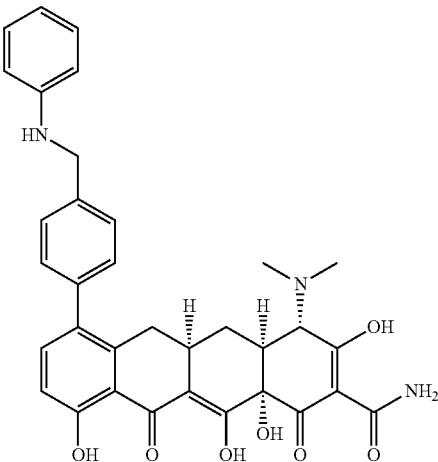
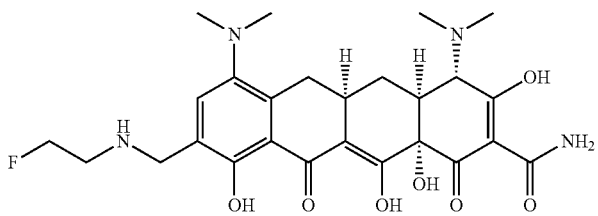
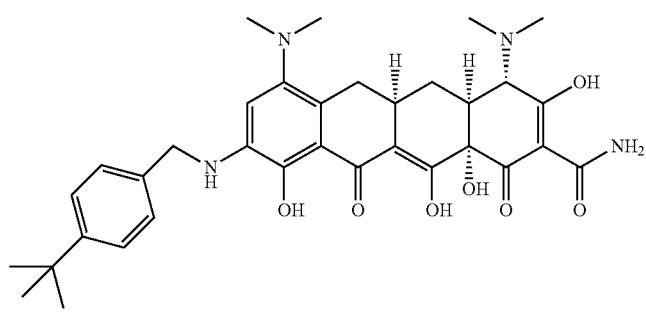

TABLE 1-continued
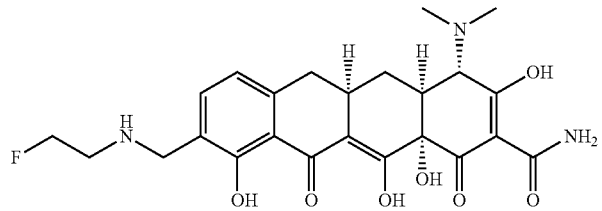
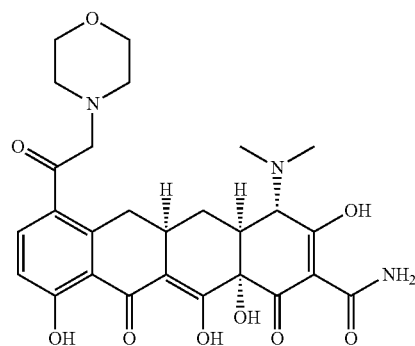
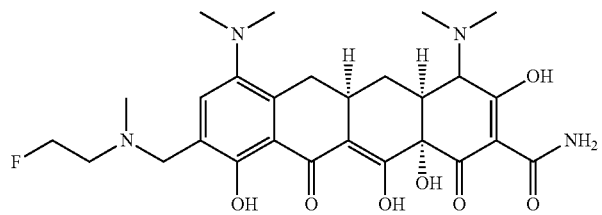
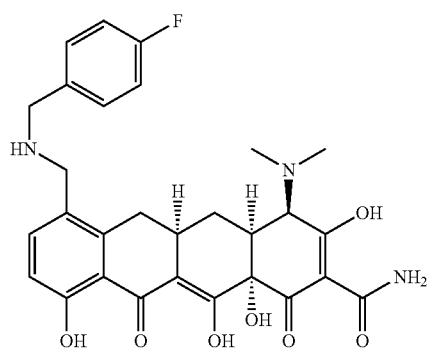
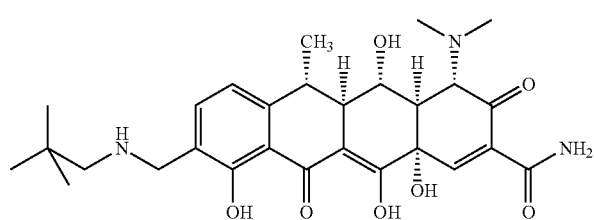

TABLE 1-continued
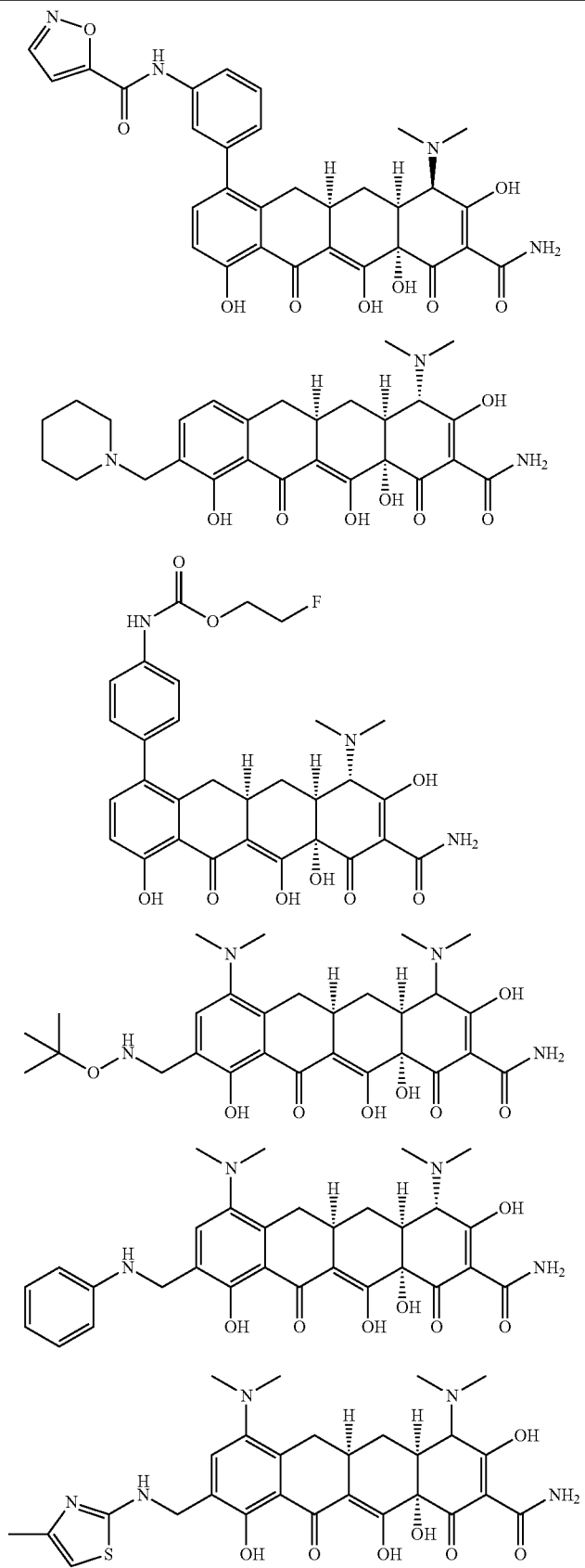

TABLE 1-continued
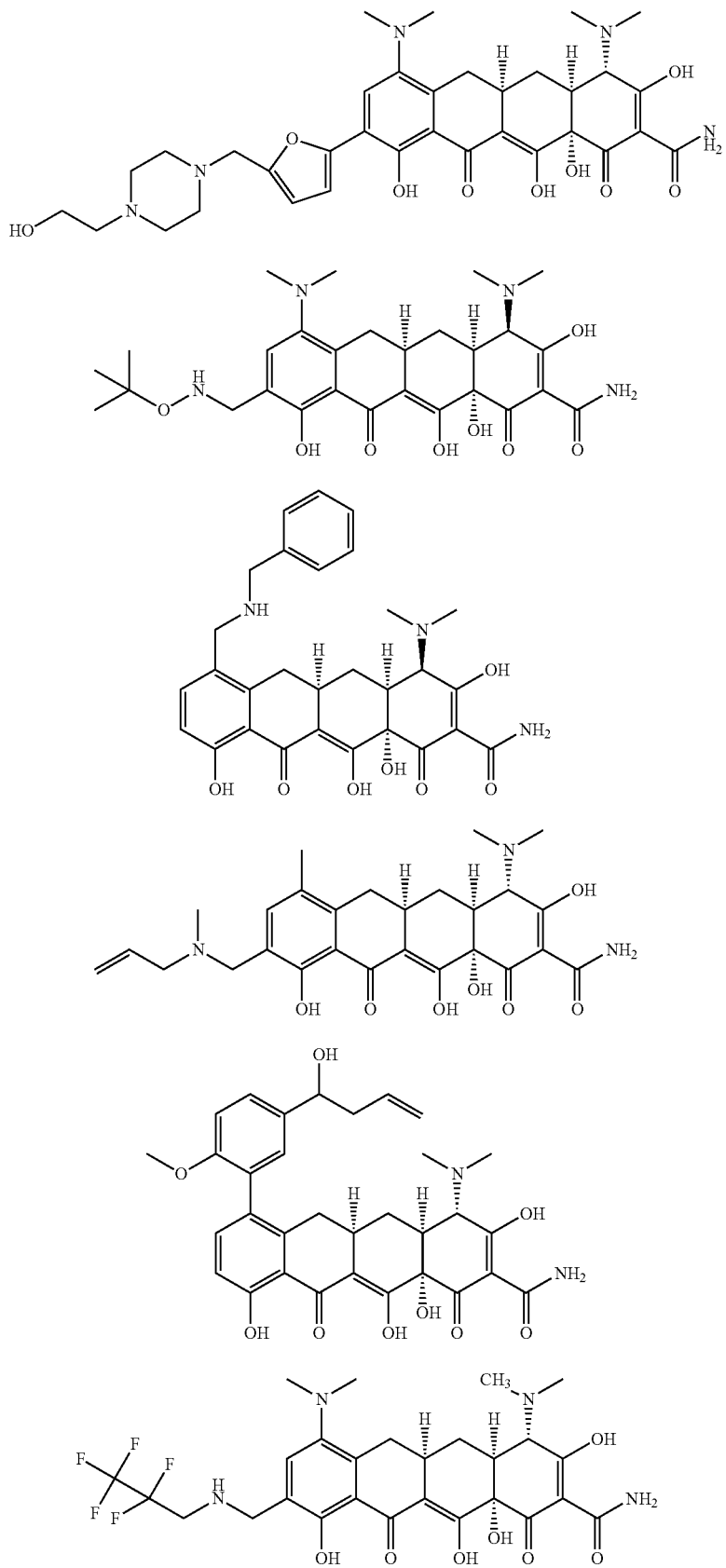

TABLE 1-continued
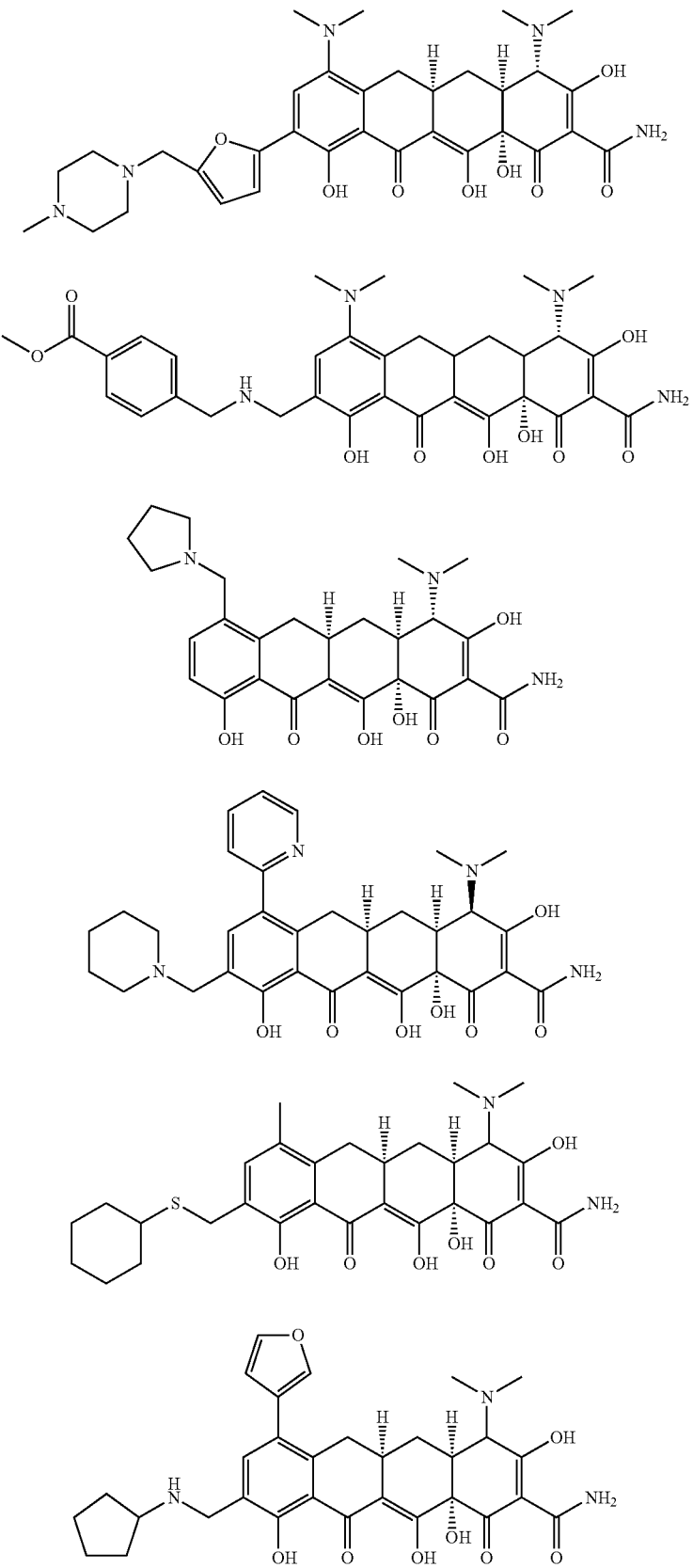

TABLE 1-continued
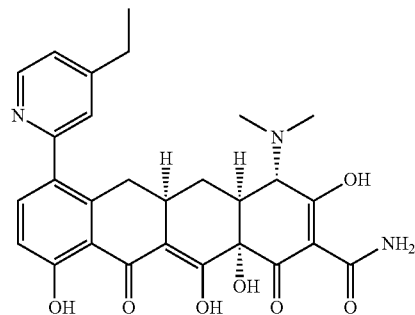
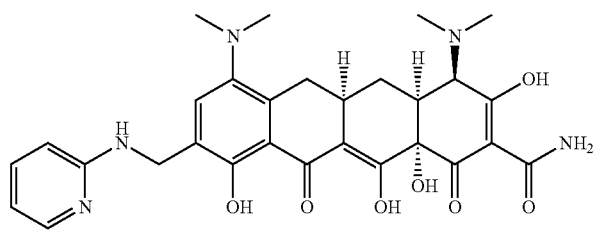
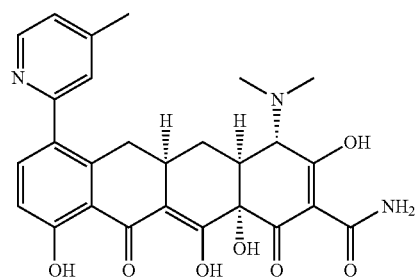
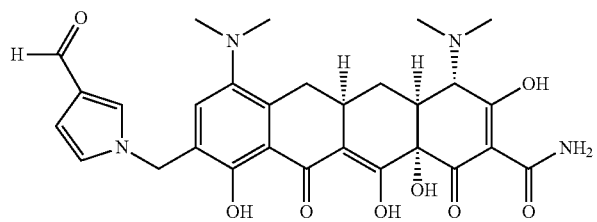
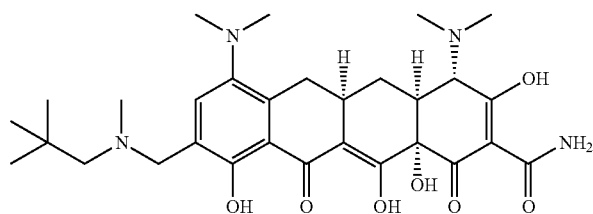
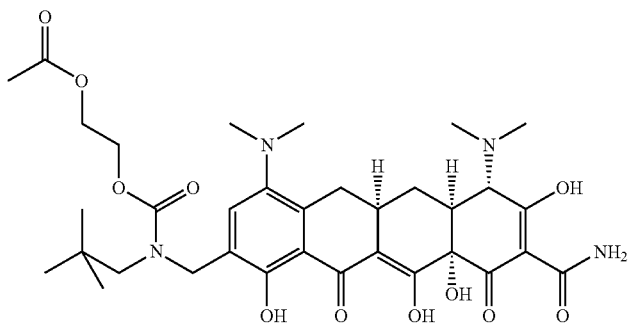

TABLE 1-continued
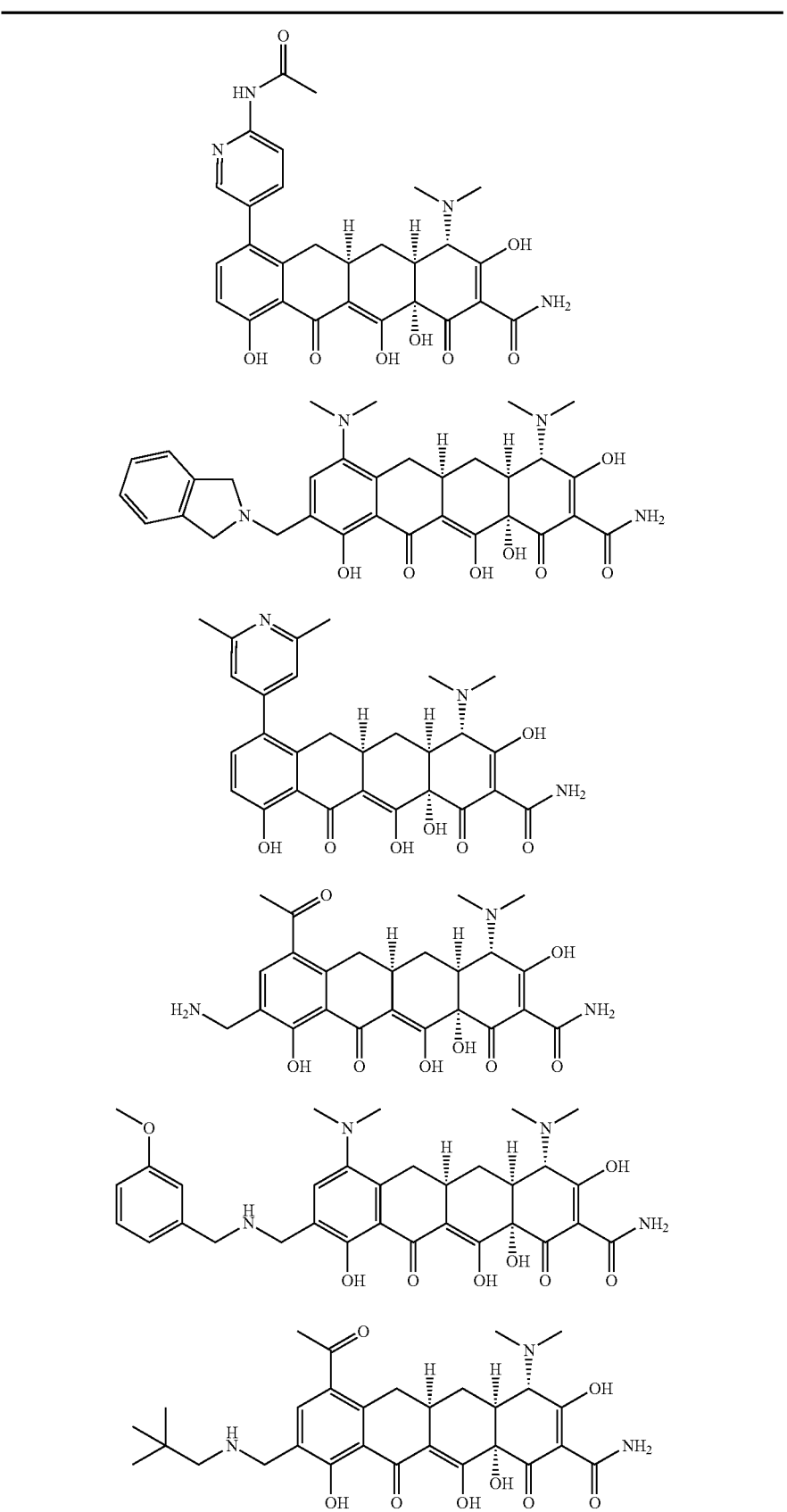

TABLE 1-continued
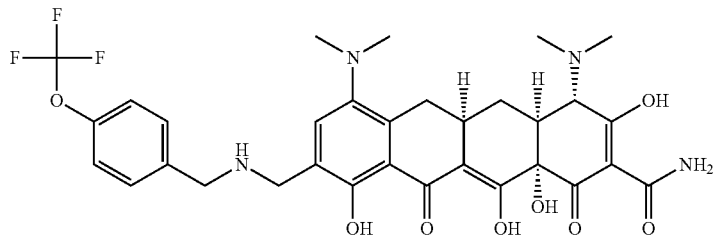
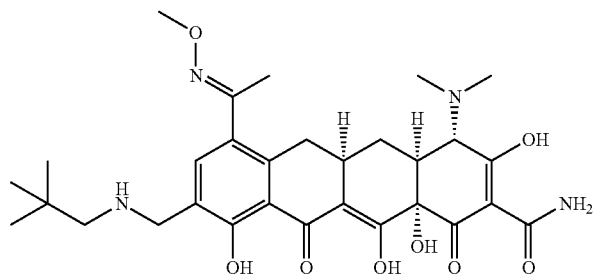
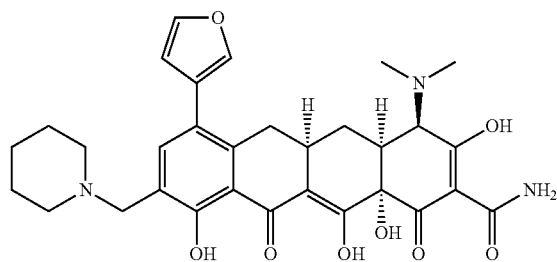
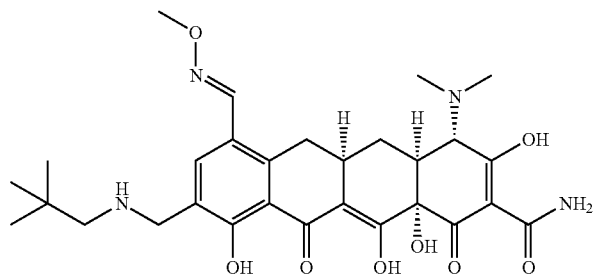
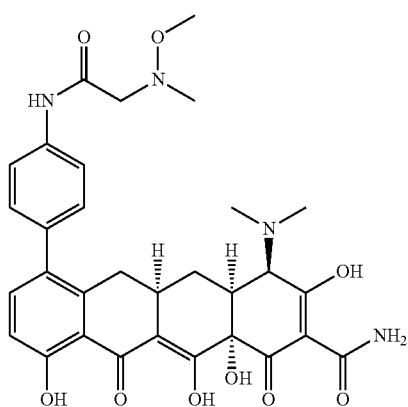

TABLE 1-continued
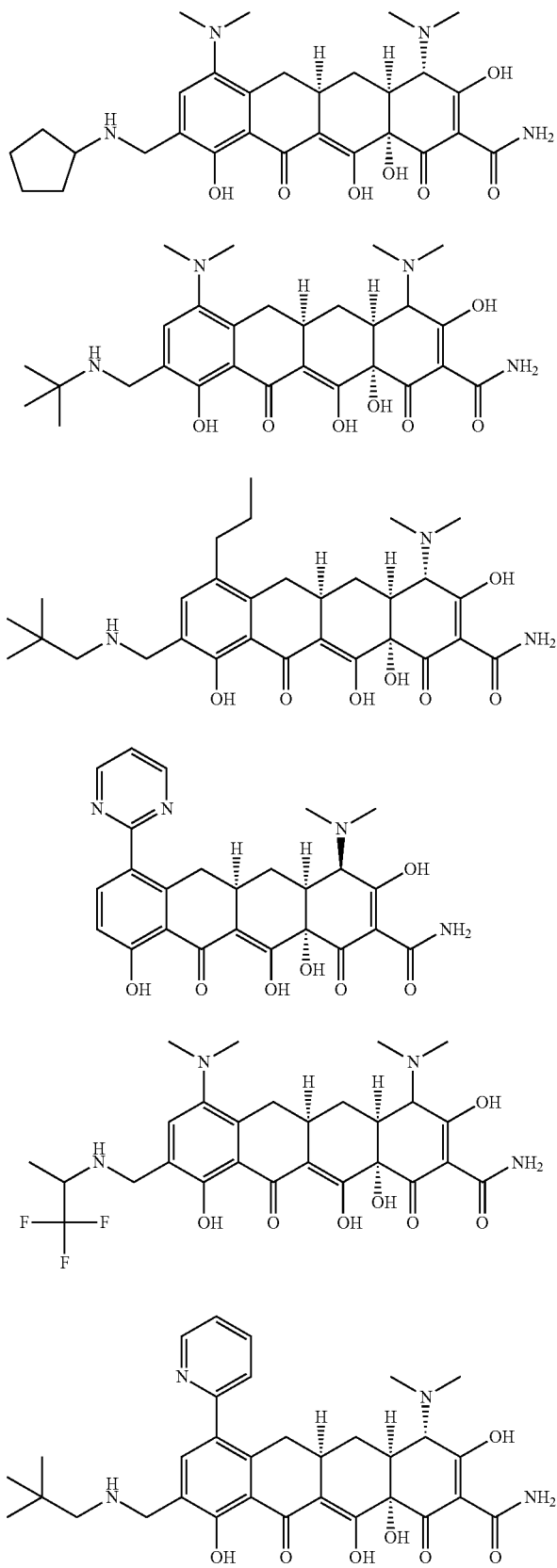

TABLE 1-continued
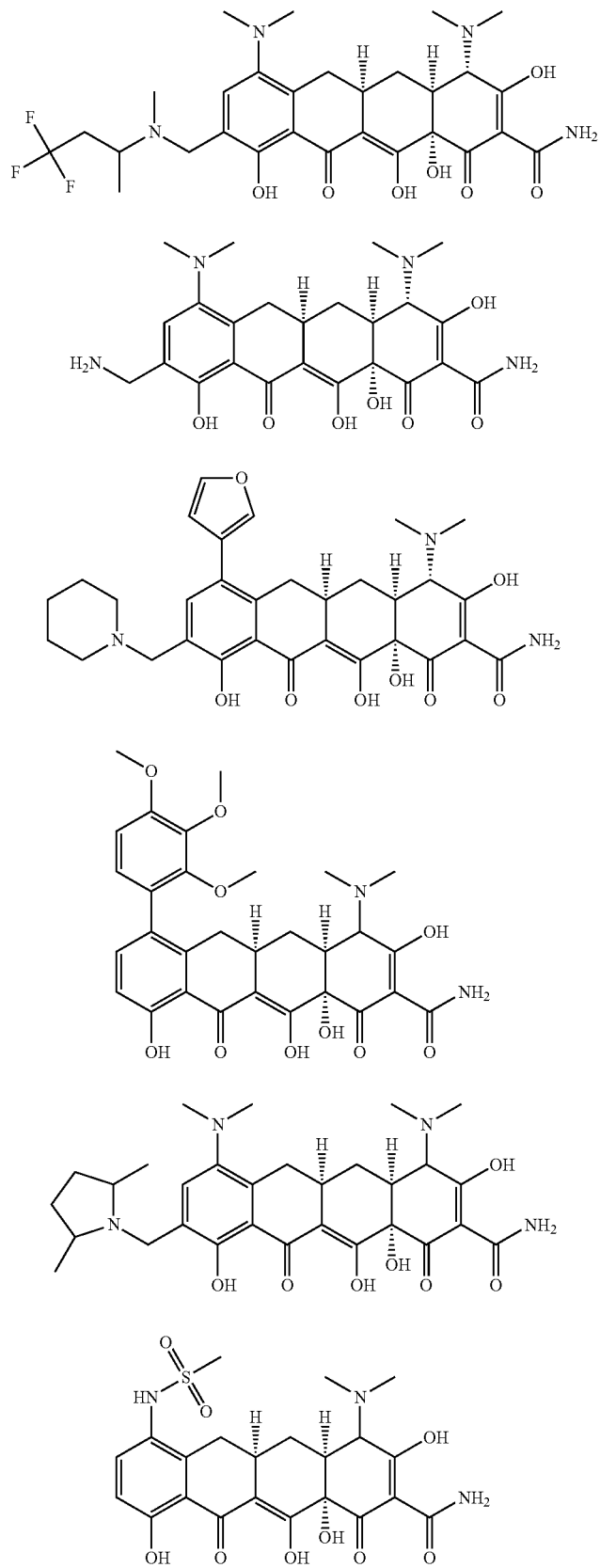

TABLE 1-continued
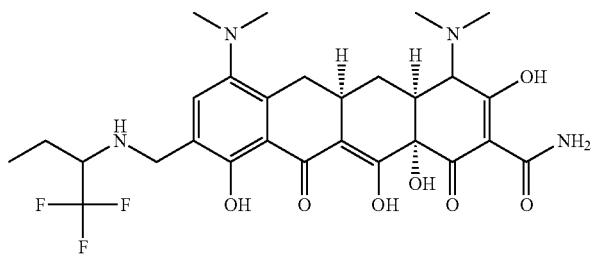
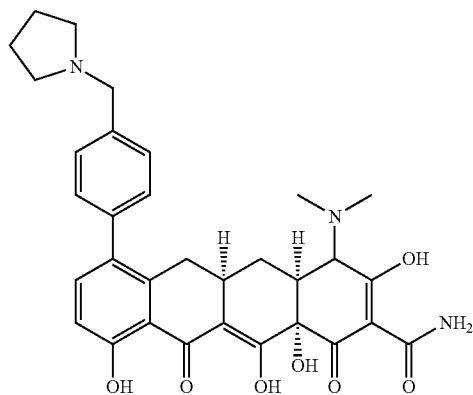
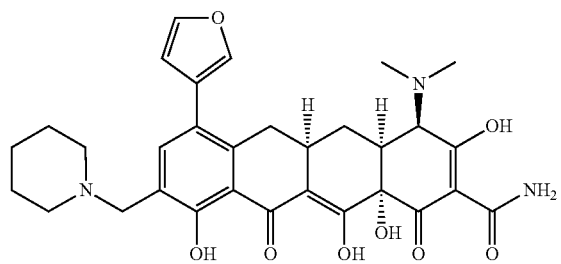
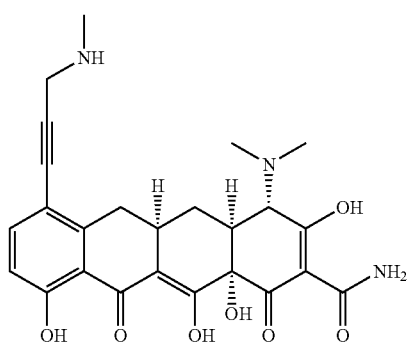
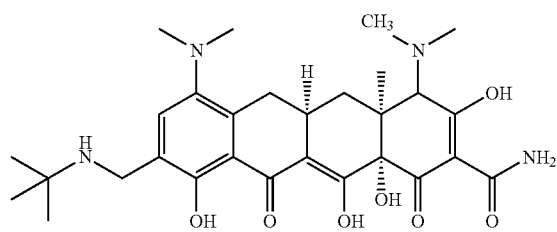

TABLE 1-continued
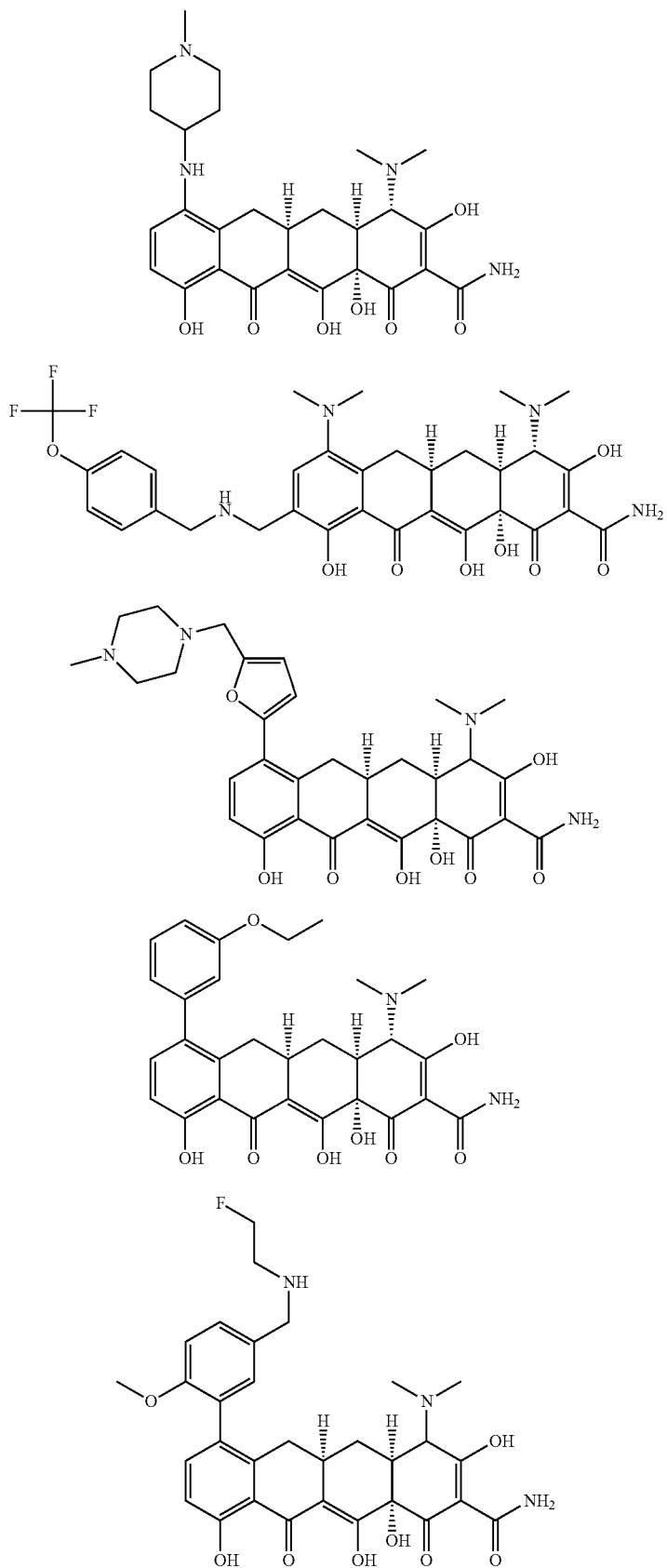

TABLE 1-continued
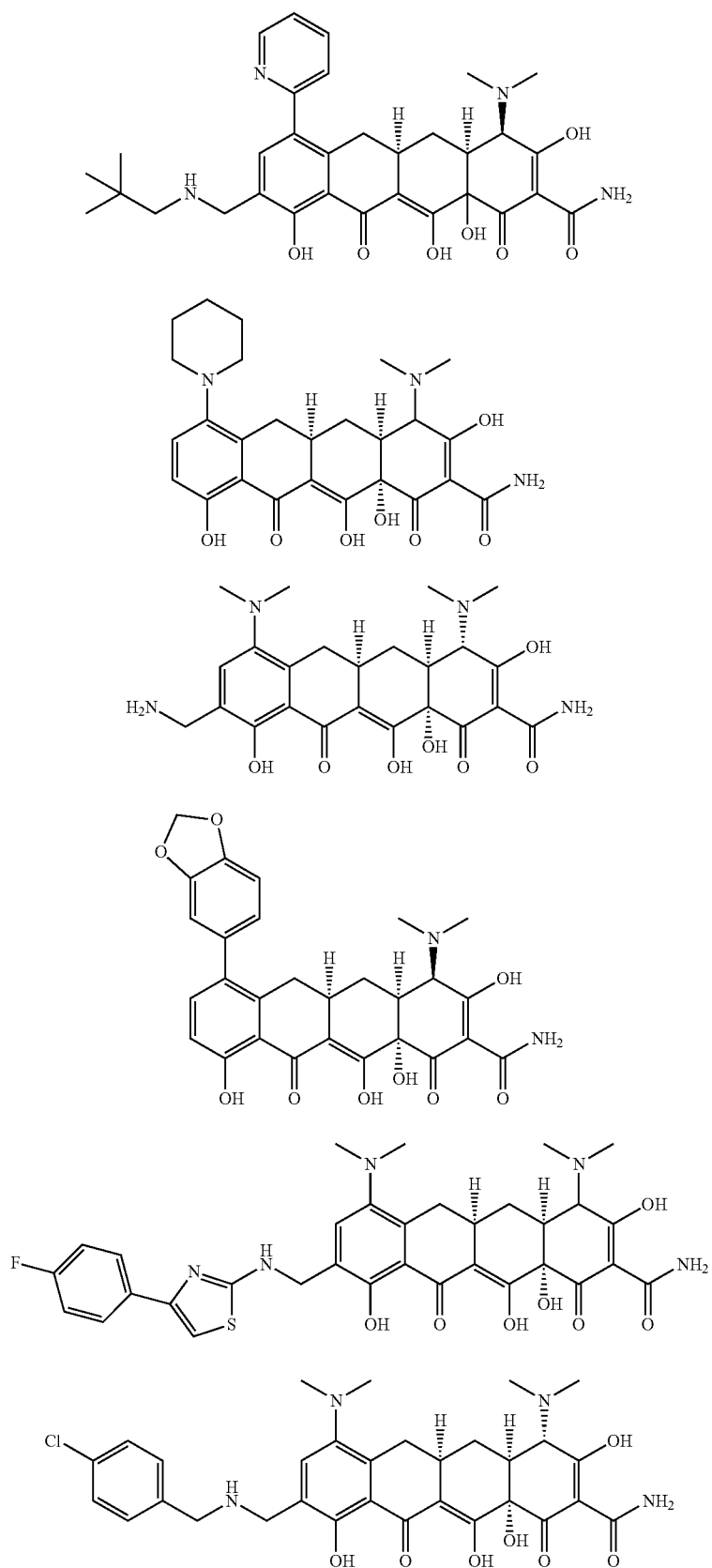

TABLE 1-continued
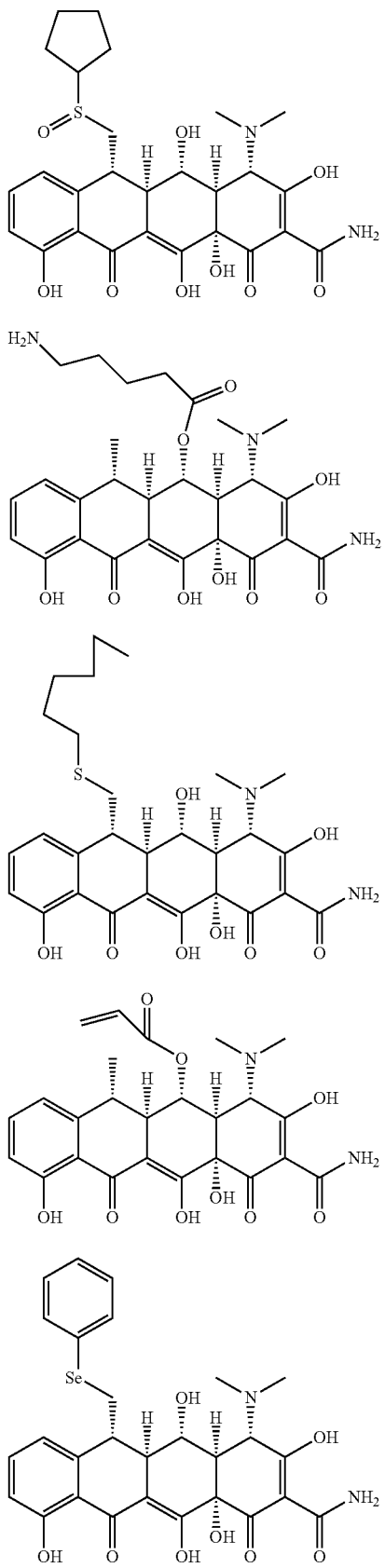

TABLE 1-continued
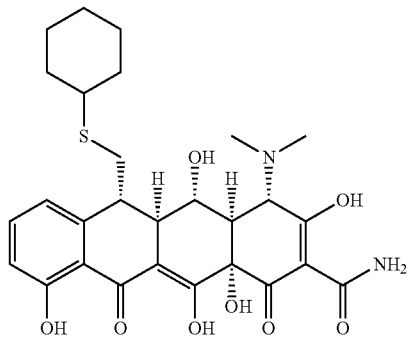
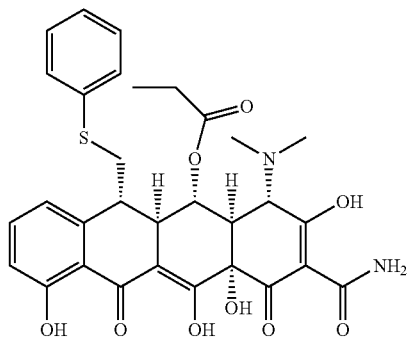
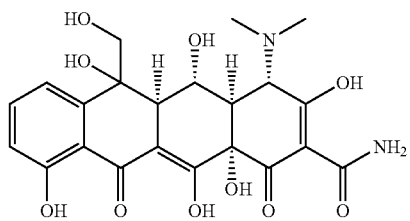
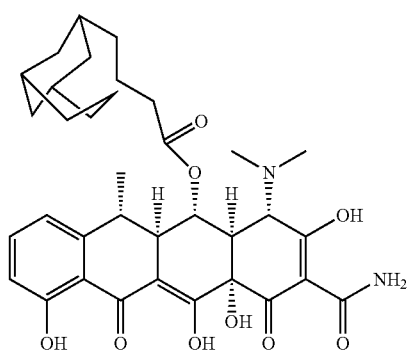
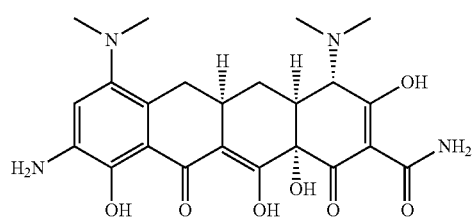

TABLE 1-continued
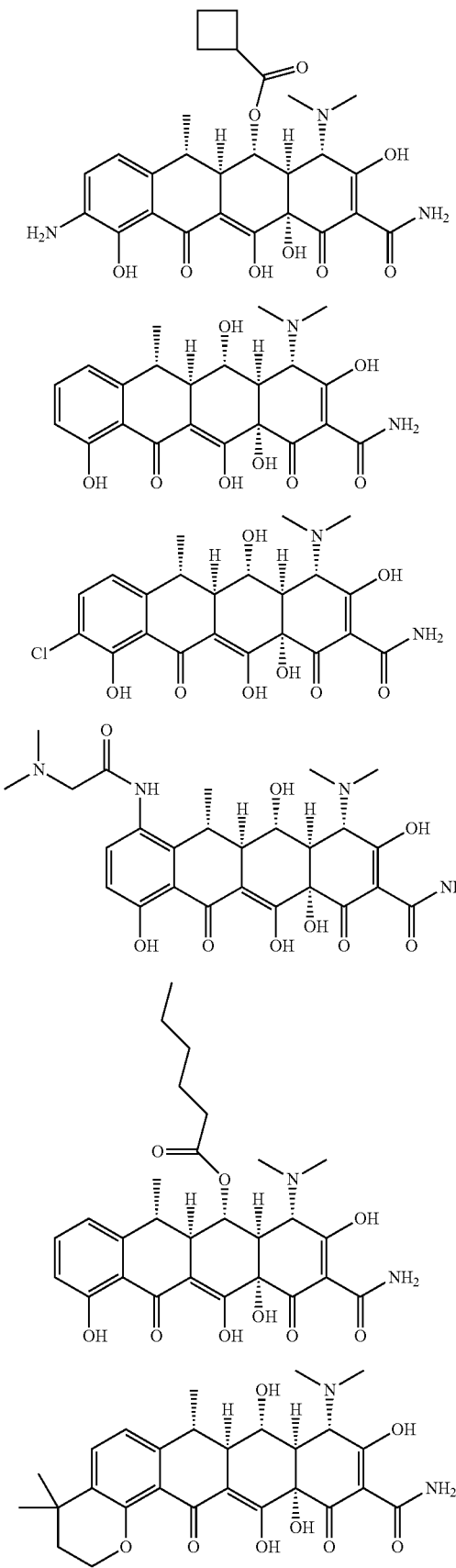

TABLE 1-continued
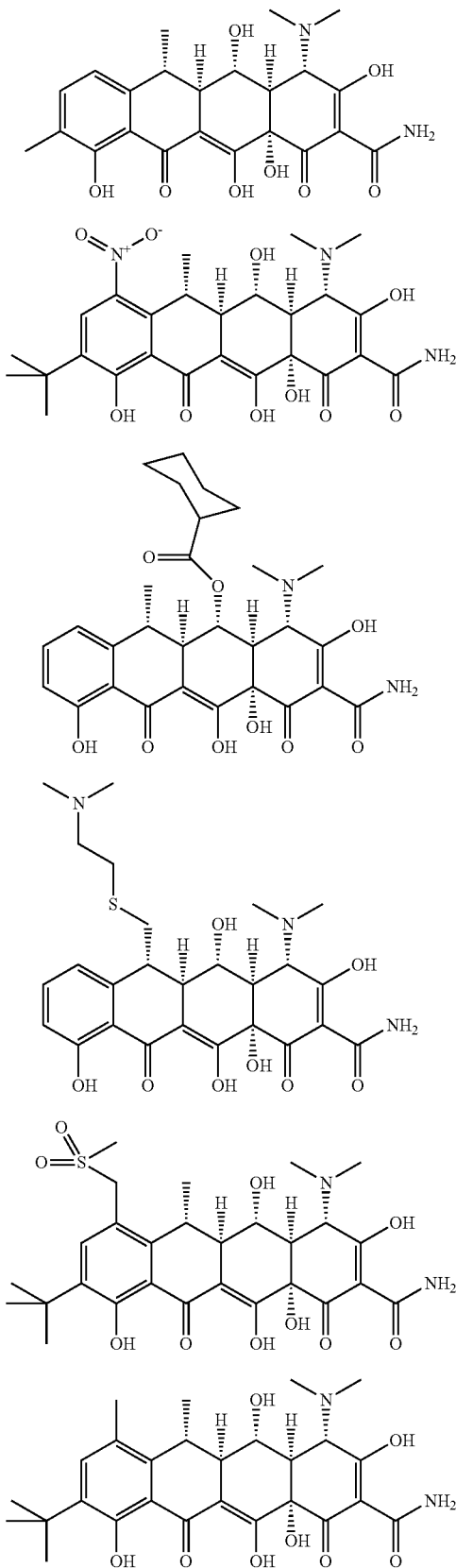

TABLE 1-continued
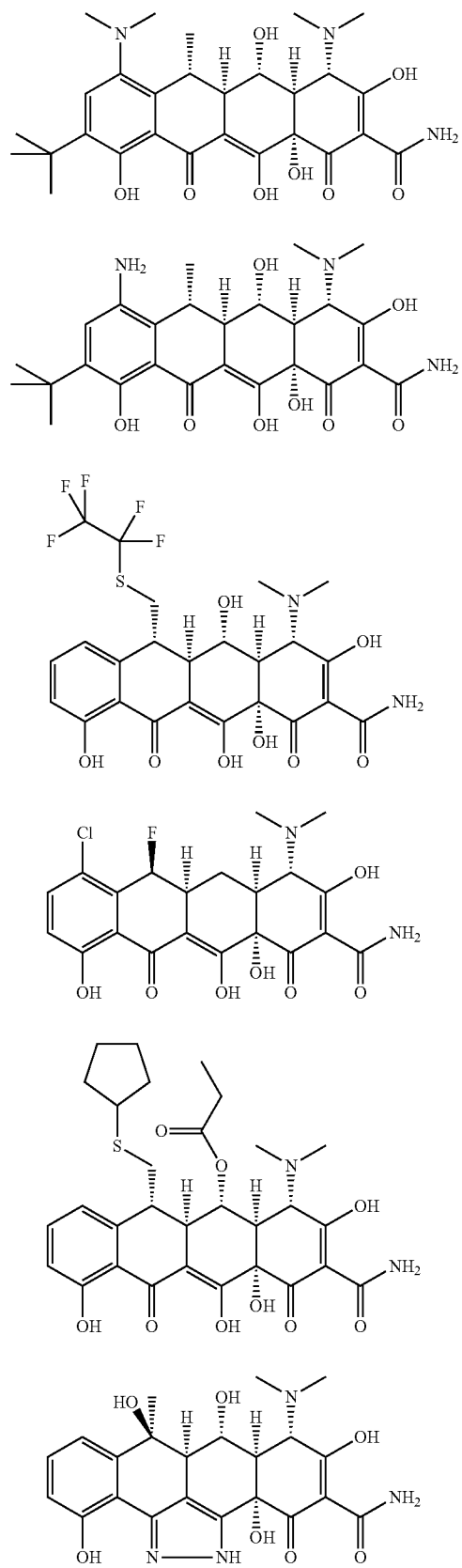

TABLE 1-continued
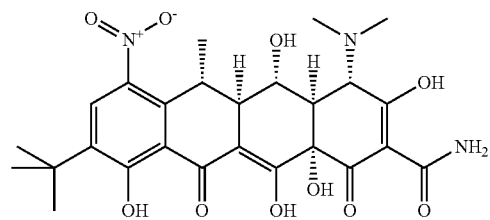
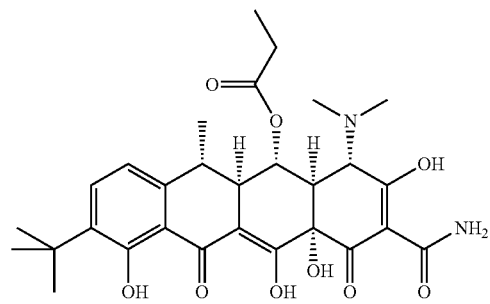
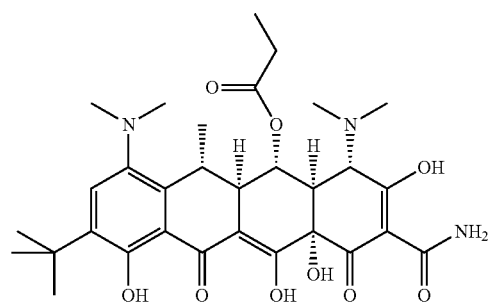
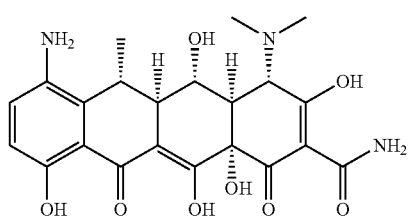
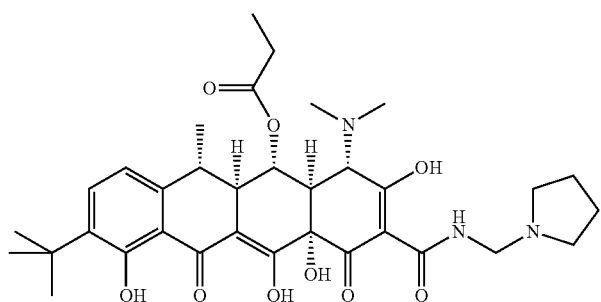

TABLE 1-continued
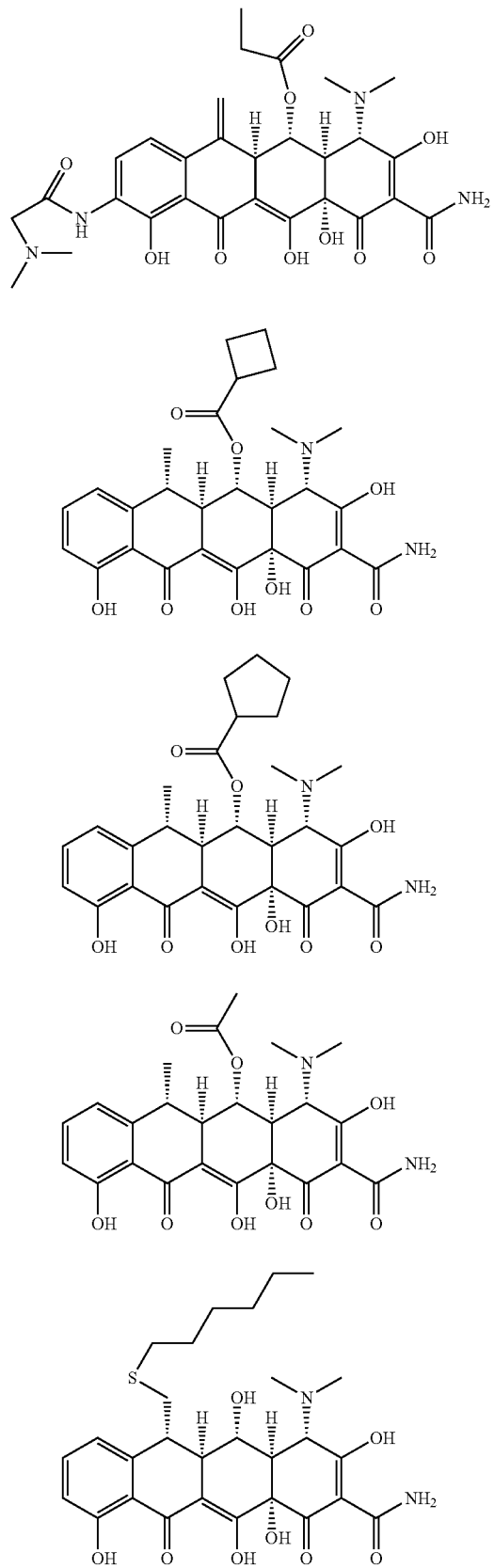

TABLE 1-continued
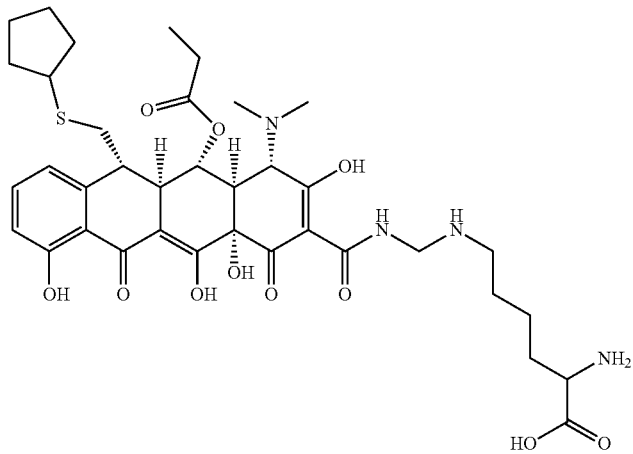
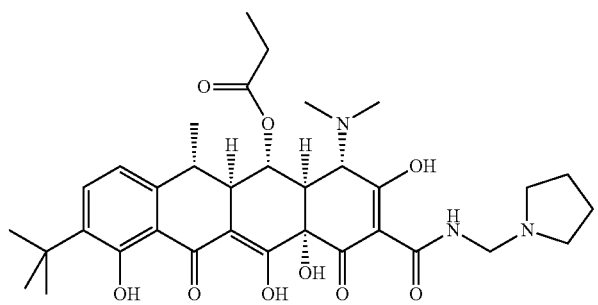
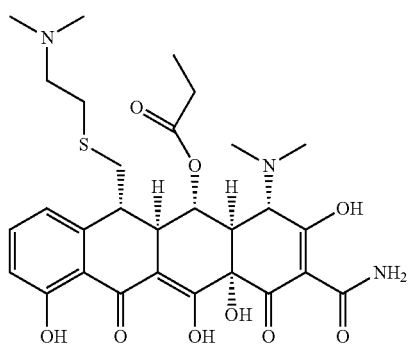
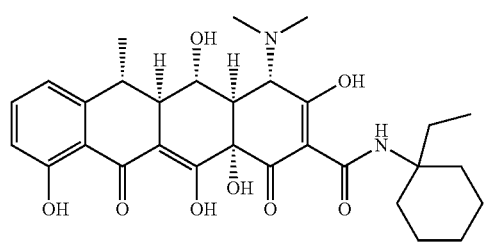

TABLE 1-continued
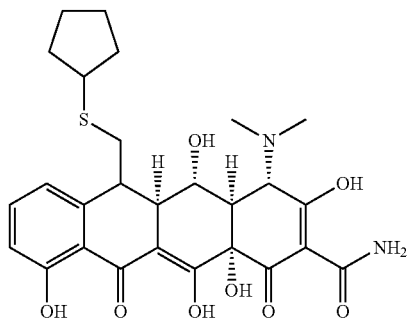
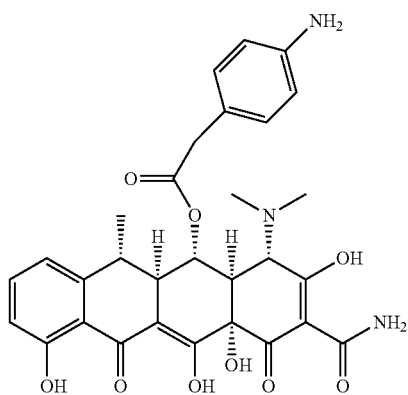
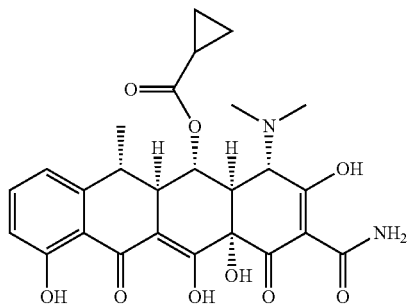
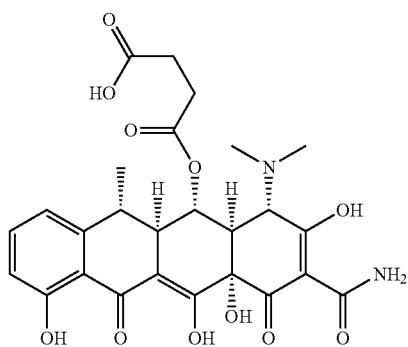

TABLE 1-continued
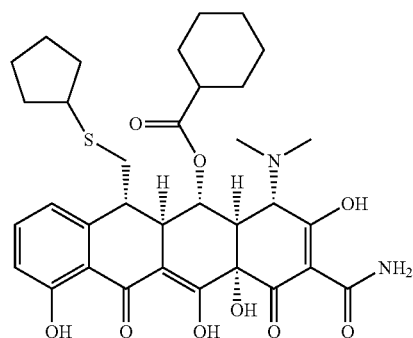
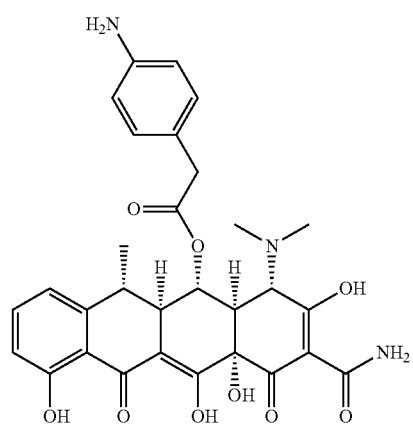
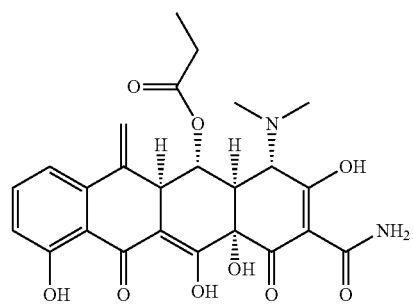
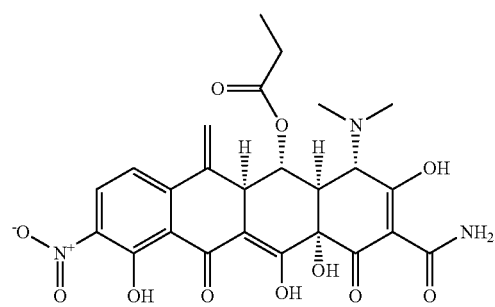
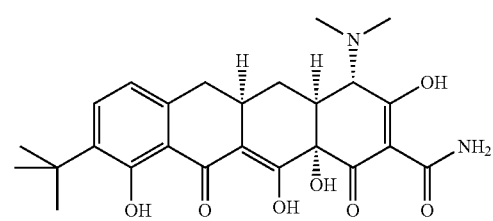

TABLE 1-continued
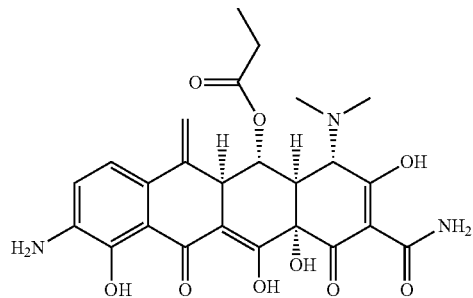
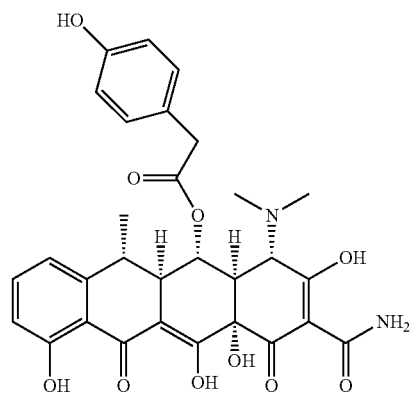
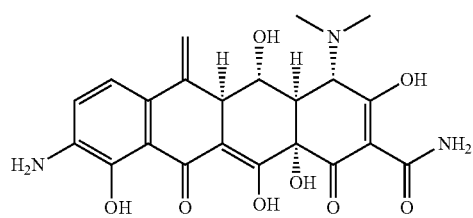
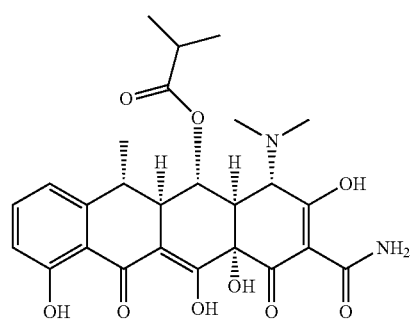
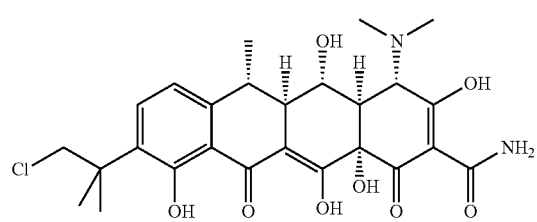

TABLE 1-continued
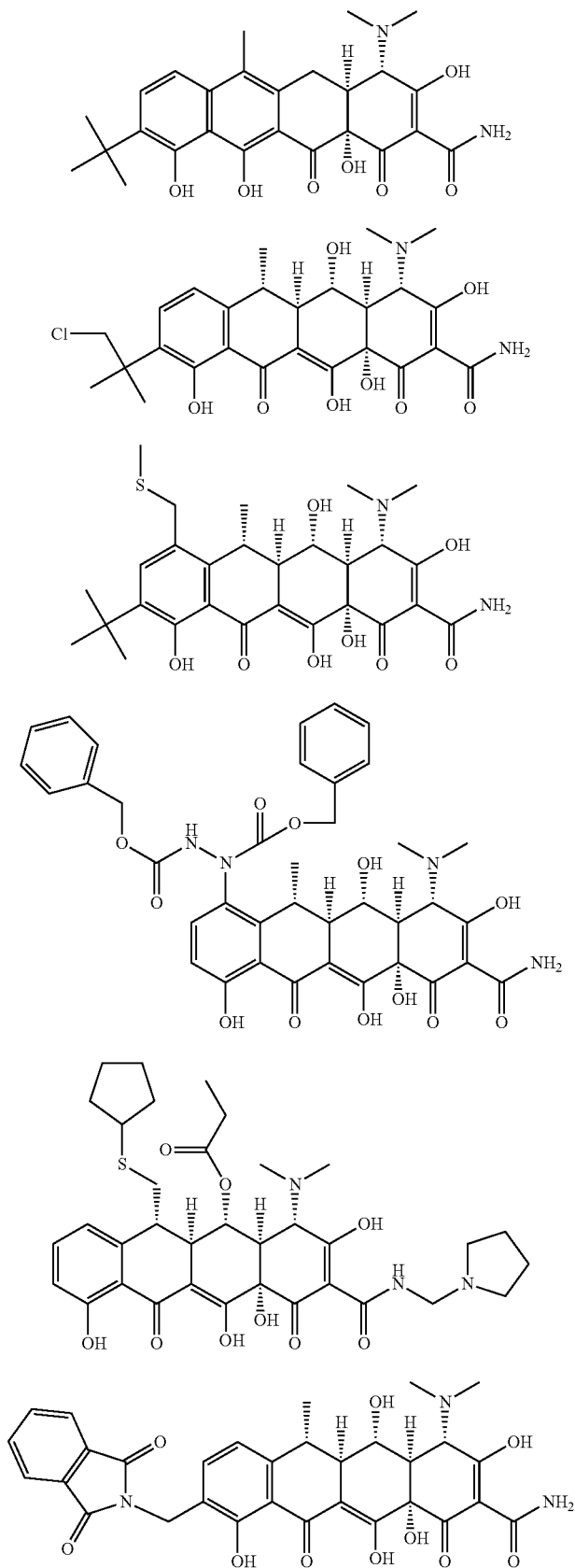

TABLE 1-continued
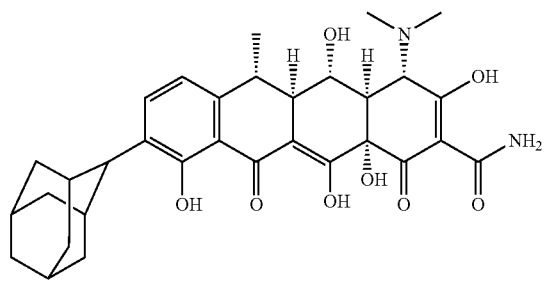
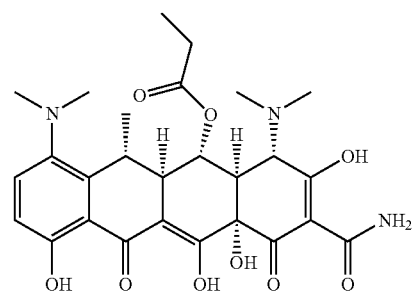
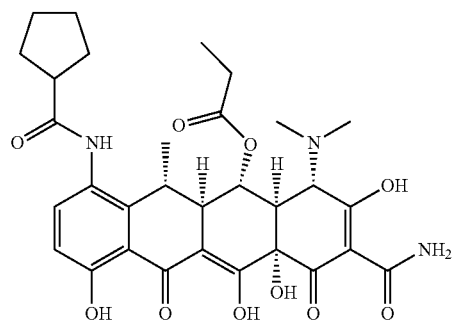
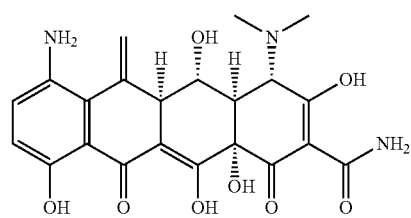
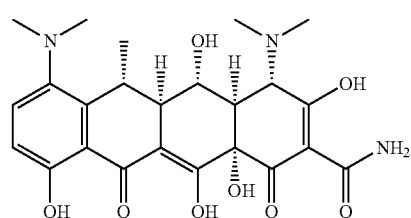

TABLE 1-continued
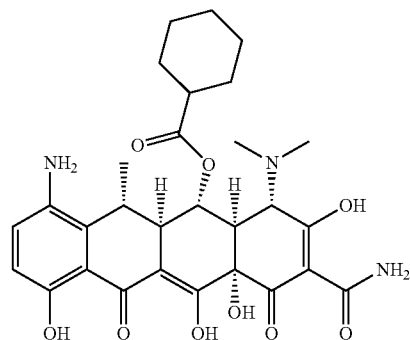
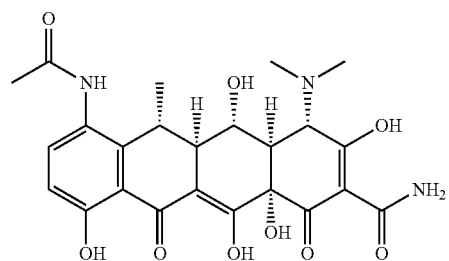
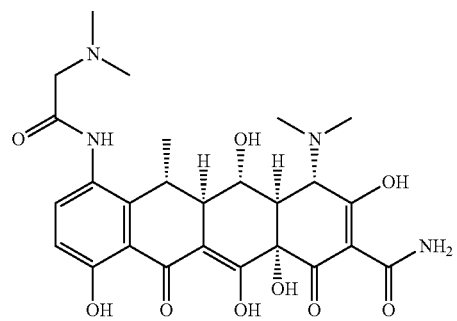
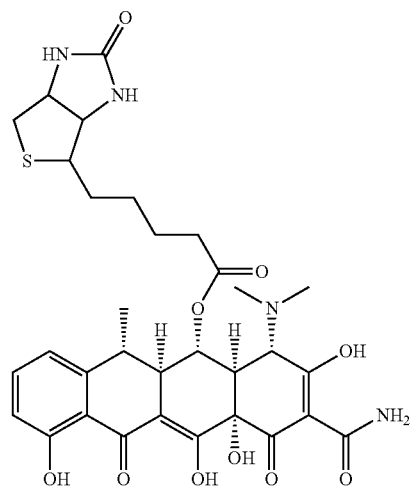

TABLE 1-continued
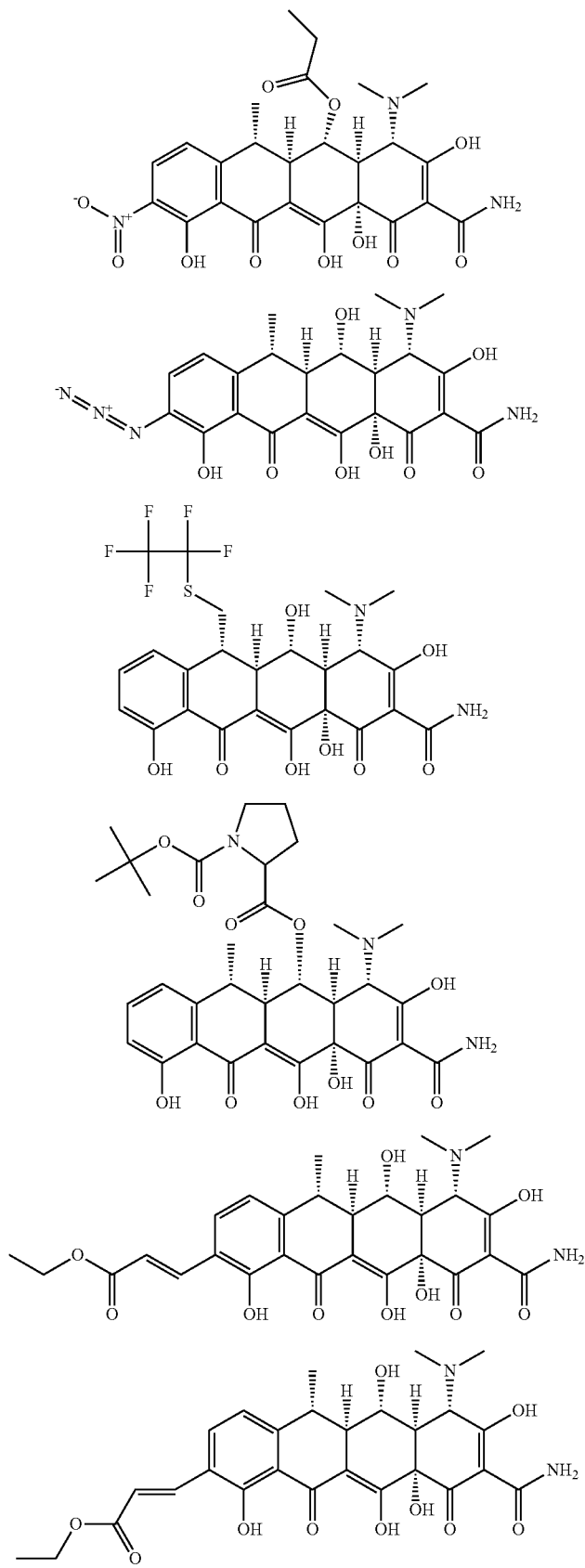

TABLE 1-continued
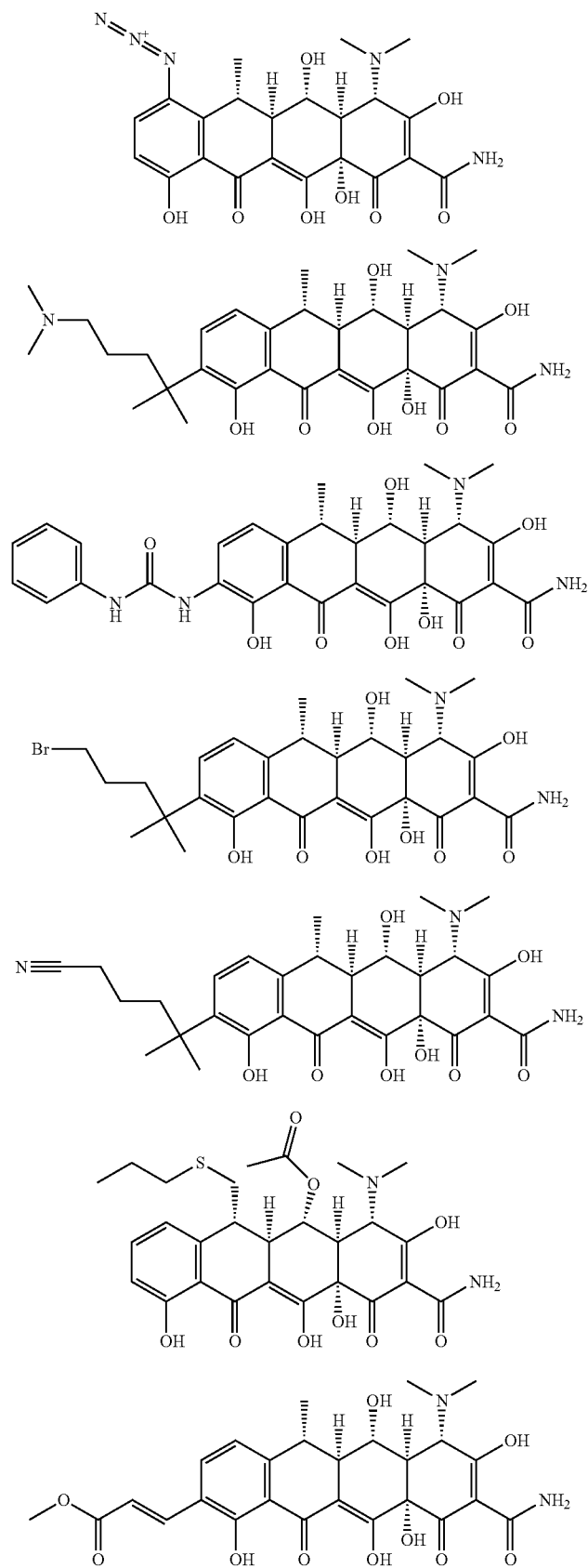

TABLE 1-continued
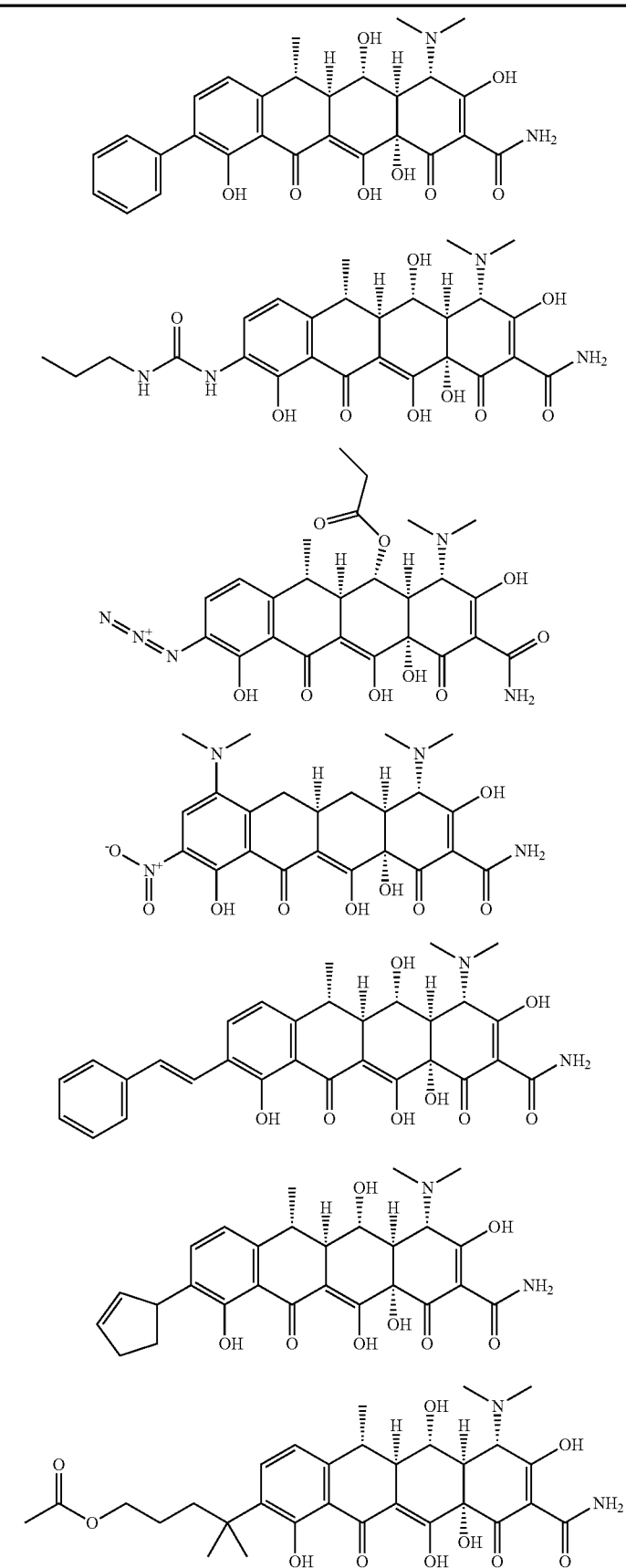

TABLE 1-continued
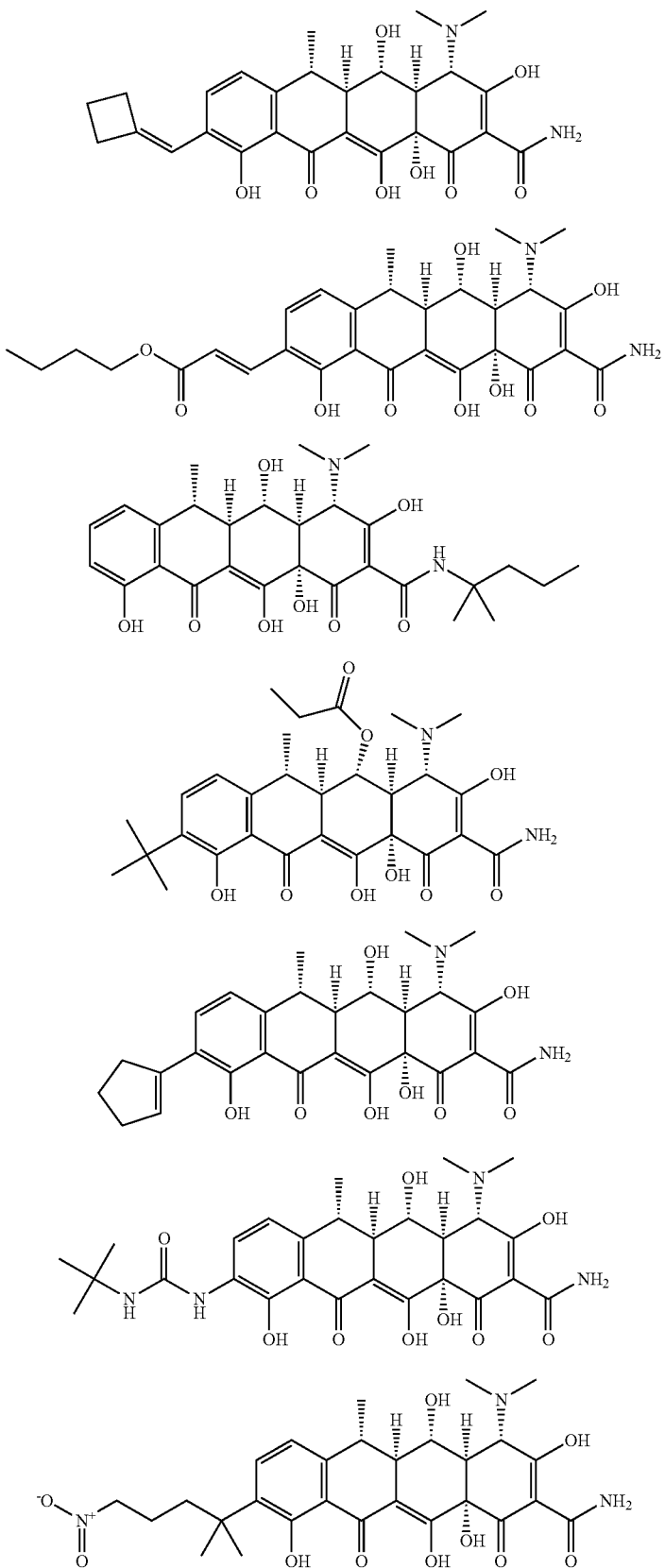

TABLE 1-continued
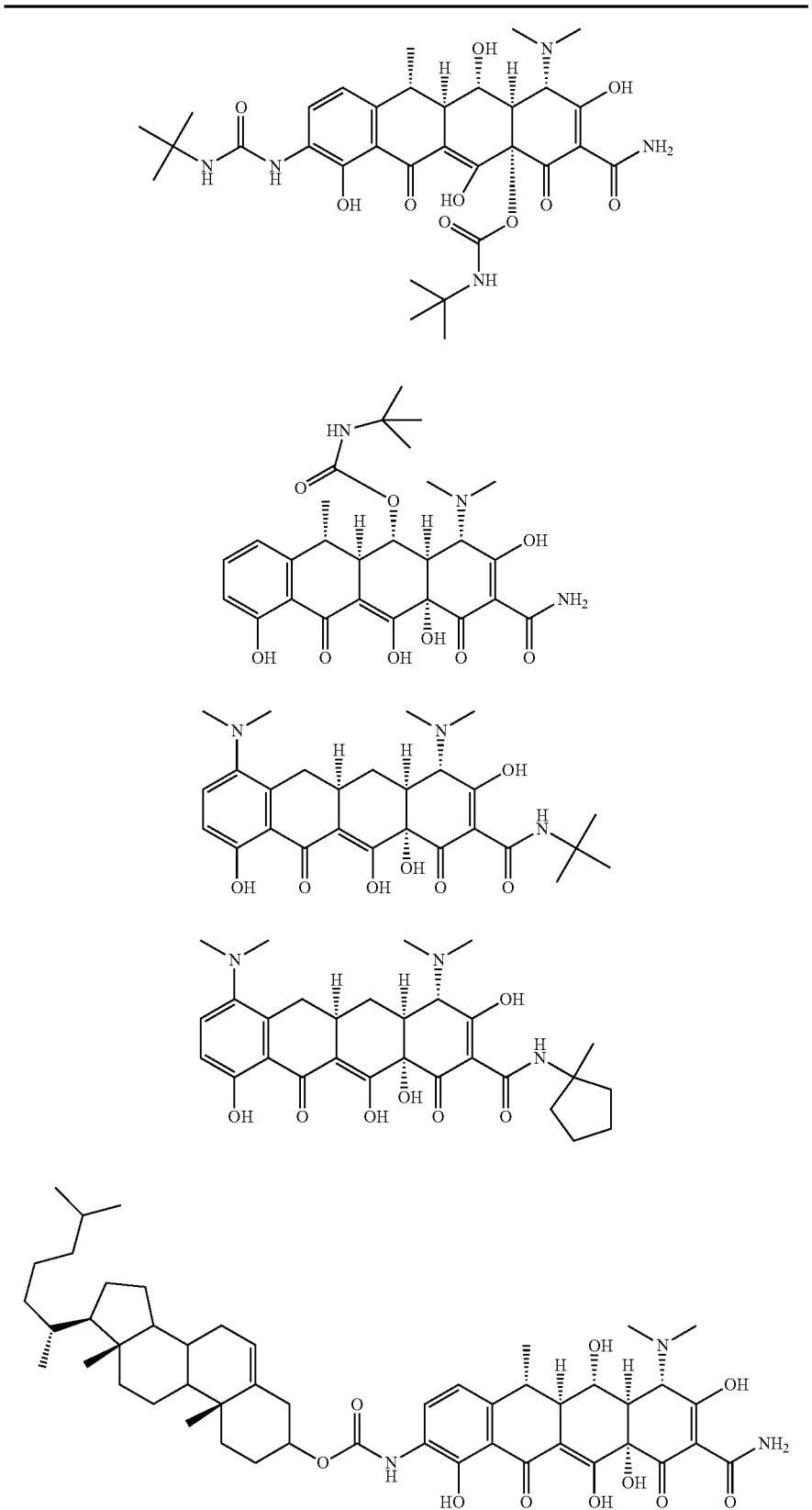

TABLE 1-continued
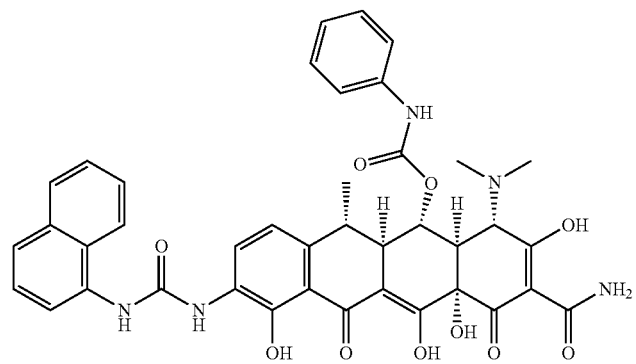
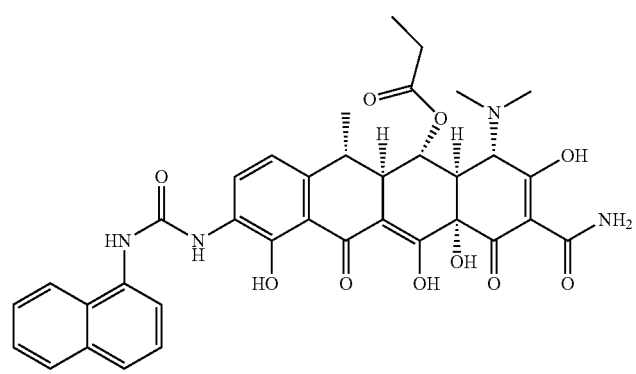
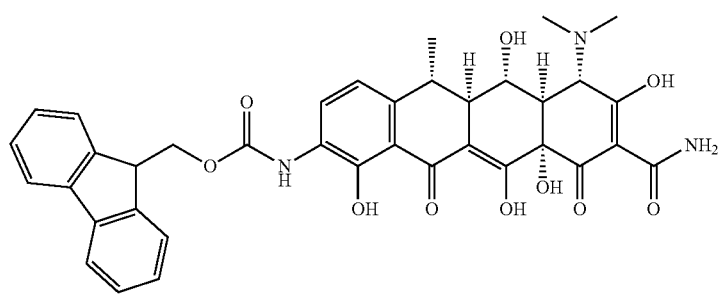
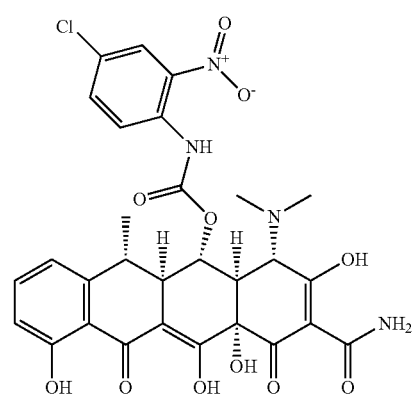

TABLE 1-continued
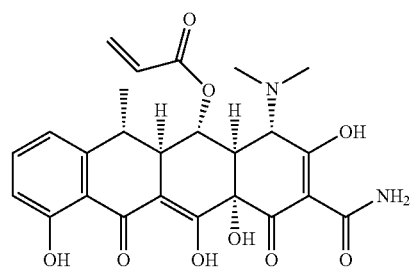
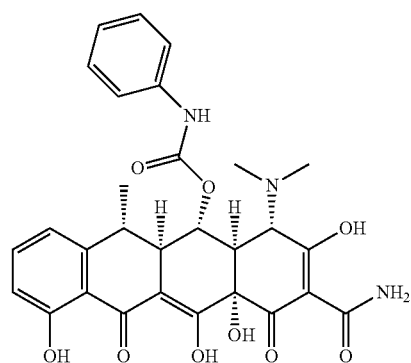
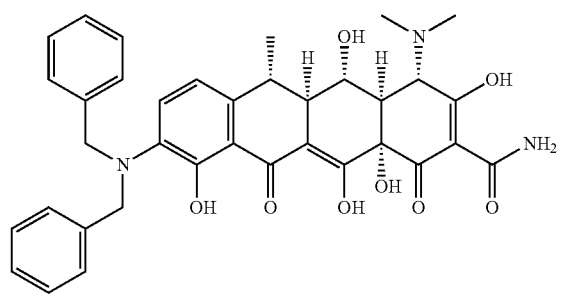
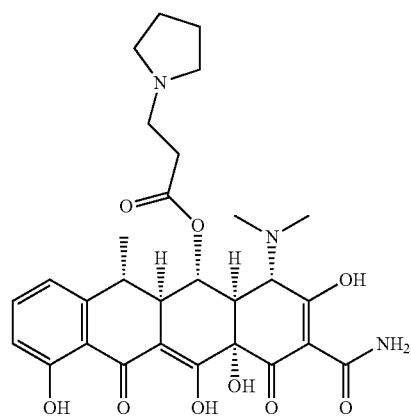

TABLE 1-continued
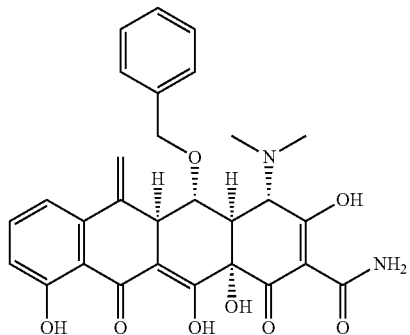
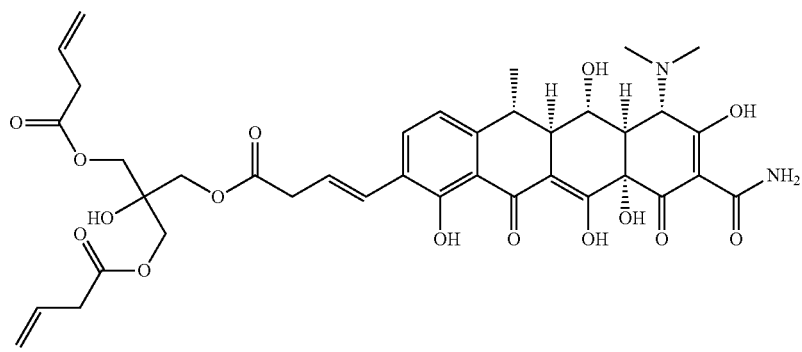
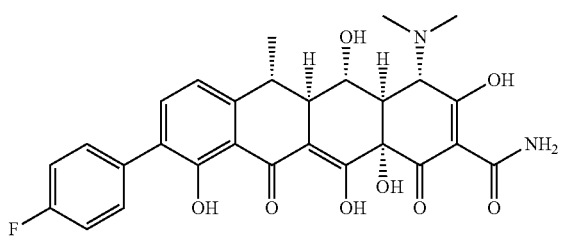
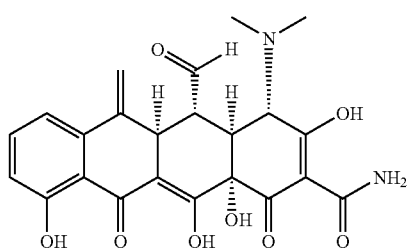
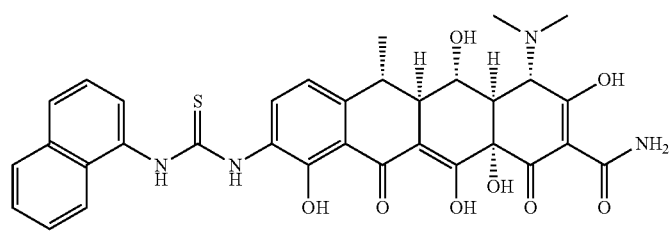

TABLE 1-continued
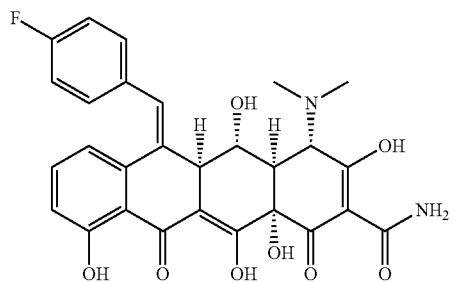
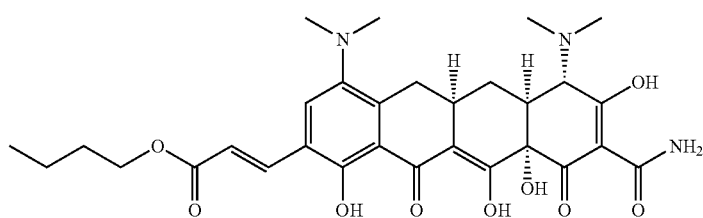
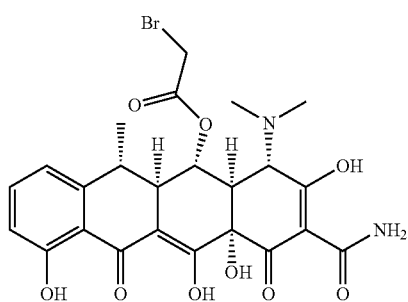
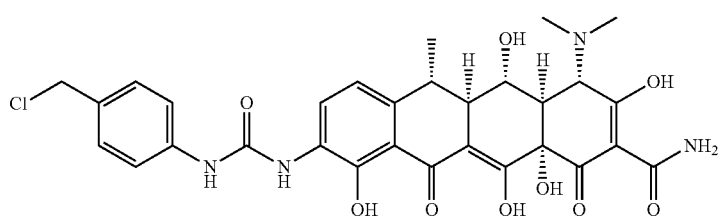
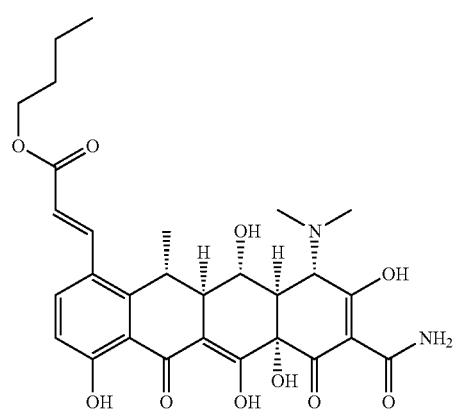

TABLE 1-continued
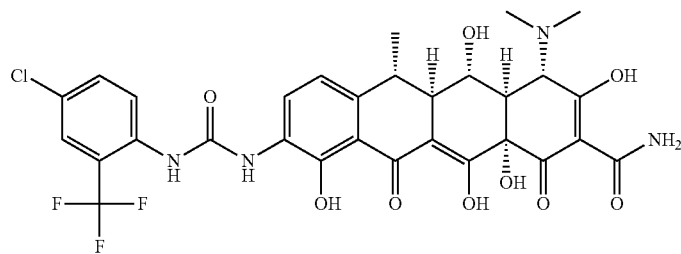
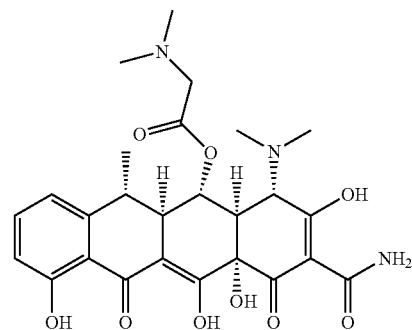
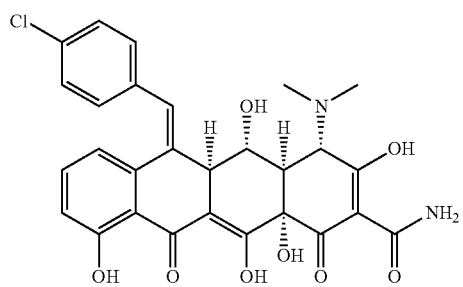
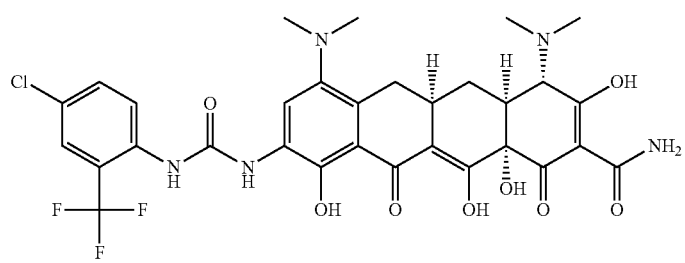
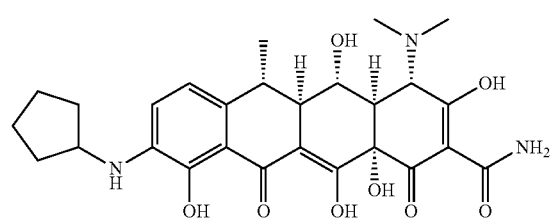

TABLE 1-continued
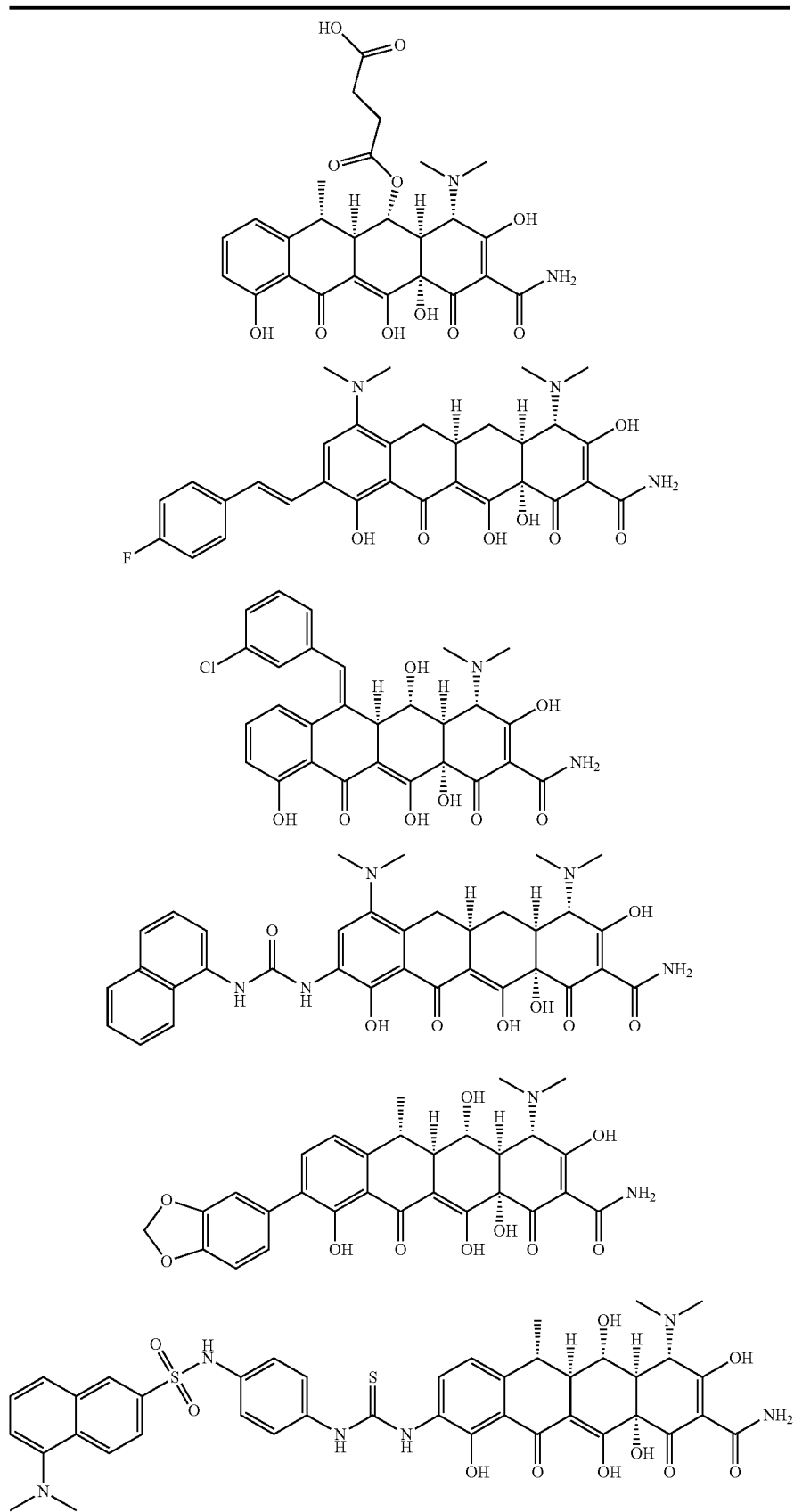

TABLE 1-continued
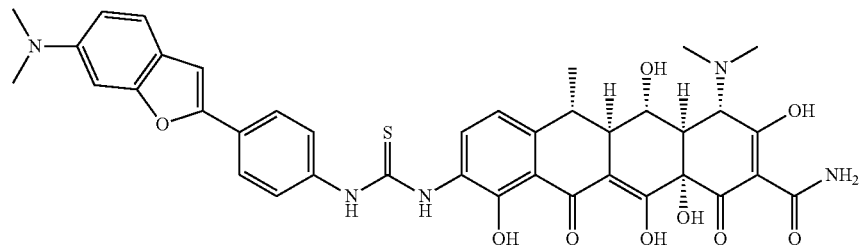
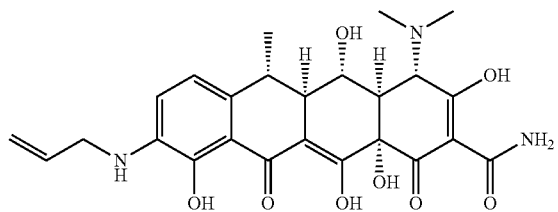
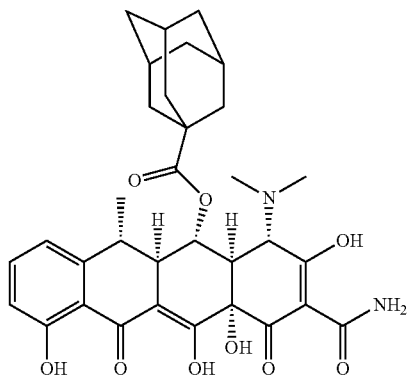
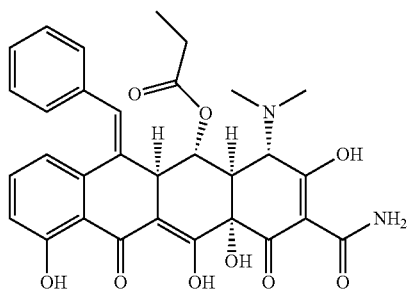
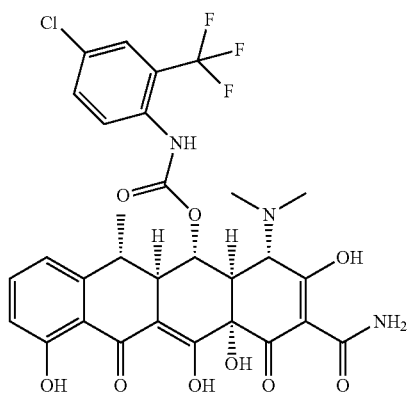

TABLE 1-continued
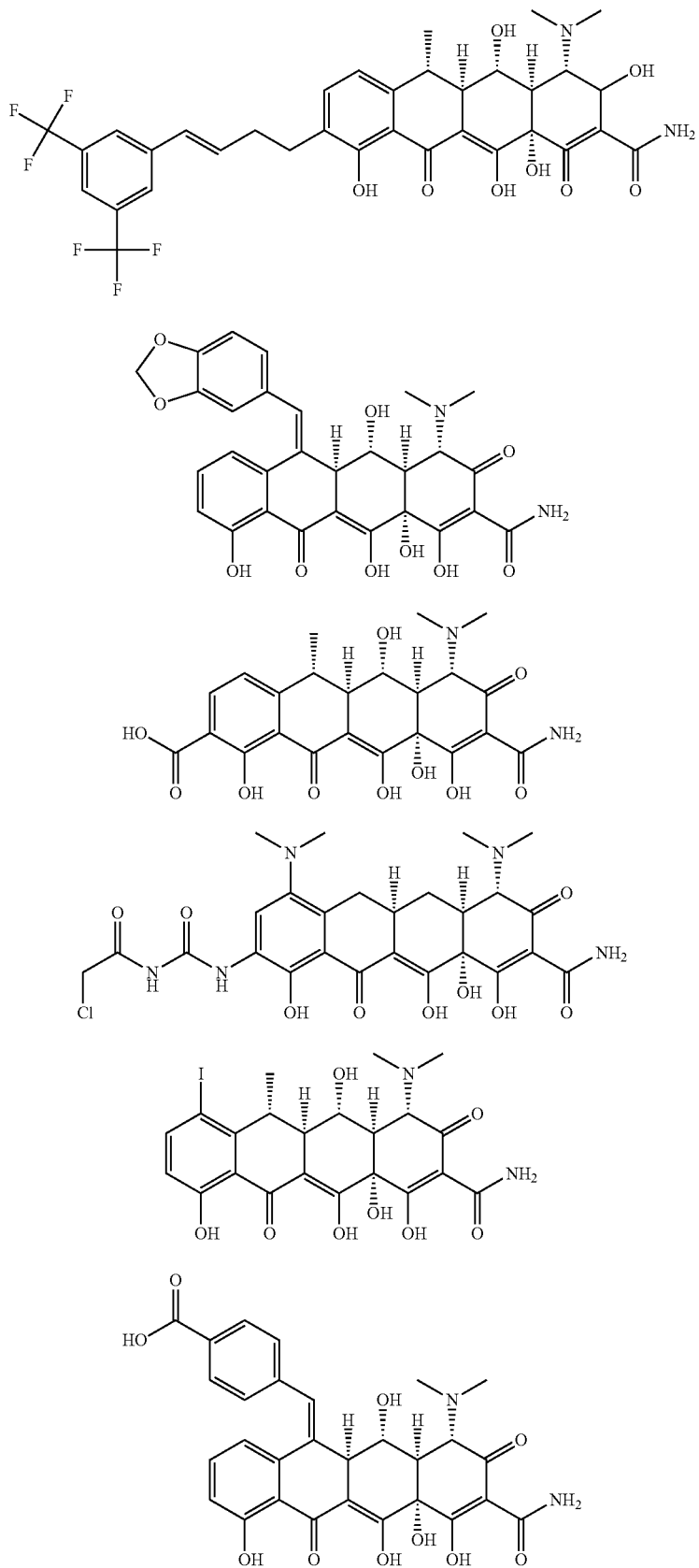

TABLE 1-continued
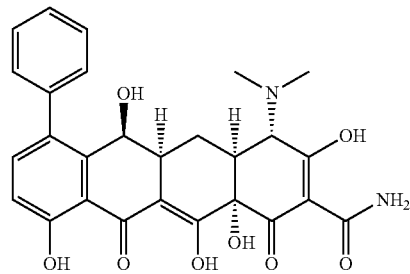
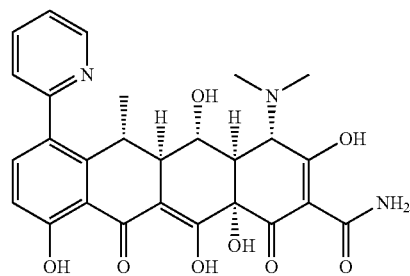
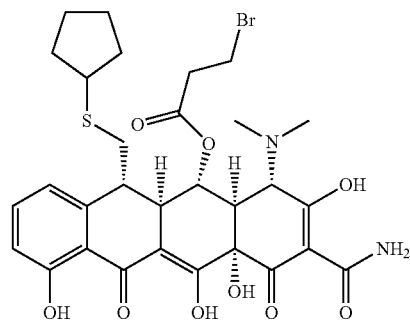
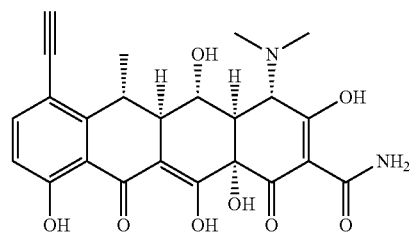
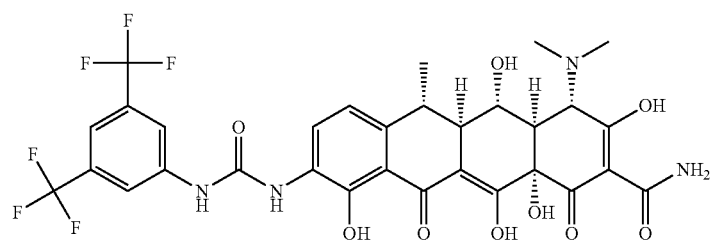

TABLE 1-continued
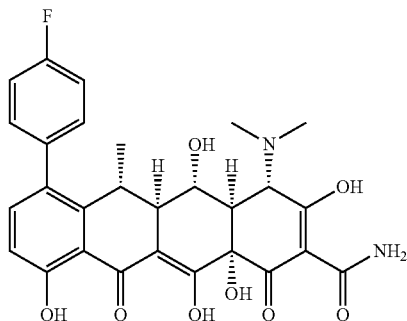
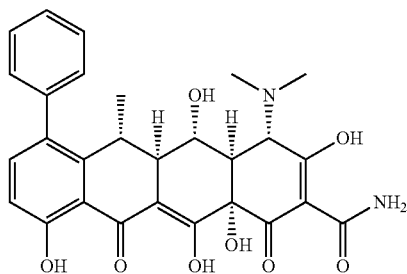
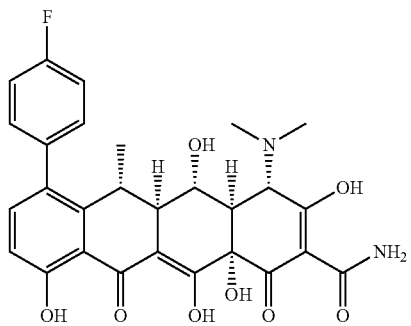
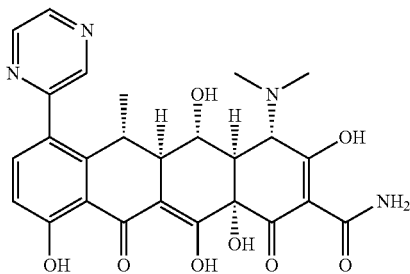
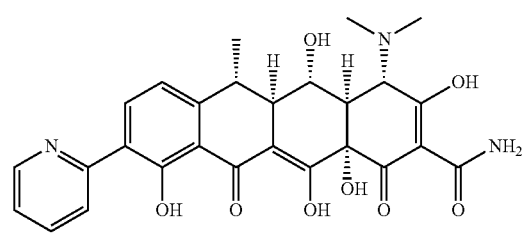

TABLE 1-continued
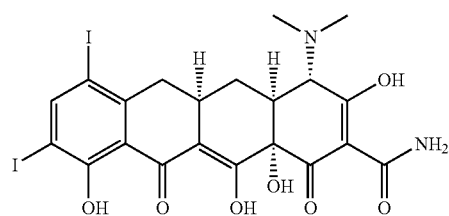
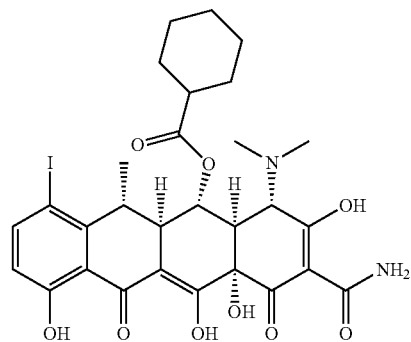
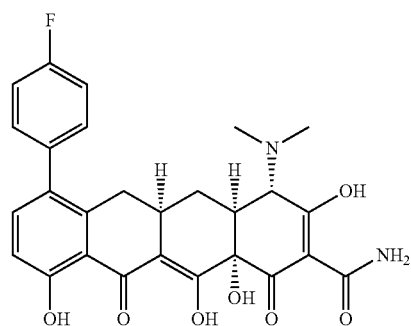
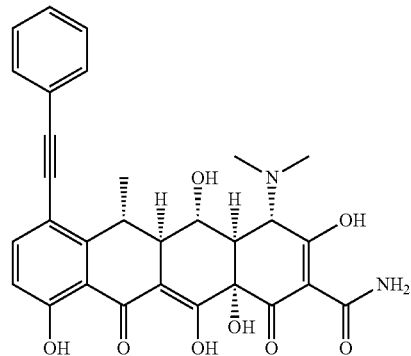
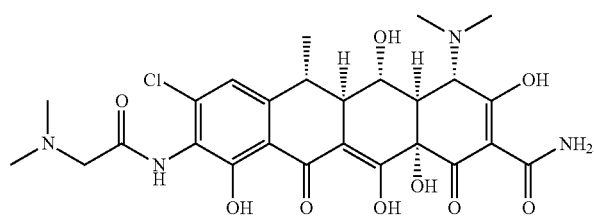

TABLE 1-continued
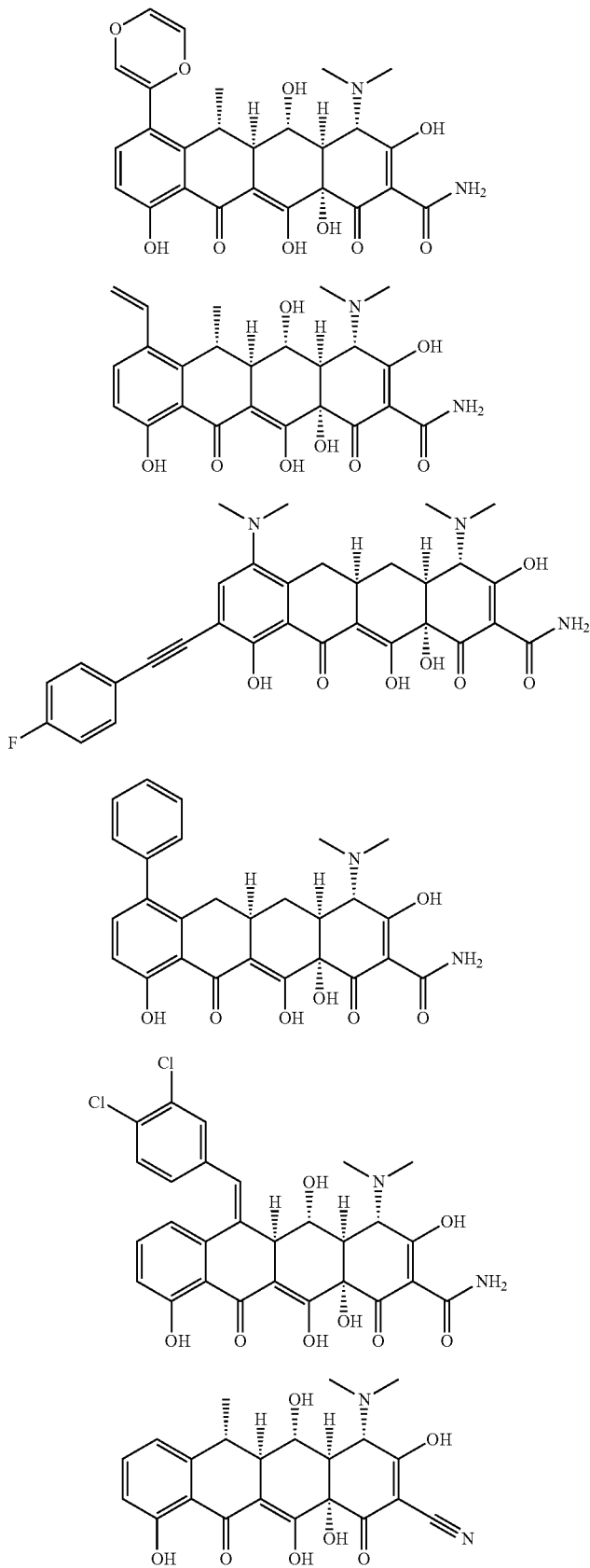

TABLE 1-continued
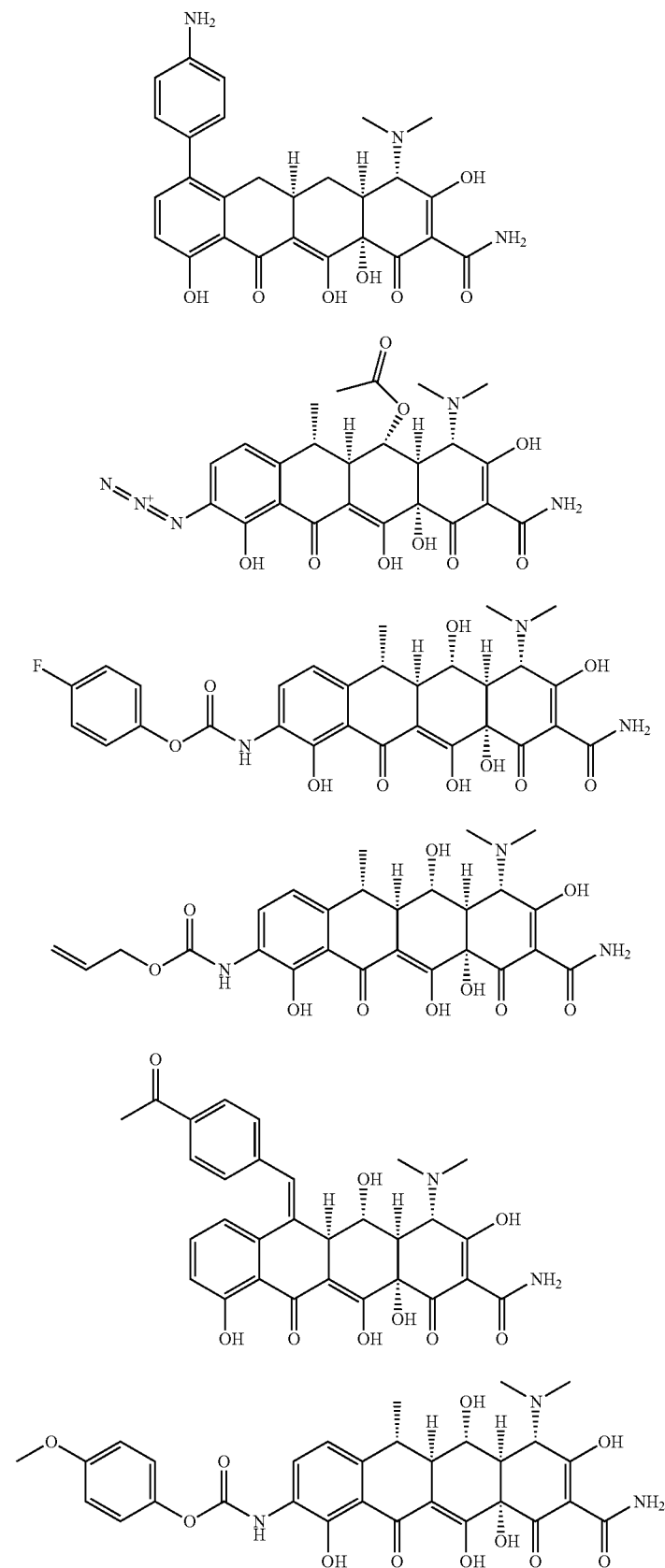

TABLE 1-continued
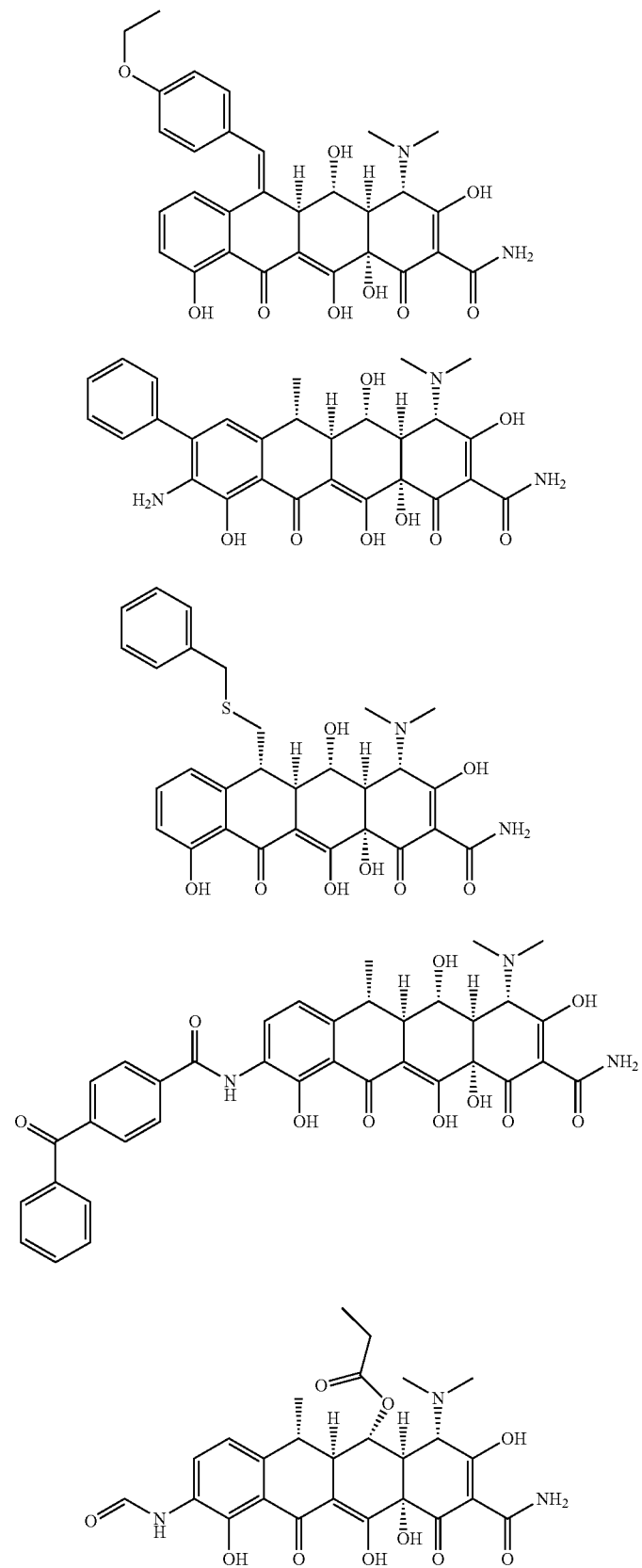

TABLE 1-continued
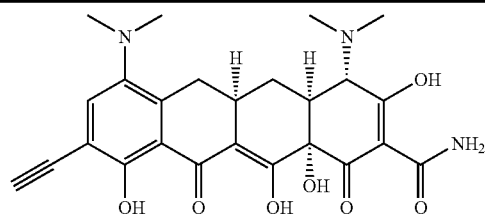
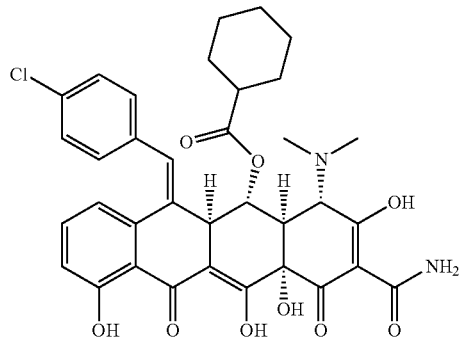
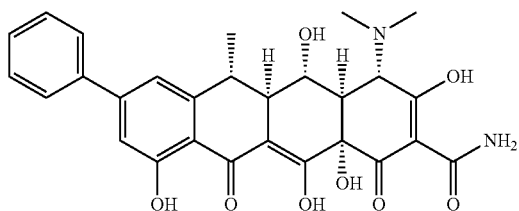
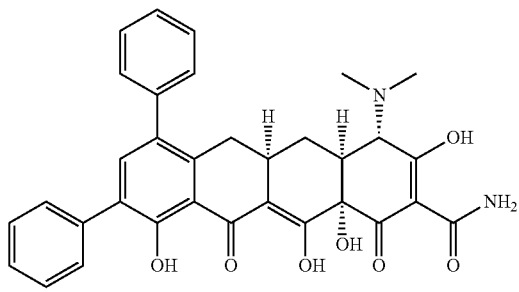
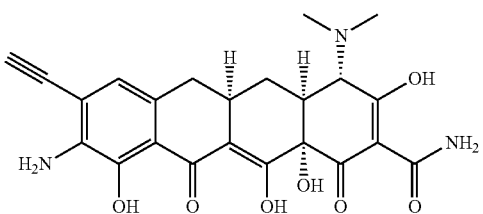
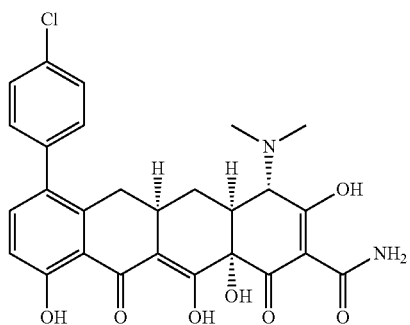

TABLE 1-continued
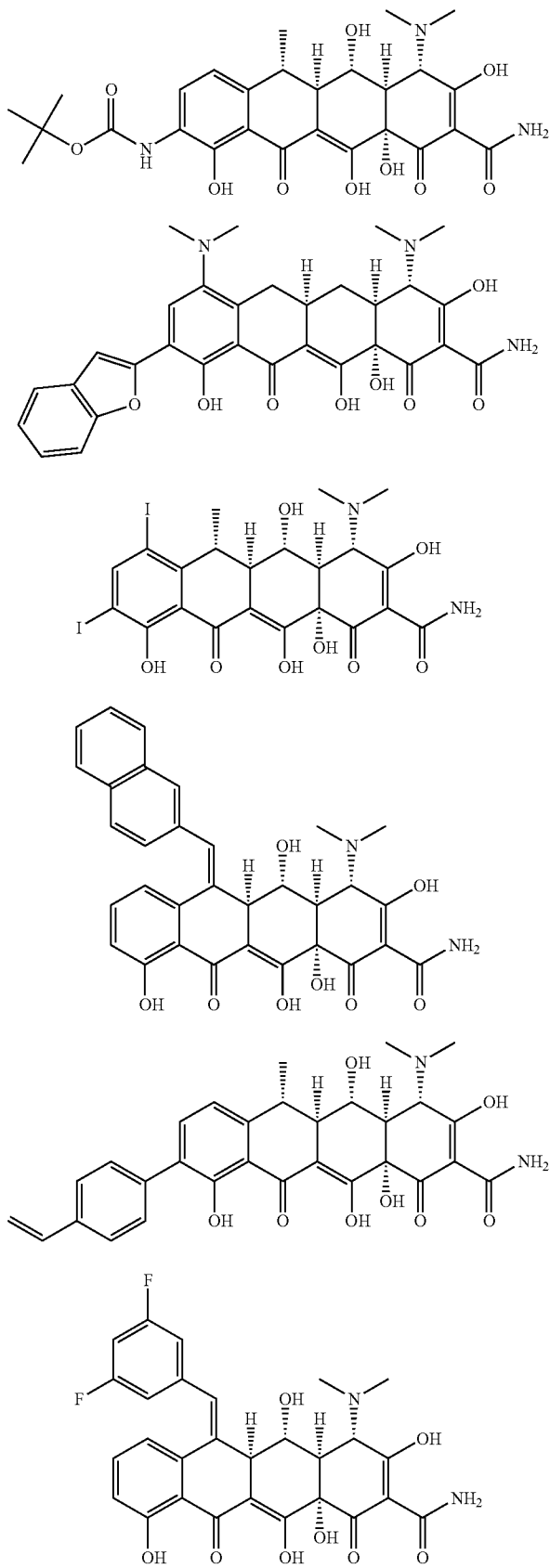

TABLE 1-continued
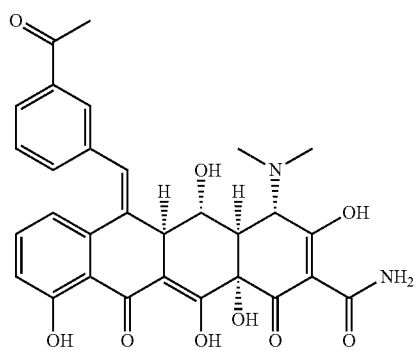
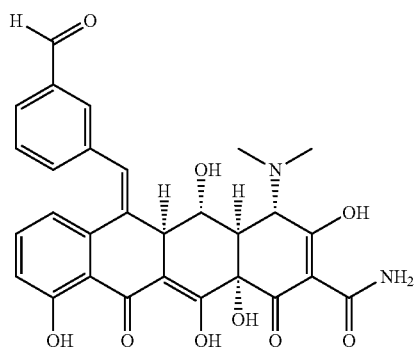
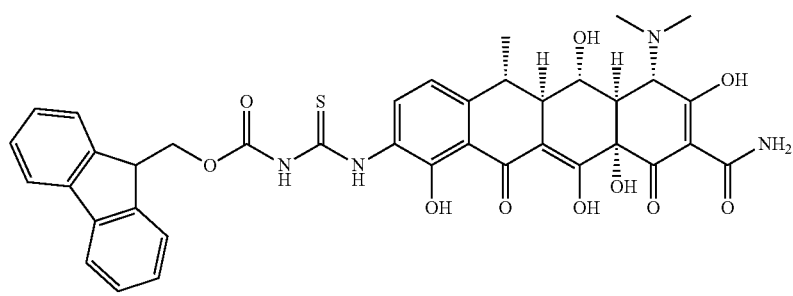
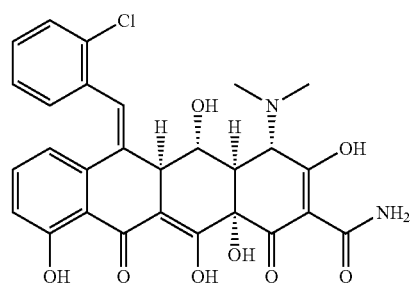
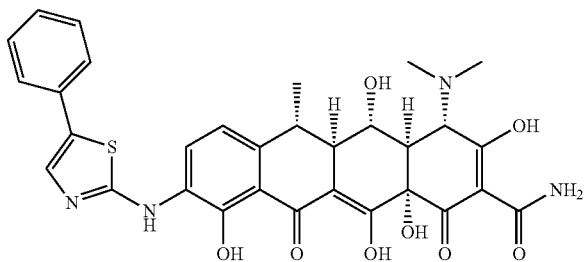

TABLE 1-continued
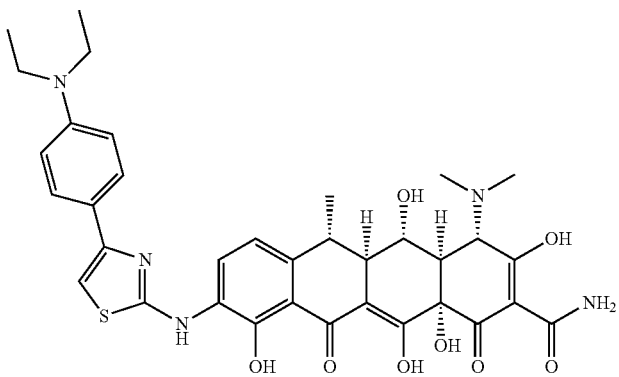
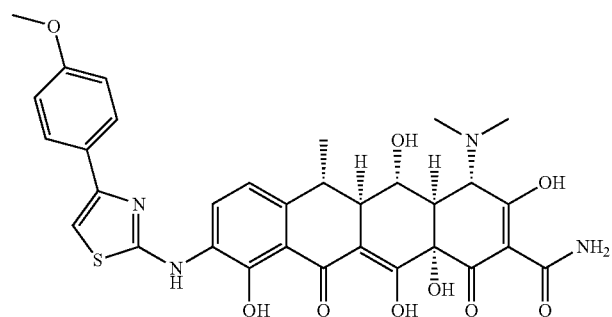
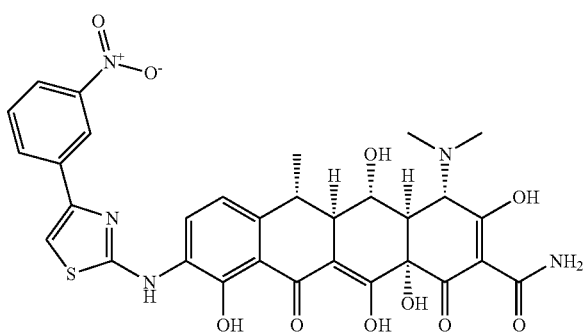
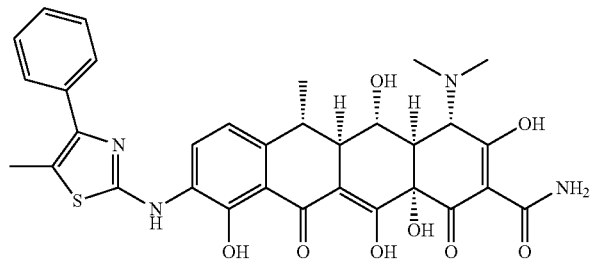

TABLE 1-continued
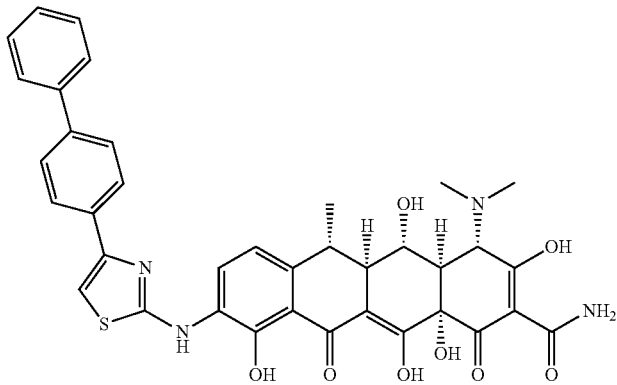
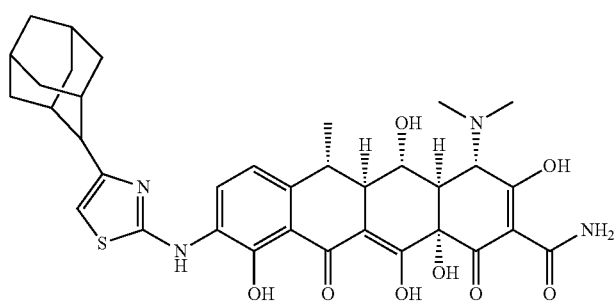
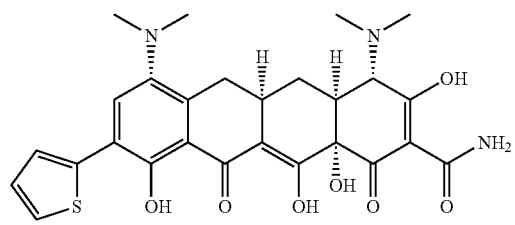
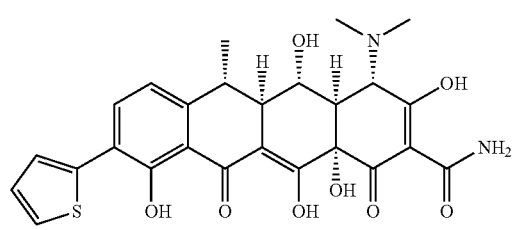
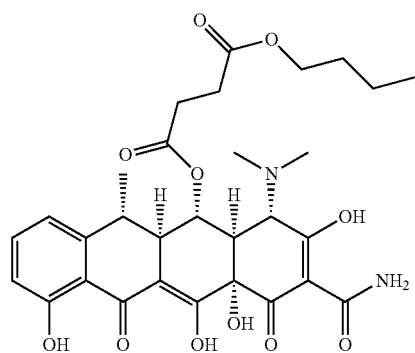

TABLE 1-continued
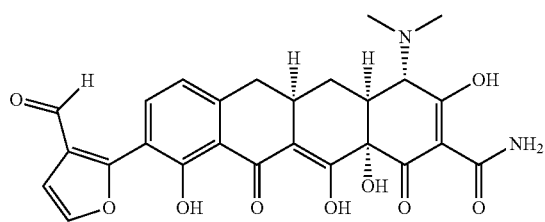
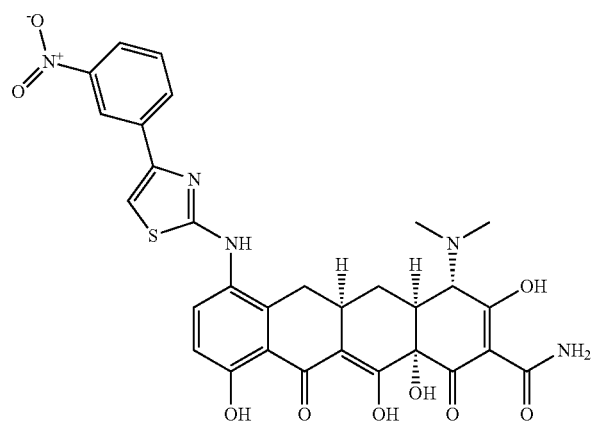
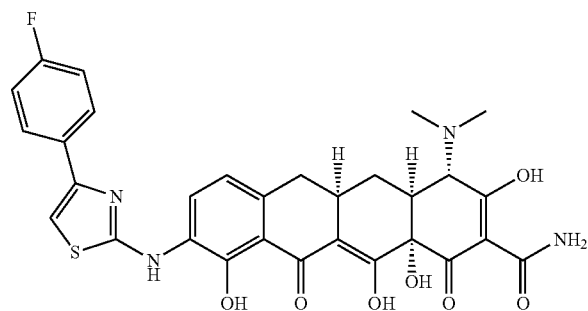

TABLE 1-continued
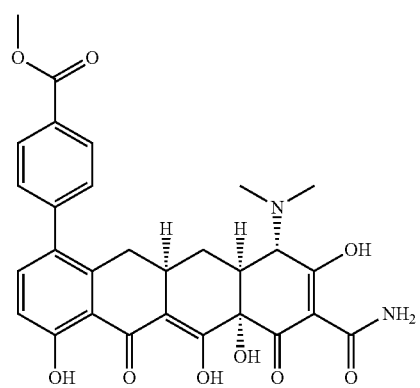
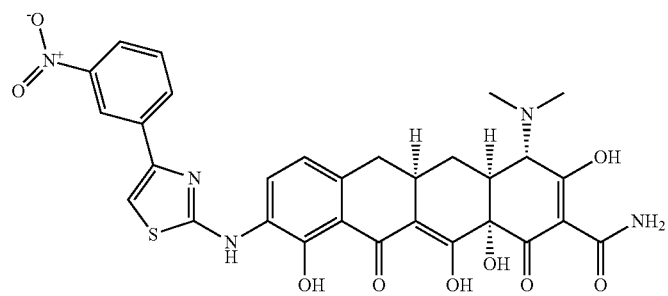
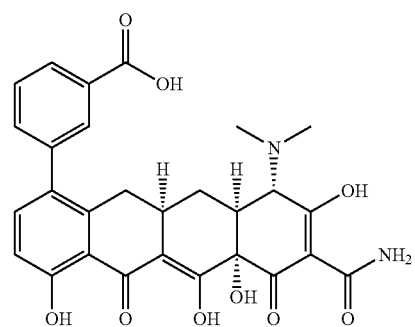
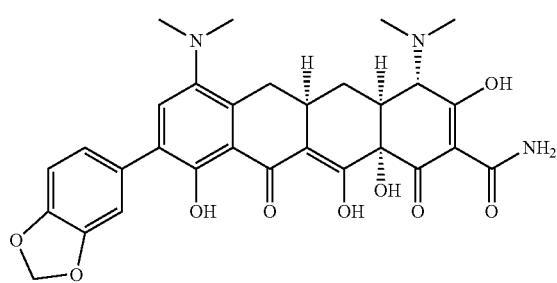

TABLE 1-continued
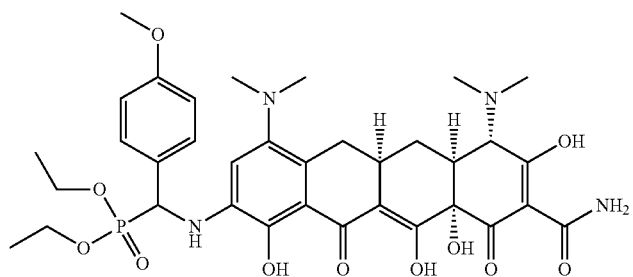
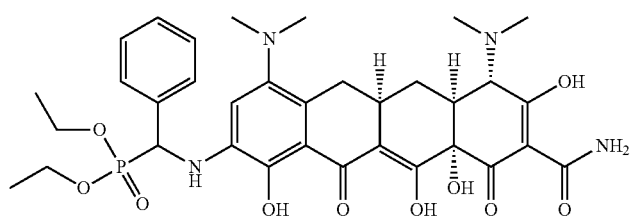
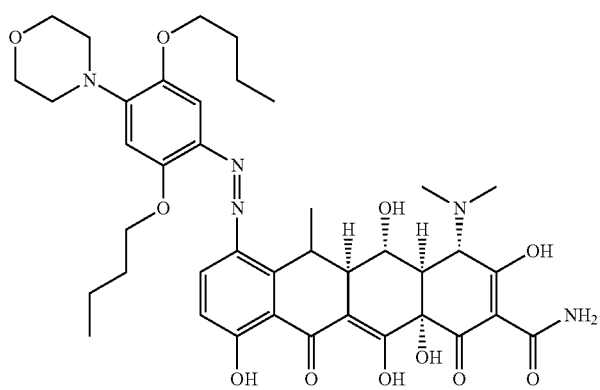
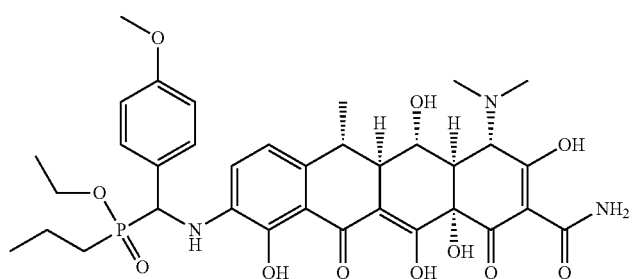
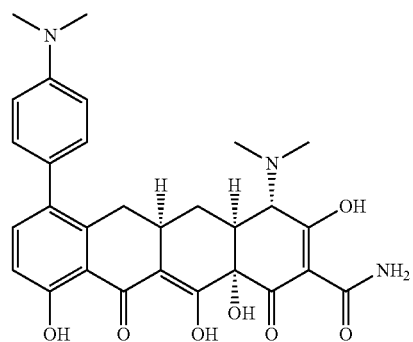

TABLE 1-continued
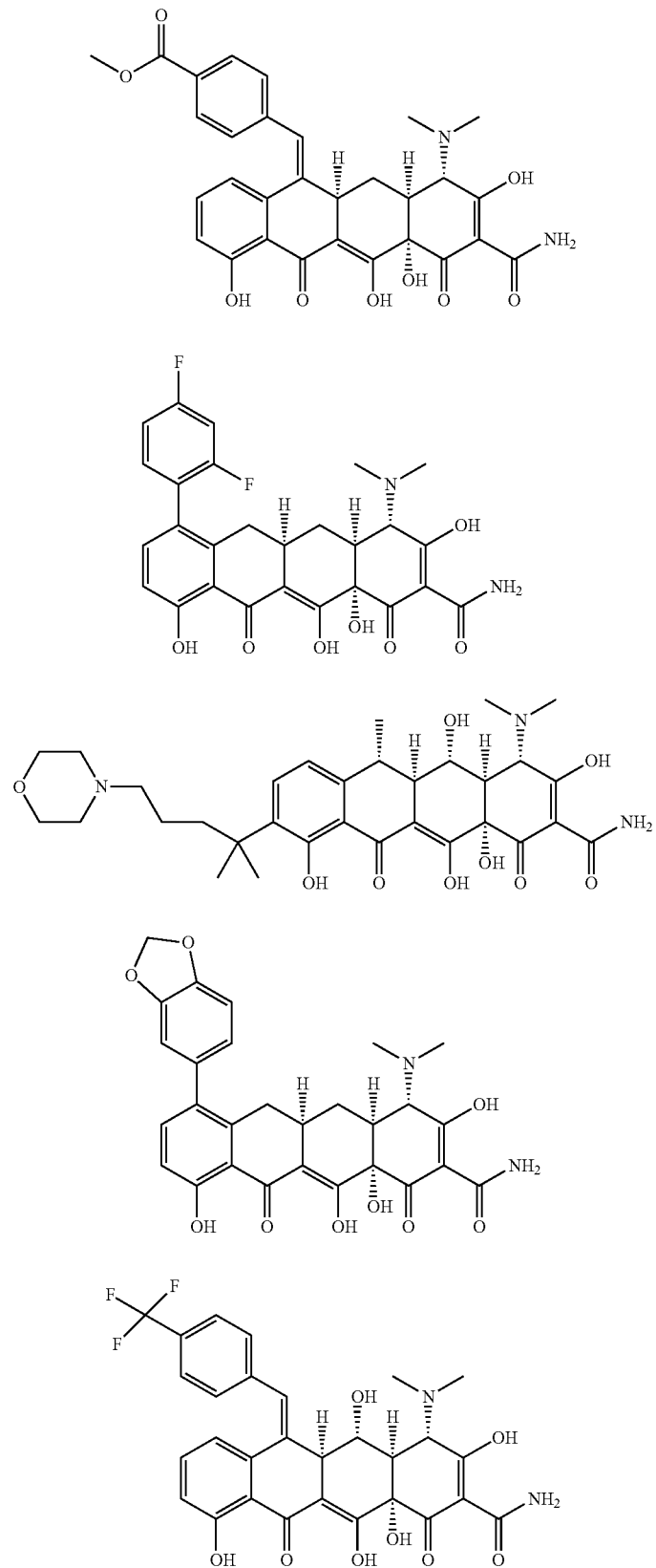

TABLE 1-continued
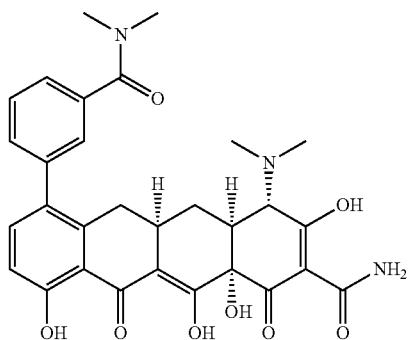
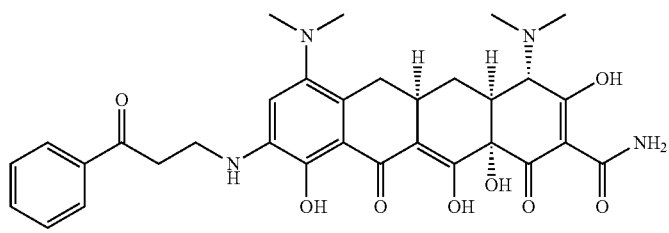
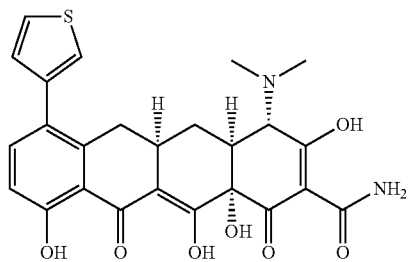
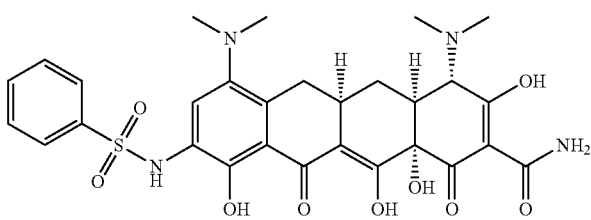
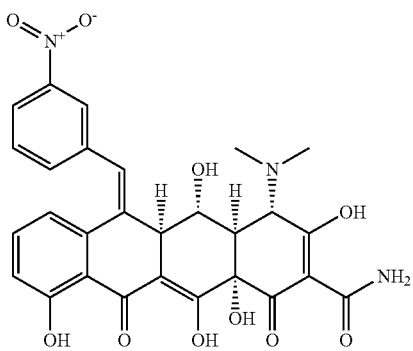

TABLE 1-continued
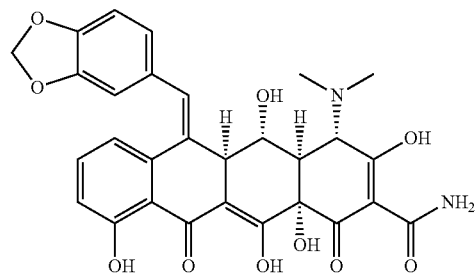
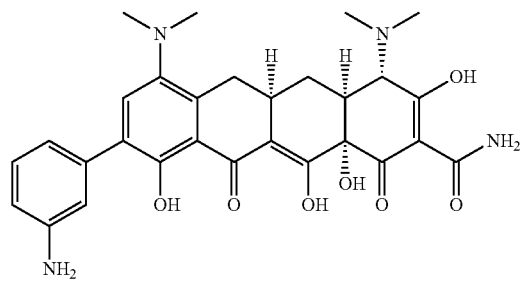
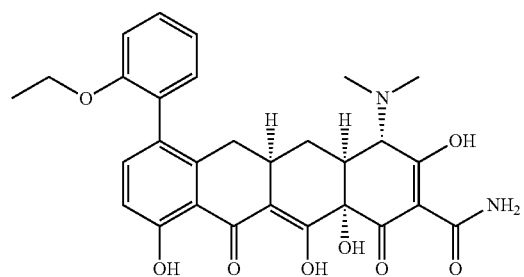
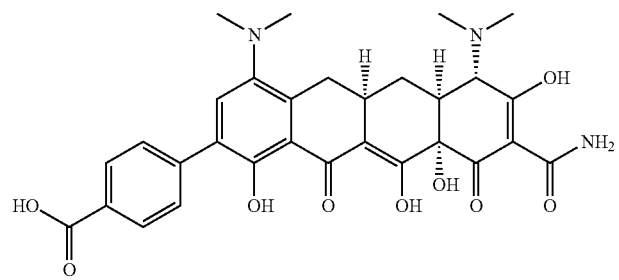
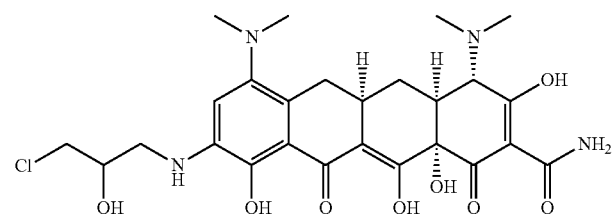
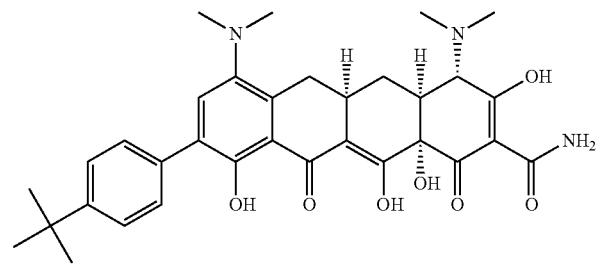

TABLE 1-continued
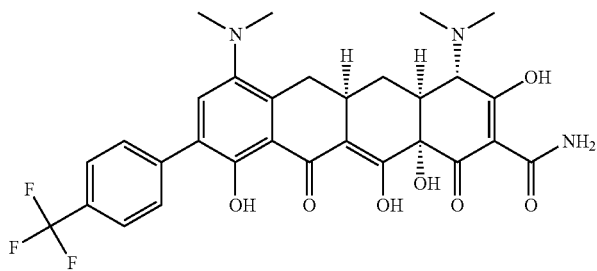
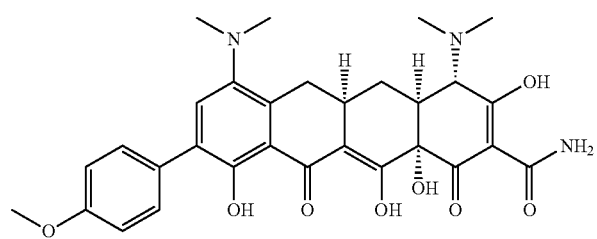
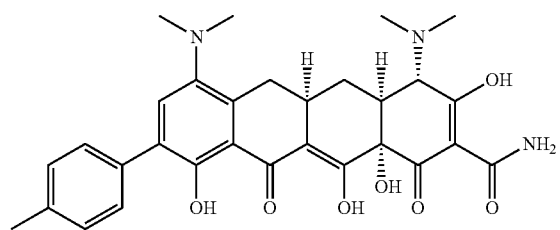
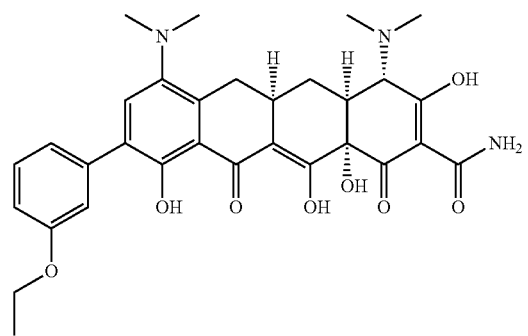
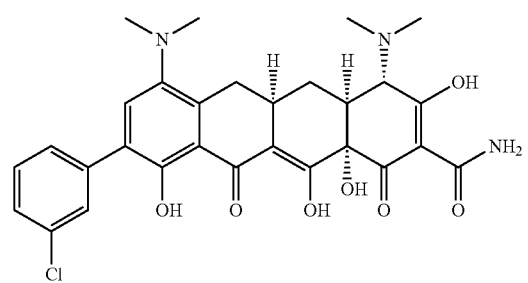

TABLE 1-continued
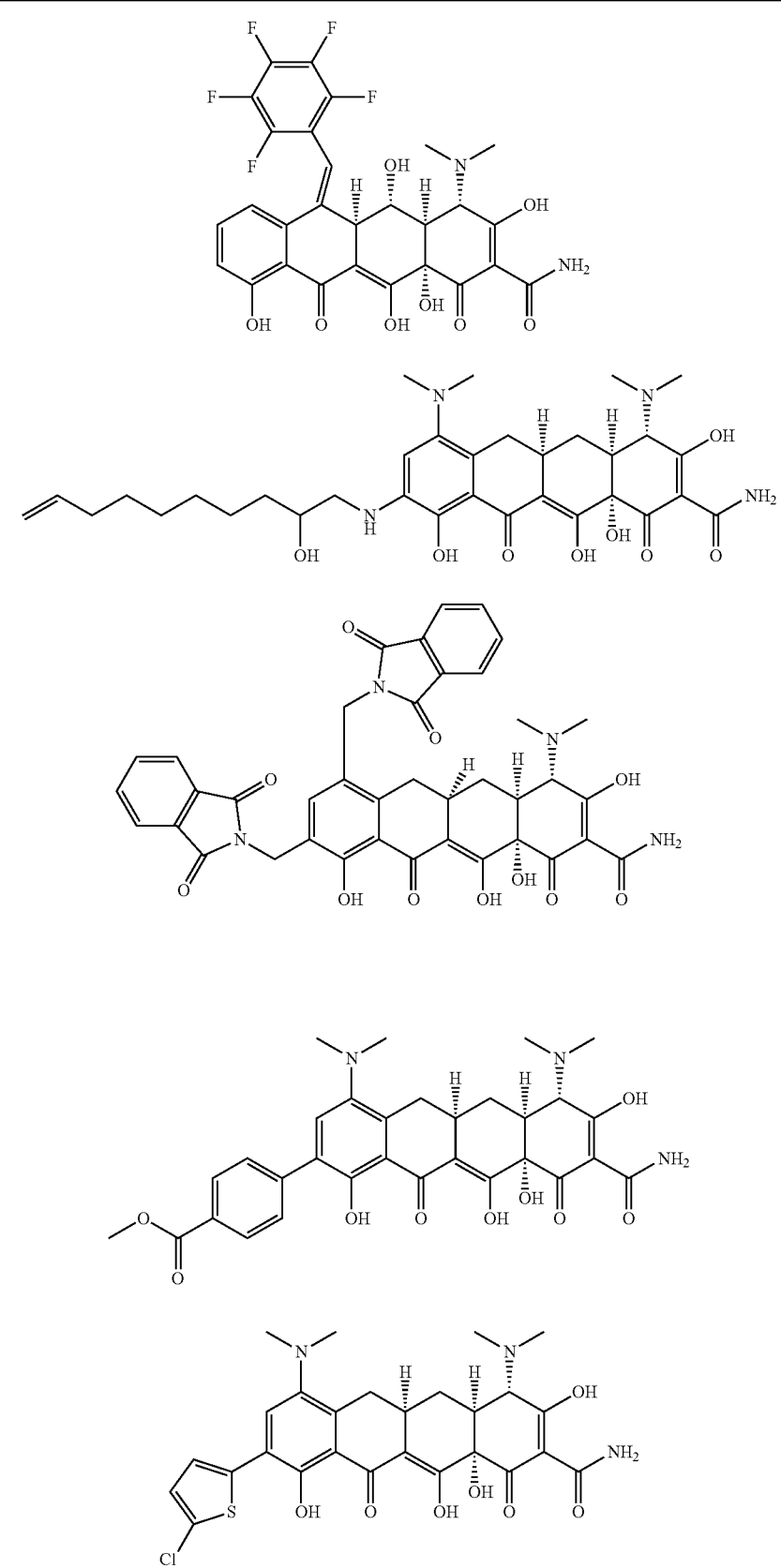

TABLE 1-continued
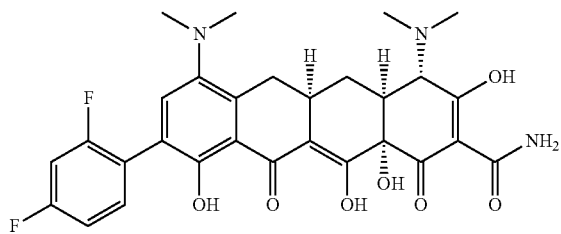
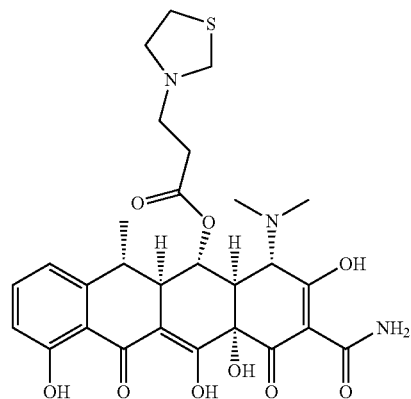
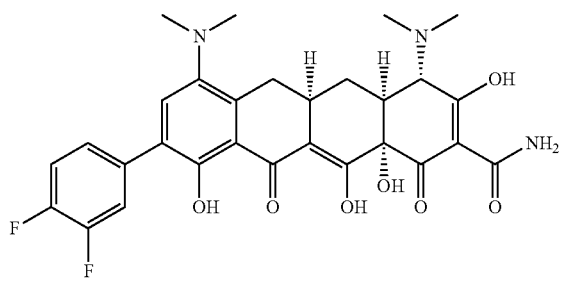
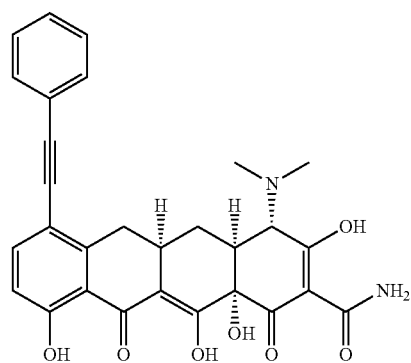
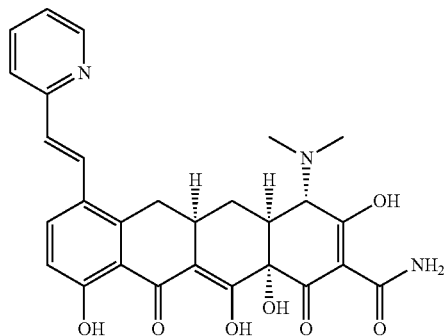

TABLE 1-continued
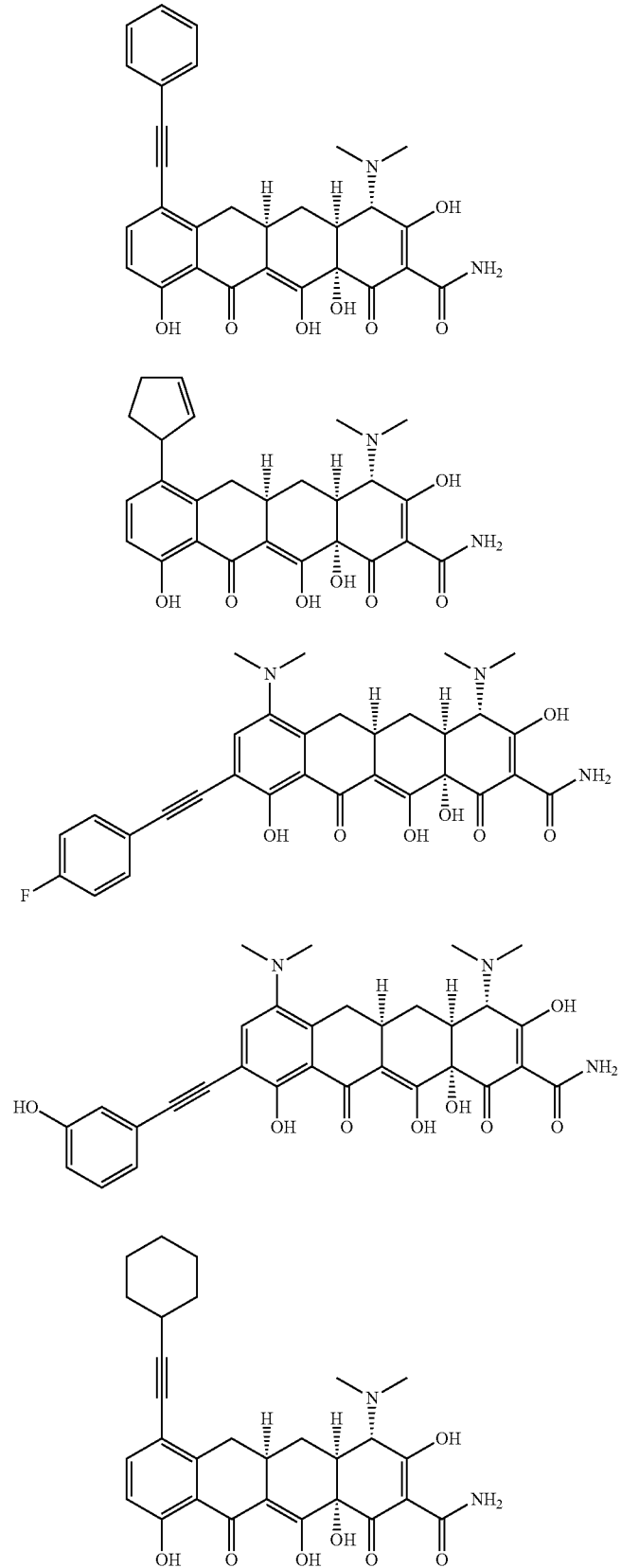

TABLE 1-continued
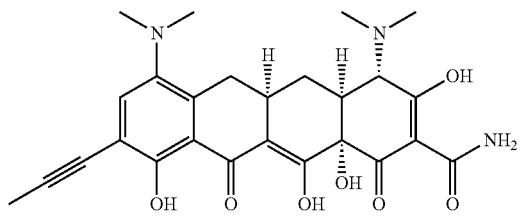
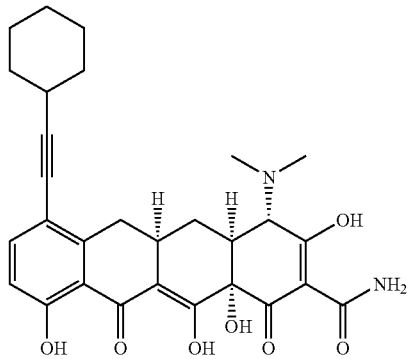
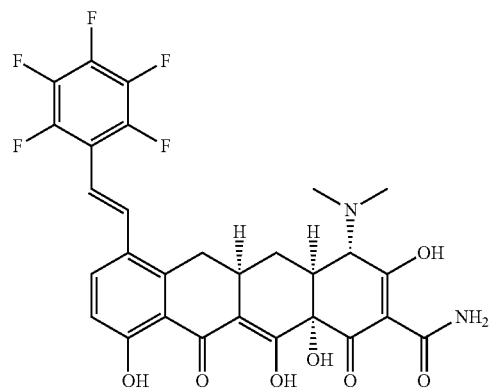
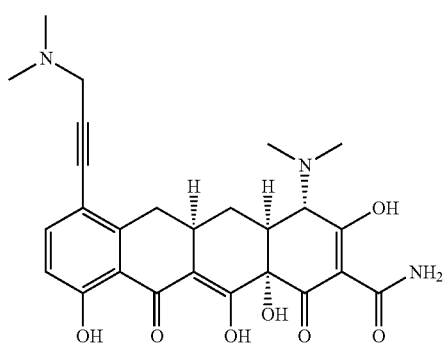
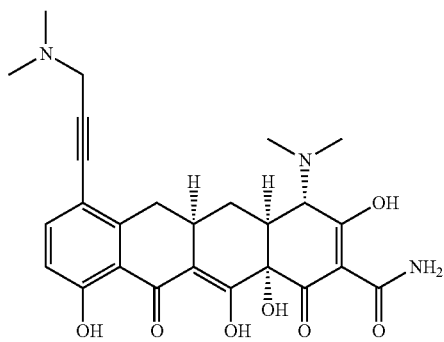

TABLE 1-continued
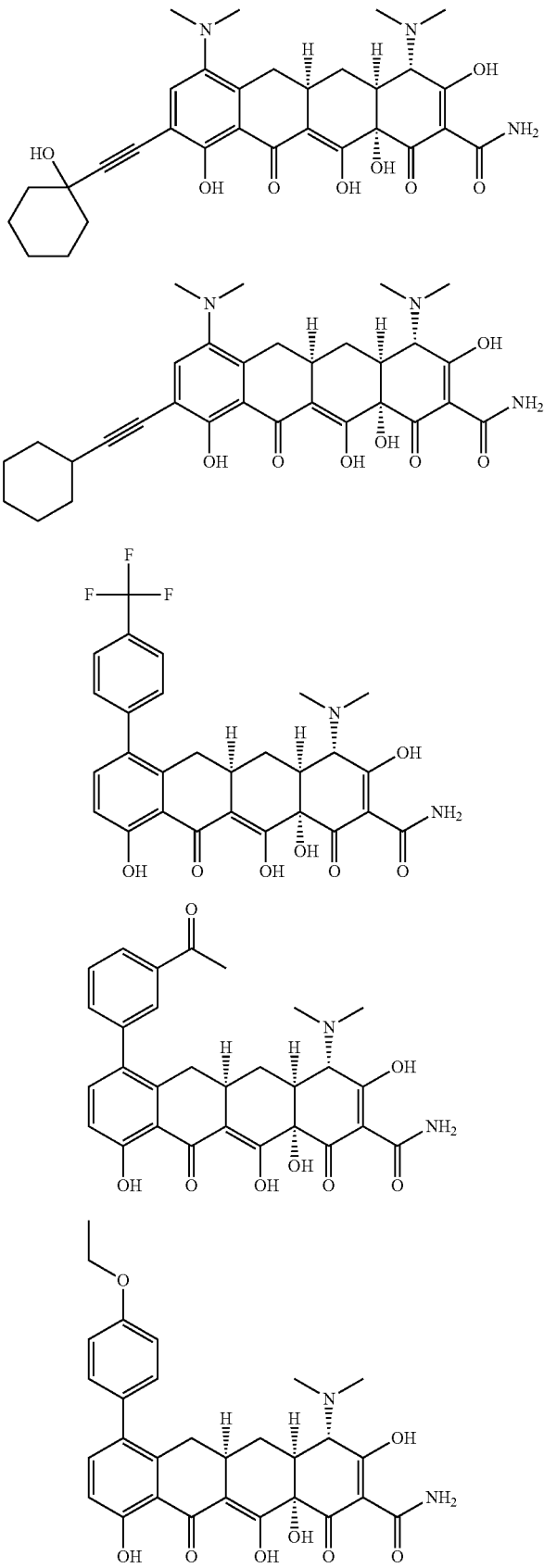

TABLE 1-continued
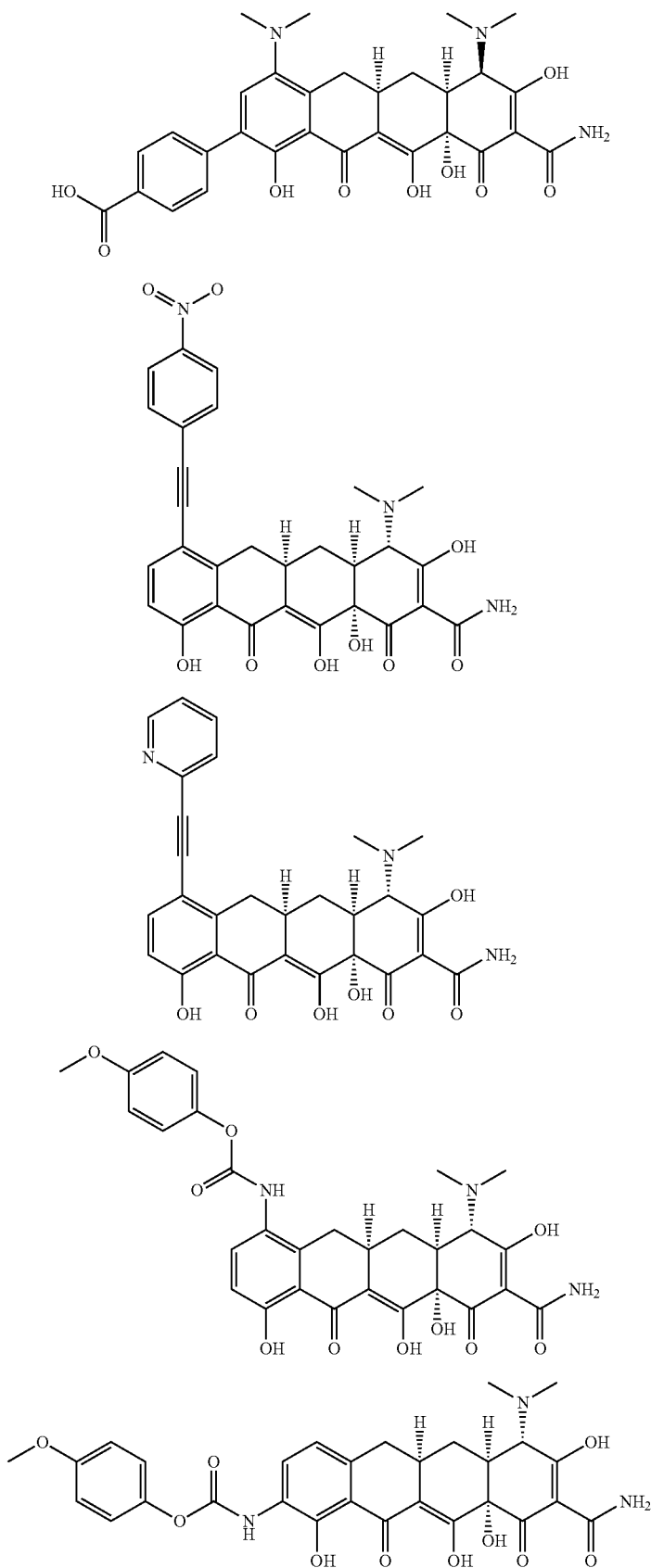

TABLE 1-continued
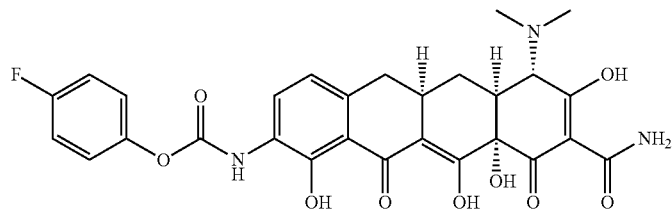
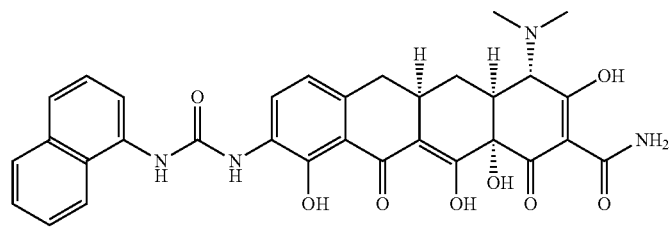
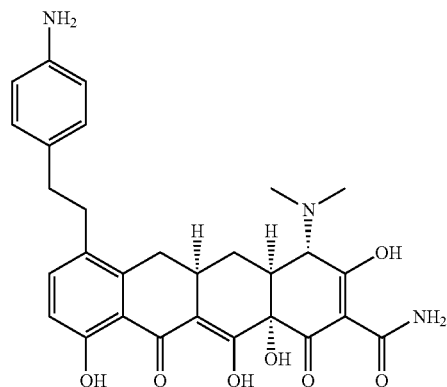
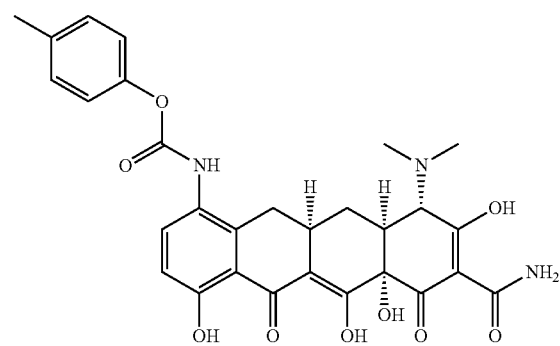
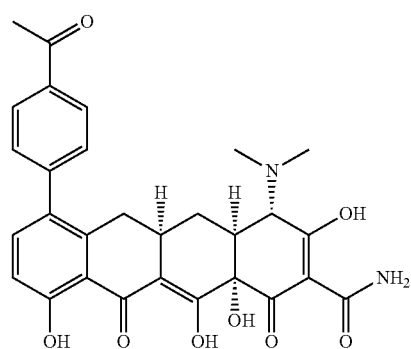

TABLE 1-continued
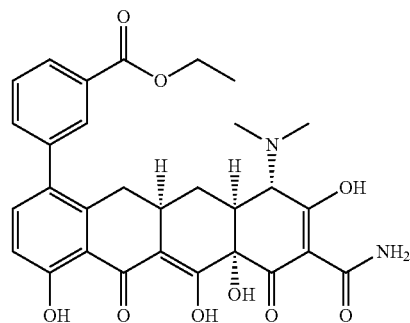
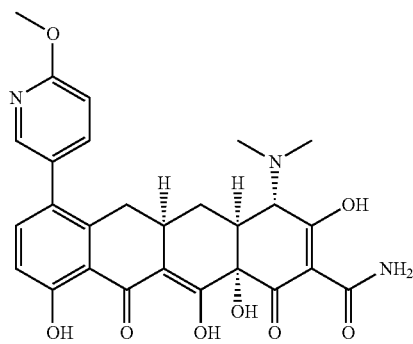
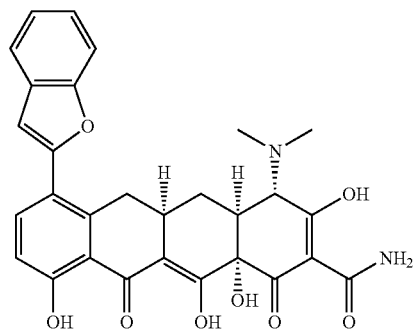
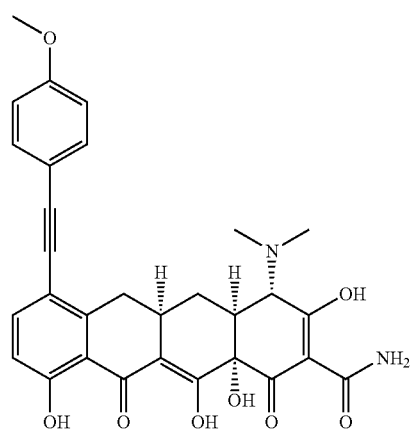

TABLE 1-continued
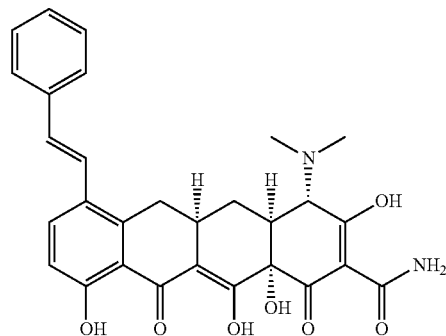
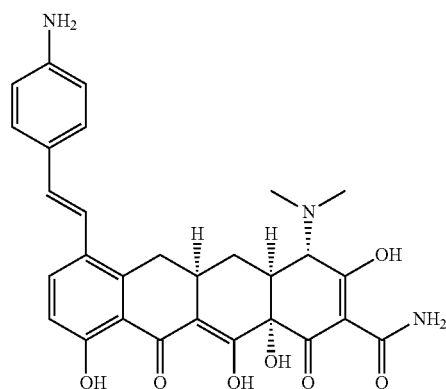
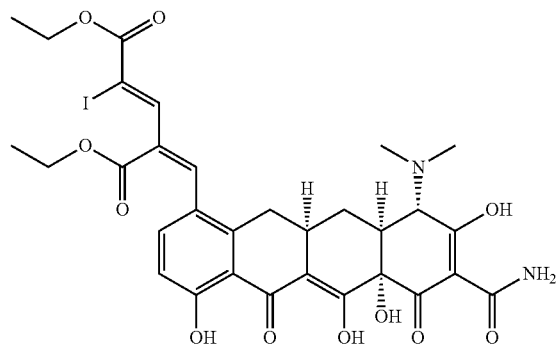
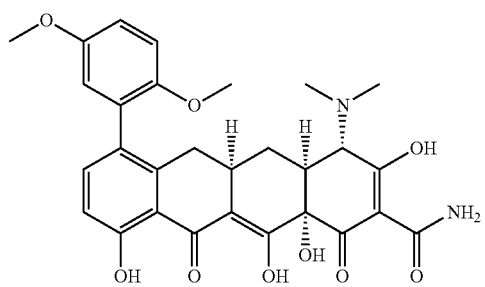
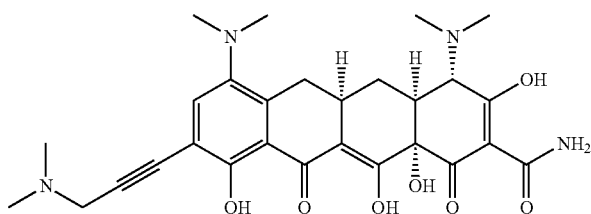

TABLE 1-continued
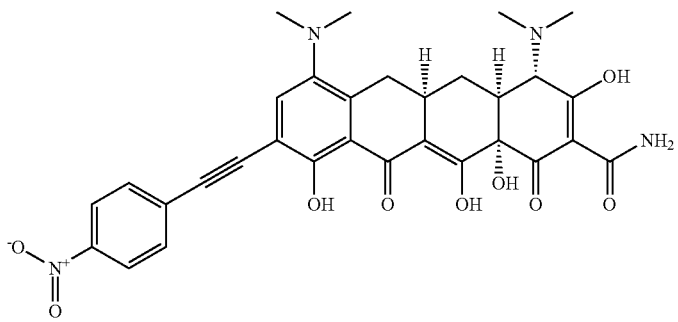
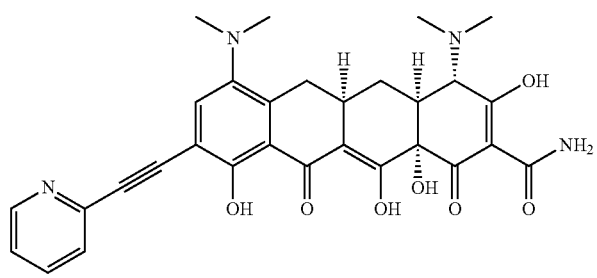
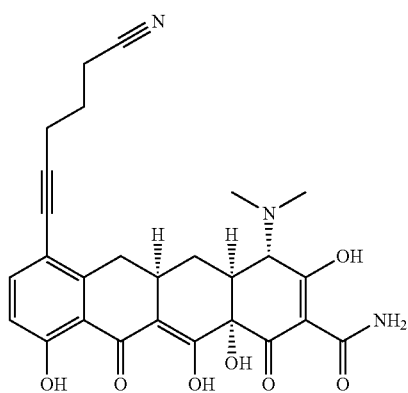
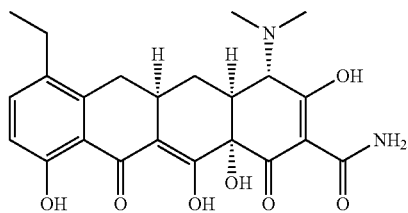
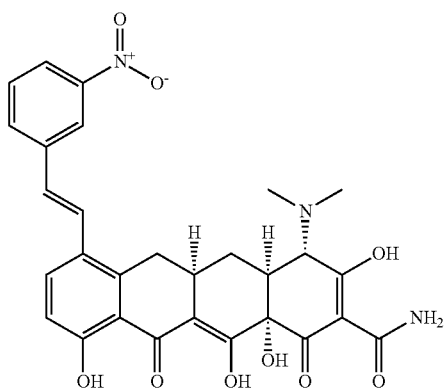

TABLE 1-continued
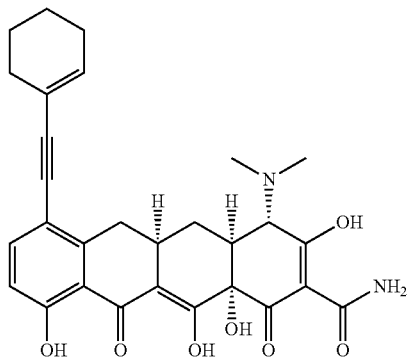
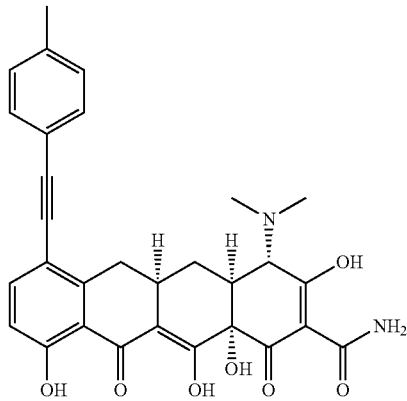
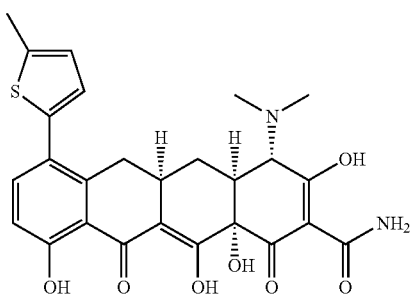
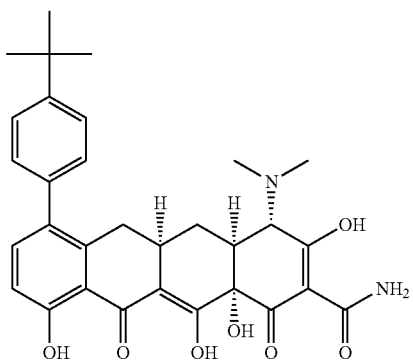

TABLE 1-continued
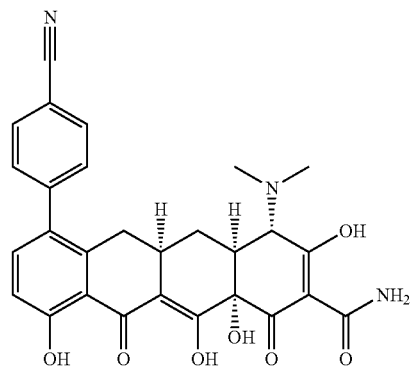
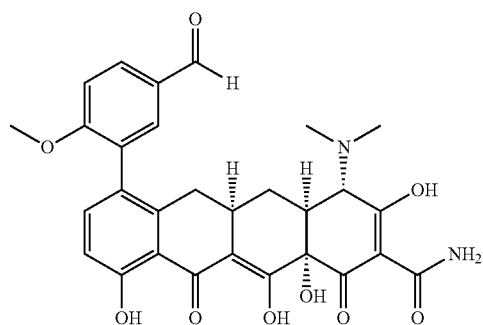
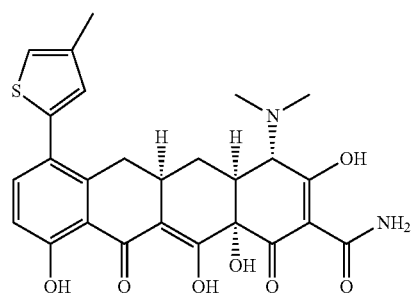
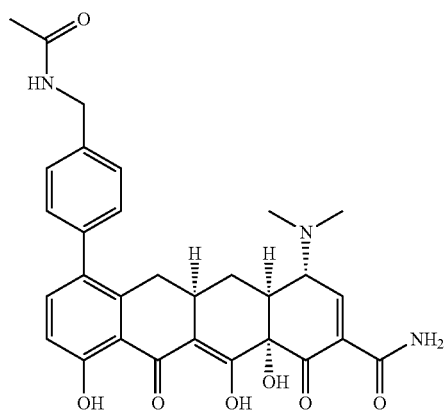

TABLE 1-continued
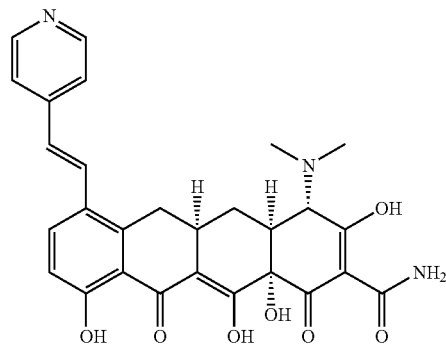
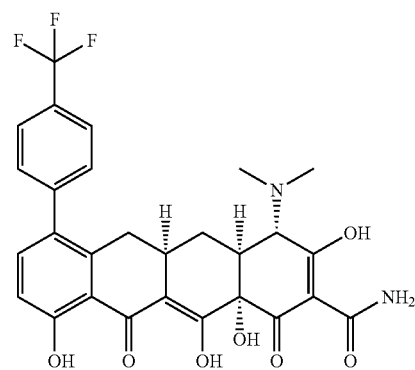
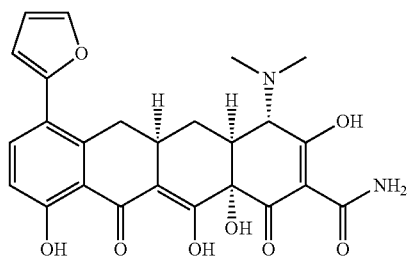
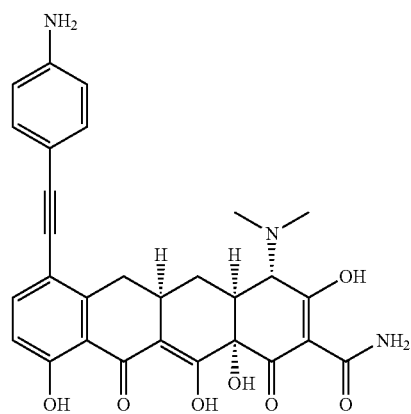

TABLE 1-continued
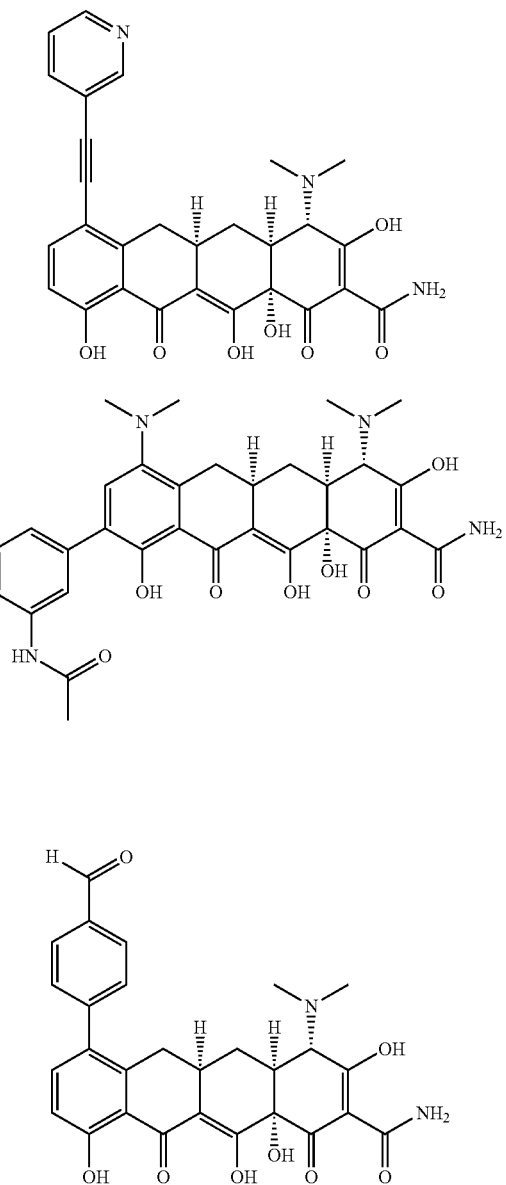
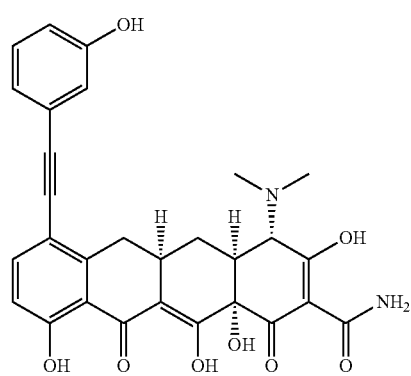

TABLE 1-continued
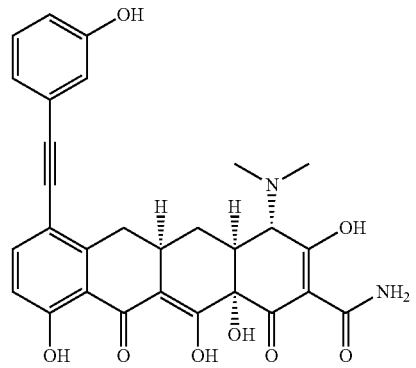
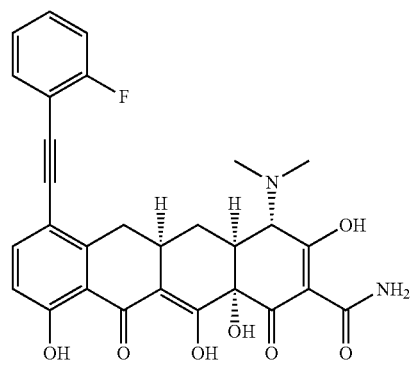
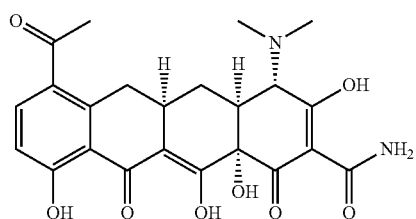
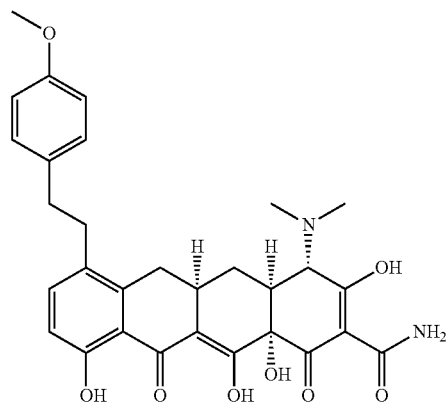

TABLE 1-continued
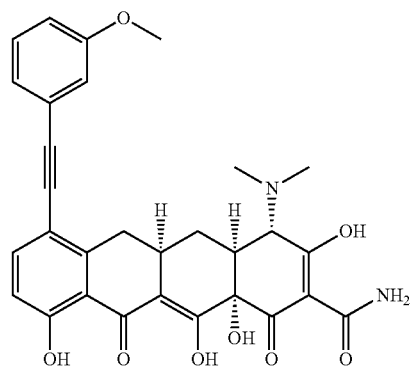
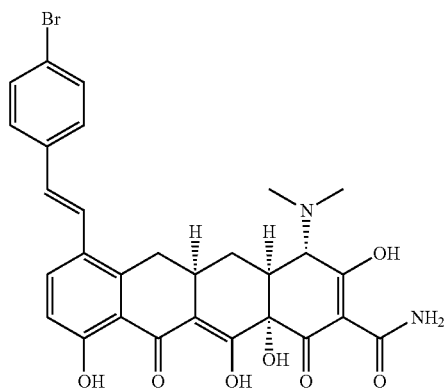
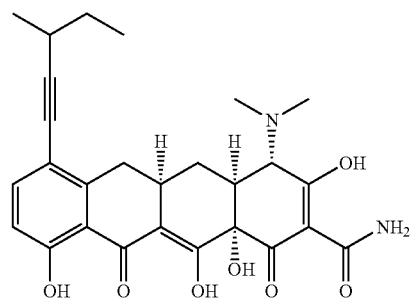
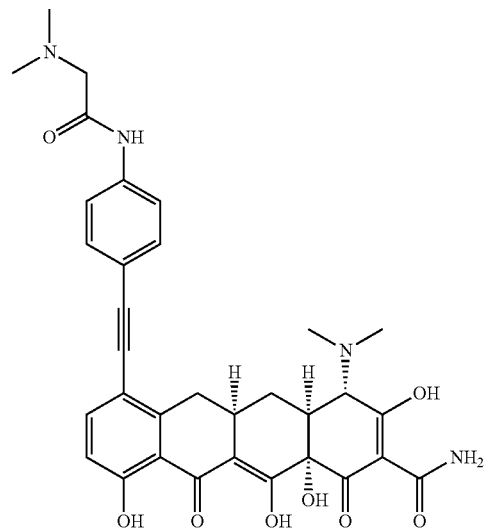

TABLE 1-continued
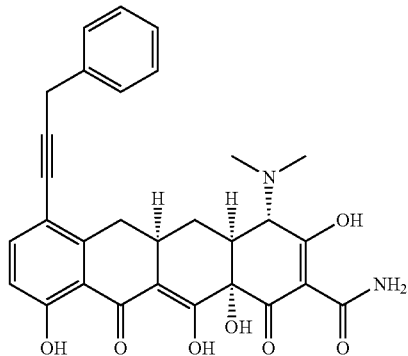
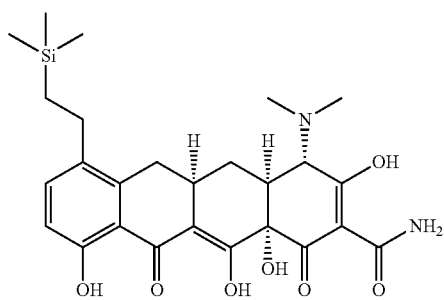
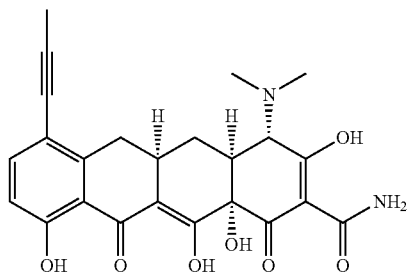
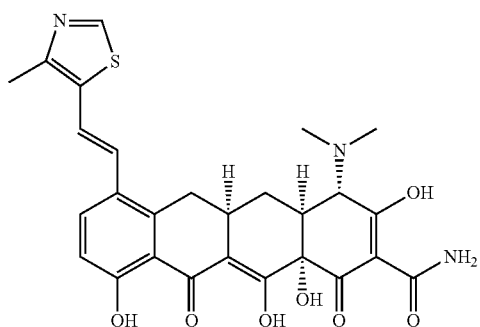
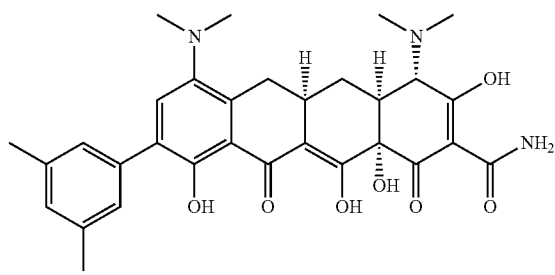

TABLE 1-continued
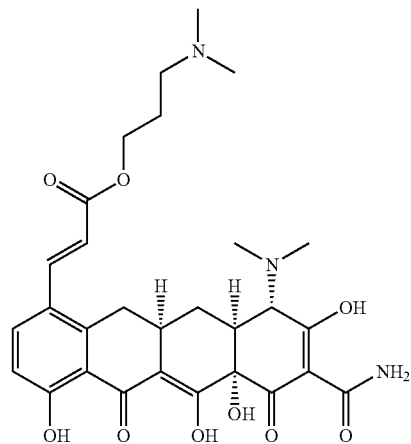
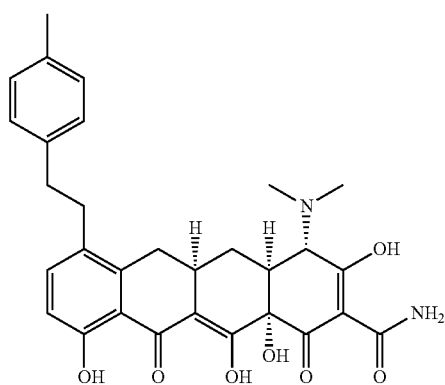
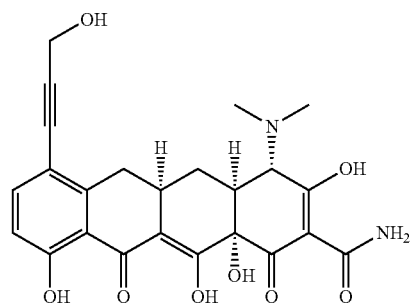
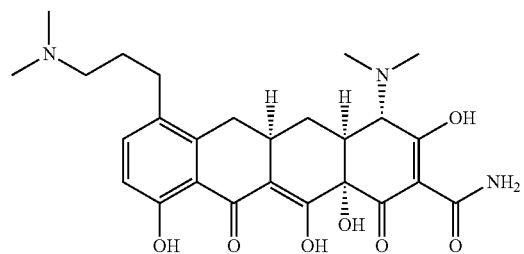

TABLE 1-continued
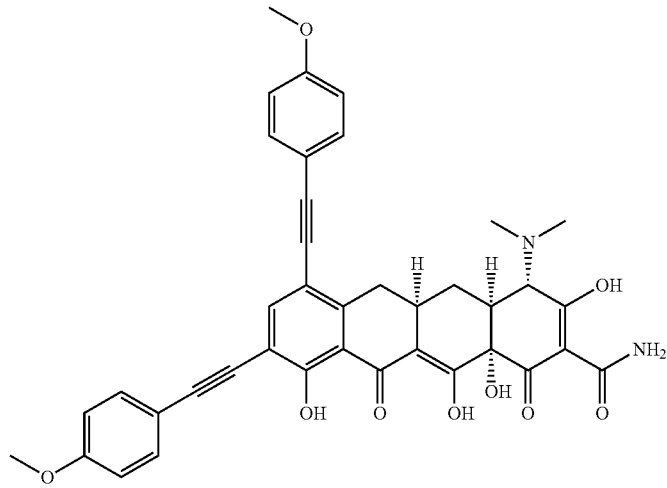
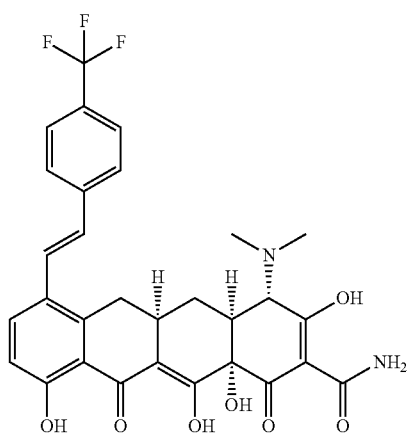
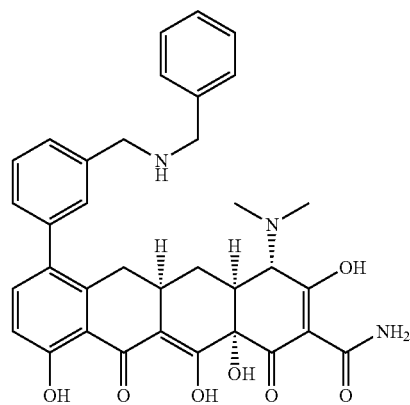

TABLE 1-continued
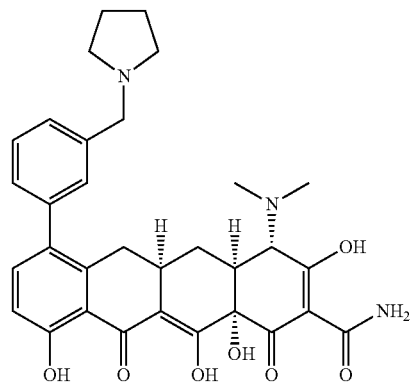
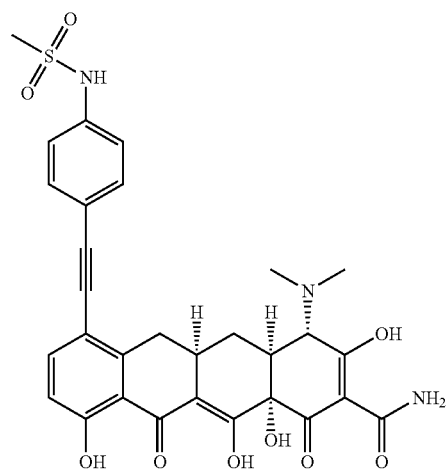
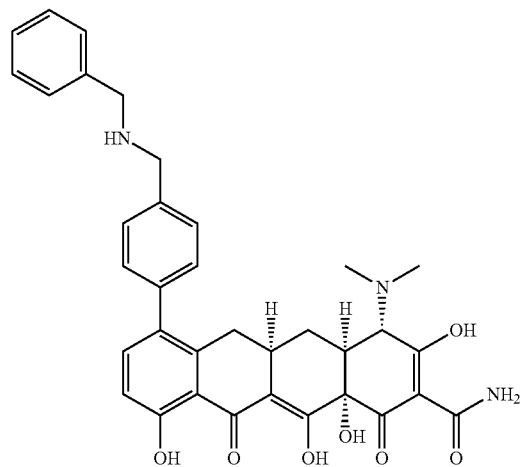

TABLE 1-continued
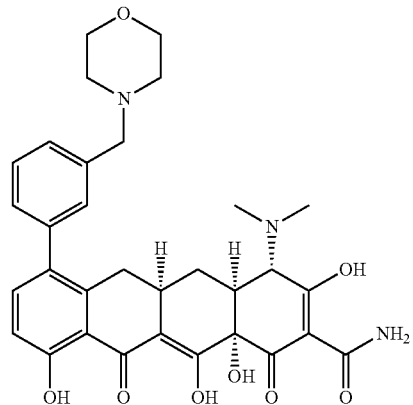
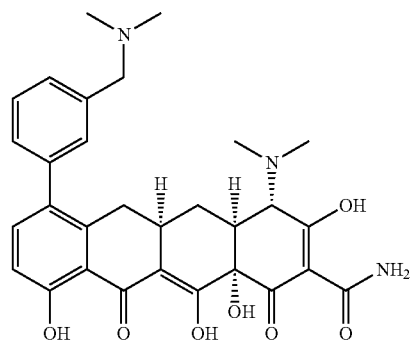
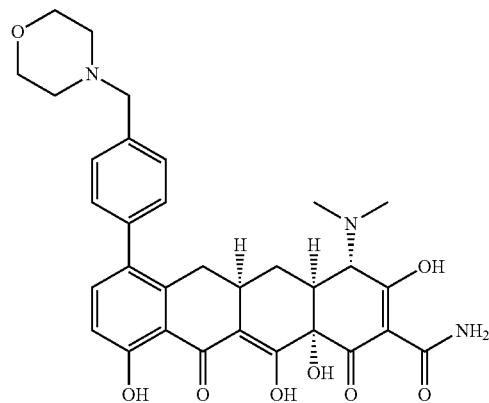
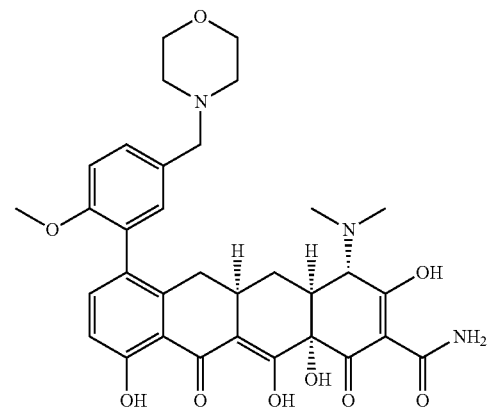

TABLE 1-continued
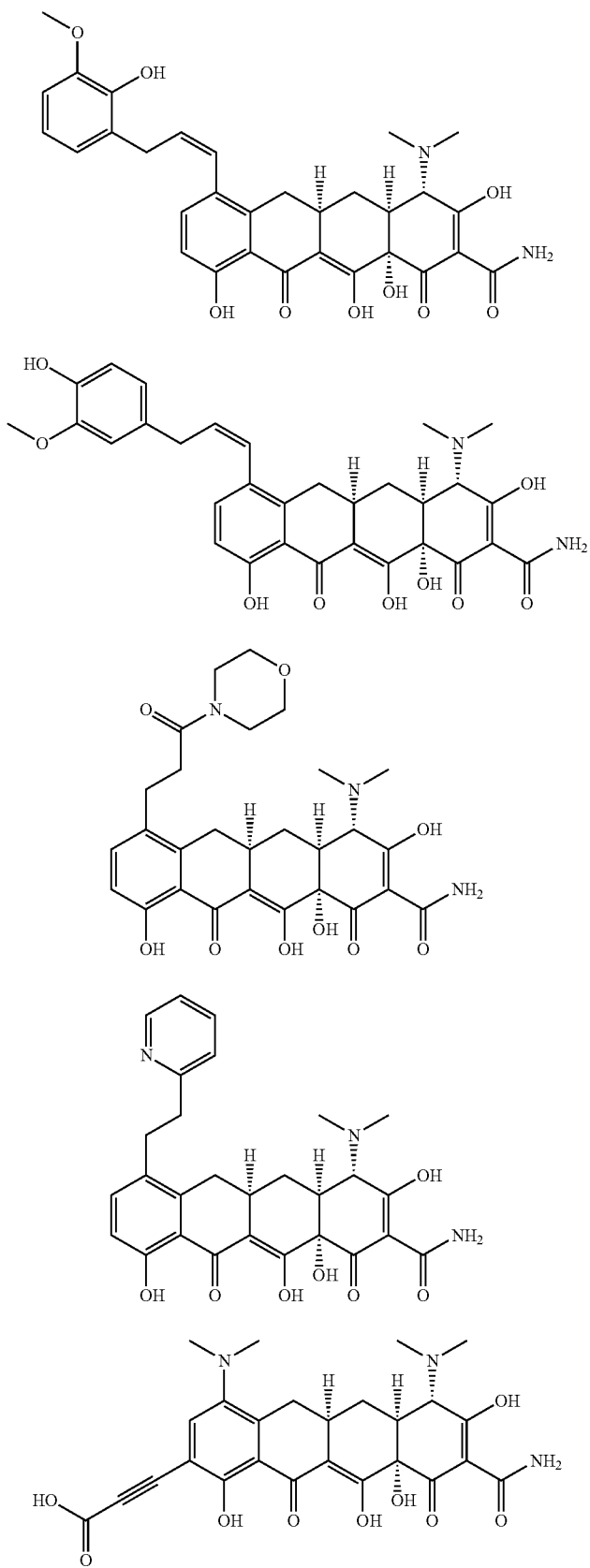

TABLE 1-continued
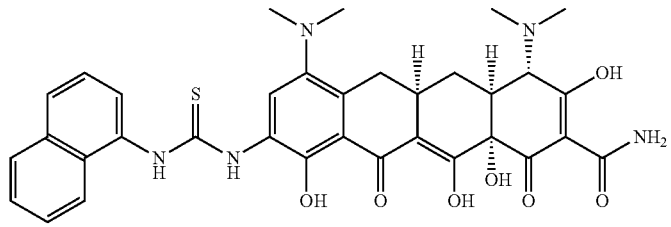
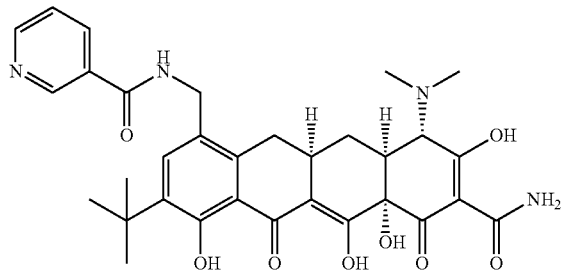
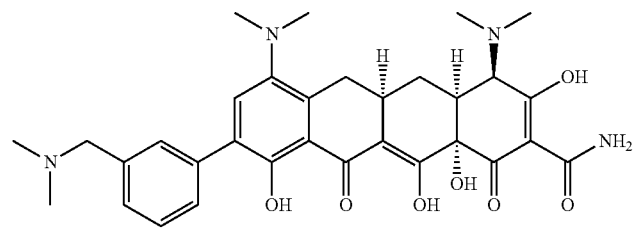
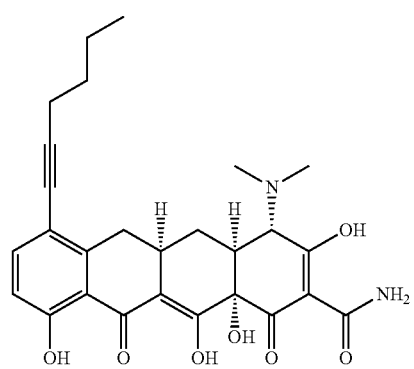
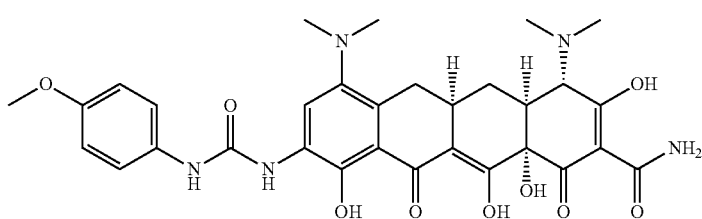

TABLE 1-continued
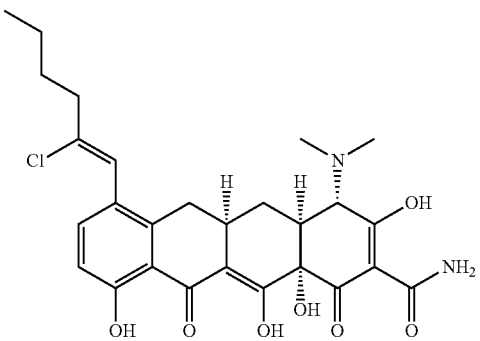
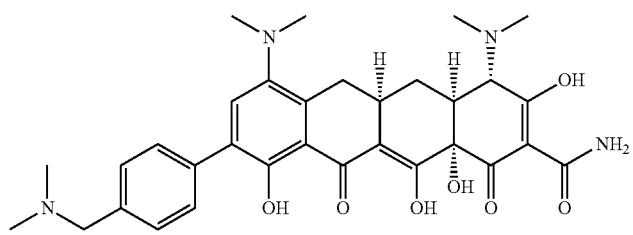
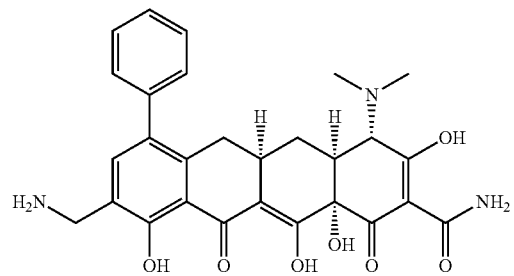
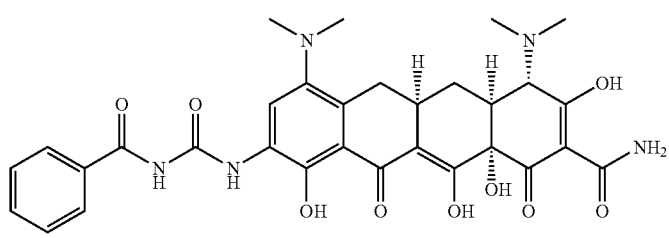
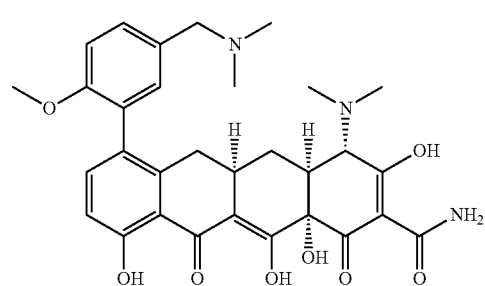

TABLE 1-continued
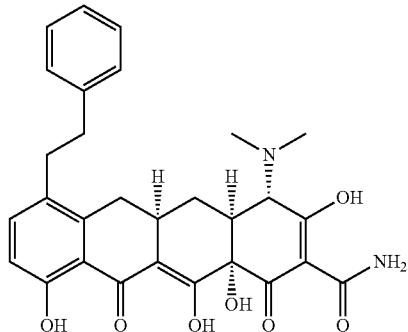
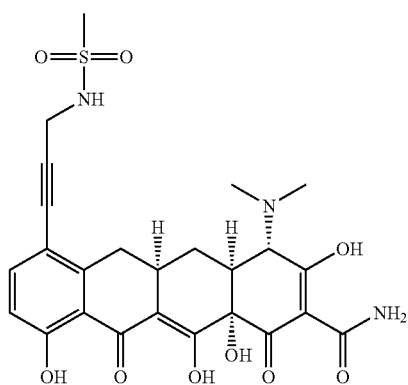
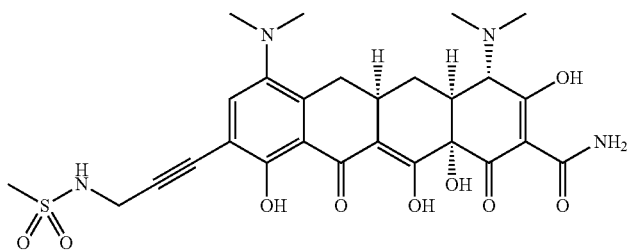
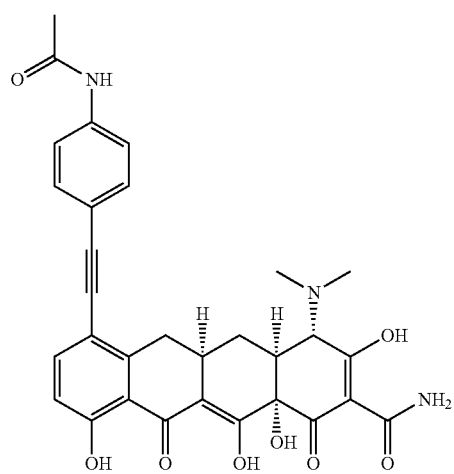

TABLE 1-continued
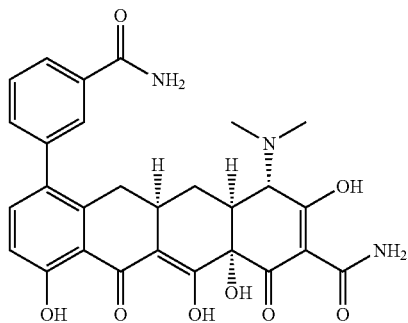
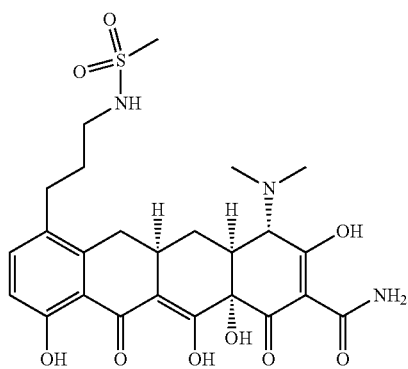
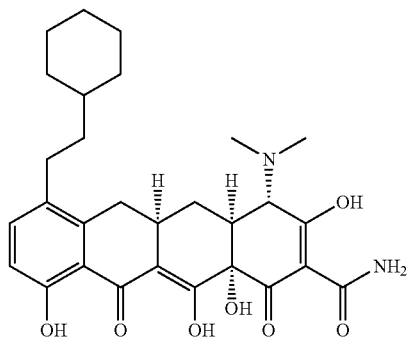
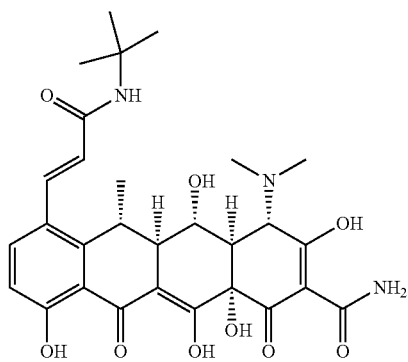
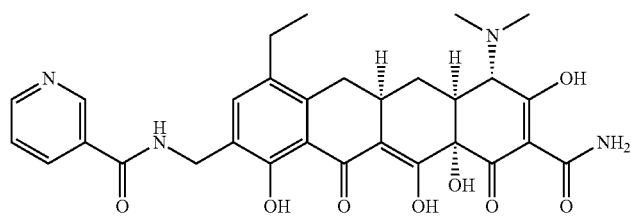

TABLE 1-continued
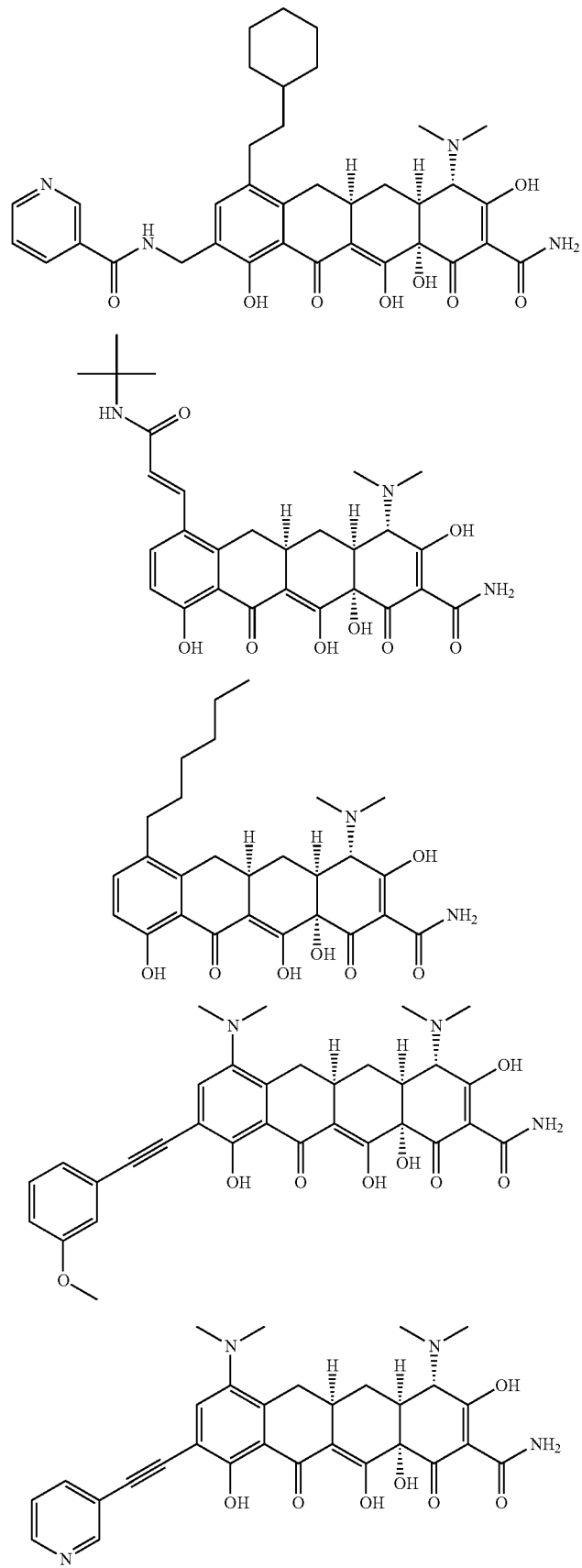

TABLE 1-continued
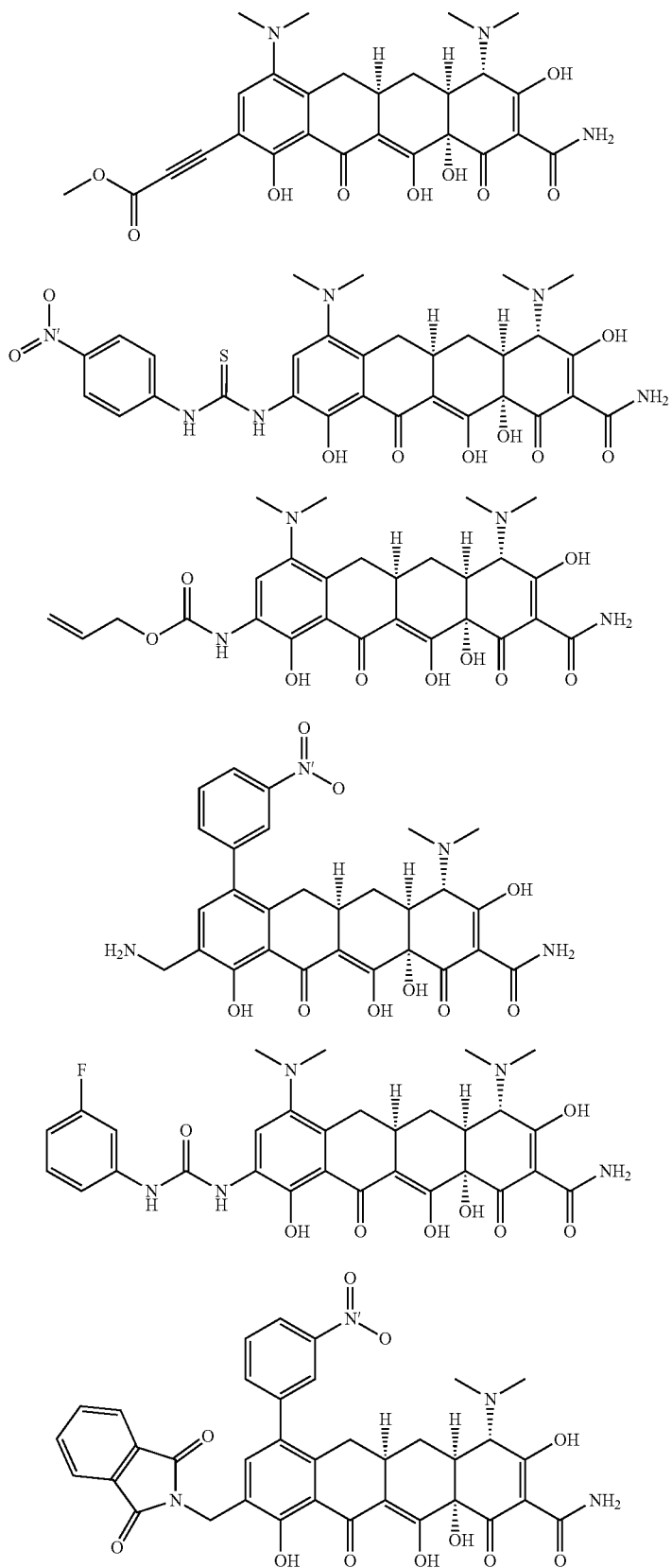

TABLE 1-continued
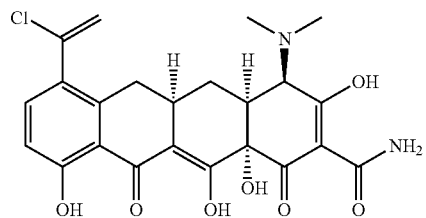
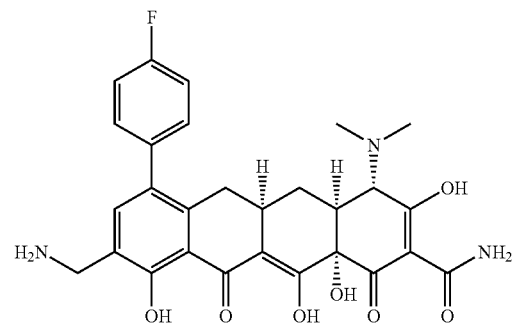
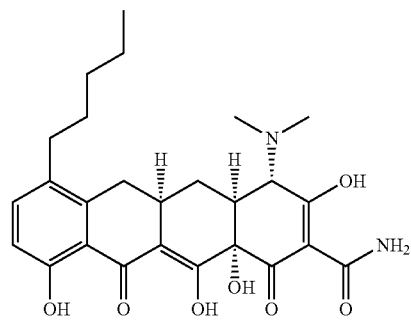
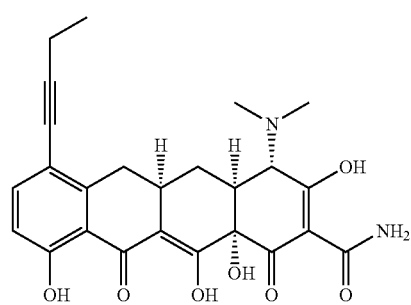
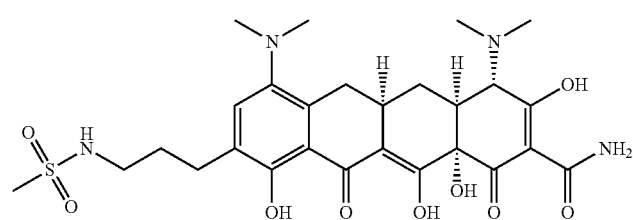

TABLE 1-continued
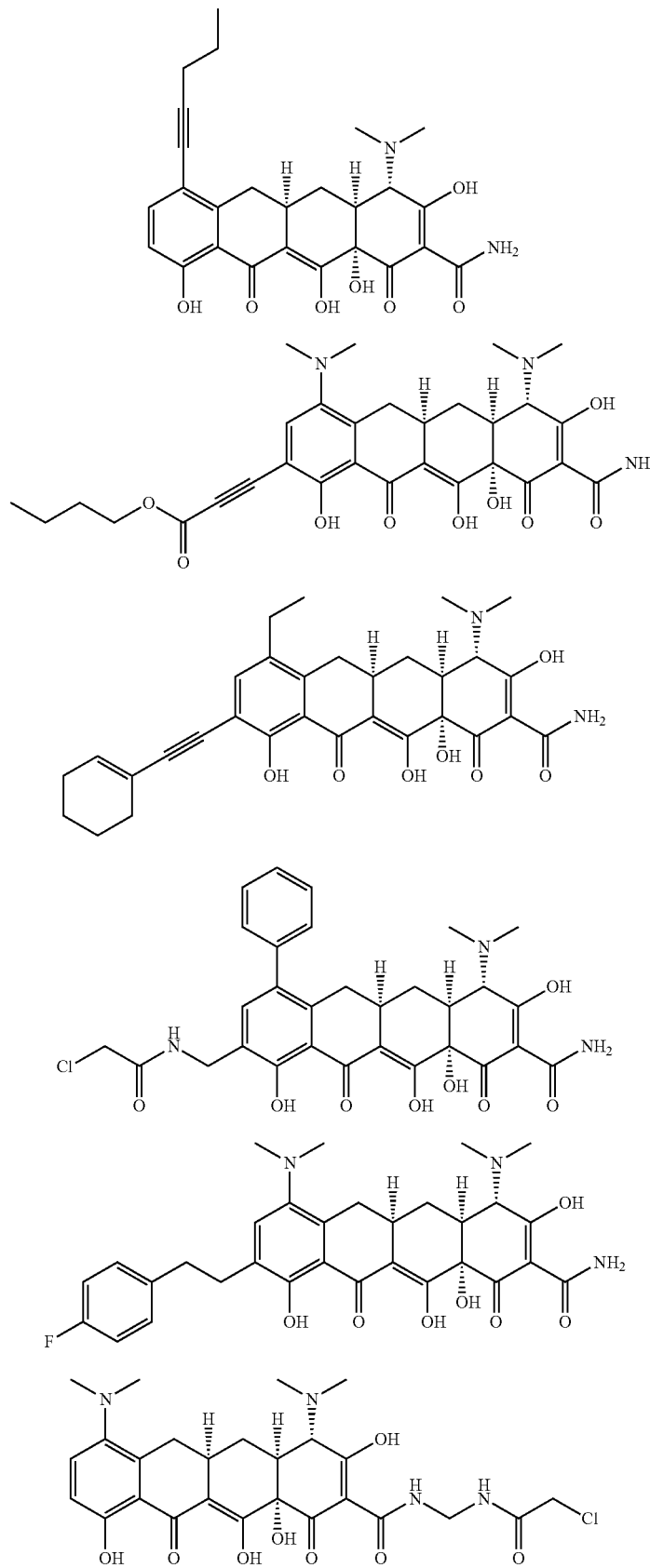

TABLE 1-continued
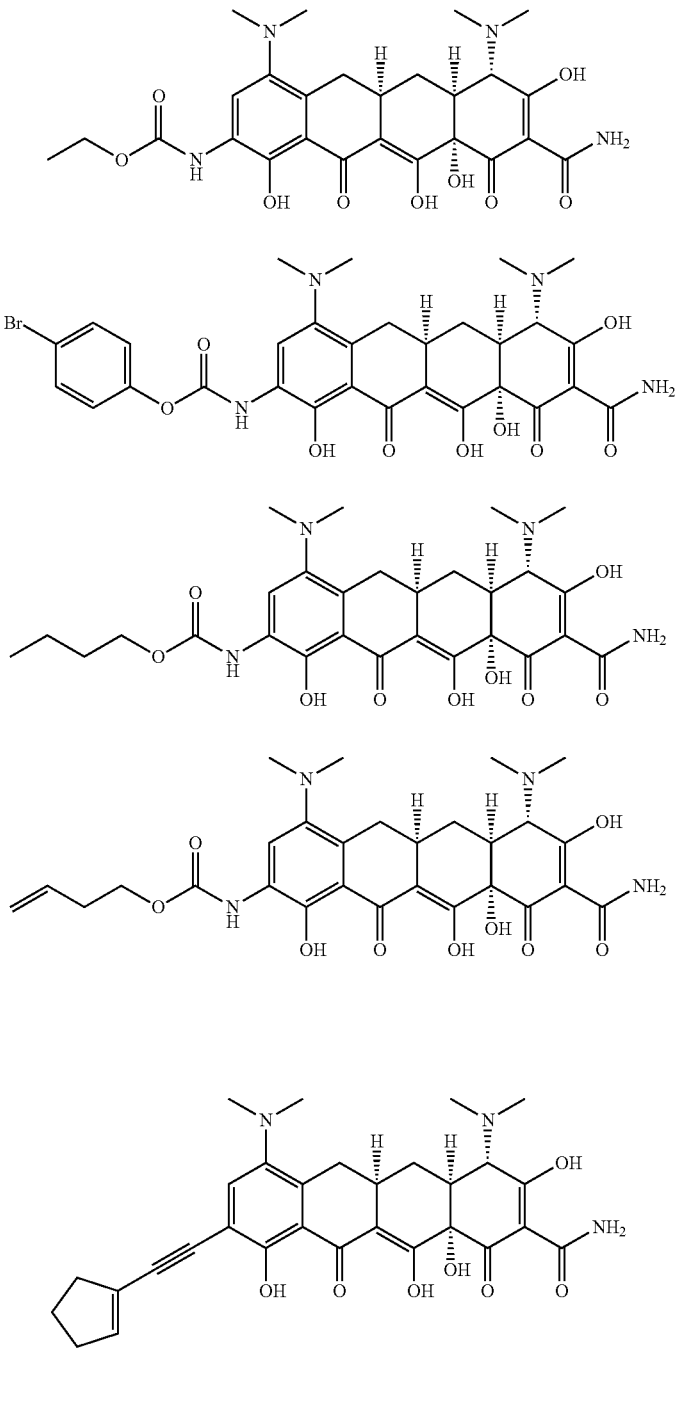
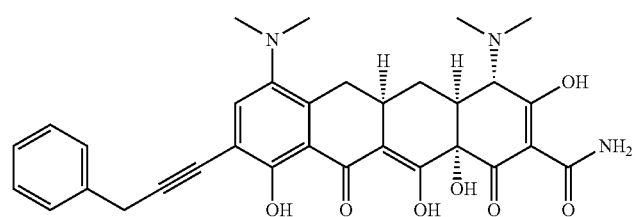

TABLE 1-continued
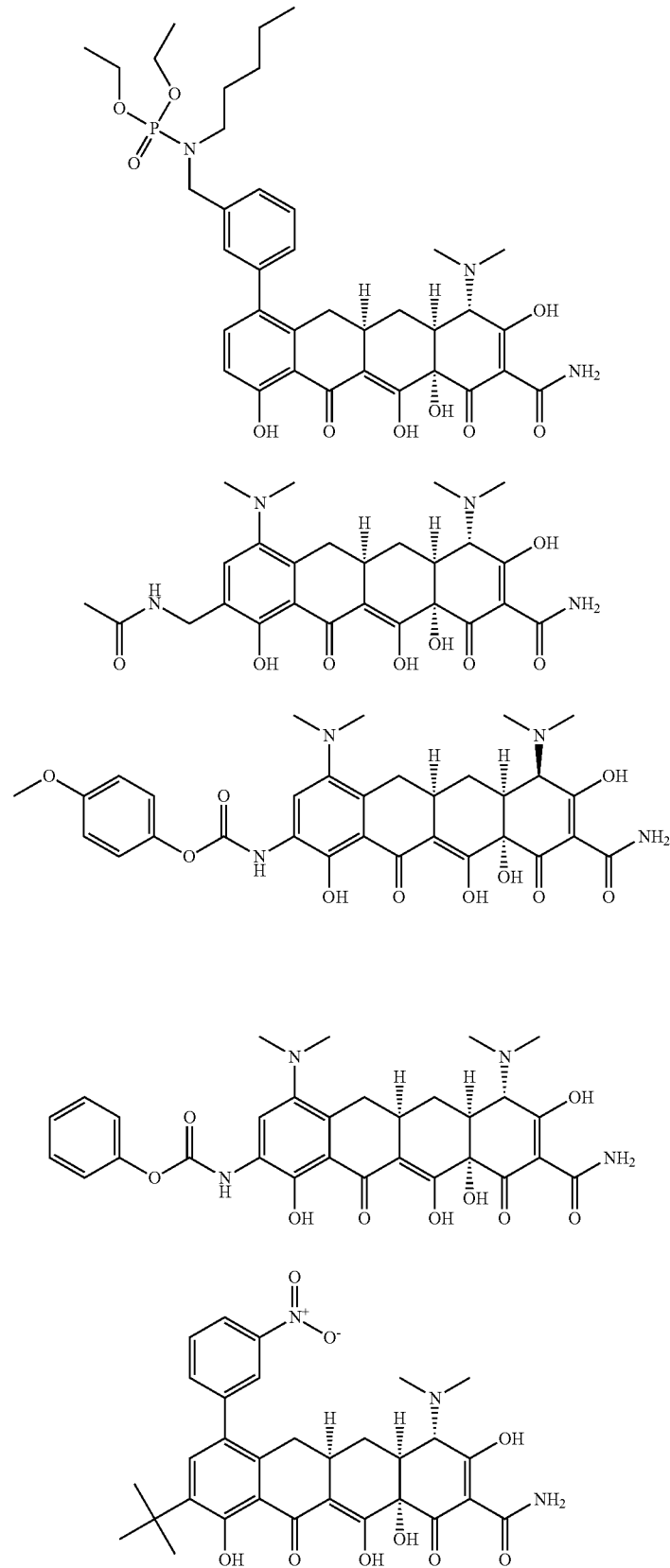

TABLE 1-continued
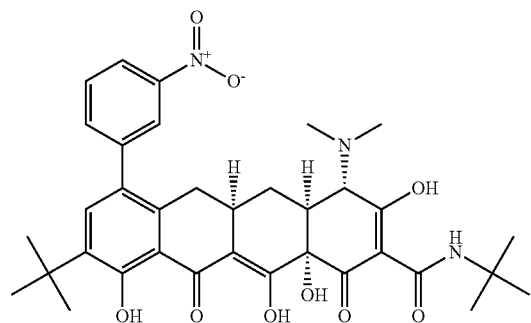
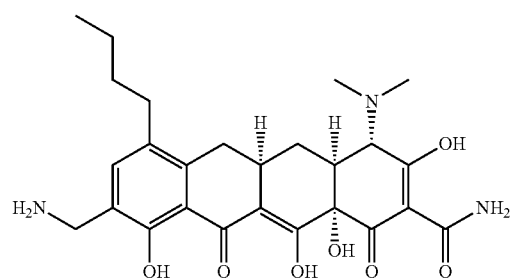
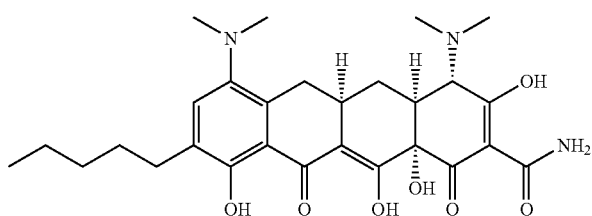
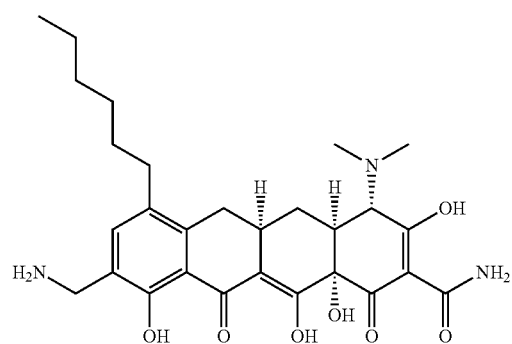
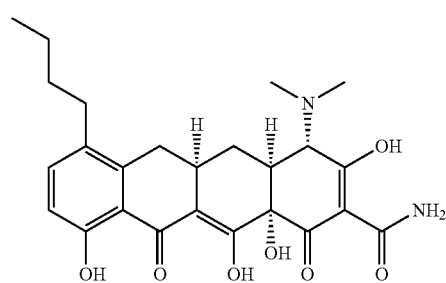

TABLE 1-continued
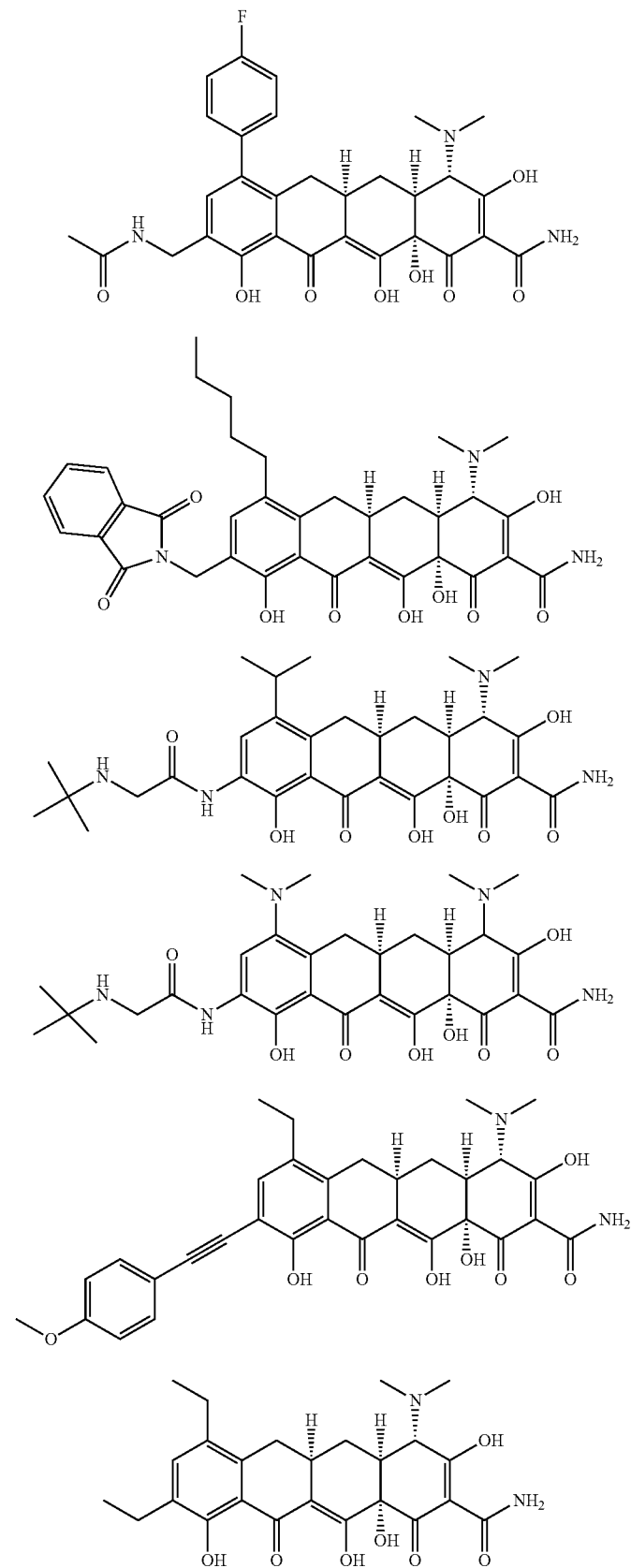

TABLE 1-continued
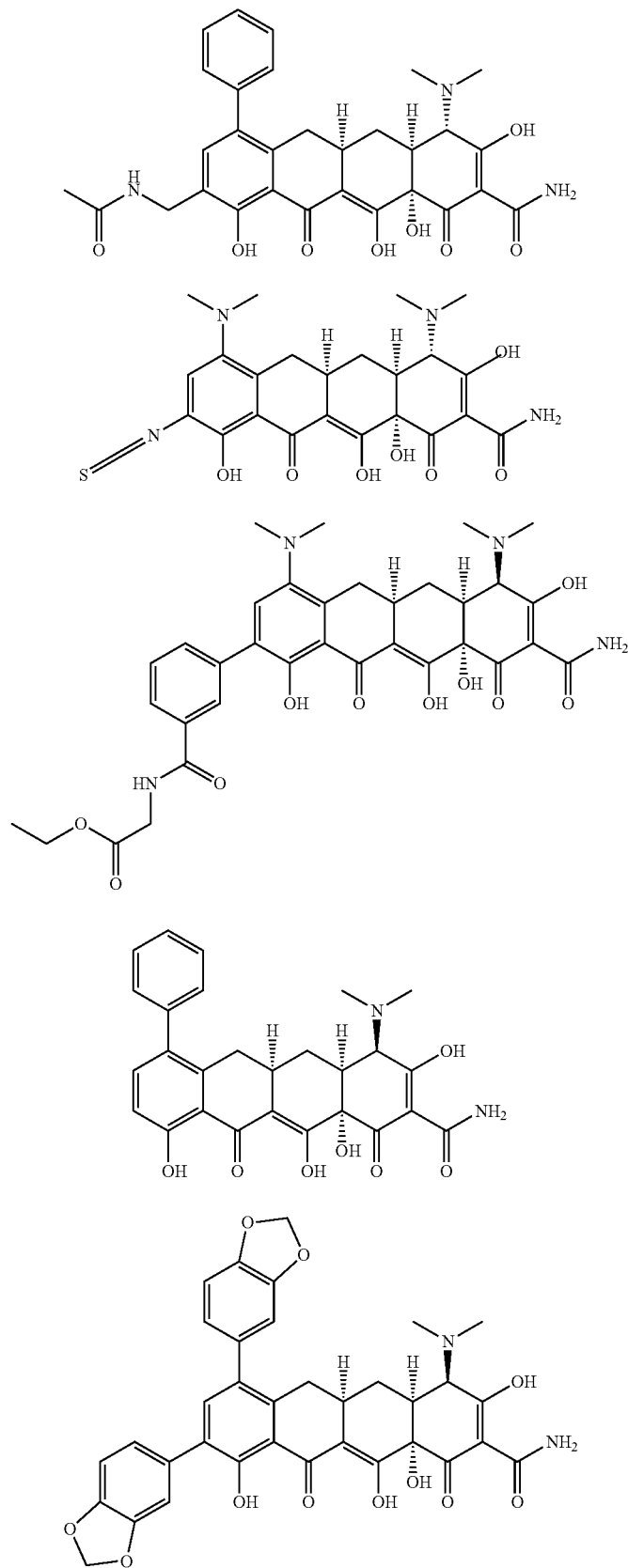

TABLE 1-continued
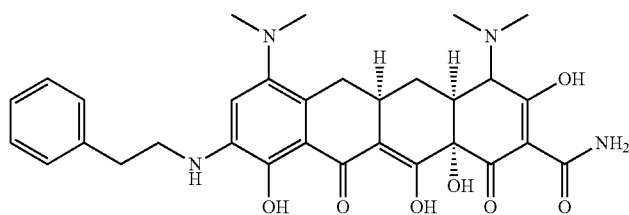
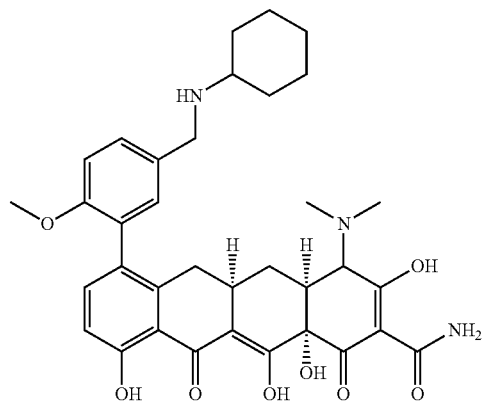
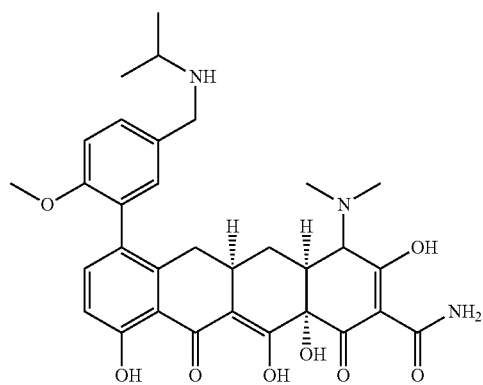
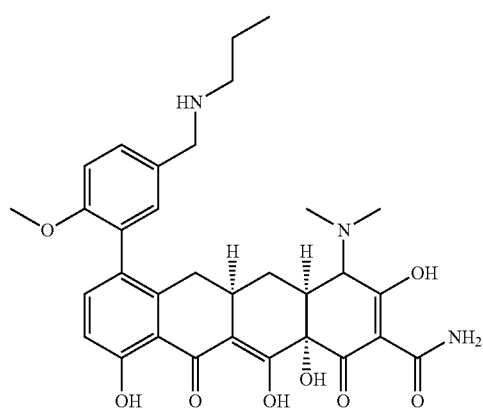

TABLE 1-continued
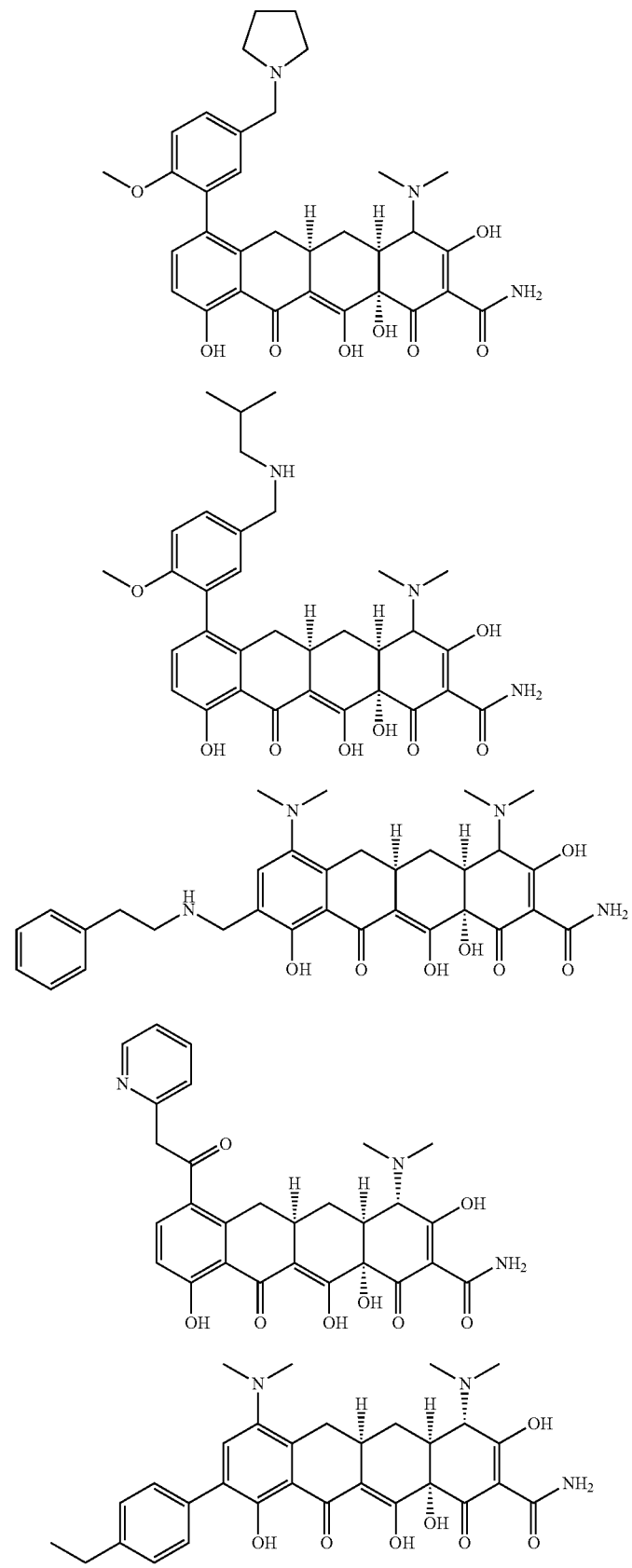

TABLE 1-continued
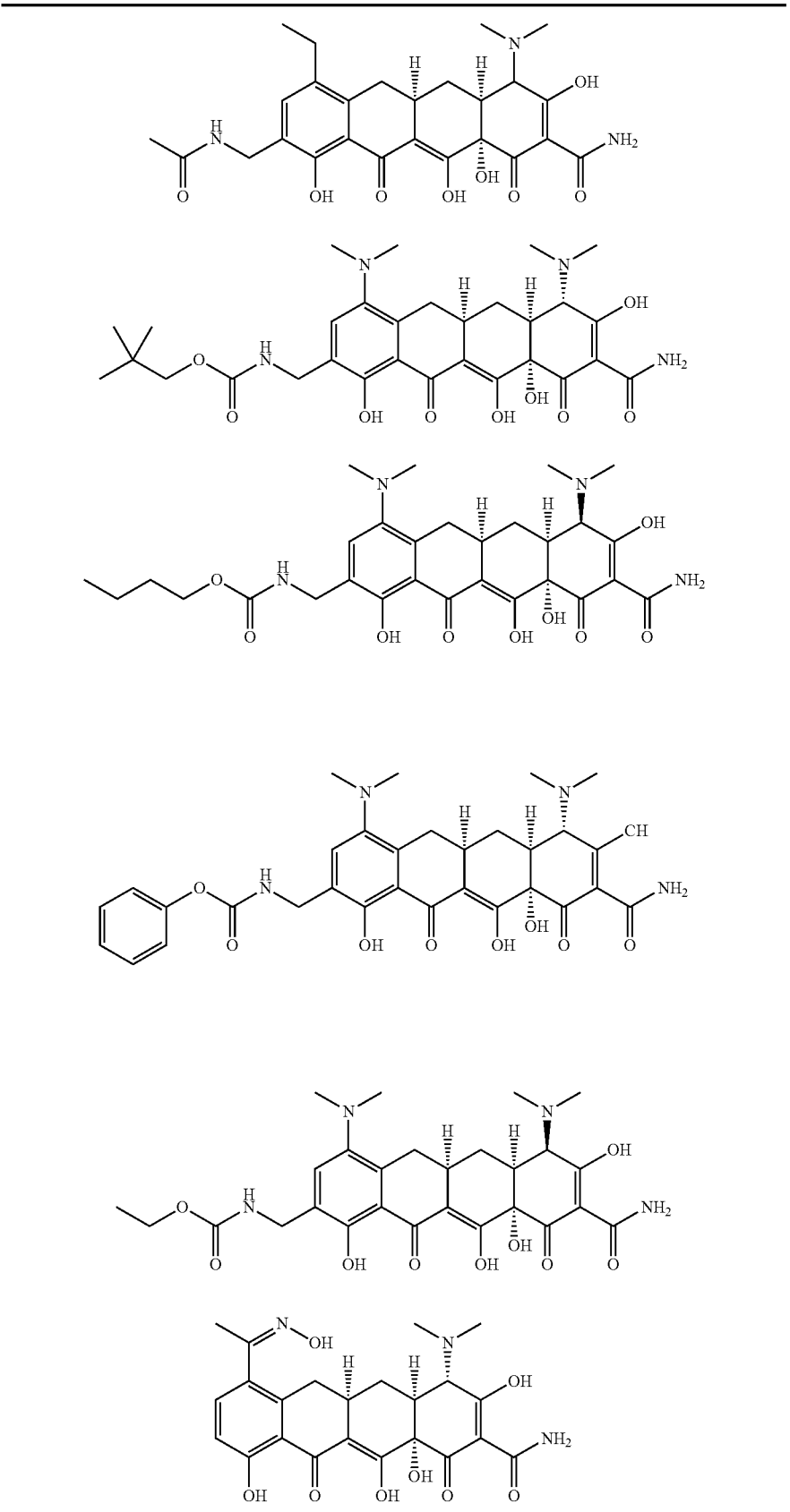

TABLE 1-continued
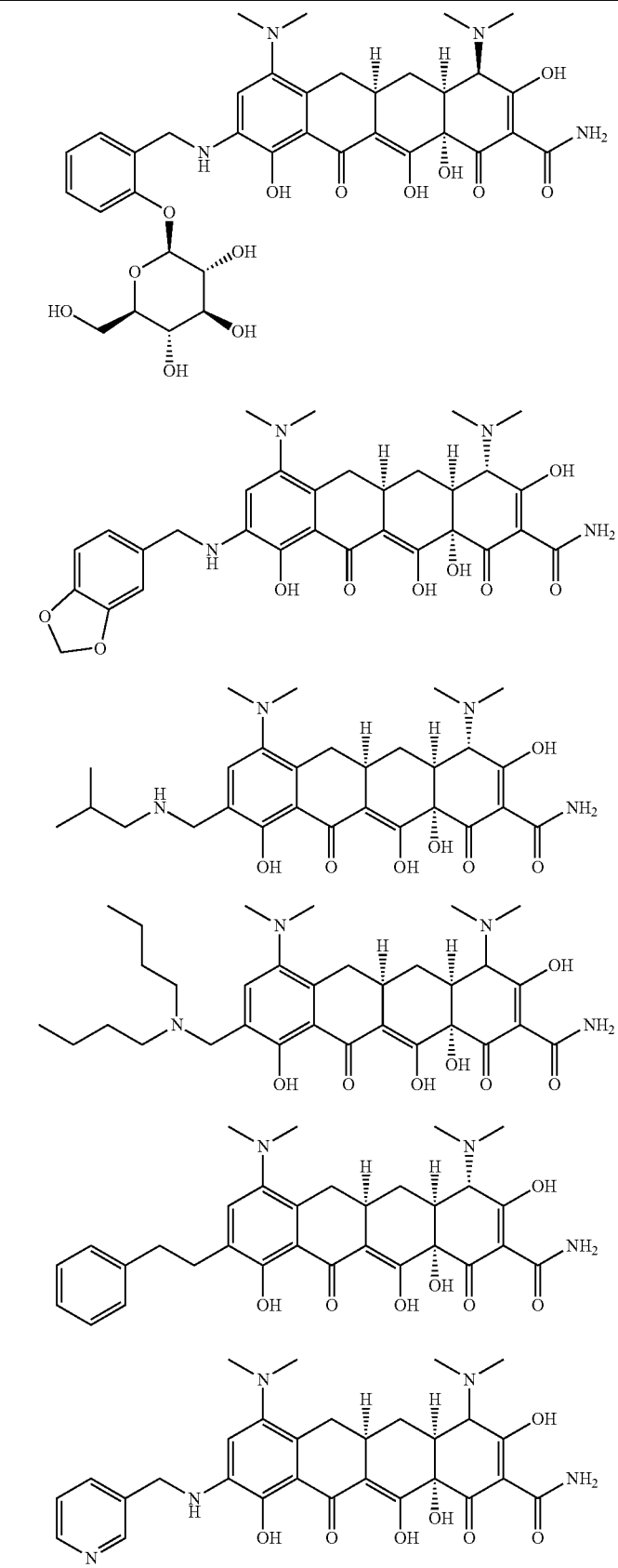

TABLE 1-continued
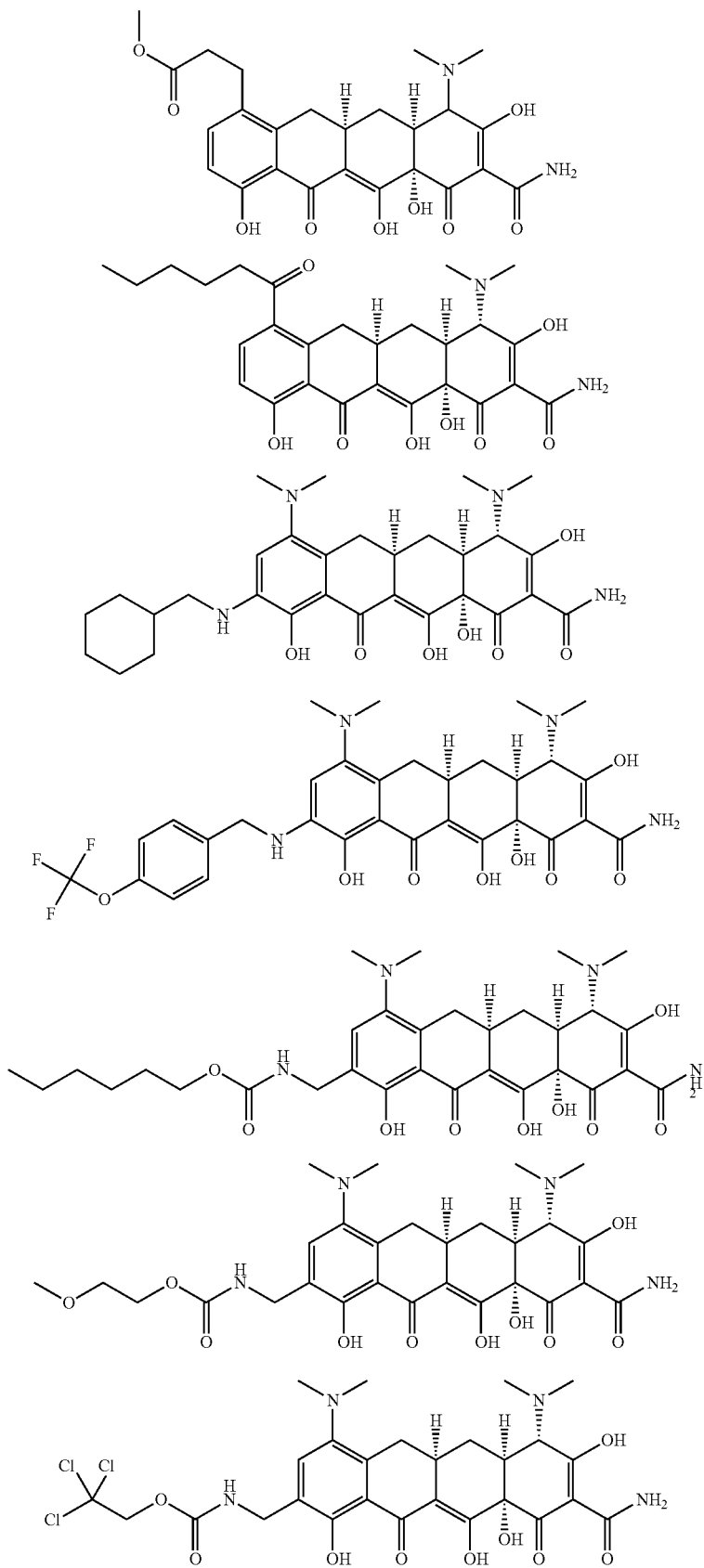

TABLE 1-continued
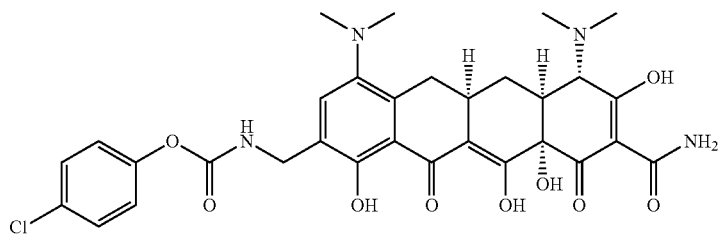
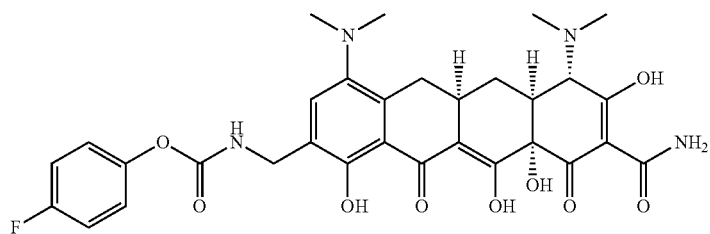
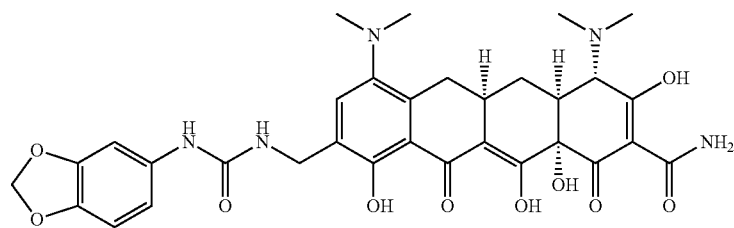
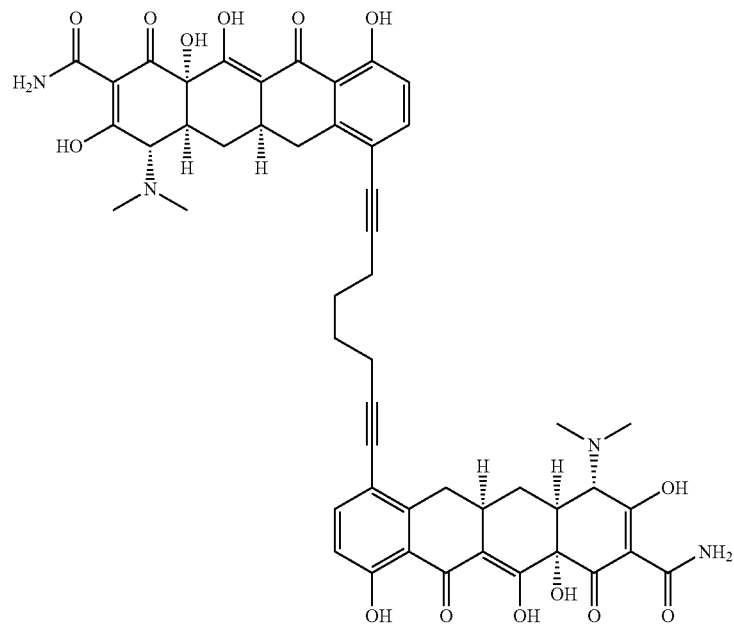

TABLE 1-continued
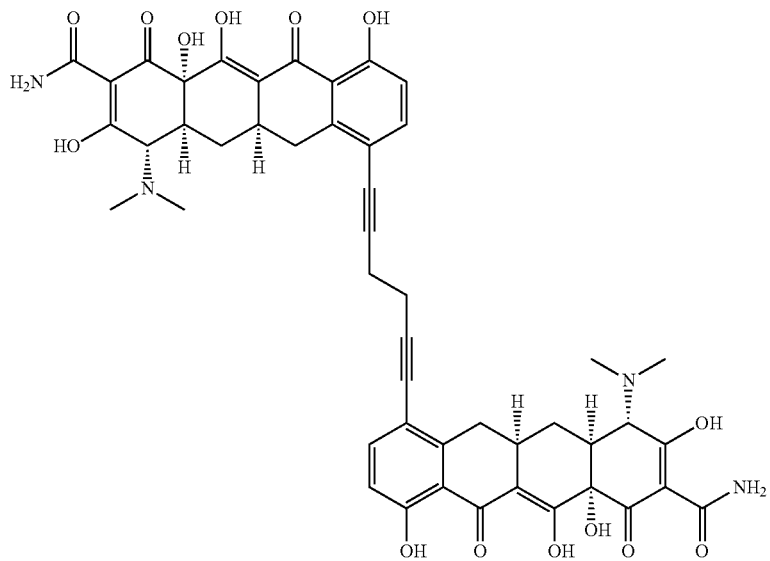
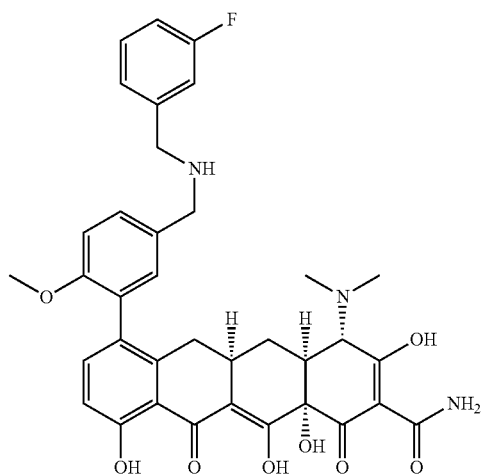
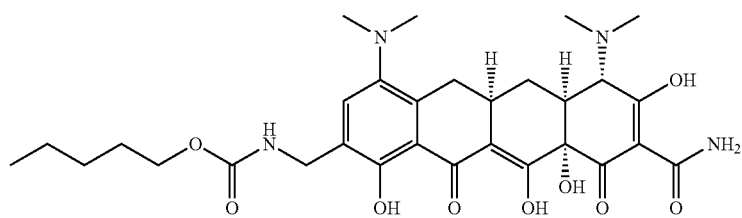

TABLE 1-continued
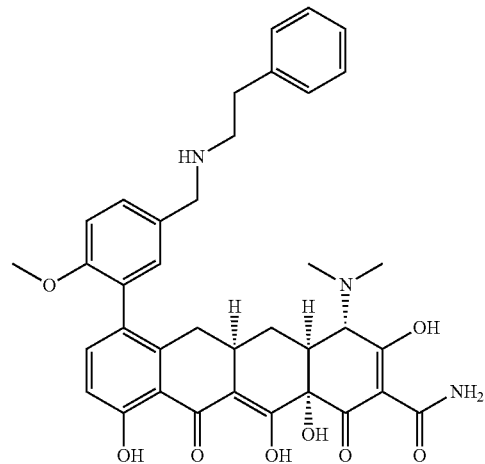
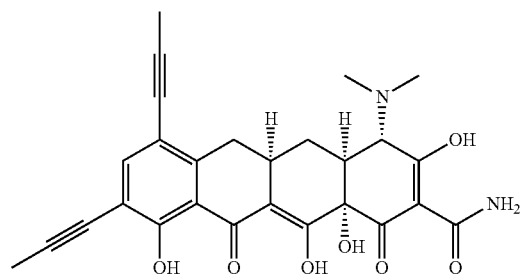
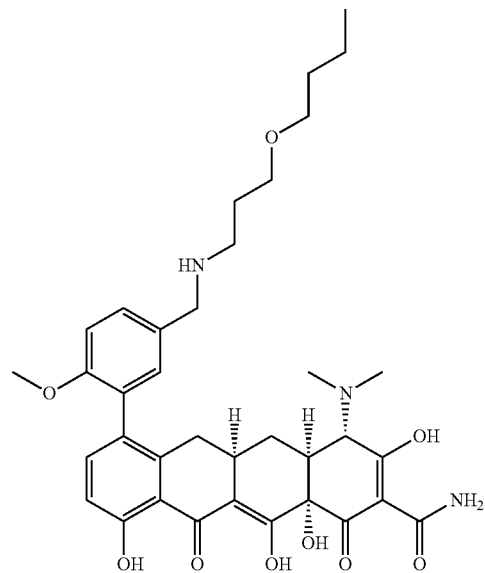

TABLE 1-continued
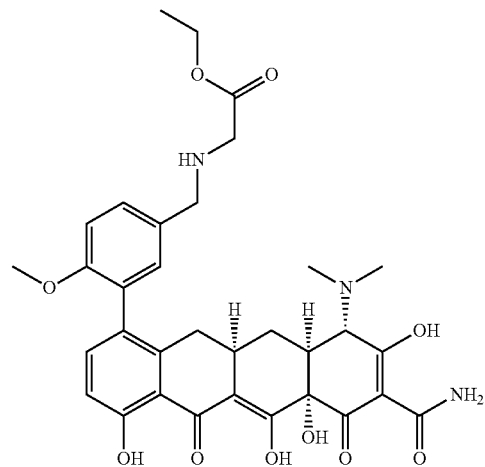
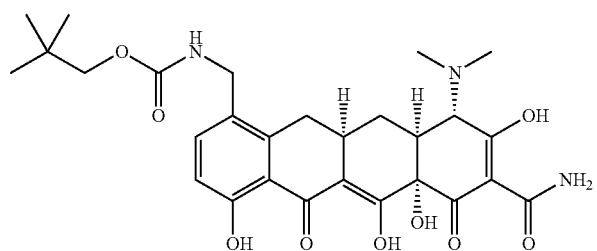
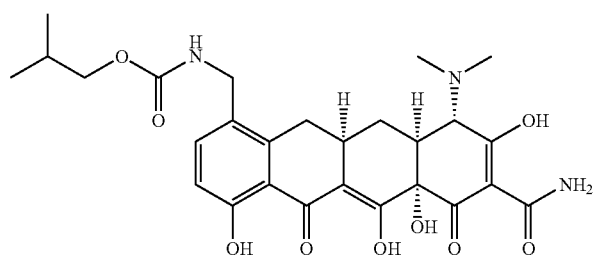
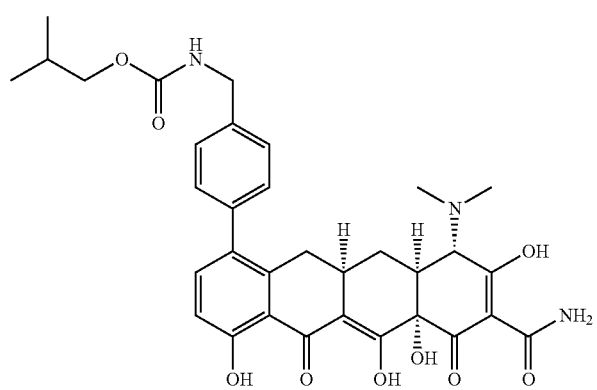
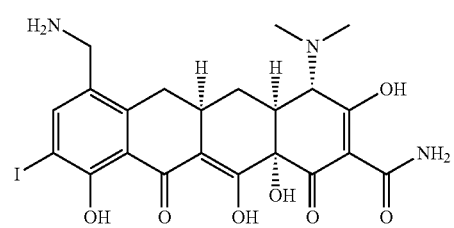

TABLE 1-continued
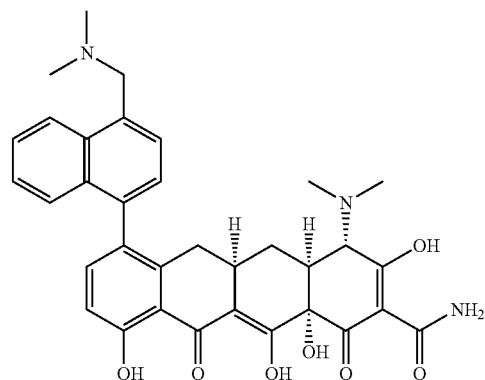
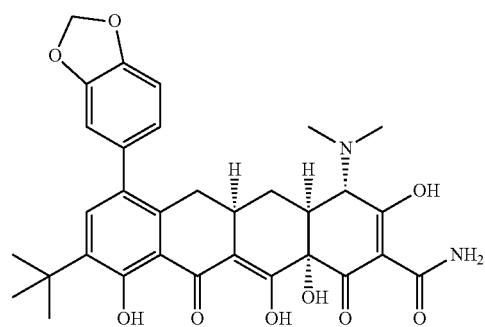
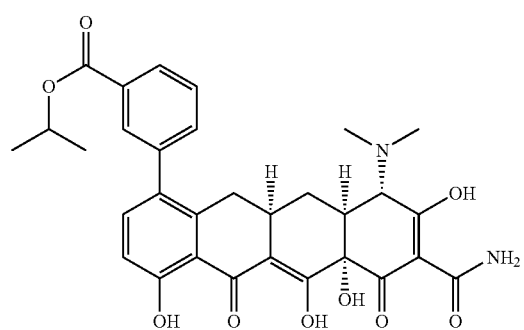
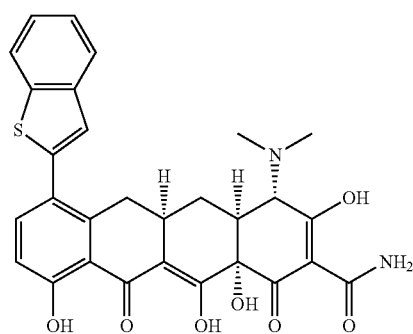

TABLE 1-continued
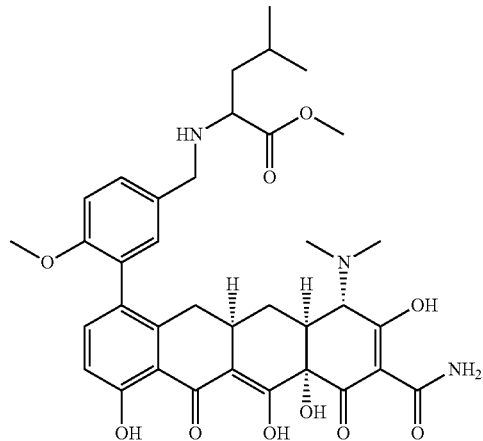
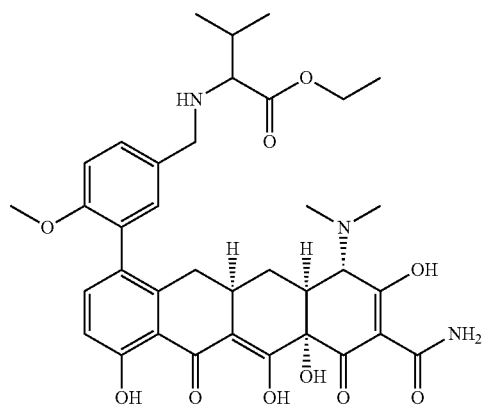
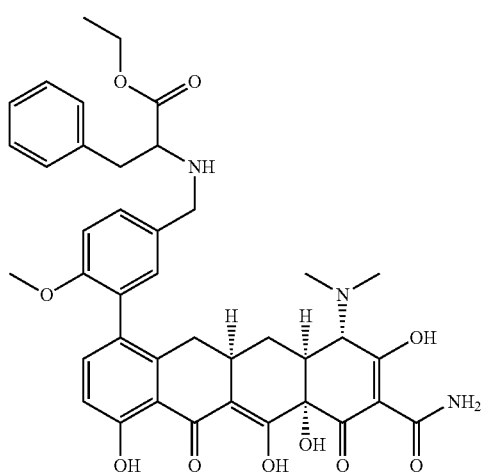

TABLE 1-continued
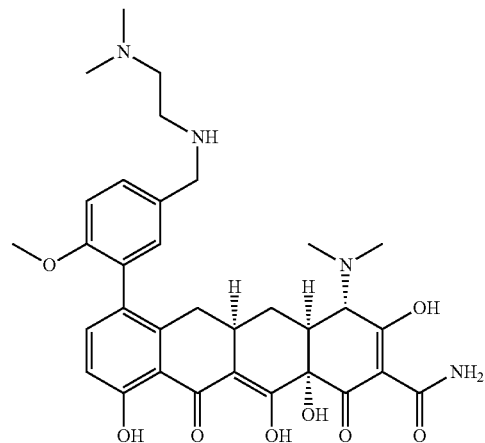
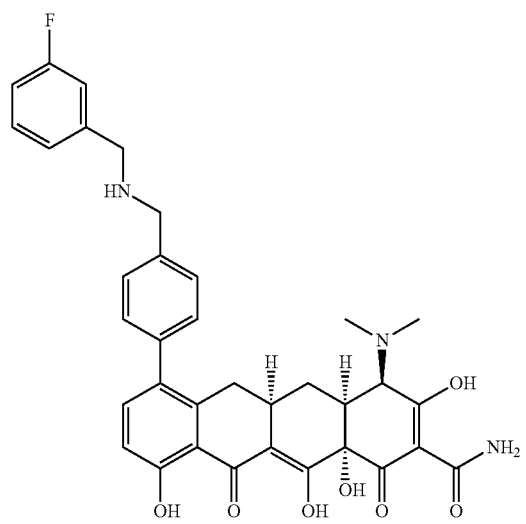
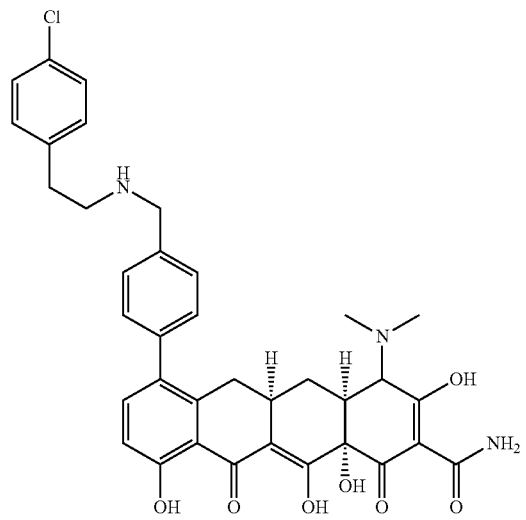

TABLE 1-continued
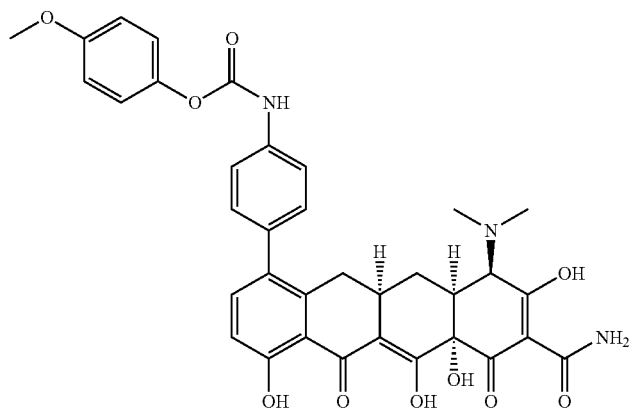
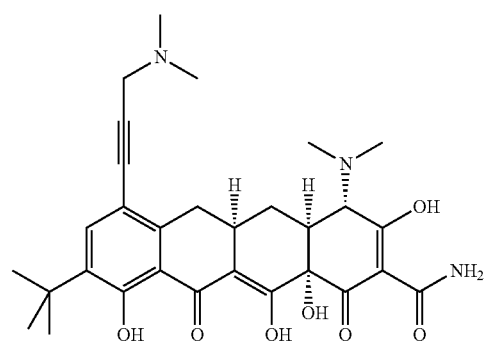
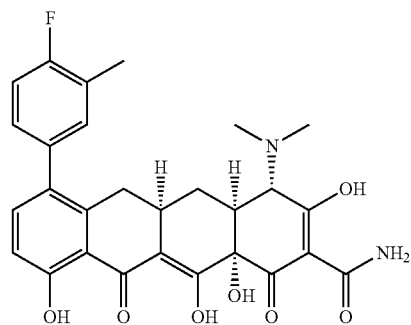
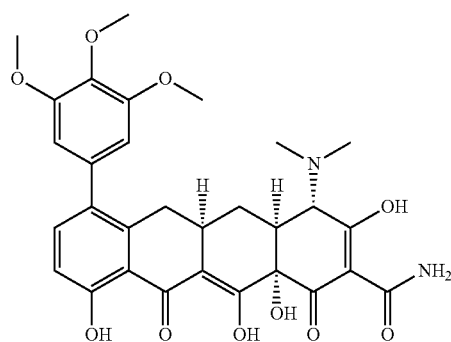

TABLE 1-continued
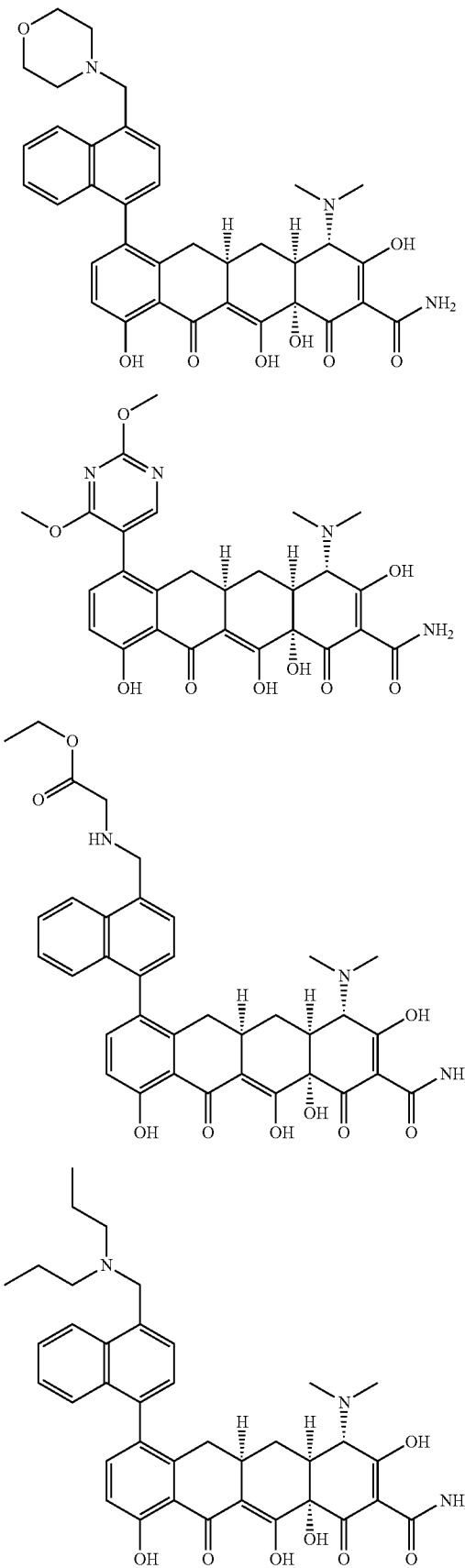

TABLE 1-continued
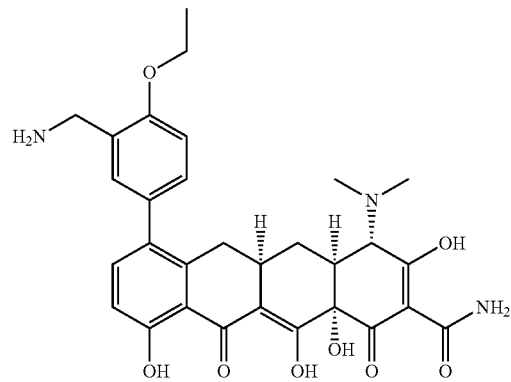
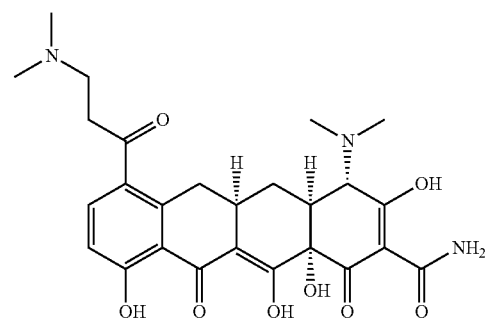
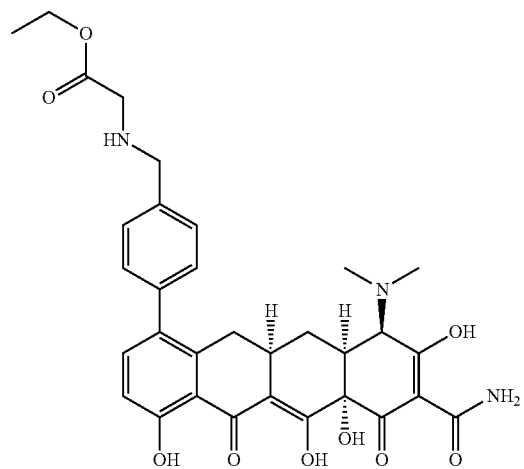
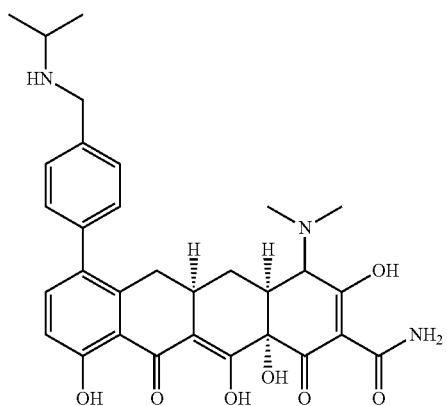

TABLE 1-continued
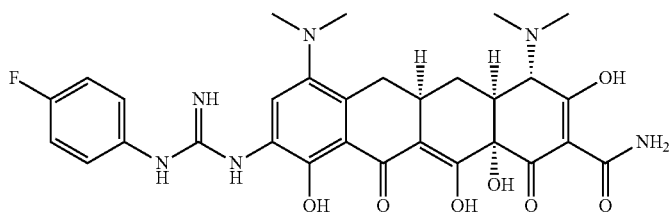
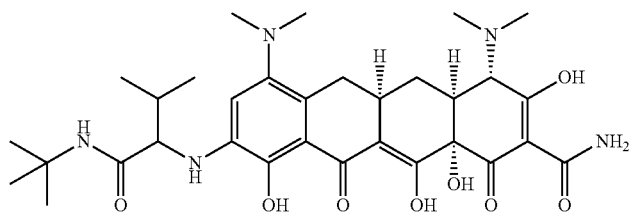
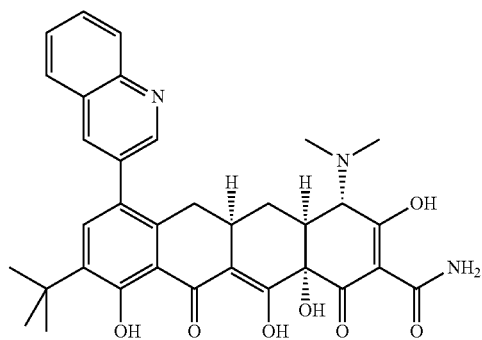
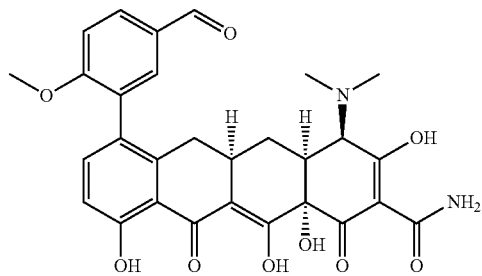
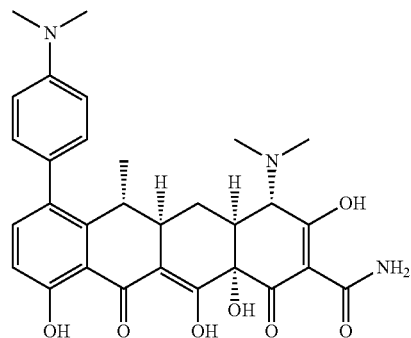

TABLE 1-continued
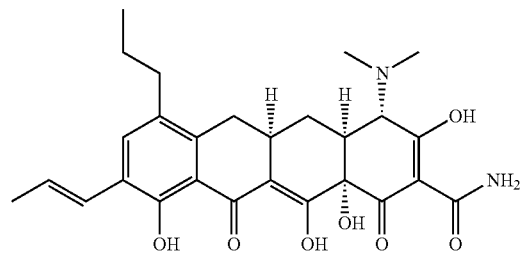
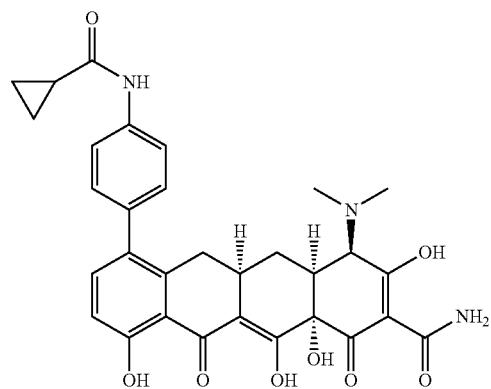
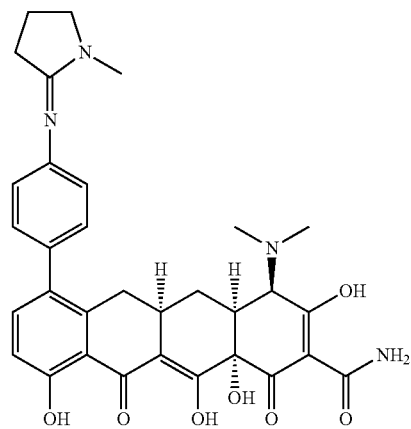
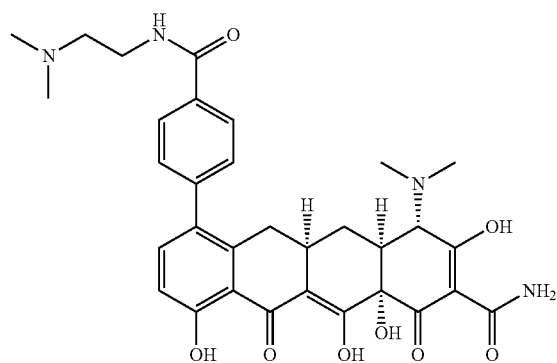

TABLE 1-continued
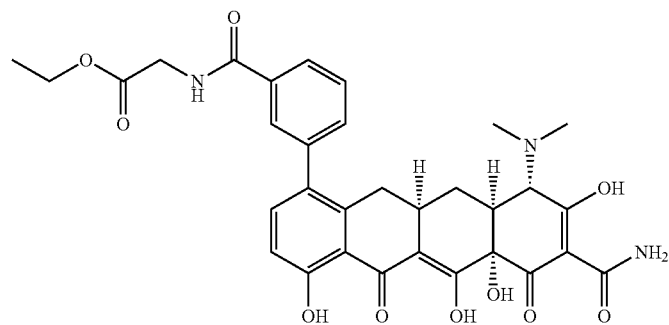
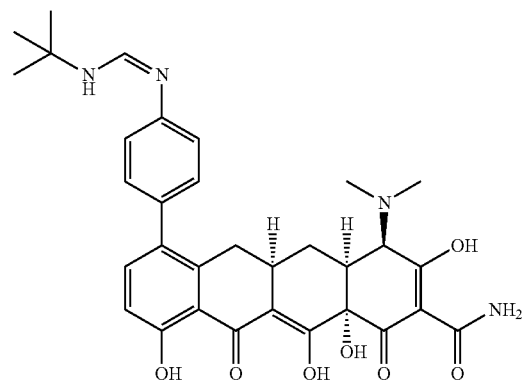
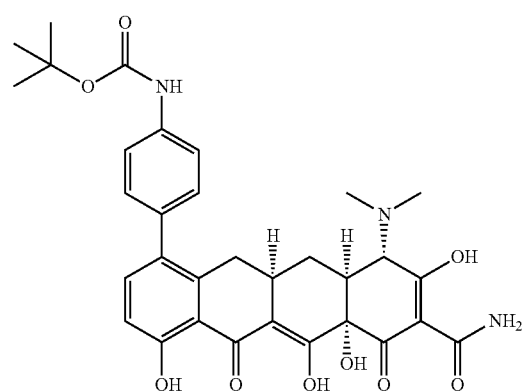
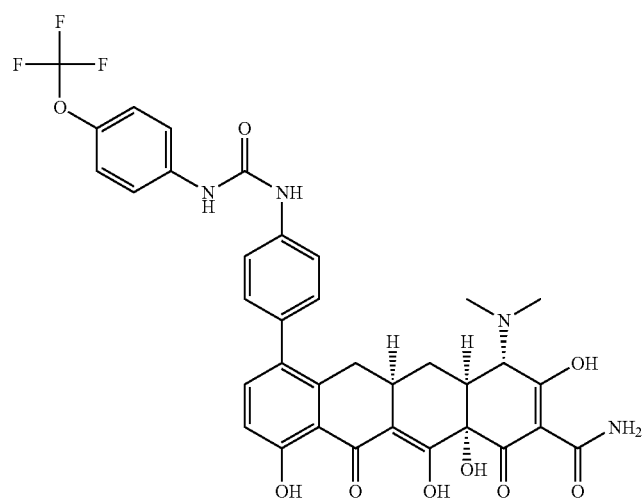

TABLE 1-continued
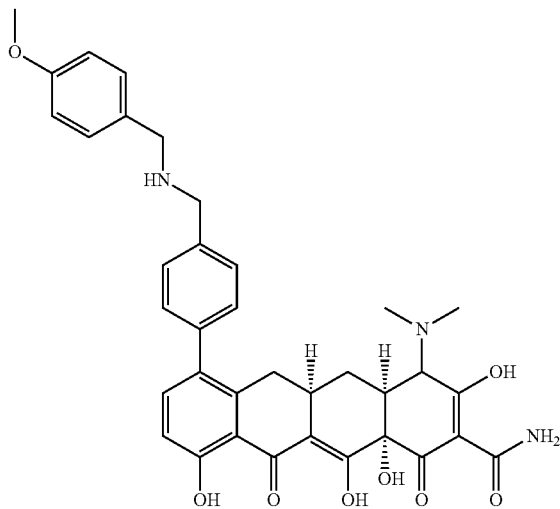
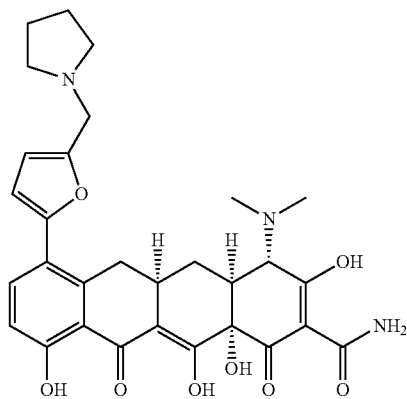
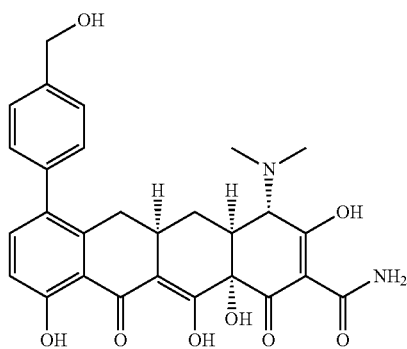
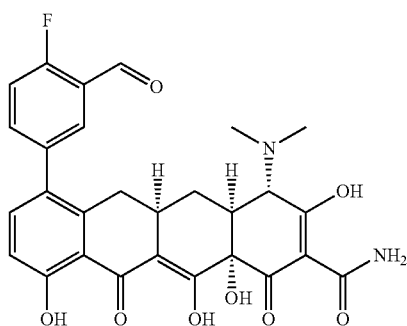

TABLE 1-continued
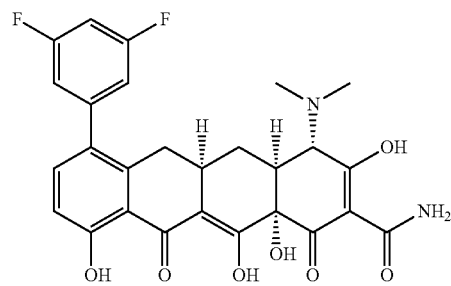
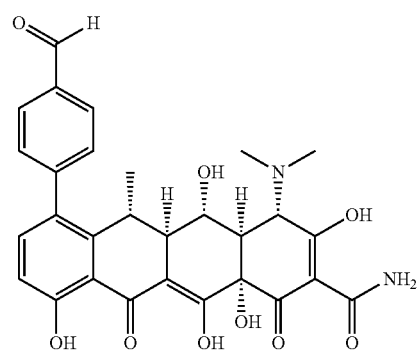
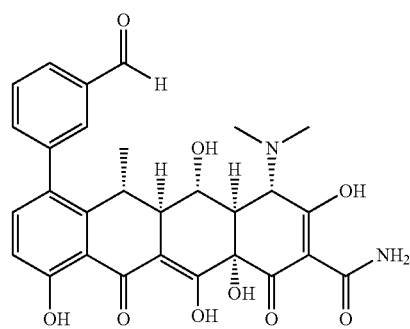
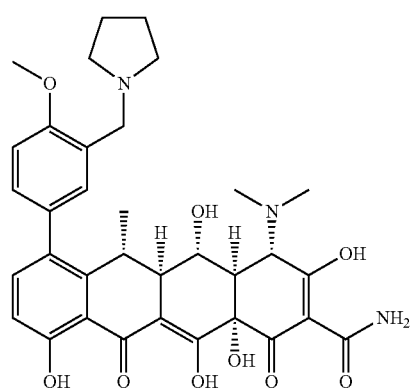

TABLE 1-continued
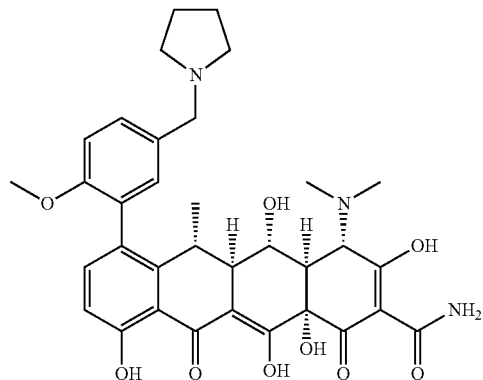
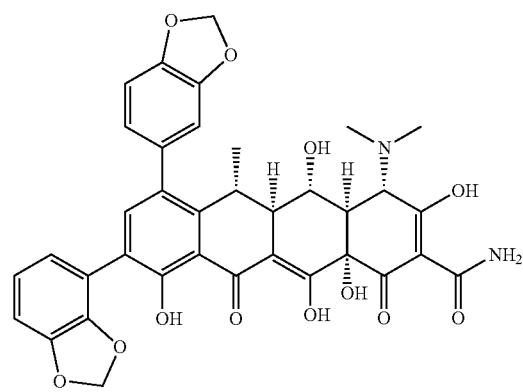
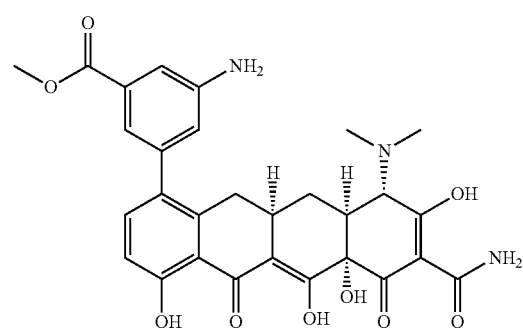
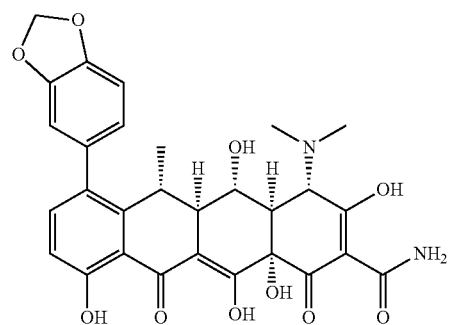

TABLE 1-continued
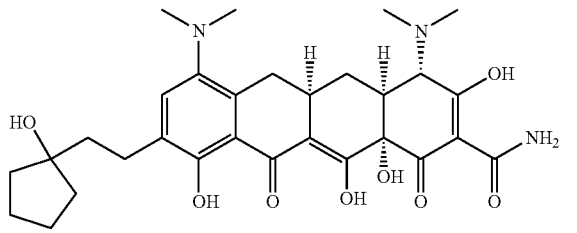
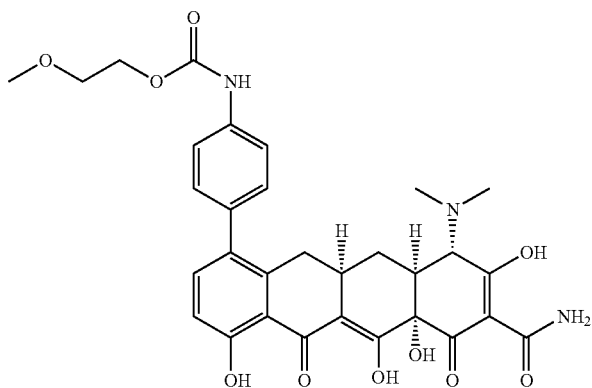
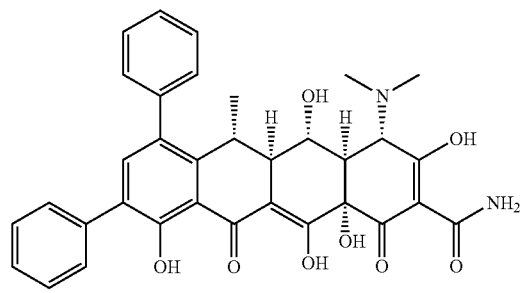
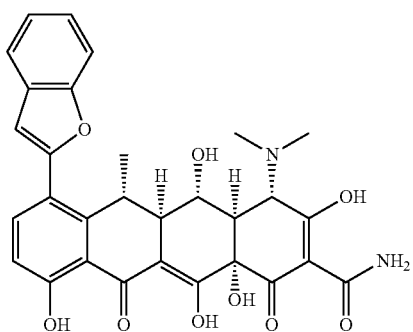
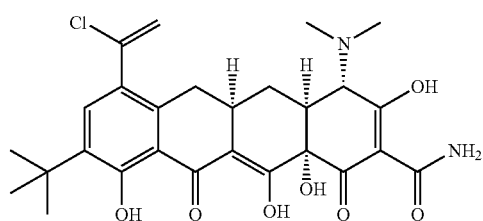

TABLE 1-continued
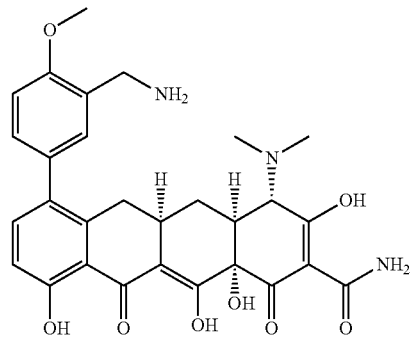
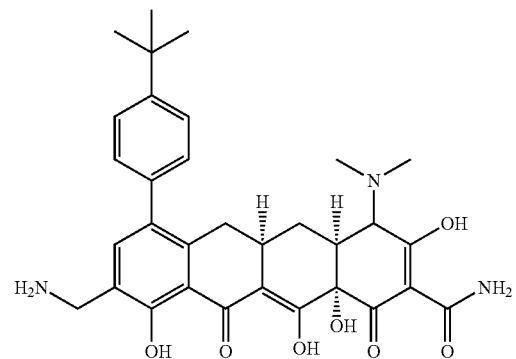
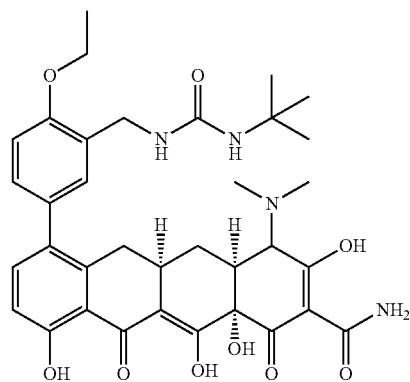
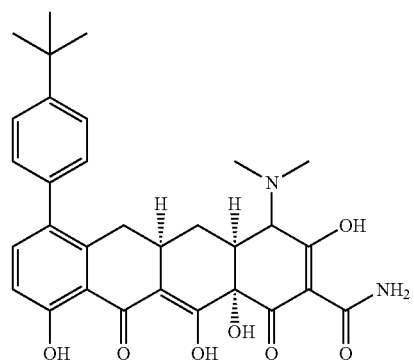

TABLE 1-continued
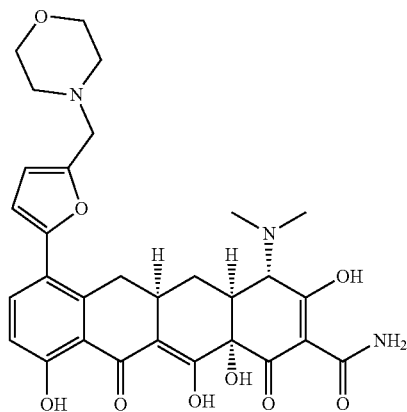
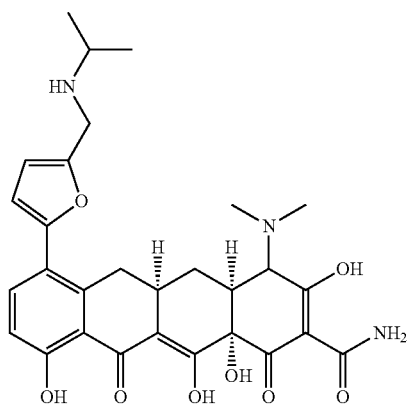
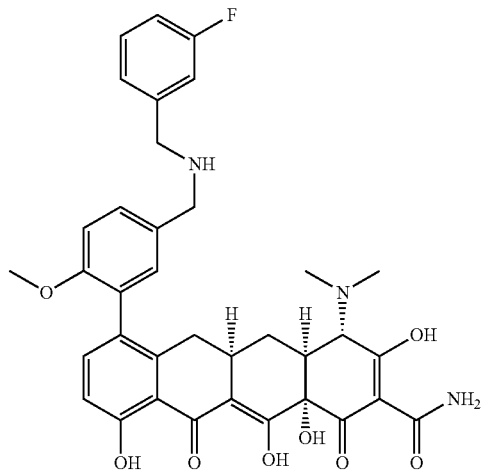
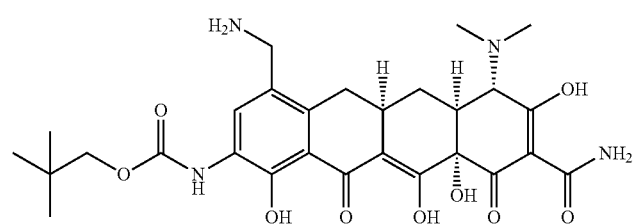

TABLE 1-continued
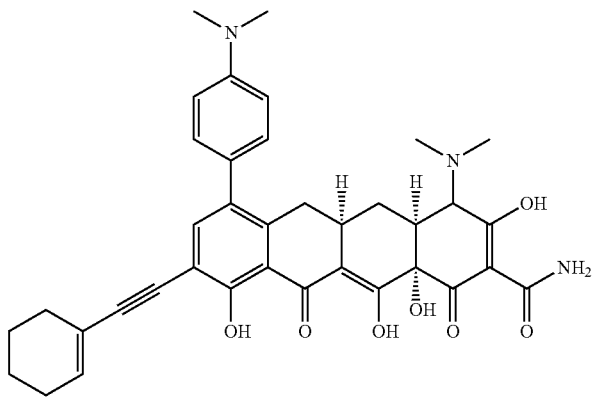
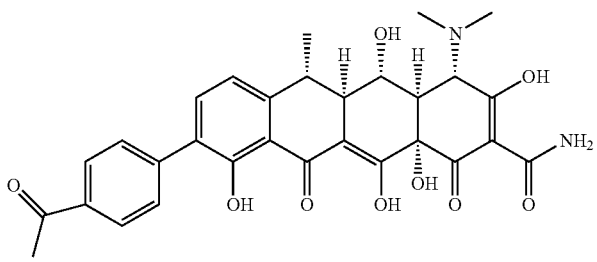
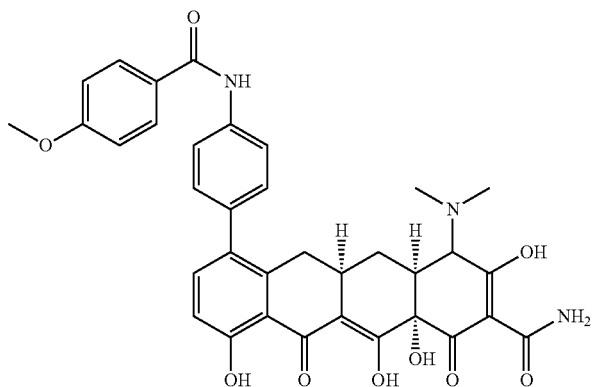
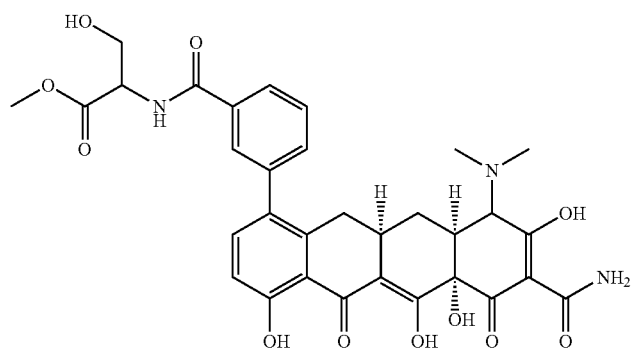

TABLE 1-continued
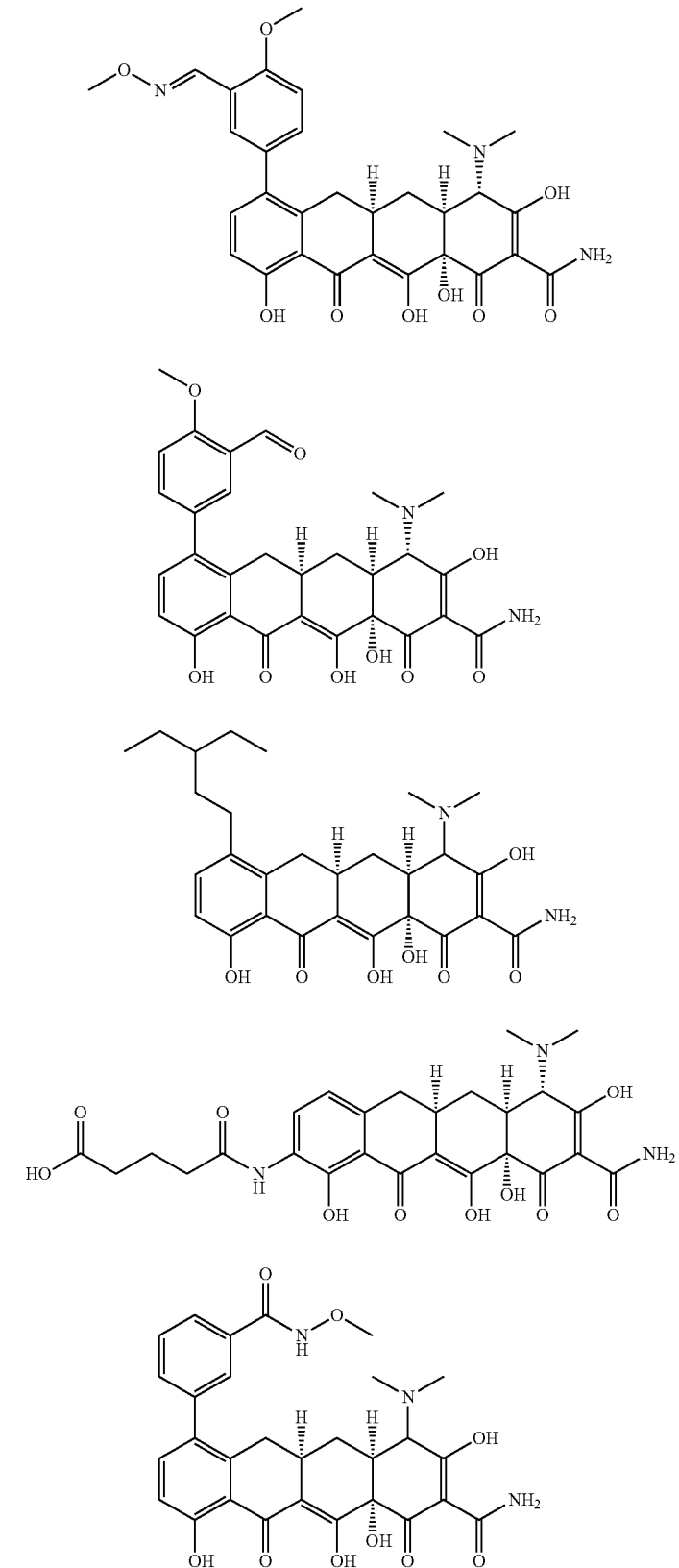

TABLE 1-continued
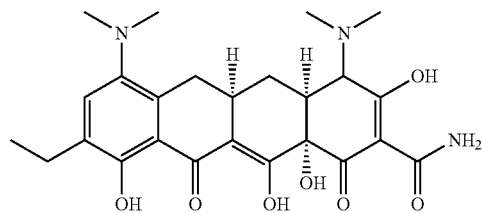
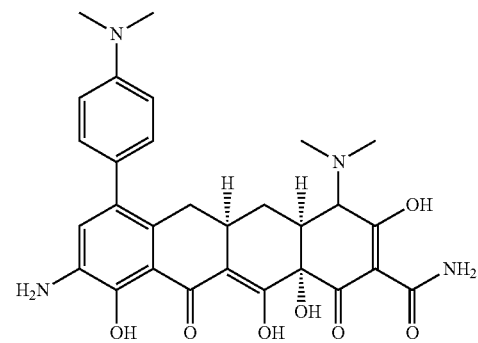
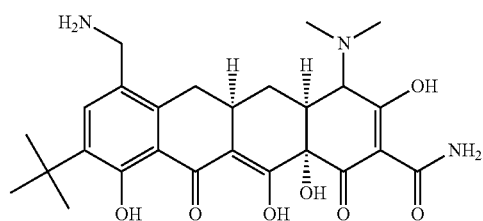
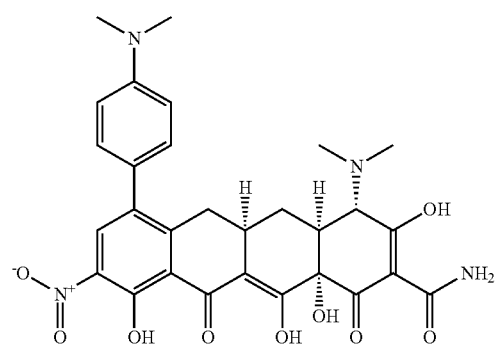
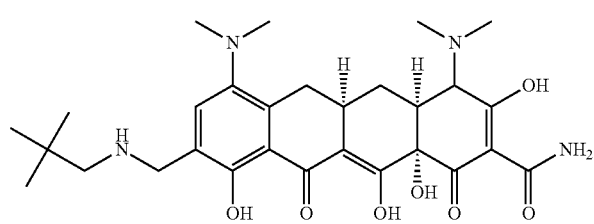

TABLE 1-continued
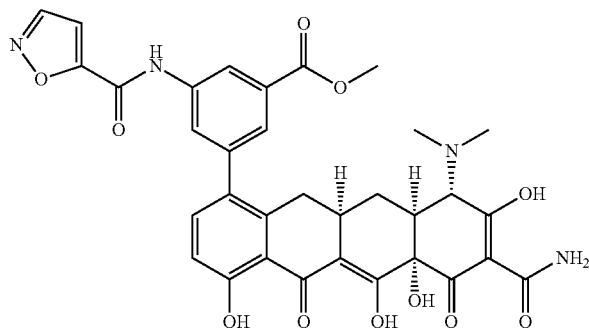
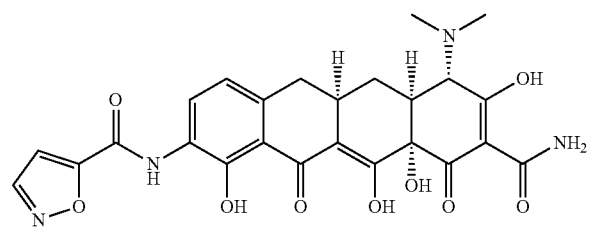
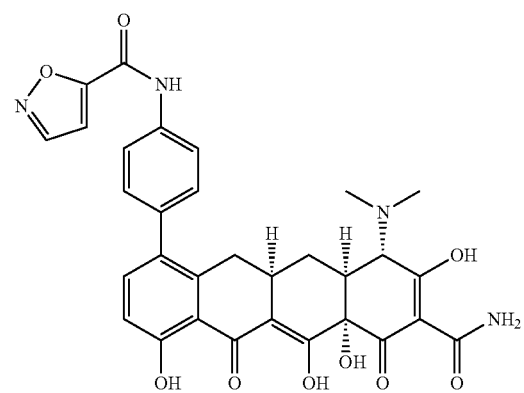
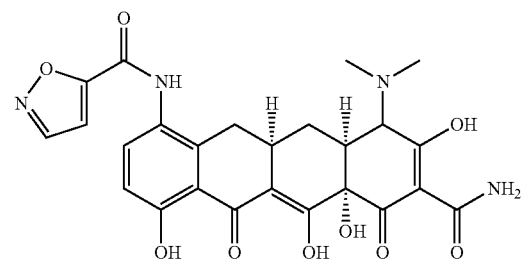
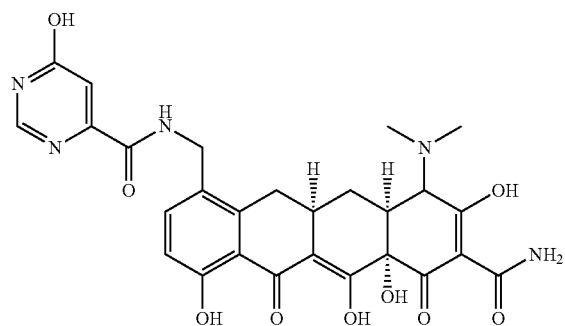

TABLE 1-continued
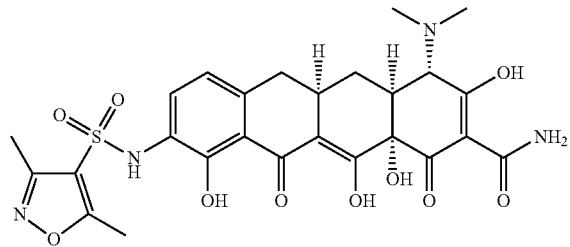
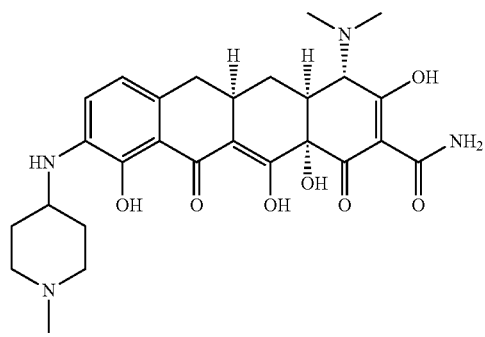
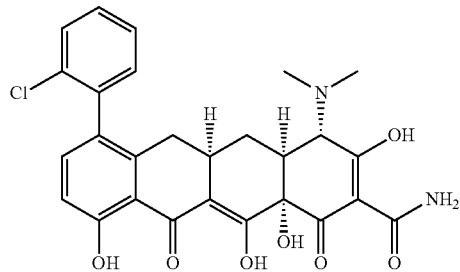
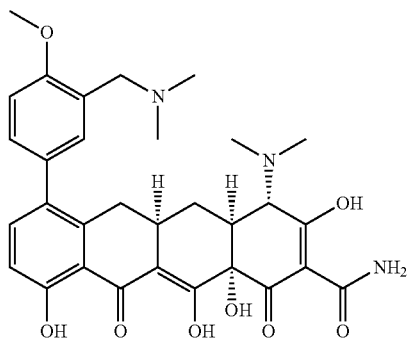
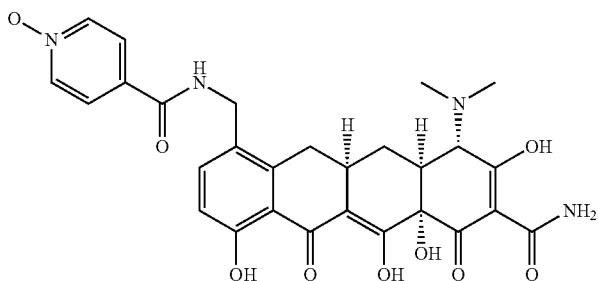

TABLE 1-continued
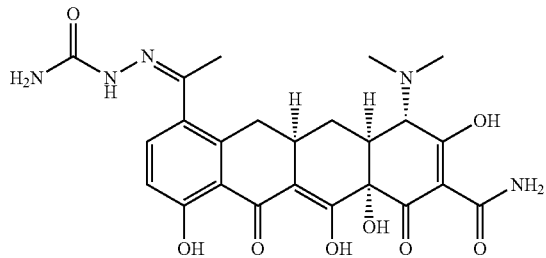
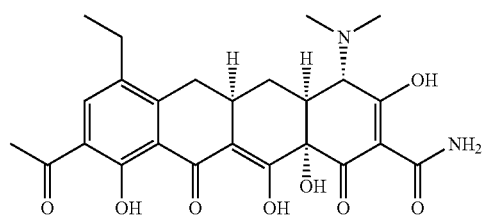
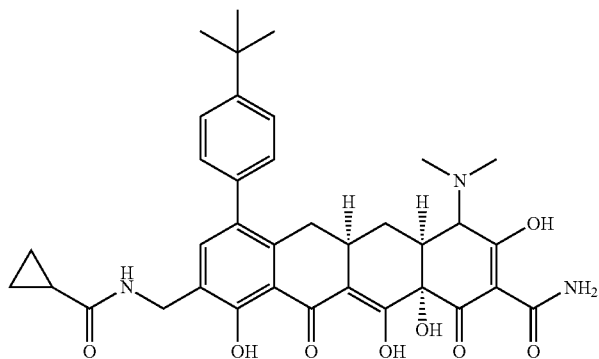
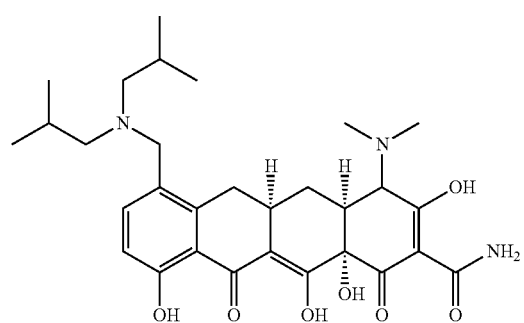
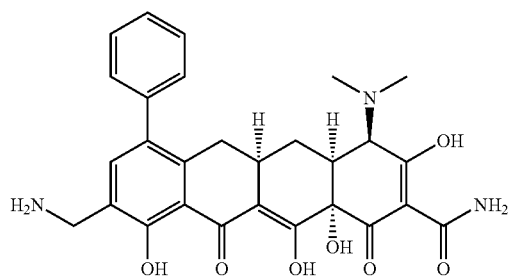

TABLE 1-continued
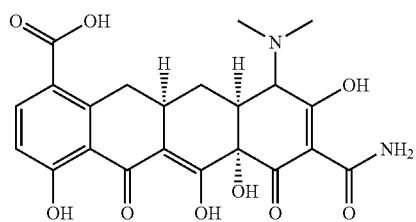
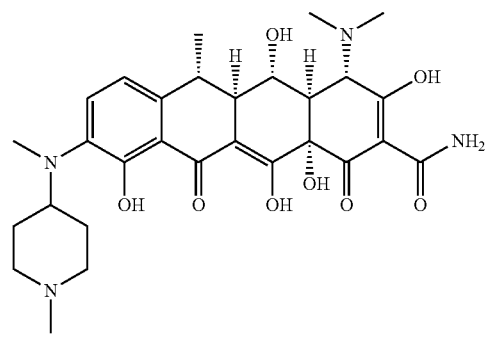
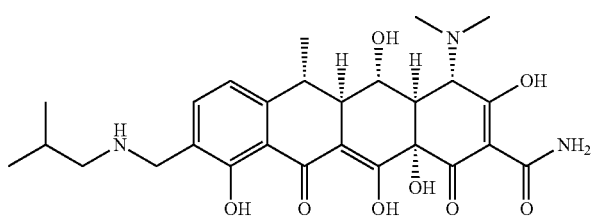
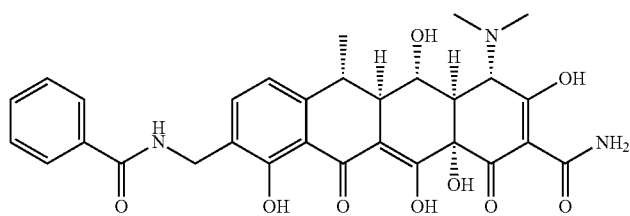
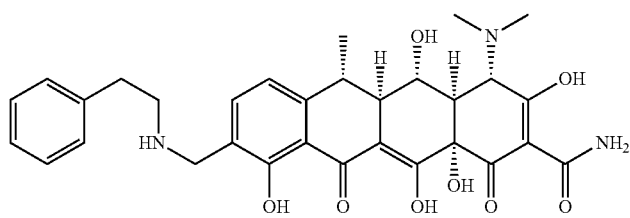
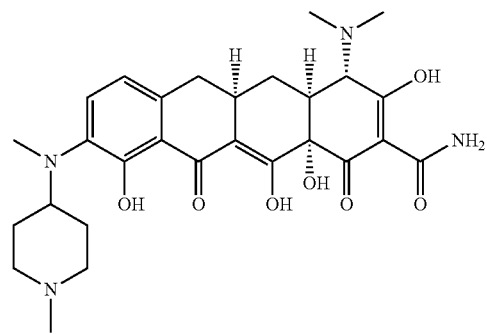

TABLE 1-continued
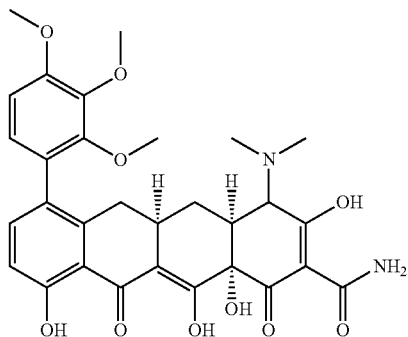
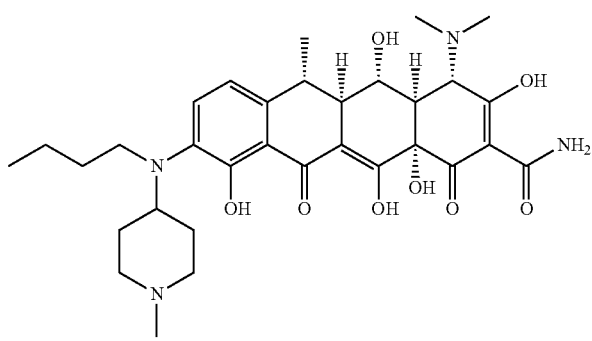
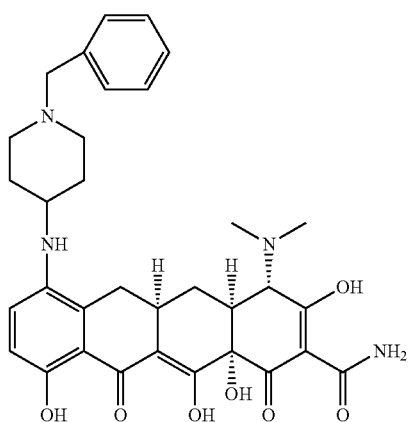
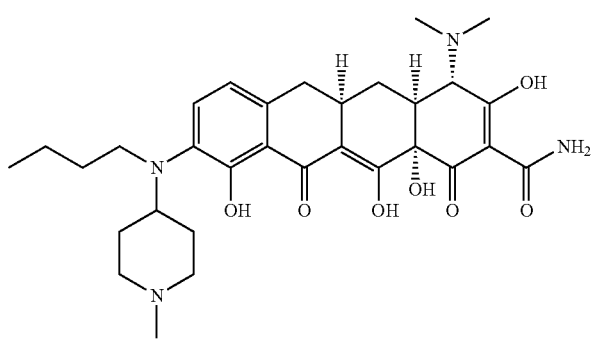
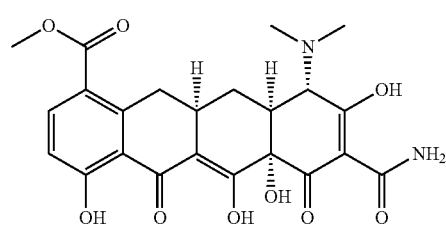

TABLE 1-continued
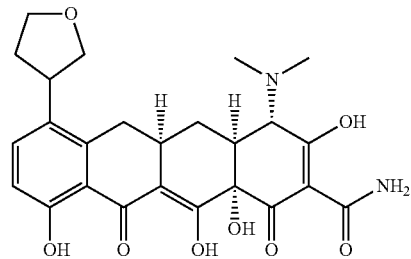
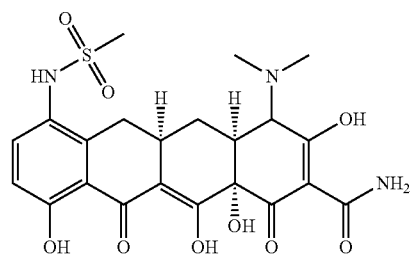
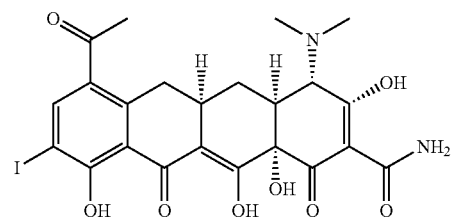
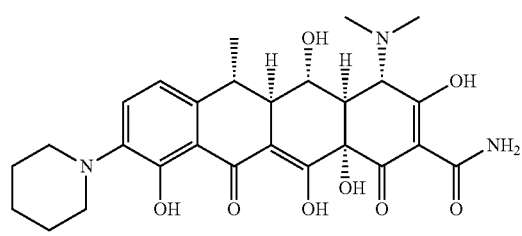
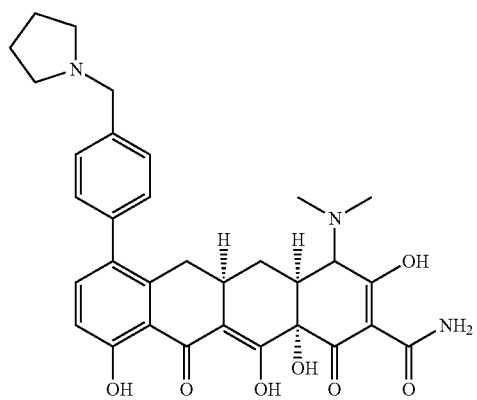

TABLE 1-continued
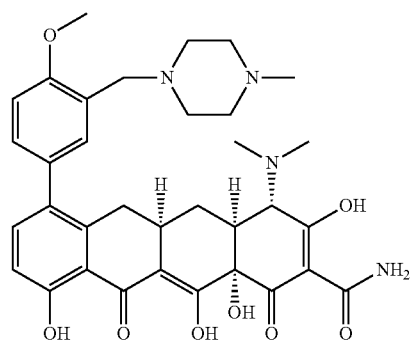
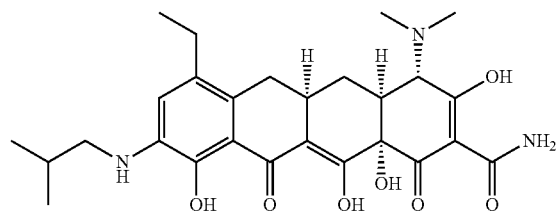
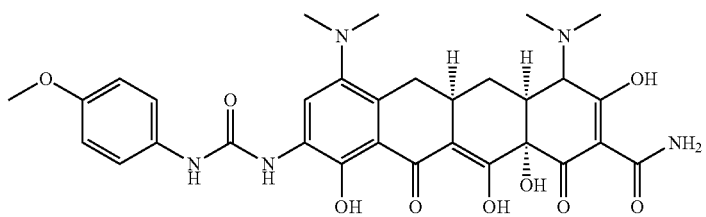
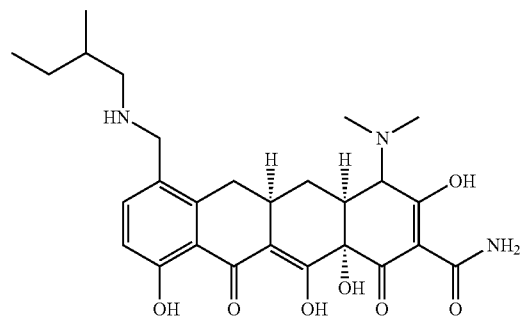
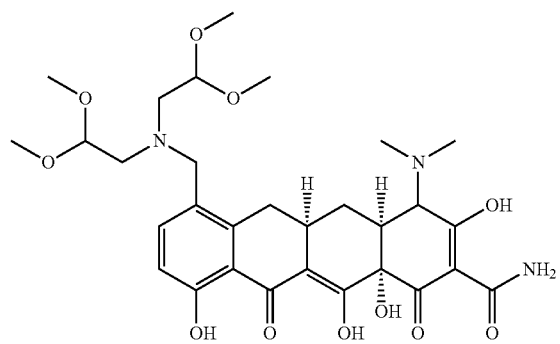

TABLE 1-continued
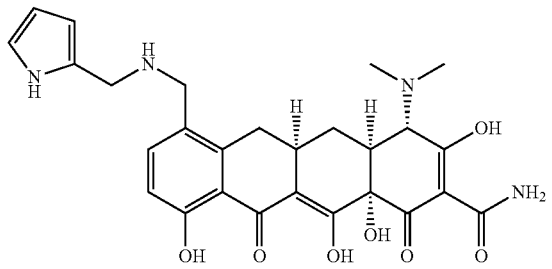
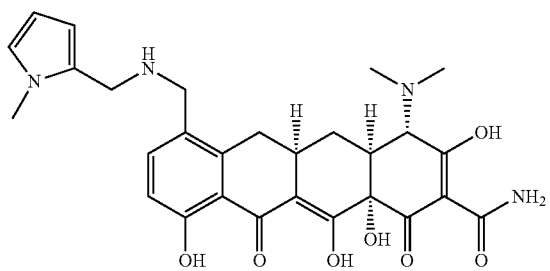
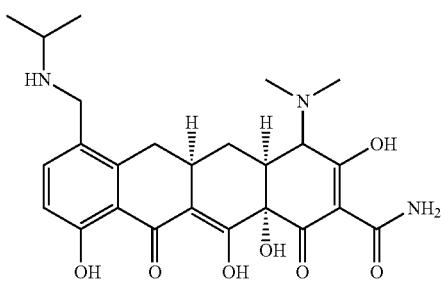
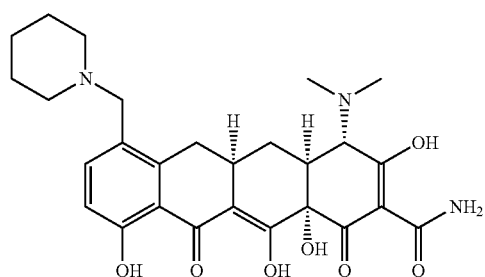
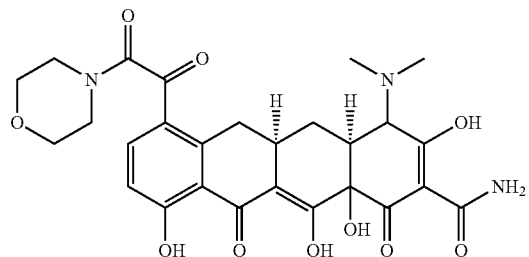

TABLE 1-continued
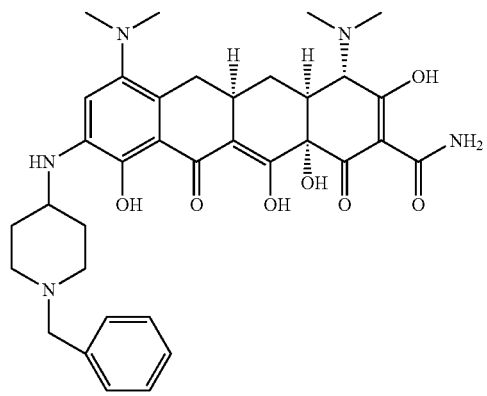
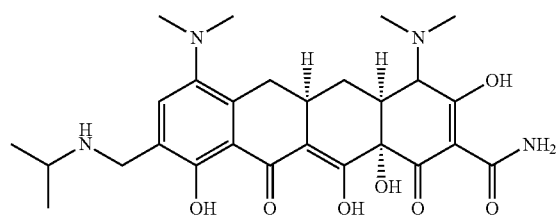
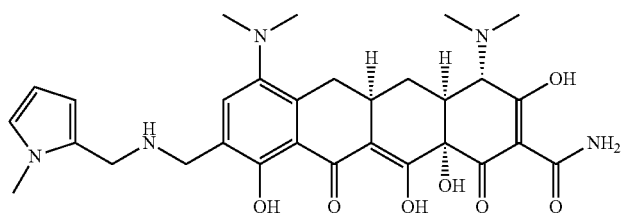
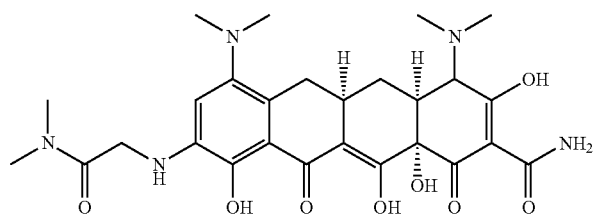
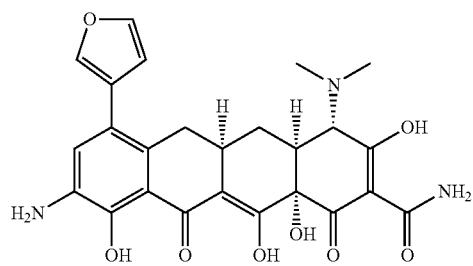

TABLE 1-continued
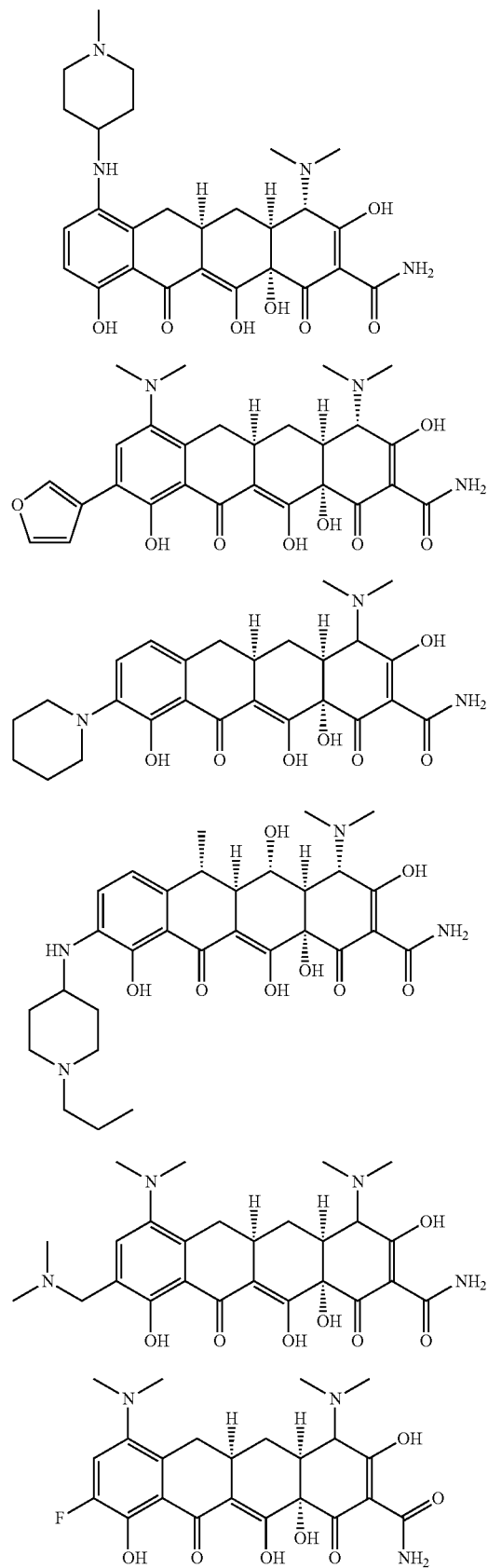

TABLE 1-continued
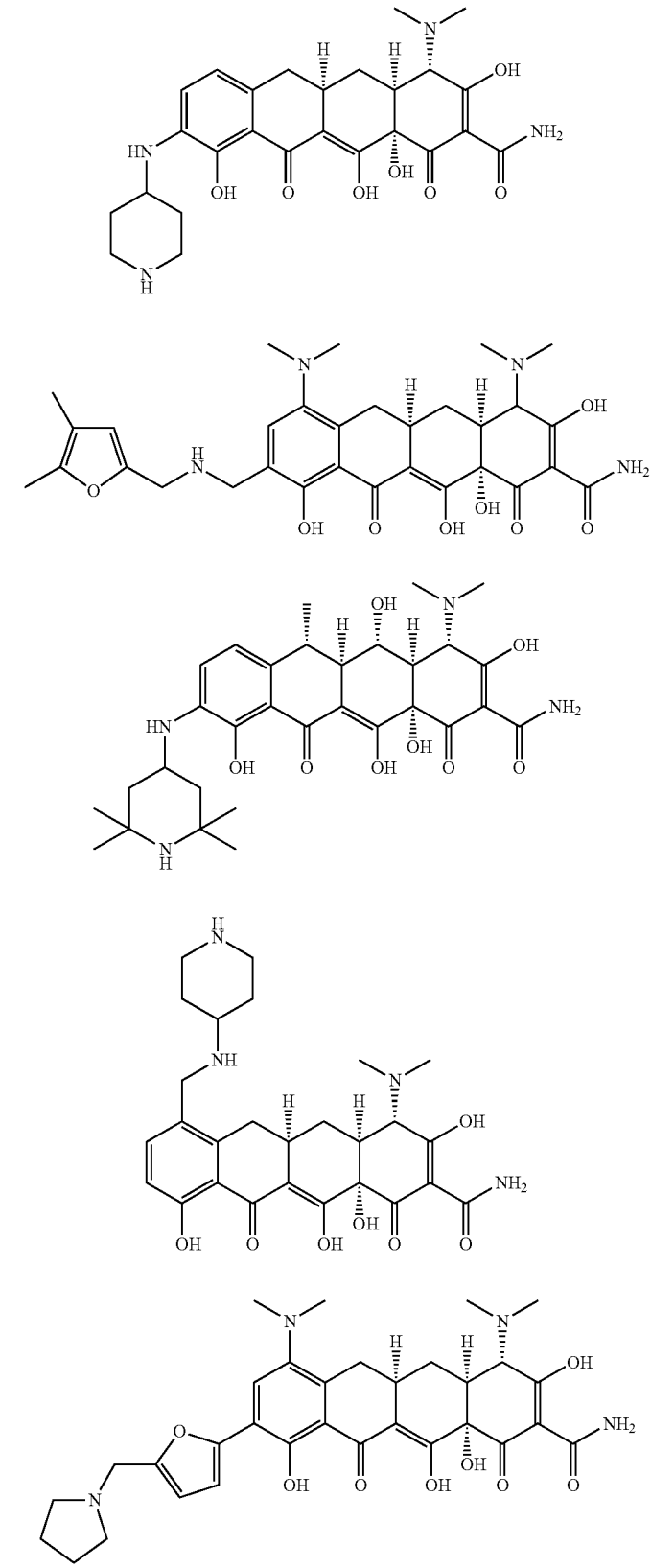

TABLE 1-continued
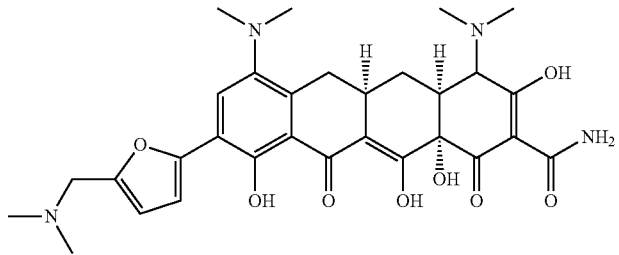
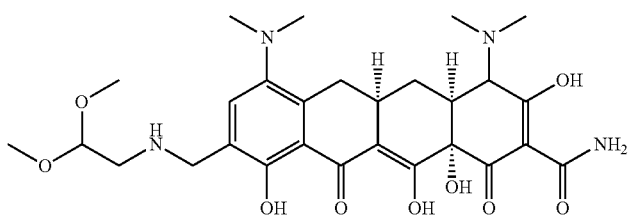
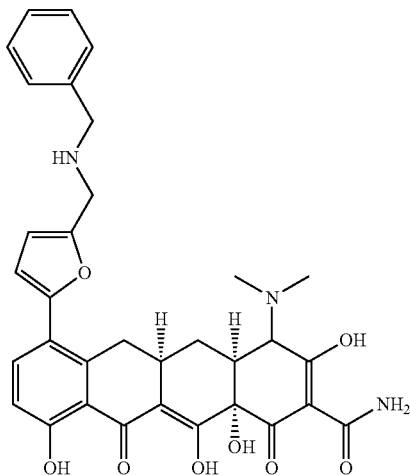
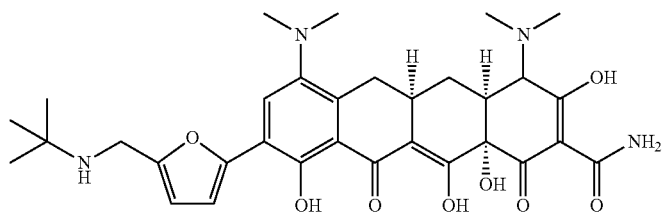
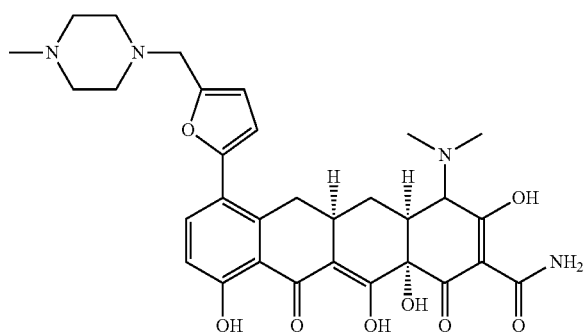

TABLE 1-continued
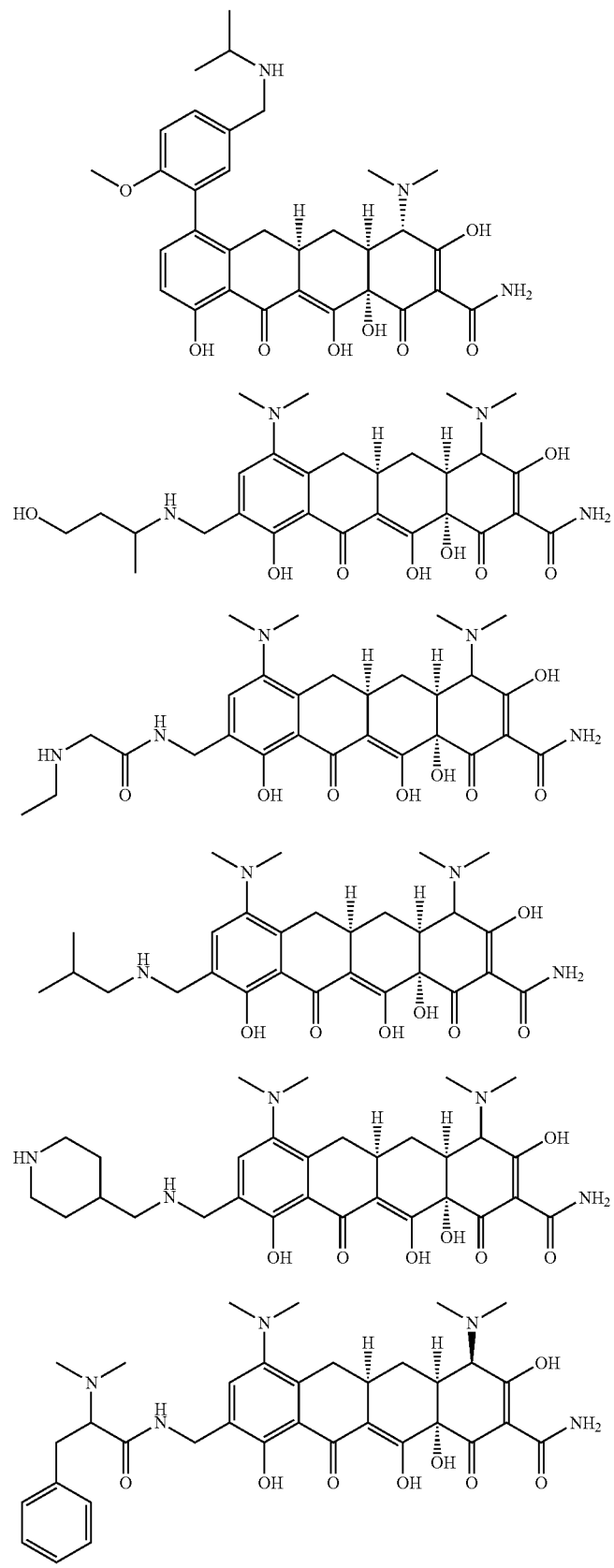

TABLE 1-continued
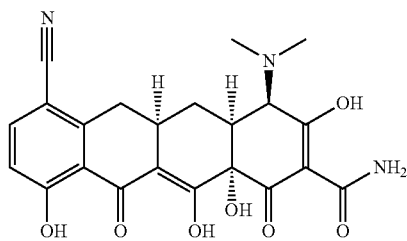
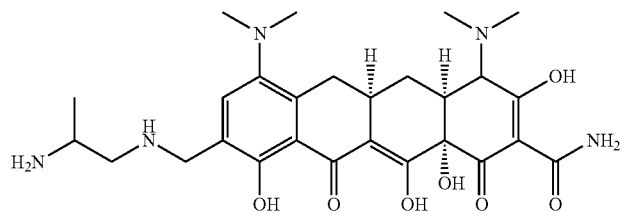
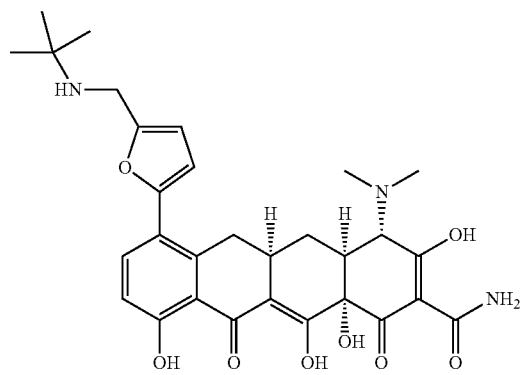
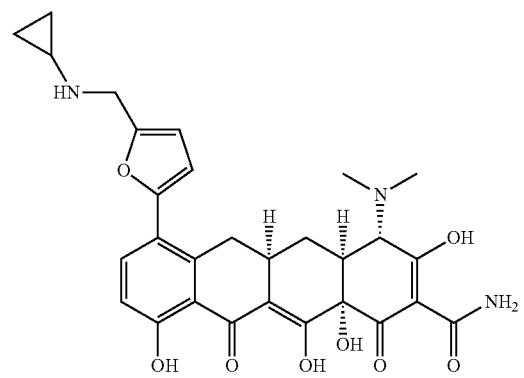
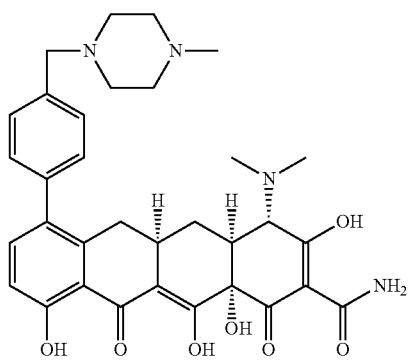

TABLE 1-continued
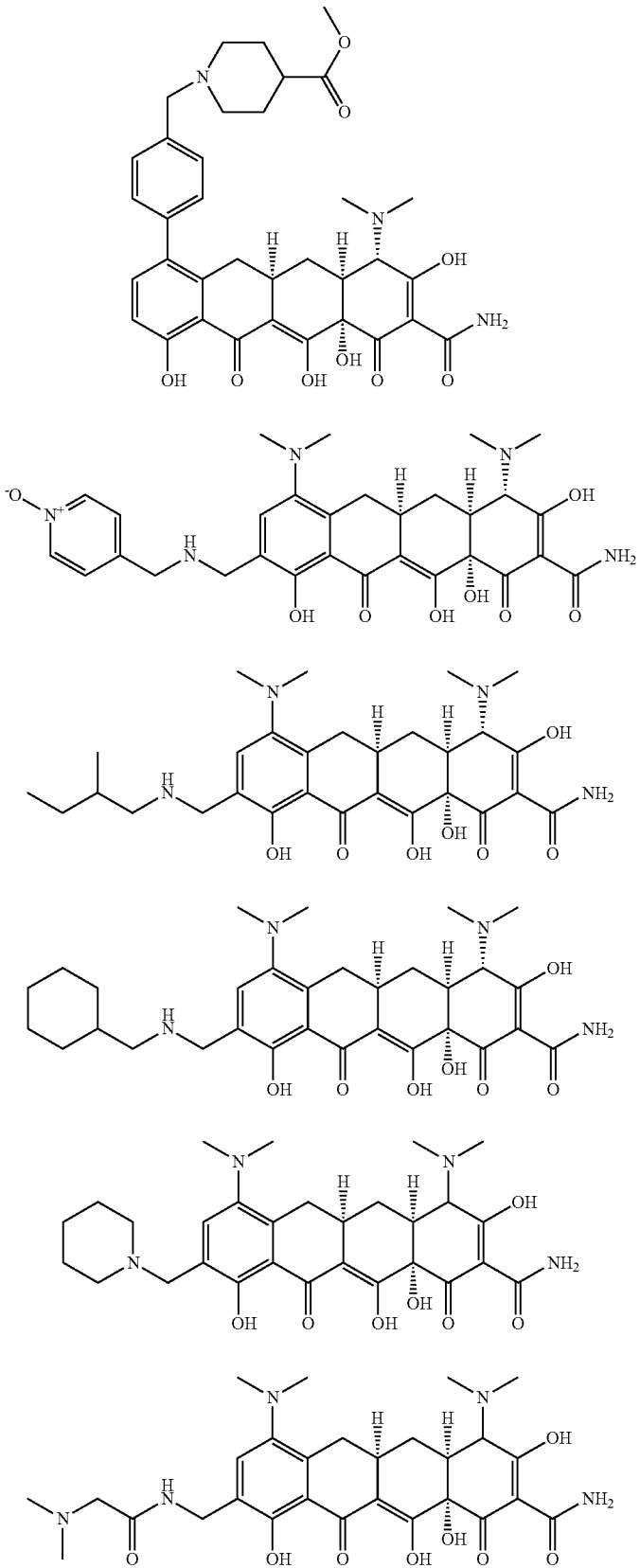

TABLE 1-continued
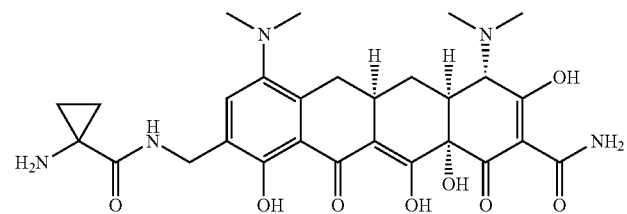
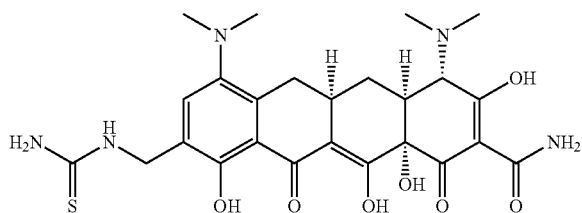
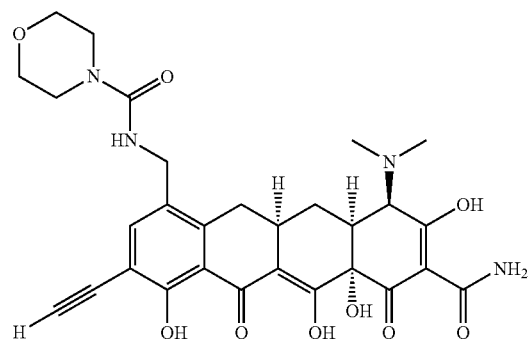
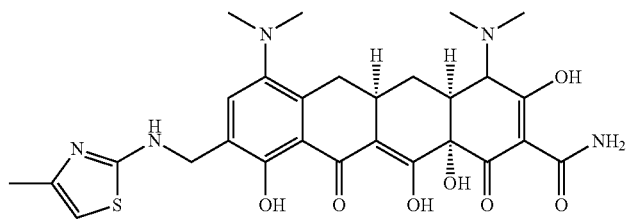
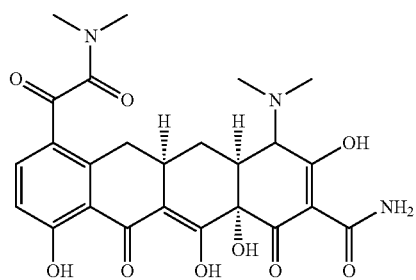
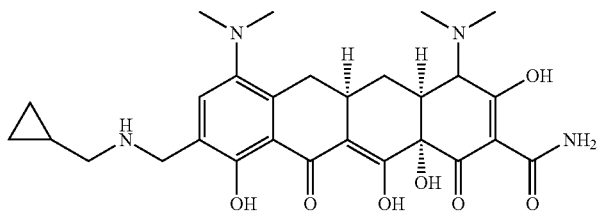

TABLE 1-continued
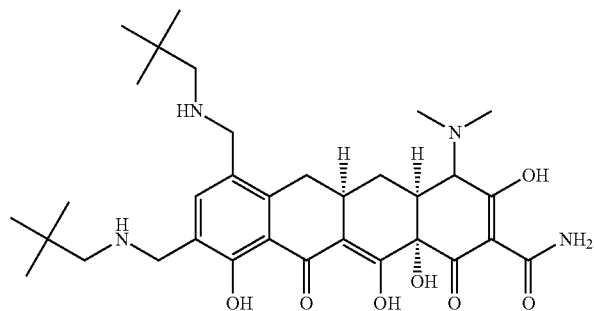
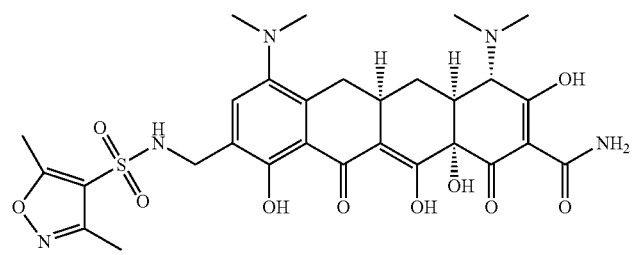
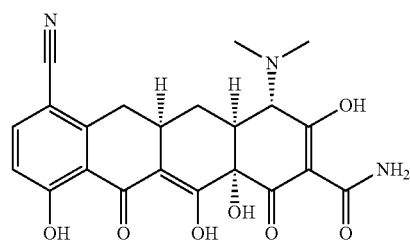
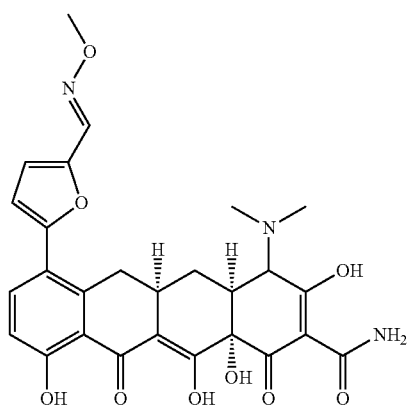
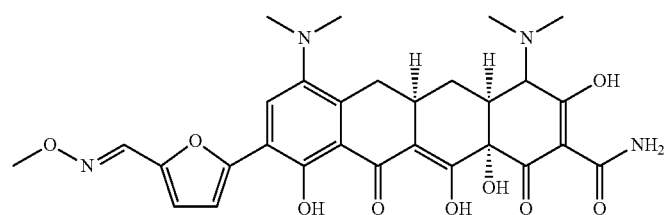

TABLE 1-continued
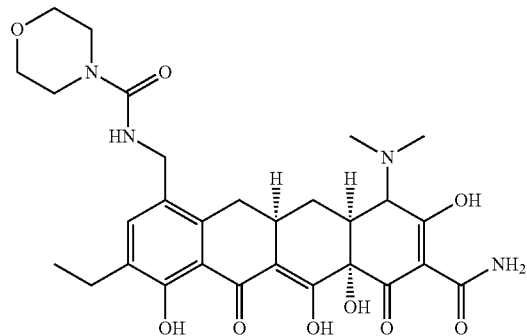
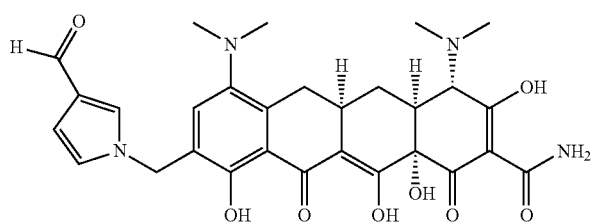
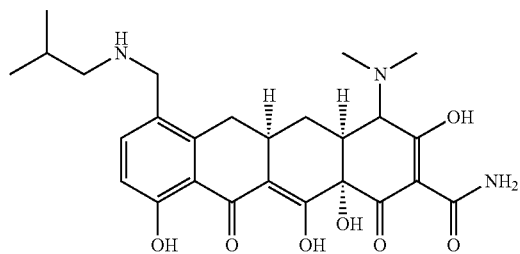
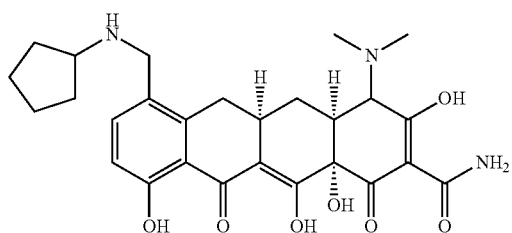
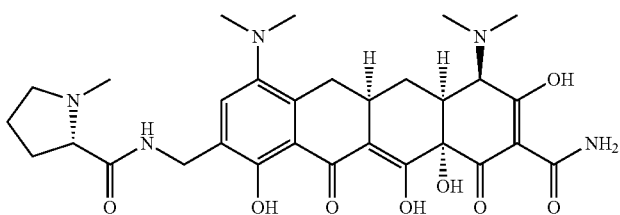
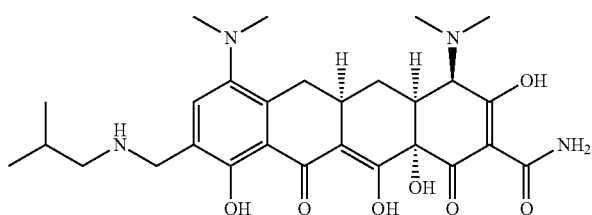

TABLE 1-continued
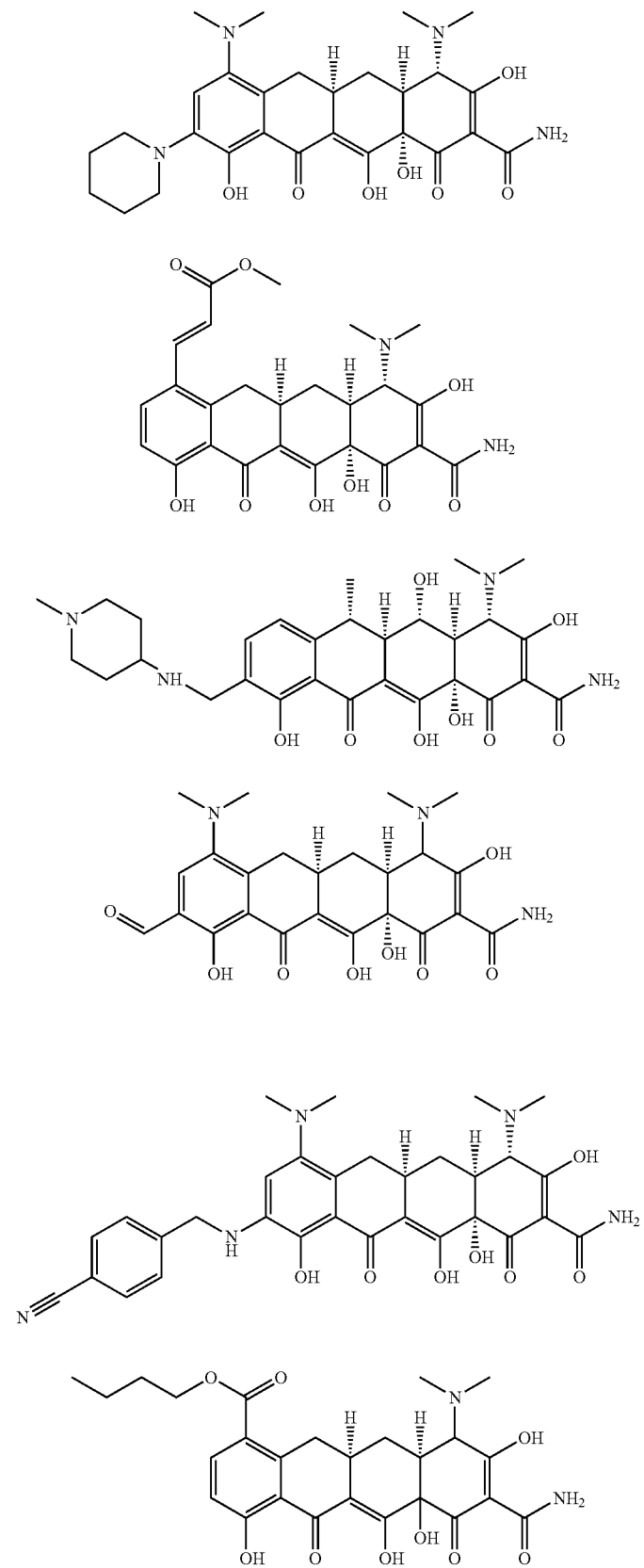

TABLE 1-continued
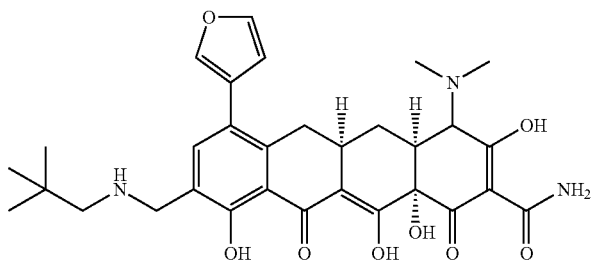
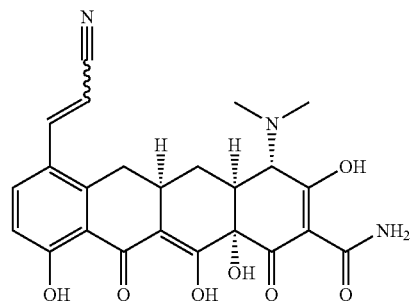
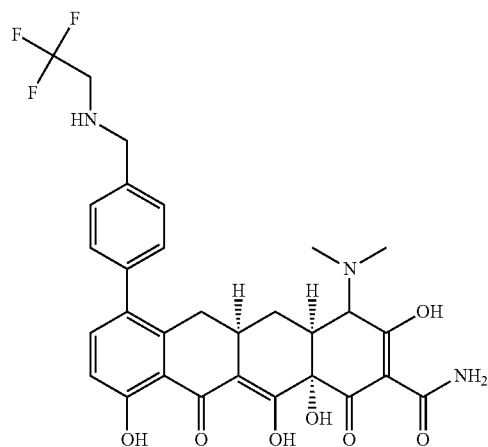
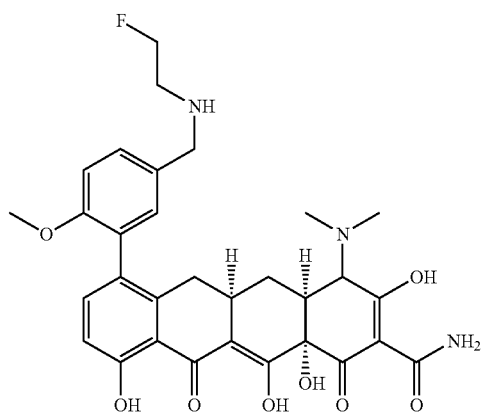

TABLE 1-continued
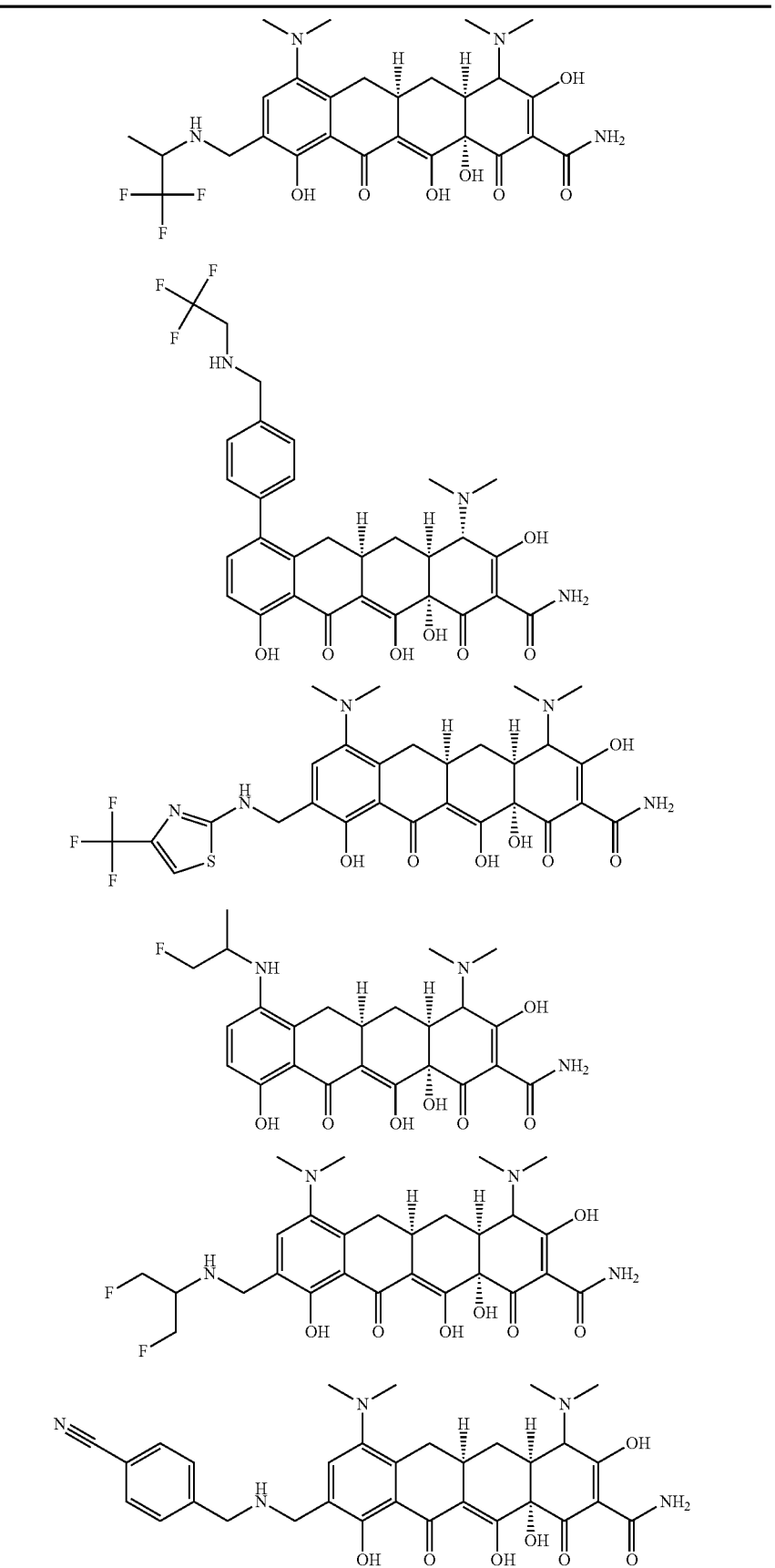

TABLE 1-continued
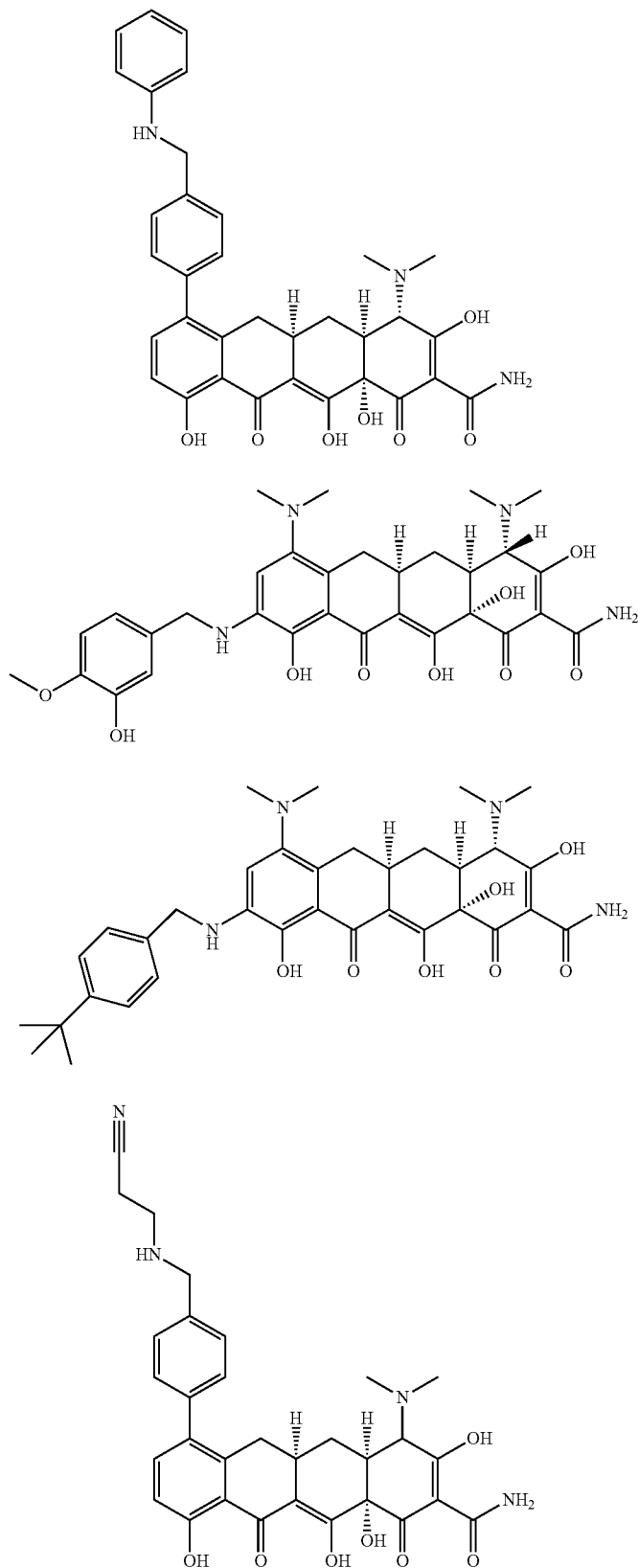

TABLE 1-continued
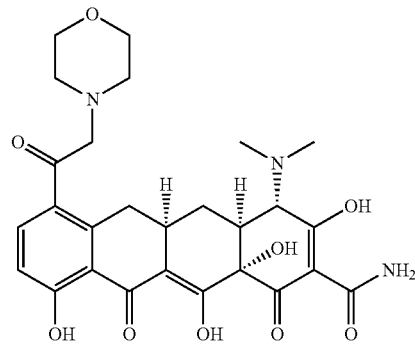
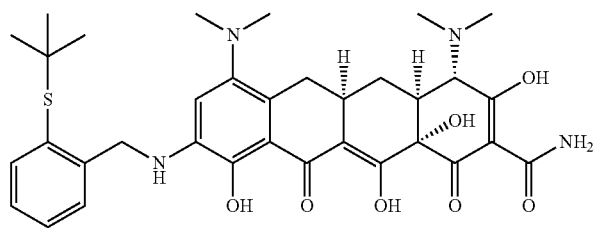
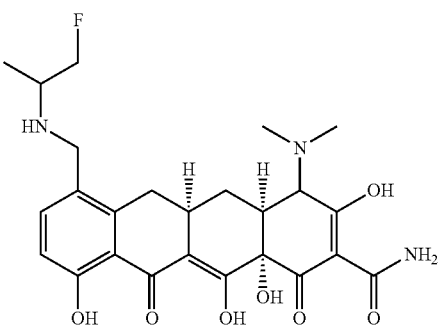
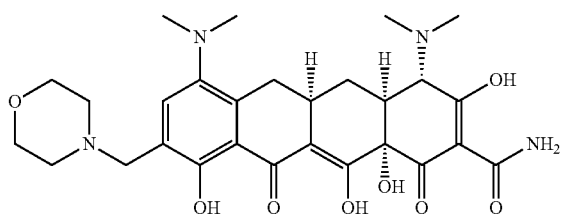
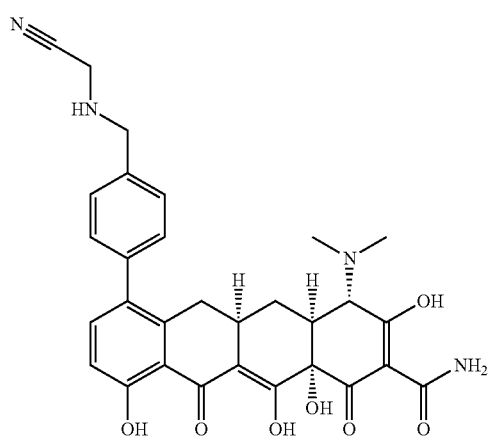

TABLE 1-continued
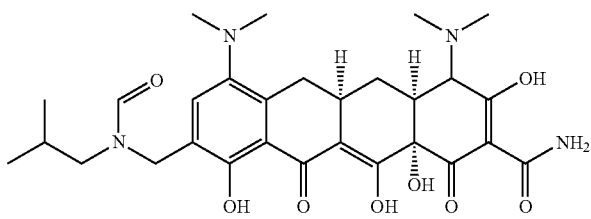
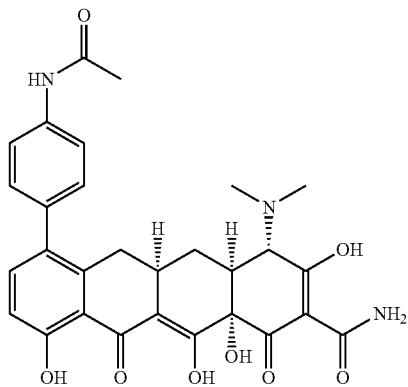
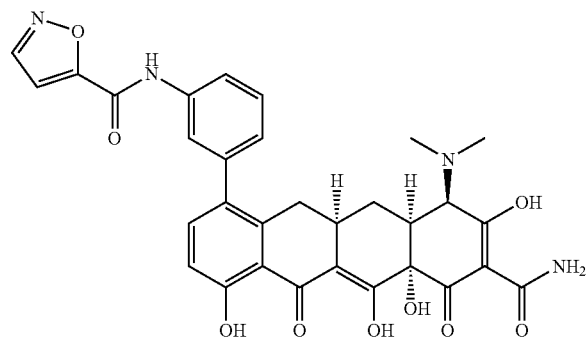
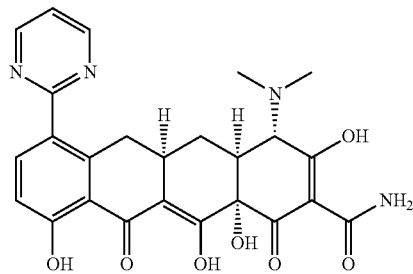
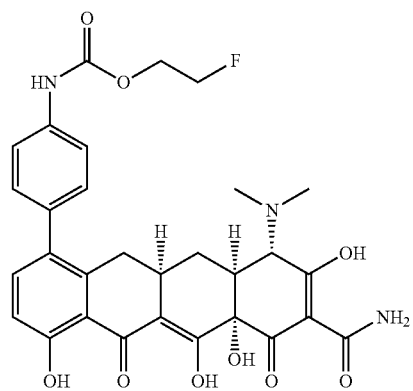

TABLE 1-continued
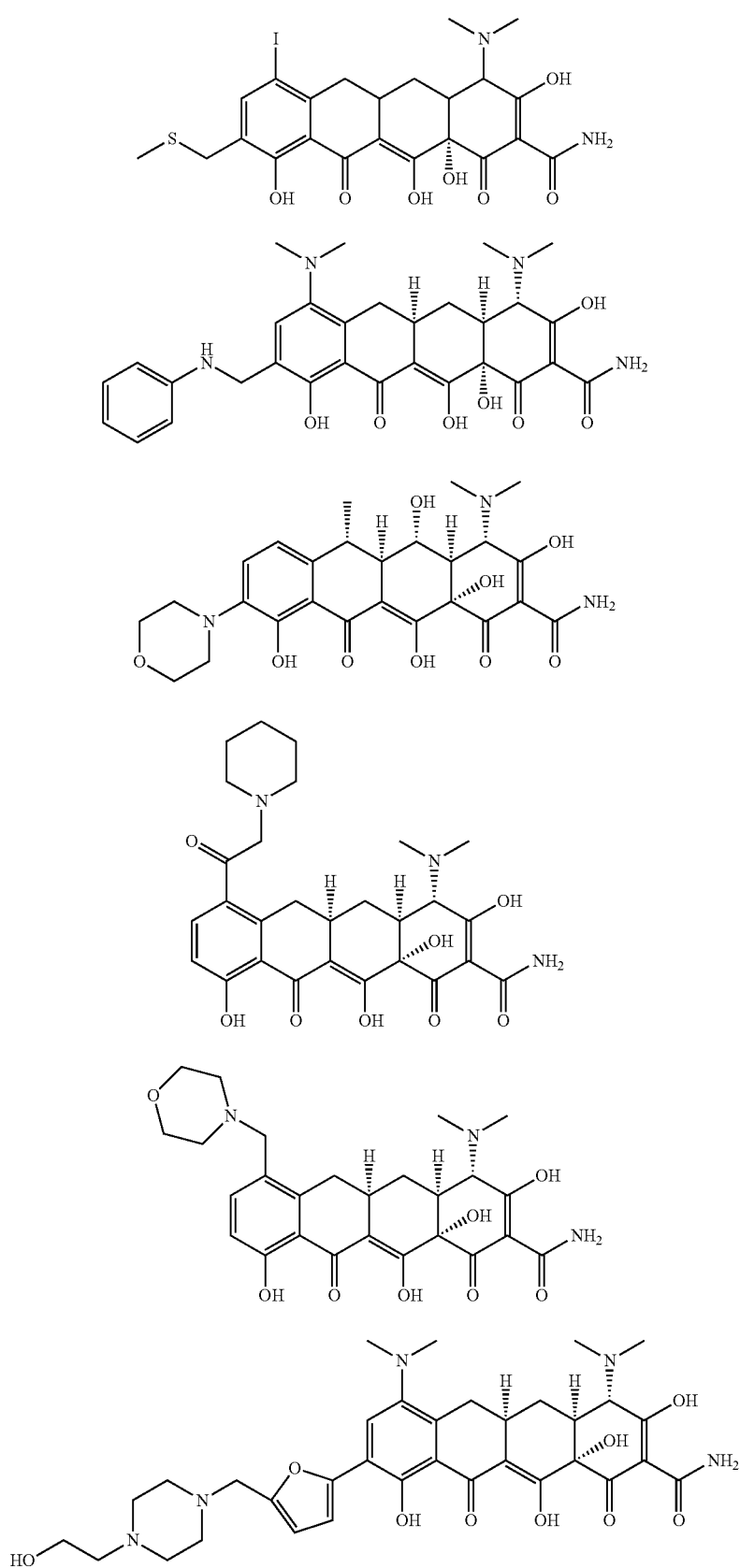

TABLE 1-continued
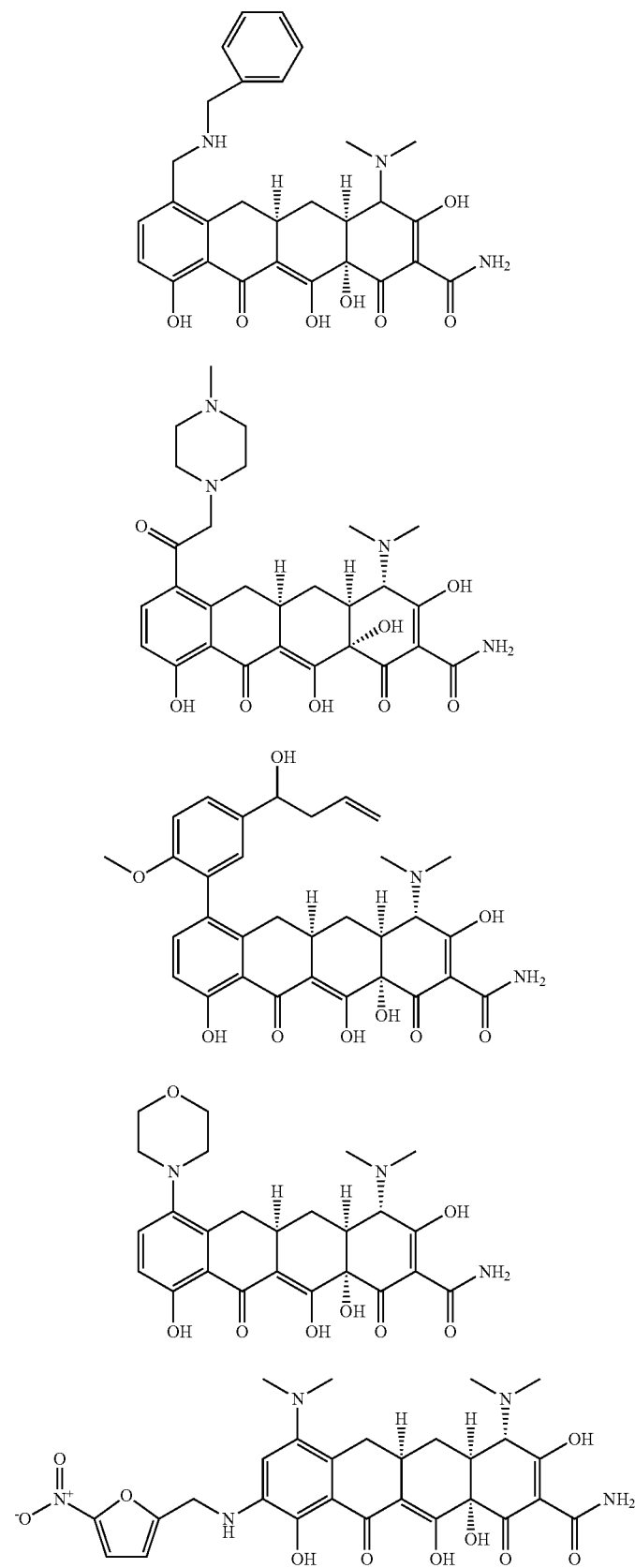

TABLE 1-continued
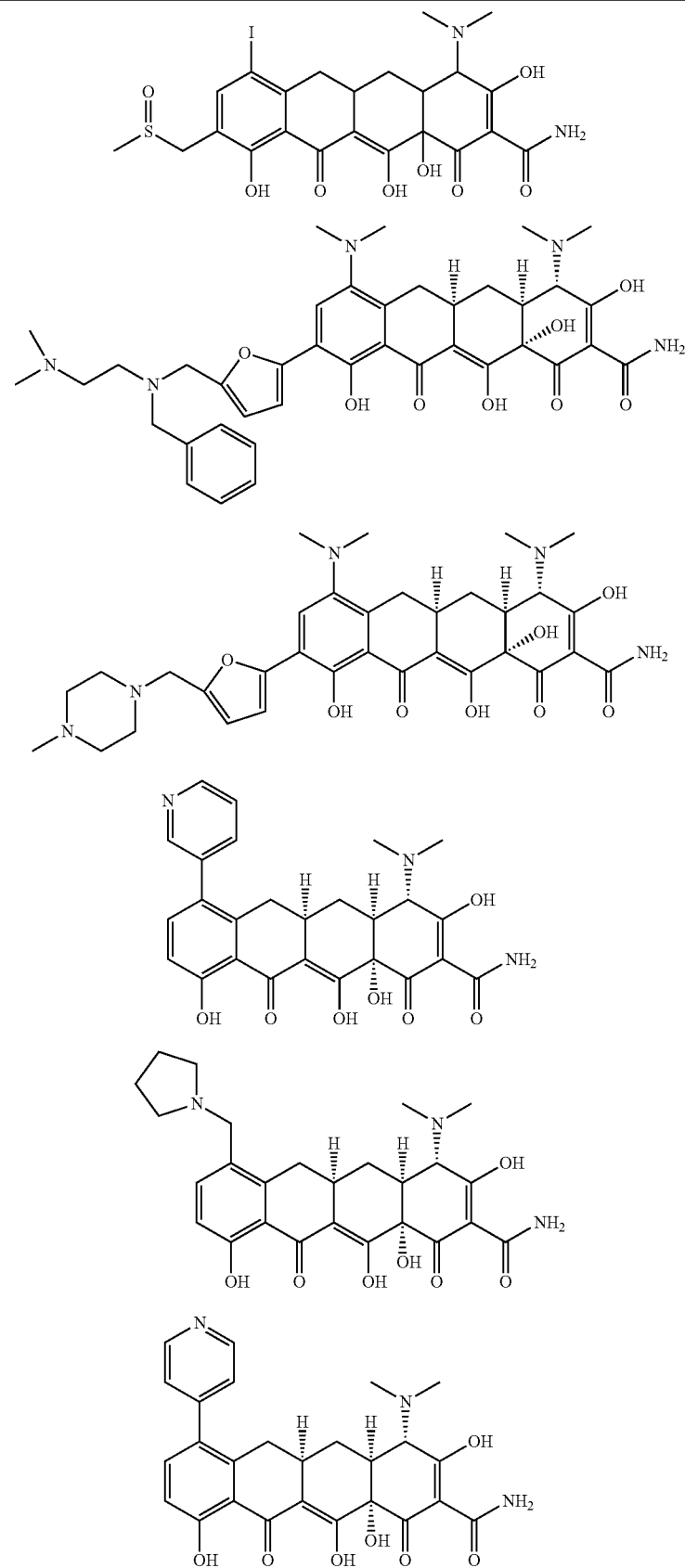

TABLE 1-continued
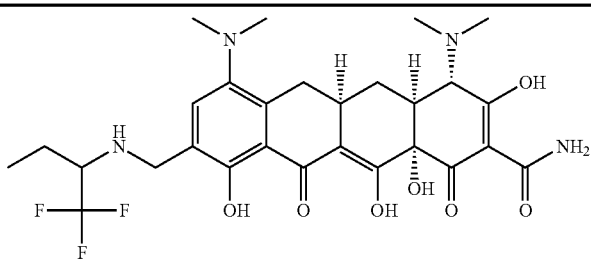
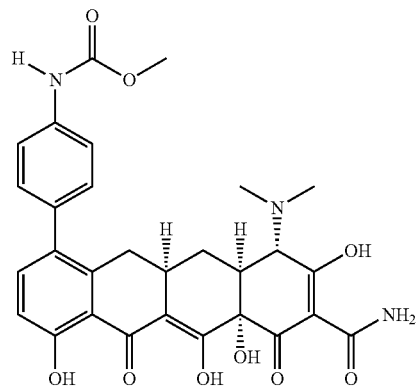
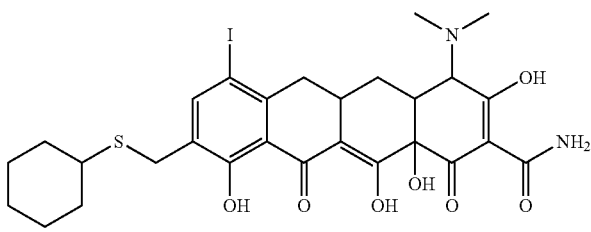
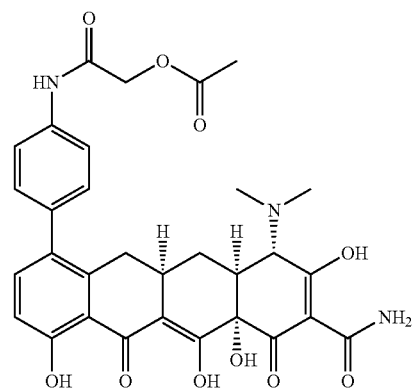
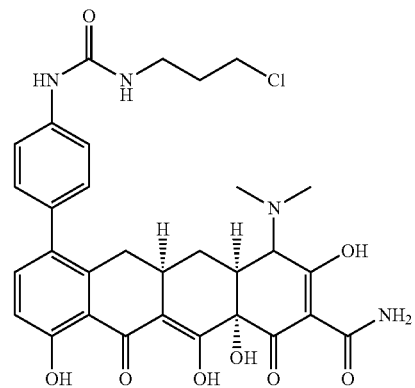

TABLE 1-continued
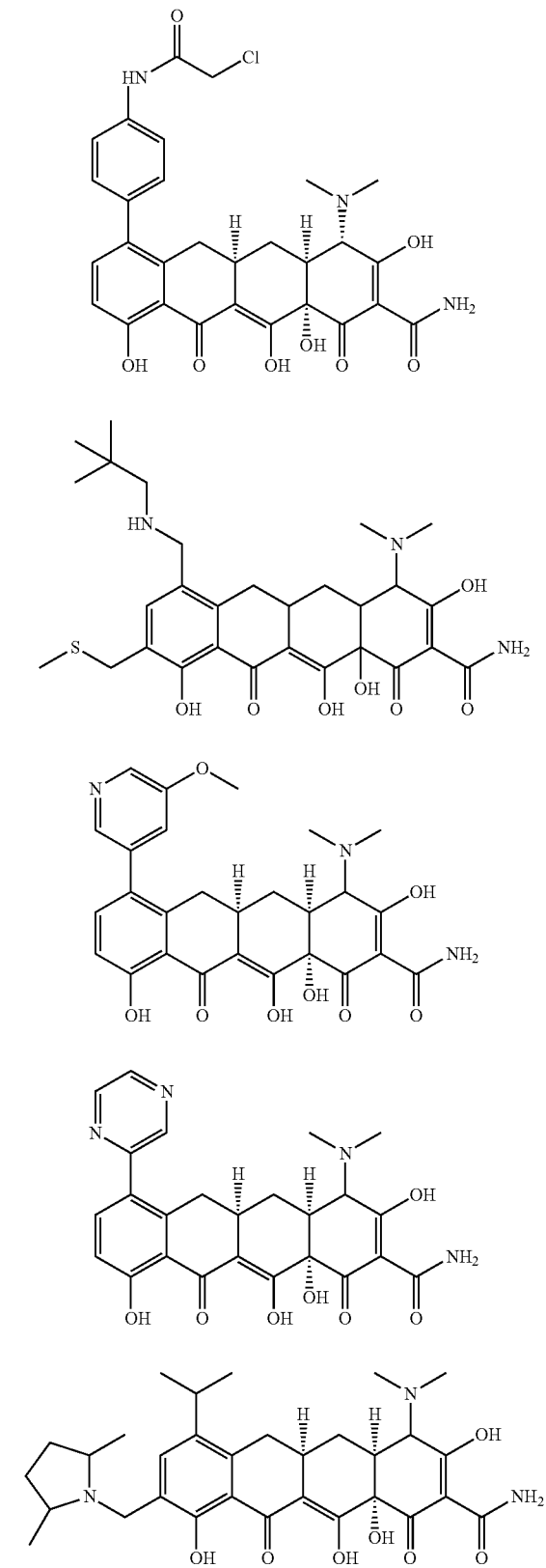

TABLE 1-continued
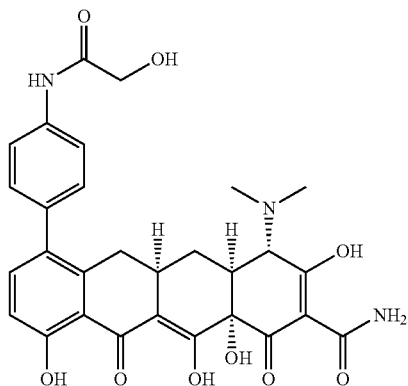
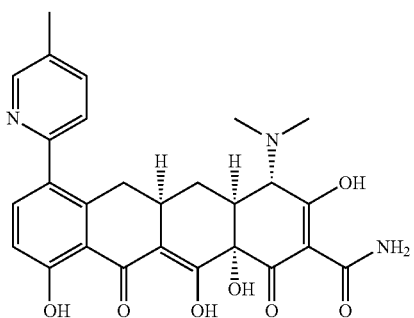
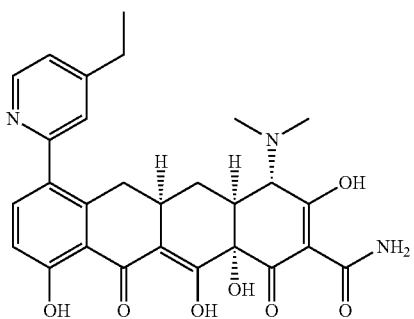
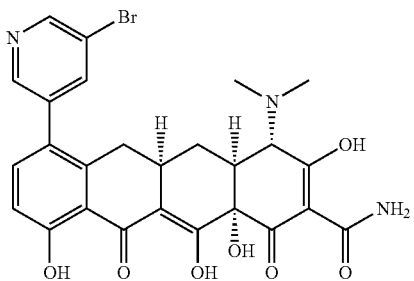
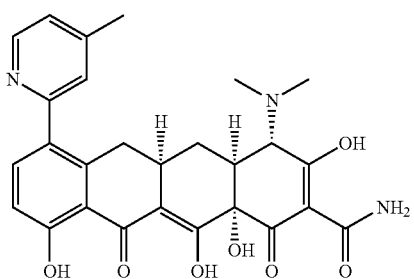

TABLE 1-continued
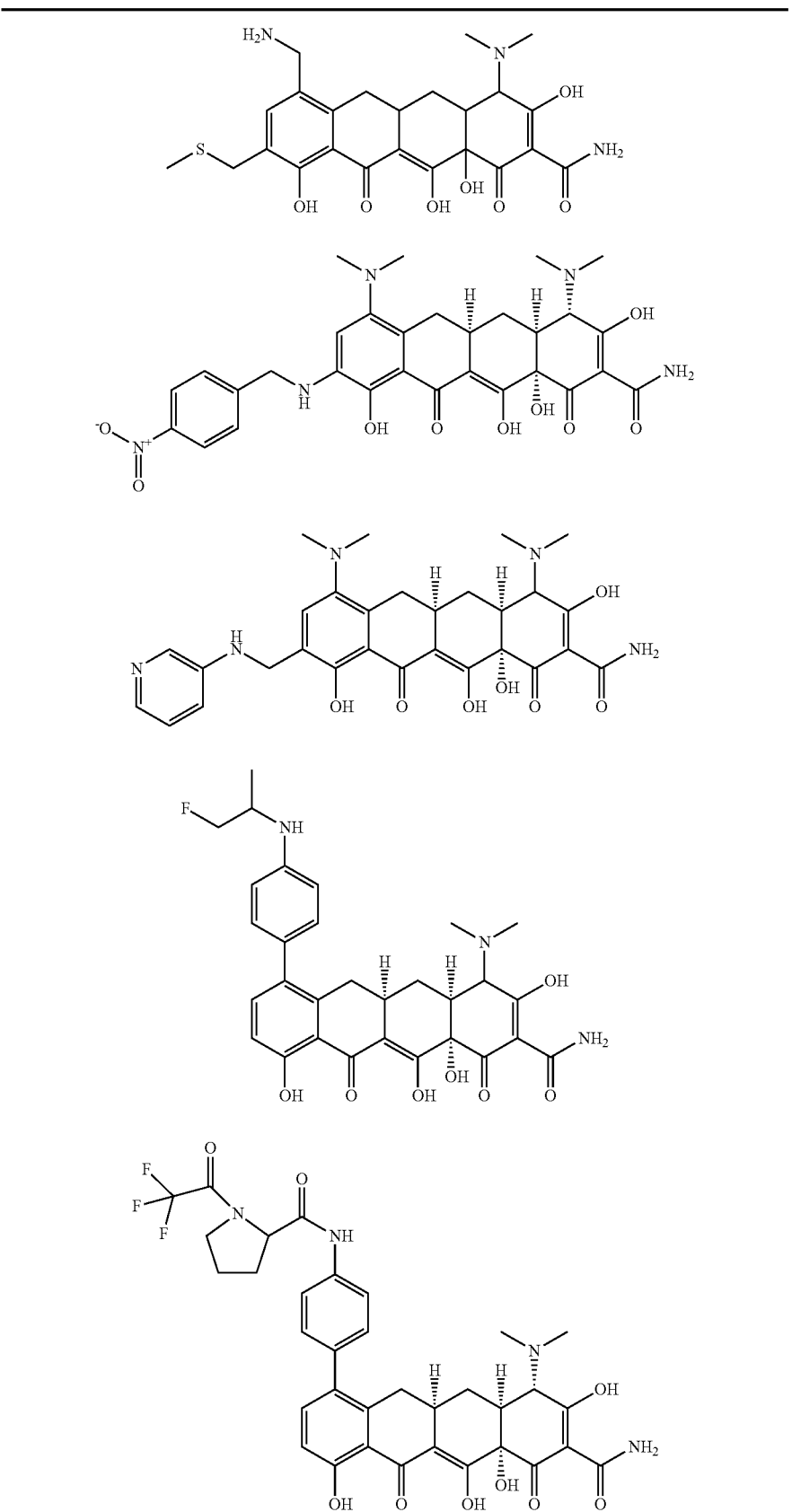

TABLE 1-continued
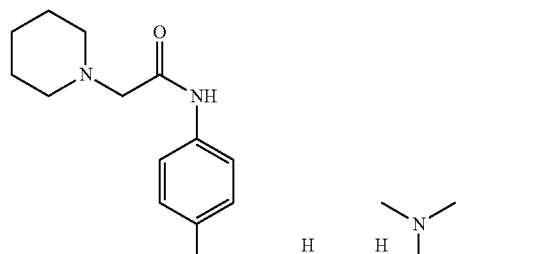
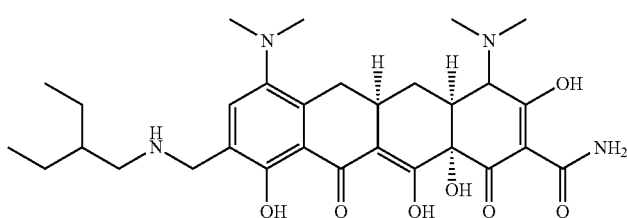
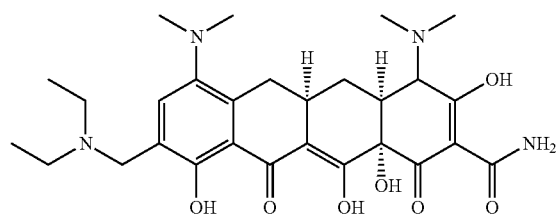
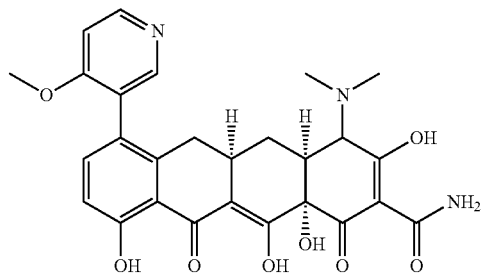
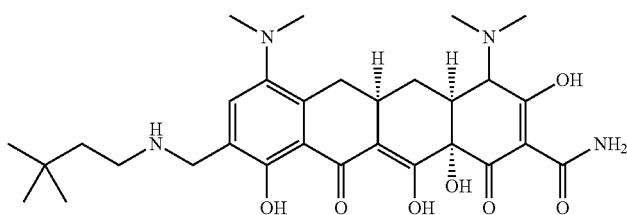
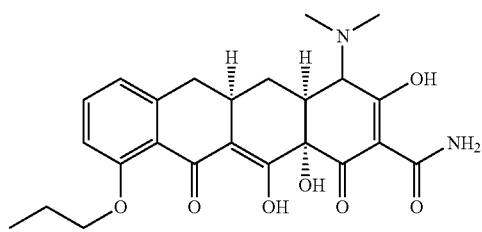

TABLE 1-continued
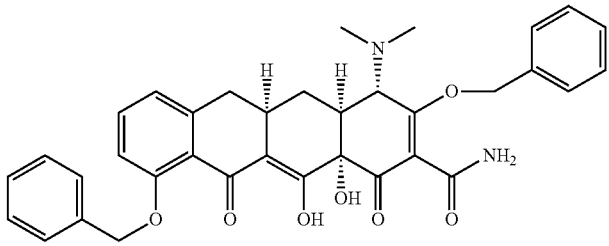
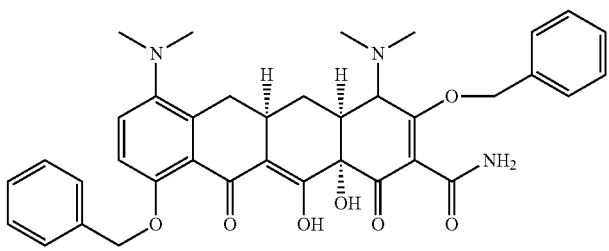
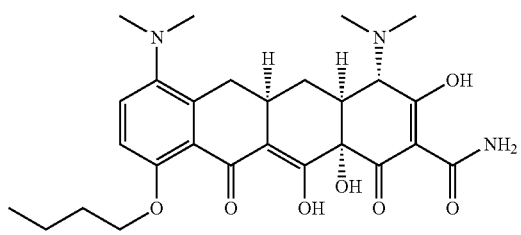
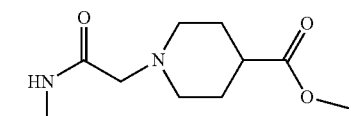
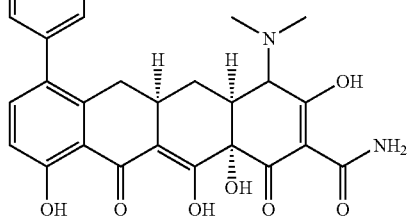
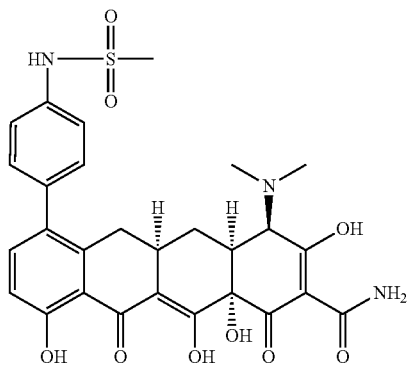

TABLE 1-continued
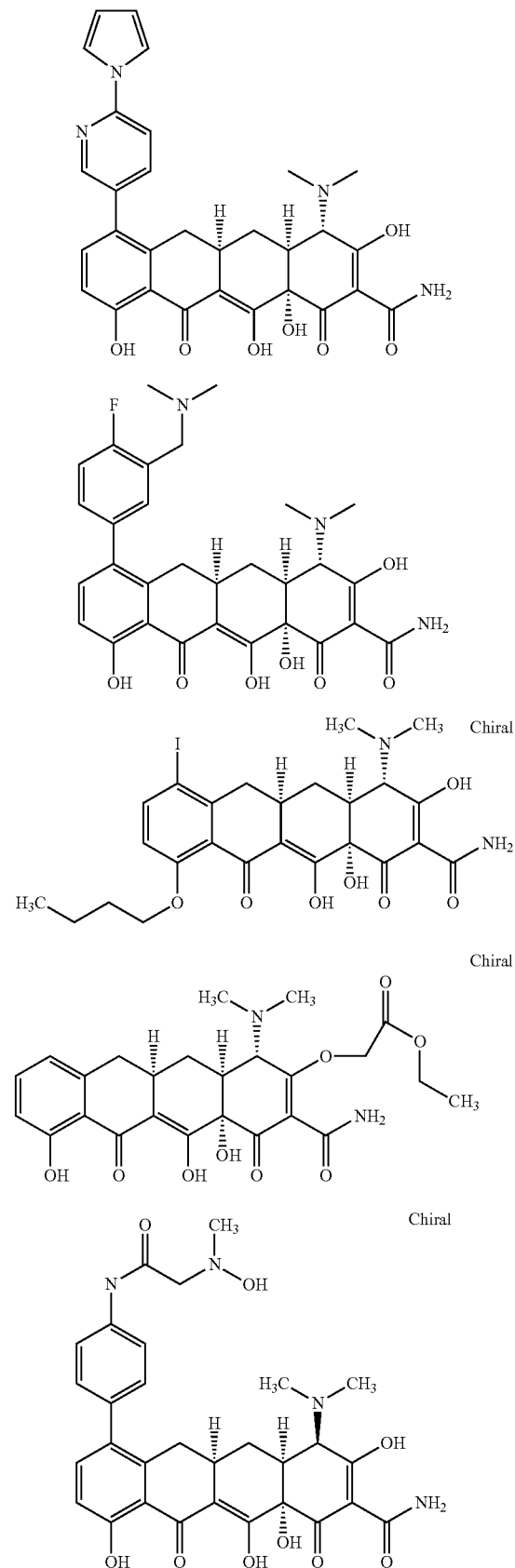

TABLE 1-continued
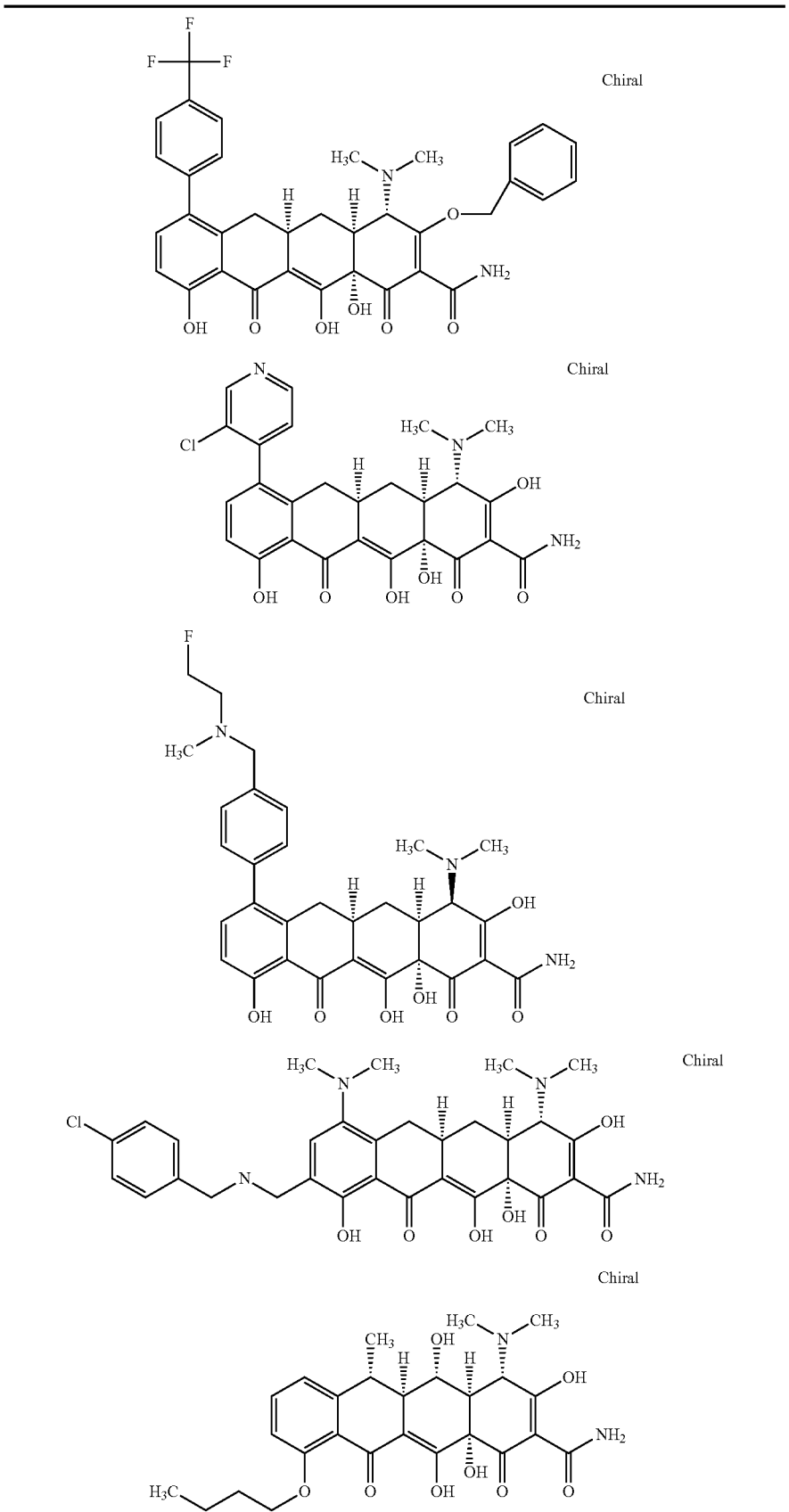

TABLE 1-continued
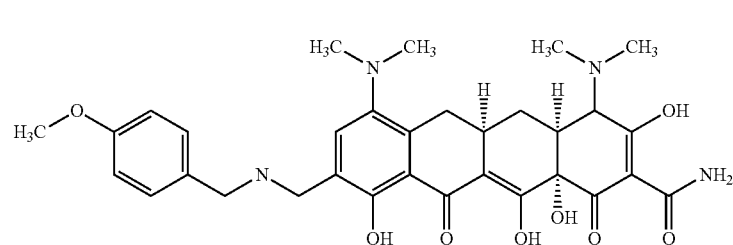
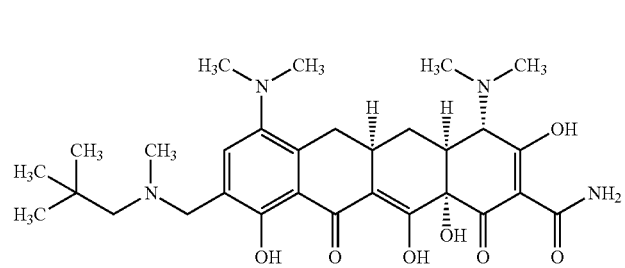
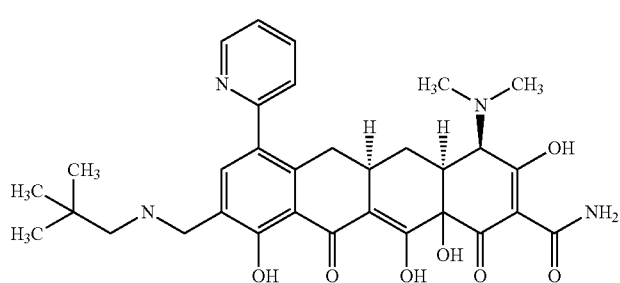
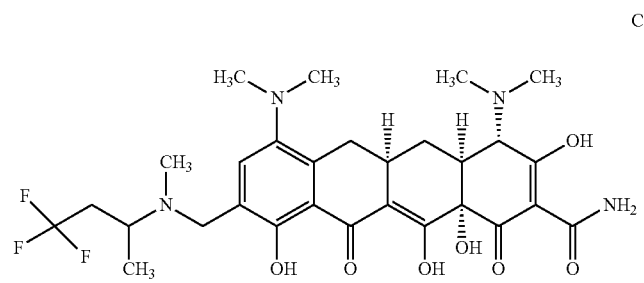
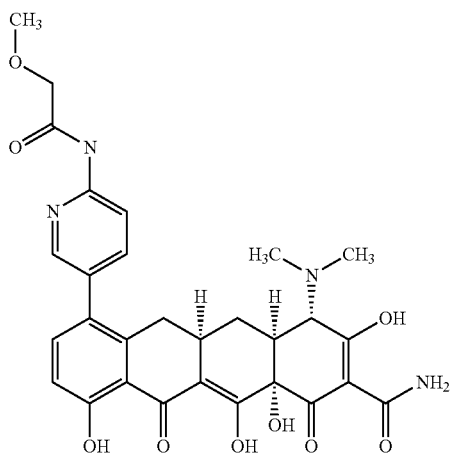

TABLE 1-continued
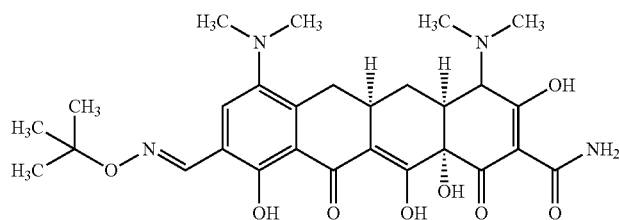
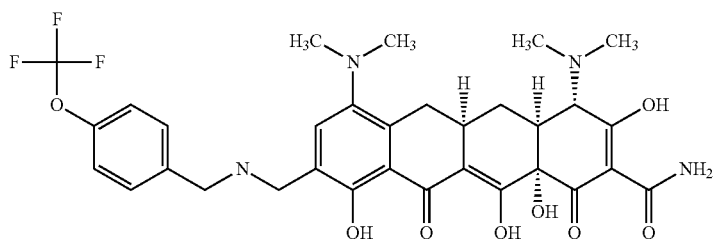
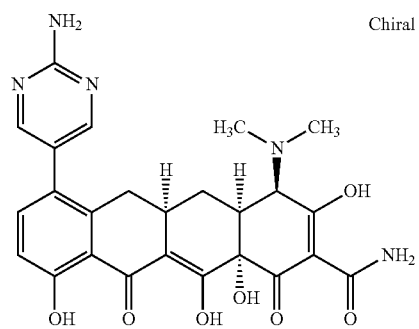
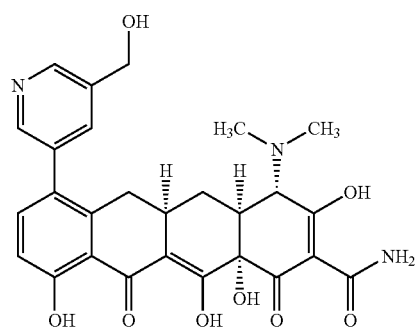
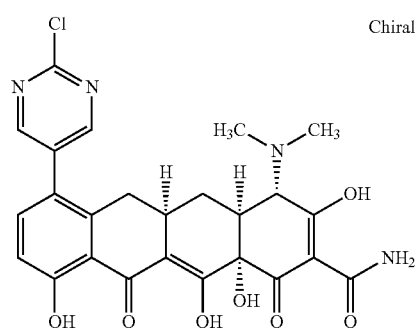

TABLE 1-continued
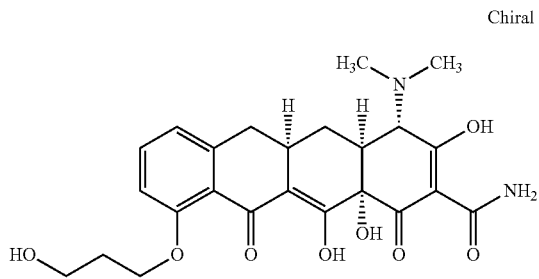
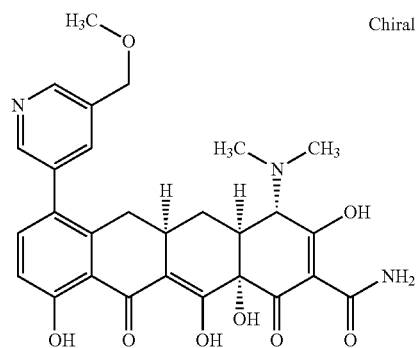
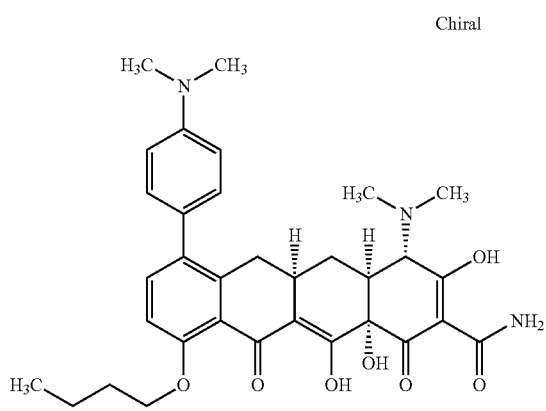
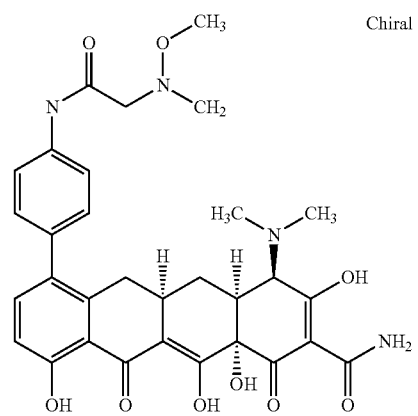

TABLE 1-continued
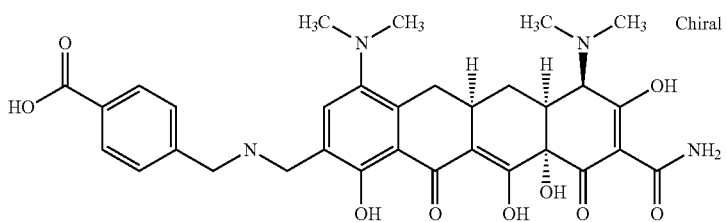
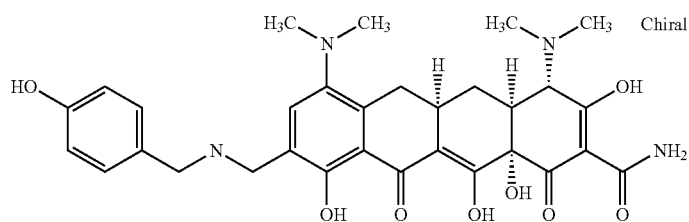
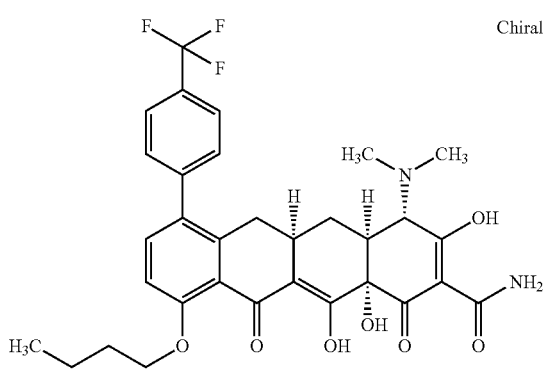
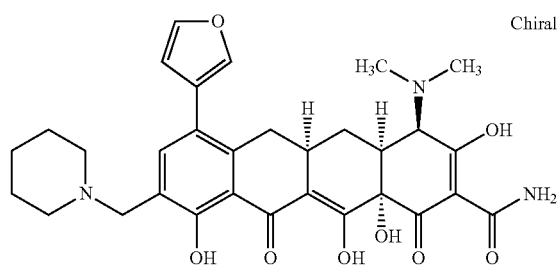
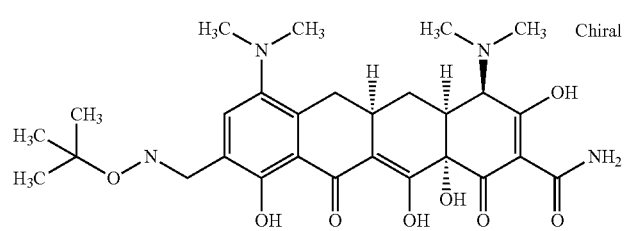

TABLE 1-continued
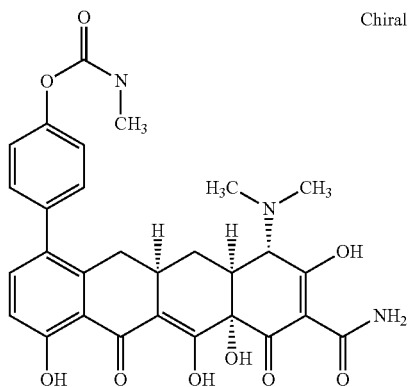
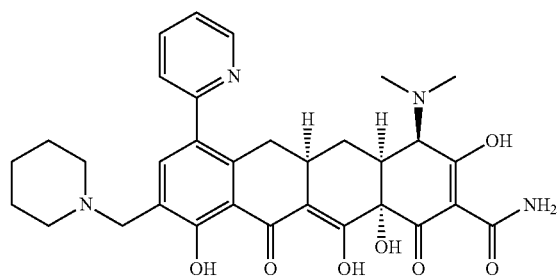
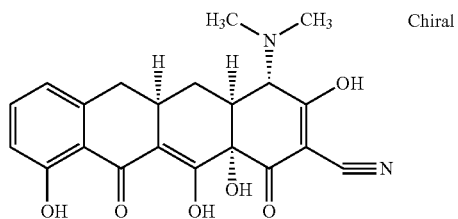
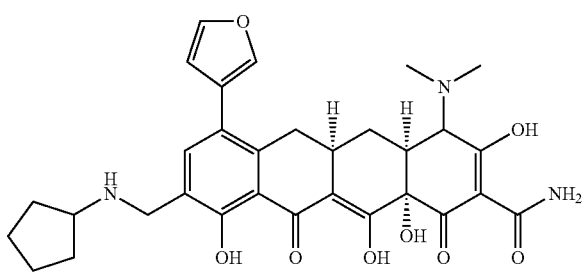
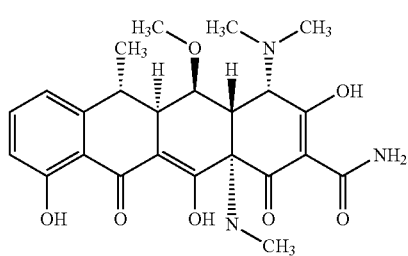

TABLE 1-continued
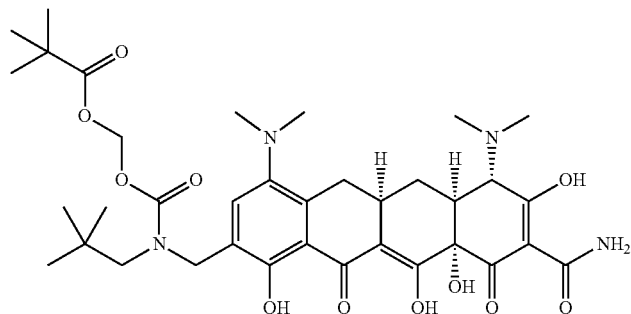
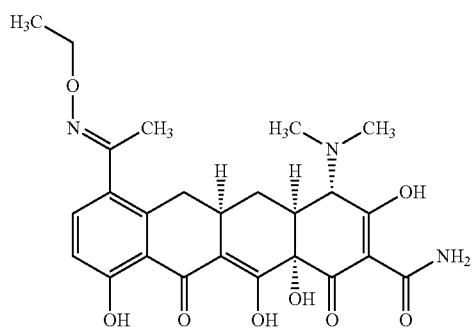
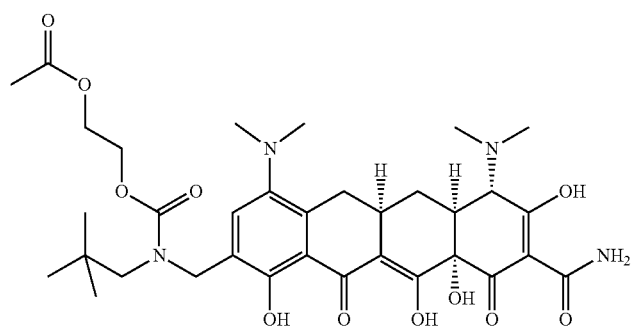
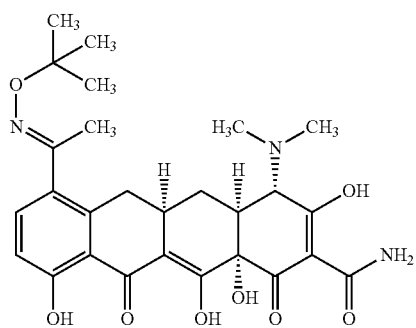
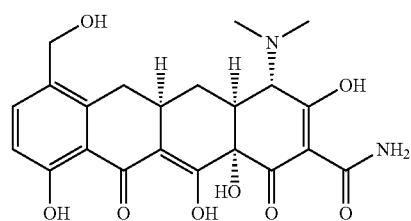

TABLE 1-continued
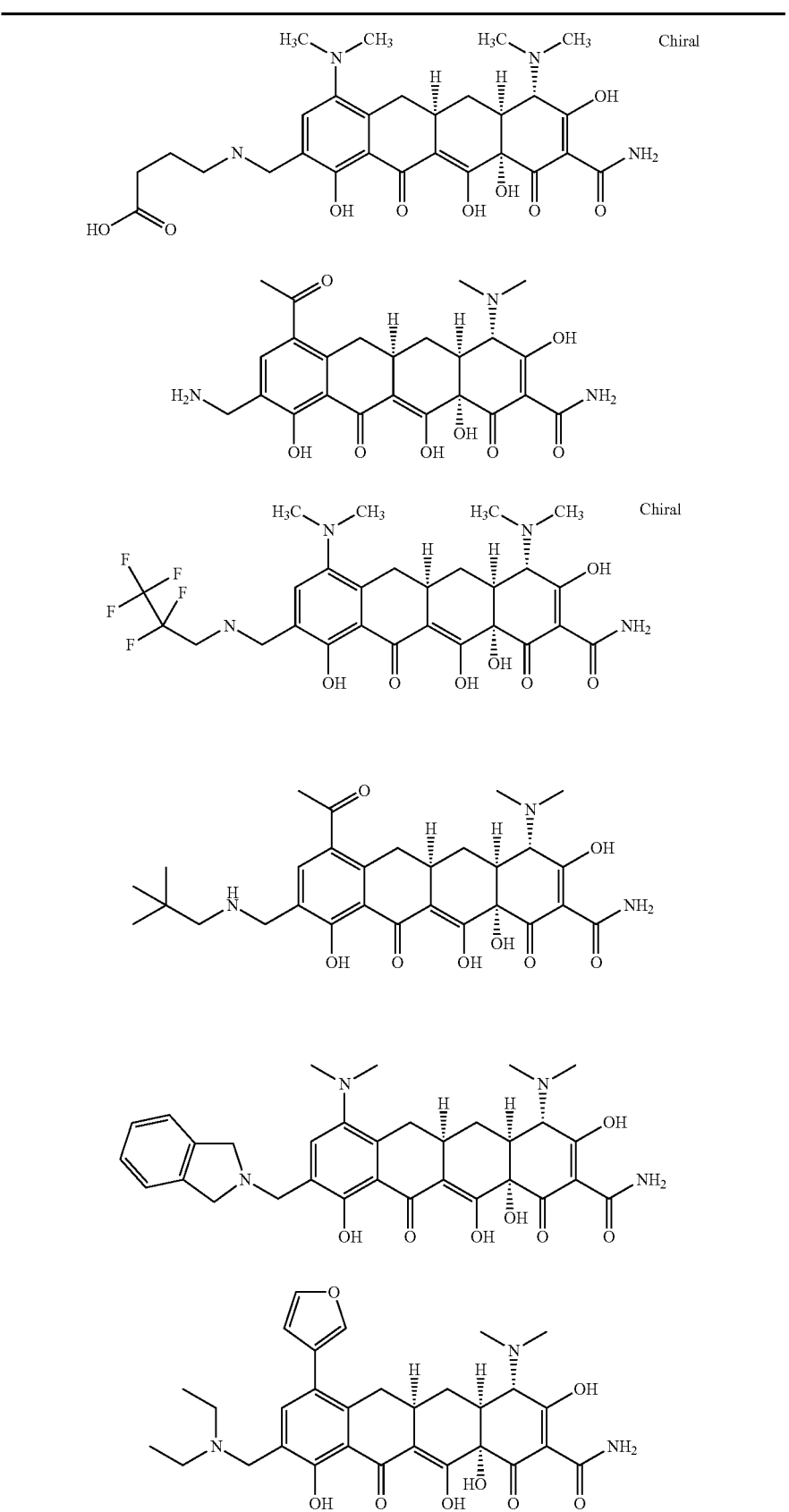

TABLE 1-continued
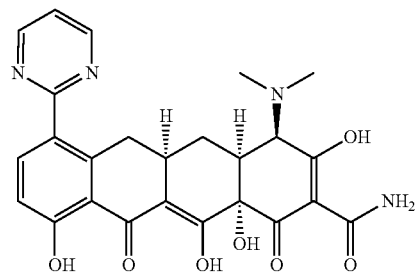
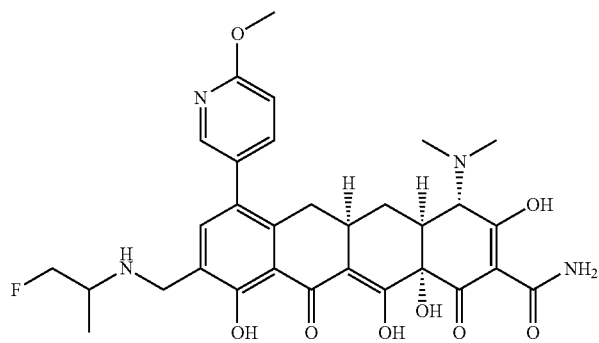
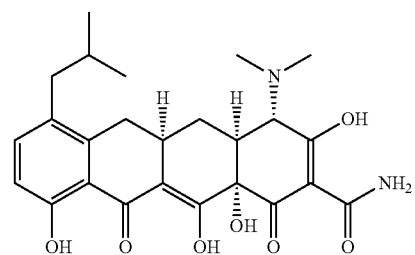
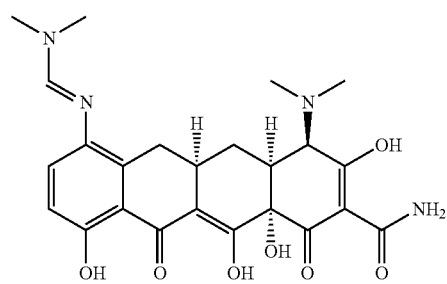
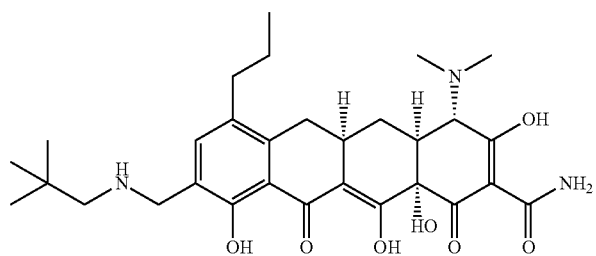

TABLE 1-continued
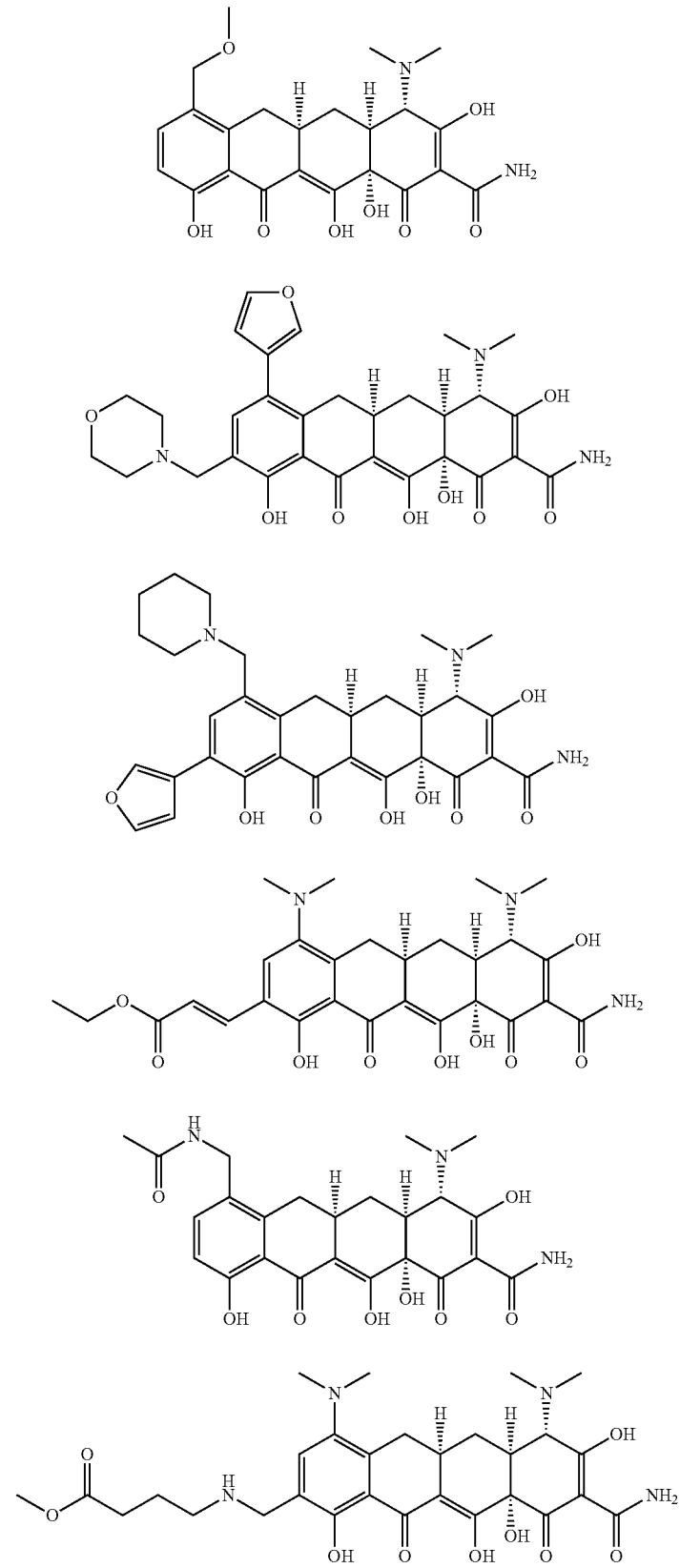

TABLE 1-continued
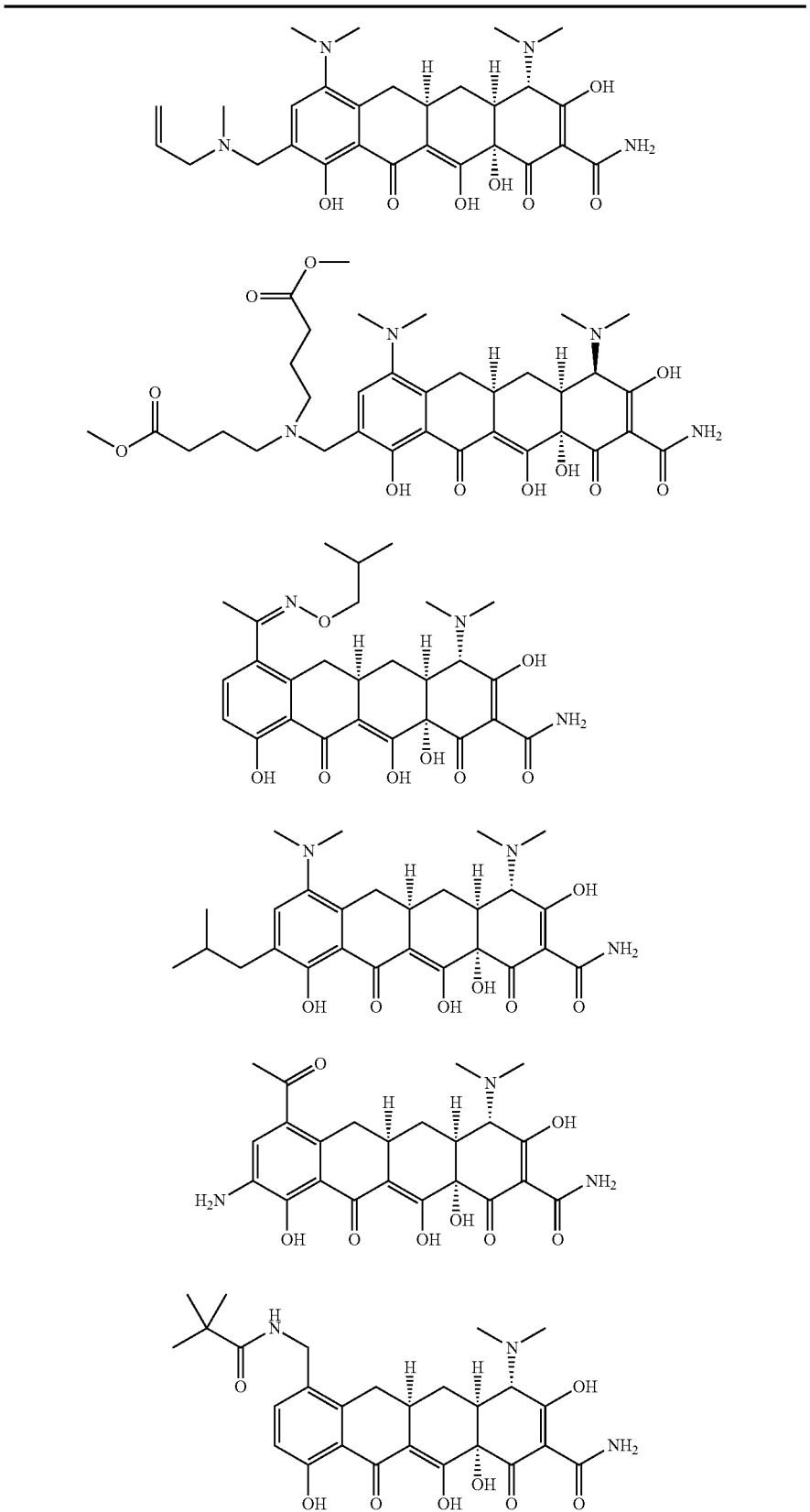

TABLE 1-continued
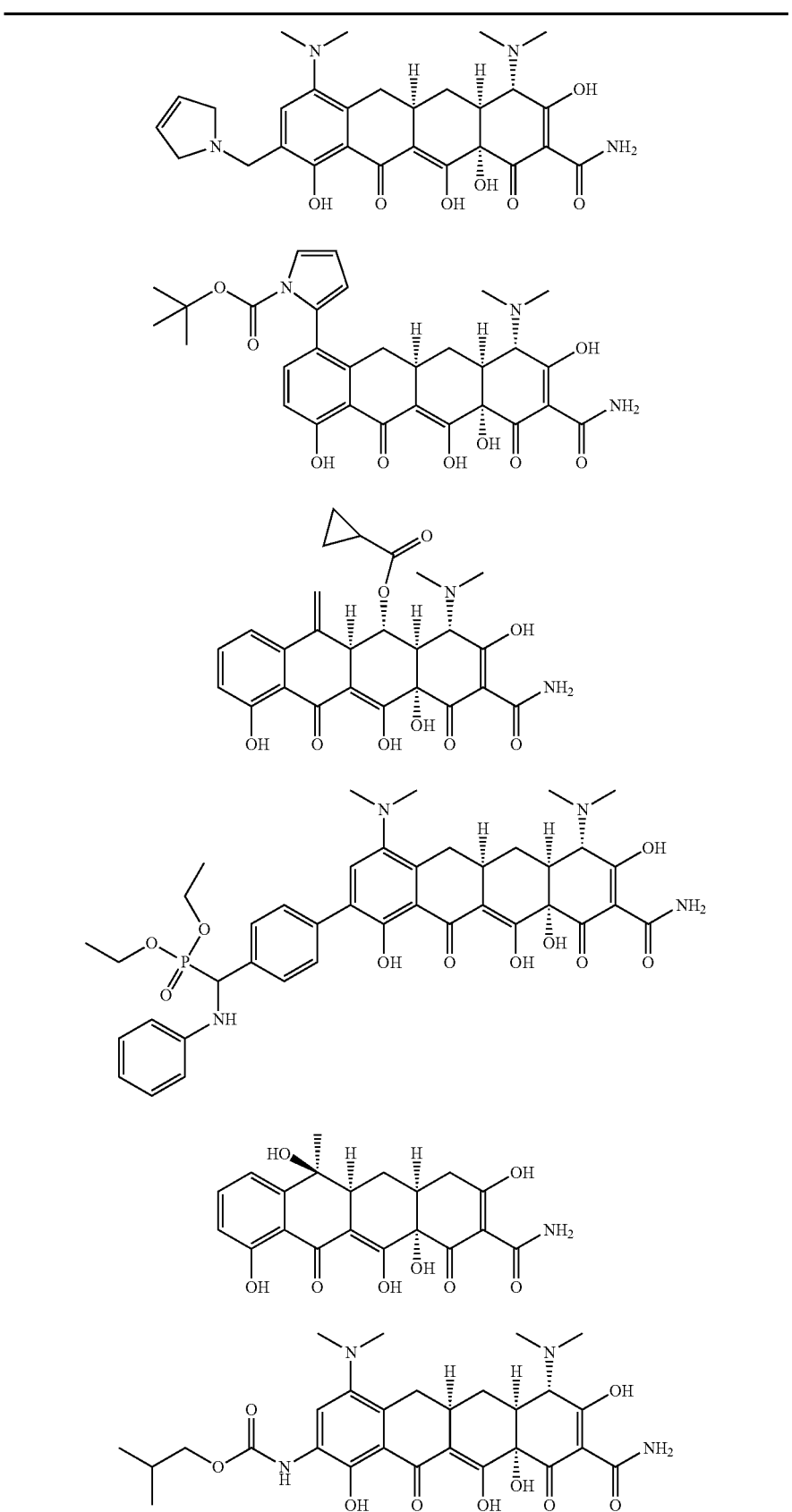

TABLE 1-continued
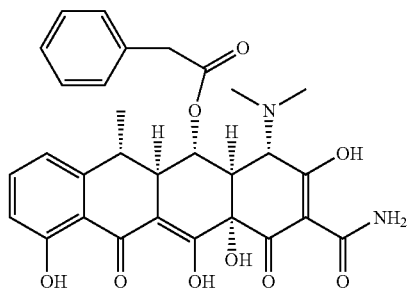
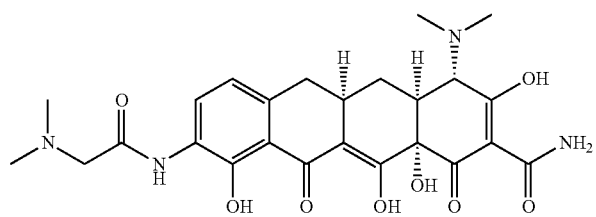
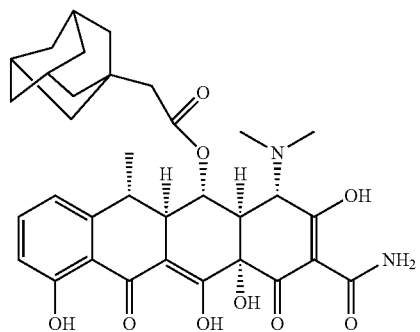
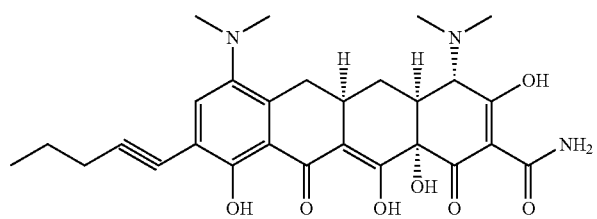
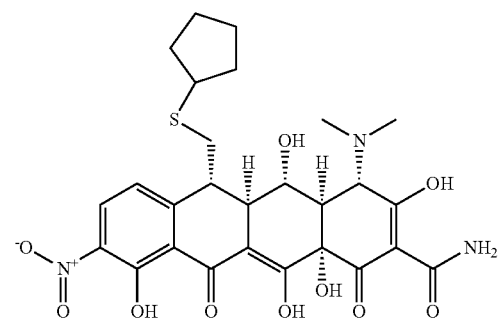

TABLE 1-continued
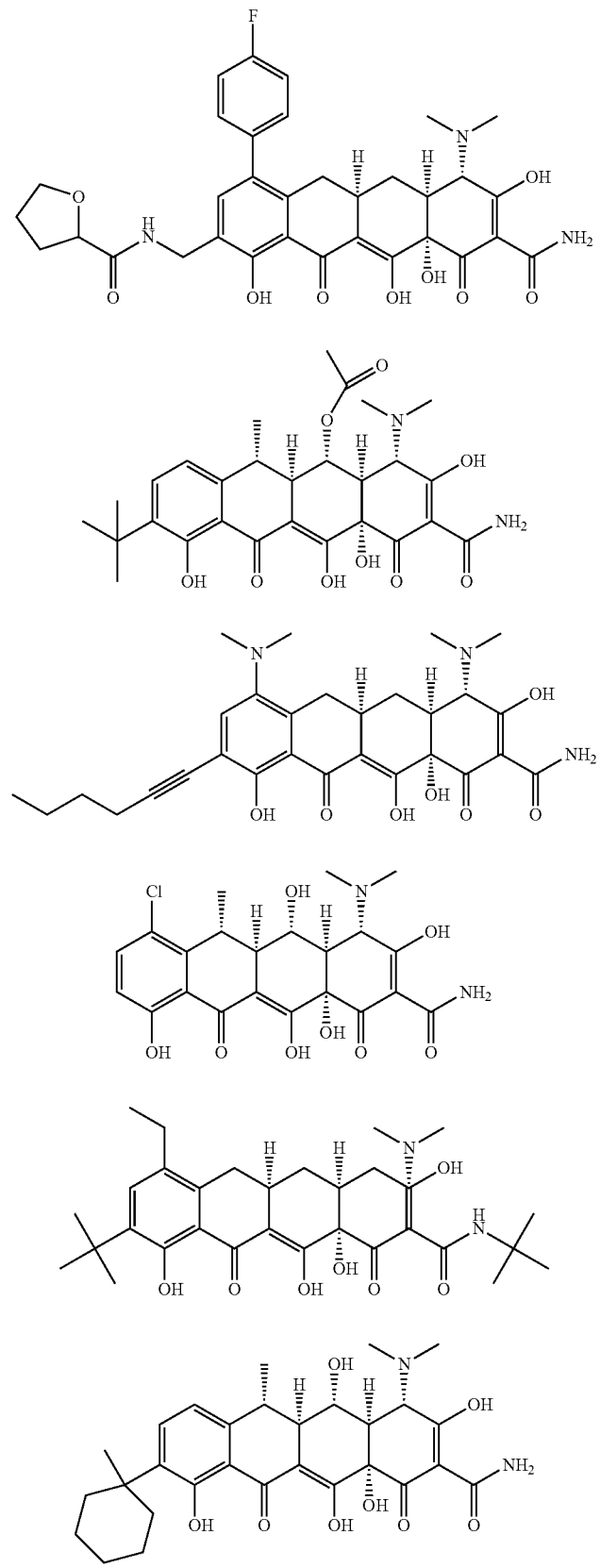

TABLE 1-continued
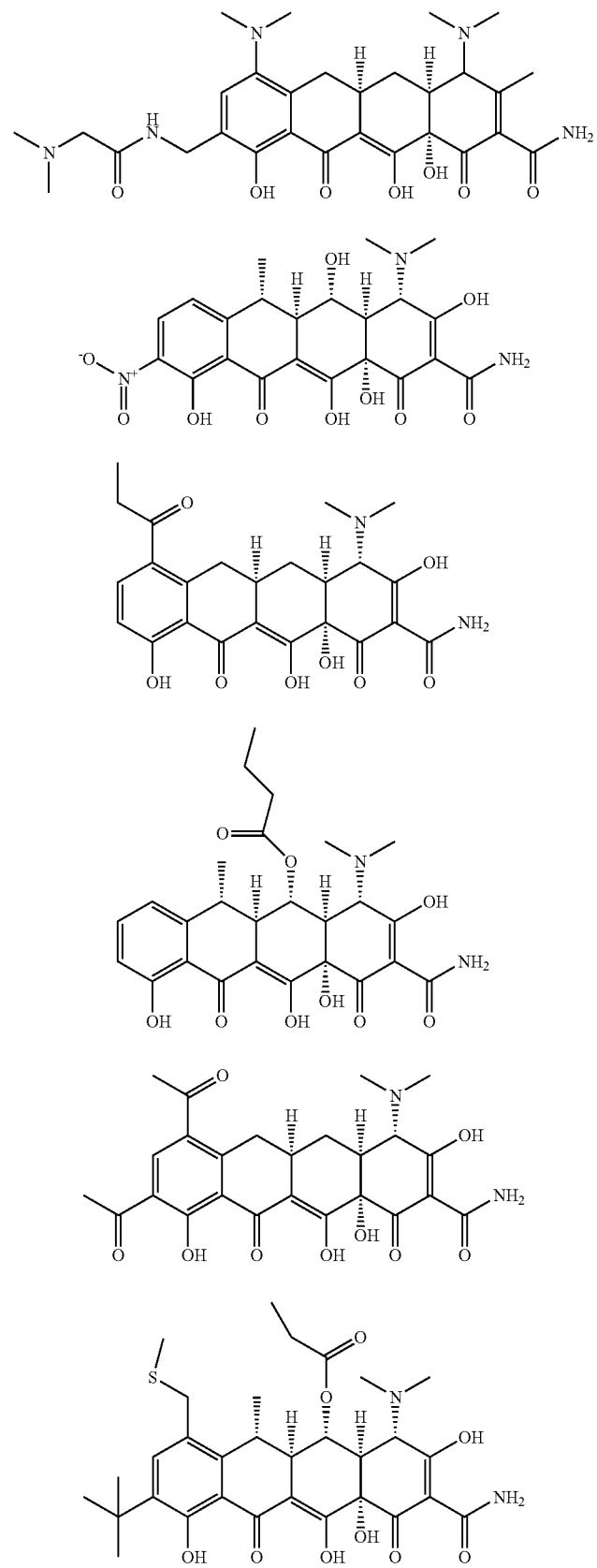

TABLE 1-continued
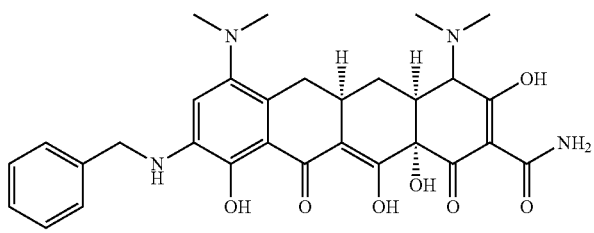
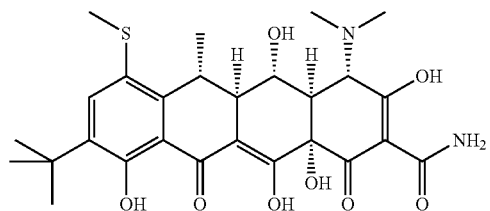
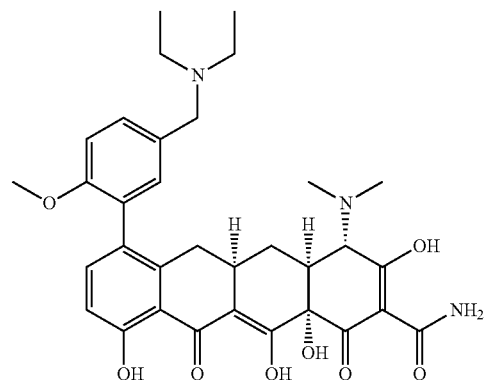
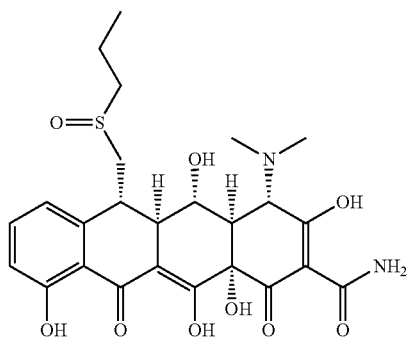
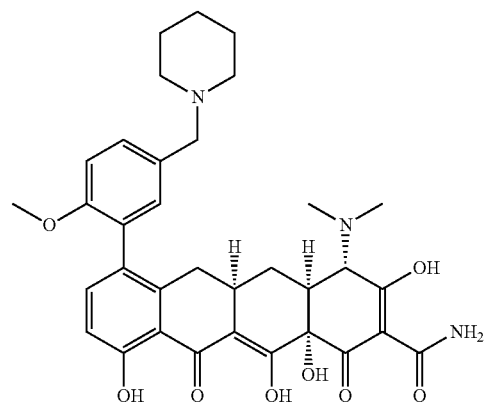

TABLE 1-continued
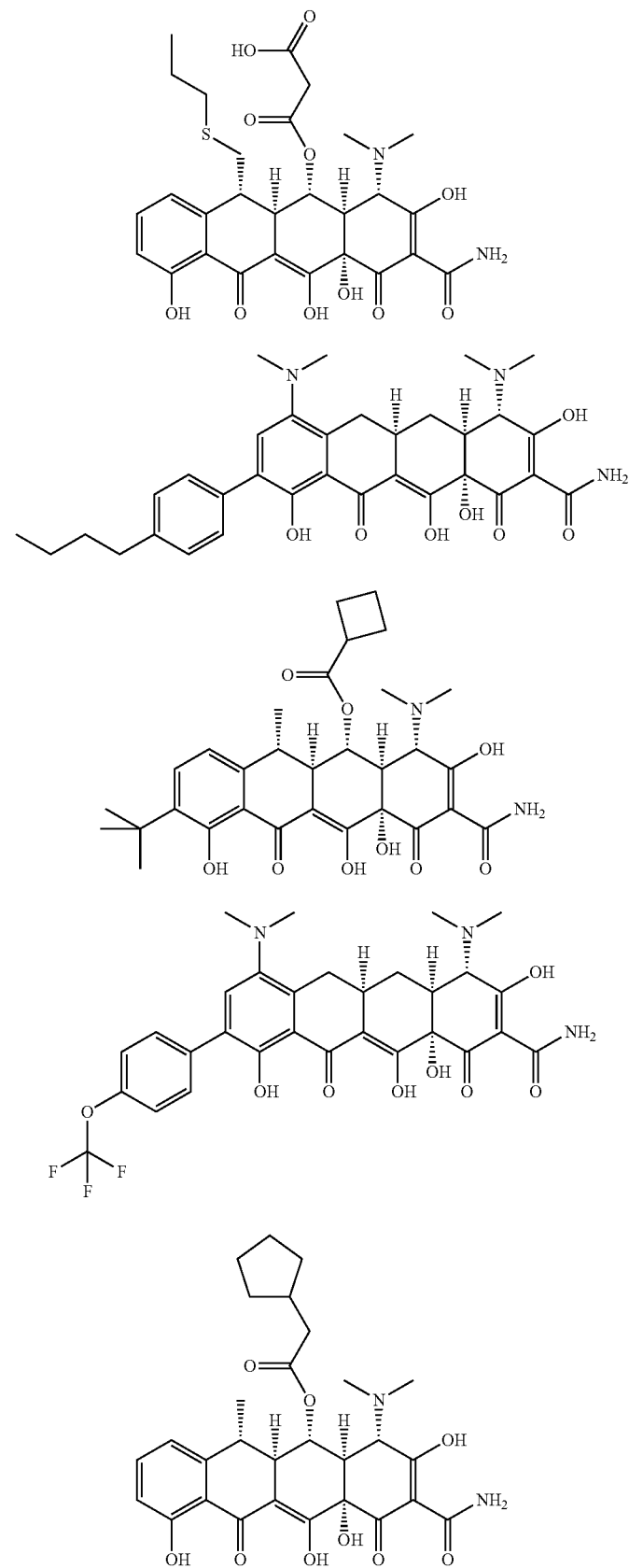

TABLE 1-continued
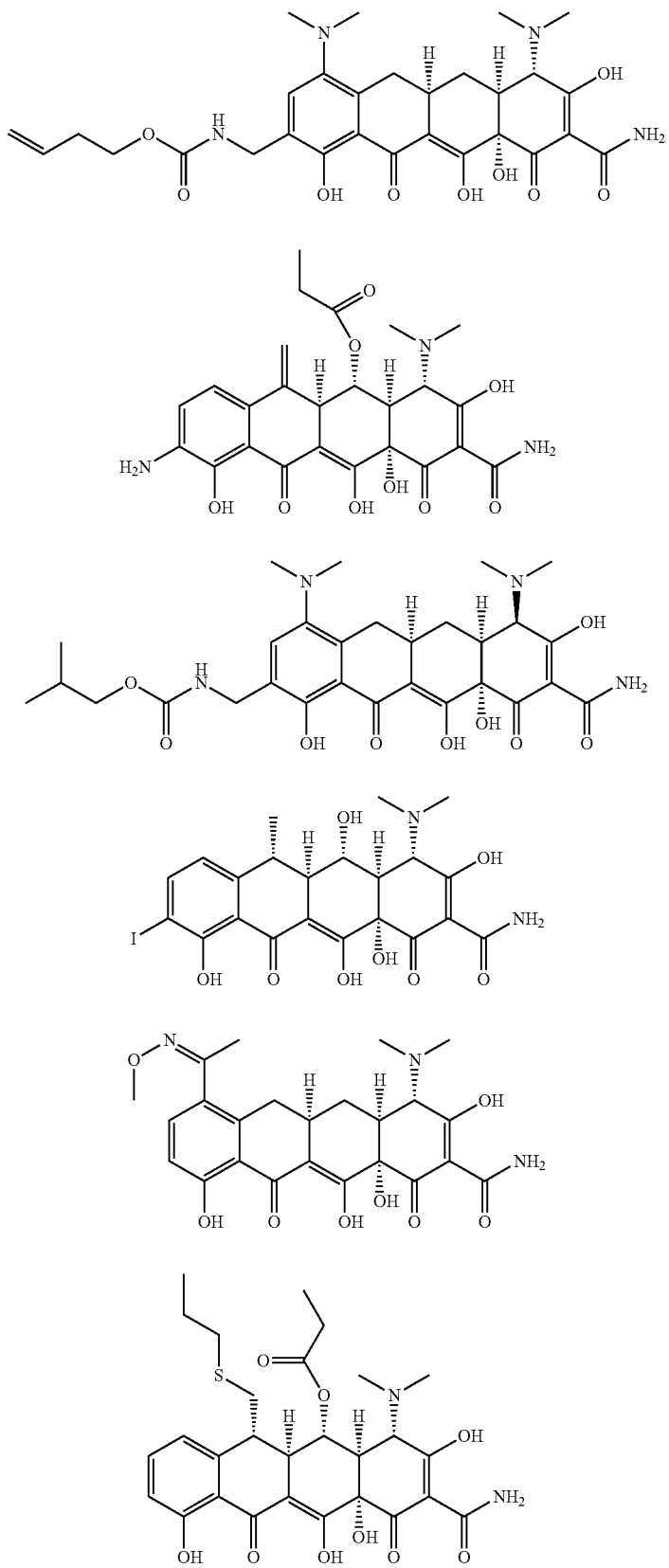

TABLE 1-continued
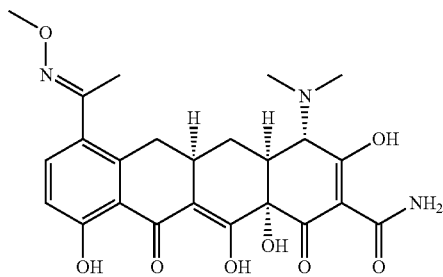
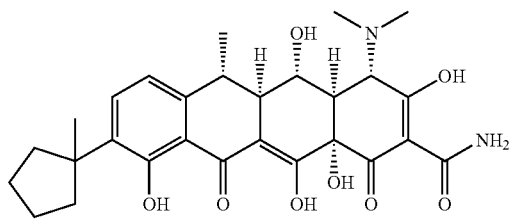
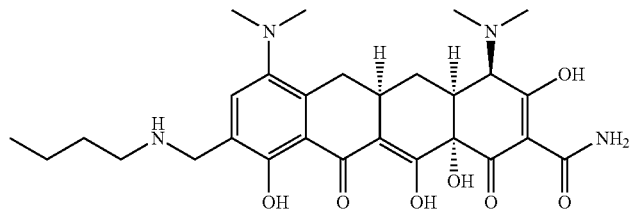
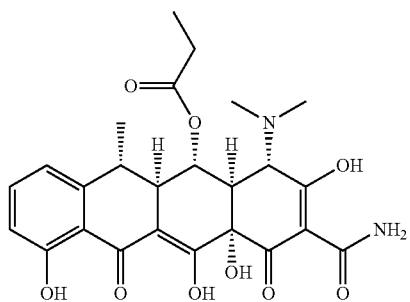
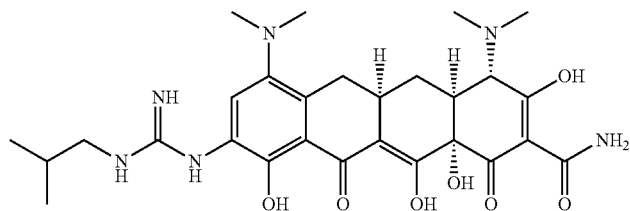
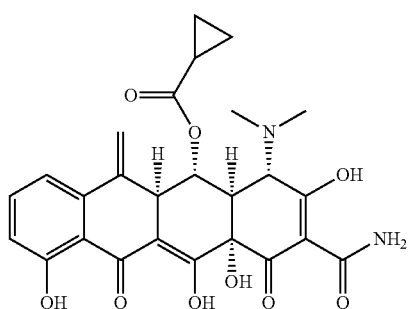

TABLE 1-continued
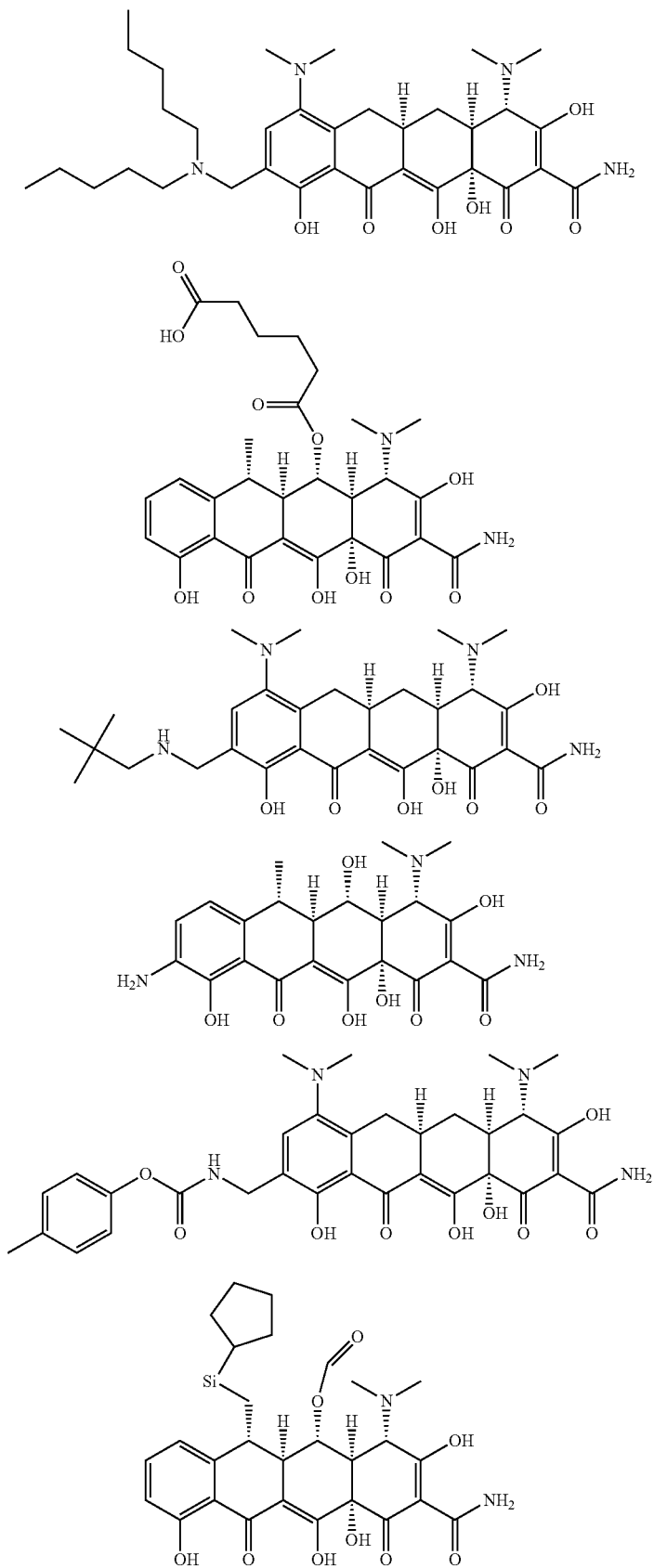

TABLE 1-continued
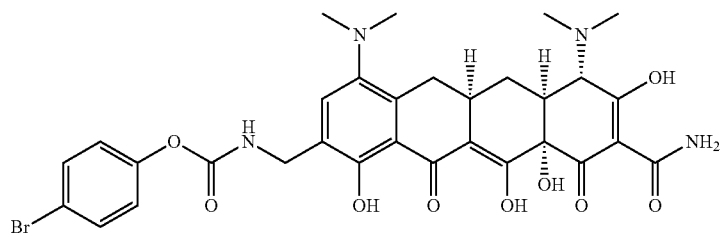
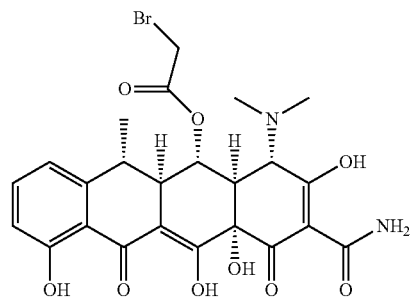
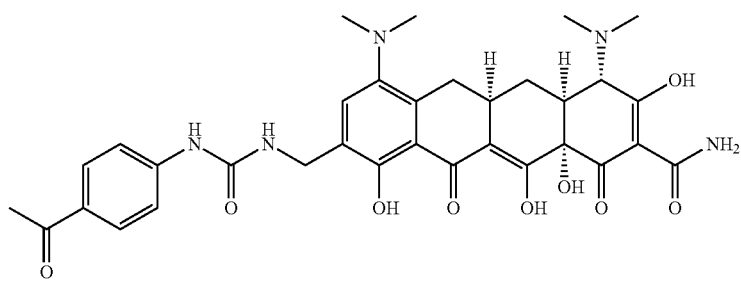
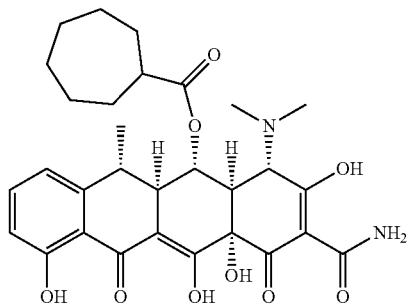
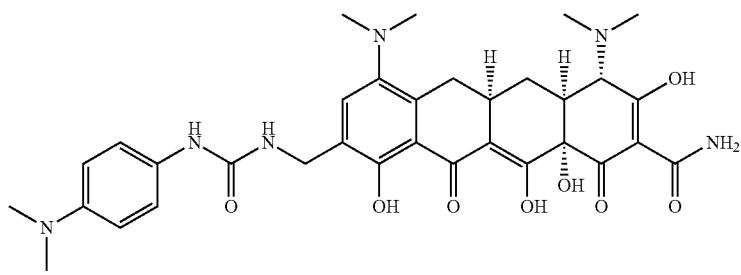

TABLE 1-continued
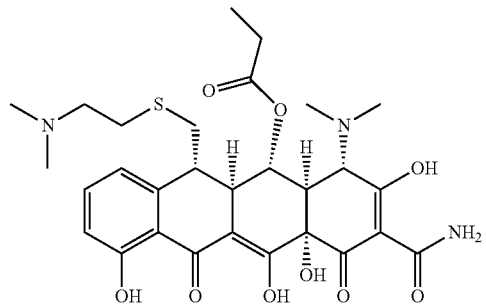
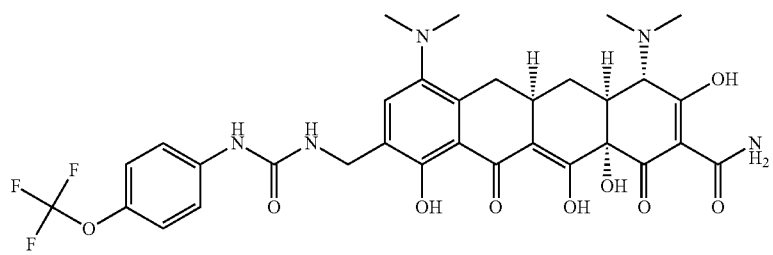
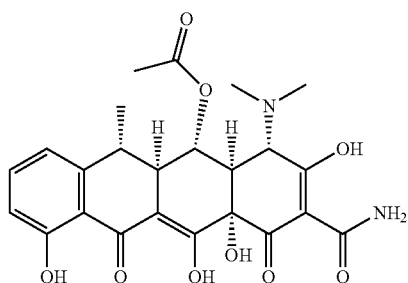
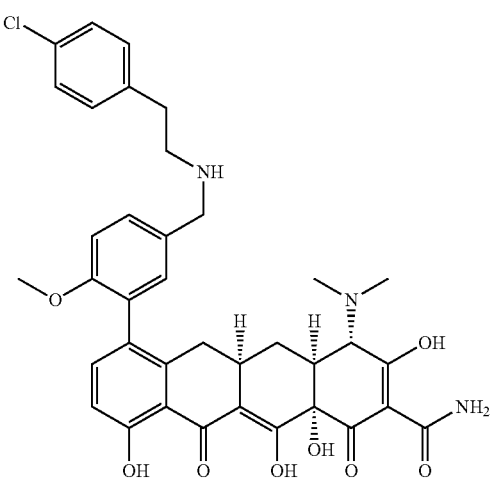

TABLE 1-continued
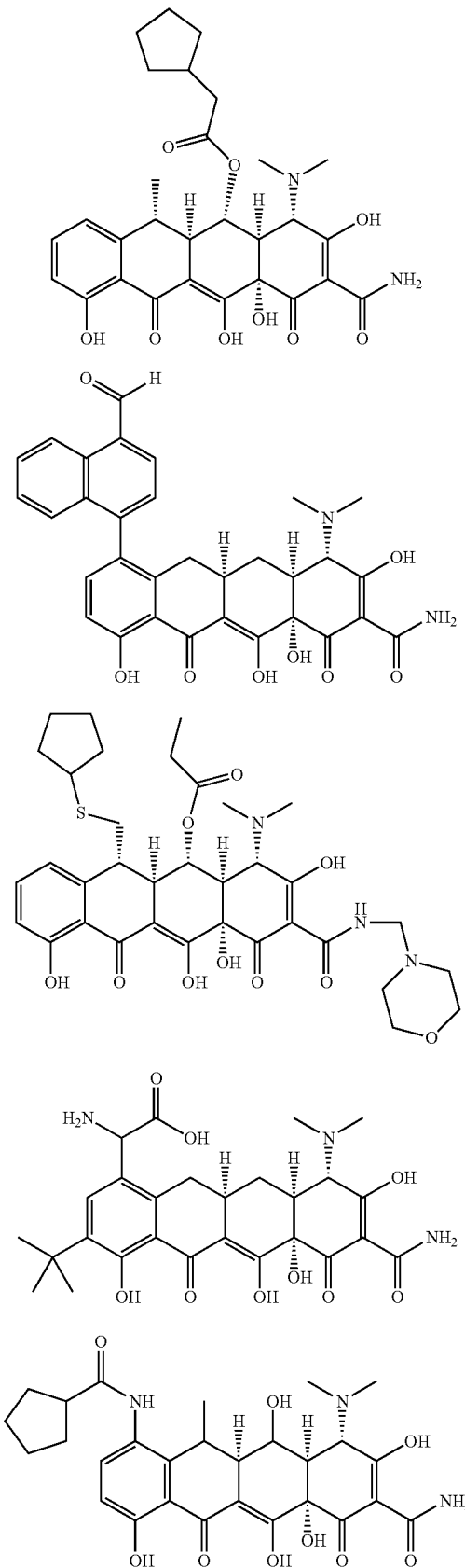

TABLE 1-continued
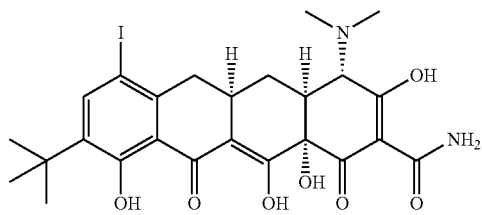
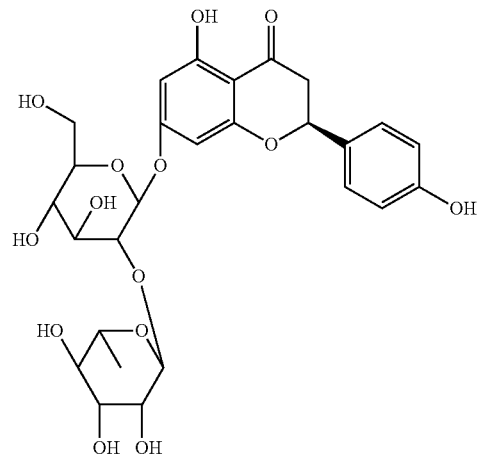
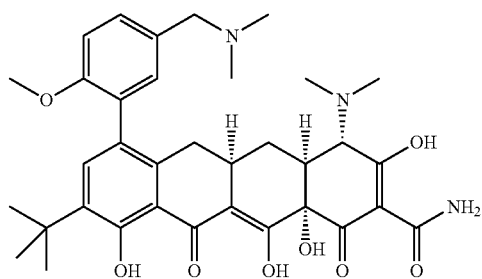
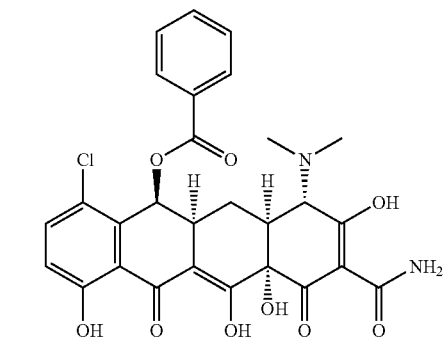
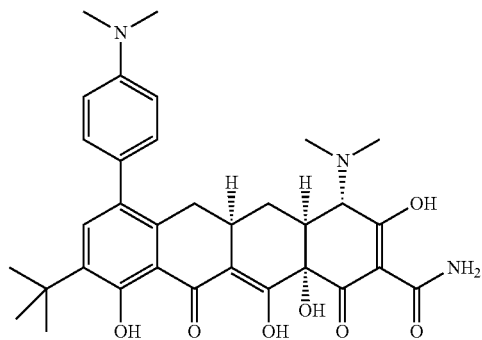

TABLE 1-continued
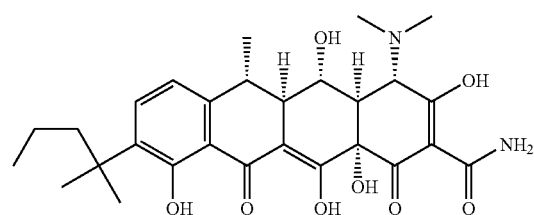
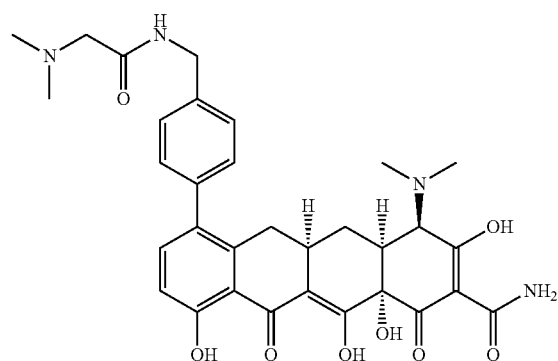
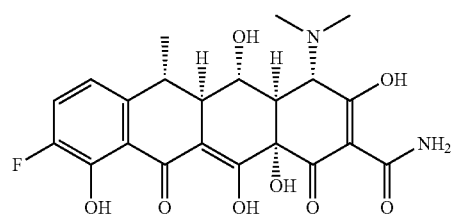
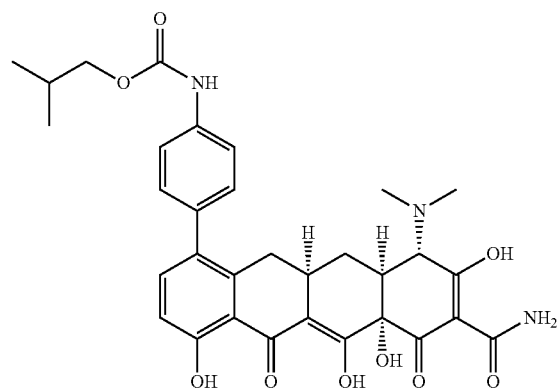
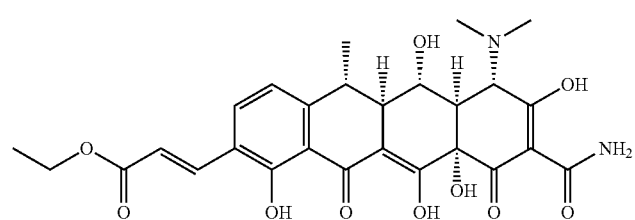

TABLE 1-continued
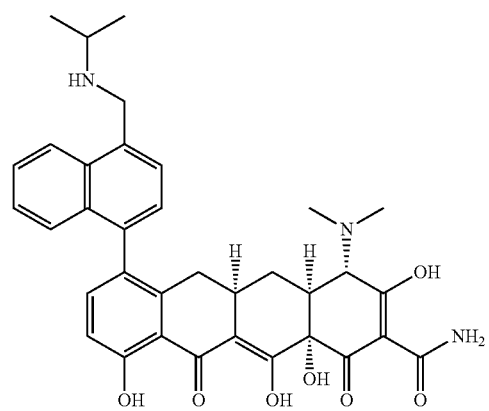
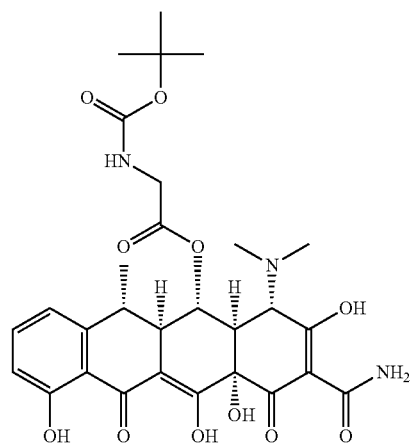
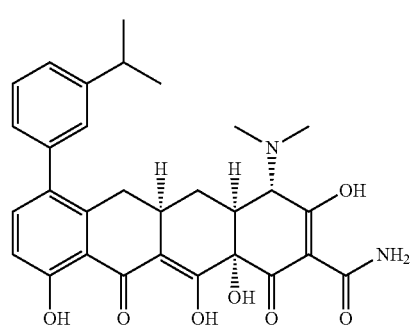
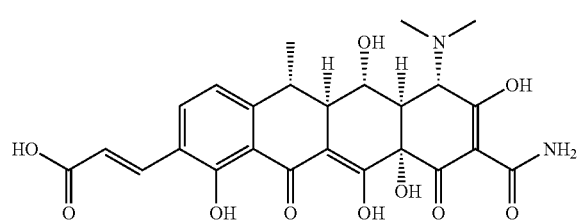

TABLE 1-continued
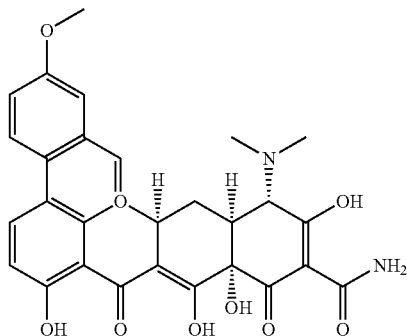
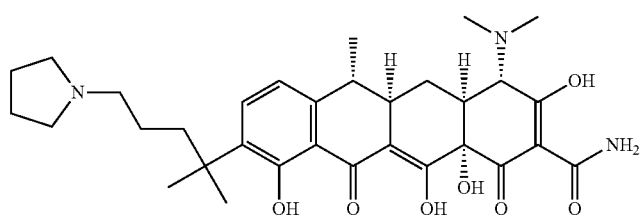
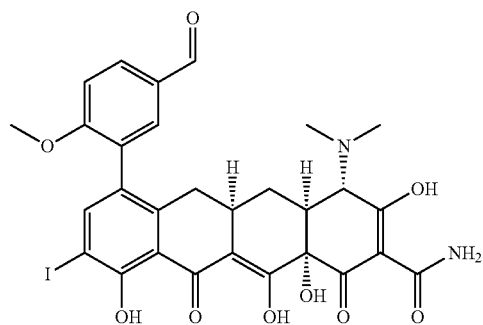
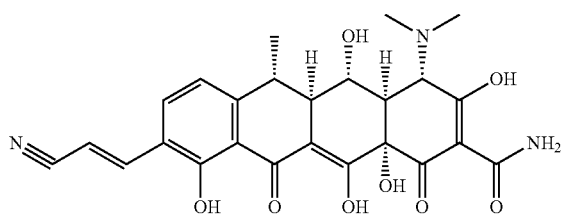
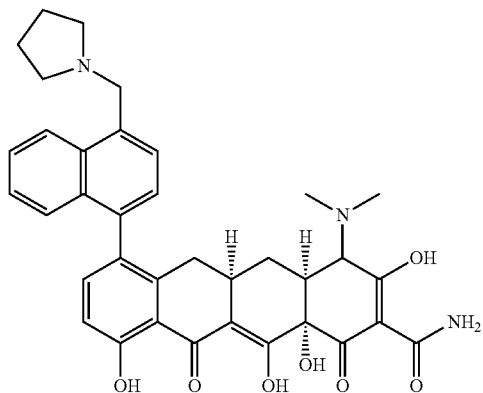

TABLE 1-continued
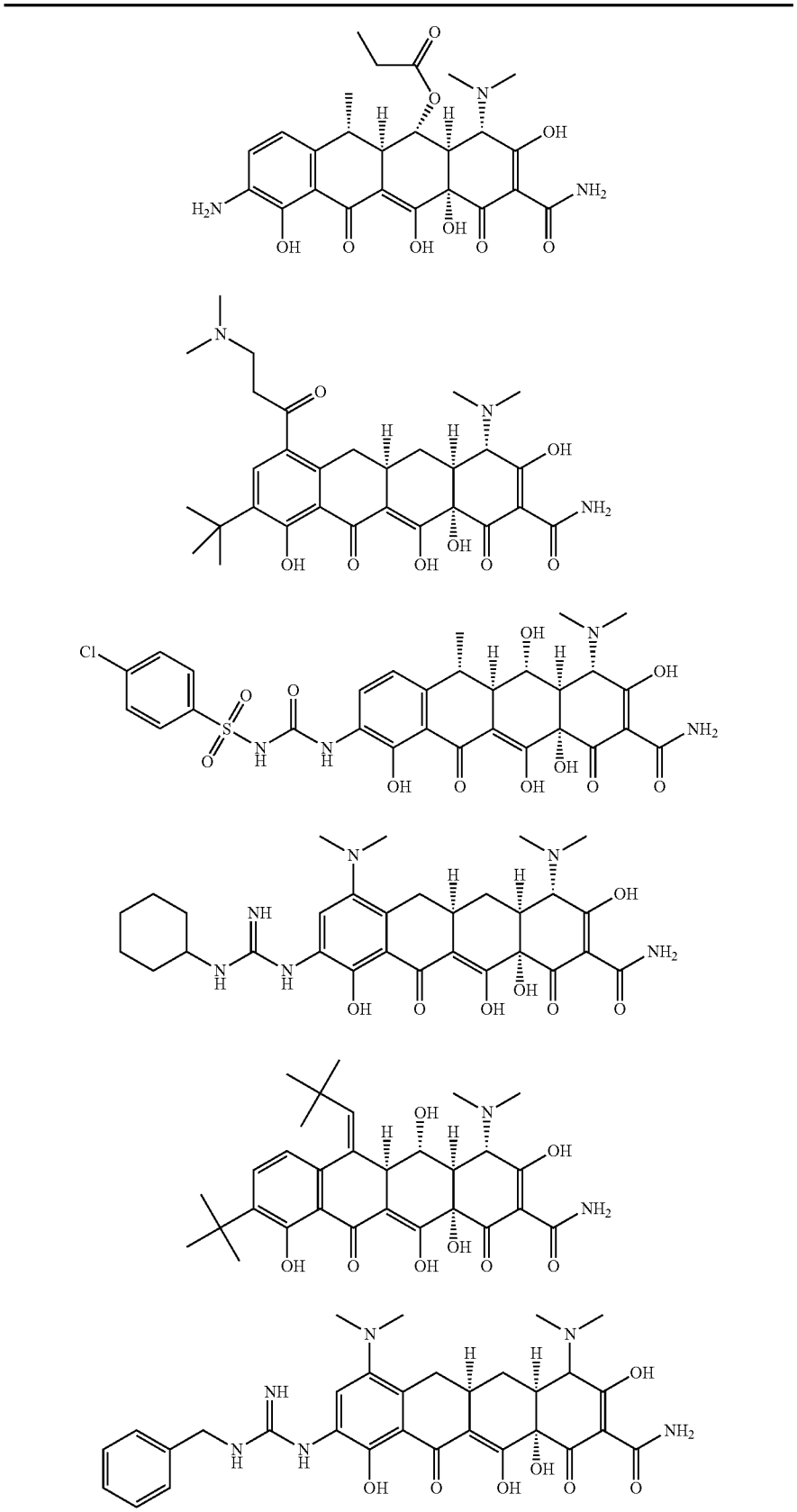

TABLE 1-continued
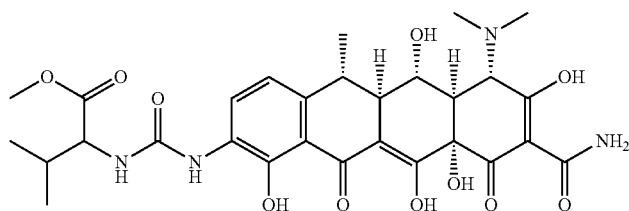
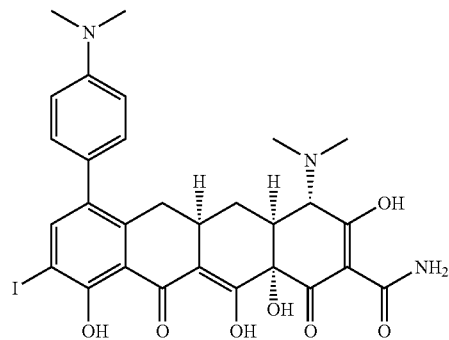
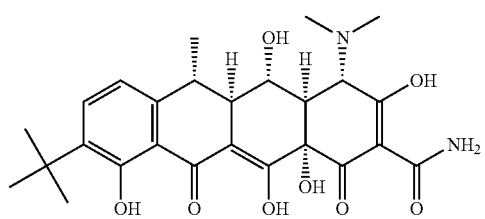
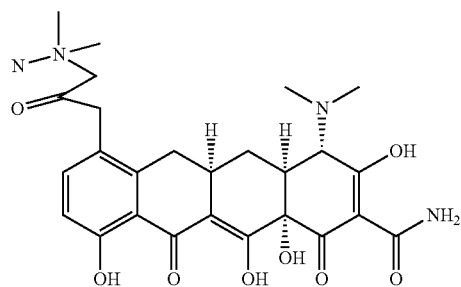
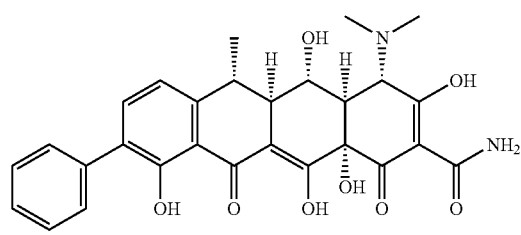

TABLE 1-continued
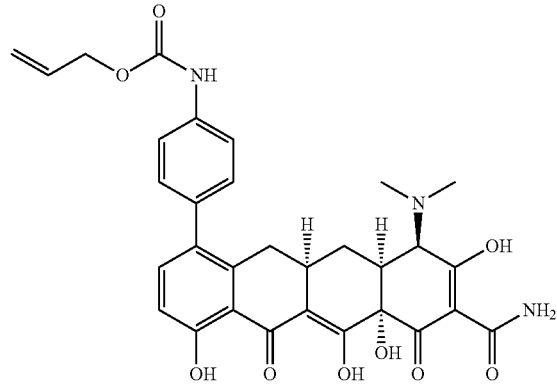
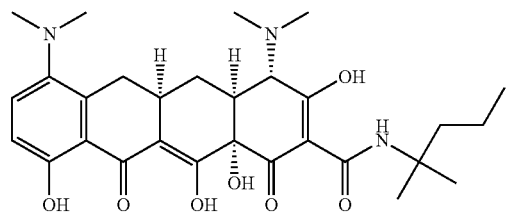
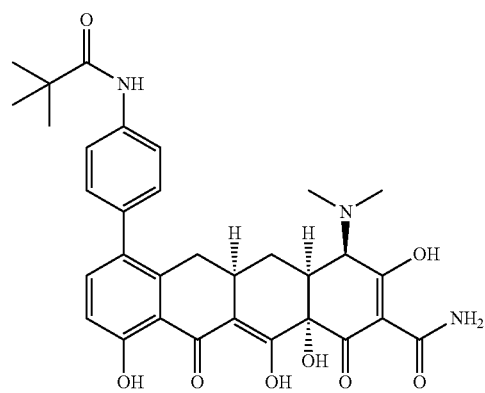
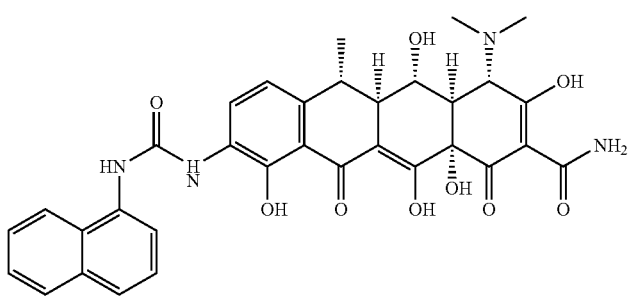
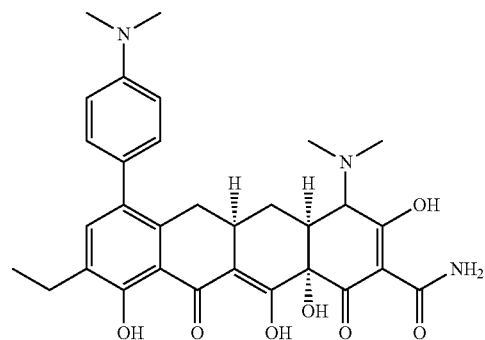

TABLE 1-continued
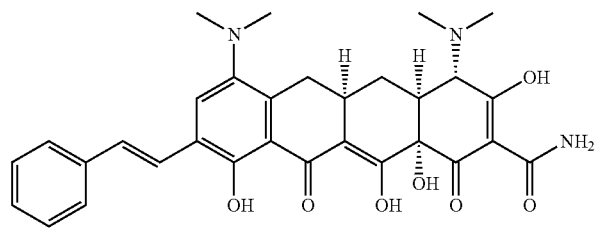
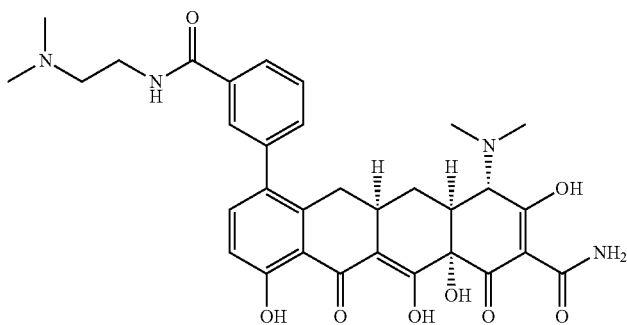
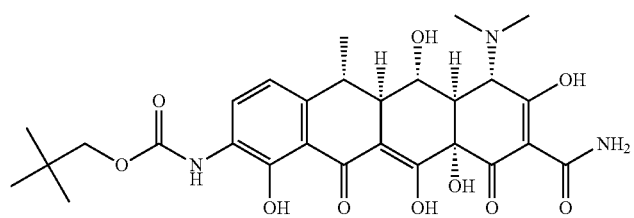
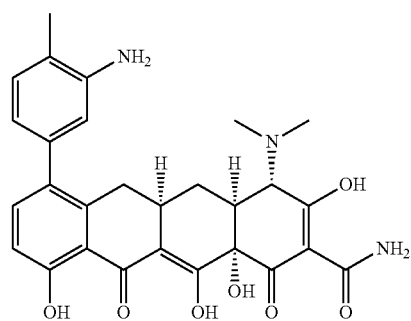
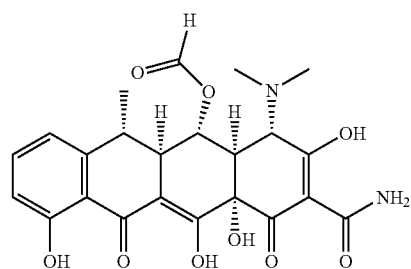

TABLE 1-continued
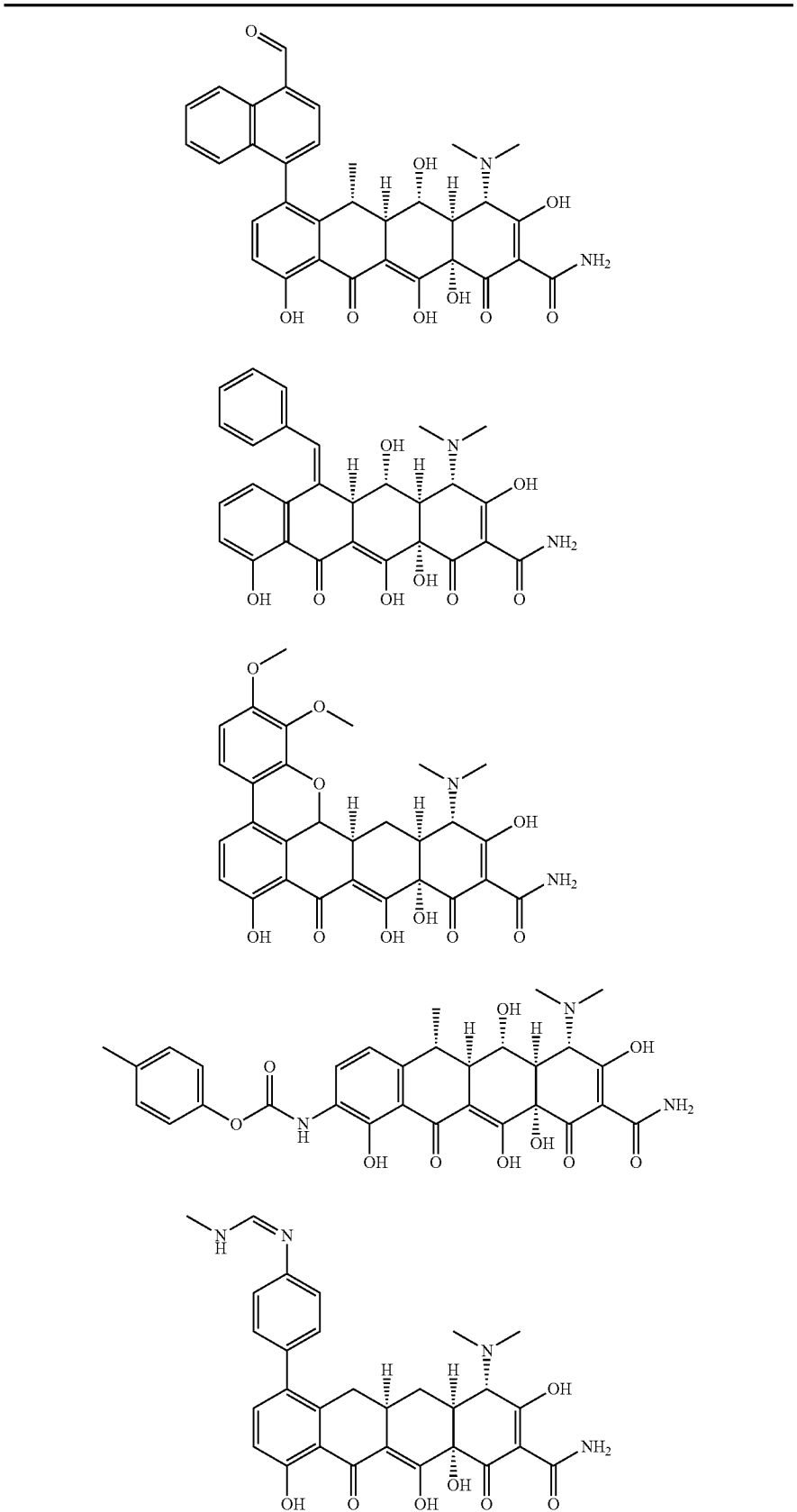

TABLE 1-continued
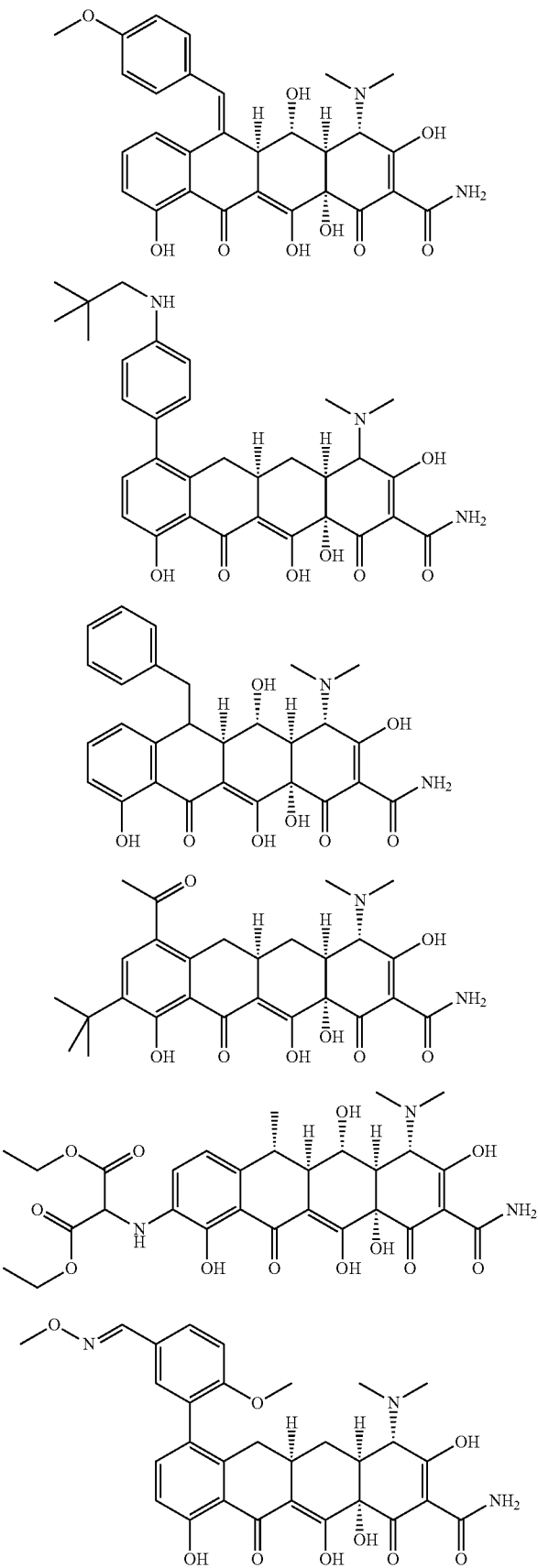

TABLE 1-continued
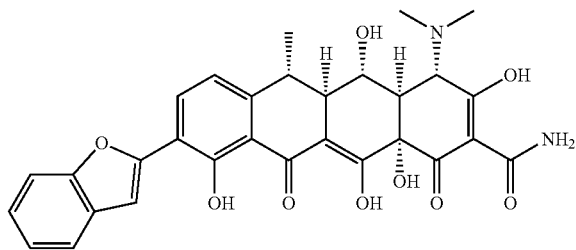
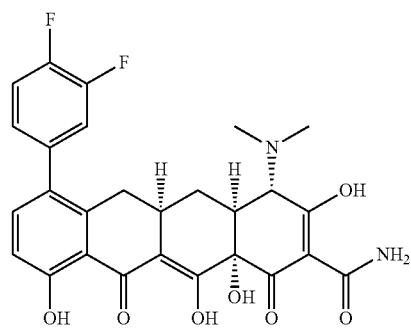
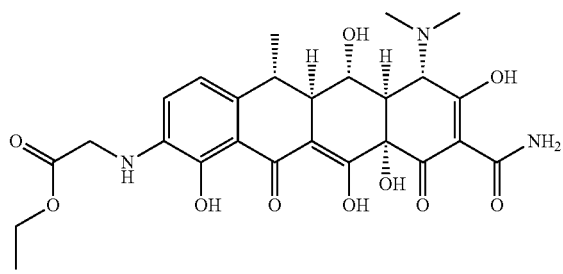
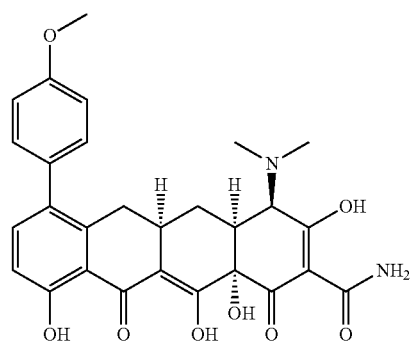
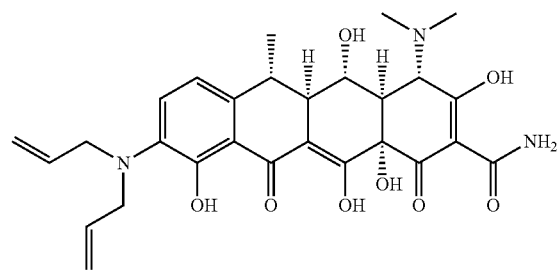

TABLE 1-continued
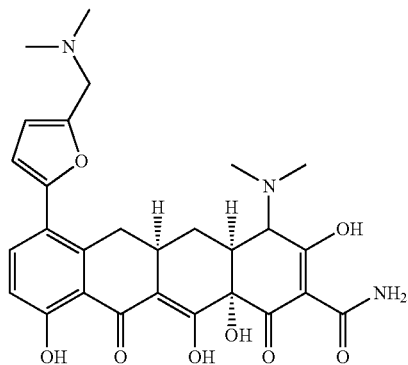
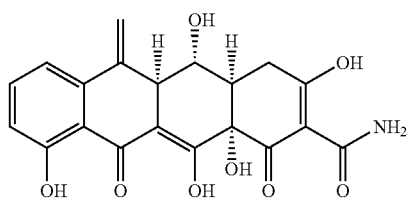
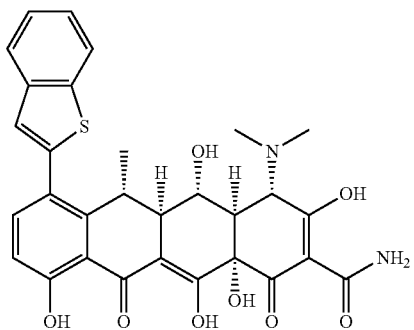
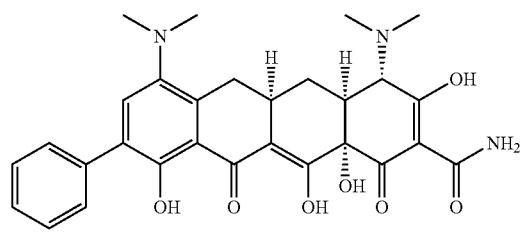
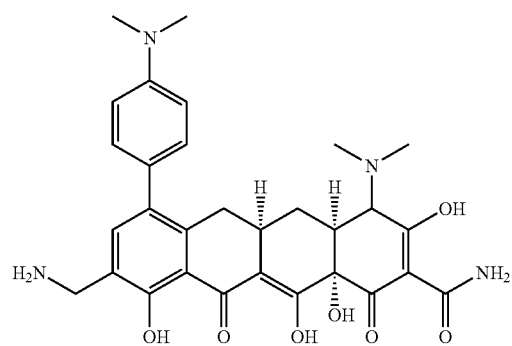

TABLE 1-continued
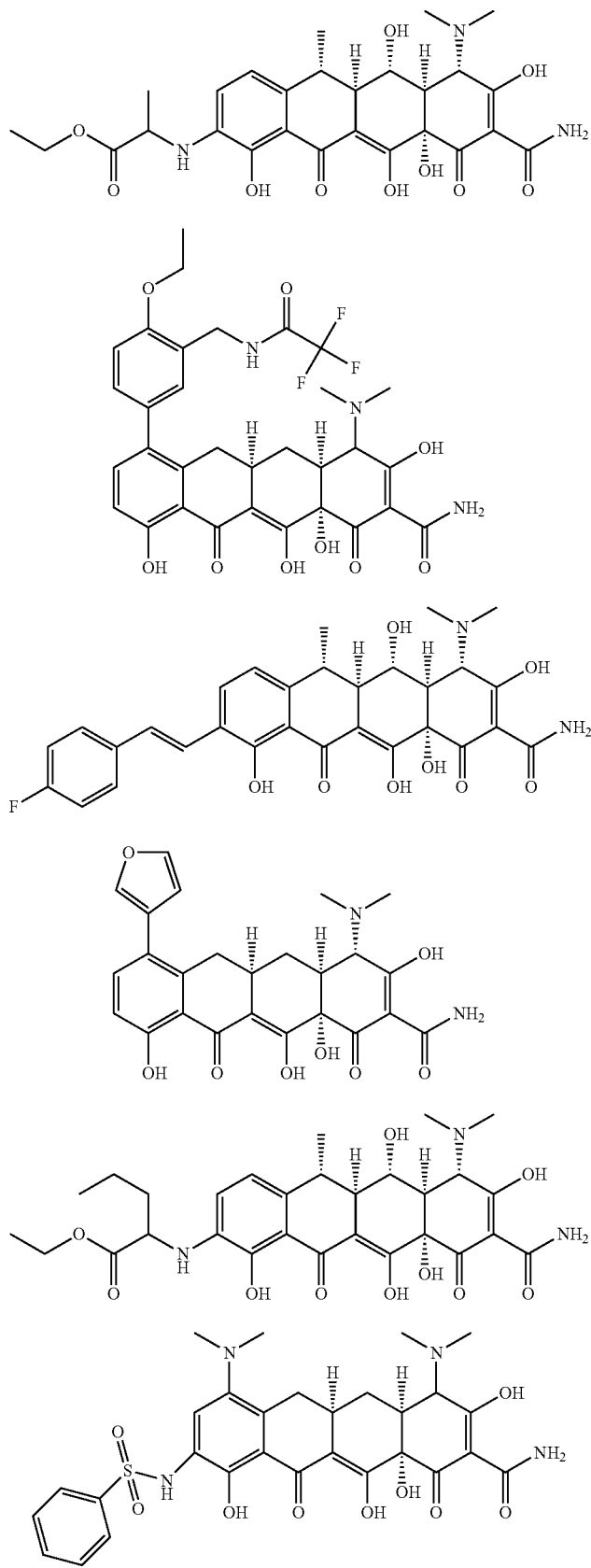

TABLE 1-continued
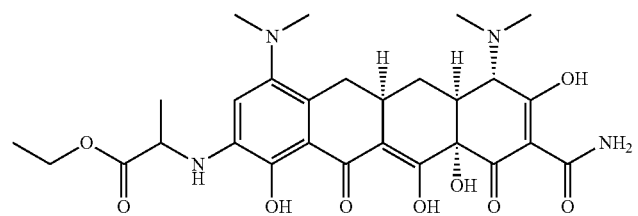
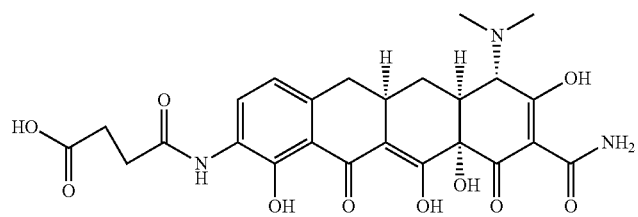
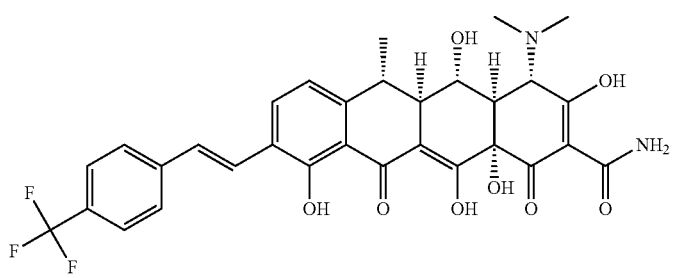
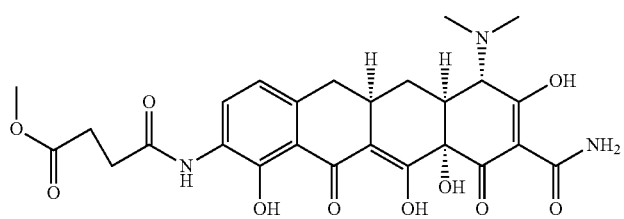
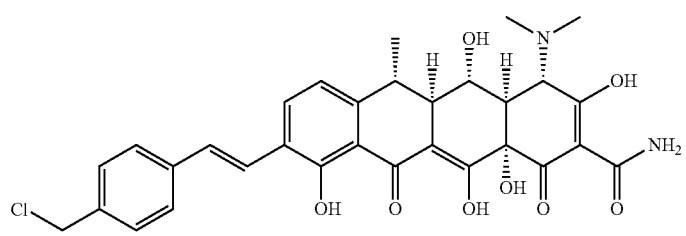
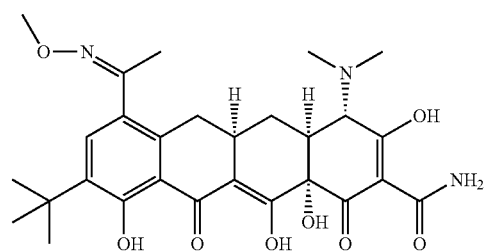

TABLE 1-continued
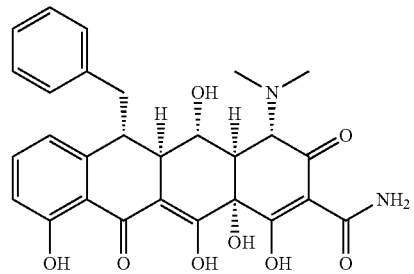
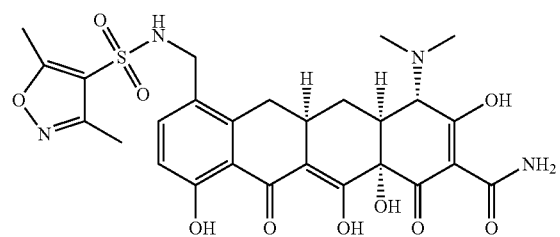
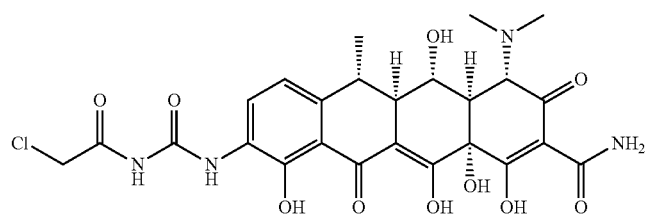
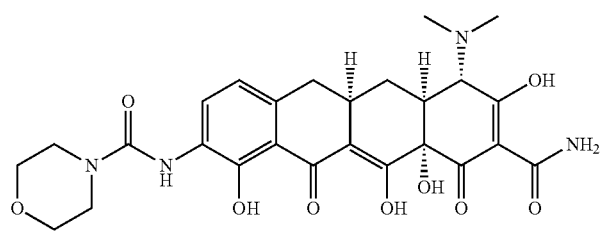
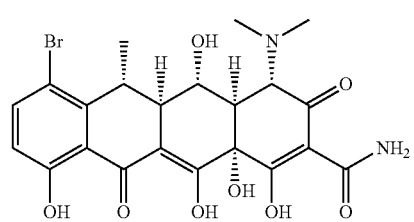
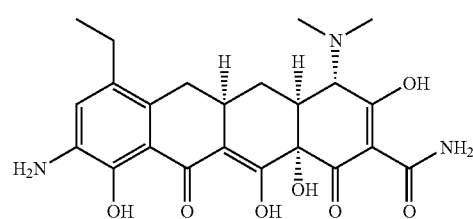

TABLE 1-continued
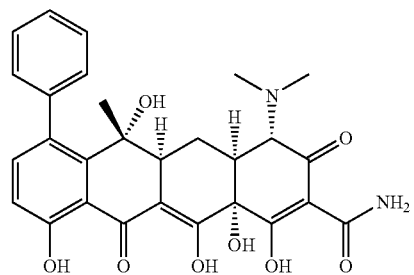
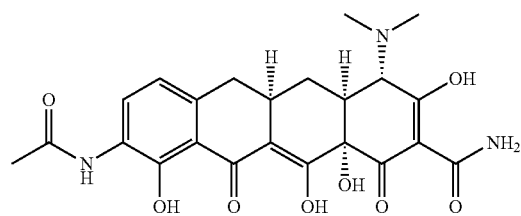
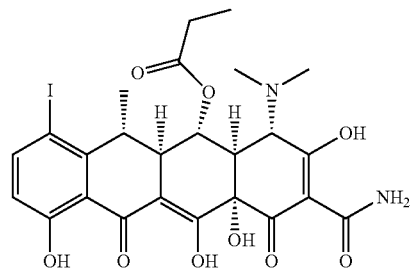
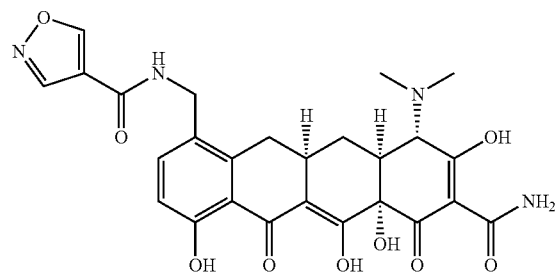
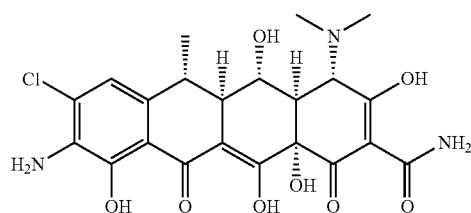
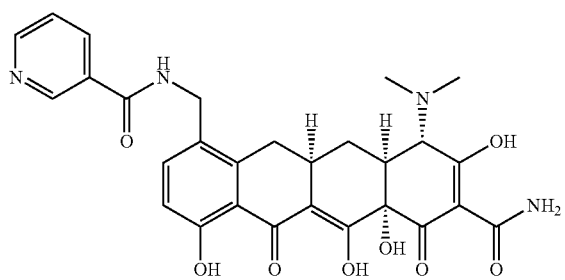

TABLE 1-continued
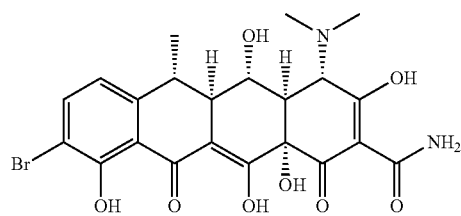
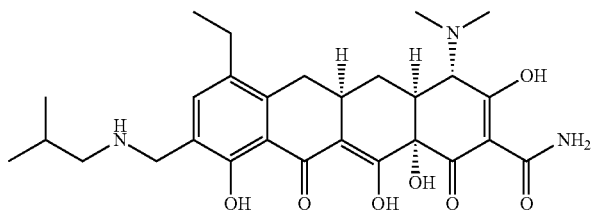
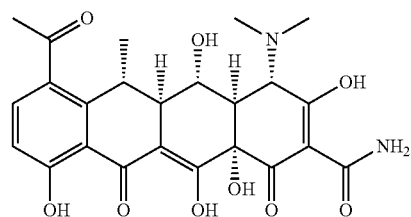
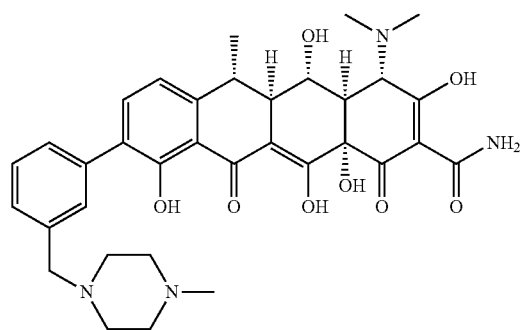
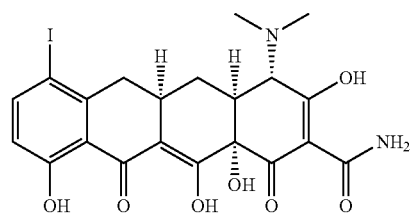
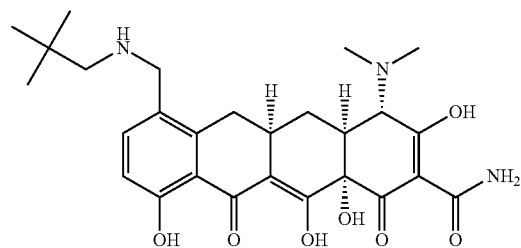

TABLE 1-continued
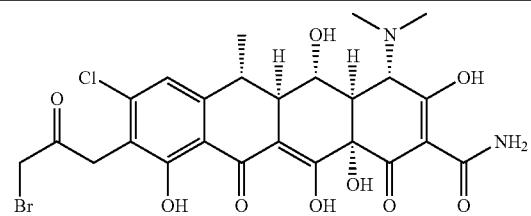
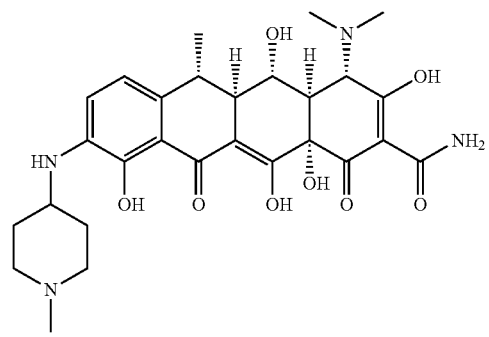
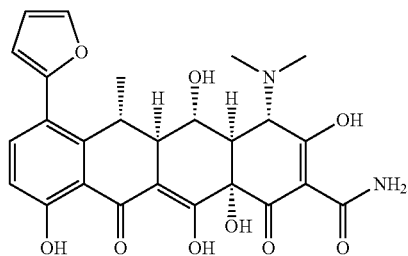
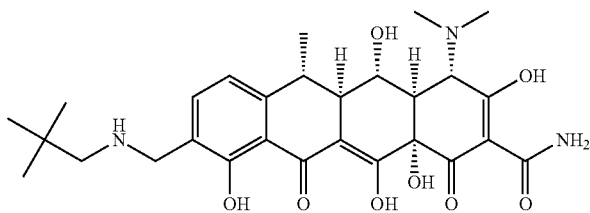
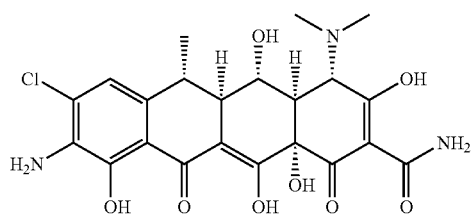
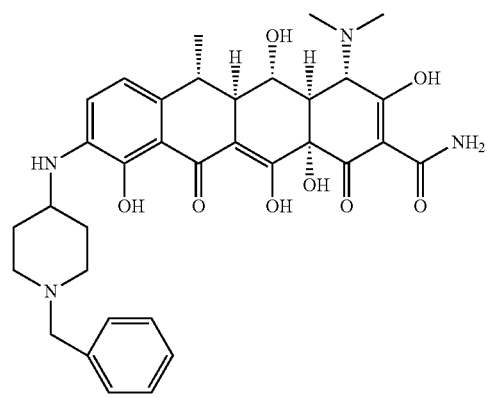

TABLE 1-continued
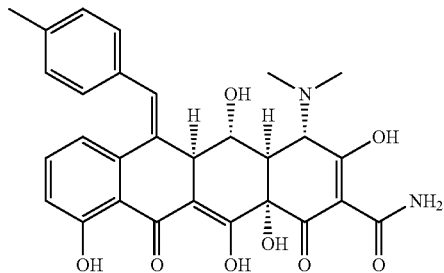
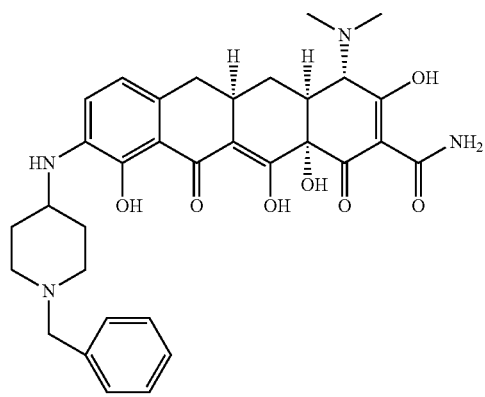
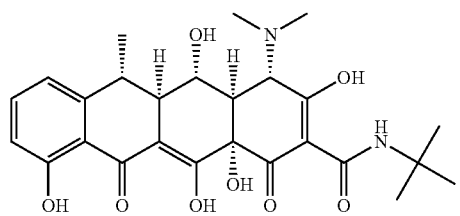
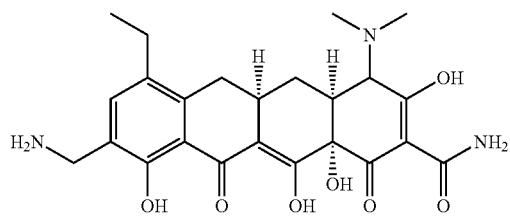
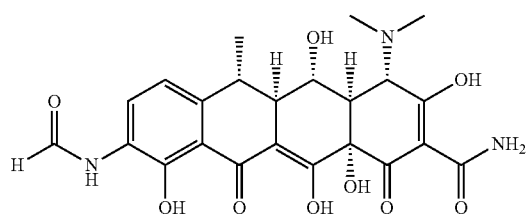
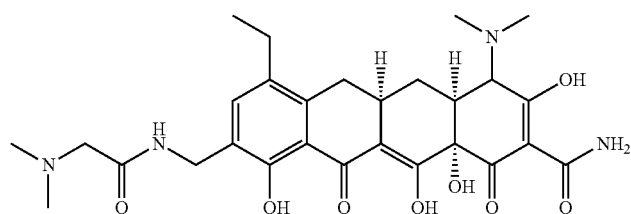

TABLE 1-continued
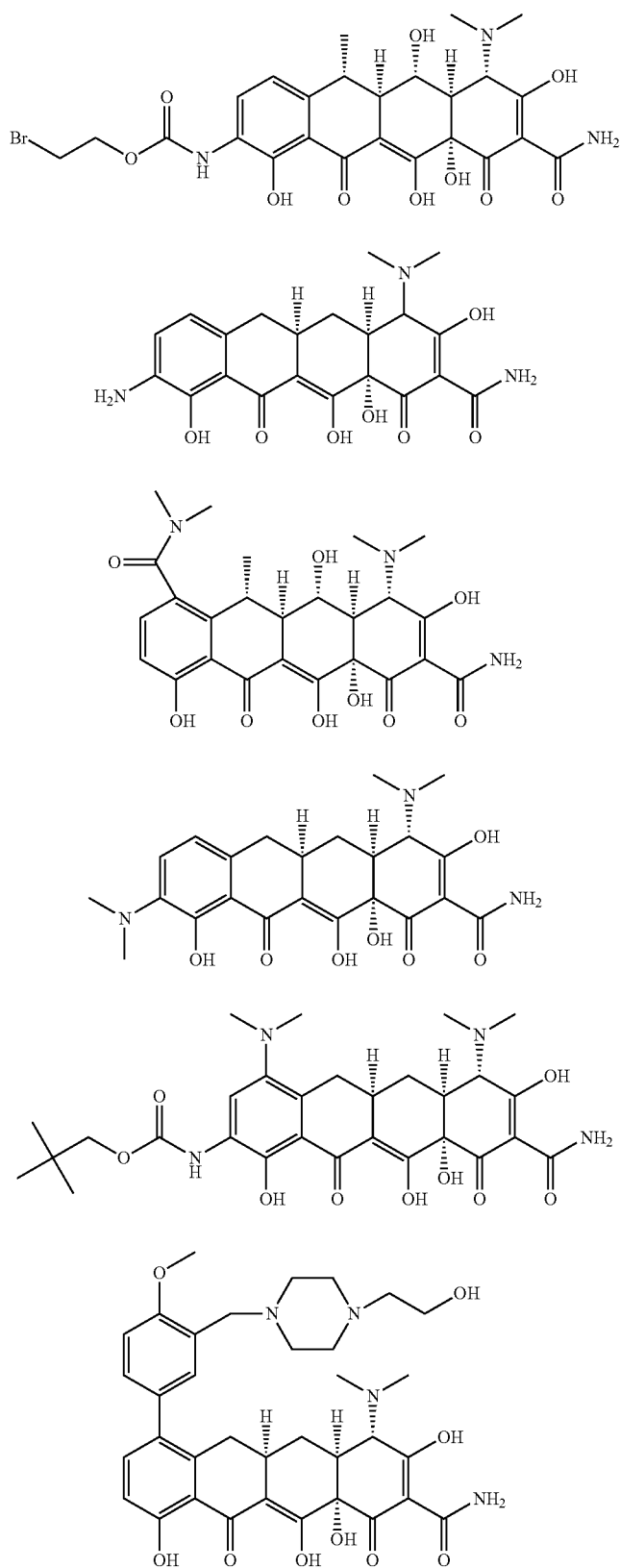

TABLE 1-continued
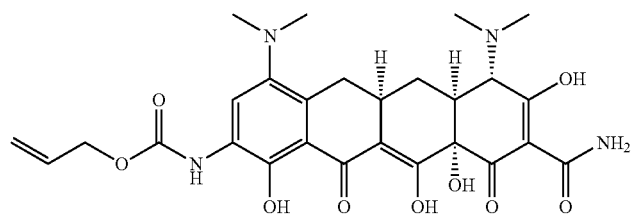
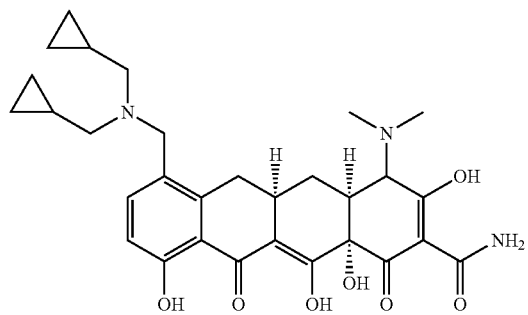
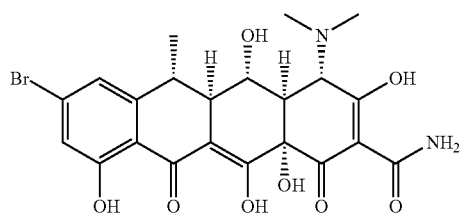
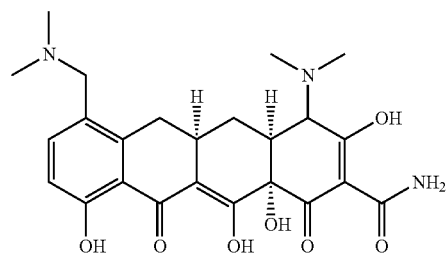
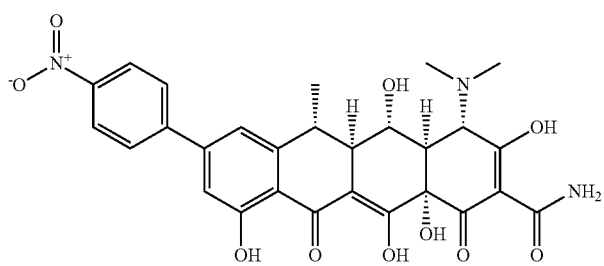
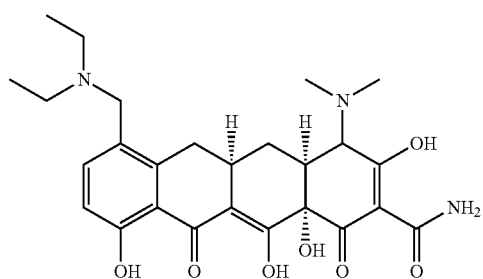

TABLE 1-continued
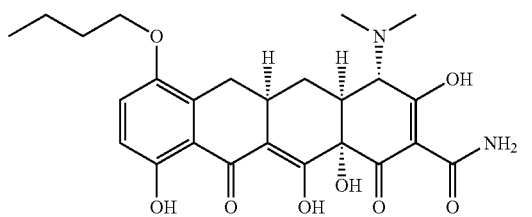
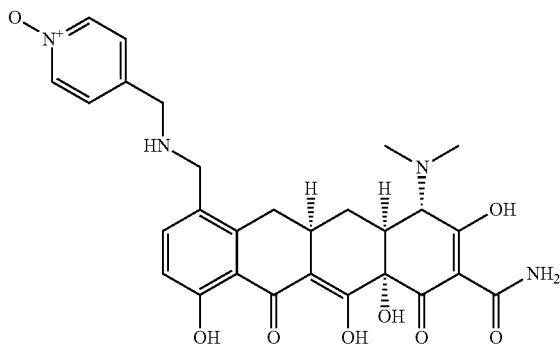
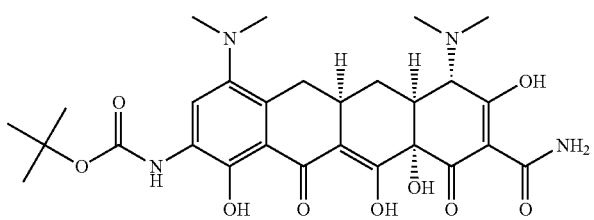
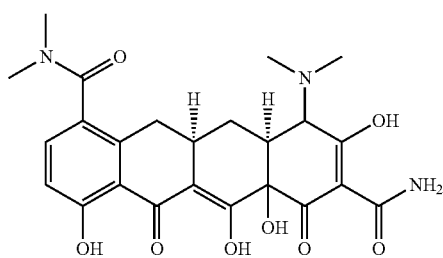
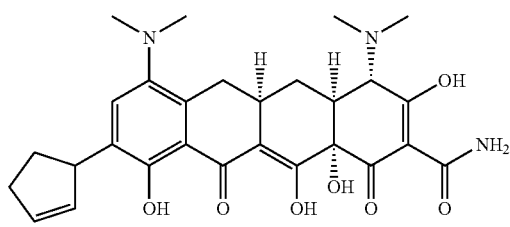
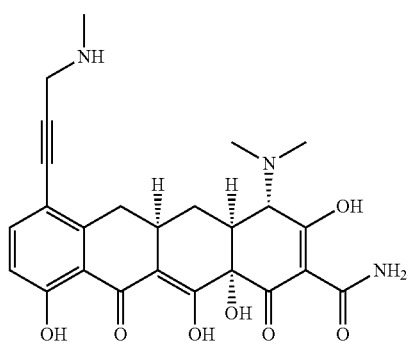

TABLE 1-continued
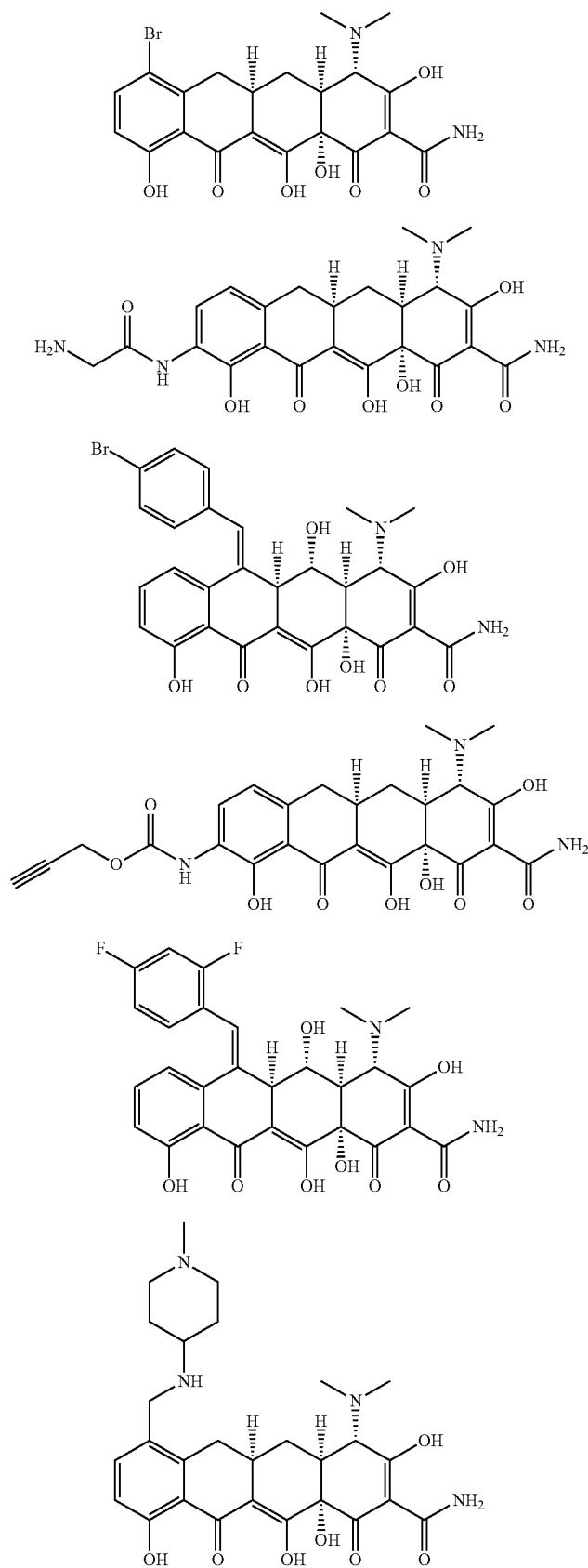

TABLE 1-continued
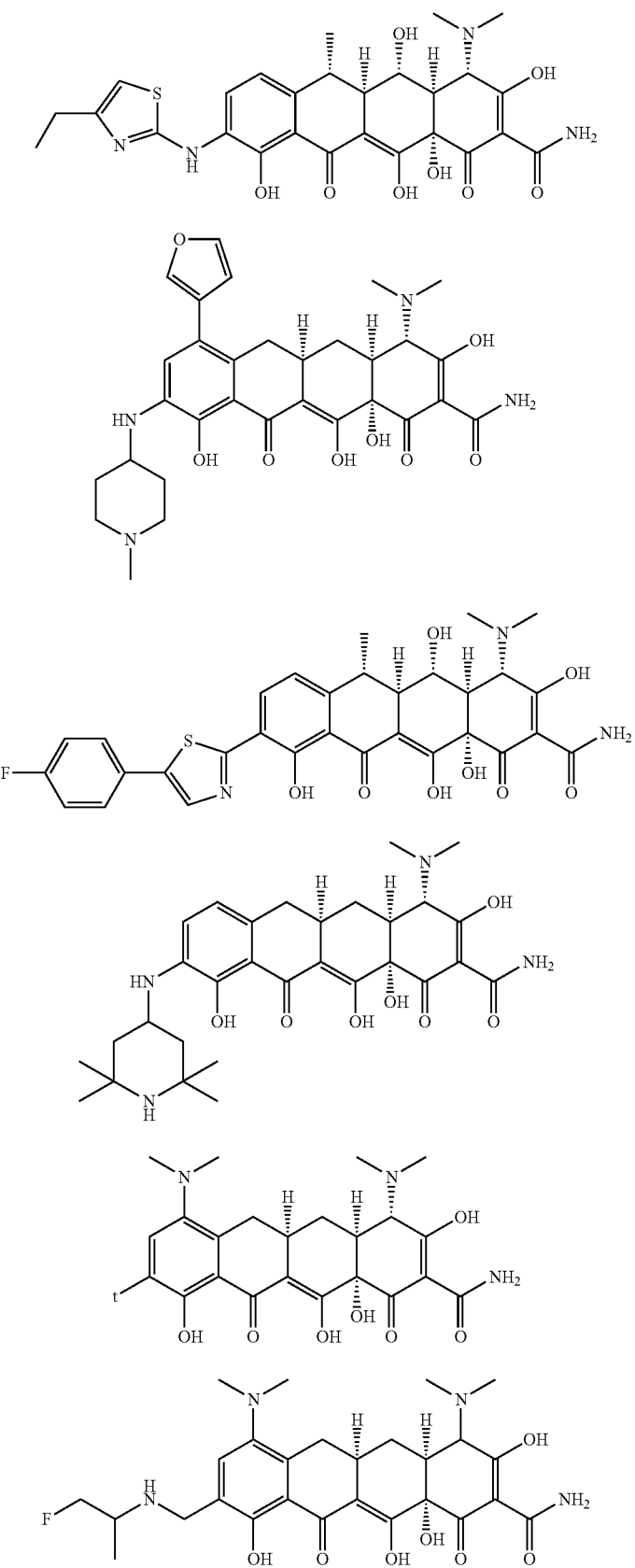

TABLE 1-continued
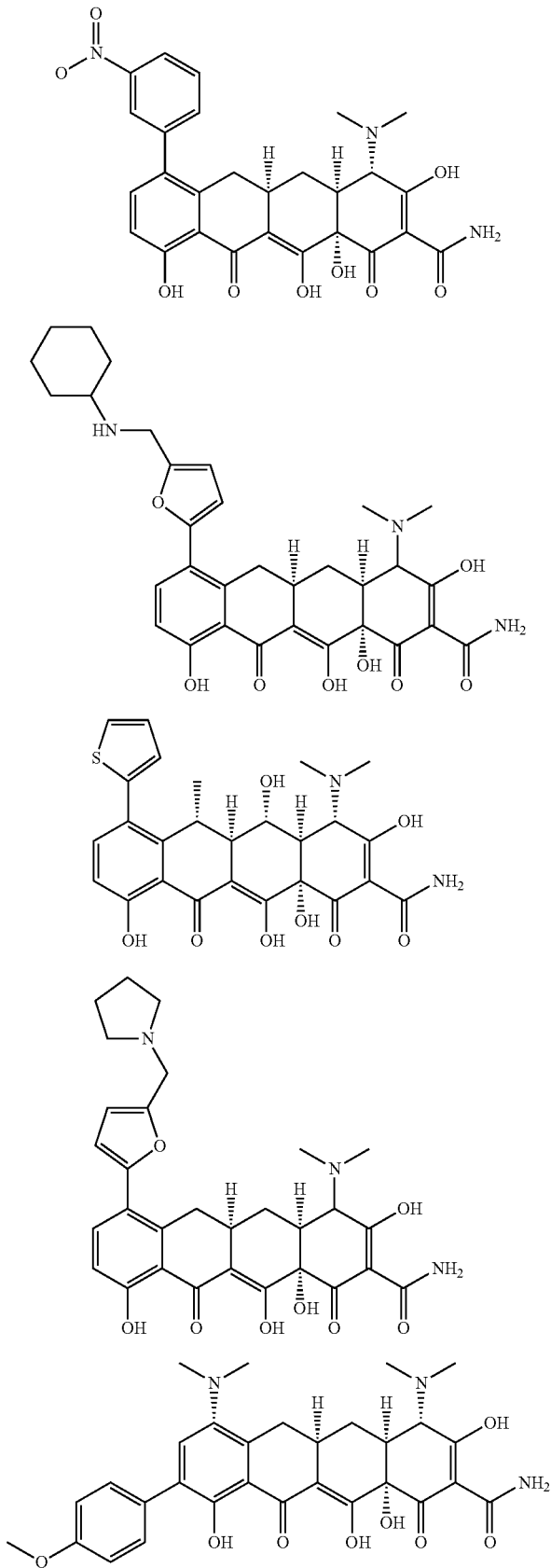

TABLE 1-continued
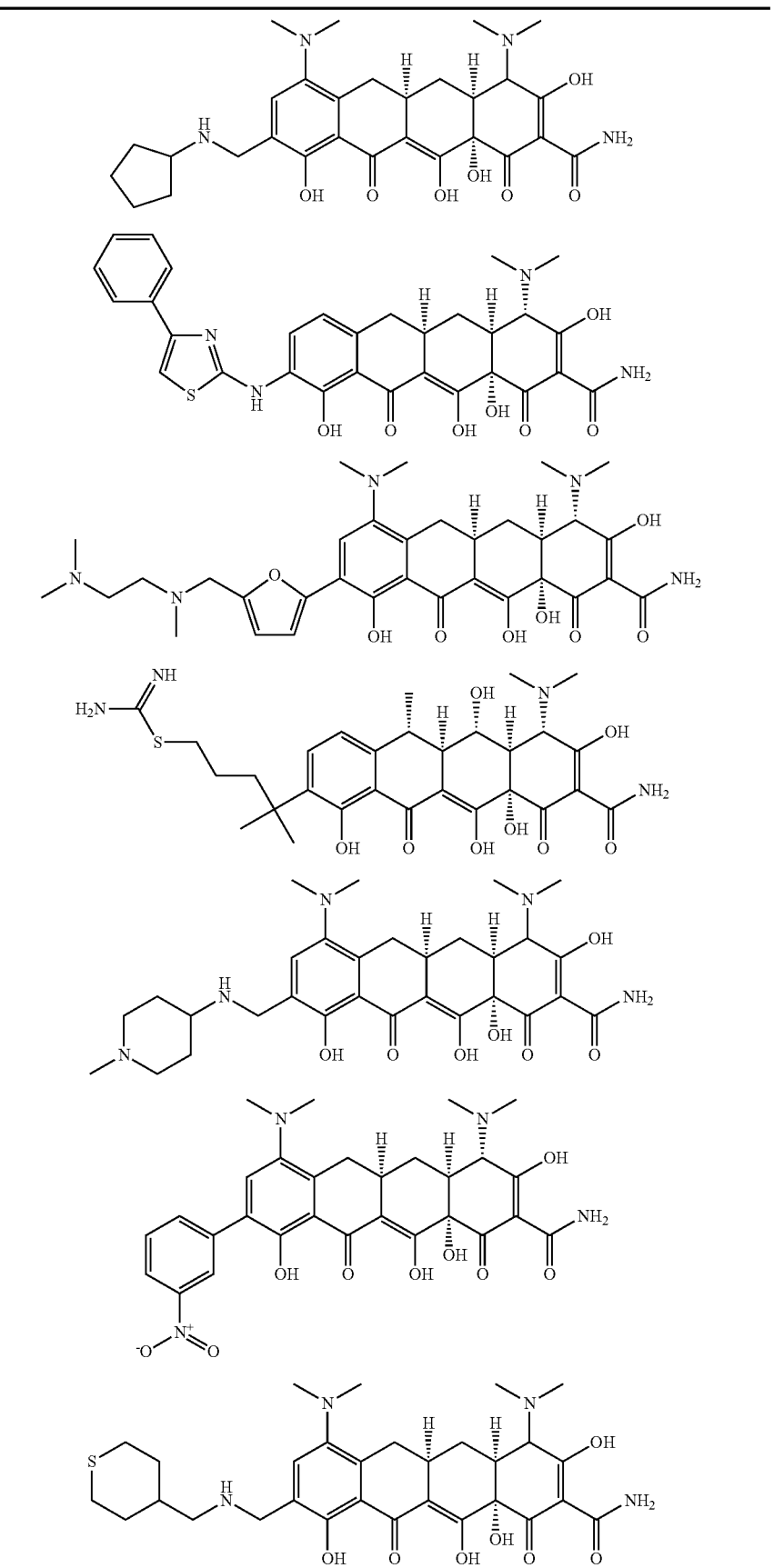

TABLE 1-continued
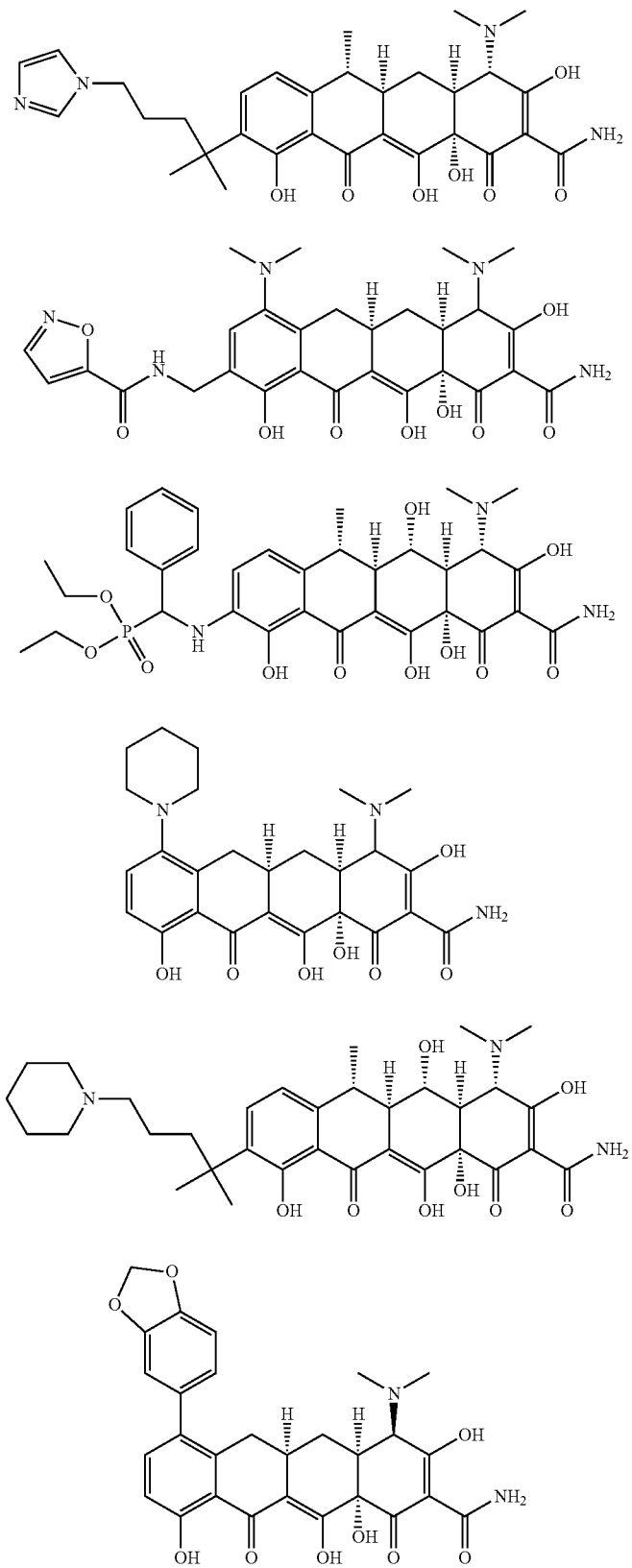

TABLE 1-continued
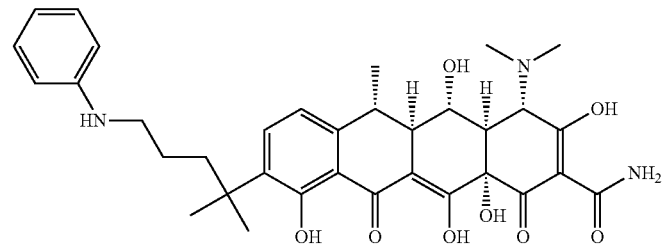
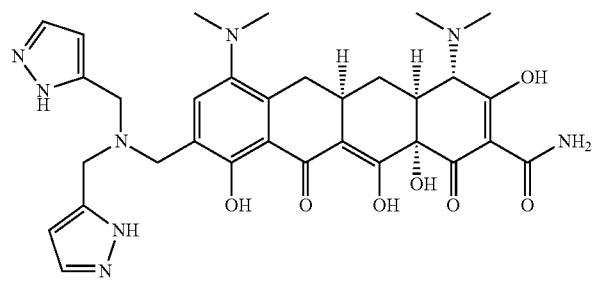
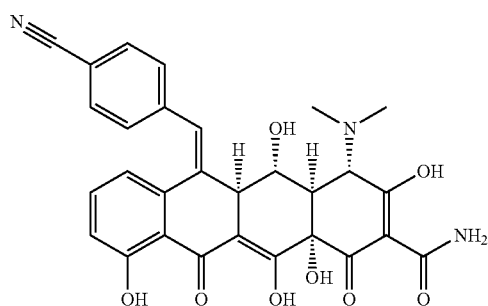
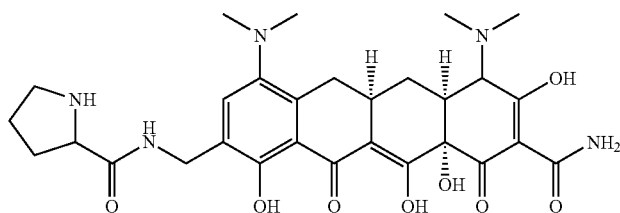
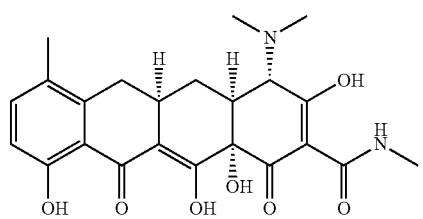
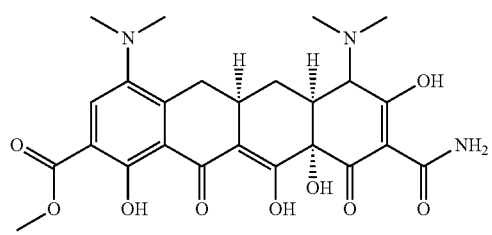

TABLE 1-continued
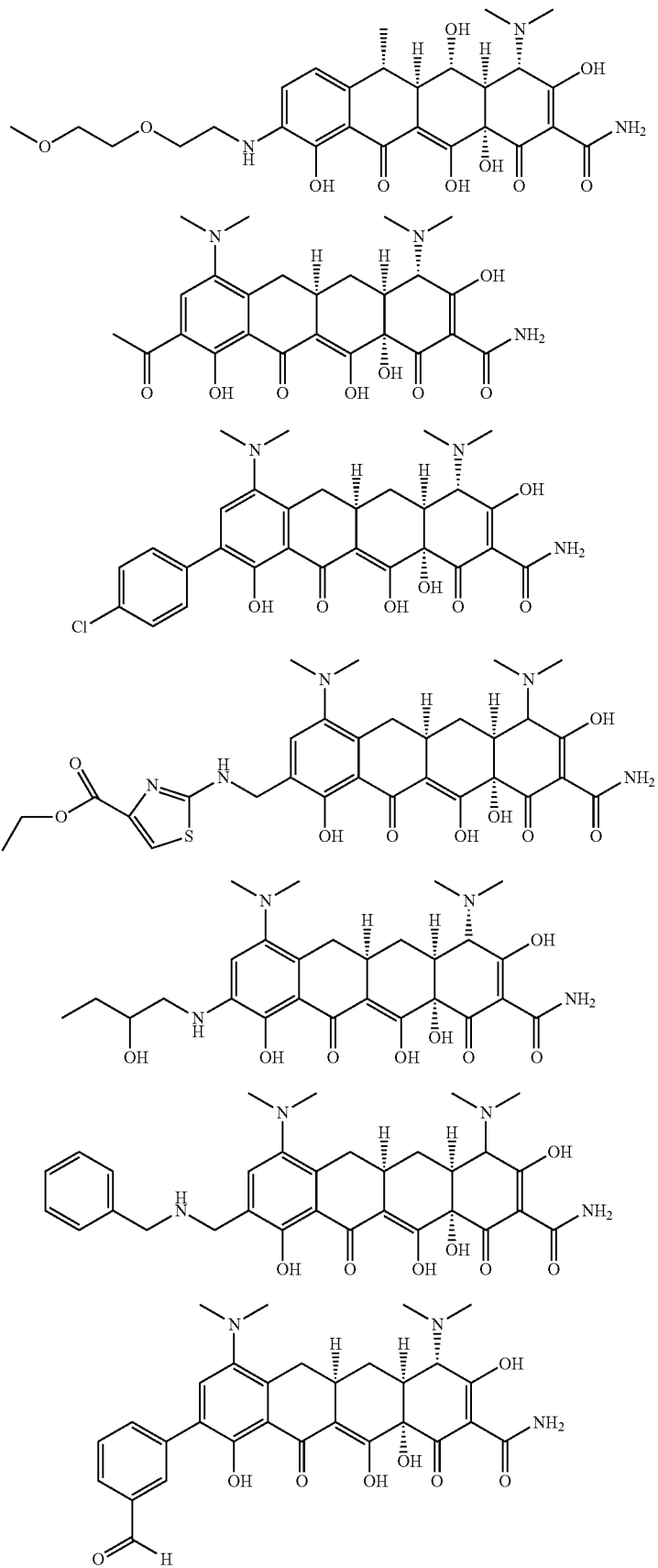

TABLE 1-continued
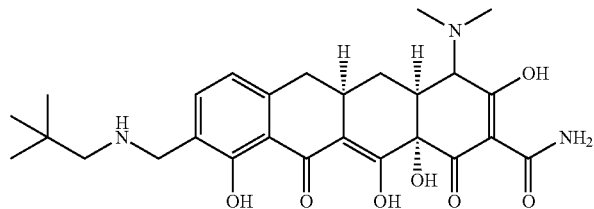
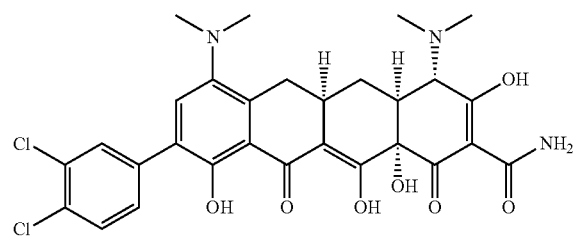
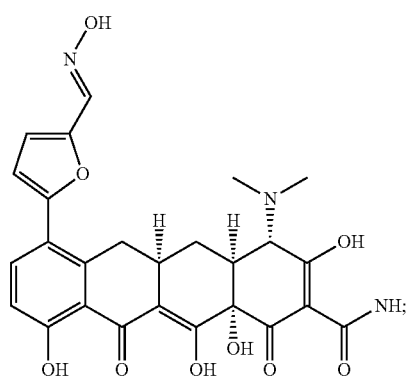
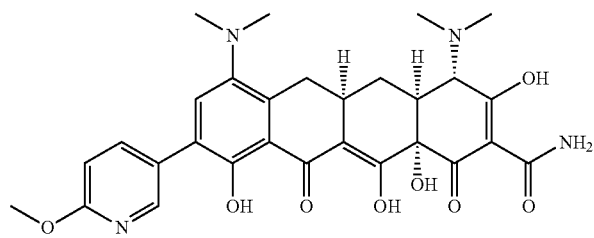
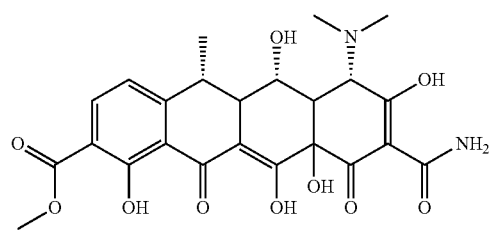
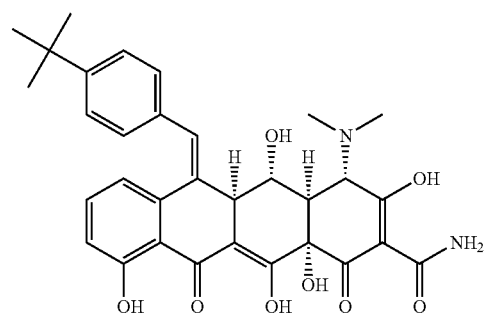

TABLE 1-continued
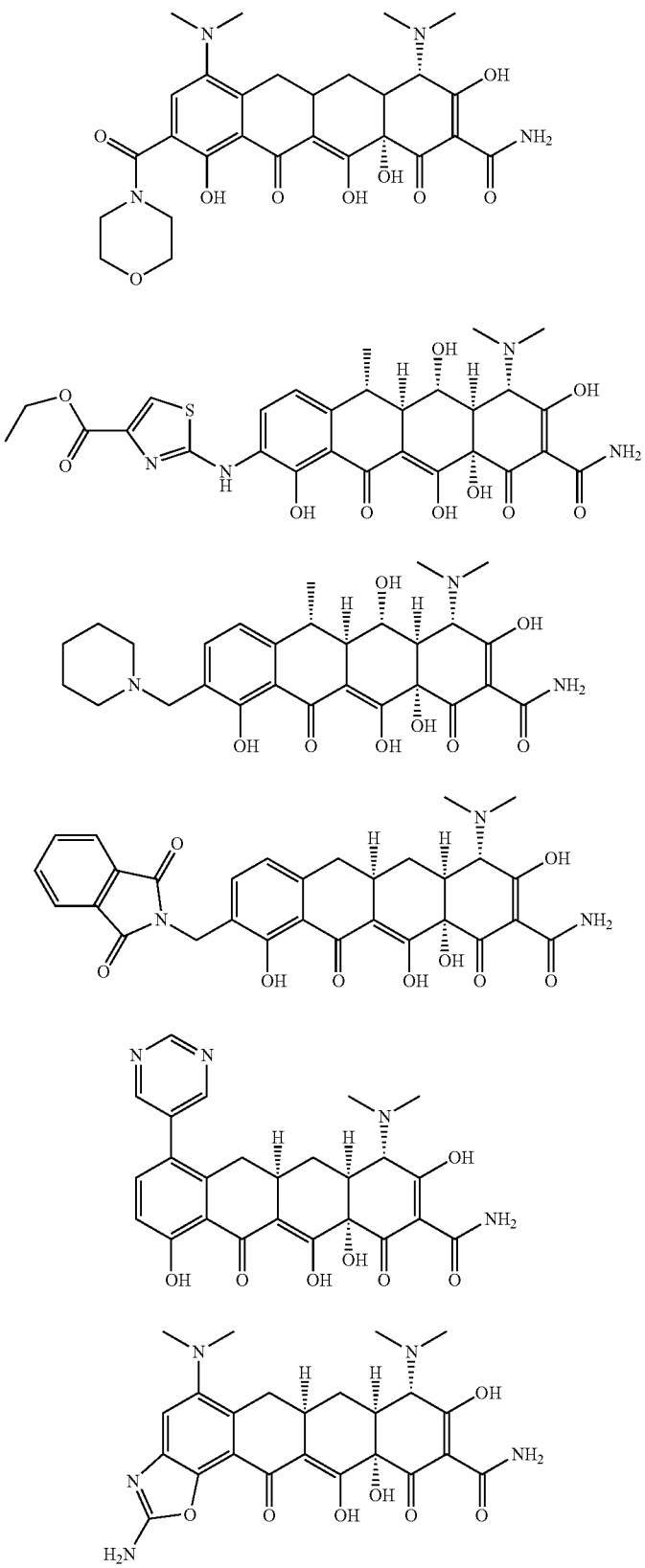

TABLE 1-continued
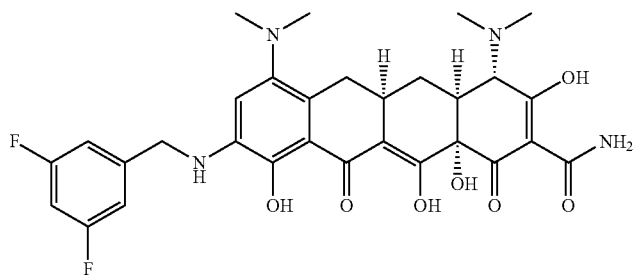
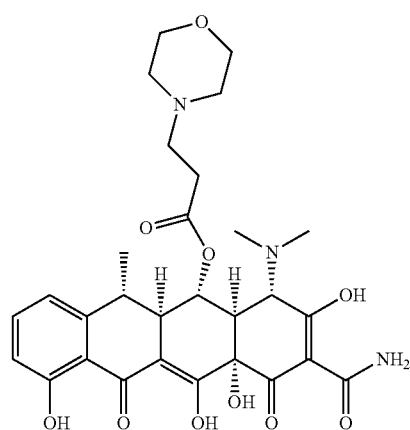
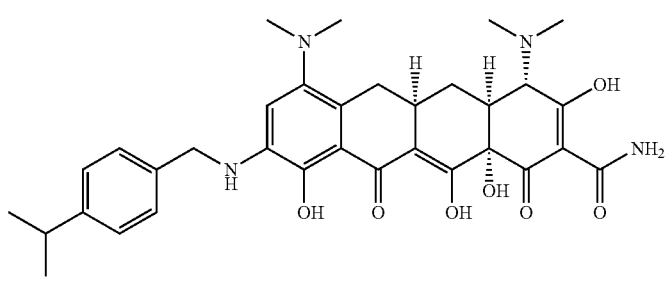
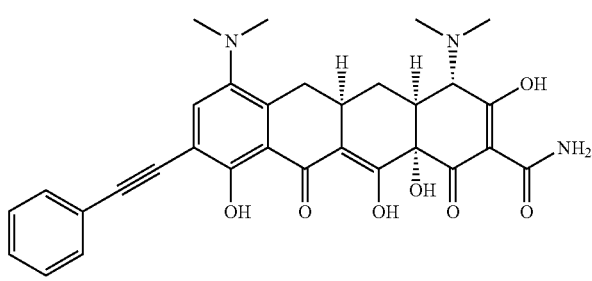

TABLE 1-continued
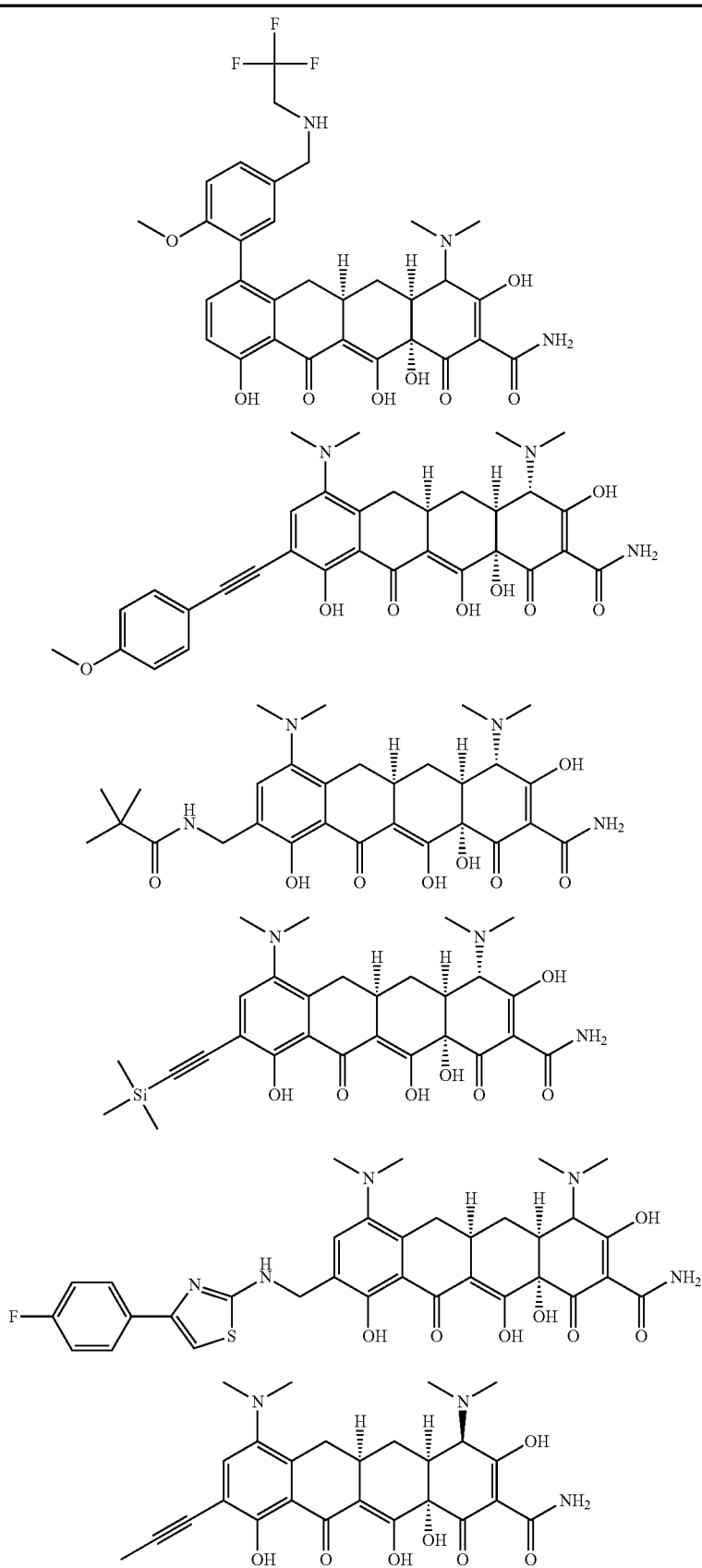

TABLE 1-continued
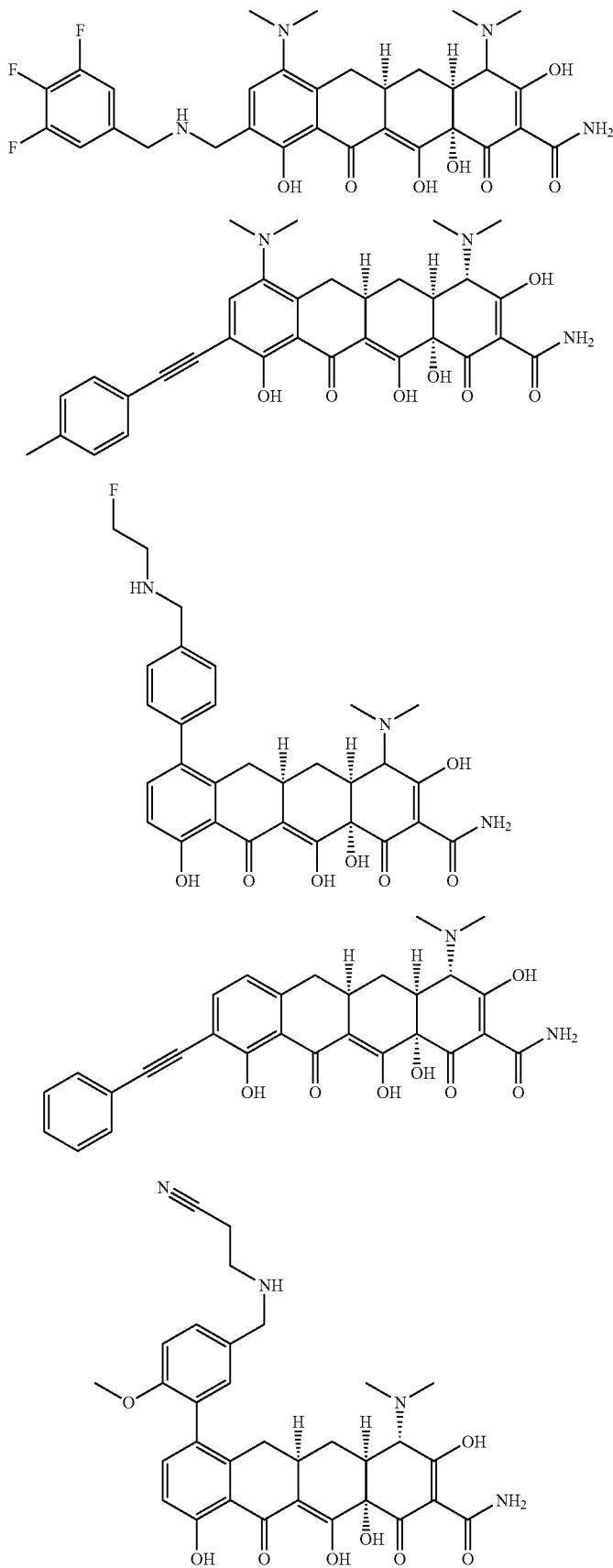

TABLE 1-continued
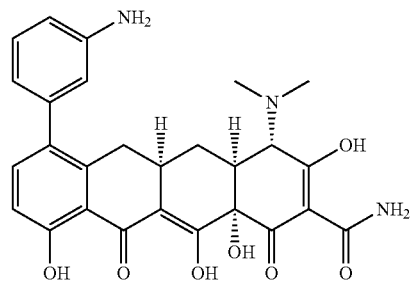
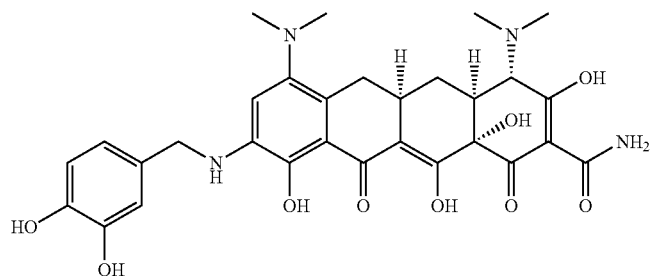
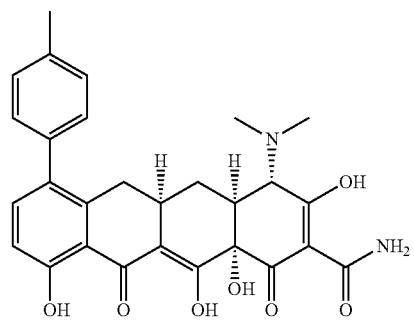
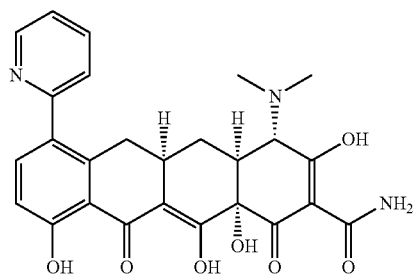
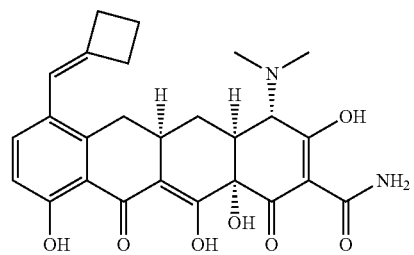

TABLE 1-continued
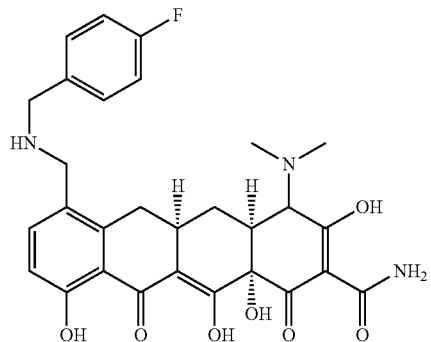
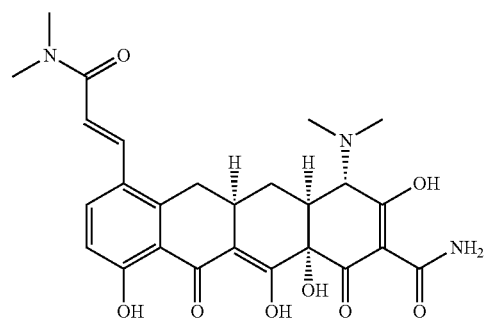
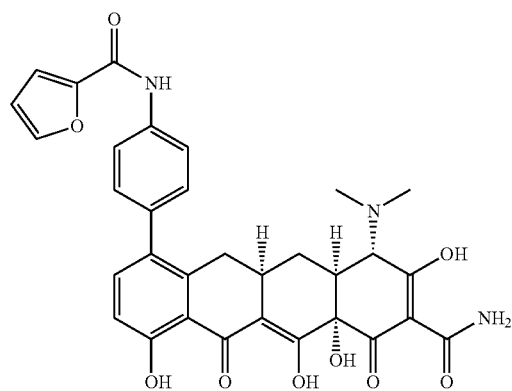
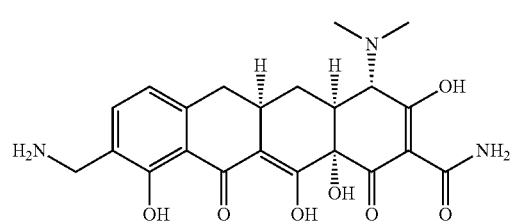

TABLE 1-continued
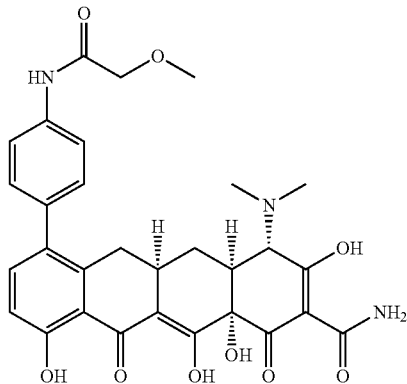
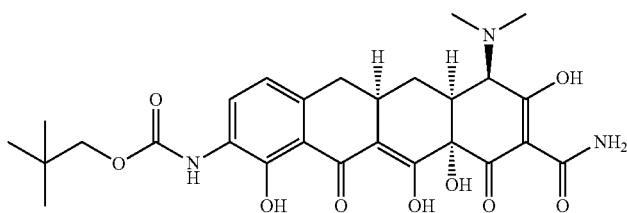
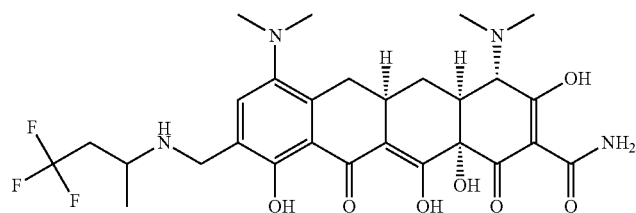
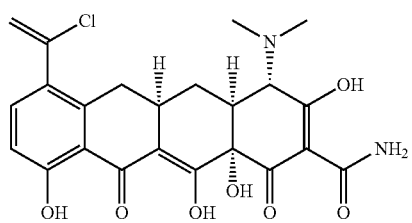
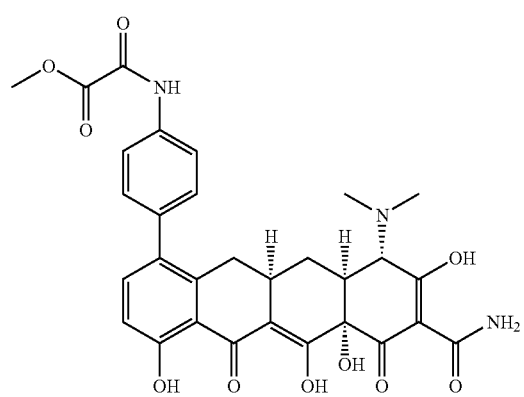

TABLE 1-continued
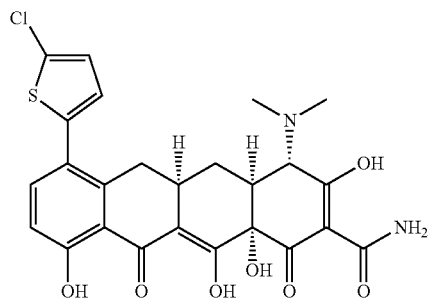
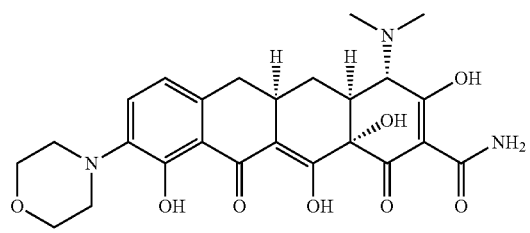
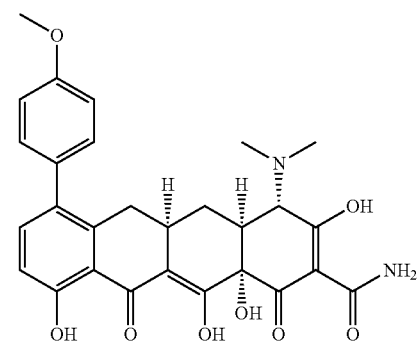
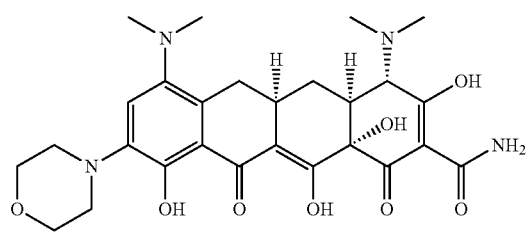
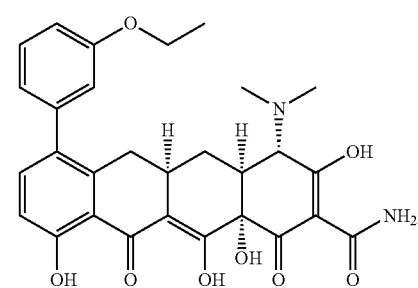

TABLE 1-continued
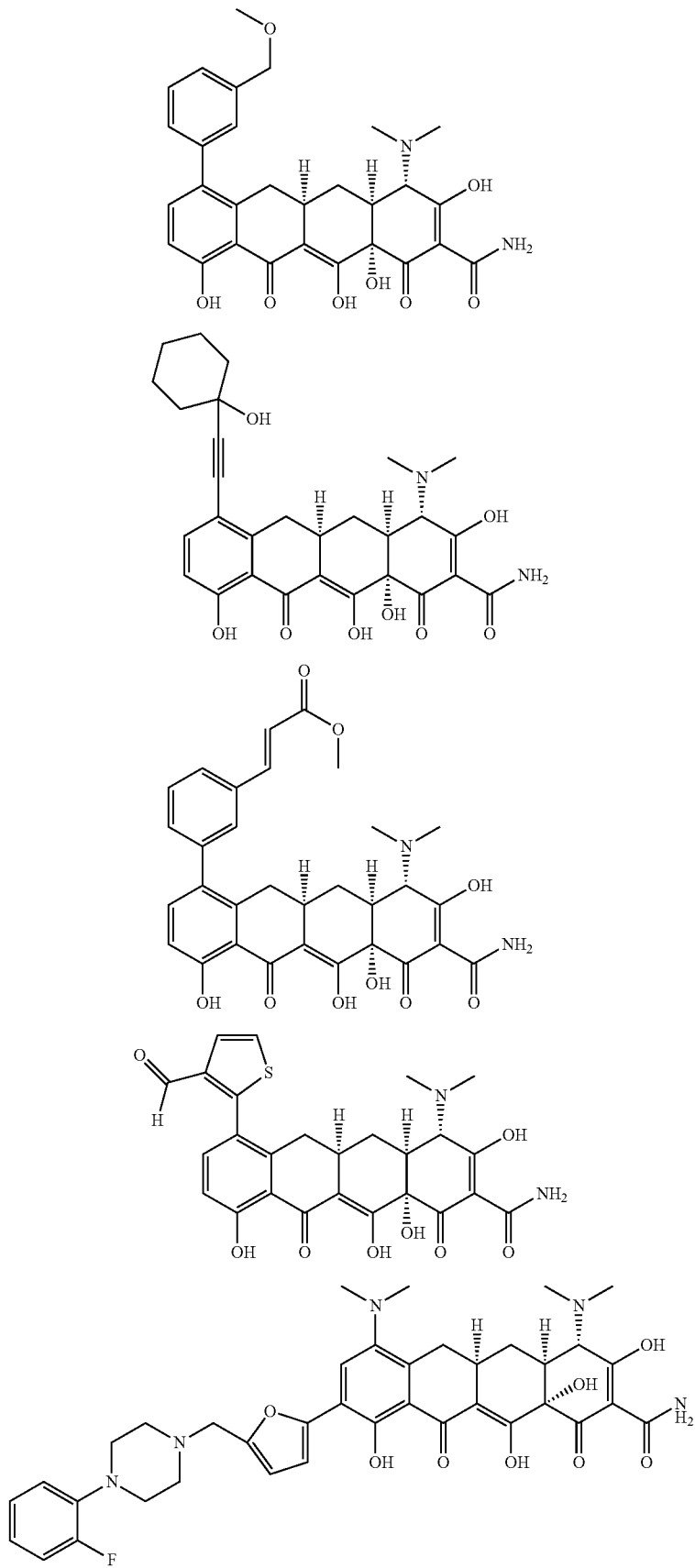

TABLE 1-continued
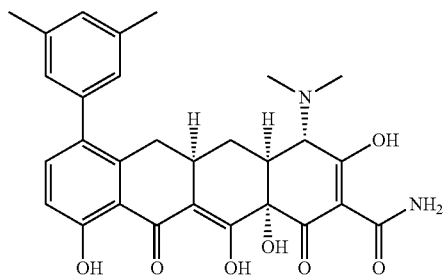
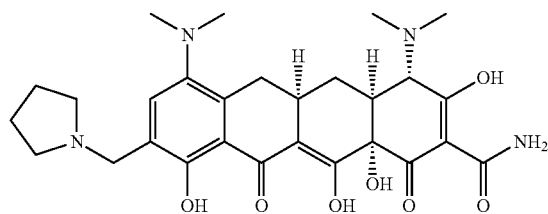
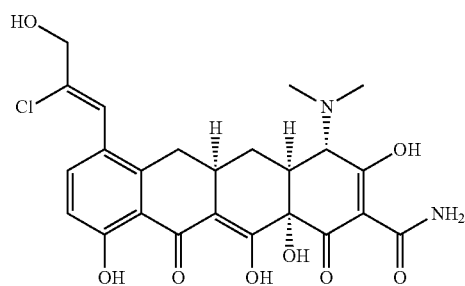
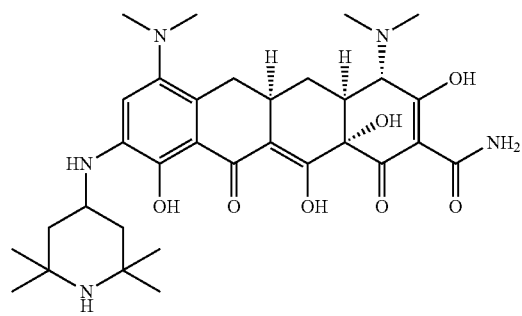
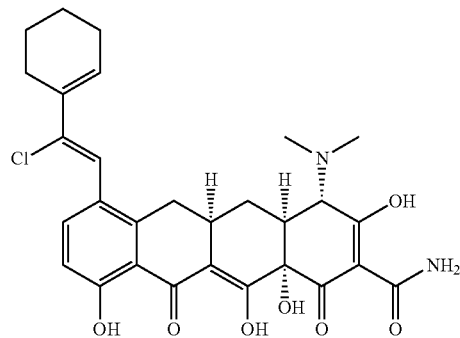

TABLE 1-continued
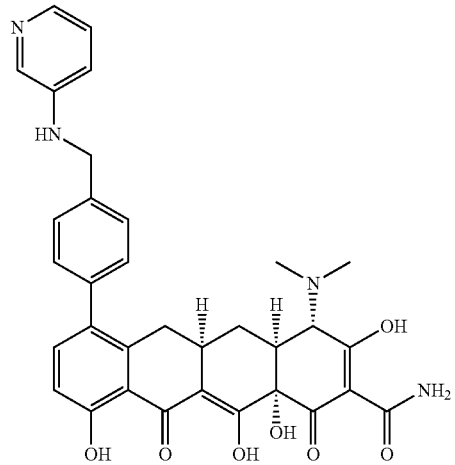
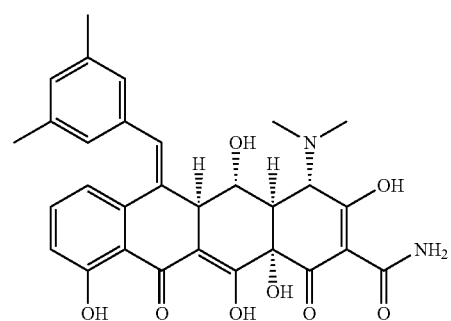
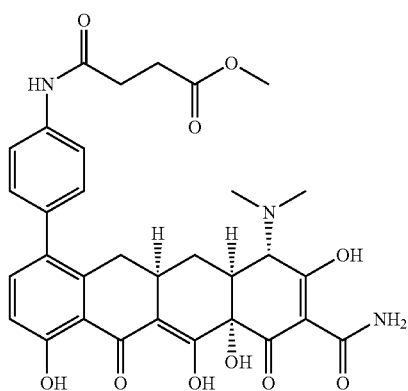
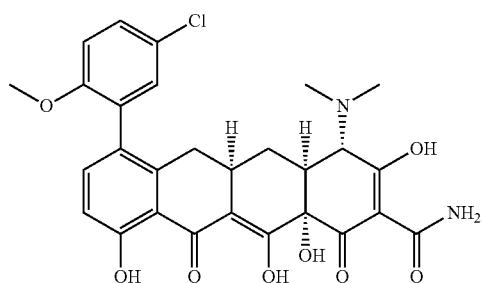

TABLE 1-continued
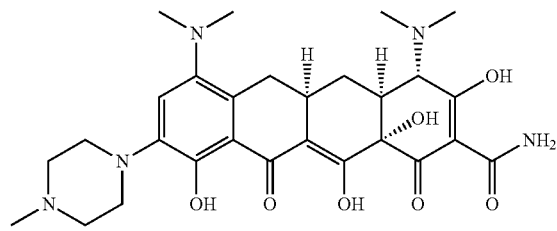
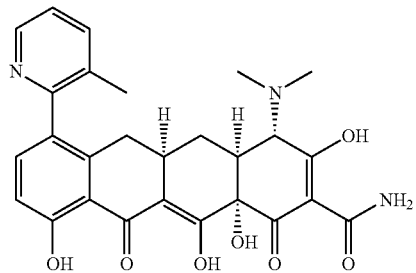
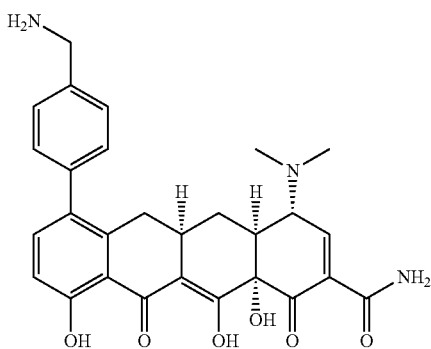
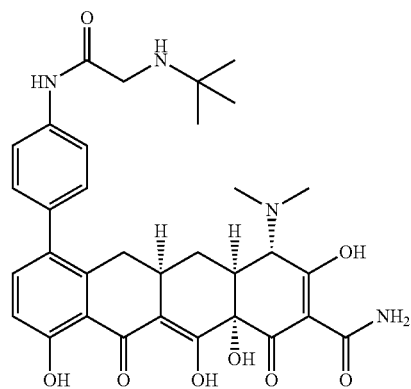
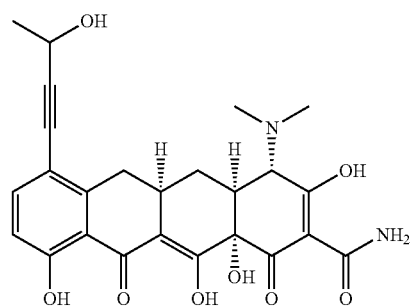

TABLE 1-continued
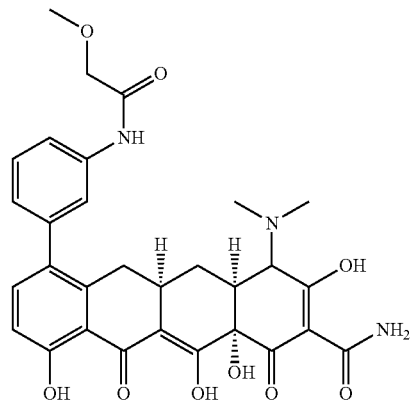
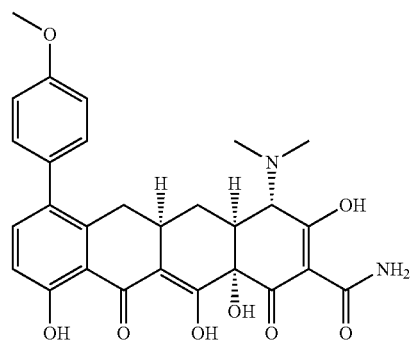
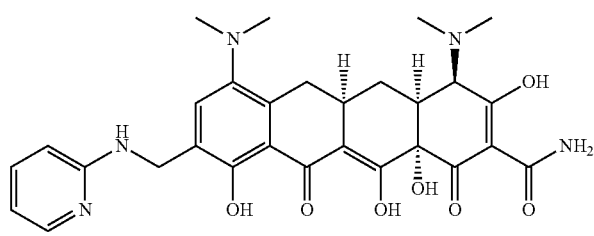
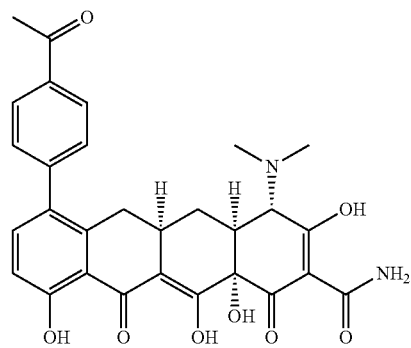

TABLE 1-continued
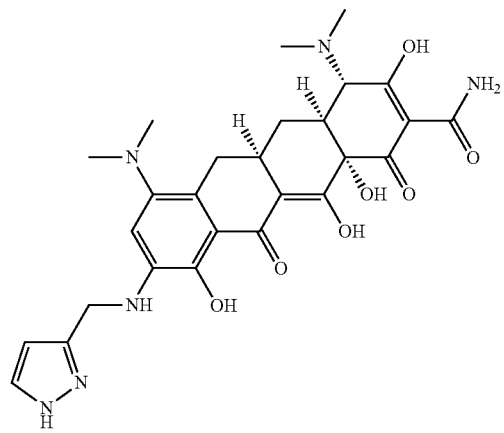
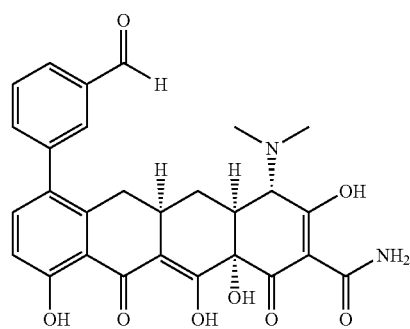
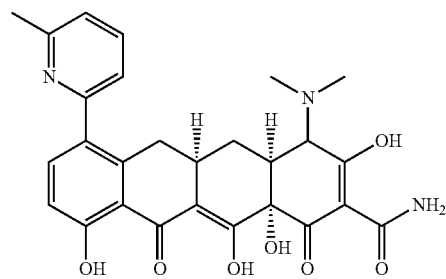
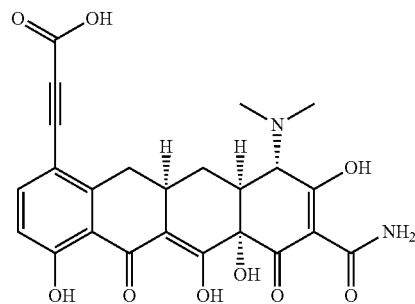

TABLE 1-continued
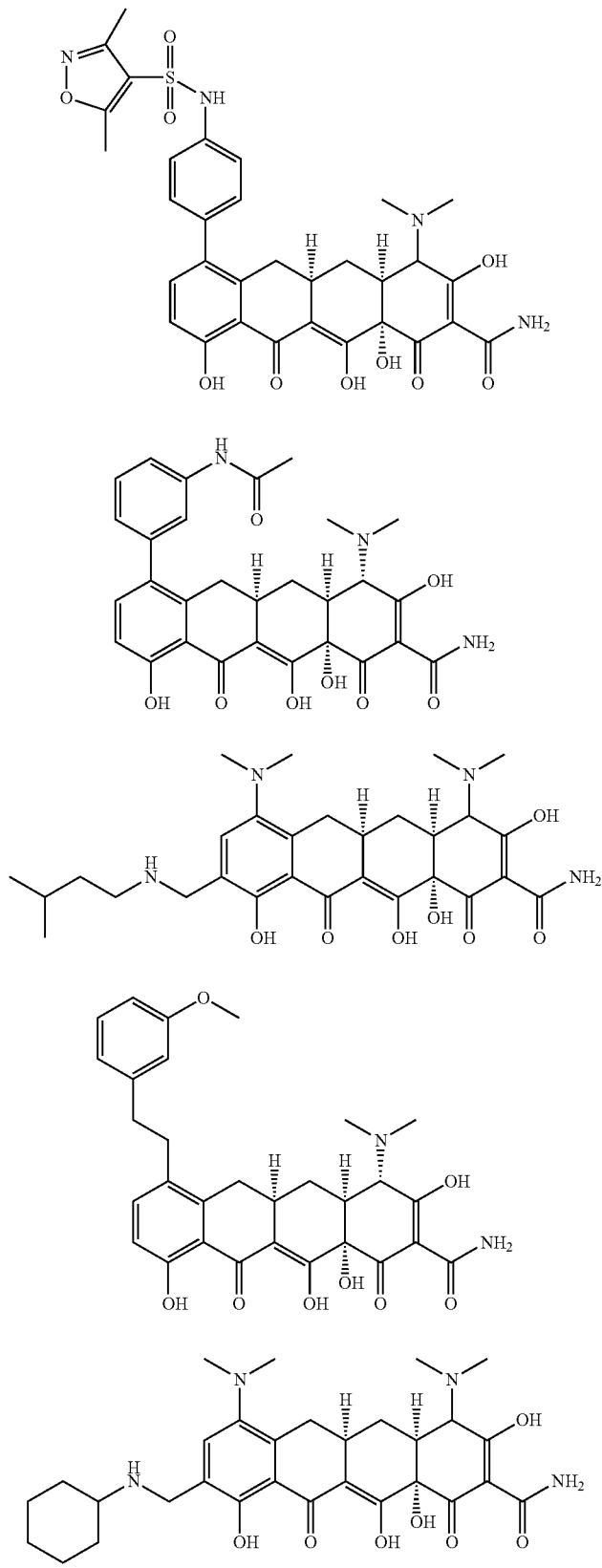

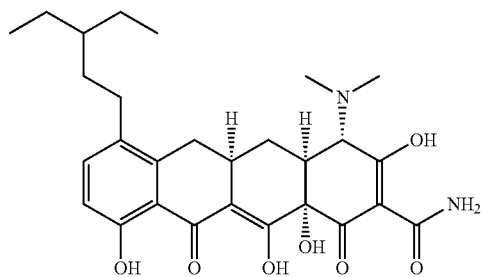
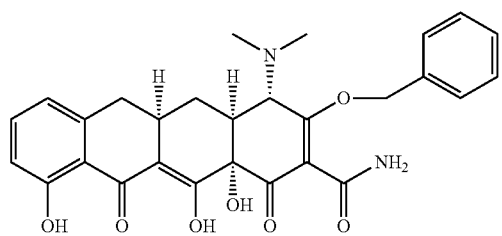
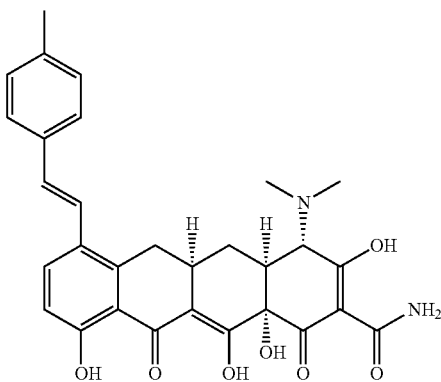
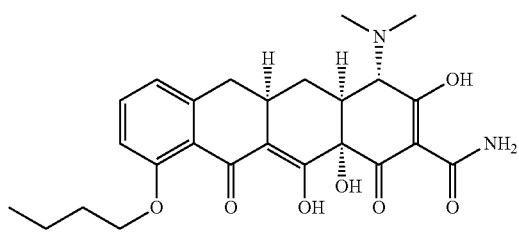
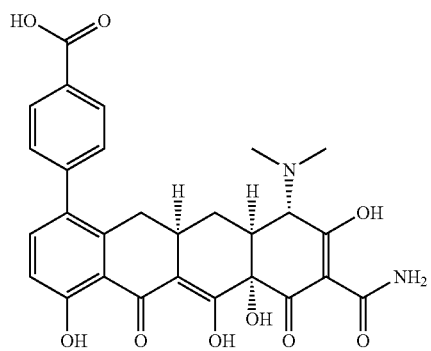

TABLE 1-continued
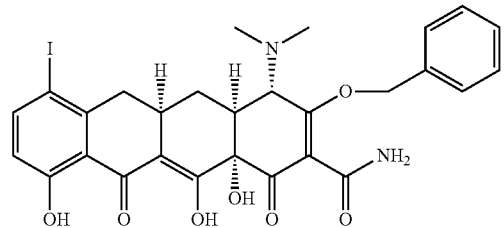
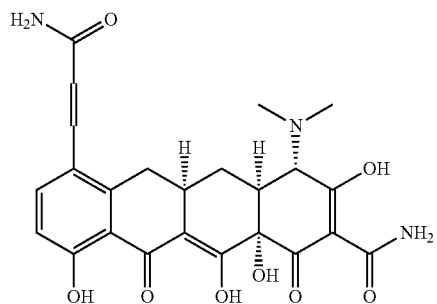
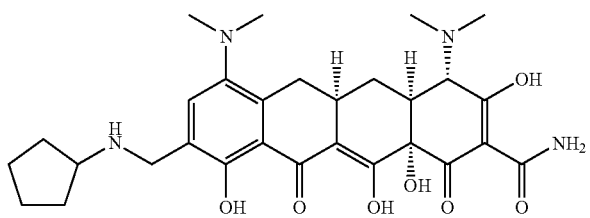
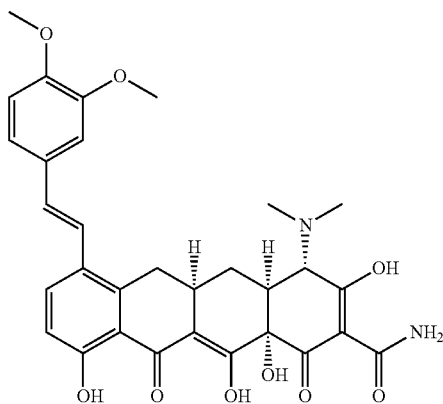
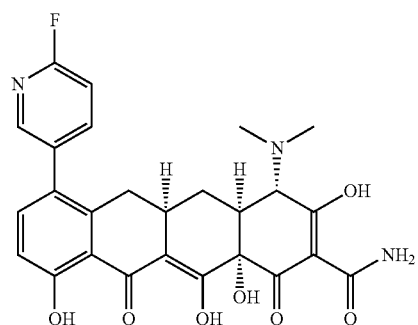

TABLE 1-continued
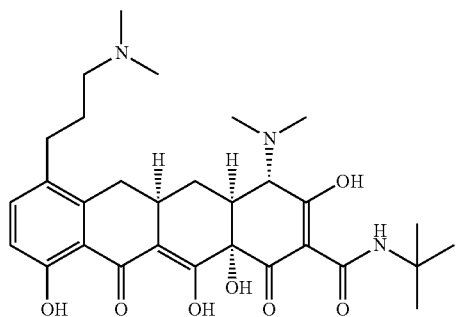
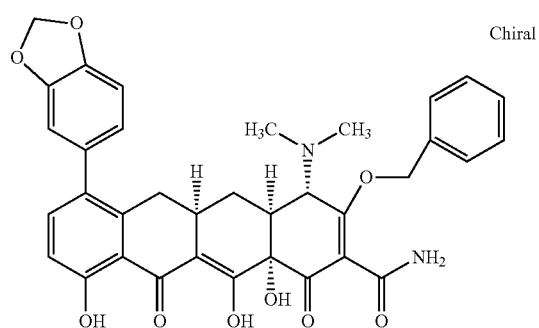
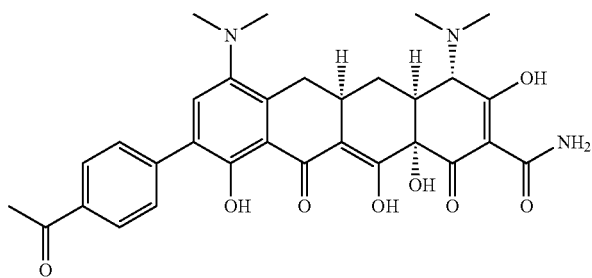
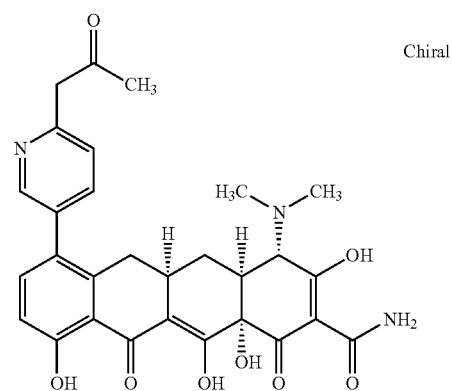

TABLE 1-continued
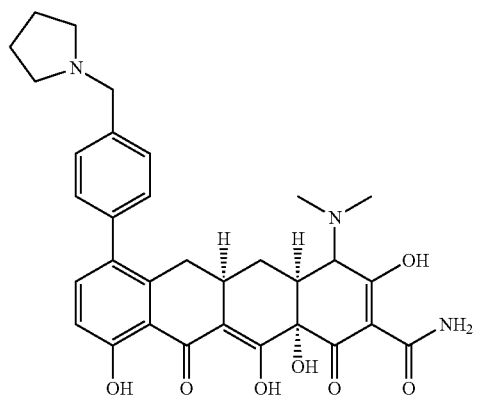
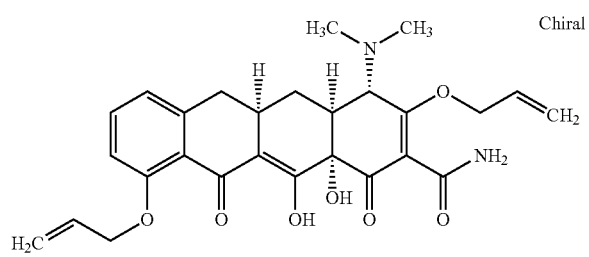
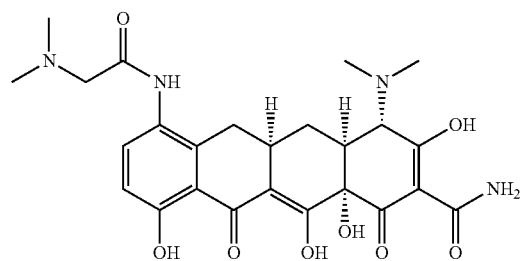
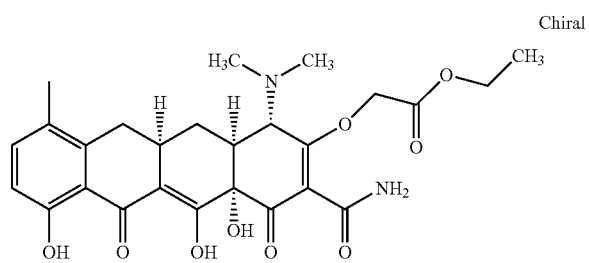
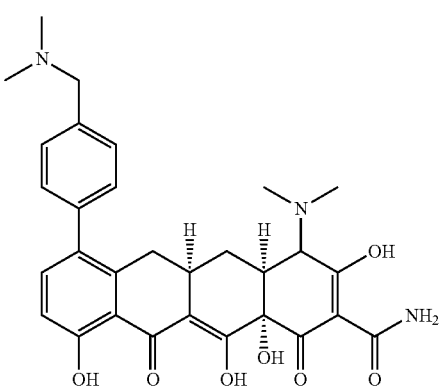

TABLE 1-continued
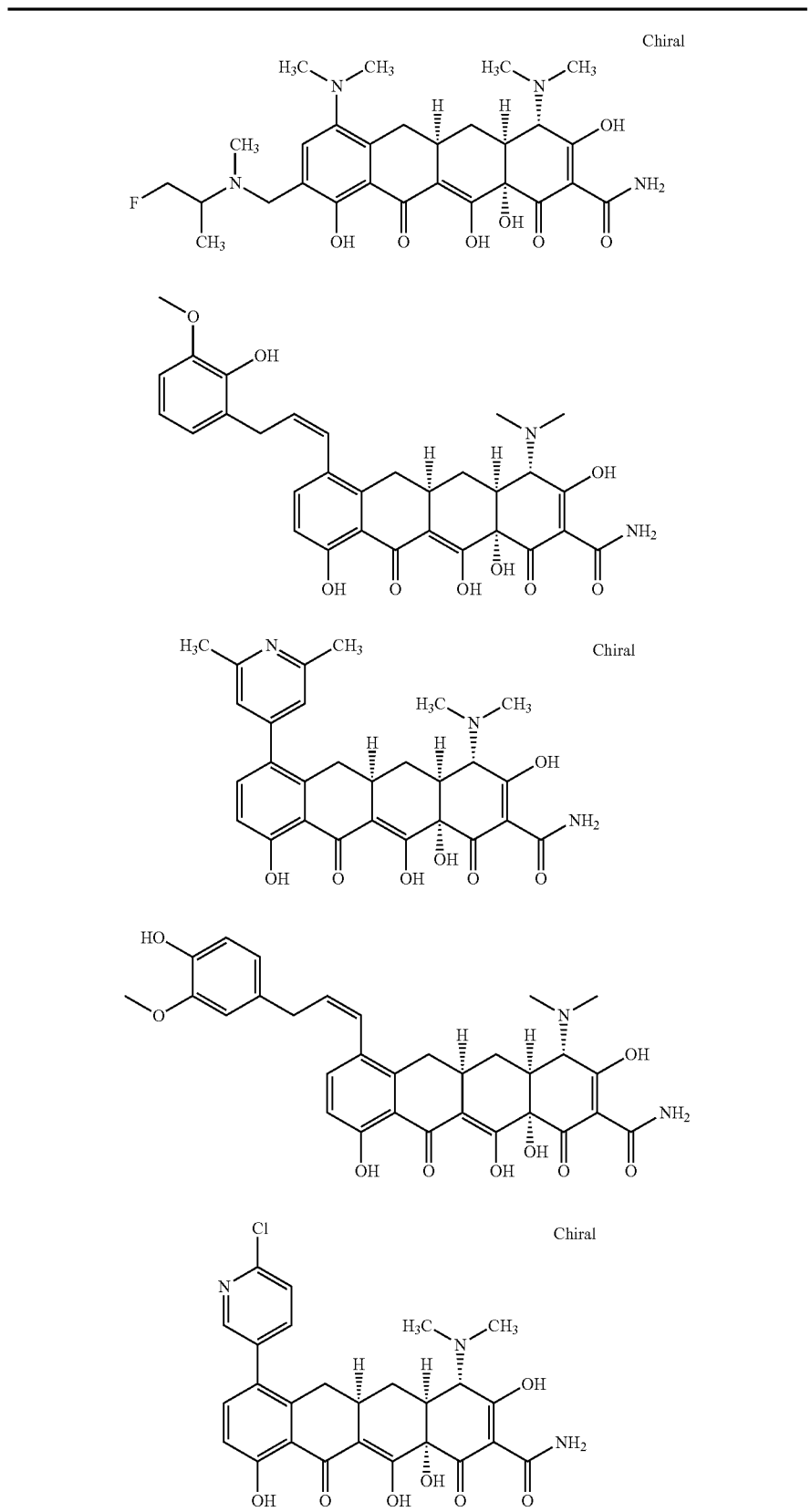

TABLE 1-continued
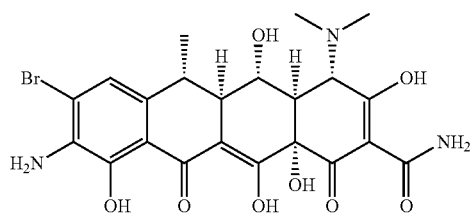
Chiral
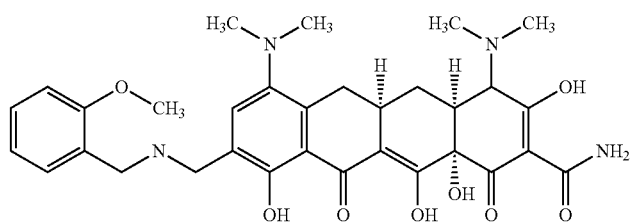
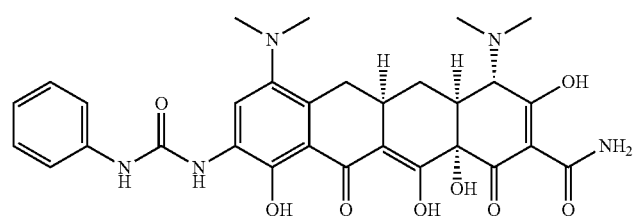
Chiral
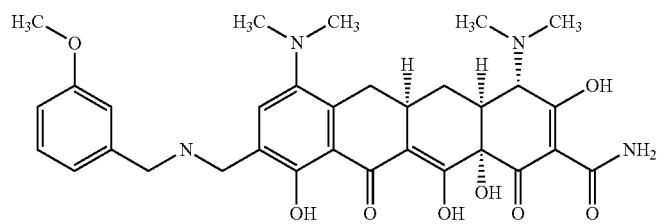
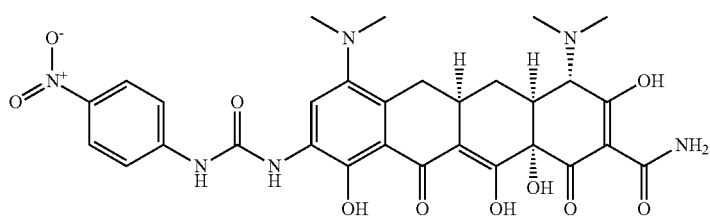
Chiral
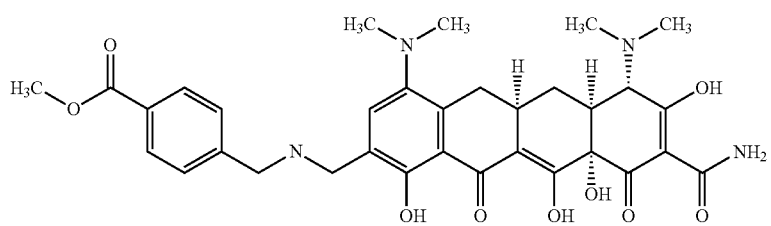

TABLE 1-continued
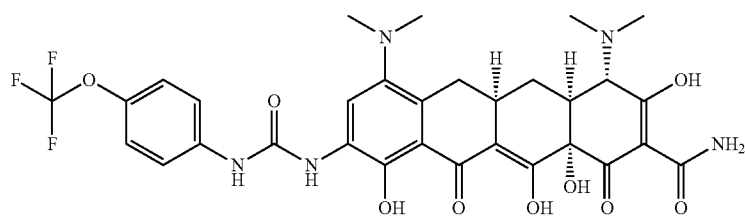
Chiral
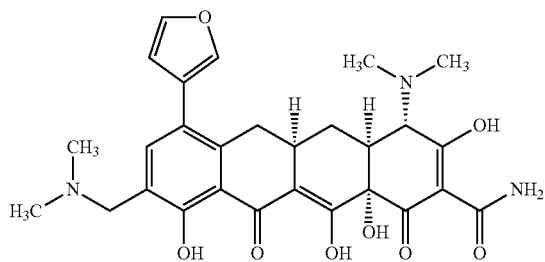
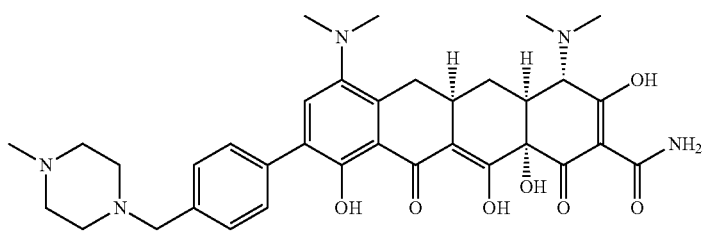
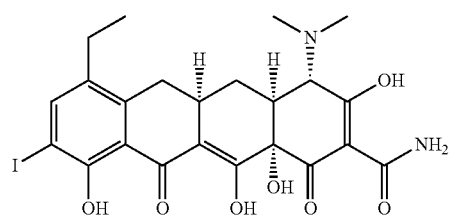
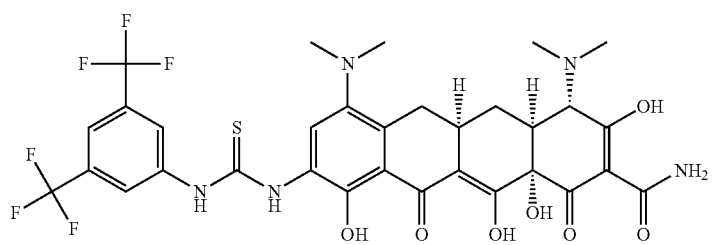
Chiral
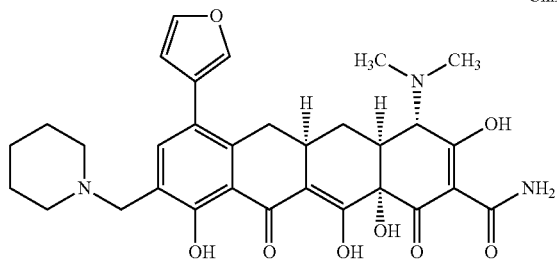

TABLE 1-continued
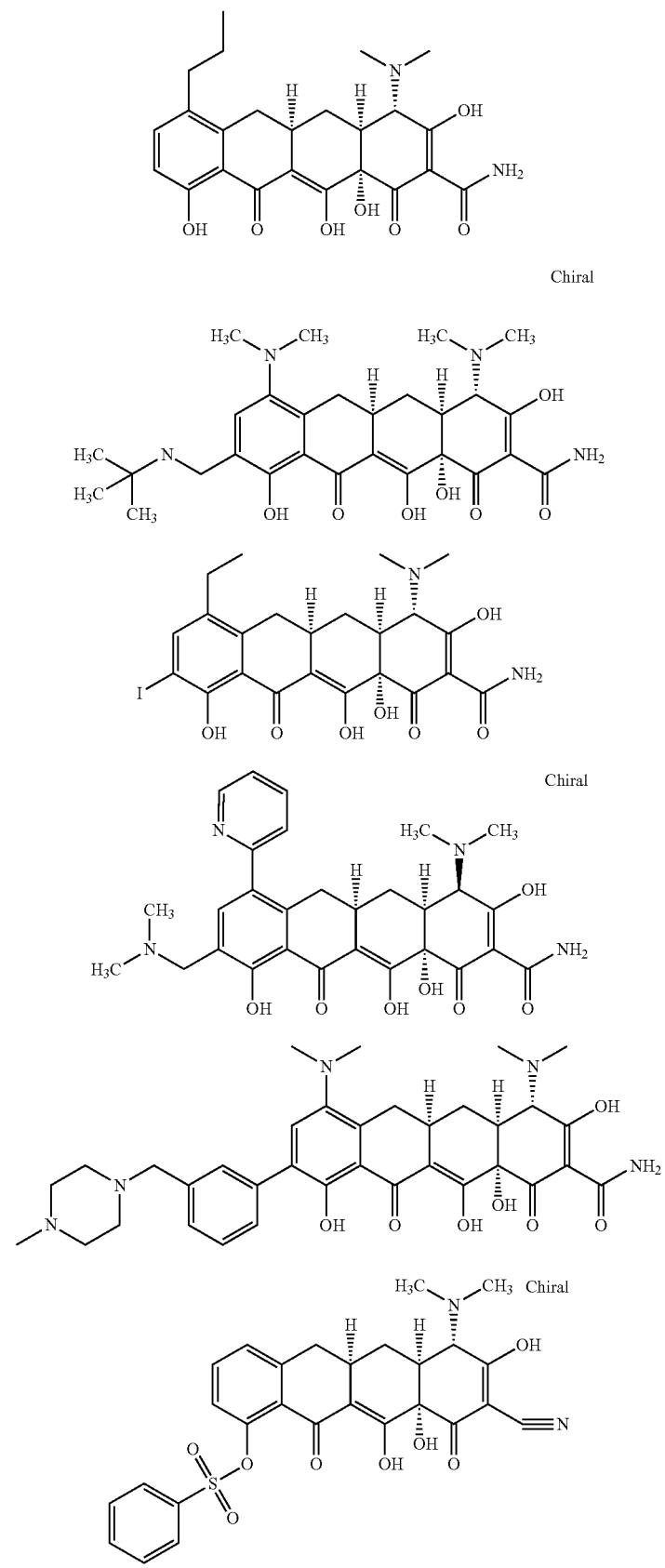

TABLE 1-continued
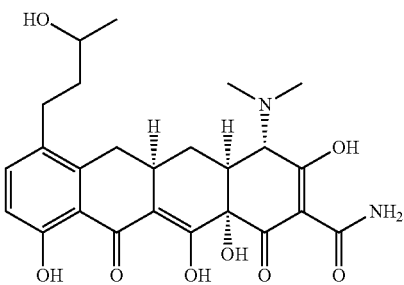
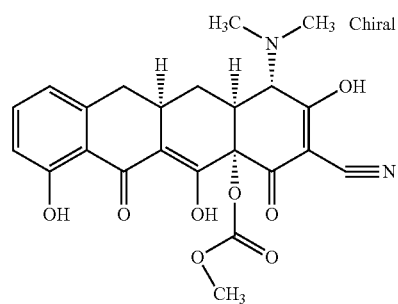
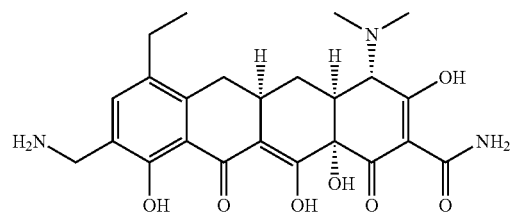
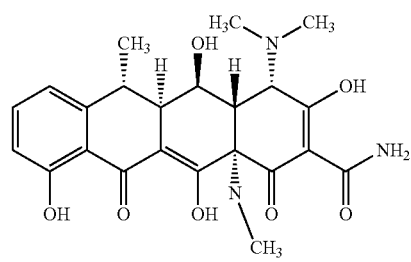
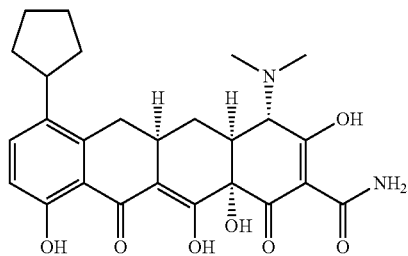
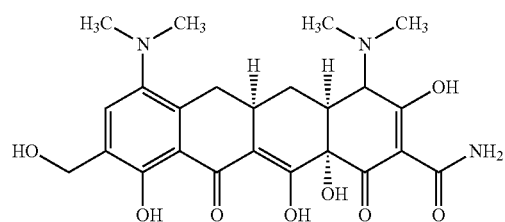

TABLE 1-continued
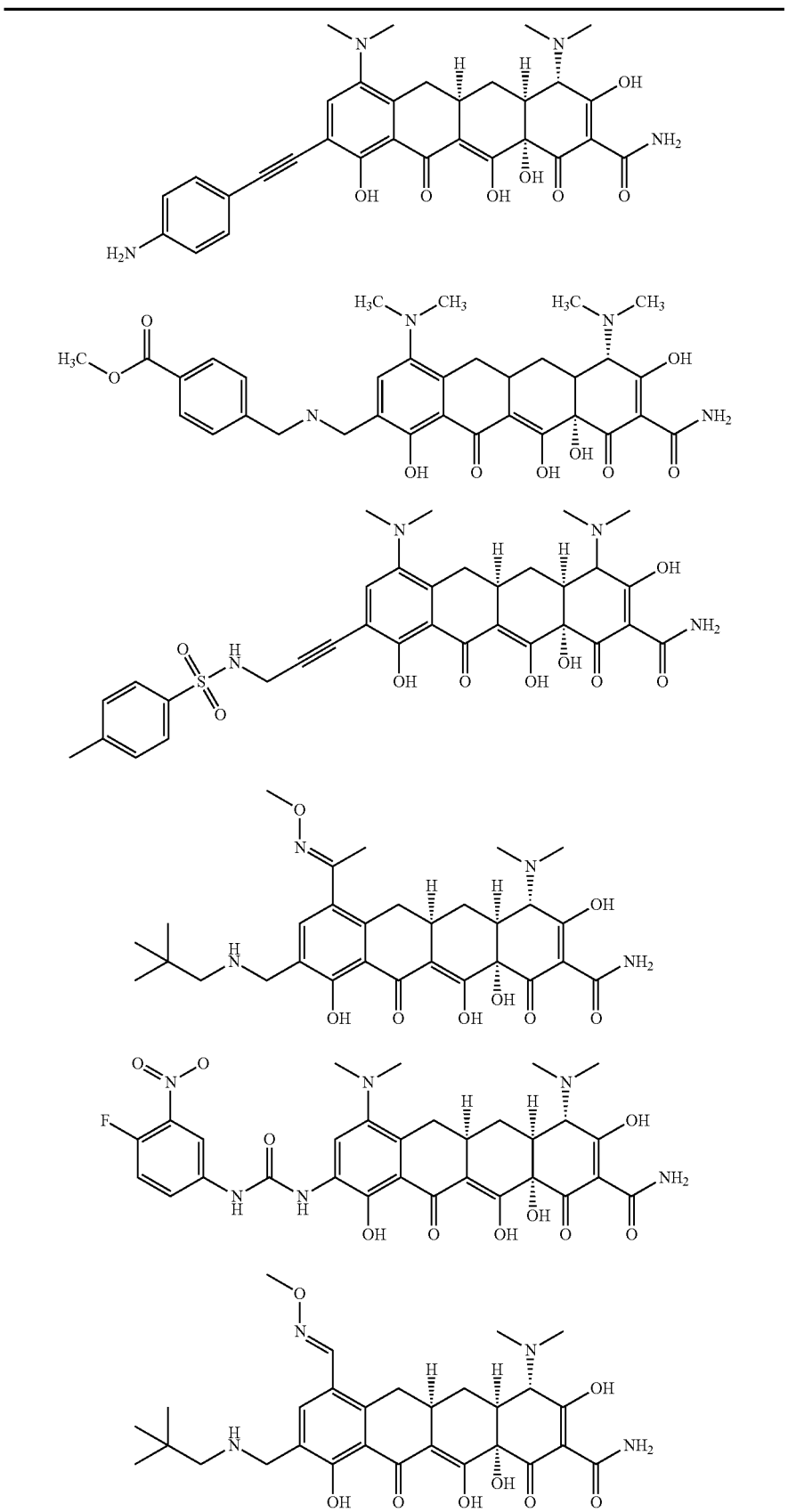

TABLE 1-continued
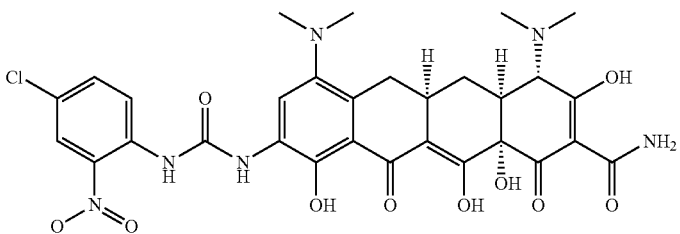
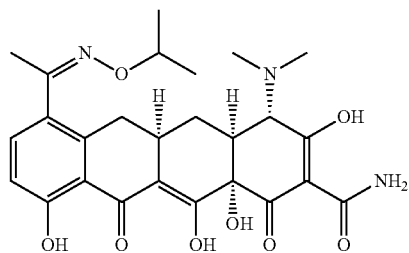
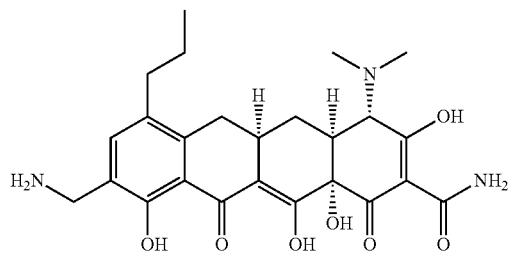
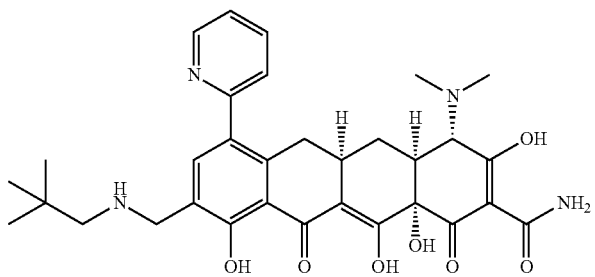
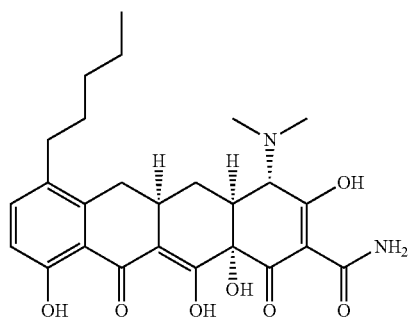
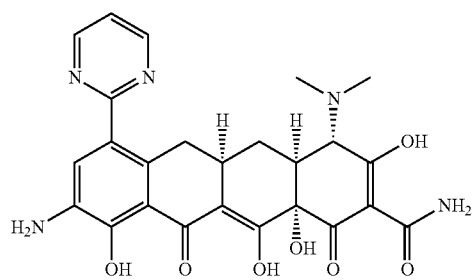

TABLE 1-continued
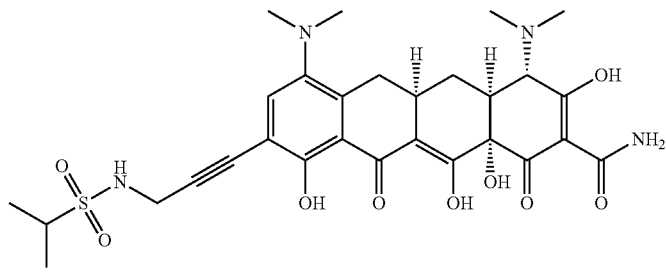
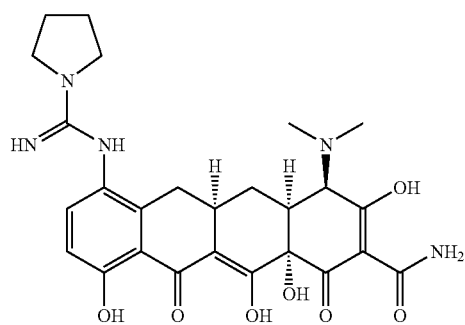
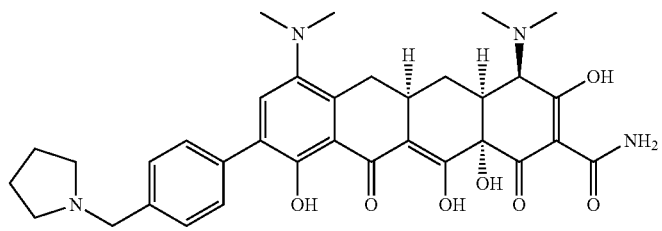
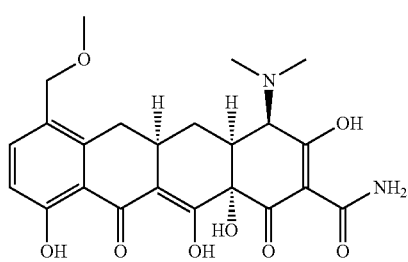
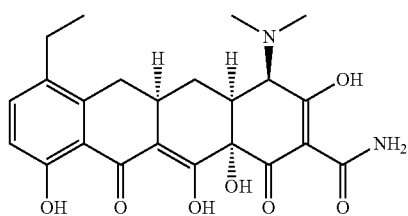
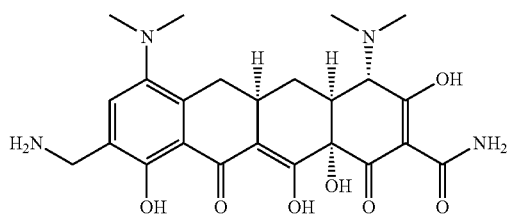

TABLE 1-continued

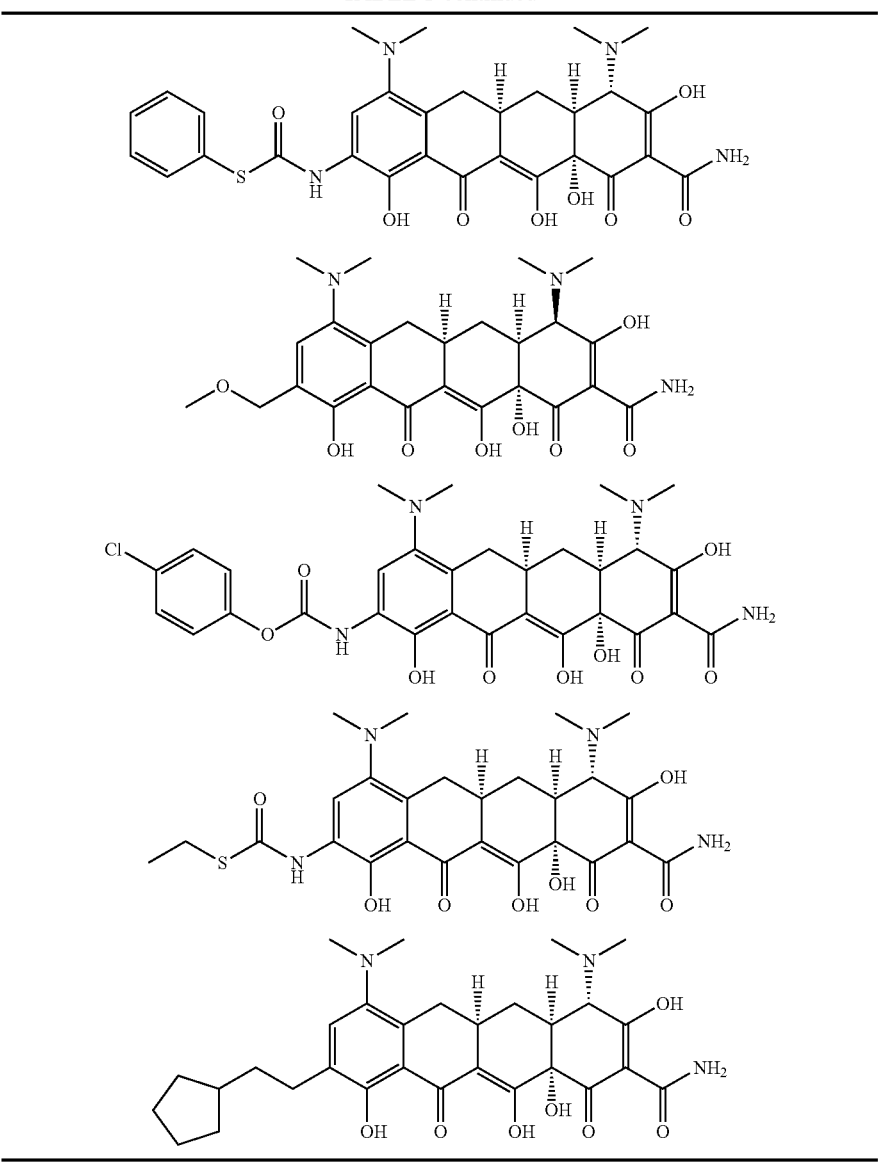

In a further embodiment, the substituted tetracycline compounds are have a suitable oral bioavailability for the treatment of malaria, e.g., after the substituted tetracycline compounds are orally administered to the subject, the compounds are able to perform their intended function, e.g., treat malaria. Examples of methods which can be used to calculate the bioavailability of a particular compound include methods known in the art as well as the methods described in U.S. Ser. No. 60/318,580, incorporated herein by reference.

In one embodiment, the substituted tetracycline compounds do not include compounds which inhibit excess phospholipase $A_2$ activity or production, as measured by the assay given in U.S. Pat. No. 6,043,231. In another embodiment, the substituted tetracycline compounds of the invention do not include compounds which inhibit inducible nitric oxide synthase expression, as measured by the assay given in U.S. Pat. No. 5,919,395. In another embodiment, the substituted tetracycline compounds of the invention do not include compounds which cause a decrease in the amount of nitric oxide produced endogenously by a mammalian-system, as measured by the method given in U.S. Pat. No. 5,789,395. Each of these three patents are hereby incorporated herein by reference in their entirety.

The term "subject" includes animals which are susceptible to malaria, e.g. reptiles, birds, and mammals (e.g. dogs, cattle, pigs, cats, horses, bears, sheep, mice, rats, rabbits, squirrels, and most advantageously humans).

In a further embodiment, malaria for treatment using the compositions and methods of the invention is resistant to one or more anti-malarial compounds such as proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, and pyronaridine.

The methods of the invention also include administering the compounds of the invention in combination with a supplementary compound. "Supplementary compounds" include anti-malarial compounds and compounds that treat the symptoms of malaria. Supplementary compounds may treat malaria directly, headache, malaise, anemia, splenomegaly, and/or fever.

The term "in combination with" a supplementary compound is intended to include simultaneous administration of the substituted tetracycline compound and the supplementary compound, administration of the substituted tetracycline compound first, followed by the supplementary compound and administration of the supplementary compound first, followed by the substituted tetracycline compound.

For example, a "supplementary compound" can include anti-malarial compounds such as proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, and phosphatidylcholin synthesis inhibitors, such as G25 (1,16-hexadecamethylenebis(N-methylpyrrolidinium) dibromide). Other anti-malarial compounds not recited here can also be administered, such as those which may be developed in the future or ones under current investigation.

In one embodiment, the anti-malarial activity of the anti-antimalarial compound is increased when administered in combination with a substituted tetracycline compound of the invention, thereby reducing the effective amount of the anti-malarial compound required as compared to the amount required when the antimalarial agent is administered alone. In one embodiment, the coadministration of a substituted tetracycline compound of the invention reduces the effective amount of the anti malarial agent by 1 fold, 2 fold, 3 fold, 4 fold, 5 fold, 6 fold, 7 fold, 8 fold, 9 fold, or 10 fold, as compared to the effective amount of the antimalarial agent alone, e.g., without the aid of a substituted tetracycline compound or another synergistic agent.

The invention also features a packaged malarial treatment, including one or more substituted tetracycline compounds packaged with instructions for using an effective amount of the compound to treat malaria. In an embodiment, the substituted tetracycline compound is not oxytetracycline, demeclocycline, doxycycline, chlorotetracycline, minocycline, or tetracycline.

The substituted tetracycline compounds of the invention can be synthesized using the methods described in Examples 1 and 2 and in the following schemes. All novel substituted tetracycline compounds described herein are included in the invention as compounds. One of ordinary skill in the art will appreciate that although the methods are illustrated generally for the synthesis of 7 substituted tetracycline compounds, similar procedures can be used to generate the corresponding 9 position substituted tetracycline compounds. Furthermore, although the schemes are generally shown for one particular substituted tetracycline compound (e.g., sancycline), the schemes and methods are generally applicable to other substituted tetracycline compounds (e.g., tetracycline, minocycline, doxycycline, etc.).

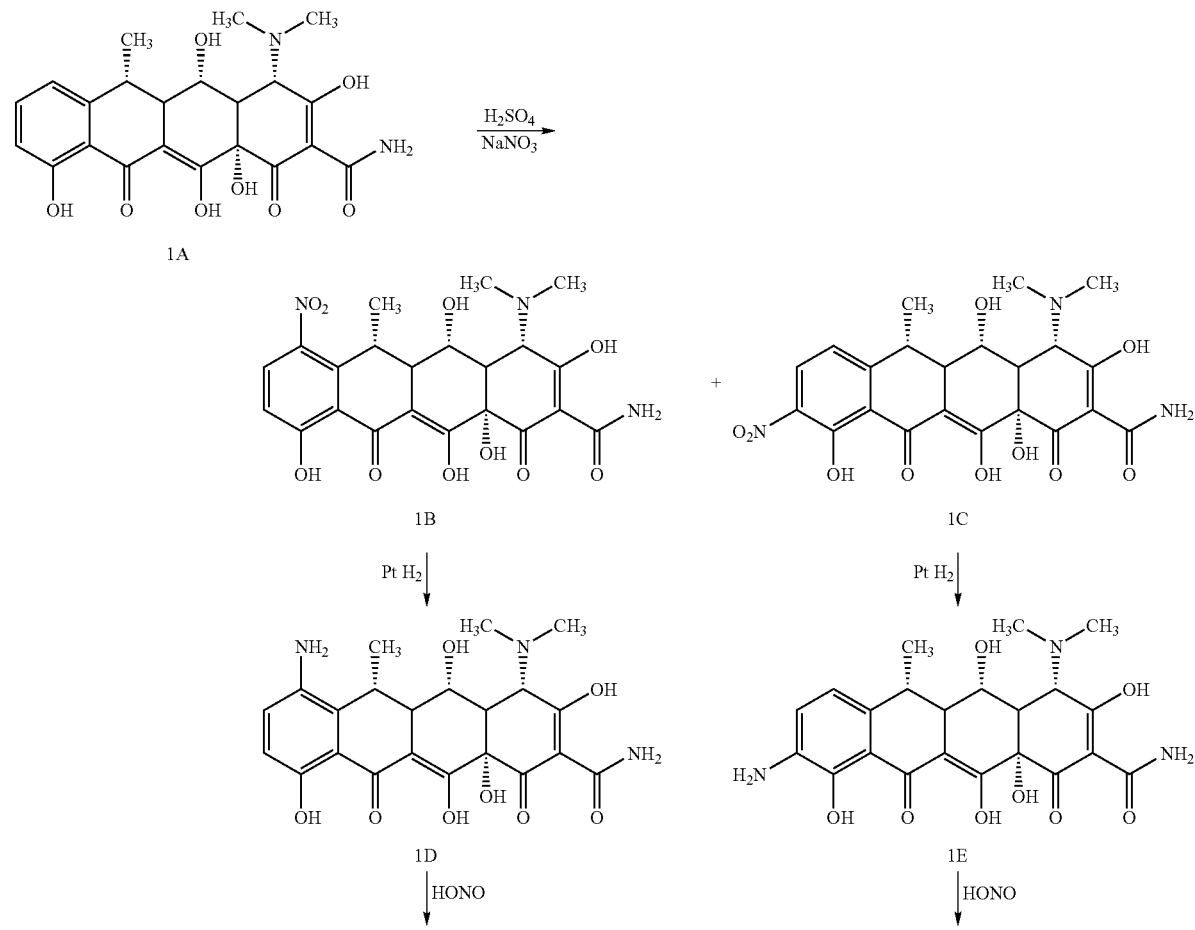

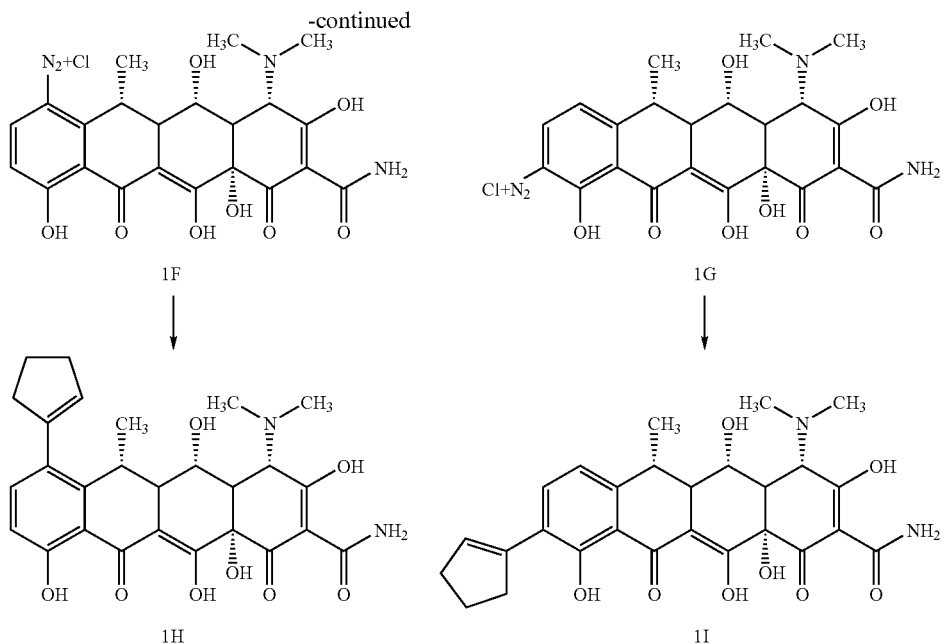

9- and 7-substituted tetracyclines can be synthesized by the method shown in Scheme 1. As shown in Scheme 1,9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate halogenated reagent (e.g., $R^9Br$, wherein $R^9$ is an aryl, alkenyl, or alkynyl moiety) to yield the desired compound (e.g., in Scheme 1, 7-cyclopent-1-enyl doxycycline (1H) and 9-cyclopent-1-enyl doxycycline (1I)).

SCHEME 2

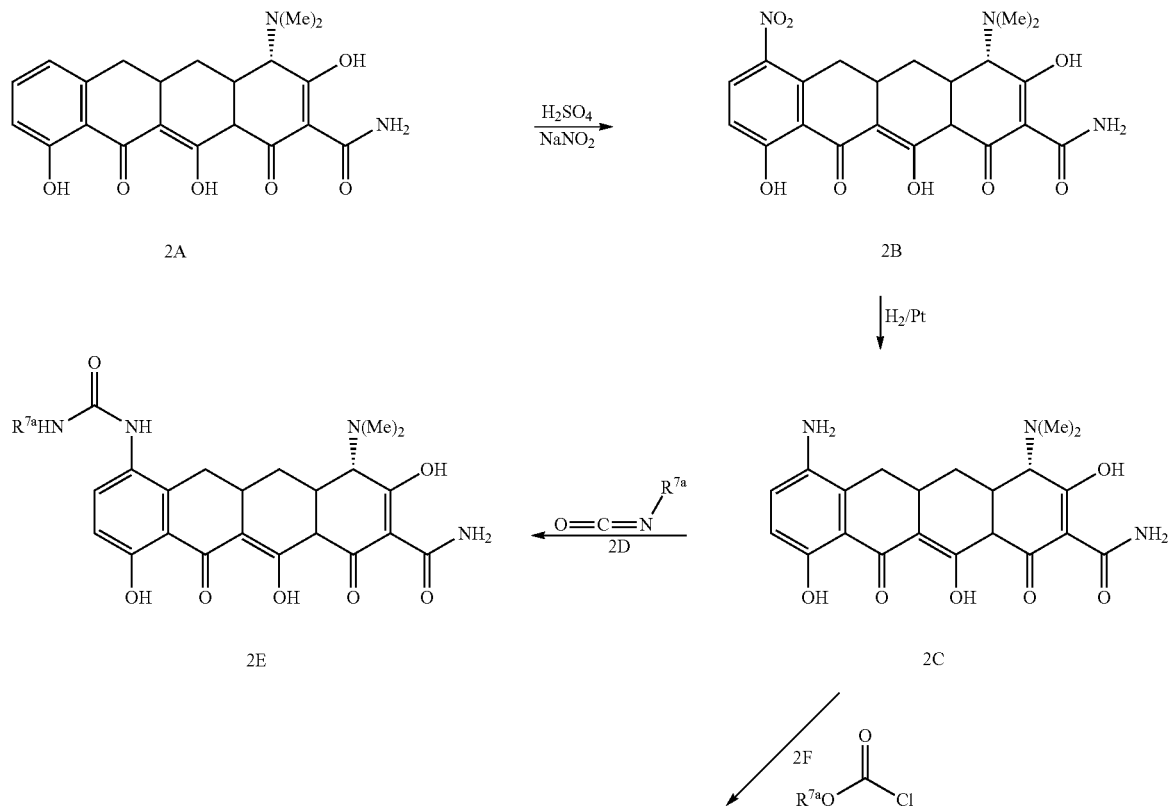

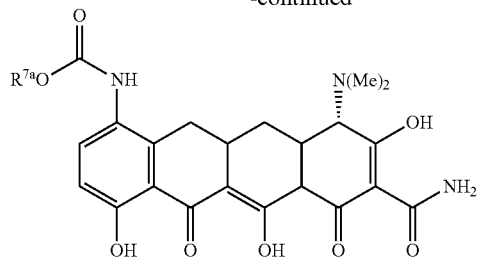

2G

As shown in Scheme 2, substituted tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

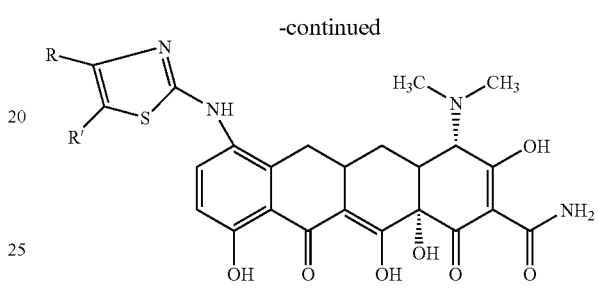

3F

As shown in Scheme 3, substituted tetracycline compounds of the invention, wherein $R^7$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

SCHEME 3

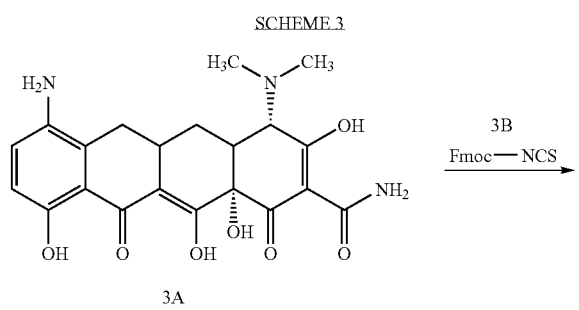

SCHEME 4

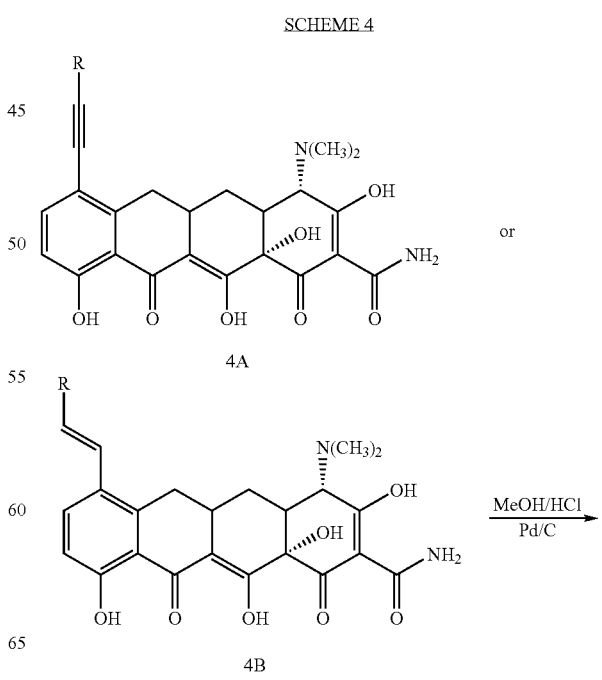

915
-continued

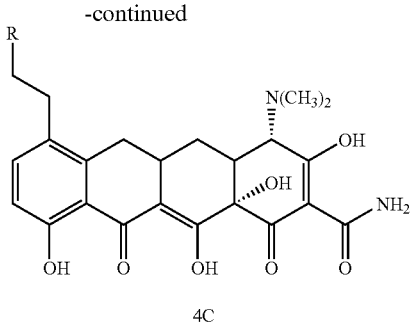

4C

916
-continued

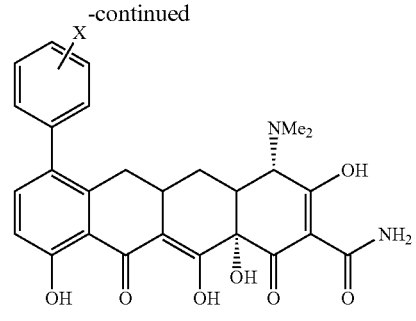

5D 7-alkenyl substituted tetracycline compounds, such as 7-alkynyl sancycline (4A) and 7-alkenyl sancycline (4B), can be hydrogenated to form alkyl 7-substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (5B) is treated with an aqueous base (e.g., $Na_2CO_3$) and an appropriate boronic acid (5C) and under an inert atmosphere. The reaction is catalyzed with a palladium catalyst (e.g., $Pd(OAc)_2$). The product (5D) can be purified by methods known in the art (such as HPLC). Other 7-aryl and alkynyl substituted tetracycline compounds can be synthesized using similar protocols.

The 7-substituted tetracycline compounds of the invention can also be synthesized using Stille cross couplings. Stille cross couplings can be performed using an appropriate tin reagent (e.g., R—$SnBu_3$) and a halogenated tetracycline compound, (e.g., 7-iodosancycline). The tin reagent and the iodosancycline compound can be treated with a palladium catalyst (e.g., $Pd(PPh_3)_2Cl_2$ or $Pd(AsPh_3)_2Cl_2$) and, optionally, with an additional copper salt, e.g., CuI. The resulting compound can then be purified using techniques known in the art.

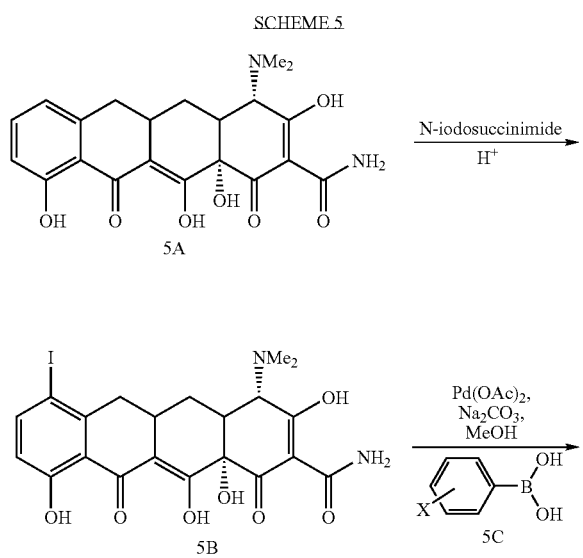

SCHEME 6

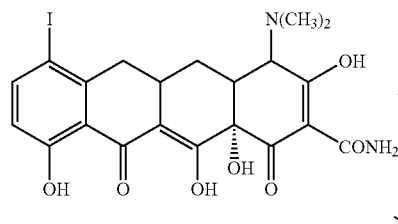

6A

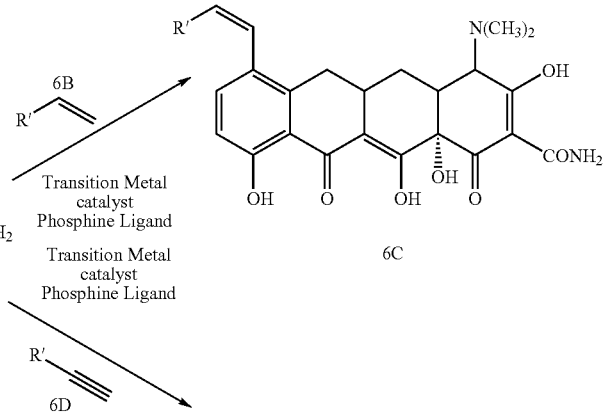

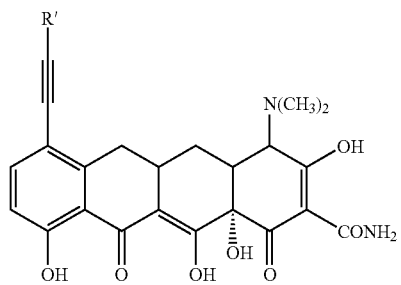

6E

The compounds of the invention can also be synthesized using Heck-type cross coupling reactions. As shown in Scheme 6, Heck-type cross-couplings can be performed by suspending a halogenated tetracycline compound (e.g., 6-iodosancycline, 6A) and an appropriate palladium or other transition metal catalyst (e.g., Pd(OAc)₂ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art.

SCHEME 7

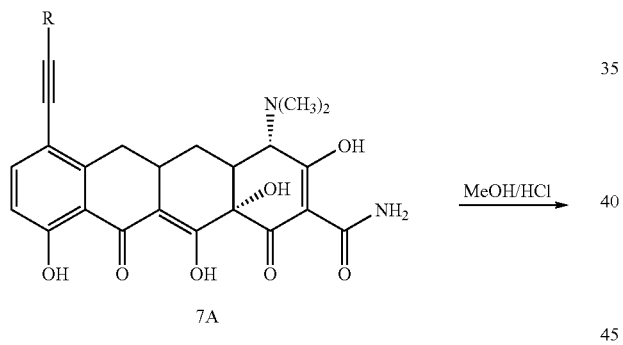

To prepare 7-(2'-Chloro-alkenyl)-tetracycline compounds, the appropriate 7-(alkynyl)-sancycline (7A) is dissolved in saturated methanol and hydrochloric acid and stirred. The solvent is then removed to yield the product (7B).

SCHEME 8

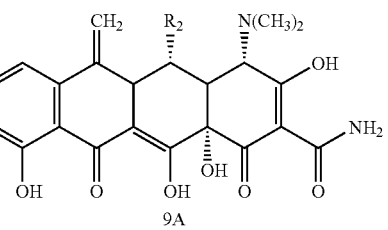

As depicted in Scheme 8,5-esters of 9-substituted tetracycline compounds can be formed by dissolving the 9-substituted compounds (8A) in strong acid (e.g. HF, methanesulphonic acid, and trifluoromethanesulfonic acid) and adding the appropriate carboxylic acid to yield the corresponding esters (8B).

SCHEME 9

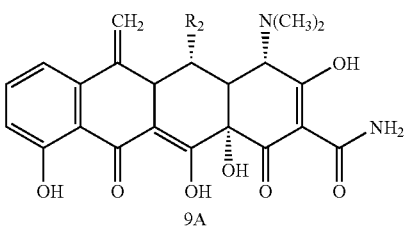

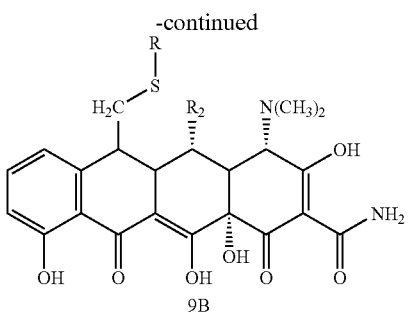

9B 13-substituted thiols can be synthesized by the method outlined in Scheme 9, above. Generally, 13-substituted thiol ethers (9B) can be synthesized by heating a tetracycline salt (9A) (such as methacycline hydrochloride), AIBN (2,2'-azobisisobutyronitrile), and a thiol in ethanol at reflux for six hours under an inert atmosphere.

As shown in Scheme 10 below, 7 and 9 aminomethyl tetracyclines may be synthesized using reagents such as hydroxymethyl-carbamic acid benzyl ester.

SCHEME 10

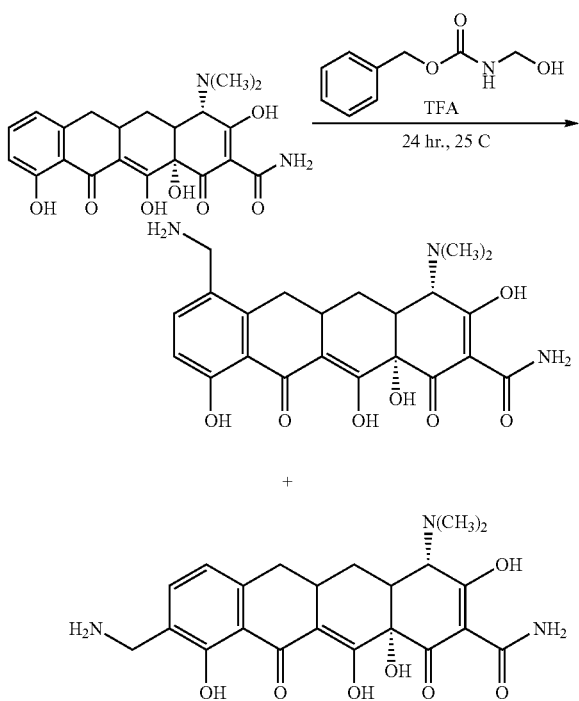

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. It also includes aminoalkyls, which may be further substituted. The term alkyl further includes alkyl groups, which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer. Likewise, preferred cycloalkyls have from 4-7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids. Examples of halogenated alkyl groups include fluoromethyl, difluoromethyl, trifluoromethyl, chloromethyl, dichloromethyl, trichloromethyl, perfluoromethyl, perchloromethyl, perfluoroethyl, perchloroethyl, etc.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin, methylenedioxyphenyl).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain).

Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties where an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds where the nitrogen is bound to at least one additional alkyl group. The term "dialkyl amino" includes groups where the nitrogen atom is bound to at least two additional alkyl groups. The term "arylamino" and "diarylamino" include groups where the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties which contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups which include aryl or heteroaryl moieties bound to an amino group which is bound to the carbon of a carbonyl or thiocarbonyl group. The terms "alkylaminocarboxy," "alkenylaminocarboxy," "alkynylaminocarboxy," and "arylaminocarboxy" include moieties where alkyl, alkenyl, alkynyl and aryl moieties, respectively, are bound to a nitrogen atom which is in turn bound to the carbon of a carbonyl group.

The term "carbonyl" or "carboxy" includes compounds and moieties which contain a carbon connected with a double bond to an oxygen atom, and tautomeric forms thereof. Examples of moieties which contain a carbonyl include aldehydes, ketones, carboxylic acids, amides, esters, anhydrides, etc. The term "carboxy moiety" or "carbonyl moiety" refers to groups such as "alkylcarbonyl" groups where an alkyl group is covalently bound to a carbonyl group, "alkenylcarbonyl" groups where an alkenyl group is covalently bound to a carbonyl group, "alkynylcarbonyl" groups where an alkynyl group is covalently bound to a carbonyl group, "arylcarbonyl" groups where an aryl group is covalently attached to the carbonyl group. Furthermore, the term also refers to groups where one or more heteroatoms are covalently bonded to the carbonyl moiety. For example, the term includes moieties such as, for example, aminocarbonyl moieties, (where a nitrogen atom is bound to the carbon of the carbonyl group, e.g., an amide), aminocarbonyloxy moieties, where an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "urea" includes compounds that containing a carbonyl group linked to two nitrogens. For example, NH(C=O)NHAr is an aromatic urea group.

The term "thiocarbonyl" or "thiocarboxy" includes compounds and moieties which contain a carbon connected with a double bond to a sulfur atom. The term "thiocarbonyl moiety" includes moieties which are analogous to carbonyl moieties. For example, "thiocarbonyl" moieties include aminothiocarbonyl, where an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties where an alkyl, alkenyl, or alkynyl group is bonded to a sulfur atom which is covalently bonded to an alkynyl group.

The term "hydroxy" or "hydroxyl" includes groups with an —OH or —O.

The term "halogen" includes fluorine, bromine, chlorine, iodine, etc. The term "perhalogenated" generally refers to a moiety where all hydrogens are replaced by halogen atoms.

The terms "polycyclyl" or "polycyclic" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "heterocycle" or "heterocyclic" includes saturated, unsaturated, aromatic ("heteroaryls" or "heteroaromatic") and polycyclic rings which contain one or more heteroatoms. Examples of heterocycles include, for example, benzodioxazole, benzofuran, benzoimidazole, benzothiazole, benzothiophene, benzoxazole, deazapurine, furan, indole, indolizine, imidazole, isooxazole, isoquinoline, isothiaozole, methylenedioxyphenyl, napthridine, oxazole, purine, pyrazine, pyrazole, pyridazine, pyridine, pyrimidine, pyrrole, quinoline, tetrazole, thiazole, thiophene, and triazole. Other heterocycles include morpholine, piprazine, piperidine, thiomorpholine, and thioazolidine. The heterocycles may be substituted or unsubstituted. Examples of substituents include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof. The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

In another aspect, this invention further pertains to a pharmaceutical composition which includes an effective amount of a substituted tetracycline compound to treat malaria in a subject and a pharmaceutically acceptable carrier.

This invention also pertains to the use of a compound of formula I in the preparation of medicament to treat or prevent malaria in a subject.

The pharmaceutical composition may also include a supplementary compound. "Supplementary compounds" include anti-malarial compounds and compounds that treat the symptoms of malaria. Supplementary compounds may treat malaria directly, headache, malaise, anemia, splenomegaly, and/or fever. Examples of supplementary anti-malarial compounds include proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, and combinations thereof.

The language "pharmaceutically acceptable carrier" includes substances capable of being co-administered with the substituted tetracycline compound(s), and which allow the substituted tetracycline compound to perform its intended function, e.g., treat or prevent malaria. Examples of such carriers include solutions, solvents, dispersion media, delay agents, emulsions and the like. The use of such media for pharmaceutically active substances are well known in the art. Any other conventional carrier suitable for use with the substituted tetracycline compounds of the present invention are included.

For example, one or more compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Some of the substituted tetracycline compounds of the invention suitably may be administered to a subject in a protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. Also, where an appropriate acidic group is present on a compound of the invention, a pharmaceutically acceptable salt of an organic or inorganic base can be employed such as an ammonium salt, or salt of an organic amine, or a salt of an alkali metal or alkaline earth metal such as a potassium, calcium or sodium salt.

The substituted tetracycline compounds can be administered to a subject in accordance with the invention by any of a variety of routes such as topical (including transdermal, buccal or sublingual), and parenteral (including intraperitoneal, subcutaneous, intravenous, intradermal or intramuscular injection). In one embodiment, the substituted tetracycline compounds are administered orally.

For parenteral application, particularly suitable are solutions, preferably oily or aqueous solutions as well as suspensions, emulsions, or implants, including suppositories. Therapeutic compounds will be formulated in sterile form in multiple or single dose formats such as being dispersed in a fluid carrier such as sterile physiological saline or 5% saline dextrose solutions commonly used with injectables.

For enteral or oral administration, particularly suitable are tablets, dragees or capsules having talc and/or carbohydrate carrier binder or the like, the carrier preferably being lactose and/or corn starch and/or potato starch. A syrup, elixir or the like can be used where a sweetened vehicle is employed. Sustained release compositions can be formulated including those where the active component is protected with differentially degradable coatings, e.g., by microencapsulation, multiple coatings, etc.

For topical applications, the substituted tetracycline compound(s) can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

The actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

For purposes of the comparison the doses other particular tetracycline related compounds are summarized. The adult dose for tetracycline, oxytetrcycline, and chlortetracycline is generally 250 mg every 6 hours by mouth with 500 mg in serious infections. For children under 50 kg, doxycycline 4 mg/kg is generally given on the first day with 2 mg/kg in subsequent days. For intramuscular tetracycline, the appropriate adult dose is generally 100 mg 2 to 3 times daily. For intravenous/intrapleural tetracycline, the usually adult dose is generally 500 mg twice daily.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

The language "effective amount" of the substituted tetracycline compound is that amount necessary or sufficient to control malaria in a subject, e.g., to prevent or ameliorate the various morphological and somatic symptoms of malaria. The effective amount can vary depending on such factors as the size and weight of the subject, the type of illness, or the particular substituted tetracycline compound. For example, the choice of the substituted tetracycline compound can affect what constitutes an "effective amount". One of ordinary skill in the art would be able to study the aforementioned factors and make the determination regarding the effective amount of the substituted tetracycline compound without undue experimentation. An in vivo assay also can be used to determine an "effective amount" of a substituted tetracycline compound. The ordinarily skilled artisan would select an appropriate amount of a substituted tetracycline compound for use in the aforementioned in vivo assay. Preferably, the effective amount of the substituted tetracycline compound is effective to treat a subject, e.g., human, suffering from malaria.

The term "subject" includes animals which are capable of having malaria. Examples of subject include, but are not limited to, birds (i.e. geese, ducks), reptiles, ruminants (e.g., cattle and goats), mice, rats, hamsters, dogs, cats, horses, pigs, sheep, lions, tigers, bears, monkeys, chimpanzees, and, in a preferred embodiment, humans.

The invention is further illustrated by the following examples, which should not be construed as further limiting. The contents of all references, pending patent applications and published patents, cited throughout this application are hereby expressly incorporated by reference.

EXEMPLIFICATION OF THE INVENTION

Compounds of the invention may be made as described below, with modifications to the procedure below within the skill of those of ordinary skill in the art.

Example 1

Synthesis of 7-Substituted Tetracyclines

7 Iodo Sancycline

One gram of sancycline was dissolved in 25 mL of TFA (trifluoroacetic acid) that was cooled to 0 C (on ice). 1.2 equivalents of N-iodosuccinimide (NIS) was added to the reaction mixture and reacted for forty minutes. The reaction was removed from the ice bath and was allowed to react at room temperature for an additional five hours. The mixture was then analyzed by HPLC and TLC, was driven to completion by the stepwise addition of NIS. After completion of the reaction, the TFA was removed in vacuo and 3 mL of MeOH was added to dissolve the residue. The methanolic solution was the added slowly to a rapidly stirring solution of diethyl ether to form a greenish brown precipitate. The 7-iodo isomer of sancycline was purified by treating the 7-iodo product with activated charcoal, filtering through Celite, and subsequent removal of the solvent in vacuo to produce the 7-isomer compound as a pure yellow solid in 75% yield.

MS (M+H) (formic acid solvent) 541.3.

\Rt: Hypersil C18 BDS Column, 11.73

$^1$H NMR (Methanol $d_4$-300 MHz) δ 7.87-7.90 (d, 1H), 6.66-6.69 (d, 1H), 4.06 (s, 1H), 2.98 (s, 6H), 2.42 (m, 1H), 2.19 (m, 1H), 1.62 (m, 4H), 0.99 (m, 2H)

7-Phenyl Sancycline 7-iodosancycline, 150 mg (0.28 mM), Pd(OAc)$_2$ and 10 mL of MeOH are added to a flask with a stir bar and the system degassed 3× using argon. Na$_2$CO$_3$ (87 mg, 0.8 mM) dissolved in water and argon degassed is added via syringe is added along with phenylboronic acid (68 mg, 0.55 mM) in MeOH that was also degassed. The reaction was followed by HPLC for 2 hours and cooled to room temperature. The solution was filtered, and dried to produce a crude mixture. The solid was dissolved in dimethylformamide and injected onto a preparative HPLC system using C18 reverse-phase silica. The fraction at 36-38 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 42% yield as a yellow solid.

Rt 21.6 min: MS (M+H, formic acid solvent): 491.3

$^1$H NMR (Methanol $d_4$-300 MHz) δ 7.87 (d, J=8.86 Hz, 1H), 7.38 (m, 5H), 6.64 (d, 8.87 Hz, 1H), 4.00 (s, 1H), 3.84 (s, 2H), 3.01 (s, 6H), 2.46 (m, 2H), 1.63 (m, 4H), 0.95 (m, 2H)

7-(4'-Chlorophenyl)Sancycline 7-iodosancycline, 500 mg (0.91 mM), Pd(OAc)$_2$ 21 mg, and 20 mL of MeOH are added to a flask with a stir bar and the system degassed 3× using argon. Na$_2$CO$_3$ (293 mg, 2.8 mM) dissolved in water and argon degassed is added via syringe is added along with 4-Cl-phenylboronic acid (289 mg, 1.85 mM) in MeOH that was also degassed. The reaction was followed by HPLC for 45 minutes and cooled to room temperature. The solution was filtered, and dried to produce a crude mixture. The solid was dissolved in dimethylformamide and injected onto a preparative HPLC system using C18 reverse-phase silica. The fraction at 39 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 57% yield as a yellow solid.

Rt 20.3 min: MS (M+H, formic acid solvent): 525.7

$^1$H NMR (Methanol $d_4$-300 MHz) δ 7.49-7.52 (d, J=8.54 Hz, 1H), 6.99-7.01 (d, 8.61 Hz, 1H), 4.12 (s, 1H), 3.67 (m, 1H), 3.06 (s, 6H), 2.58 (m, 2H), 1.62 (m, 4H), 1.01 (m, 2H)

7-(4'-Fluorophenyl)Sancycline 7-iodosancycline, 200 mg (0.3 mM), Pd(OAc)$_2$ 8.3 mg, and 10 mL of MeOH are added to a flask with a stir bar and the system degassed 3× using argon. Na$_2$CO$_3$ (104 mg, 1.1 mM) dissolved in water and argon degassed is added via syringe is added along with 4-F-phenylboronic acid (104 mg, 0.7 mM) in MeOH that was also degassed. The reaction was followed by HPLC for 20 minutes and cooled to room temperature. The solution was filtered, and dried to produce a crude mixture. The solid was dissolved in dimethylformamide and injected onto a preparative HPLC system using C18 reverse-phase silica. The fraction at 19-20 minutes was isolated, and the solvent removed in vacuo to yield the product plus salts. The salts were removed by extraction into 50:25:25 water, butanol, ethyl acetate and dried in vacuo. This solid was dissolved in MeOH and the HCl salt made by bubbling in HCl gas. The solvent was removed to produce the product in 47% yield as a yellow solid.

Rt 19.5 min: MS (M+H, formic acid solvent): 509.4

$^1$H NMR (Methanol $d_4$-300 MHz) δ 6.92-6.95 (d, 1H), 7.45-7.48 (d, 1H), 7.15-7.35 (m, 4H), 4.05 (s, 1H), 3.62 (m, 1H), 3.08 (s, 6H), 2.55 (m, 2H), 1.65 (m, 4H), 1.00 (m, 2H)

7-(4'-Iodo-1',3'-carboethoxy-1',3'-butadiene)Sancycline

7-I-Sancycline (1 gm, 1.86 mmol), was dissolved in 25 mL of acetonitrile and was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen. Ethyl propiolate (1 mL) and triethylamine (1 mL) were added to the suspension. It turned to a brown solution upon addition of Et$_3$N. The reaction mixture was then heated to 70 degrees C. for two hours. Progress of the reaction was monitored by HPLC. It was then cooled down to room temperature and was filtered through celite. Evaporation of the solvent gave a brown solid, which was then purified on preparative HPLC to give a yellow solid.

7-(2'-Chloroethenyl)-Sancycline

To a solution/suspension of 0.65 g (1 mmol) of 7-iodo sancycline, 0.05 g tetrakis triphenyl phosphinato palladate, 0.012 g palladium acetate, 0.05 g copper (I) iodide in 10 mL acetonitrile, 2 mL triethylamine and 0.5 g trimethylsilyl acetylene was added at room temperature. The reaction proceeded for two hours before being filtered through a celite bed and concentrated. The crude product was purified by preparative HPLC. The collected fractions were concentrated and the residue was taken up in about 1 mL of methanol and 2 mL of HCl saturated methanol. The product was precipitated with ether. The solids were filtered off and dried under reduced pressure. NMR spectroscopy and LC-MS showed that the compound was 7-(2-chloroethenyl) sancycline.

7-(4'-aminophenyl)Sancycline

To a solution of 200 mg of 7-(4-nitrophenyl) sancycline in 50 mL methanol, 10 mg of 10% palladium on charcoal catalyst was added. The reaction mixture was shaken under 40 psi hydrogen pressure for 2 hours and was then filtered followed by concentration. The residue was further purified by preparative HPLC. 35 mg was isolated as the HCl salt and the structure was proved by NMR and LC-MS to be 7-(4-aminophenyl)sancycline.

7-(N,N-Dimethylpropynyl)-Sancycline

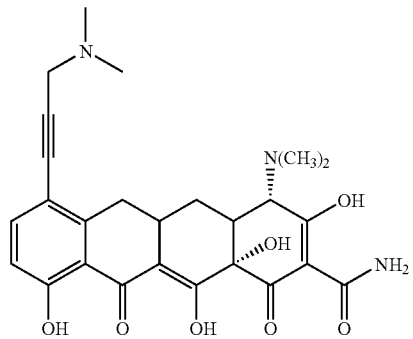

7-I-Sancycline (1 gm, 1.86 mmol), taken in 25 mL of acetonitrile was degassed and purged with nitrogen (three times). To this suspension Pd(OAc)$_2$ (20 mg, 0.089 mmol), CuI (10 mg, 0.053 mmol), (o-tolyl)$_3$P (56 mg, 0.183 mmol) were added and purged with nitrogen for few minutes. N,N-Dimethylpropyne (308 mg, 3.72 mmol) and triethylamine (1 mL) were added to the suspension. It was turned into a brown solution upon addition of Et$_3$N. The reaction mixture was then heated to 70° C. for 3 hours. Progress of the reaction was monitored by HPLC. It was then cooled down to room temperature and was filtered through celite. Evaporation of the solvent gave a brown solid, which was then purified on preparative HPLC to give a yellow solid. The structure of this compound has been characterized using $^1$H NMR, HPLC, and MS.

7-(2'-Chloro-3-Hydroxypropenyl)-Sancycline

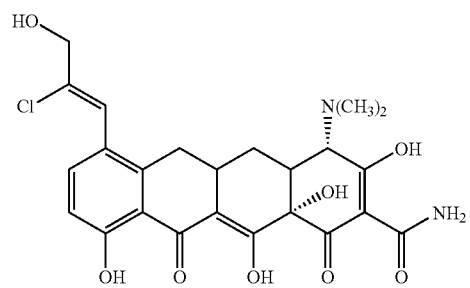

7-(alkynyl)-sancycline (100 mg) was taken in 20 ml of saturated MeOH/HCl and stirred for 20 min. The solvent was then evaporated to give a yellow powder. The structure of this compound has been characterized using $^1$H NMR, HPLC, and MS.

7-(3'-Methoxyphenylethyl)-Sancycline

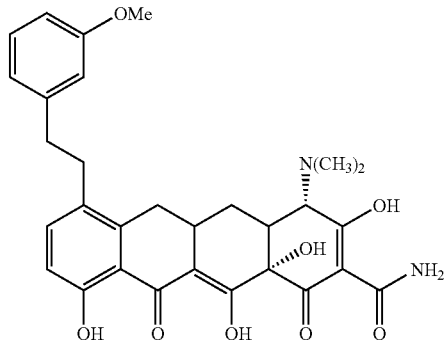

7-(3'-Methoxyphenylethynyl)-sancycline (1 mmol) was taken in saturated solution of MeOH/HCl. To this solution 10% Pd/C was added and was subjected to hydrogenation at 50 psi for 12 hrs. It was then filtered through celite. The solvent was evaporated to give a yellow powder. Finally, it was precipitated from MeOH/diethylether. The structure of this compound has been characterized using $^1$H NMR, HPLC, and MS.

(2-Dimethylamino-Acetylamino)-Sancycline

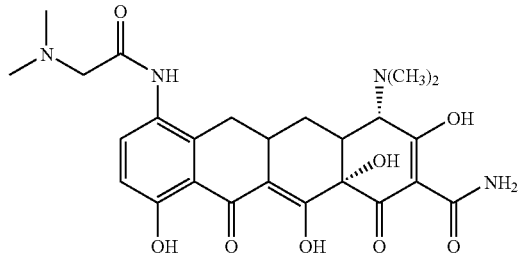

N,N-Dimethylglycine (1.2 mmol) was dissolved in DMF (5 mL) and O-Benzotriazol-1-yl-N,N,N',N'-tramethyluronium hexafluorophosphate (HBTU, 1.2 mmol) was added. The solution was then stirred for 5 minutes at room temperature. To this solution, 7-aminosancycline (1 mmol) was added, followed by the addition of diisopropylethyl amine (DIEA, 1.2 mmol). The reaction was then stirred at room temperature for 2 hours. The solvent, DMF, was removed on vacuum. The crude material was dissolved in 5 mL of MeOH and filtered using autovials and purified using preparative HPLC. The structure of the product has been characterized using $^1$H NMR, HPLC, and MS.

7-(N-Methylsulphonamidopropargylamine) Sancycline

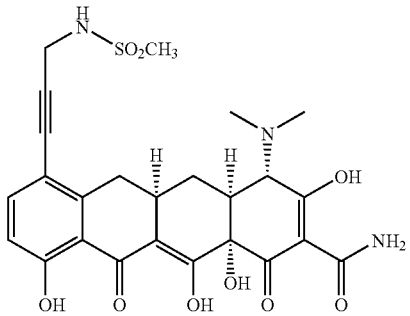

To a mixture of 7-iodosancycline mono trifluoroacetic acid salt (1 g; 1.53 mmoles), palladium II acetate (17.2 mg; 0.076 mmoles), tetrakis triphenylphosphine palladium (176.8 mg; 0.153 mmoles), and copper (I) iodide (49 mg; 0.228 mmoles) was added 15 ml of reagent grade acetonitrile in a clean dry 2 necked round bottom flask. The reaction was purged with a slow steam of argon gas, with stirring, for 5 minutes before the addition (in one portion as a solid) of N-methylsulphonamidopropargyl amine. The sulphonamide was prepared by a method known in the art (J. Med. Chem. 31(3) 1988; 577-82). This was followed by one milliliter of triethylamine (1 ml; 0.726 mg; 7.175 mmoles) and the reaction was stirred, under an argon atmosphere, for approximately 1.0 hour at ambient temperature. The reaction mixture was suctioned filtered through a pad of diatomaceous earth and washed with acetonitrile. The filtrates were reduced to dryness under vacuo and the residue was treated with a dilute solution of trifluororoacetic acid in acetonitrile to adjust the pH to approximately 2. The residue was treated with more dilute trifluoroacetic acid in acetonitrile, resulting in the formation of a precipitate, which was removed via suction filtration. The crude filtrates were purified utilizing reverse phase HPLC with DVB as the solid phase; and a gradient of 1:1 methanol/acetonitrile 1% trifluoroacetic acid and 1% trifluoroacetic acid in water. The appropriate fractions were reduced to dryness under reduced pressure and solid collected. The product was characterized via $^1$H NMR, mass spectrogram and LC reverse phase.

7-(2'-methoxy-5'-formylphenyl)sancycline

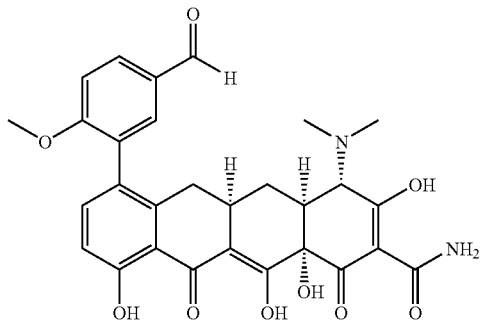

7-iodo-sancycline (1 g, 1.53 mmol), Pd(OAc)$_2$ (34 mg, 0.153 mmol), and MeOH (50 mL) were combined in a 250 mL 2 neck round bottom flask equipped with a condenser and argon line. The solution was then purged with argon (15 min) while heated in an oil bath to approximately 70° C. Sodium carbonate (482 mg, 4.58 mmol) was dissolved in water (3-5 mL) and added to reaction flask. The flask was then purged with argon for another 5 minutes. 2-Methoxy-5-formylphenyl boronic acid (333 mg, 1.83 mmol) was dissolved in MeOH (5 mL) and added to reaction flask. The flask was then purged again with argon for 10 minutes. The reaction was monitored to completion within 3 hours. The contents of the flask were filtered through filter paper and the remaining solvent was evacuated. To make the hydrochloric acid salt, the residue was dissolved in MeOH (sat. HCl) to make the HCl salt. The solution was then filtered and the solvent was evacuated. The product was then characterized by $^1$H NMR, LC-MS.

7-(2'-Methoxy-5'-N,N'-Dimethylaminomethylphenyl)Sancycline

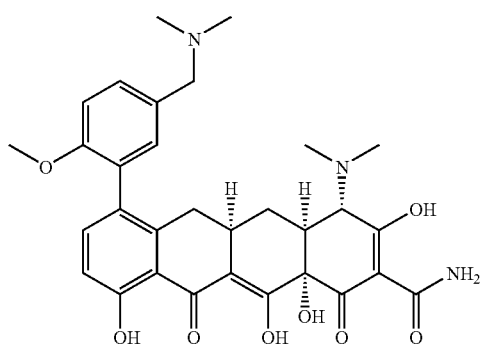

7-(2'-methoxy-5'-formylphenyl)sancycline (1 g, 1.82 mmol), dimethylamine HCl (297 mg, 3.64 mmol), triethylamine (506 µL, 3.64 mmol), and 1,2-DCE (7 mL) were combined in a 40 mL vial. The contents were dissolved within several minutes of shaking or stirring. Sodium triacetoxyborohydride (772 mg, 3.64 mmol) was then added as a solid. The reaction was monitored by HPLC and LC-MS and was complete within 3 hours. The reaction was quenched with MeOH (20 mL) and the solvent was subsequently evacuated. The residue was redissolved in 3 mL DMF and separated on a C-18 column. Fractions from the prep column dried down in-vacuo and the HCl salt was made by dissolving contents in methanol (sat. HCl). The solvent was reduced and a yellow powder obtained. Characterized by $^1$H NMR, LC-MS, HPLC.

7-Furanyl Sancycline 7-iodo sancycline (1.3 mg) and Pd(OAc)$_2$ were taken in 100 mL of methanol and purged with argon for five minutes at 70° C. To this solution was added a solution of sodium carbonate (44 mg) in water (previously purged with argon). A yellow precipitate was obtained and the mixture was heated for another ten minutes. 3-Furanyl boronic acid (333 mg, solution in DMF, purged with argon) was then added and the mixture was heated for another two hours at 70° C. The reaction was monitored by MPLC/MS. When the reaction was complete, the mixture was filtered through celite and the solvent was removed to give a crude material. The crude material was purified by precipitating it with ether (200 ml). The yellow precipitate was filtered and purified using preparative HPLC. The hydrochloride salt was made by dissolving the material in MeOH/HCl and evaporating to dryness. The identity of the resulting solid was confirmed using HPLC, MS, and NMR.

4S-(4α,12aα)]-4-Dimethylamino-7-ethynyl-3,10,12,12a-tetrahydroxy-1,11-dioxo-1,4, 4a,5,5a,6,11,12a-octahydro-naphthacene-2-carboxamide 300 mg of 7-iodosancycline 6A was dissolved in 20 mL of acetonitrile and 2.0 mL triethylamine, 50.0 mg Pd(PPh$_3$)$_4$, 50 mg CuI, 12.5 mg Pd(OAc)$_2$ was added followed by 0.5 mL of trimethylsilylacetylene. The reaction was stirred at room temperature for 4 hours, filtered through a divinyl-benzene cartridge (25 g), and concentrated in vacuo to yield 280 mg of the crude material (monitored by LC/MS). The TMS group was removed by dissolving the crude material in methanol, and adding 250 mg of K$_2$CO$_3$ while stirring for 4 hours at room temperature to yield compound 6E (Scheme 11). The mixture was filtered through a divinylbenzene cartridge. The solvent was removed in vacuo to yield the 7-ethynyl sancycline 6E (Scheme 11) in 60% yield by HPLC.

General Method for Synthesis of 7-acetyl sancycline and 7-carbonylalkyl derivatives of Sancycline 7-ethynyl sancycline 6E (Scheme 11, 300 mg) or ethynyl substituted derivatives of 7-ethynyl sancycline are dissolved in 0.1 mL water, 2 mL of H$_2$SO$_4$, optionally with HgSO$_4$ (170 mg) and stirred overnight at room temperature. The aqueous layer is extracted into butanol, CH$_2$Cl$_2$ or an equivalent and the solvent is removed to yield the crude compound 11A (Scheme 11). 7-acetyl sancycline (11A, Scheme 11) is isolated via C18 reverse-phase HPLC or by other methods in the art to yield pure compound in good yield. M+H=457.4

Conversion of 7-acetyl or 7-carbonylalkyl derivatives of sancycline to oximes or O-alkyl oximes 1 gram of 7-acetyl or 7-carbonylalkyl derivatives of sancycline 11A (Scheme 11, 2 mmol) and hydroxylamine HCl are dissolved in methanol or ethanol and stirred at room temperature for 2 or more hours. The compounds are isolated as the syn and anti isomers appropriately by preparative C18-HPLC or by other methods in the art to yield 7-oximecarbonyl alkyl derivatives of sancycline or 7-O-substituted oximecarbonyl derivatives in good yield. 7-acetyl-oxime (Scheme 11, 11B); M+H=473.5. 11C 7-acetyl-oxime-O-methyl ether; M+H=487.5. The syn or anti isomers are both attainable by fractionation of HPLC solvent volumes.

General Methods and Conversion of 7-acetyl or 7-carbonylalkyl derivatives of sancycline to 7-carbonyl-α-amino derivatives 1 gram of 7-acetyl or 7-carbonylalkyl derivatives of sancycline 11A (Scheme 11, 2 mmol) is reacted with bromine (4 mmol) or typical halogenating agent (NBS, NCS or equivalent, 2-4 mmol) to produce the α-halogenated derivative 11D (Br, Cl) as crude solid. This compound is isolated by extraction or other methods in the art and may be reacted with nucleophilic amines (2-4 mmol) or other nucleophiles (C or O-based) to yield α-amino derivatives of 7-acetyl 11E or other 7-carbonylalkyl derivatives of sancycline.

Scheme 11
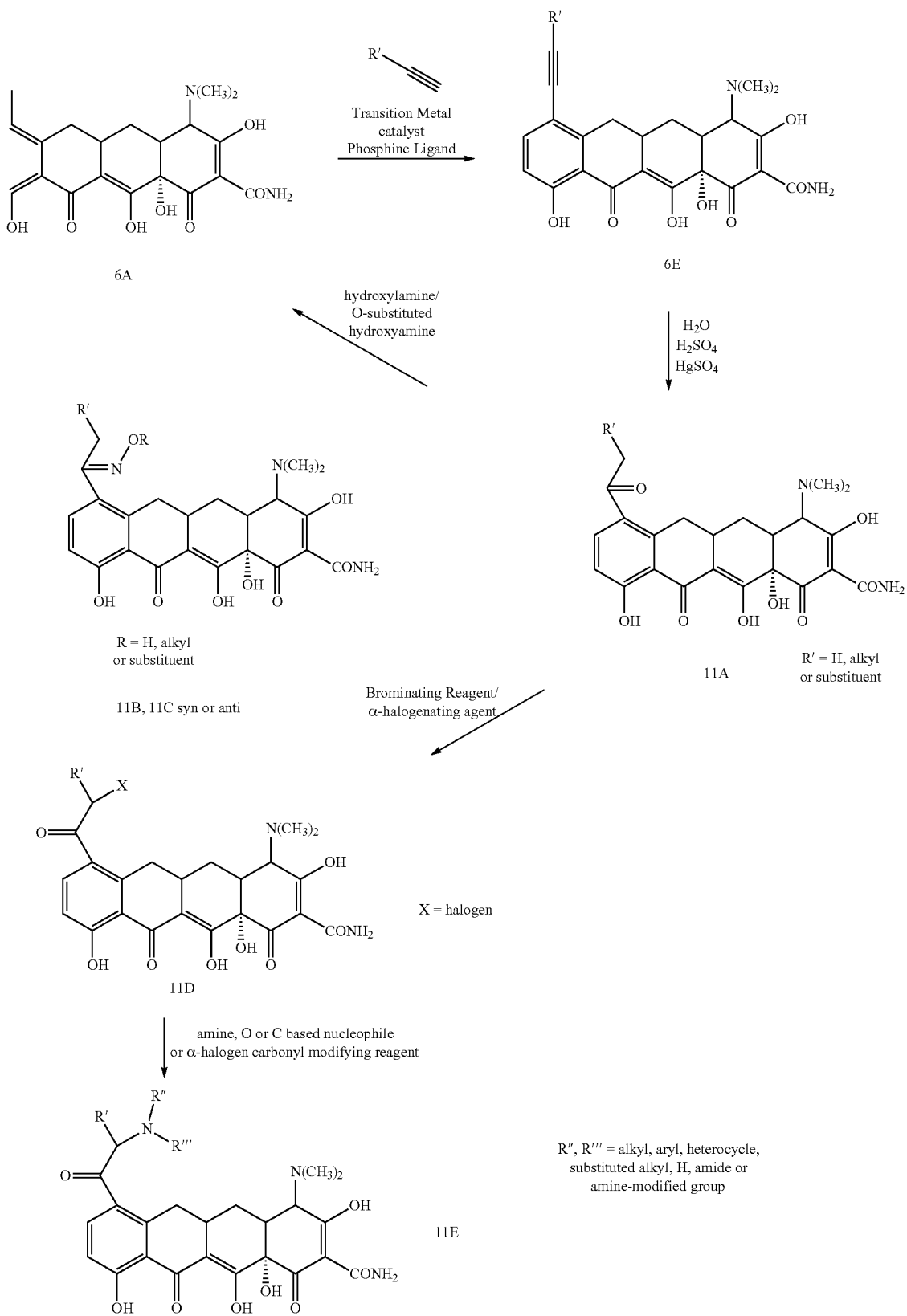

Example 2

Preparation of 9-Substituted Minocyclines

Preparation of 9-Iodominocycline

To 200 ml of 97% methanesulfonic acid was slowly added, at ambient temperature, portionwise [30 g; 56.56 mM] of minocycline-bis-hydrochloride salt. The dark yellow brown solution was then stirred at ambient temperature while [38 g; 169.7 mM] of N-iodosuccinimide was added, in six equal portions, over 3.0 hours time. The reaction was monitored via analytical LC, noting the disappearance of the starting material.

The reaction was slowly quenched into 2 L of ice cold water containing [17.88 g; 1134.1 mM] of sodium thiosulfate with rapid stirring. This quench was stirred for approximately 30 minutes at ambient temperature. The aqueous layer was then extracted with 6×200 ml of ethyl acetate before the aqueous was poured onto [259.8 g; 3.08M] of sodium hydrogen carbonate containing 300 ml of n-butanol. The phases were split and the aqueous extracted with 4×250 ml of n-butanol. The organic fractions were combined and washed with 3×250 ml of water and once with 250 ml of saturated brine. The resulting organic phase was reduced to dryness under reduced pressure. The residue was suspended in methanol (~600 ml) and anhydrous HCl gas was bubbled into this mixture until solution occurred This solution was reduced to dryness under reduced pressure. The filtrates were reduced to dryness under reduced pressure. The resulting material was triturated with 300 ml of methyl t-butyl ether and isolated via filtration. This material was redissolved in 300 ml of methanol and treated with 0.5 g of wood carbon, filtered and filtrates reduced to dryness under reduced pressure. The material was again powdered under methyl t-butyl ether, isolated via suction filtration and washed with more ether, and finally hexanes. The material was vacuum dried to give 22.6 g of a light yellow brown powder.

General Procedure for Preparation of 9-Alkynyl Minocycline Compounds 1 mmol 9-iodo minocycline, 50 mg tetrakis triphenylphosphinato palladate, 12 mg palladium acetate, 32 mg copper (I) iodide are dissolved/suspended in 10 ml acetonitrile. 2 to 5 ml triethylamine and 3 to 5 mmol alkynyl derivative is added. The reaction mixture is vigorously stirred between ambient temperature to 70° C. The reaction time is 2-24 hours. When the reaction is completed the dark suspension is filtered through a celite bed and concentrated. The crude product is purified by prep HPLC. The combined fractions are concentrated and taken up in ~1 ml methanol. ~3 ml HCl saturated methanol is added, and the product is precipitated with ether.

General Procedure for Preparation of 9-Aryl Minocycline Compounds 0.15 mmol of 9-iodominocycline, PdOAc (3.2 mg), 229 µl 2M $Na_2CO_3$ and 2 equivalents of phenyl boronic acid were dissolved/suspended in 10 ml methanol. The reaction flask was purged with argon and the reaction run for a minimum of four hours or until HPLC monitoring shows consumption of starting material and/or the appearance of products. The suspension was filtered through celite, and subject to purification by prep HPLC on a divinylbenzene or CIE reverse-phase column.

9-(4-Trifluoromethoxyphenylureido)-Methyl Minocycline

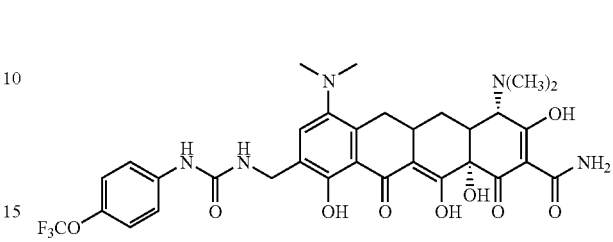

To 3 mL of dimethylformamide was added 150 mg (0.25 mmol) of 9-methyl aminominocycline trihydrochloride and 67 mL (0.50 mmol) of triethylamine at 25° C. With stirring, 75 mL (0.50 mmol) of 4-trifluoromethoxyphenylisocyanate was added and the resulting reaction mixture was stirred at 25° C. for two hours. The reaction was monitored by analytical HPLC (4.6×50 mm reversed phase Luna C18 column, 5 minute linear gradient 1-100% B buffer, A buffer was water with 0.1% trifluoroacetic acid, B buffer was acetonitrile with 0.1% trifluoroacetic acid). Upon completion, the reaction was quenched with 1 mL of water and the pH adjusted to approximately 2.0 with concentrated HCl. The solution was filtered and the compound purified by preparative HPLC. The product yield was 64 mg (37% yield). The purity of the product was 95%, as determined by LCMS (M+1=690).

9-(4'Carboxy phenyl) Minocycline

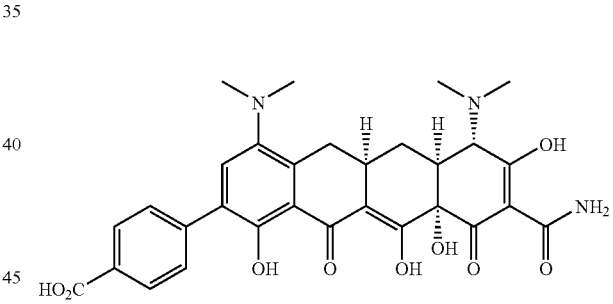

In a clean, dry reaction vessel, was placed 9-iodominocycline [500 mg; 0.762 mmoles]bis HCl salt, palladium (II) acetate [17.2 mg; 0.076 mmoles] along with 10 ml of reagent grade methanol. The solution was immediately purged, with stirring, with a stream of argon gas for approximately 5 minutes. The reaction vessel was brought to reflux and to it was sequentially added via syringe 2M potassium carbonate solution [1.91 ml; 3.81 mmoles], followed by a solution of p-carboxyphenyl boronic acid [238.3 mg; 1.53 mmoles]in 5 ml of reagent DMF. Both of these solutions were previously degassed with argon gas for approximately 5 minutes. The reaction was heated for 45 minutes, the progress was monitored via reverse phase HPLC. The reaction was suctioned filtered through a pad of diatomaceous earth and washed with DMF. The filtrates were reduced to an oil under vacuum and residue treated with t-butylmethyl ether. Crude material was purified via reverse phase HPLC on DVB utilizing a gradient of water and methanol/acetonitrile containing 1.0% trifluoroacetic acid. Product confirmed by mass spectrum: found M+1 578.58; the structure corroborated with $^1$H NMR.

Example 3

Assessment of Antimalarial Activity In Vitro

The following protocol is adapted from *Antimicrob. Agents Chemother.* 40:1600-1603, 1996 and was used in the instant examples.

Preparation of parasites: Strains of *P. falciparum* were grown continuously in culture. A 6% suspension of human type A+ erythrocytes were prepared in culture medium which consists of powdered RPMI 1640 diluted in sterile water with 25 mM HEPES, 32 mM $NaHCO_3$ and 10% heat-inactivated human type A+ fresh frozen plasma (in acid-citrate-dextrose anticoagulant). Stock cultures were maintained in 5 mL of the 6% erythrocyte suspension in 25 mL tissue culture flasks. The flasks were flushed with a gas mixture of 5% $CO_2$, 5% $O_2$ and 90% $N_2$. The flasks were then sealed and incubated at 37° C. The cultures were maintained so that less than 2% of the erythrocytes were infected at any one time. For experiments, samples of the stock cultures were diluted in culture medium containing sufficient noninfected type A+human erythrocytes to yield a final hematocrit of 1.5% and parasitemia of 0.25 to 0.5% in preparation of addition to the microtiter plates.

Preparation of Drugs: all Compounds were Dissolved Initially in Dmso at a Stock concentration of 20 mg/mL. The final dilution contained less than 1% DMSO which has no measurable effect on the parasites in this system.

Microtiter plate setup: 25 μl of the culture medium was placed in each well of a 96 well microtiter plate. 25 μl of the DMSO drug solution was added to two separate wells of the plate. After the drugs were added to the wells, an automatic diluter was used to make serial twofold dilutions. A constant volume (200 μl) of the parasitized erythrocyte suspension was added to each well of the microtiter plate except for the controls. The control were treated with 200 μl of an equivalent suspension of nonparasitized type A human erythrocytes. The total volume in every well was 225 μl. After preparation, the plates were placed in a humidified airtight box with a mixture of 5% $O_2$, 5% $CO_2$ and 90% $N_2$, sealed and placed in an incubator at 30° C. for 24 to 48 hours.

Harvesting parasites and scintillation counting: At the end of the second incubation period, each plate was harvested using a automated cell harvester. The instrument essentially aspirates and deposits the particulate contents of each of the wells onto small disks of filter paper which are then thoroughly washed with distilled water. Each disk is then counted using a scintillation counter.

Table 2, which follows, shows the relative MIC values obtained for certain substituted tetracycline compounds of the invention. * represents good inhibition of parasite growth,  represents very good inhibition of parasite growth, * represent extremely good inhibition of parasite growth. MIC represents the minimum concentration of the compound that inhibits *P. falciparum* growth after incubation at 30° C. for 24 to 48 hours.

TABLE 2

| ID | STRUCTURE | M + H | Mol Weight | Toxicity | Activity |
|----|-----------|-------|------------|----------|----------|
| A  | 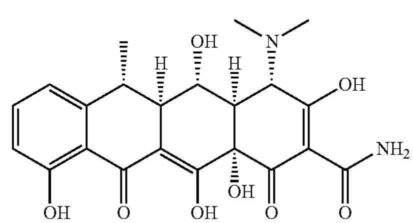          |       | 444.4402   |          | ***      |
| B  | 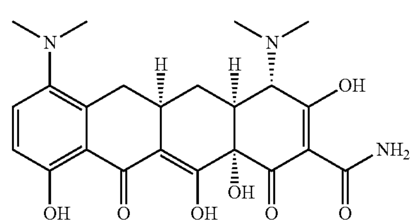          |       | 457.4822   |        | *      |
| C  | 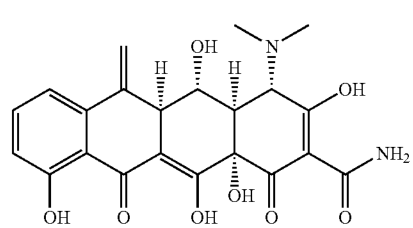          |       | 442.4244   |        | *      |

TABLE 2-continued

| ID | STRUCTURE | M + H | Mol Weight | Toxicity | Activity |
|---|---|---|---|---|---|
| D | 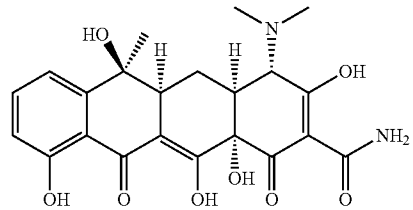 | | 444.4402 |  | * |
| E | 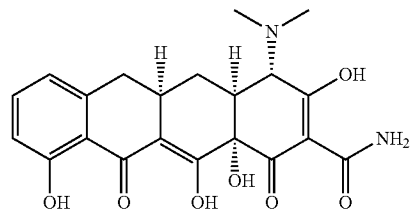 | | 414.414 | * | *** |
| F | 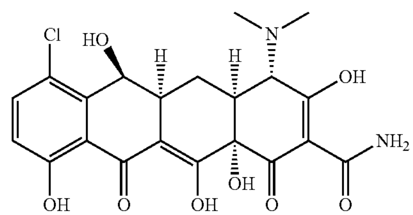 | | 464.8585 | | *** |
| G | 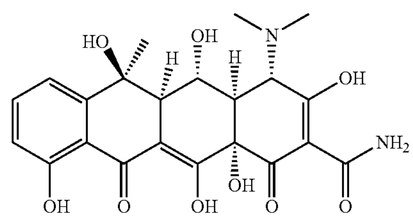 | | 460.4396 |  | * |
| H | 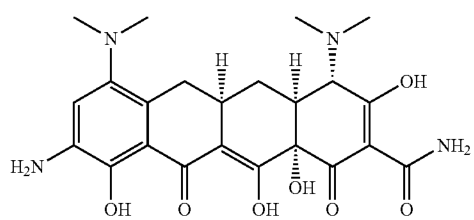 | 473.4 | 472.4968 | | ** |
| I | 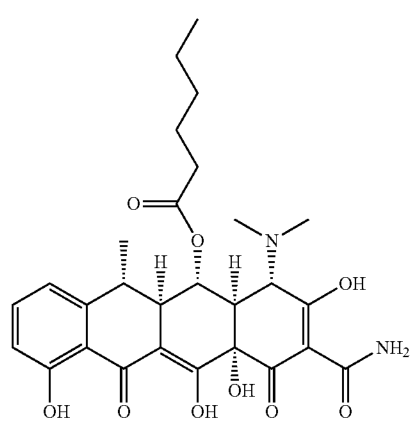 | 543.6 | 542.5846 | * | ** |

TABLE 2-continued

| ID | STRUCTURE | M + H | Mol Weight | Toxicity | Activity |
|----|-----------|-------|------------|----------|----------|
| J  | 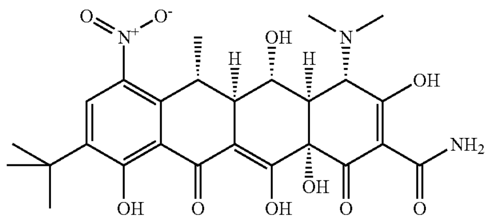          | 546.5 | 545.545    |          | **       |
| K  | 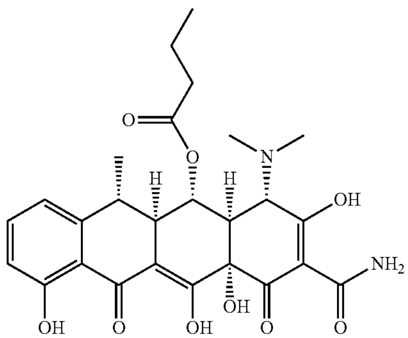          | 515.5 | 514.531    | *        | **       |
| L  | 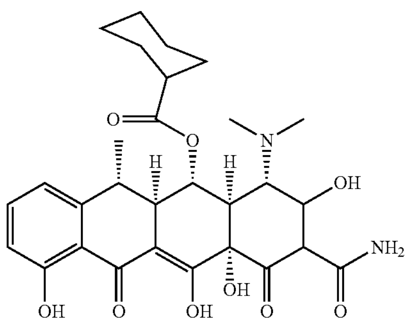          | 555.6 | 554.5956   | *        | **       |
| M  | 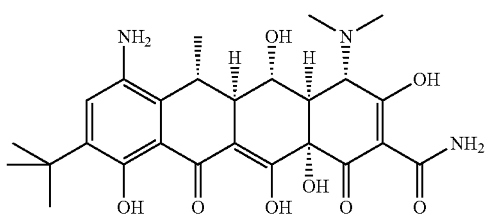          | 516.6 | 515.562    |          | **       |
| N  | 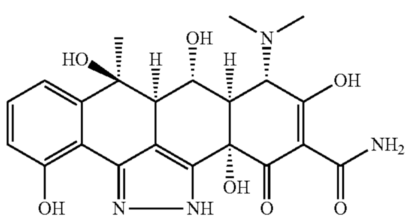          | 557.5 | 456.4542   |          | **       |
| O  | 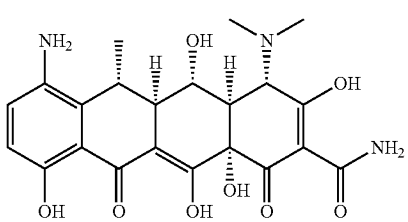          | 460.4 | 459.4548   |          | **       |

TABLE 2-continued

| ID | STRUCTURE | M + H | Mol Weight | Toxicity | Activity |
|---|---|---|---|---|---|
| P | 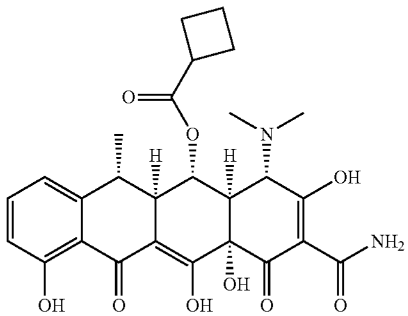 | 527 | 526.542 | * | ** |
| Q | 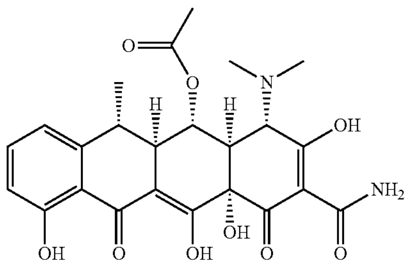 | 487.5 | 486.4774 | | ** |
| R | 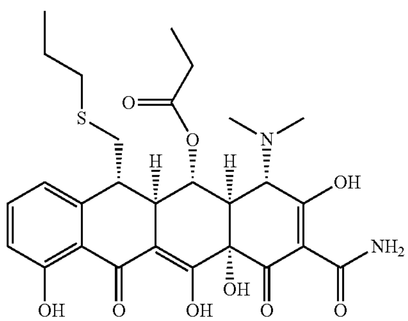 | 575.6 | 574.6446 | | ** |
| S | 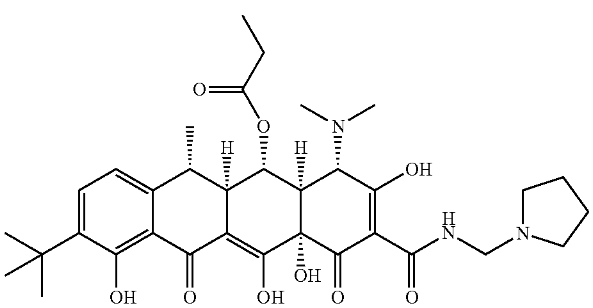 | 640.5 | 639.7442 | | * |
| T | 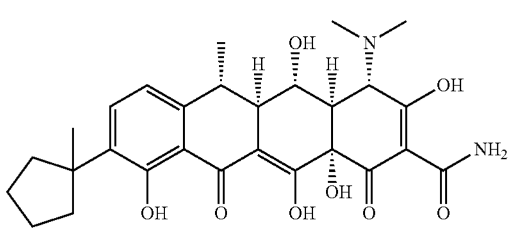 | 527.6 | 526.5852 | * | *** |

TABLE 2-continued
| ID | STRUCTURE | M + H | Mol Weight | Toxicity | Activity |
|---|---|---|---|---|---|
| U | 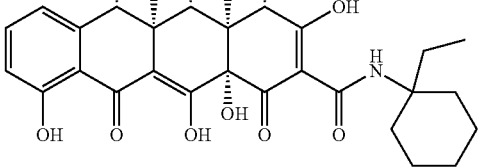 | 555.4 | 554.6388 | | ** |
| V | 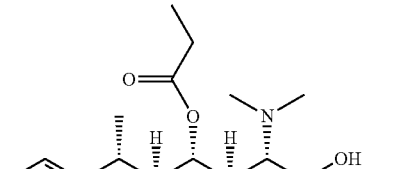 | 501.3 | 500.5042 | * | ** |
| W | 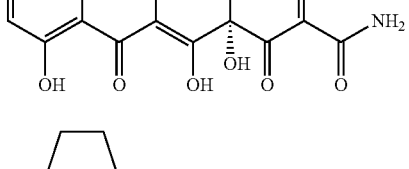 | 545.4 | 544.6184 | * | ** |
| X | 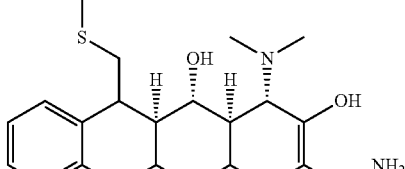 | 513.5 | 512.5152 | | * |
| Y | 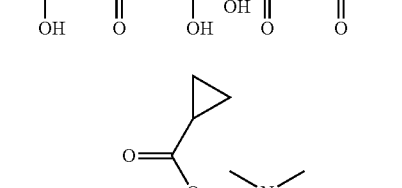 | 499.3 | 498.4884 | | * |

TABLE 2-continued

| ID | STRUCTURE | M + H | Mol Weight | Toxicity | Activity |
|----|-----------|-------|------------|----------|----------|
| Z  | 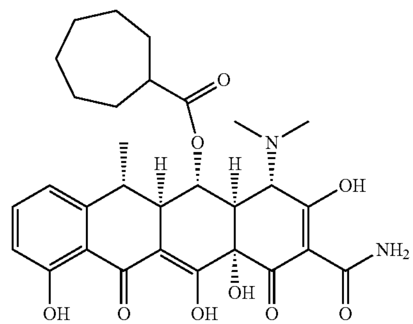          | 569.4 | 568.6224   |          | ** |
| AA | 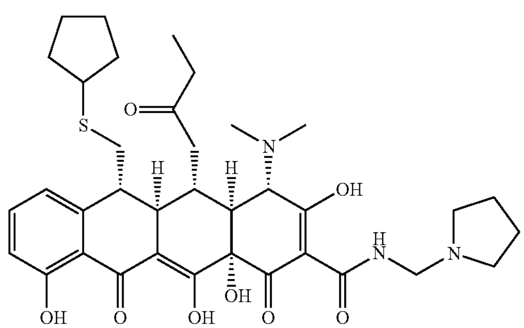          | 684.8 | 683.8152   | *        | * |
| AB | 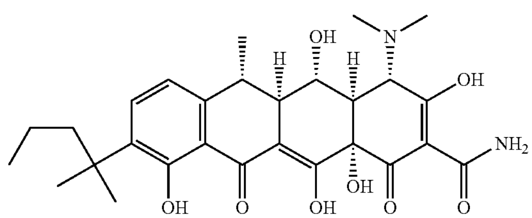          | 529   | 528.601    |          | ** |
| AC | 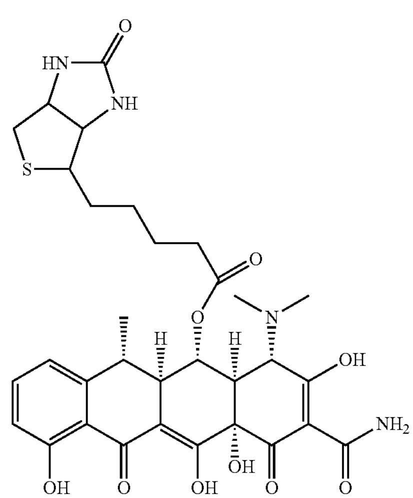          | 671.3 | 670.733    |          | * |

TABLE 2-continued

| ID | STRUCTURE | M + H | Mol Weight | Toxicity | Activity |
|---|---|---|---|---|---|
| AD | 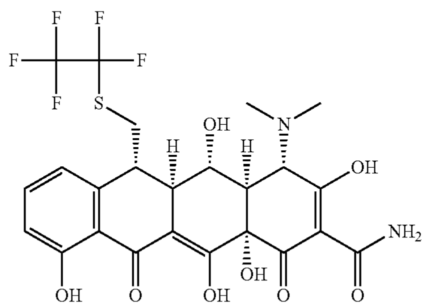 | 595 | 594.5063 | | ** |
| AE | 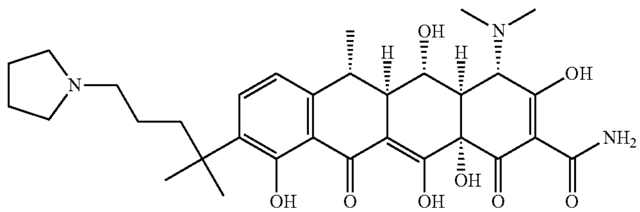 | | 597.707 | | * |
| AF | 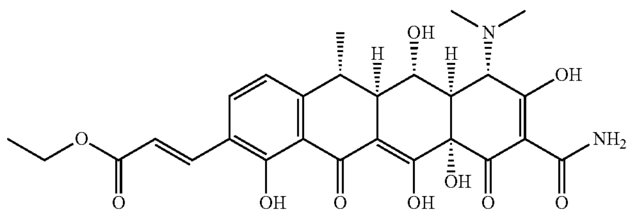 | 543 | 542.5414 | | * |
| AG | 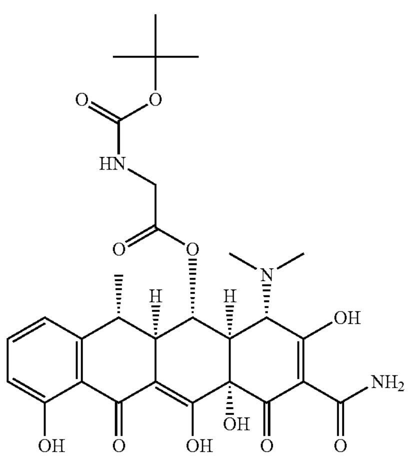 | 602 | 601.609 | | * |
| AH | 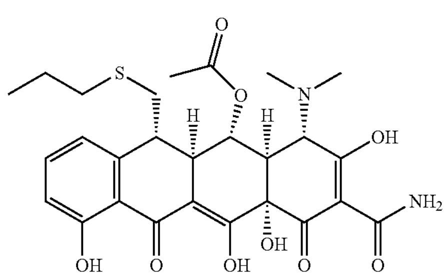 | 561 | 560.6178 | | ** |

TABLE 2-continued

| ID | STRUCTURE | M + H | Mol Weight | Toxicity | Activity |
|---|---|---|---|---|---|
| AI | 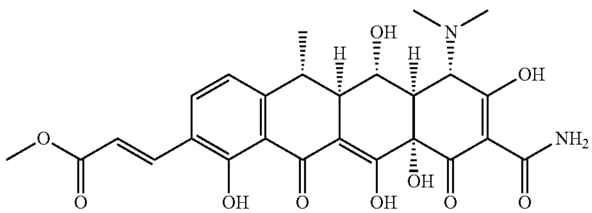 | | 528.5146 | | ** |
| AJ | 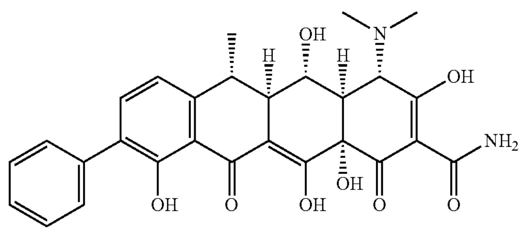 | 529 | 520.5378 | | ** |
| AK | 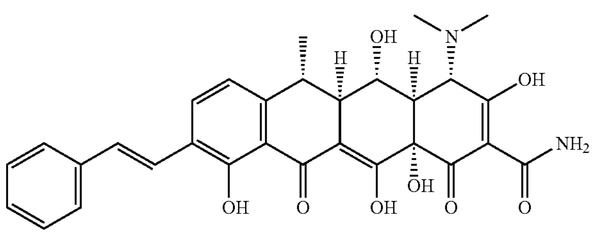 | | 546.5756 | * | ** |
| AL | 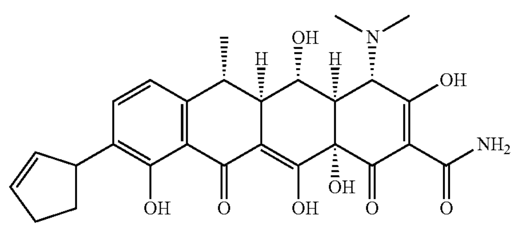 | | 510.5426 | | * |
| AM | 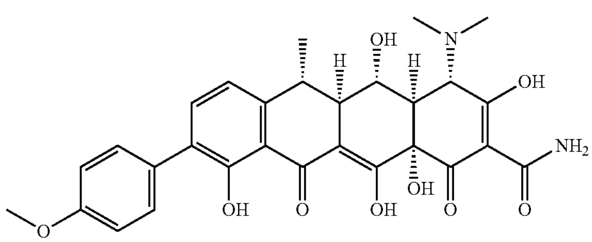 | 551 | 550.564 | * | ** |
| AN | 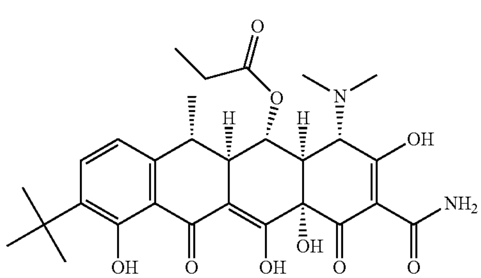 | 557 | 556.6114 |  |  |

TABLE 2-continued
| ID | STRUCTURE | M + H | Mol Weight | Toxicity | Activity |
|---|---|---|---|---|---|
| AO | 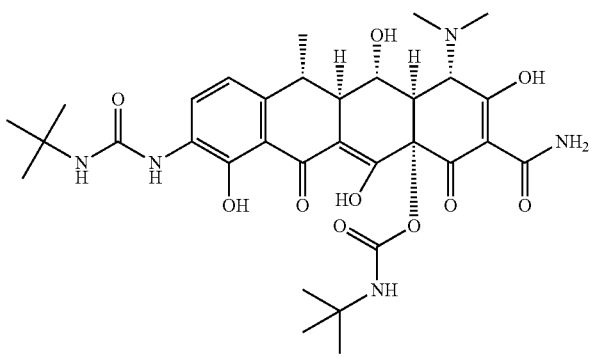 | | 657.7192 | | * |
| AP | 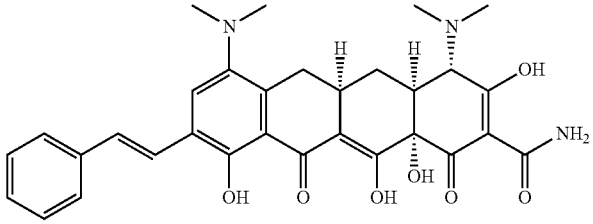 | 560 | 559.6176 | * | ** |
| AQ | 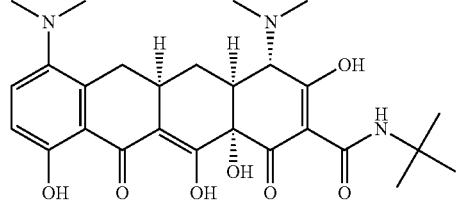 | 514 | 513.5894 | | ** |
| AR | 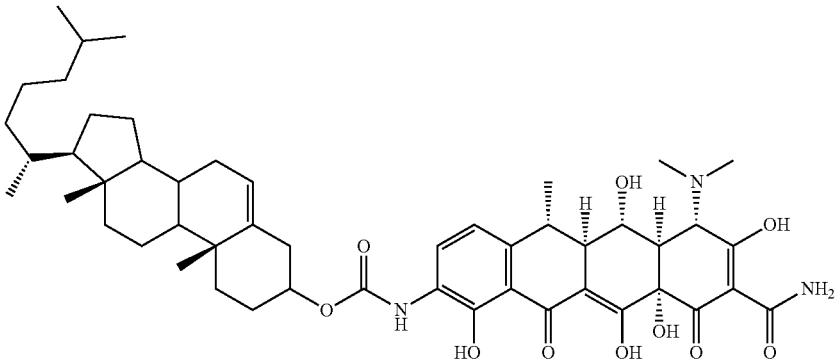 | | 872.1092 | | * |
| AS | 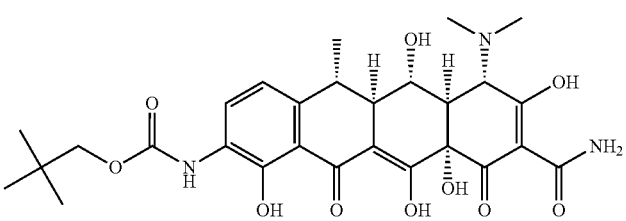 | | 573.5986 | * | ** |

TABLE 2-continued

| ID | STRUCTURE | M + H | Mol Weight | Toxicity | Activity |
|---|---|---|---|---|---|
| AT | 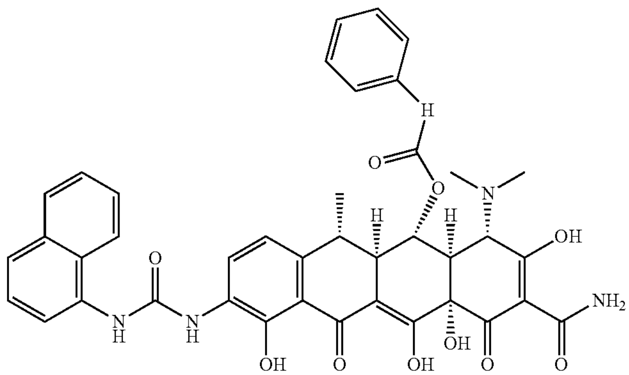 | | 747.7598 | | * |
| AU | 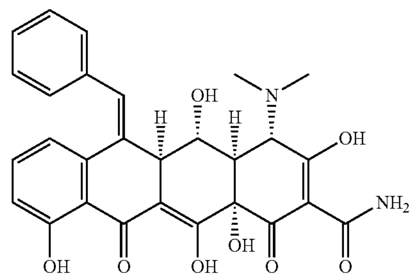 | | 518.522 | | * |
| AV | 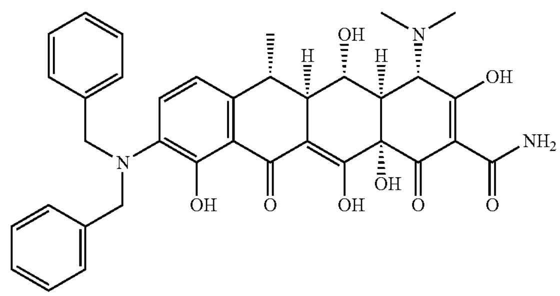 | 640 | 639.7036 | | ** |
| AW | 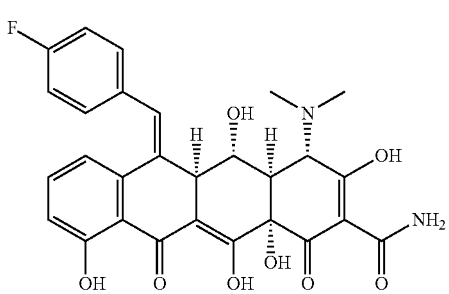 | 537 | 536.5125 | | * |
| AX | 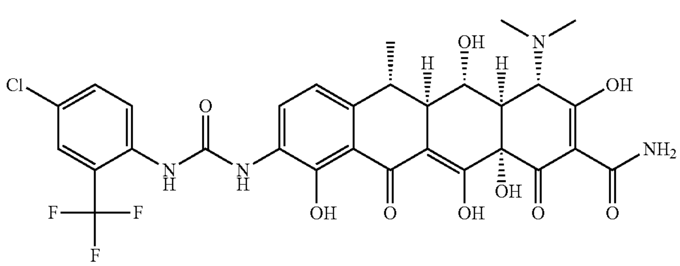 | | 681.0208 | * | ** |

TABLE 2-continued

| ID | STRUCTURE | M + H | Mol Weight | Toxicity | Activity |
|---|---|---|---|---|---|
| AY | 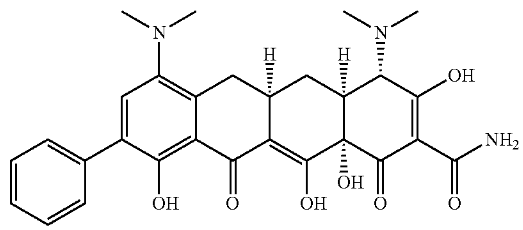 | 534 | 533.5798 | | ** |
| AZ | 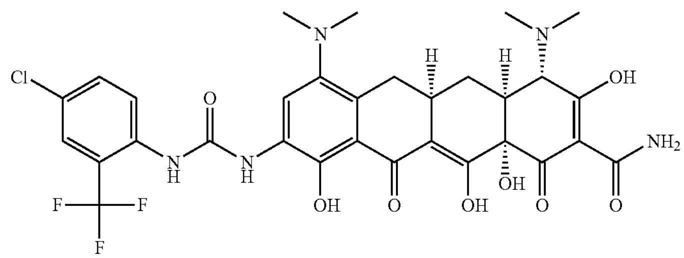 | | 694.0628 | | ** |
| BA | 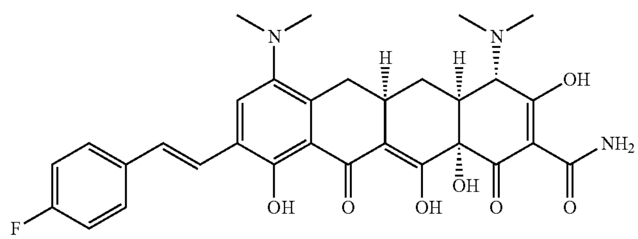 | | 577.6081 | * | ** |
| BB | 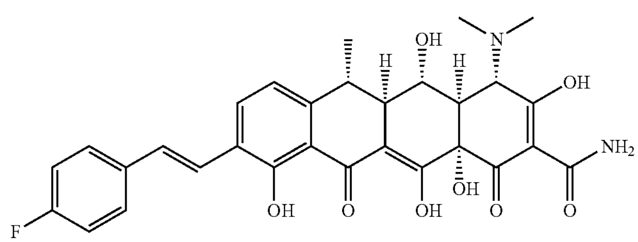 | | 564.5661 | * | ** |
| BC | 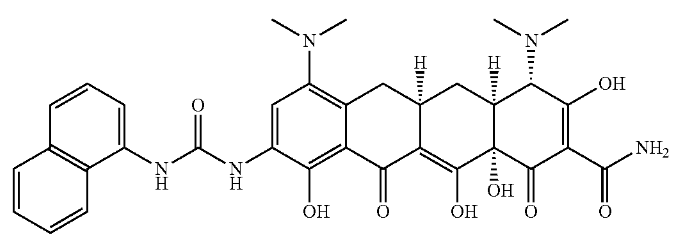 | | 641.6792 | ** | * |
| BD | 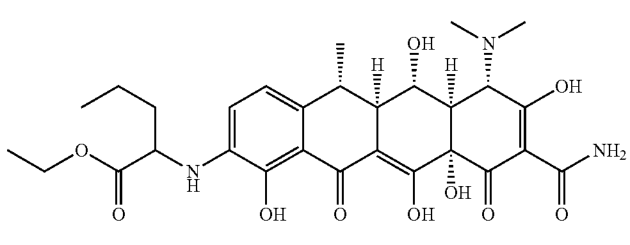 | 588 | 587.6254 | | ** |

TABLE 2-continued

| ID | STRUCTURE | M + H | Mol Weight | Toxicity | Activity |
|----|-----------|-------|------------|----------|----------|
| BE | 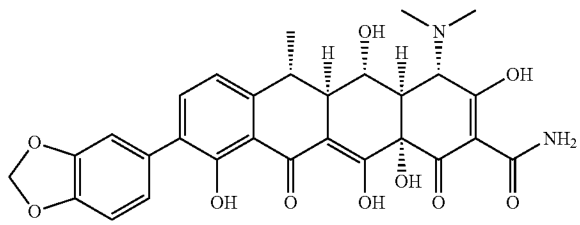 | | 564.5476 | * | ** |
| BF | 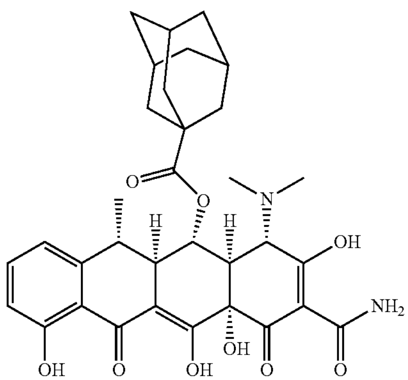 | 607.3 | 606.6712 | * | *** |
| BG | 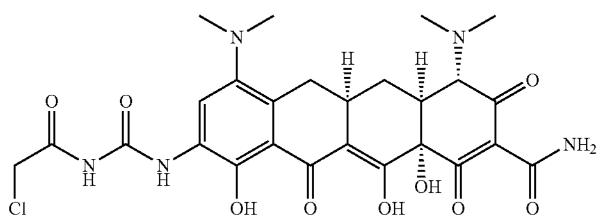 | | 592.0041 | | * |
| BH | 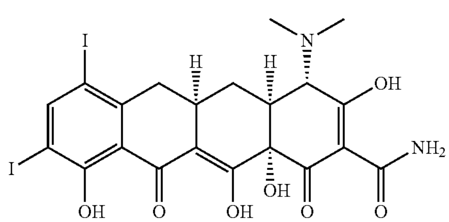 | 667 | 666.2072 | * | ** |
| BI | 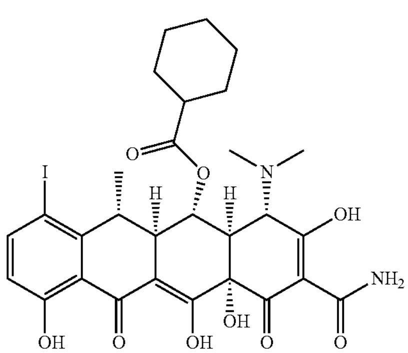 | 681 | 680.4922 | | ** |

TABLE 2-continued

| ID | STRUCTURE | M + H | Mol Weight | Toxicity | Activity |
|---|---|---|---|---|---|
| BJ | 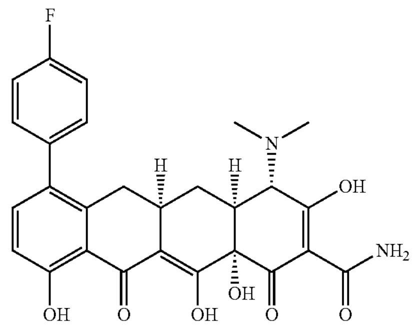 | 509.3 | 508.5021 | * | ** |
| BK | 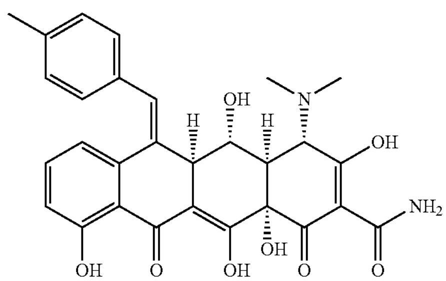 | 533.3 | 532.5488 | | ** |
| BL | 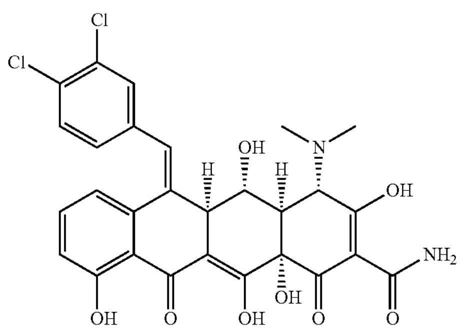 | 588.3 | 587.4122 | | ** |
| BM | 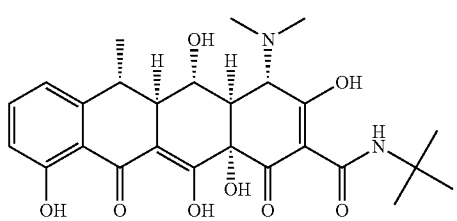 | 501.4 | 500.5474 | * | |
| BN | 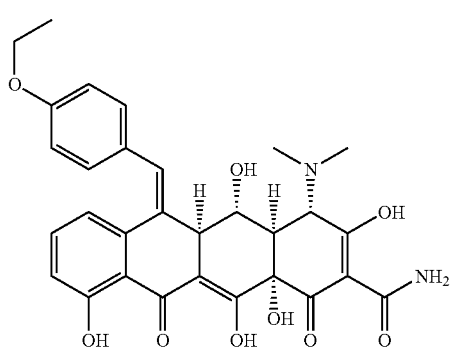 | 563.3 | 562.575 | | ** |

TABLE 2-continued

| ID | STRUCTURE | M + H | Mol Weight | Toxicity | Activity |
|---|---|---|---|---|---|
| BO | 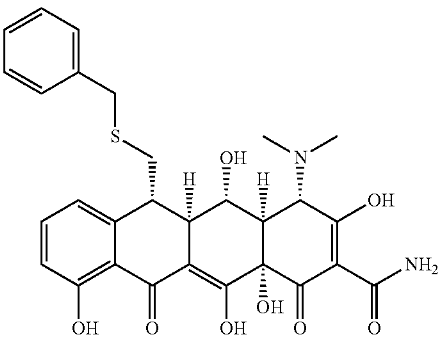 | 567.3 | 566.6246 | | * |
| BP | 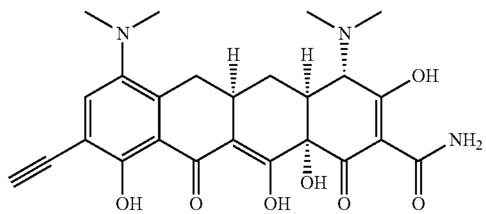 | 482.2 | 481.5042 | | * |
| BQ | 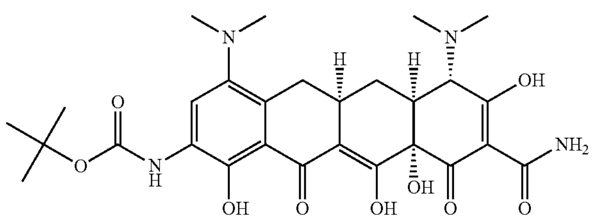 | | 572.6138 | * | * |
| BR | 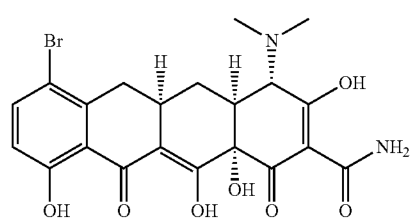 | 494.1 | 493.3101 | * | ** |
| BS | 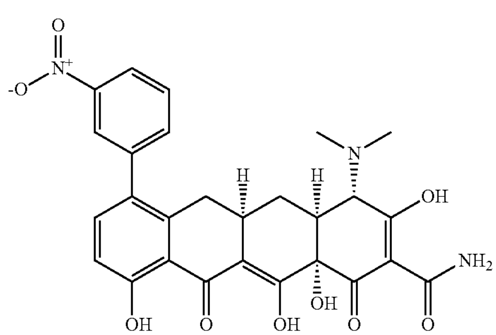 | | 535.5092 | * | *** |
| BT | 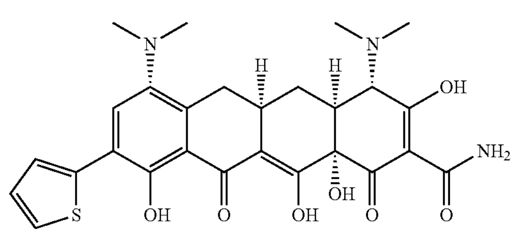 | 540.2 | 539.602 | * | ** |

TABLE 2-continued

| ID | STRUCTURE | M + H | Mol Weight | Toxicity | Activity |
|---|---|---|---|---|---|
| BU | 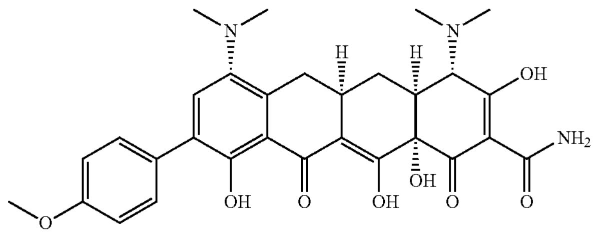 | 564.6 | 563.606 | * | ** |
| BV | 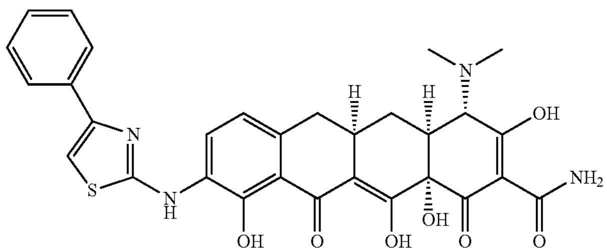 | 589.3 | 588.6338 | | ** |
| BW | 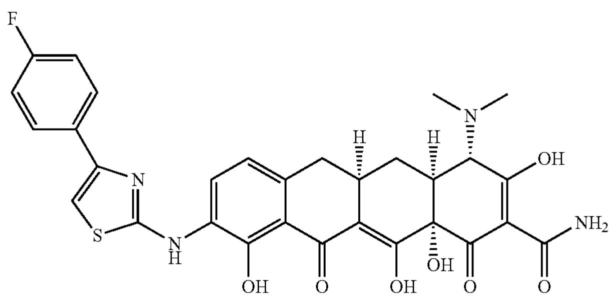 | 607.3 | 606.6243 | * | ** |
| BX | 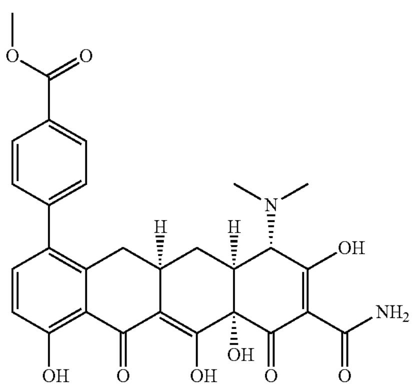 | 549.3 | 548.5482 | * | ** |
| BY | 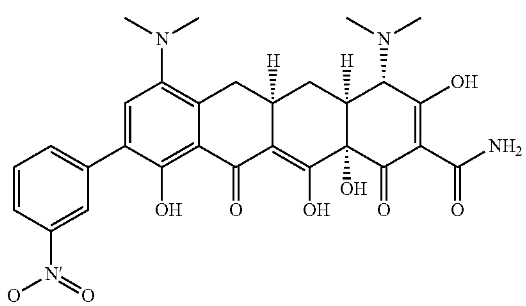 | 579.3 | 578.5774 | * | * |

TABLE 2-continued

| ID | STRUCTURE | M + H | Mol Weight | Toxicity | Activity |
|---|---|---|---|---|---|
| BZ | 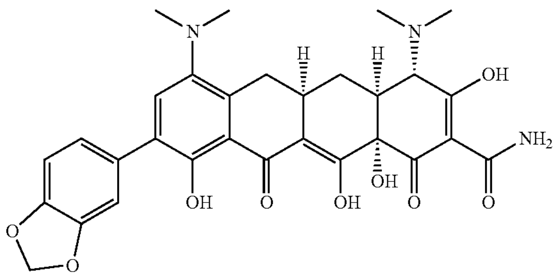 | 578.3 | 577.5896 | | ** |
| CA | 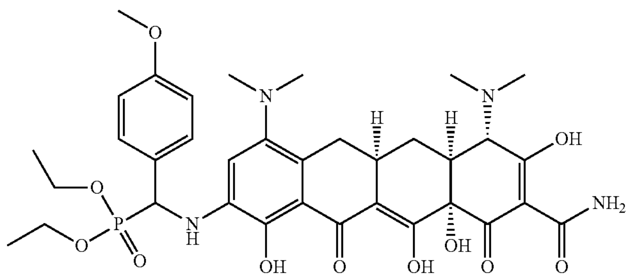 | 729.4 | 728.73446 | ** | * |
| CB | 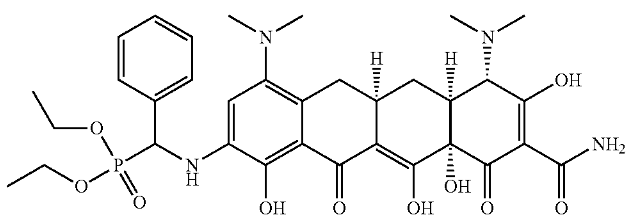 | 699.4 | 698.70826 | ** | * |
| CC | 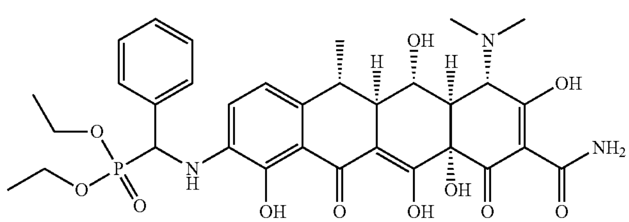 | 686.4 | 685.66626 | | ** |
| CD | 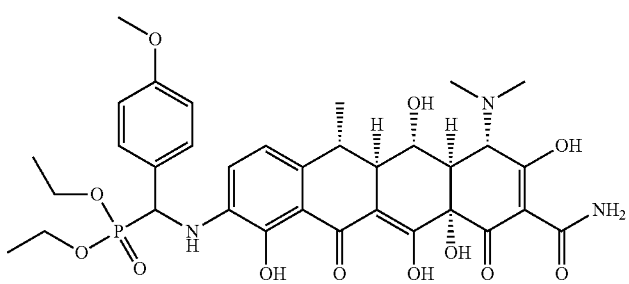 | 716.3 | 715.69246 | | ** |

TABLE 2-continued

| ID | STRUCTURE | M + H | Mol Weight | Toxicity | Activity |
|---|---|---|---|---|---|
| CE | 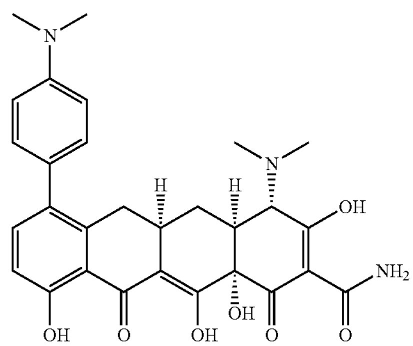 | 534.3 | 533.5798 | * | ** |
| CF | 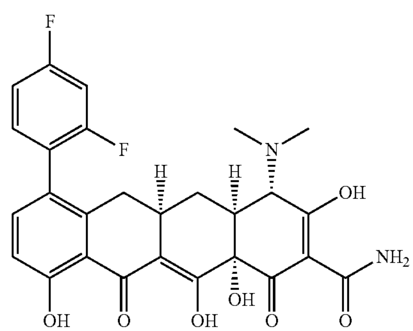 | 527.3 | 526.4926 | * | *** |
| CG | 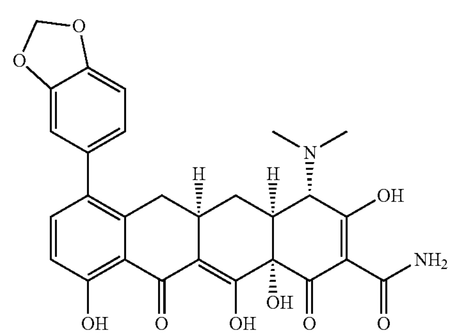 | 535.2 | 534.5214 | * | ** |
| CH | 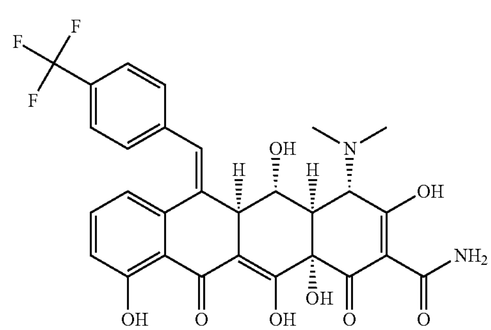 | 587.2 | 586.5203 | * | ** |

TABLE 2-continued
| ID | STRUCTURE | M + H | Mol Weight | Toxicity | Activity |
|---|---|---|---|---|---|
| CI | 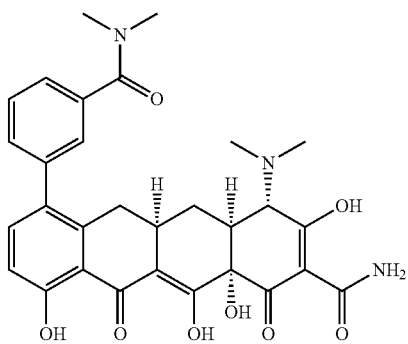 | 562.3 | 561.5902 |  | * |
| CJ | 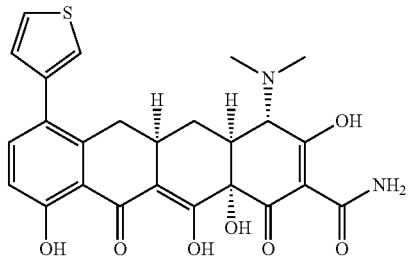 | 497.2 | 496.5338 | * | ** |
| CK | 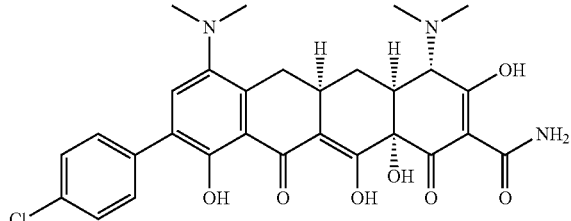 | 569.2 | 568.0249 |  | ** |
| CL | 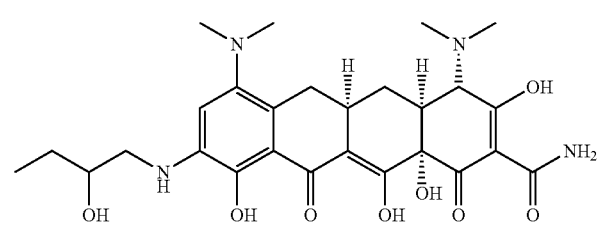 | 545.3 | 544.6034 |  | ** |
| CM | 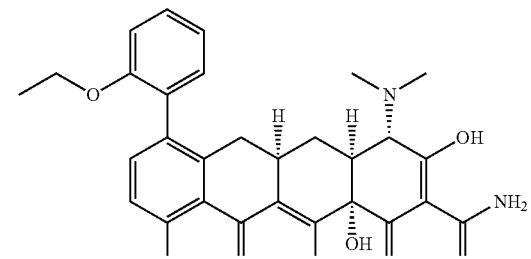 | 535.3 | 534.5646 | * | *** |

TABLE 2-continued

| ID | STRUCTURE | M + H | Mol Weight | Toxicity | Activity |
|---|---|---|---|---|---|
| CN | 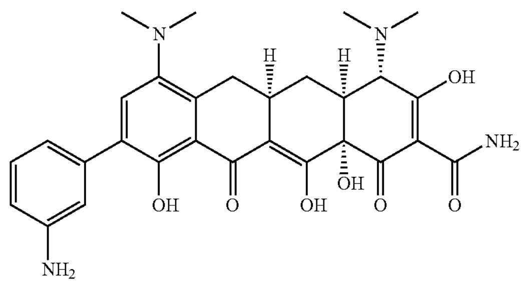 | 549.3 | 548.5944 | | ** |
| CO | 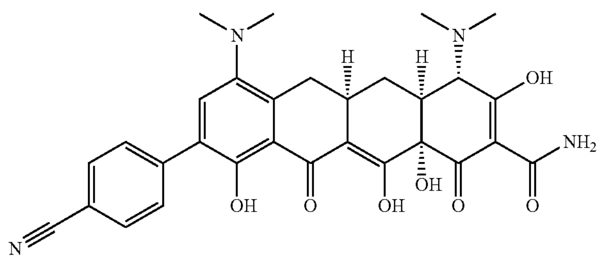 | | 558.5896 | | ** |
| CP | 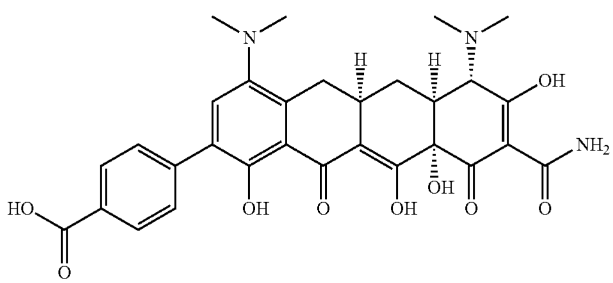 | | 577.5896 | * | ** |
| CQ | 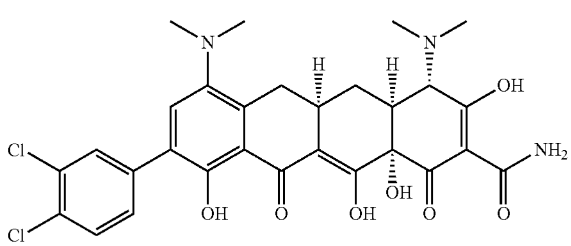 | 603.3 | 602.47 | * | * |
| CR | 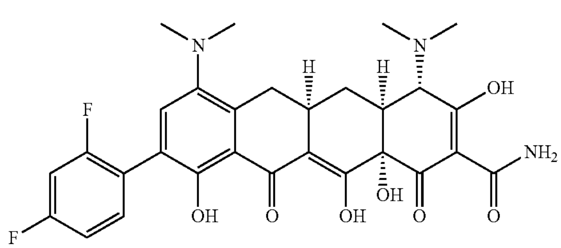 | 570.3 | 569.5608 | * | ** |

TABLE 2-continued
| ID | STRUCTURE | M + H | Mol Weight | Toxicity | Activity |
|---|---|---|---|---|---|
| CS | 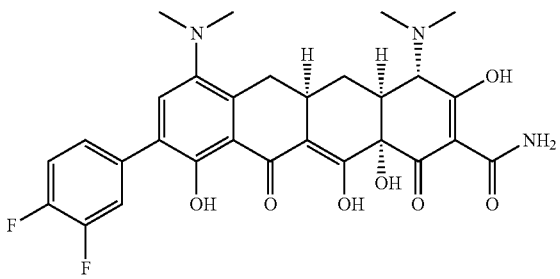 | 570.3 | 569.5608 | * | * |
| CT | 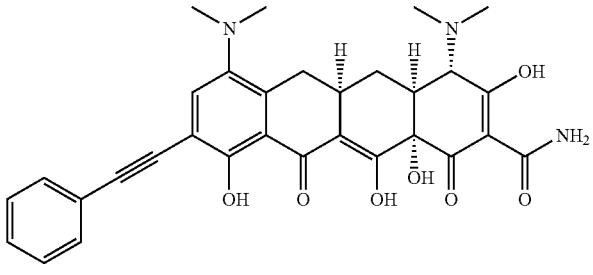 | 558.3 | 557.6018 | * | ** |
| CU | 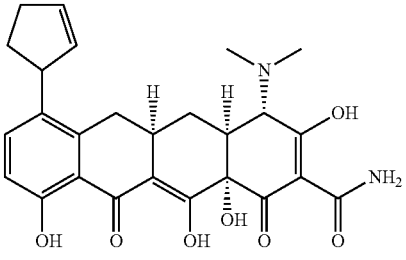 | 481.2 | 480.5164 | * | ** |
| CV | 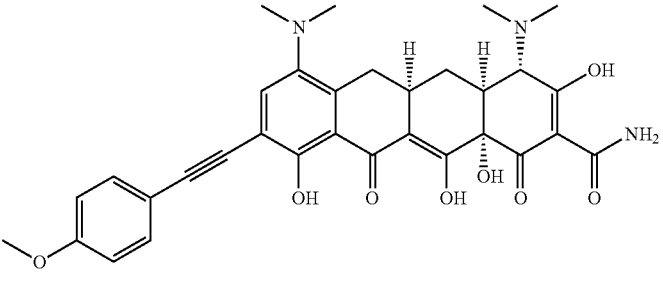 | 588.3 | 587.628 | * | ** |
| CW | 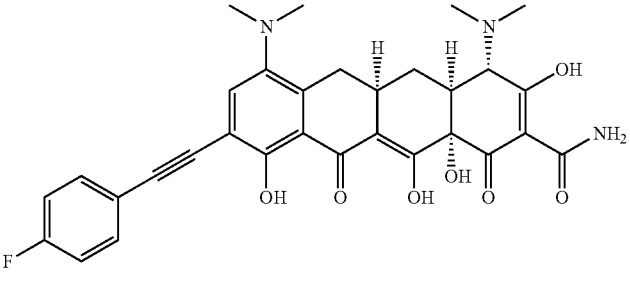 | 576.2 | 575.5923 | * | ** |

TABLE 2-continued

| ID | STRUCTURE | M + H | Mol Weight | Toxicity | Activity |
|---|---|---|---|---|---|
| CX | 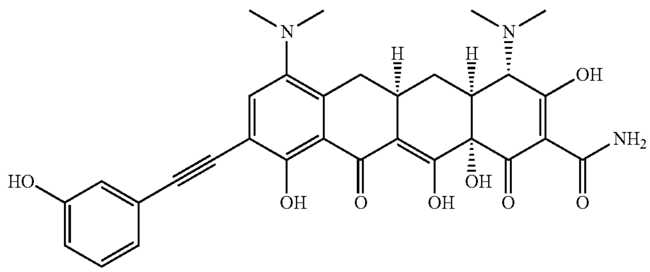 | 574.2 | 573.6012 | * | * |
| CY | 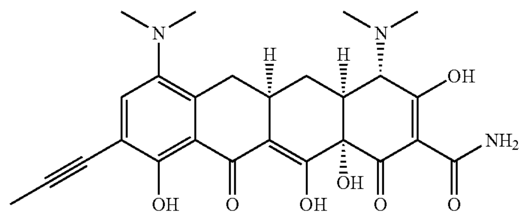 | 496.2 | 495.531 | ** | * |
| CZ | 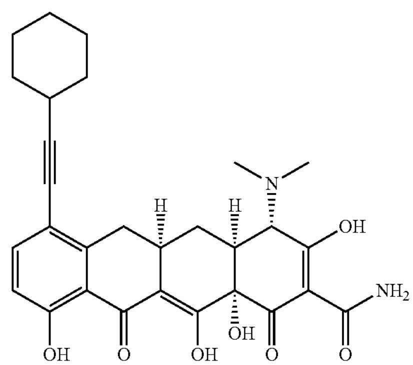 | 521.2 | 520.581 | * | ** |
| DA | 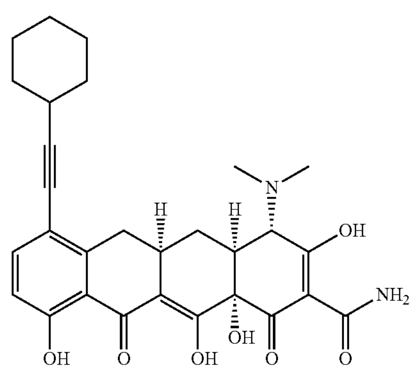 | 521.2 | 520.581 | * | ** |

TABLE 2-continued

| ID | STRUCTURE | M + H | Mol Weight | Toxicity | Activity |
|----|-----------|-------|------------|----------|----------|
| DB | 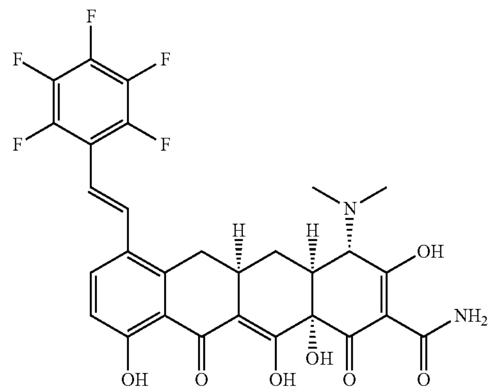 | 607.1 | 606.5019 | * | ** |
| DC | 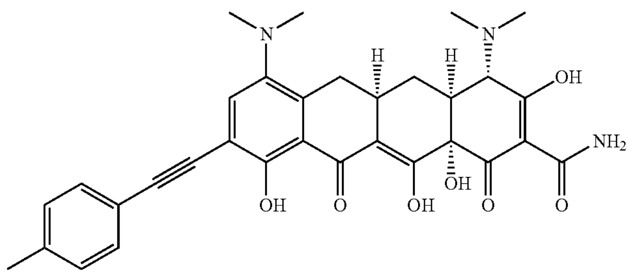 | 572.3 | 571.8286 | * | *** |
| DD | 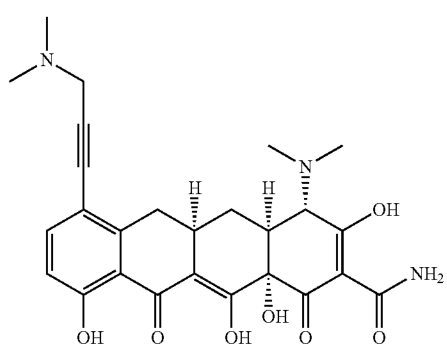 | 496.3 | 495.531 |  | * |
| DE | 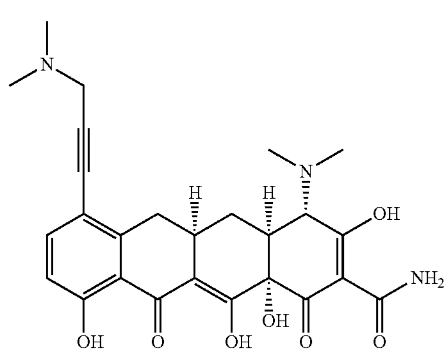 | 496.3 | 495.531 | | *** |

TABLE 2-continued
| ID | STRUCTURE | M + H | Mol Weight | Toxicity | Activity |
|---|---|---|---|---|---|
| DF | 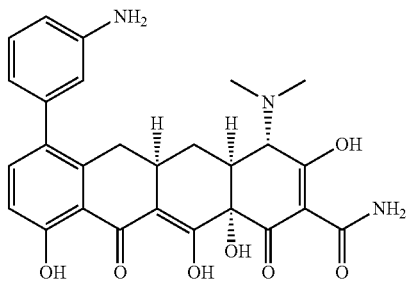 | 506.3 | 505.5262 |  | * |
| DG | 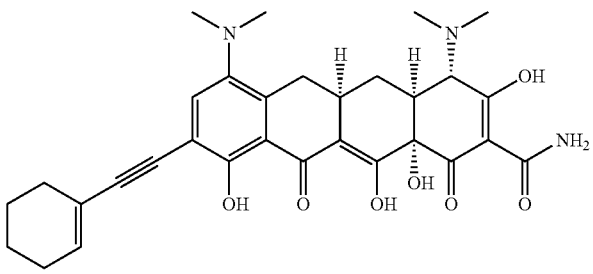 | 562.3 | 561.6334 | * | ** |
| DH | 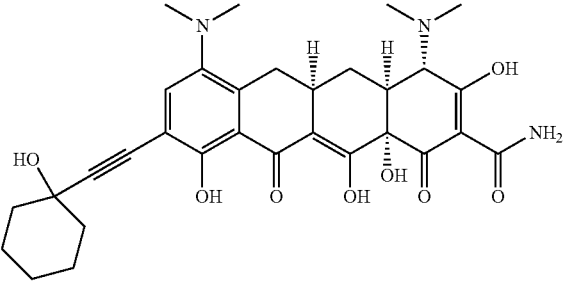 | 533.2 | 579.6486 |  |  |
| DI | 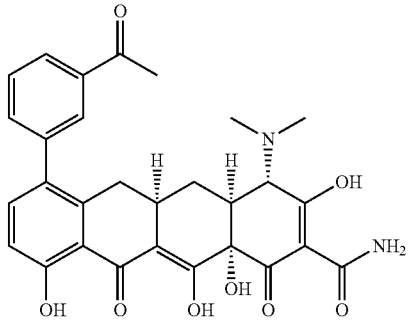 | 533.2 | 532.5488 | * | *** |
| DJ | 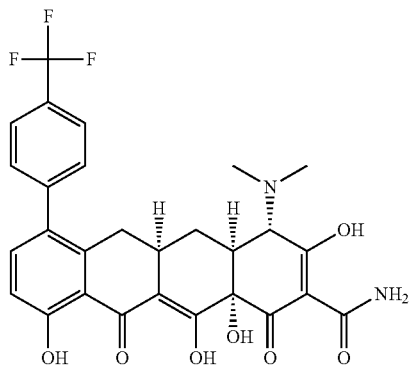 | 559.2 | 558.5099 | * | ** |

TABLE 2-continued
| ID | STRUCTURE | M + H | Mol Weight | Toxicity | Activity |
|---|---|---|---|---|---|
| DK | 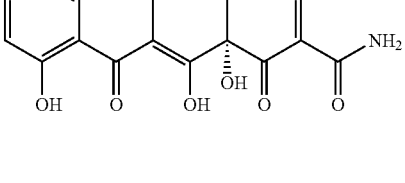 | 505.3 | 504.5384 | * | ** |
| DL | 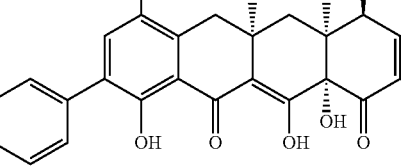 | 578.3 | 577.5896 | ** | * |
| DM | 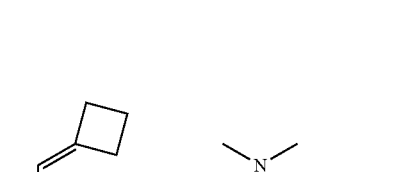 | 481.2 | 480.5164 | * | ** |
| DN | 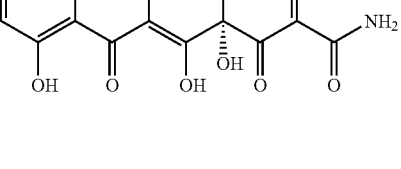 | 535.2 | 534.5646 | * | ** |

TABLE 2-continued

| ID | STRUCTURE | M + H | Mol Weight | Toxicity | Activity |
|----|-----------|-------|------------|----------|----------|
| DO | 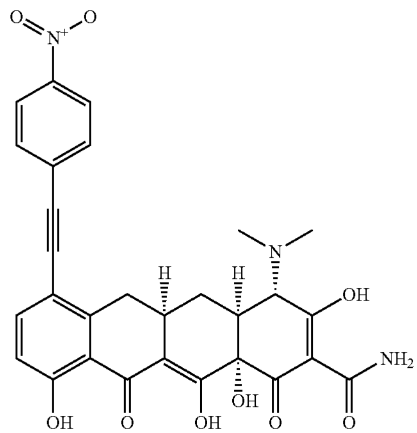 | 560.2 | 559.5312 | * | ** |
| DP | 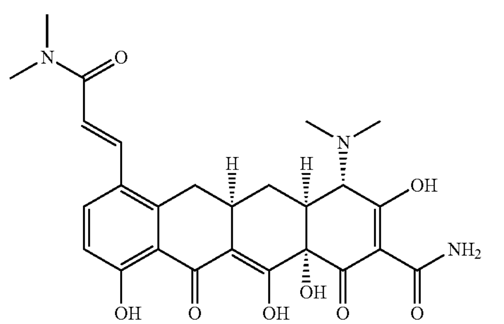 | 512.2 | 511.5304 |  | * |
| DQ | 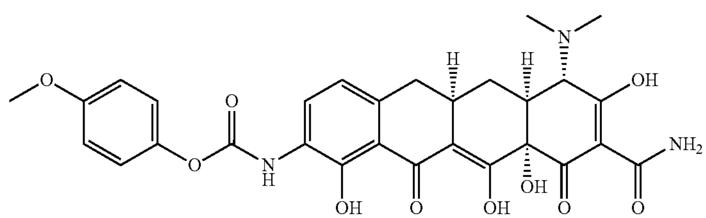 | 580.2 | 579.5622 | * | * |
| DS | 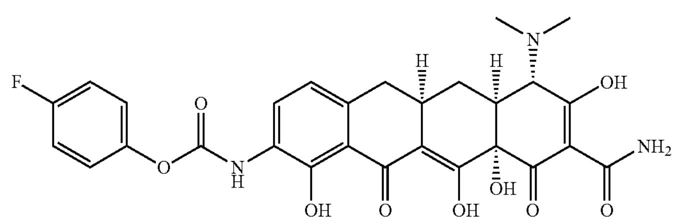 | 568.2 | 567.5265 | ** | * |
| DT | 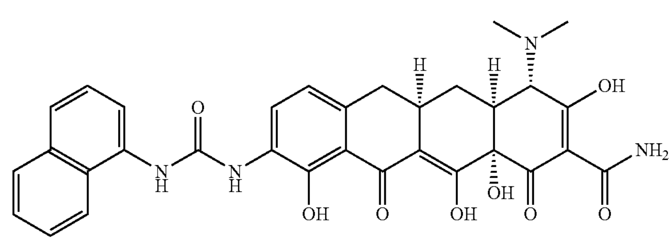 | 599.3 | 598.611 | ** | * |

TABLE 2-continued

| ID | STRUCTURE | M + H | Mol Weight | Toxicity | Activity |
|---|---|---|---|---|---|
| DU | 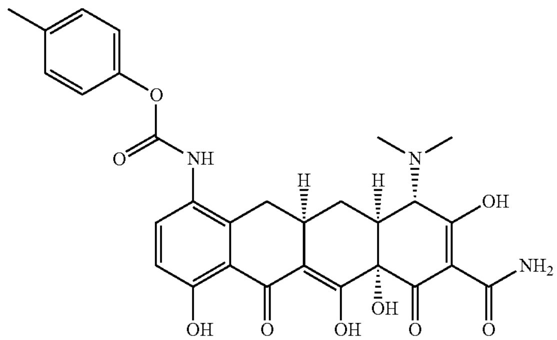 | 564.2 | 563.5628 | ** | * |
| DV | 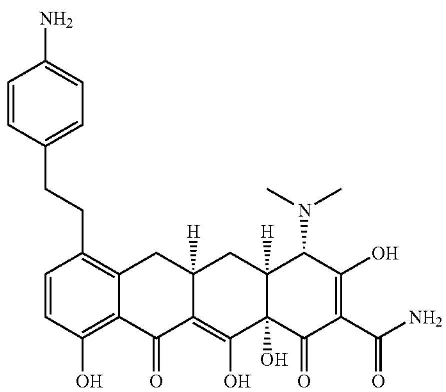 | 543.3 | 533.5798 | * | ** |
| DW | 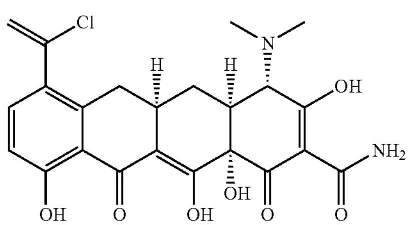 | 475.2 | 474.8969 | * | ** |
| DX | 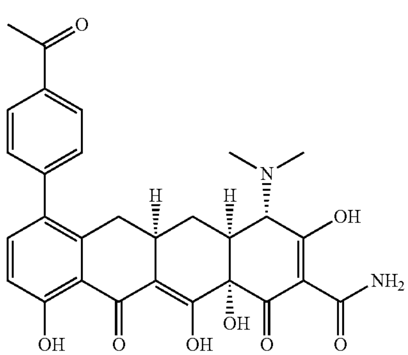 | 533.3 | 532.5488 | * | ** |

TABLE 2-continued
| ID | STRUCTURE | M + H | Mol Weight | Toxicity | Activity |
|---|---|---|---|---|---|
| DY | 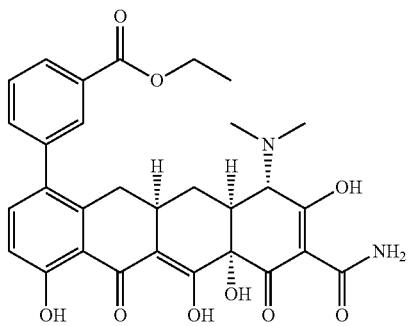 | 563.3 | 562.575 | * | ** |
| DZ | 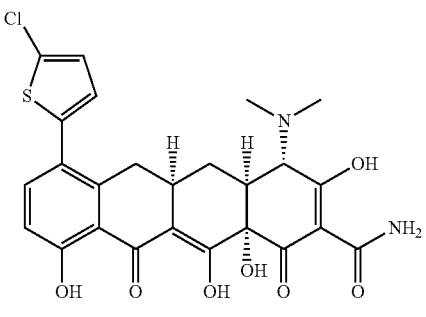 | 531.2 | 530.9789 | * | ** |
| EA | 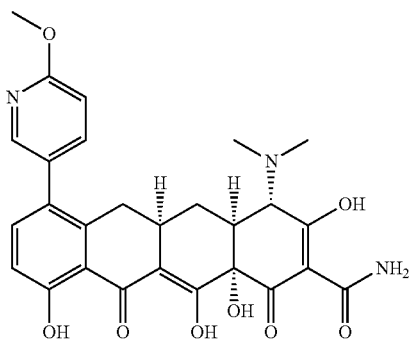 | 522.3 | 521.5256 | * | *** |
| EB | 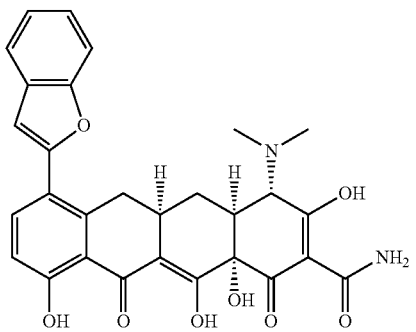 | 531.3 | 530.533 | * | ** |

TABLE 2-continued

| ID | STRUCTURE | M + H | Mol Weight | Toxicity | Activity |
|---|---|---|---|---|---|
| EC | 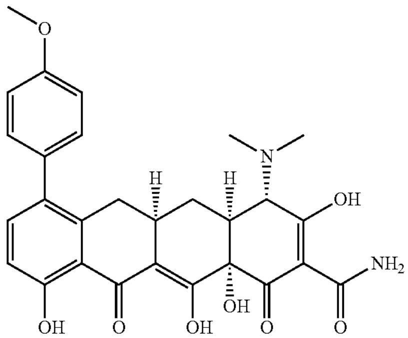 | 521.3 | 520.5378 | * | ** |
| ED | 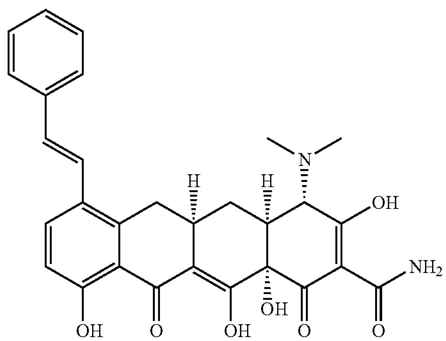 | 517.3 | 516.5494 | * | ** |
| EE | 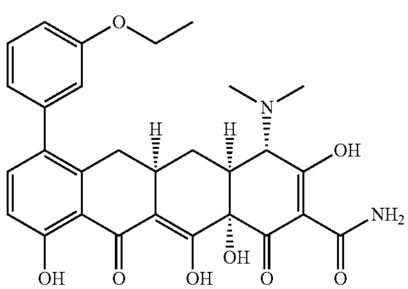 | | 534.5646 | * | ** |
| EF | 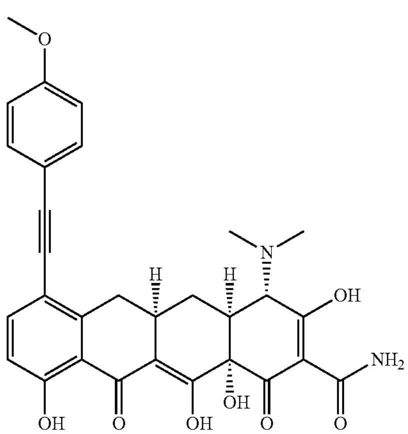 | | 544.5598 | * | ** |

TABLE 2-continued

| ID | STRUCTURE | M + H | Mol Weight | Toxicity | Activity |
|---|---|---|---|---|---|
| EG | 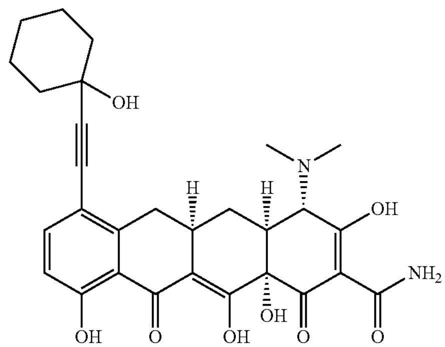 | 537.2 | 536.5804 |  |  |
| EH | 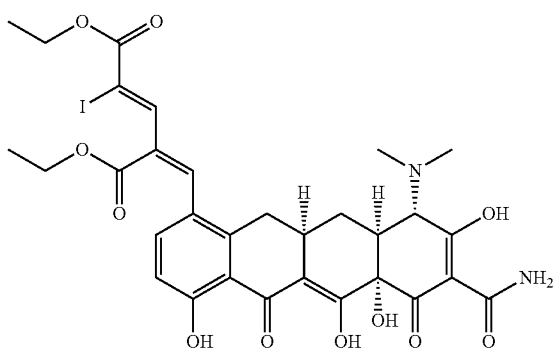 | 737.2 | 736.513 | ** | * |
| EI | 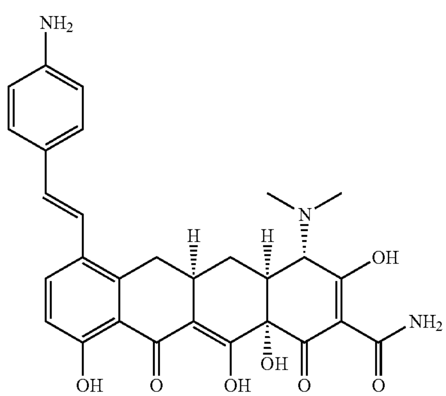 | 532.2 | 531.564 | * | *** |
| EJ | 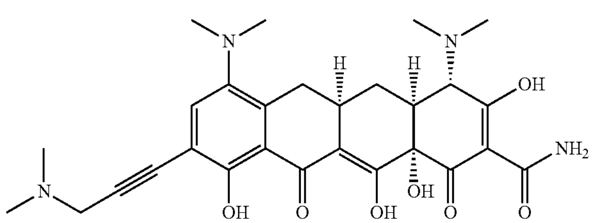 | 539.4 | 538.5992 | ** | * |

TABLE 2-continued

| ID | STRUCTURE | M + H | Mol Weight | Toxicity | Activity |
|---|---|---|---|---|---|
| EK | 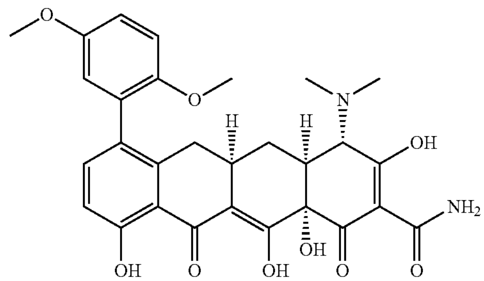 | 551.2 | 550.564 | * | ** |
| EL | 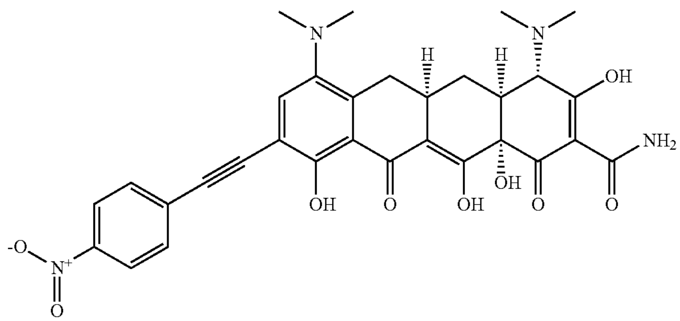 | 603.3 | 602.5994 | * | * |
| EM | 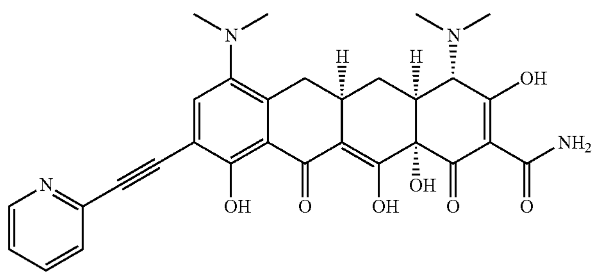 | 559.3 | 558.5896 | ** | * |
| EN | 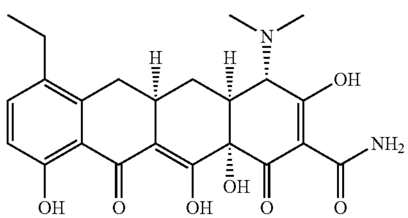 | 443.2 | 442.4676 | * | ** |
| EO | 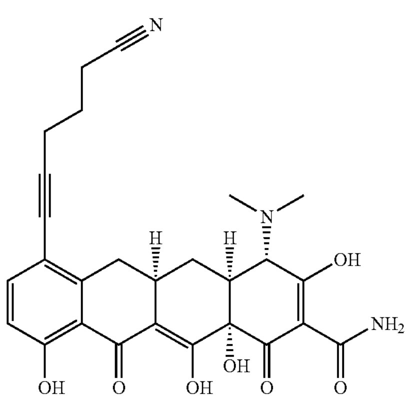 | 506.3 | 505.5262 | * | ** |

TABLE 2-continued

| ID | STRUCTURE | M + H | Mol Weight | Toxicity | Activity |
|----|-----------|-------|------------|----------|----------|
| EP | 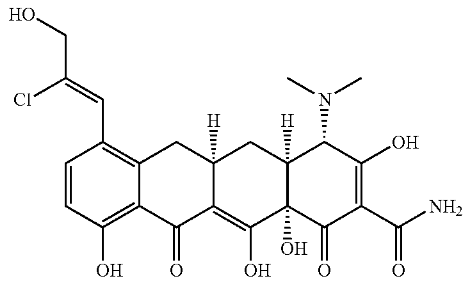 | 505.2 | 504.9231 |  |  |
| EQ | 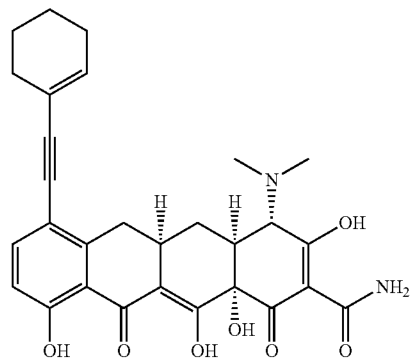 | 519.2 | 518.5652 | * | ** |
| ER | 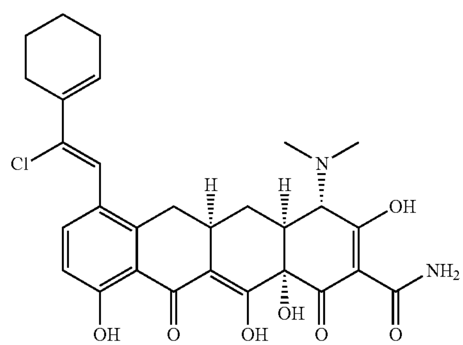 | 555.3 | 555.0261 | * | ** |
| ET | 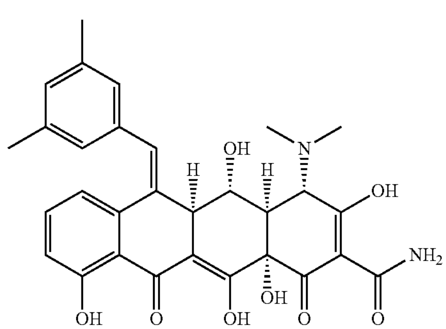 | 547.3 | 546.5756 | * | * |

TABLE 2-continued

| ID | STRUCTURE | M + H | Mol Weight | Tox-icity | Activity |
|----|-----------|-------|------------|-----------|----------|
| EU | 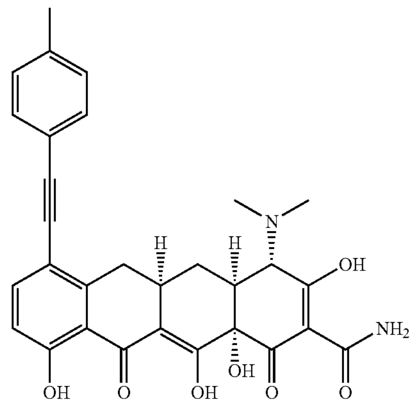 | 529.3 | 528.5604 | * | ** |
| EV | 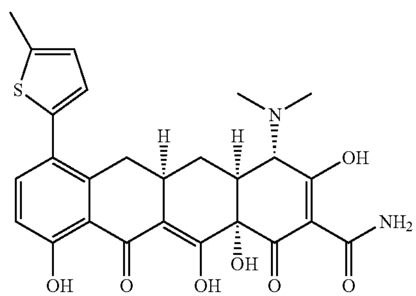 | 511.3 | 510.5606 | * | ** |
| EW | 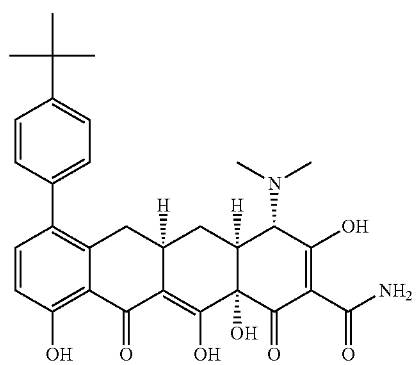 | 547.3 | 546.6188 | * | ** |
| EX | 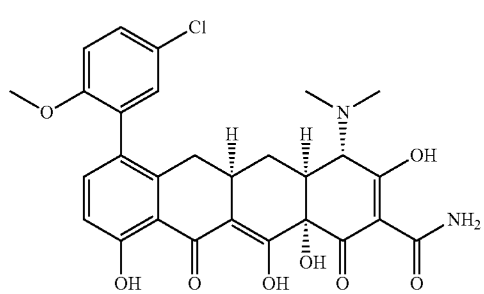 | 555.3 | 554.9829 | * | ** |

TABLE 2-continued

| ID | STRUCTURE | M + H | Mol Weight | Toxicity | Activity |
|---|---|---|---|---|---|
| EY | 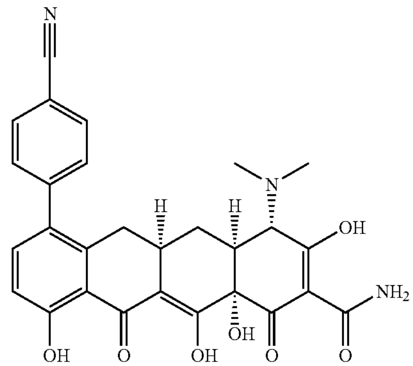 | 516.3 | 515.5214 | * | ** |
| EZ | 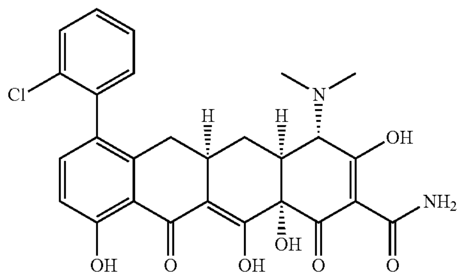 | 525.3 | 524.9567 | * | ** |
| FA | 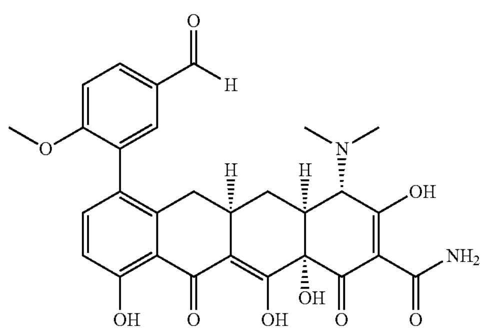 | 549.2 | 548.5482 | * | *** |
| FB | 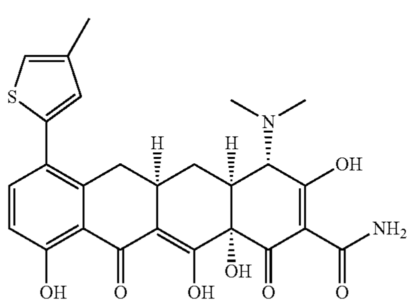 | 511.3 | 510.5606 | * | ** |

TABLE 2-continued

| ID | STRUCTURE | M + H | Mol Weight | Toxicity | Activity |
|---|---|---|---|---|---|
| FC | 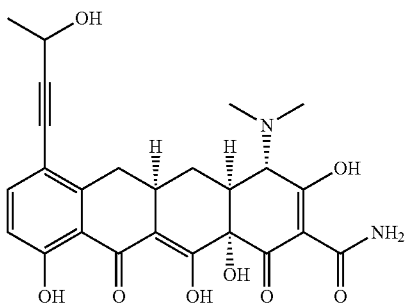 | 483.3 | 482.489 |  |  |
| FD | 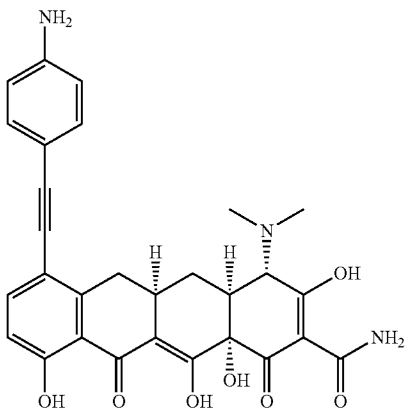 | 530.3 | 529.5482 | * | *** |
| FE | 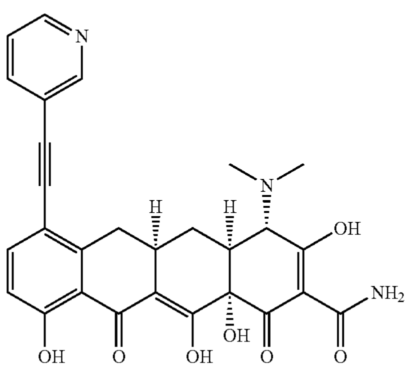 | 516.2 | 515.5214 | * | ** |
| FF | 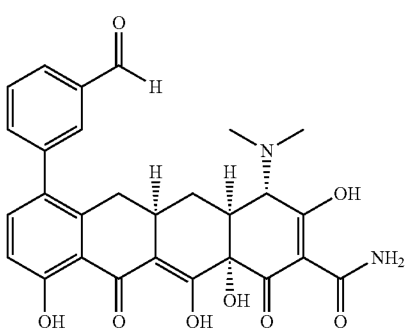 | 519.2 | 518.522 | * | ** |

TABLE 2-continued

| ID | STRUCTURE | M + H | Mol Weight | Toxicity | Activity |
|---|---|---|---|---|---|
| FG | 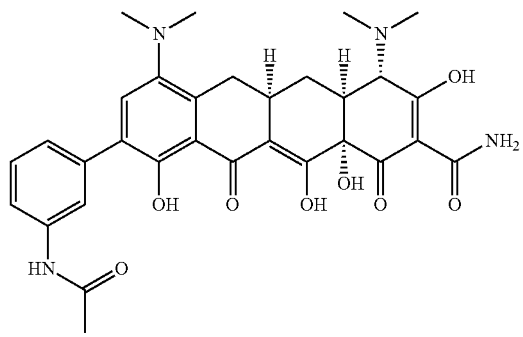 | 591.2 | 590.6316 | ** | * |
| FH | 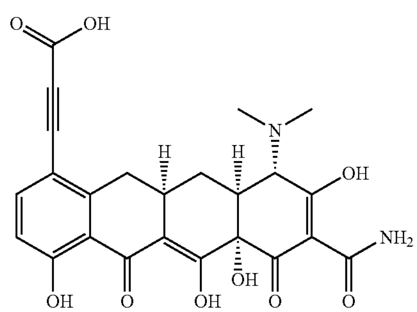 | 483.3 | 482.4458 | ** | * |
| FI | 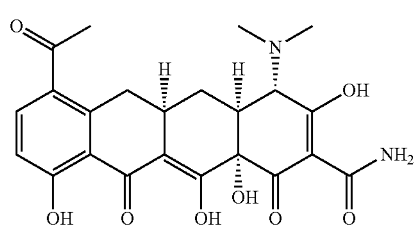 | 457.3 | 456.4512 |  | * |
| FJ | 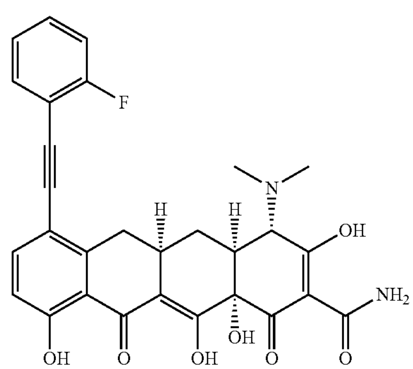 | 533.2 | 532.5241 | * | ** |

TABLE 2-continued
| ID | STRUCTURE | M + H | Mol Weight | Toxicity | Activity |
|---|---|---|---|---|---|
| FK | 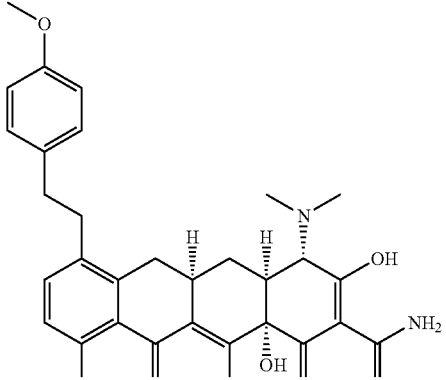 | 549.3 | 548.5914 | * | ** |
| FL | 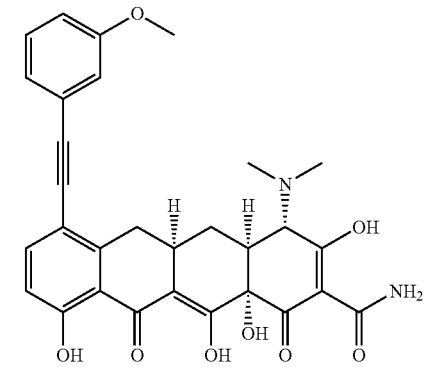 | 545.3 | 544.5598 | * | ** |
| FM | 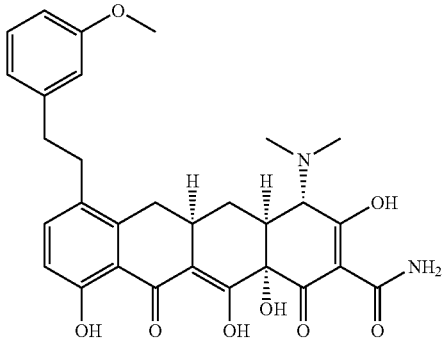 | 549.3 | 548.5914 | * | ** |
| FN | 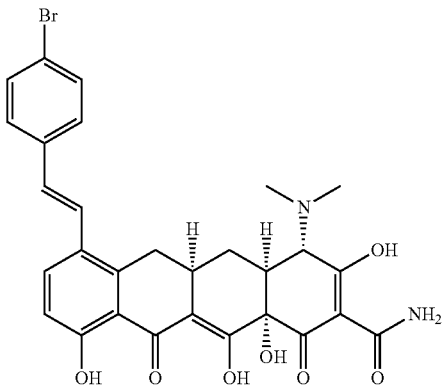 | 597.1 | 595.4455 | * | *** |

TABLE 2-continued
| ID | STRUCTURE | M + H | Mol Weight | Toxicity | Activity |
|---|---|---|---|---|---|
| FO | 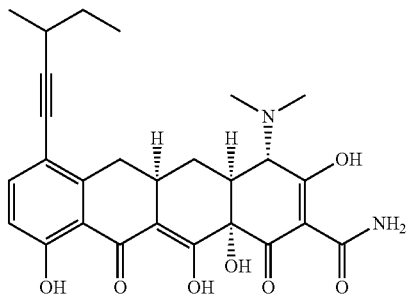 | 495.3 | 494.5432 | * | ** |
| FP | 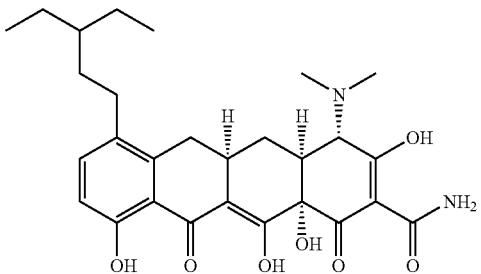 | 513.2 | 512.6016 | * | ** |
| FQ | 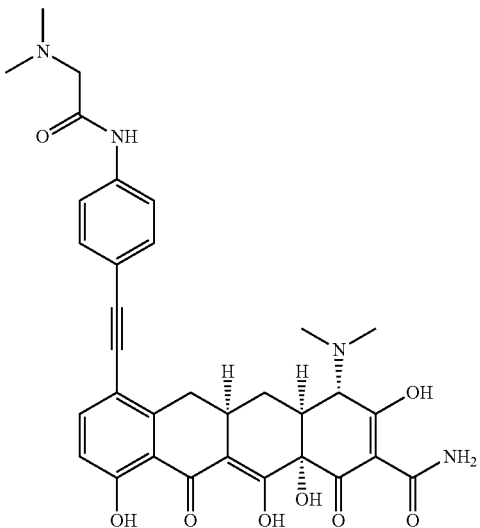 | 615.3 | 614.6536 | * | *** |
| FR | 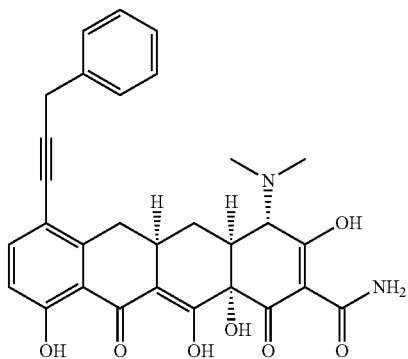 | 529.5 | 528.5604 | * | ** |

TABLE 2-continued

| ID | STRUCTURE | M + H | Mol Weight | Toxicity | Activity |
|---|---|---|---|---|---|
| FS | 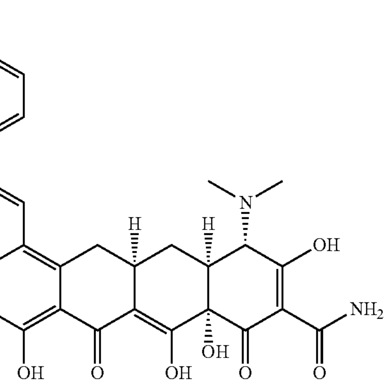 | 531.3 | 530.5762 | * | ** |
| FT | 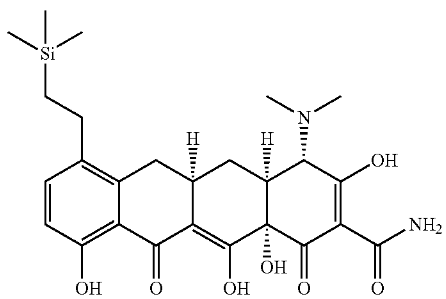 | 515.3 | 514.6498 | * | ** |
| FU | 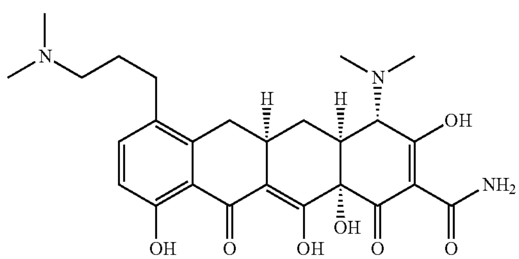 | 500.3 | 499.5626 |  | * |
| FV | 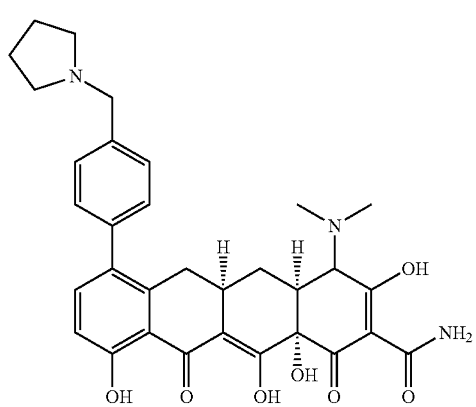 | 574.2 | 573.6444 |  | * |

TABLE 2-continued

| ID | STRUCTURE | M + H | Mol Weight | Toxicity | Activity |
|---|---|---|---|---|---|
| FW | 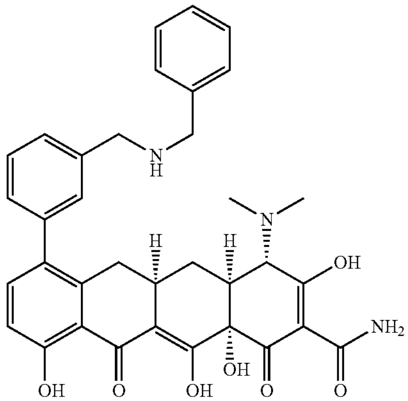 | 610.3 | 609.6774 | * | *** |
| FX | 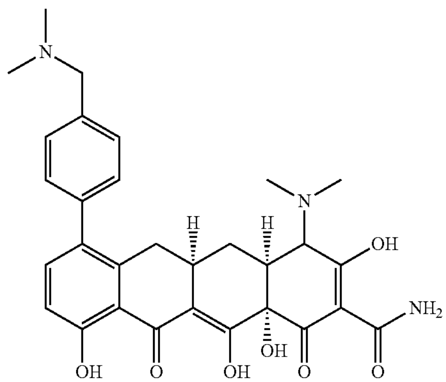 | 548.4 | 547.6066 |  | * |
| FY | 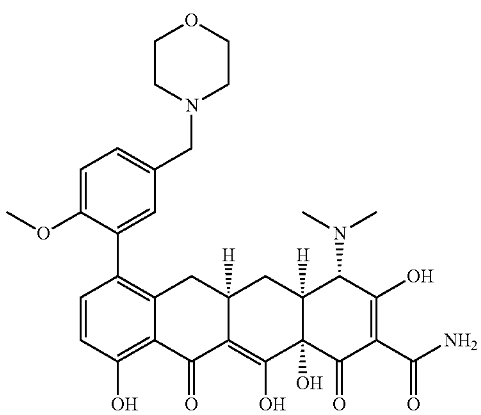 | 620.3 | 619.67 |  | * |
| FZ | 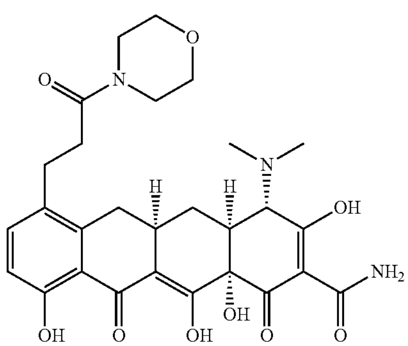 | 556.3 | 555.5834 |  |  |

TABLE 2-continued

| ID | STRUCTURE | M + H | Mol Weight | Toxicity | Activity |
|----|-----------|-------|------------|----------|----------|
| GA | 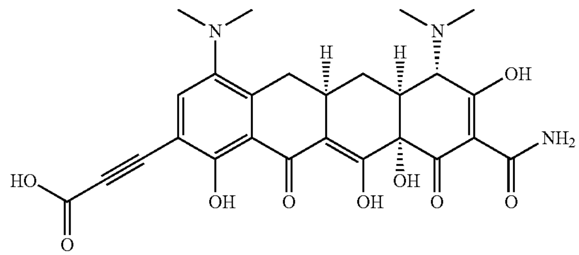 | 526.2 | 525.514 | ** | * |
| GB | 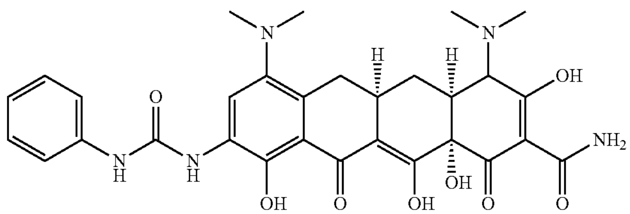 | 592.3 | 591.6194 |  | * |
| GC | 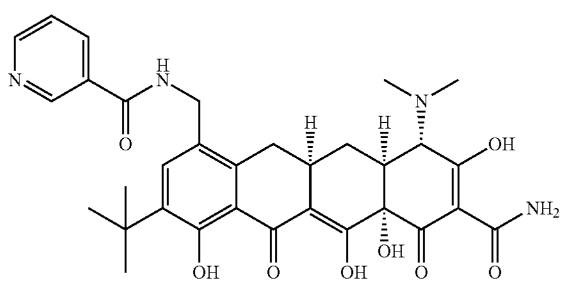 | 605.3 | 604.6584 |  |  |
| GD | 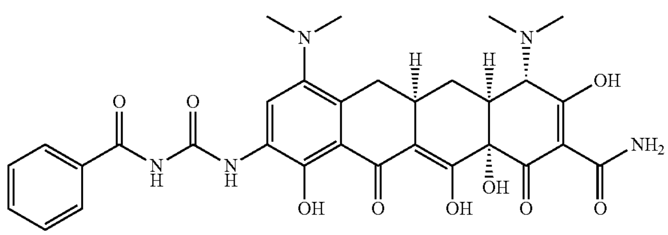 | 620.3 | 619.6298 |  |  |
| GE | 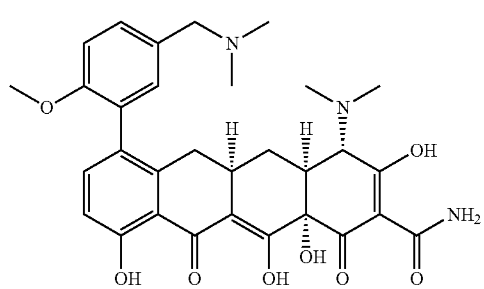 | 575.3 | 577.6328 |  | * |
| GF | 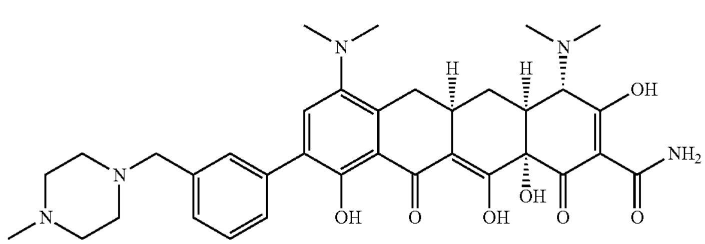 | 646.4 | 645.754 | ** | * |

TABLE 2-continued

| ID | STRUCTURE | M + H | Mol Weight | Toxicity | Activity |
|---|---|---|---|---|---|
| GG | 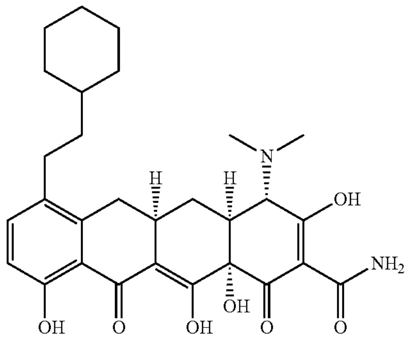 | 525.3 | 524.6126 | * | ** |
| GH | 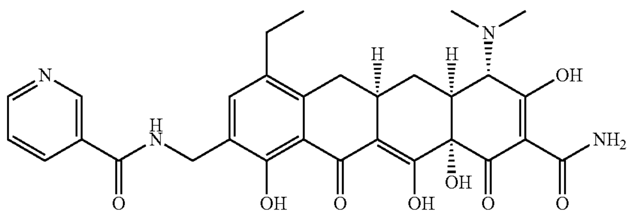 | 577.3 | 576.6048 |  |  |
| GI | 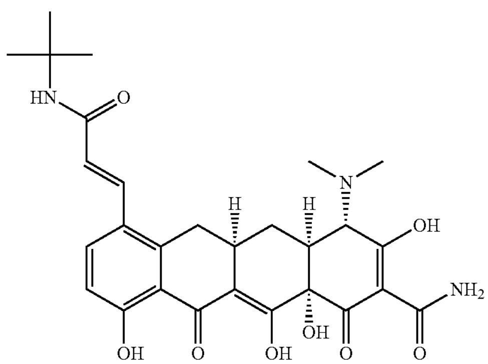 | 540.3 | 539.584 |  |  |
| GJ | 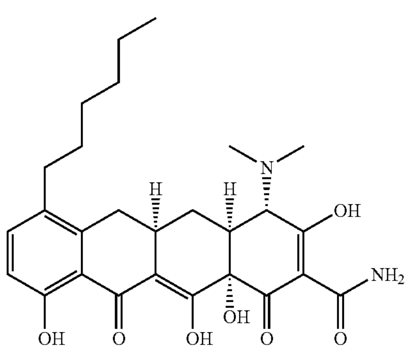 | 499.3 | 498.5748 | * | ** |

TABLE 2-continued
| ID | STRUCTURE | M + H | Mol Weight | Toxicity | Activity |
|---|---|---|---|---|---|
| GK | 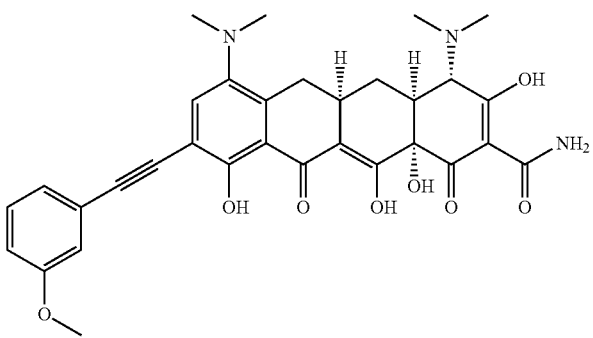 | 588.3 | 587.628 | * | ** |
| GL | 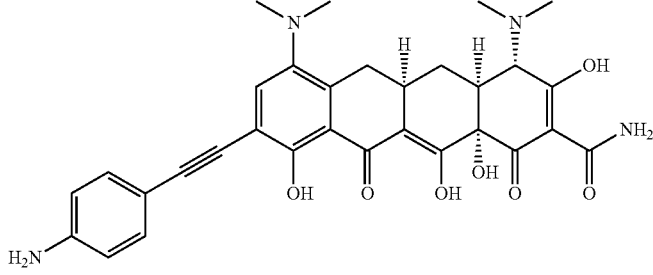 | 573.3 | 572.6164 | ** | * |
| GM | 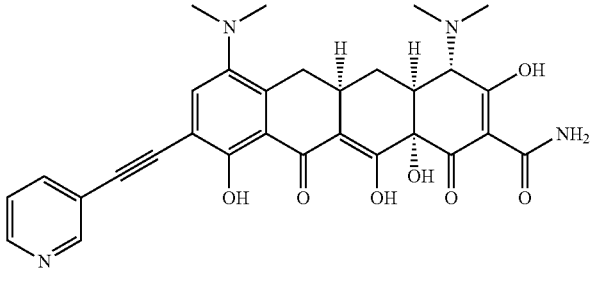 | 559.3 | 558.5896 | * | * |
| GN | 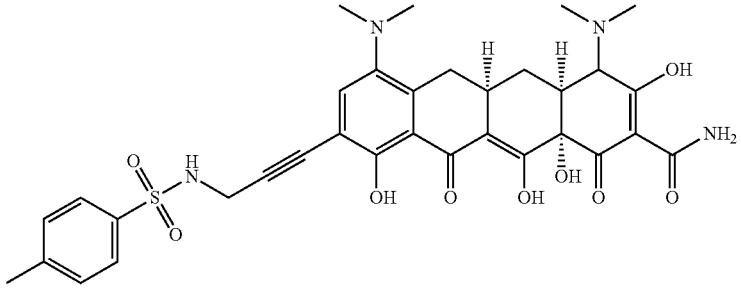 | 665.2 | 664.7288 |  |  |
| GO | 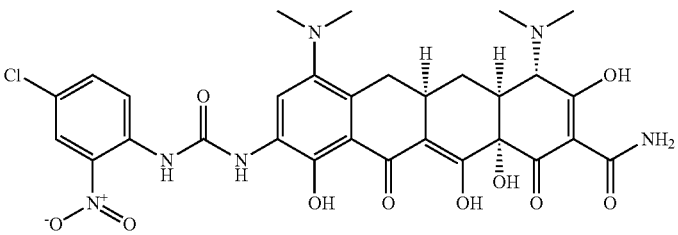 | 671.3 | 671.0621 | * | ** |

TABLE 2-continued

| ID | STRUCTURE | M + H | Mol Weight | Toxicity | Activity |
|---|---|---|---|---|---|
| GP | 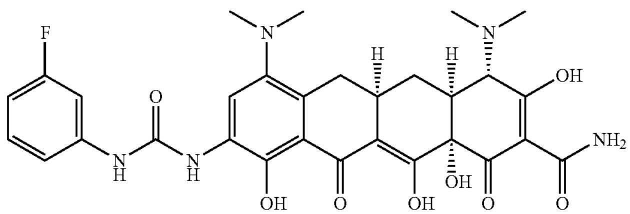 | 610.3 | 609.6099 |  | * |
| GQ | 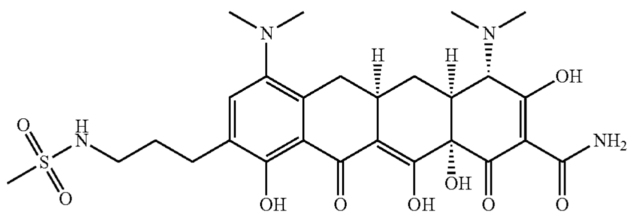 | 593.4 | 592.6628 | ** | * |
| GR | 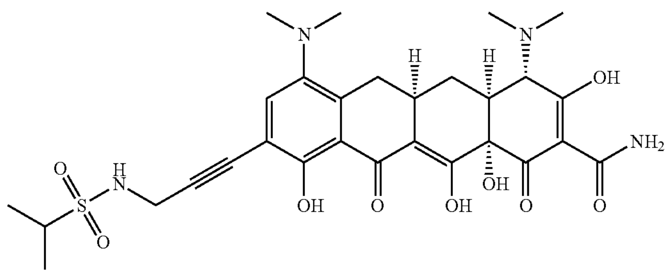 | 617.3 | 616.6848 | ** | * |
| GS | 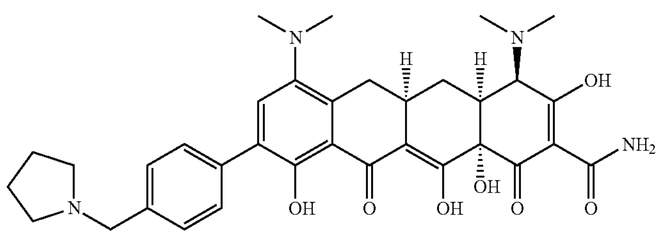 | 617.4 | 616.7126 | ** | * |
| GT | 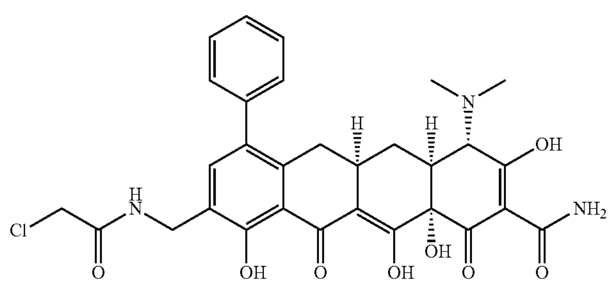 | 596.2 | 596.0353 | | *** |
| GU | 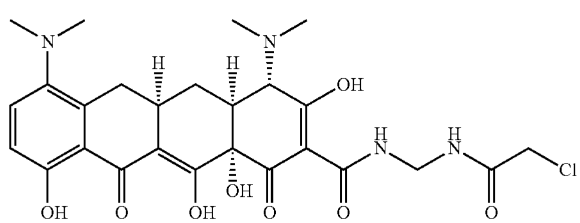 | 563.2 | 563.0059 | | ** |

TABLE 2-continued

| ID | STRUCTURE | M + H | Mol Weight | Toxicity | Activity |
|---|---|---|---|---|---|
| GV | 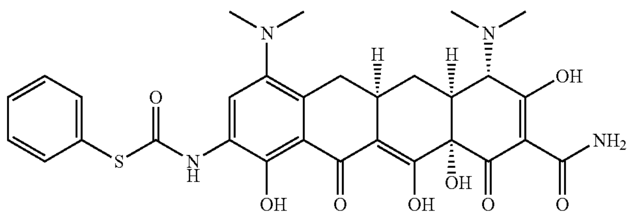 | 609.2 | 608.6648 | | * |
| GW | 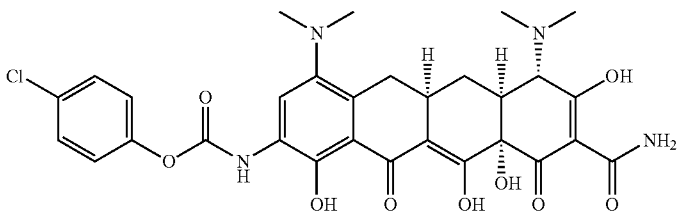 | 627.2 | 627.0493 | | * |
| GX | 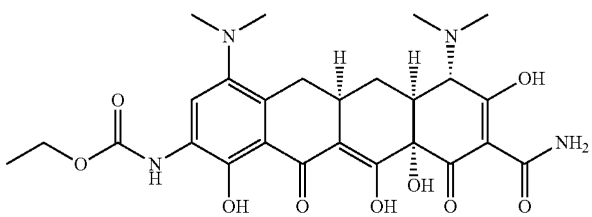 | | 544.5602 | | ** |
| GY | 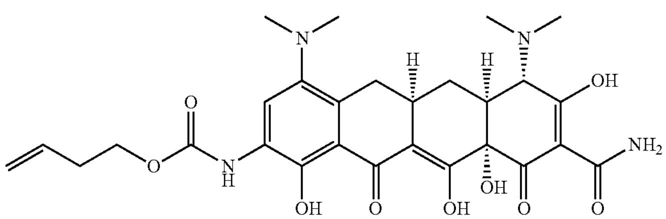 | 571.3 | 570.598 | | ** |
| GZ | 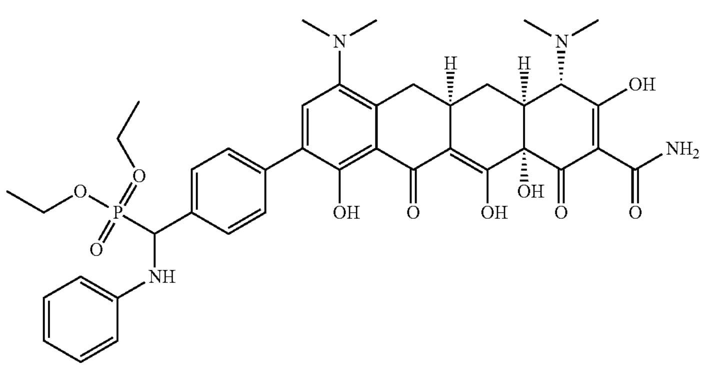 | 775.4 | 774.80586 | * | ** |
| HA | 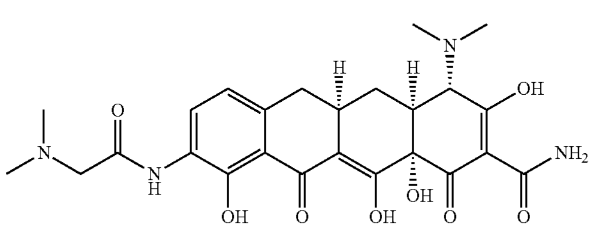 | | 514.534 |  | * |

TABLE 2-continued

| ID | STRUCTURE | M + H | Mol Weight | Toxicity | Activity |
|---|---|---|---|---|---|
| HB | 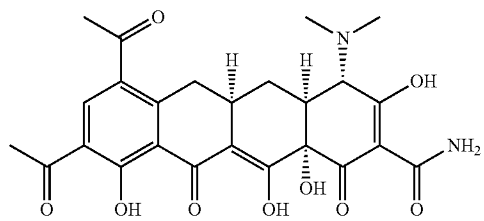 | 499.2 | 498.4884 | ** | * |
| HC | 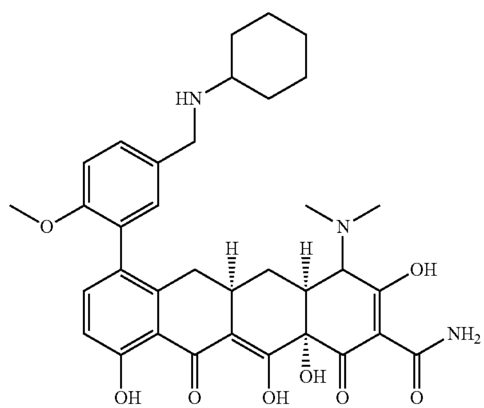 | 632.5 | 631.7242 |  | * |
| HD | 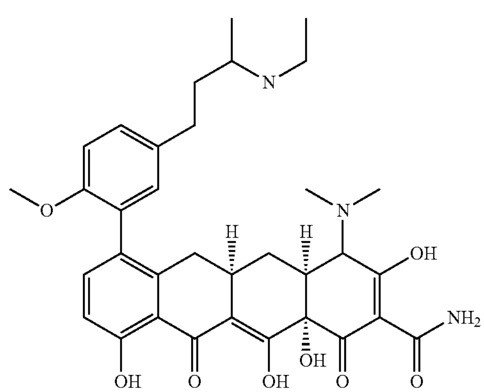 | 606.5 | 605.6864 |  | * |
| HE | 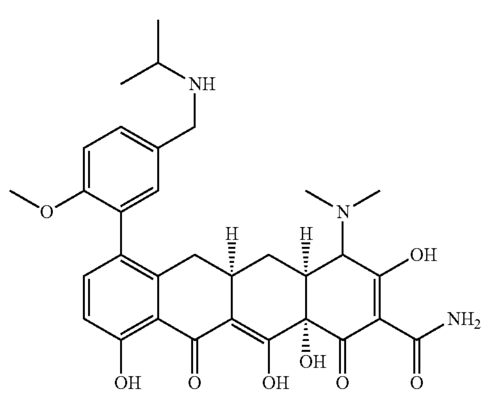 | 592.3 | 591.6596 |  | * |

TABLE 2-continued

| ID | STRUCTURE | M + H | Mol Weight | Toxicity | Activity |
|---|---|---|---|---|---|
| HF | 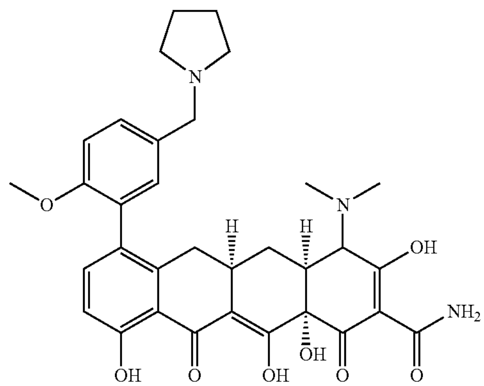 | 604.4 | 603.6706 |  | * |
| HG | 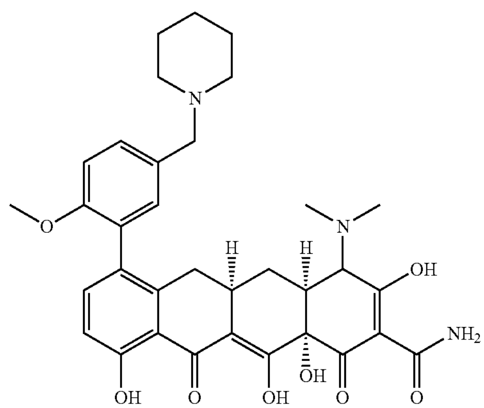 | 618.3 | 617.6974 |  | * |
| HH | 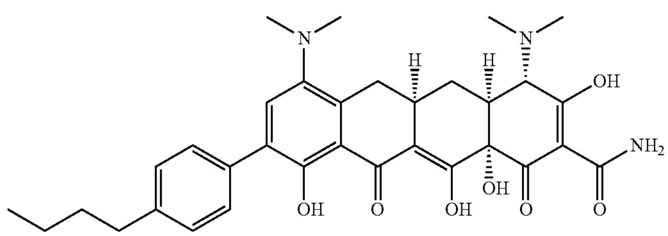 | 590.3 | 589.687 | | ** |
| HI | 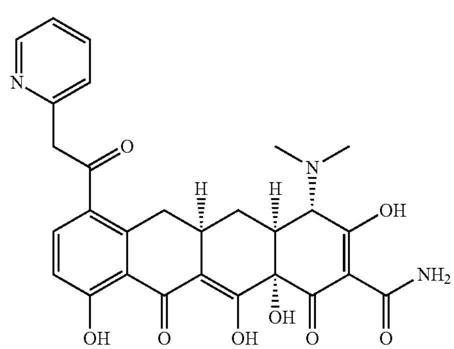 | 534.3 | 533.5366 |  | * |

TABLE 2-continued
| ID | STRUCTURE | M + H | Mol Weight | Toxicity | Activity |
|---|---|---|---|---|---|
| HJ | 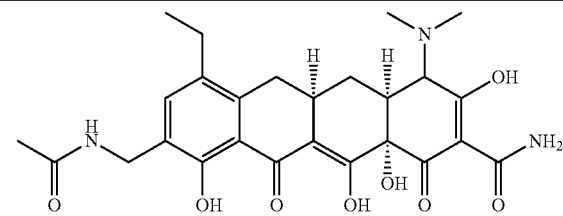 | 514.3 | 513.5462 | | ** |
| HK | 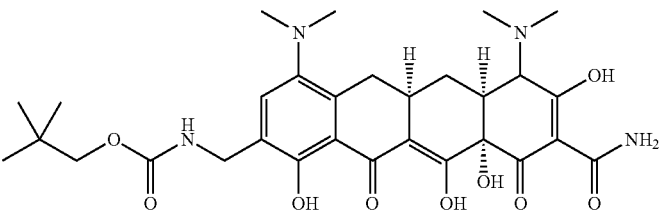 | 601.4 | 600.6674 | | * |
| HL | 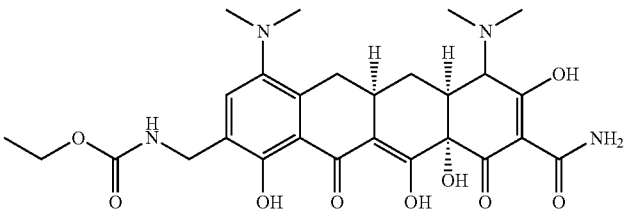 | 559.3 | 558.587 | ** | * |
| HM | 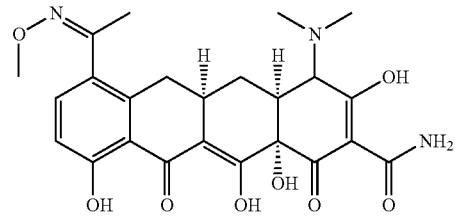 | 486.3 | 485.4926 | | *** |
| HN | 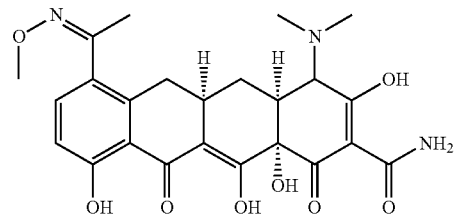 | 486.3 | 485.4926 | | *** |
| HO | 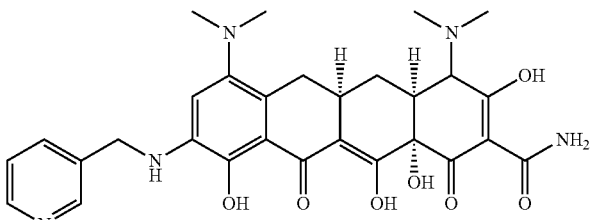 | 564.3 | 563.609 | | * |
| HP | 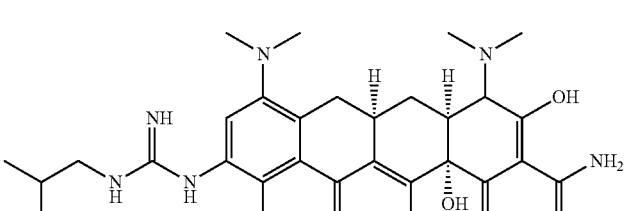 | 571.4 | 570.6442 | | * |

TABLE 2-continued

| ID | STRUCTURE | M + H | Mol Weight | Toxicity | Activity |
|---|---|---|---|---|---|
| HQ | 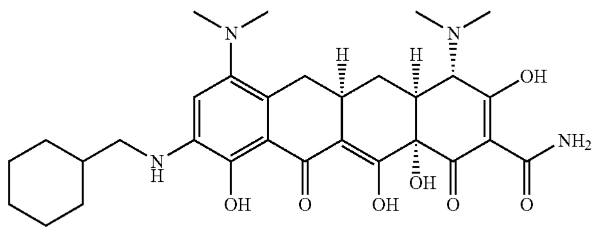 | 569.3 | 568.6686 | * | * |
| HR | 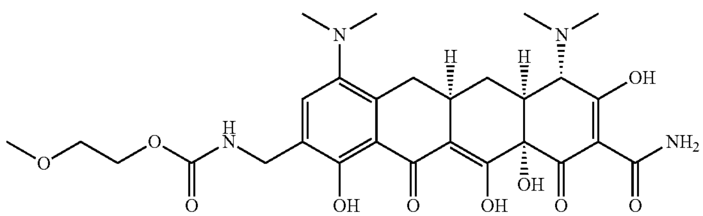 | 589.3 | 588.6132 |  |  |
| HS | 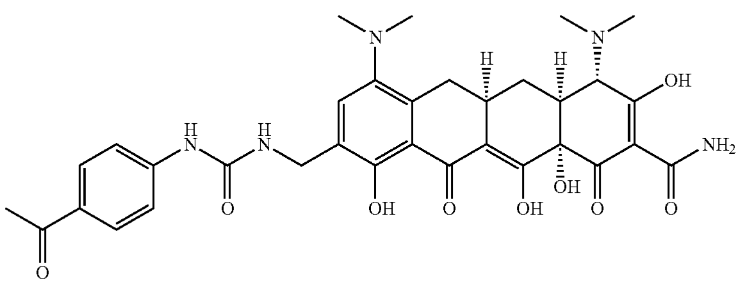 | 648.3 | 647.6834 |  |  |
| HT | 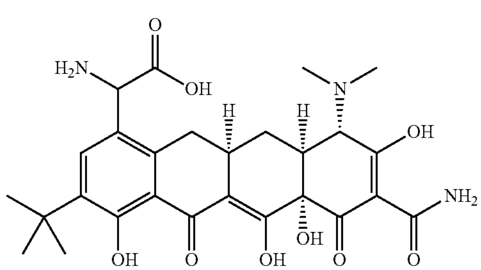 | 544.3 | 543.5724 | ** | * |
| HU | 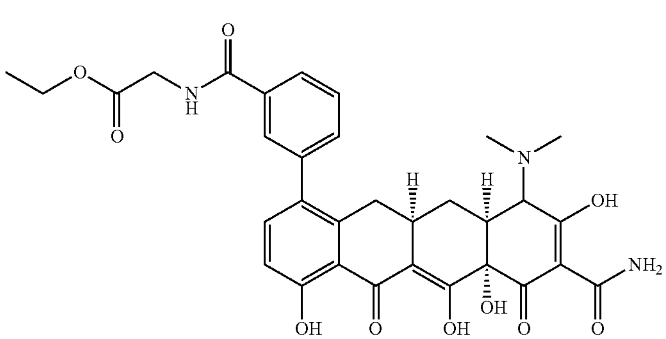 | 620.2 | 619.6268 |  | * |

TABLE 2-continued

| ID | STRUCTURE | M + H | Mol Weight | Toxicity | Activity |
|----|-----------|-------|------------|----------|----------|
| HV | 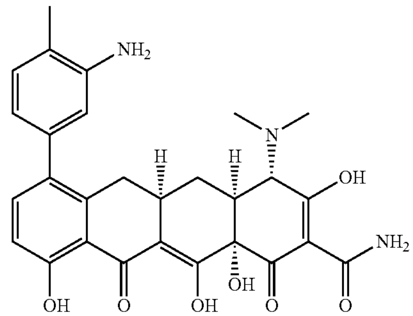 | 520.2 | 519.553 |  | * |
| HW | 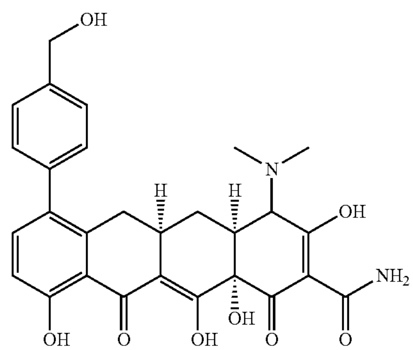 | 521.2 | 520.5378 |  | * |
| HX | 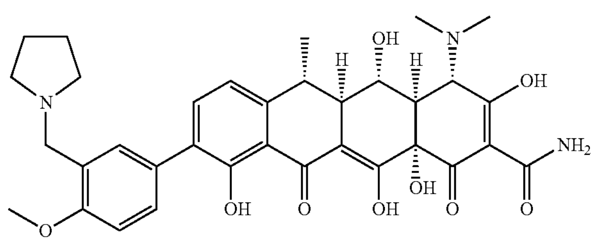 | 644.3 | 633.6968 | ** | * |
| HY | 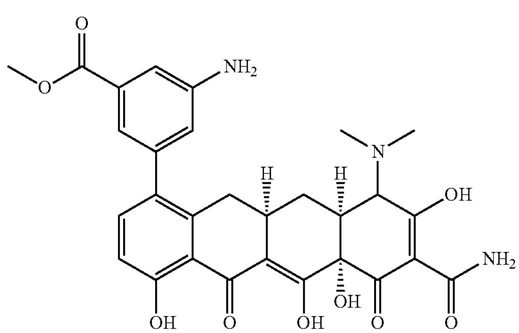 | 564.2 | 563.5628 |  | * |
| HZ | 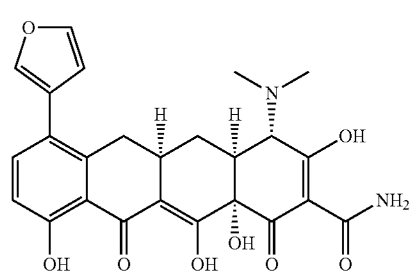 | 481.1 | 480.4732 | * | *** |

TABLE 2-continued

| ID | STRUCTURE | M + H | Mol Weight | Toxicity | Activity |
|---|---|---|---|---|---|
| IA | 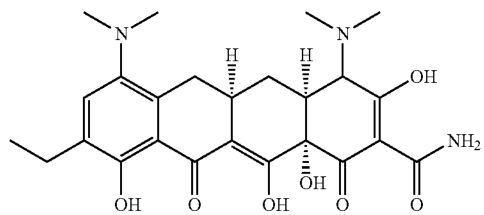 | 486.3 | 485.5358 | ** | * |
| IB | 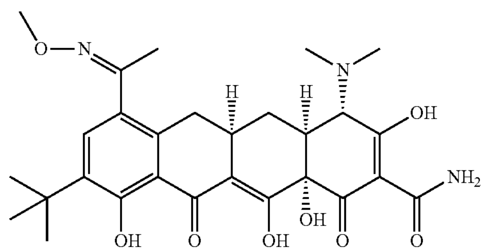 | 542.2 | 541.5998 |  |  |
| IC | 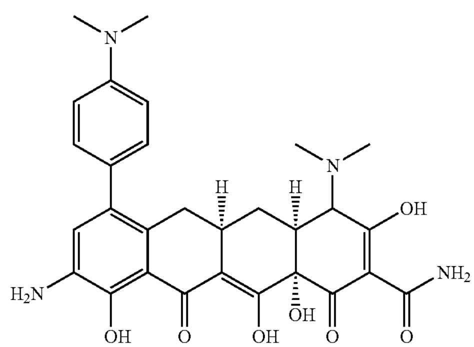 | 549.2 | 548.5944 |  |  |
| ID | 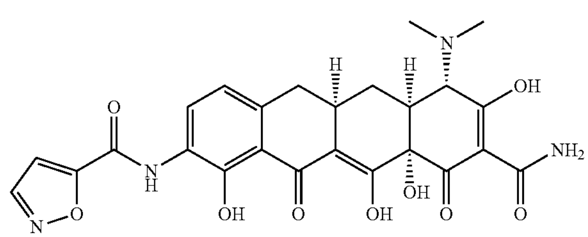 | 525.2 | 524.486 | ** | * |
| IE | 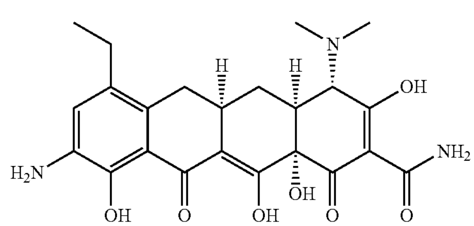 | 458.2 | 457.4822 |  |  |

TABLE 2-continued

| ID | STRUCTURE | M + H | Mol Weight | Toxicity | Activity |
|----|-----------|-------|------------|----------|----------|
| IF | 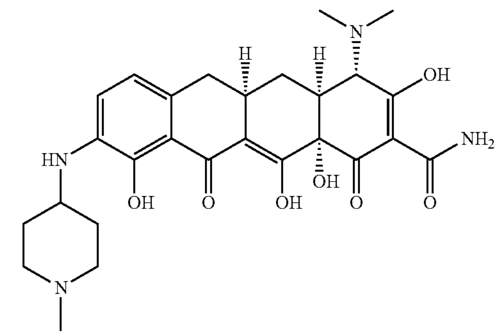 | 527.28 | 526.5882 |  |  |
| IG | 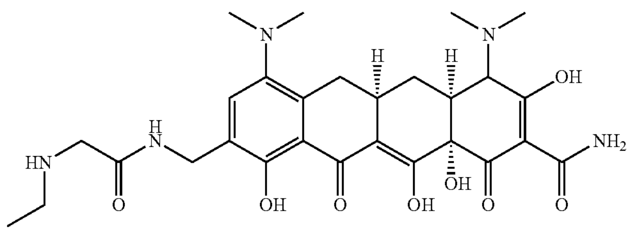 | 572.4 | 571.629 |  |  |
| IH | 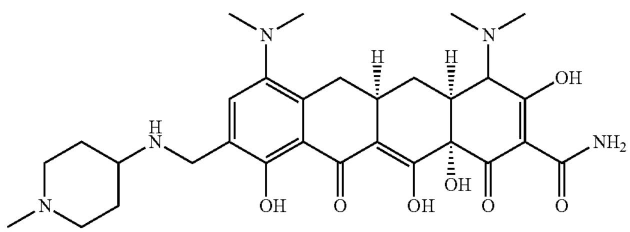 | 584.4 | 583.6832 |  |  |
| II | 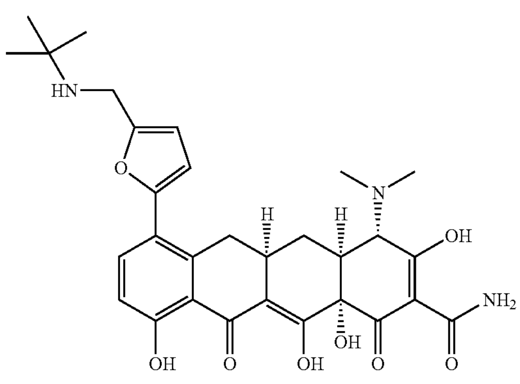 | | 565.6218 |  | * |
| IJ | 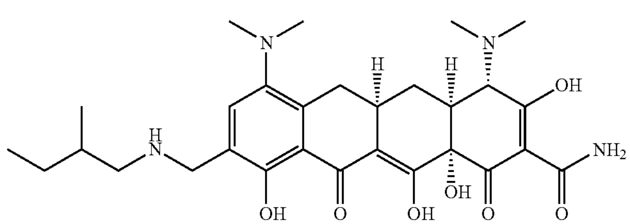 | 557.4 | 556.6576 |  | * |

TABLE 2-continued

| ID | STRUCTURE | M + H | Mol Weight | Toxicity | Activity |
|---|---|---|---|---|---|
| IK | 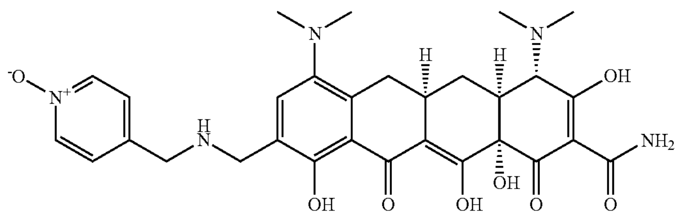 | 594.4 | 593.6352 | ** | * |
| IL | 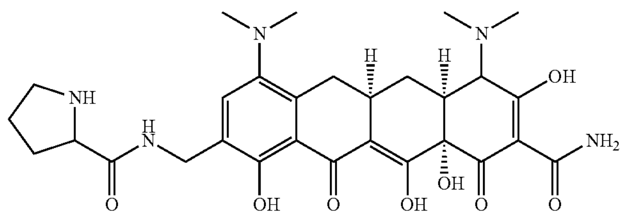 | 584.3 | 583.64 |  |  |
| IM | 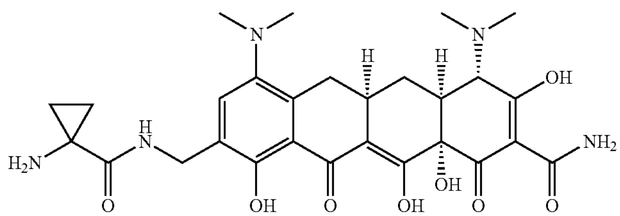 | 570.3 | 569.6132 | ** | * |
| IN | 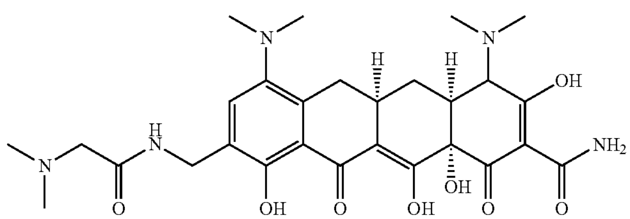 | 572.3 | 571.629 |  |  |
| IO | 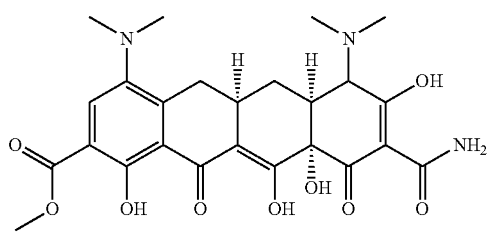 | 516.3 | 515.5188 | ** | * |
| IP | 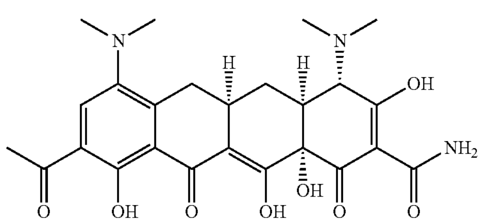 | 500.3 | 499.5194 | ** | * |

TABLE 2-continued

| ID | STRUCTURE | M + H | Mol Weight | Toxicity | Activity |
|---|---|---|---|---|---|
| IQ | 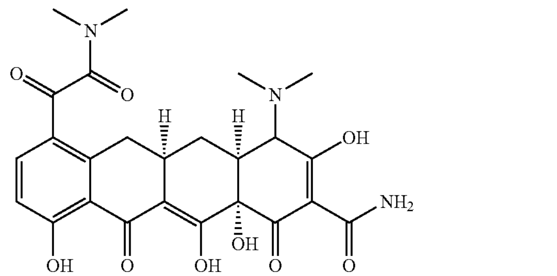 | 514.3 | 513.503 |  | * |
| IR | 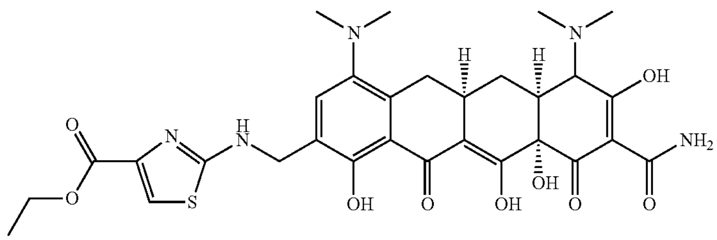 | 642.3 | 641.6946 | ** | * |
| IS | 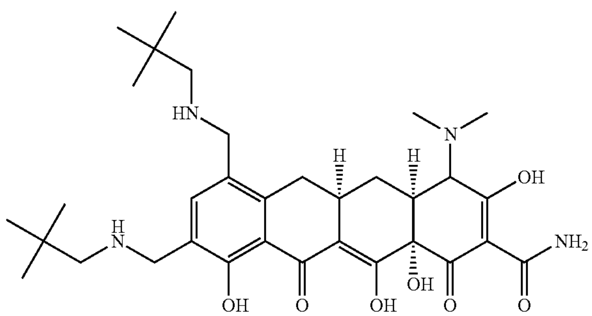 | 613.4 | 612.7648 |  | * |

Example 4

Assessment of Antimalarial Activity In Vivo

The assessment is performed with *P. vinckei*, a murine parasite that consistently causes a rapidly fatal malaria, and is an excellent model for drug efficacy. However, other murine parasites which are available (e.g. *P. berghei*) can also be studied using similar methodology.

20 gm Swiss Webster mice are inoculated intraperitoneally with $10^6$ *P. vinckei*-infected erythrocytes obtained from another infected mouse. Twelve hours after infection, treatment is initiated by the intraperitoneal injection of test compounds. Treatment is continued twice-a-day (BID) for four days. The progress of malaria infections in experimental and control (injected with diluent only) mice is followed by daily examinations of blood smears obtained from tail veins. The pharmacological endpoint is parasitemia >50%. Uninfected animals are followed for 6 weeks, and the animals that remain uninfected through this period are considered long-term cures.

The test compounds are injected into the stomach of the test mice by gavage. A number of variations of standard in vivo protocol may be utilized for specific purposes. For example, dosing intervals may be altered based on the known pharmacokinetics or observed initial efficacy data for a compound. Protocols may also be altered to more closely mimic true treatment (with delay of therapy after inoculation of parasites) or chemoprophylaxis (with treatment before the inoculation of parasites) conditions.

For all in vivo experiments, the mice are monitored daily, for at least the first two weeks of an experiment, with blood smears. Counts per 1000 erythrocytes provide parasitemias, and the parasitemias are then plotted over time, and results for control and experimental animals are compared.

Example 5

Mammalian Cytotoxicity Assay

COS-1 and CHO cell suspensions are prepared, seeded into 96-well tissue culture treated black-walled microtiter plates (density determined by cell line), and incubated overnight at 37° C., in 5% $CO_2$ and approximately 95% humidity. The following day serial dilutions of drug are prepared under sterile conditions and transferred to cell plates. Cell/Drug plates are incubated under the above conditions for 24 hours. Following the incubation period, media/drug is aspirated and 50 µl of Resazurin is added. Plates are then incubated under the above conditions for 2 hours and then in the dark at room temperature for an additional 30 minutes. Fluorescence measurements are taken (excitation 535 nm, emission 590 nm). The $IC_{50}$ (concentration of drug causing 50% growth inhibition) is then calculated. The cytotoxicity of both unsubstituted minocycline and doxycycline were found to be greater than 25 μg/ml. Substituted tetracycline compounds with good cytotoxicities are indicated with * in Table 2. Substituted tetracycline compounds with very good cytotoxicities are indicated with ** in Table 2.

Example 6

In vitro Anti-Bacterial Activity Assay

The following assay is used to determine the efficacy of the tetracycline compounds against common bacteria. 2 mg of each compound is dissolved in 100 μl of DMSO. The solution is then added to cation-adjusted Mueller Hinton broth (CAMHB), which results in a final compound concentration of 200 μg per ml. The tetracycline compound solutions are diluted to 50 μL volumes, with a test compound concentration of 0.098 μg/ml. Optical density (OD) determinations are made from fresh log-phase broth cultures of the test strains. Dilutions are made to achieve a final cell density of $1\times10^6$ CFU/ml. At OD=1, cell densities for different genera should be approximately:

| | |
|---|---|
| E. coli | $1 \times 10^9$ CFU/ml |
| S. aureus | $5 \times 10^8$ CFU/ml |
| Enterococcus sp. | $2.5 \times 10^9$ CFU/ml |

50 μl of the cell suspensions are added to each well of microtiter plates. The final cell density should be approximately $5\times10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

Equivalents

Those skilled in the art will recognize, or be able to ascertain using no more than routine experimentation, many equivalents to the specific embodiments and methods described herein. Such equivalents are intended to be encompassed by the scope of the following claims.

The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method for treating or preventing malaria in a subject, comprising administering to said subject an effective amount of a substituted tetracycline compound of formula I or a pharmaceutically acceptable salt thereof:

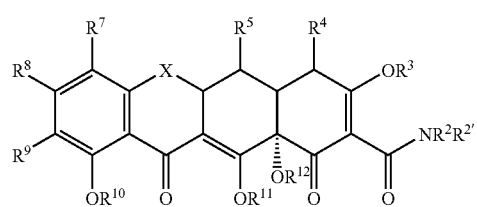

(I)

wherein:
X is $CR^{6'}R^6$;
$R^2$ and $R^{2'}$ are each hydrogen;
$R^{4'}$ and $R^{4''}$ are each alkyl;
$R^4$ is $NR^{4'}R^{4''}$;
$R^3$, $R^{11}$ and $R^{12}$ are each hydrogen;
$R^{10}$ is hydrogen;
$R^5$ is hydroxyl, hydrogen or thiol;
$R^6$ and $R^{6'}$ are independently hydrogen, hydroxyl, thiol or alkyl;
$R^7$ is substituted or unsubstituted furanyl, substituted or unsubstituted benzofuranyl, substituted or unsubstituted thienyl or substituted or unsubstituted benzothienyl;
$R^9$ is hydrogen; and
$R^8$ is hydrogen; such that malaria is treated or prevented in said subject.

2. The method of claim 1, wherein $R^5$, $R^6$, and $R^{6'}$ are each hydrogen.

3. The method of claim 1, wherein $R^7$ is substituted furanyl or substituted thienyl.

4. The method of claim 3, wherein $R^7$ is substituted with halogen, alkoxy, amino, acyl, alkyl, nitro, formyl, amido, alkenyl, alkynyl, or aryl.

5. The method of claim 4, wherein $R^7$ is substituted with alkoxy and further wherein said alkoxy is methoxy, ethoxy, propoxy, methylene dioxy, or ethylene dioxy.

6. The method of claim 4, wherein $R^7$ is substituted with alkyl and further wherein said alkyl is substituted or unsubstituted methyl, ethyl, propyl, butyl or pentyl.

7. The method of claim 6, wherein said substituted methyl, ethyl, propyl, butyl or pentyl is substituted with an amino, carbocyclic or heterocyclic group.

8. The method of claim 4, wherein $R^7$ is substituted with acyl and further wherein said acyl is acetyl.

9. The method of claim 1, wherein $R^7$ is substituted or unsubstituted benzofuranyl or substituted or unsubstituted benzothienyl.

10. The method of claim 1, wherein $R^7$ is unsubstituted thienyl or unsubstituted furanyl.

11. The method of claim 3, wherein said substituent comprises an ionizable nitrogen atom.

12. The method of claim 1, wherein $R^7$ is selected from the group consisting of:

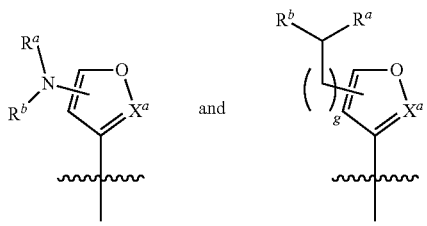

wherein:
$R^a$ and $R^b$ are each independently hydrogen, halogen, alkyl, alkenyl, alkynyl, aryl, aralkyl, alkoxy, or heterocyclic;
g is 1, 2, 3, 4, 5, 6, 7, 8, 9, 10, 11, 12, 13, 14, 15, 16, 17, 18, 19, or 20; and
$X^a$ is substituted carbon.

13. The method of claim 1, wherein said compound is selected from the group consisting of:
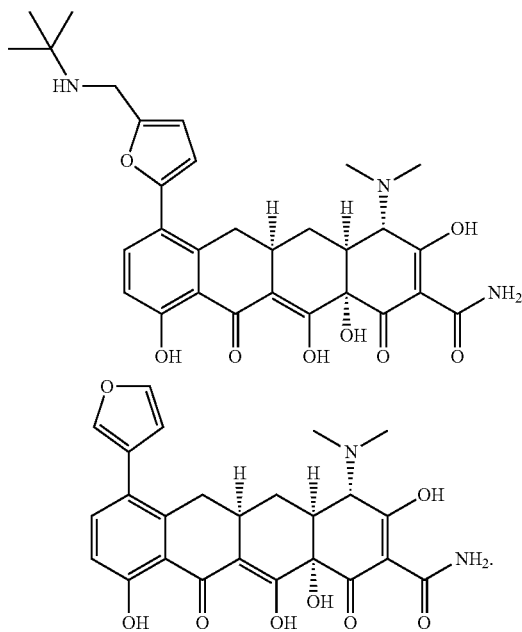
and
14. The method of claim 1, wherein said compound is selected from the group consisting of:
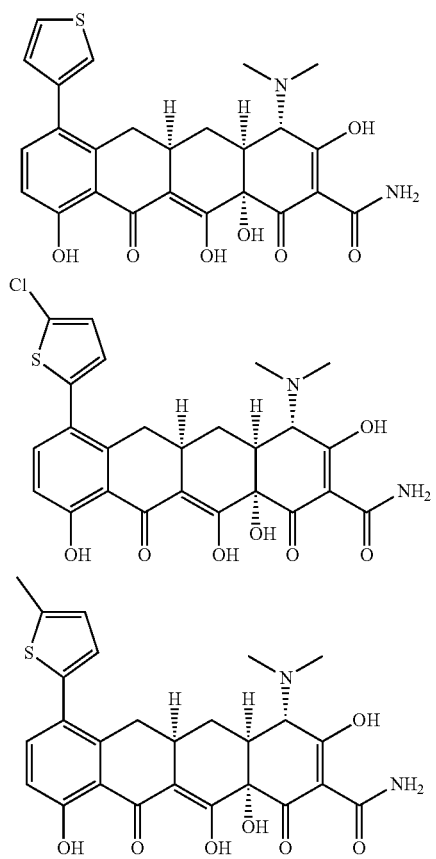
-continued
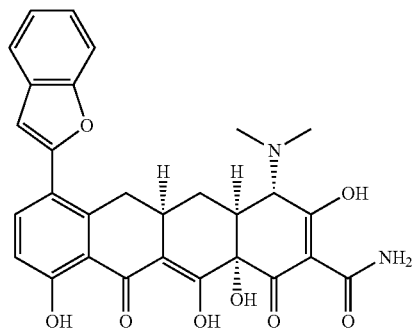
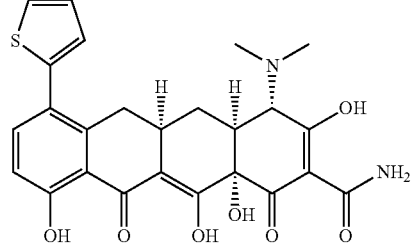
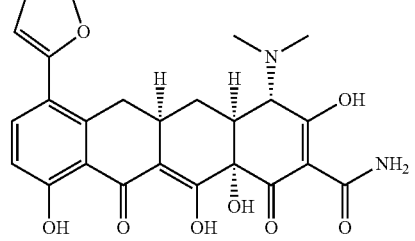
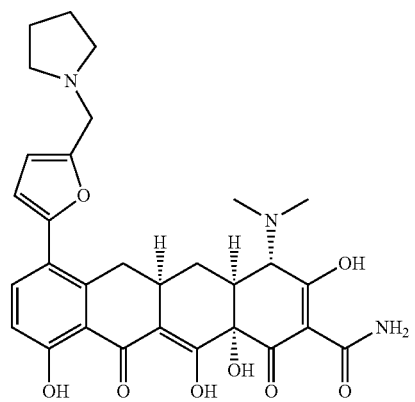
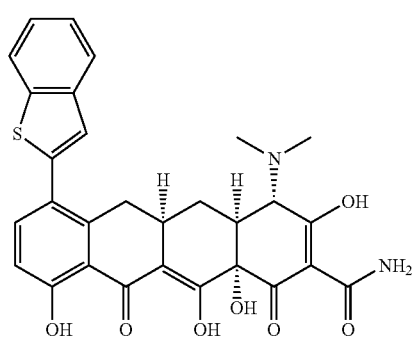

| 1049 | 1050 |
|---|---|
| -continued | -continued |
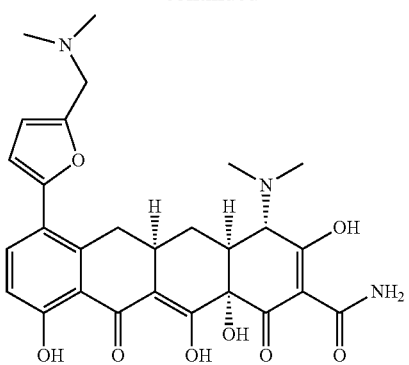
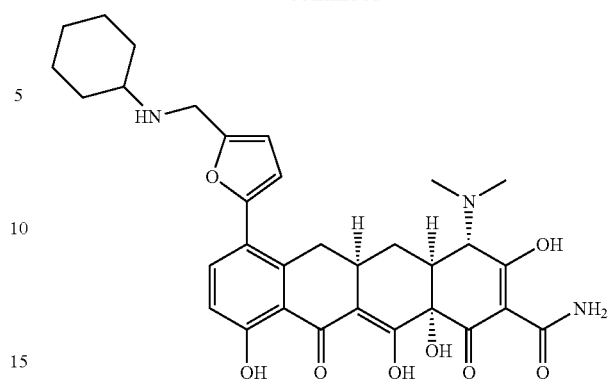
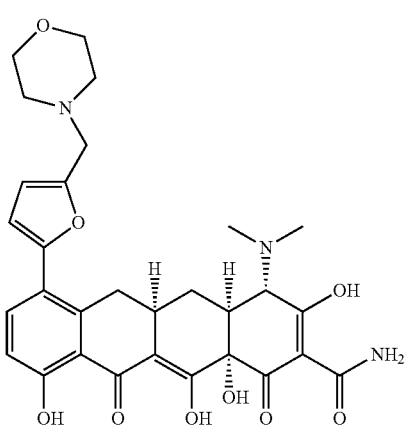
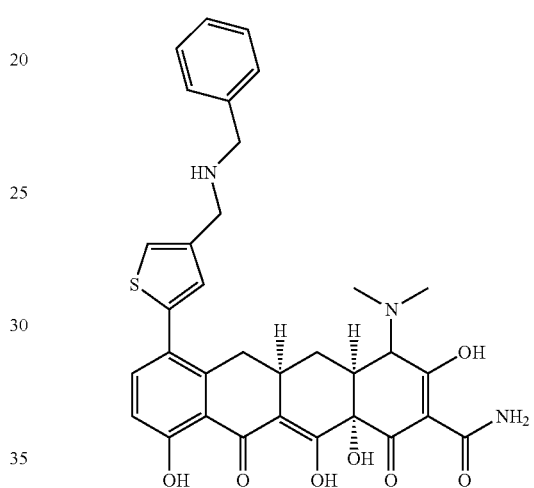
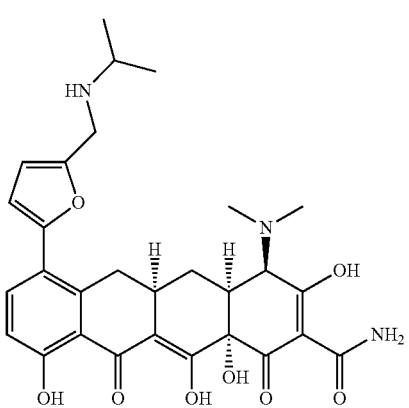
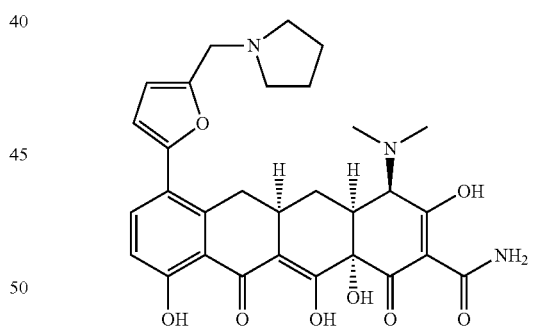
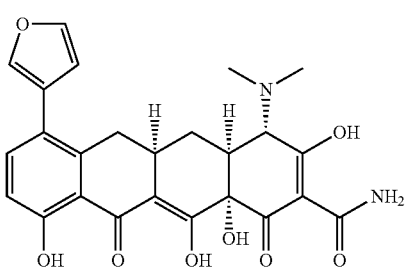
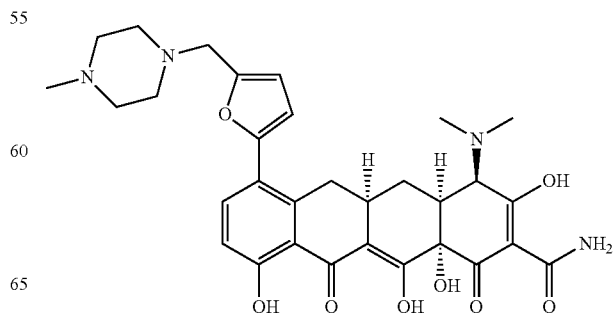

1051
-continued
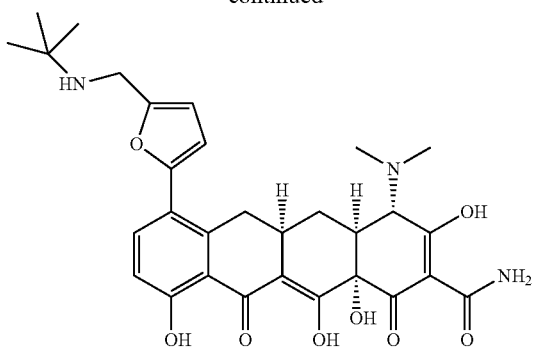
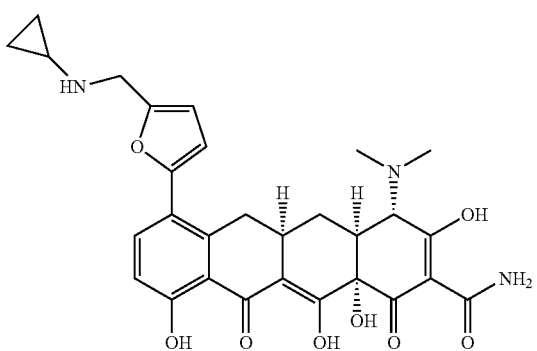
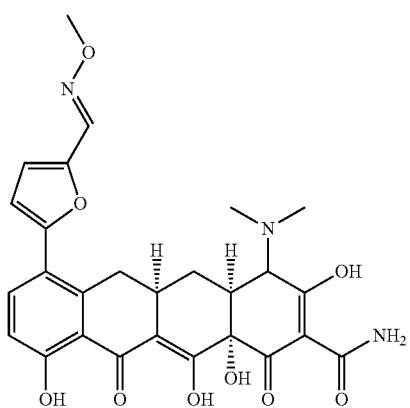
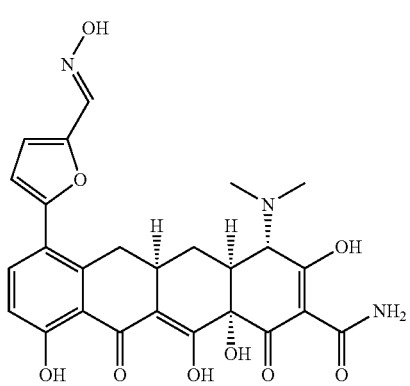
1052
-continued
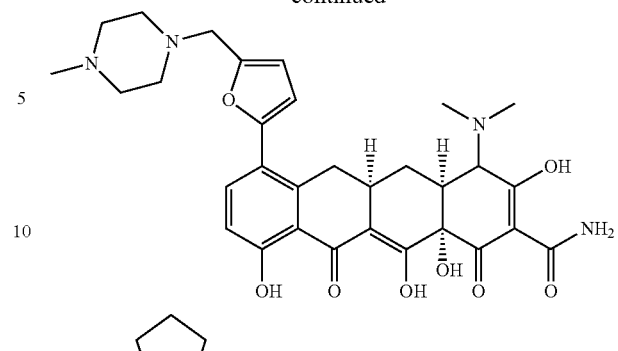
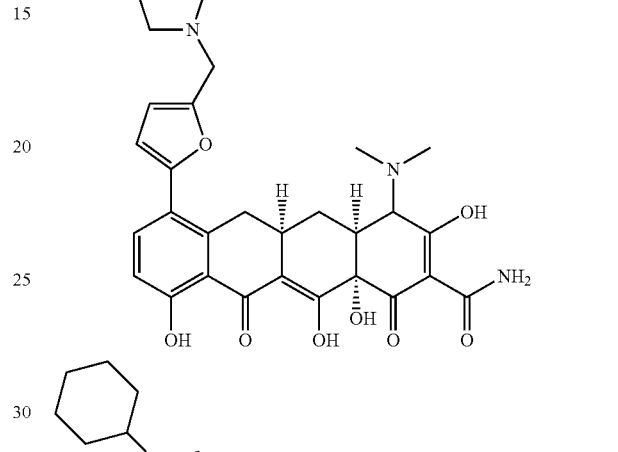
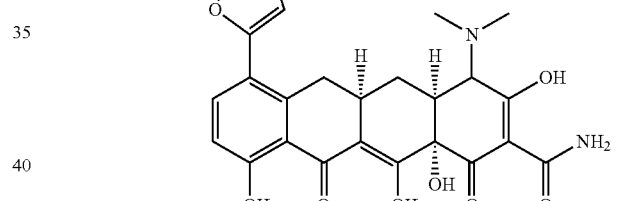
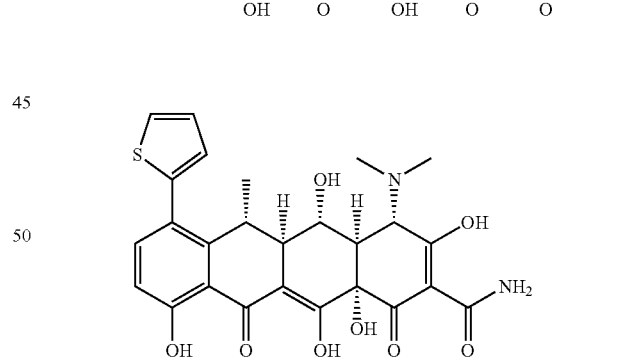
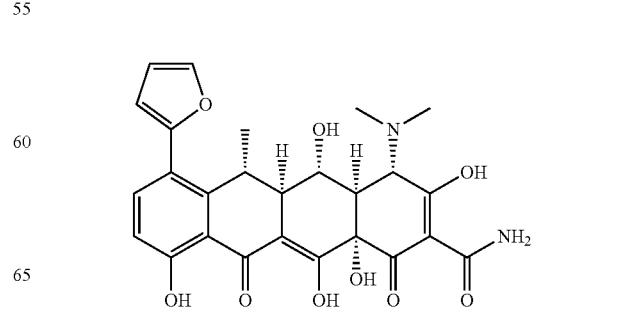

-continued

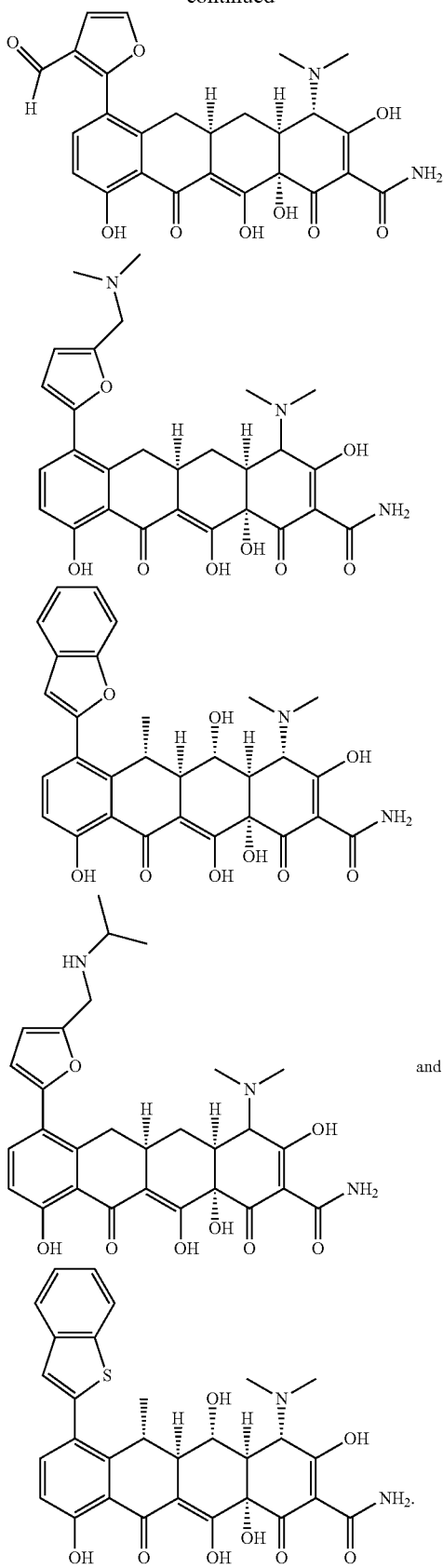

15. The method of claim 1, wherein said subject is a human.

16. The method of claim 1, wherein said substituted tetracycline compound has anti-gram positive microbial activity.

17. The method of claim 16, wherein said anti-gram positive microbial activity is greater than about 0.05 µg/ml.

18. The method of claim 17, wherein said anti-gram positive microbial activity is greater than about 5 µg/ml.

19. The method of claim 1, wherein said substituted tetracycline compound is non-antibacterial.

20. The method of claim 1, wherein said substituted tetracycline compound has a cytotoxicity of 25 µg/ml or greater.

21. The method of claim 1, wherein said substituted tetracycline compound has a MIC of 150 nM or less.

22. The method of claim 21, wherein said substituted tetracycline compound has a MIC of 50 nM or less.

23. The method of claim 22, wherein said substituted tetracycline compound has a MIC of 10 nM or less.

24. The method of claim 23, wherein said substituted tetracycline compound has a MIC of 5 nM or less.

25. The method of claim 1, wherein said malaria is caused by a *plasmodium* protozoan selected from the group consisting of: *P. falciparum, P. vivax, P. ovale*, and *P. malariae*.

26. The method of claim 1, wherein said malaria is resistant to one or more anti-malarial compounds selected from the group consisting of proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine and 1,16-hexadecamethylenebis(N-methylpyrrolidinium)dibromide.

27. The method of claim 1, further comprising administering an anti-malarial compound selected from the group consisting of: proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, 1,16-hexadecamethylenebis (N-methylpyrrolidinium)dibromide and combinations thereof.

28. A method for increasing the antimalarial activity of an antimalarial compound, comprising administering said antimalarial compound in combination with an effective amount of a substituted tetracycline compound, such that the antimalarial activity of said antimalarial compound is increased, wherein said tetracycline compound is of formula I or a pharmaceutically acceptable salt thereof:

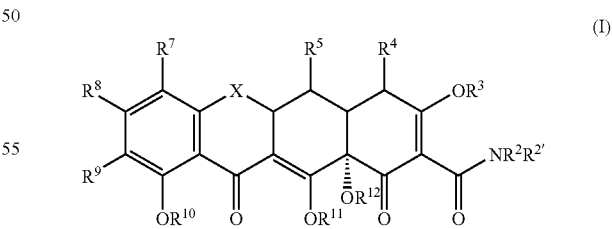

(I)

wherein:
X is $CR^{6'}R^6$;
$R^2$ and $R^{2'}$ are each hydrogen;
$R^{4'}$ and $R^{4''}$ are each alkyl;
$R^4$ is $NR^{4'}R^{4''}$;
$R^3$, $R^{11}$ and $R^{12}$ are each hydrogen;
$R^{10}$ is hydrogen;
$R^5$ is hydroxyl, hydrogen or thiol;

R⁶ and R⁶' are independently hydrogen, hydroxyl, thiol or alkyl;
R⁷ is substituted or unsubstituted furanyl, substituted or unsubstituted benzofuranyl, substituted or unsubstituted thienyl or substituted or unsubstituted benzothienyl;
R⁹ is hydrogen; and
R⁸ is hydrogen.

29. The method of claim 28, wherein said anti-malarial compound is selected from the group consisting of: proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, 1,16-hexadecamethylenebis(N-methylpyrrolidinium)dibromide and combinations thereof.

30. A method for preventing malaria in a mammal, comprising administering to said mammal an effective amount of a substituted tetracycline compound, such that malaria is prevented in said mammal, wherein said tetracycline compound is of formula I or a pharmaceutically acceptable salt thereof:

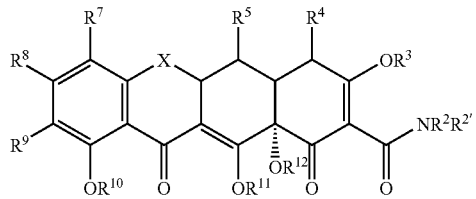

wherein:
X is CR⁶'R⁶;
R² and R²' are each hydrogen;
R⁴' and R⁴" are each alkyl;
R⁴ is NR⁴'R⁴";
R³, R¹¹ and R¹² are each hydrogen;
R¹⁰ is hydrogen;
R⁵ is hydroxyl, hydrogen or thiol;
R⁶ and R⁶' are independently hydrogen, hydroxyl, thiol or alkyl;
R⁷ is substituted or unsubstituted furanyl, substituted or unsubstituted benzofuranyl, substituted or unsubstituted thienyl or substituted or unsubstituted benzothienyl;
R⁹ is hydrogen; and
R⁸ is hydrogen.

31. The method of claim 30, wherein said substituted tetracycline compound is selected from the group consisting of:

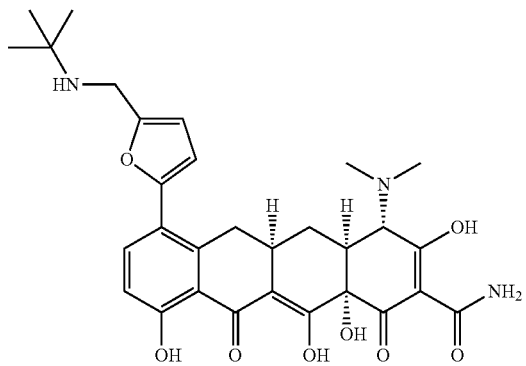

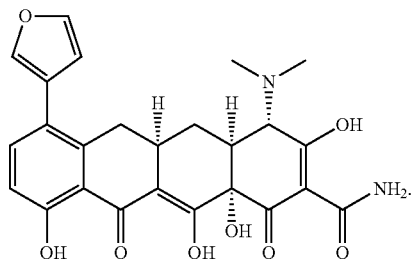

32. The method of claim 30, wherein said substituted tetracycline compound is selected from the group consisting of:

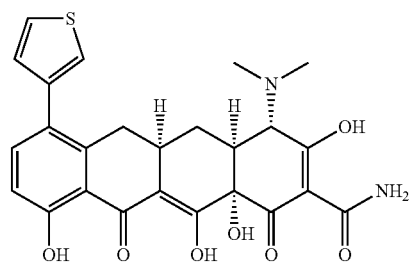

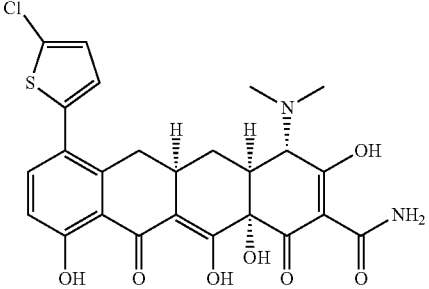

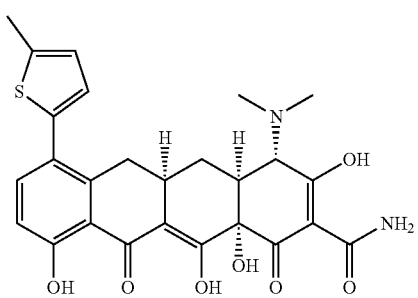

and

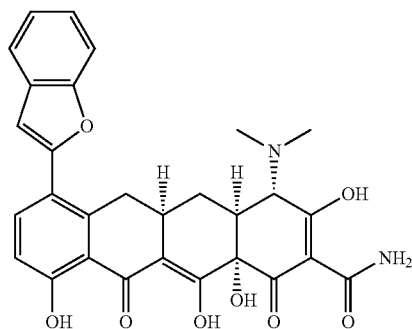

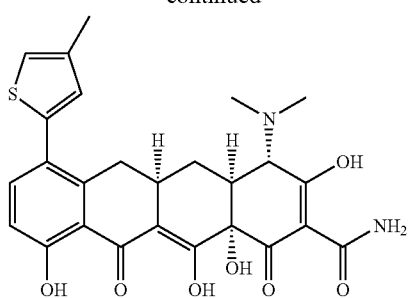
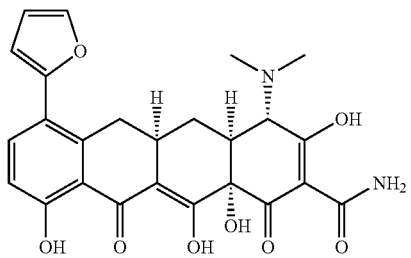
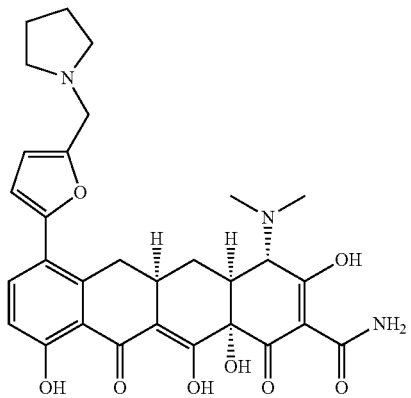
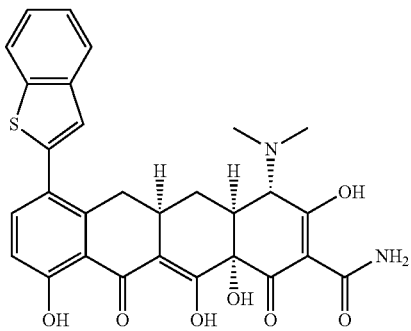
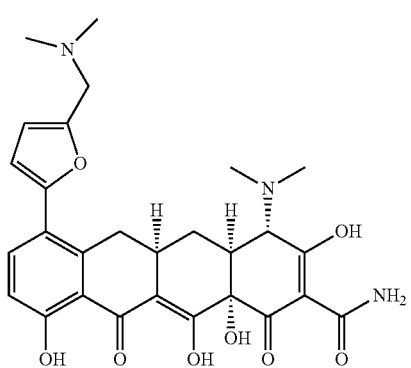
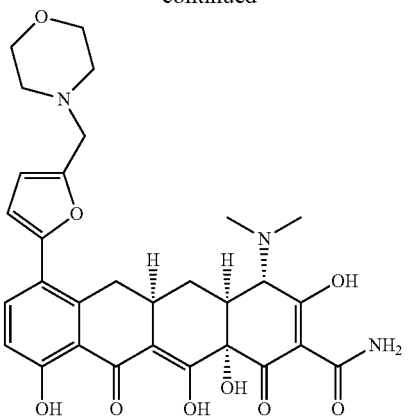
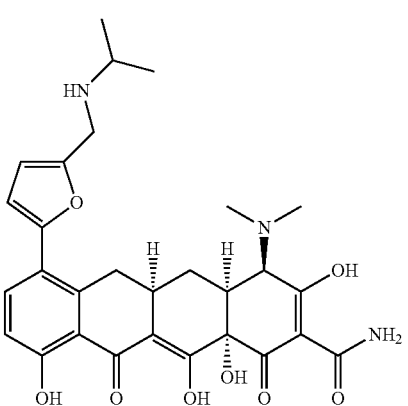
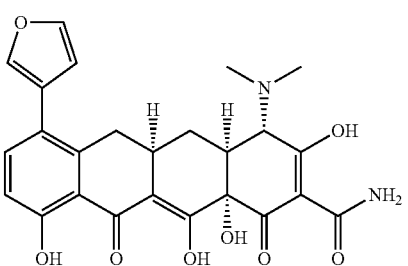
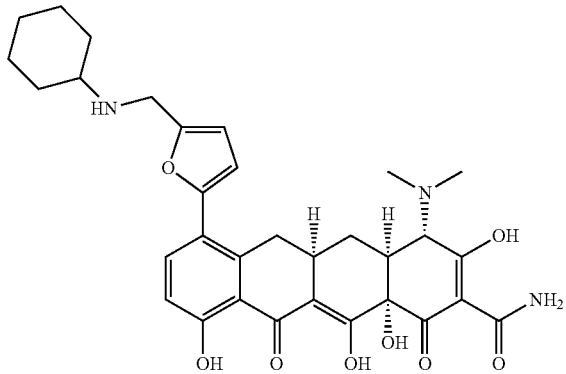

| 1059 -continued | 1060 -continued |
|---|---|
| 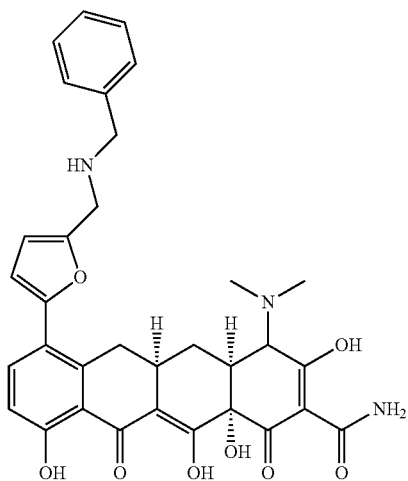 | 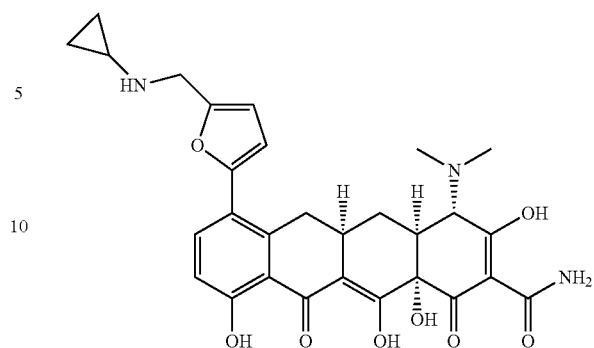 |
| 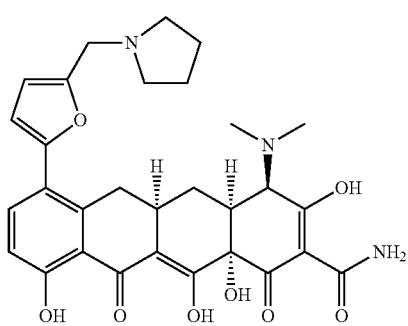 | 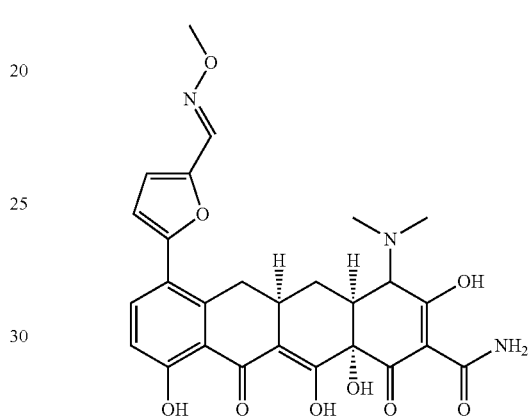 |
| 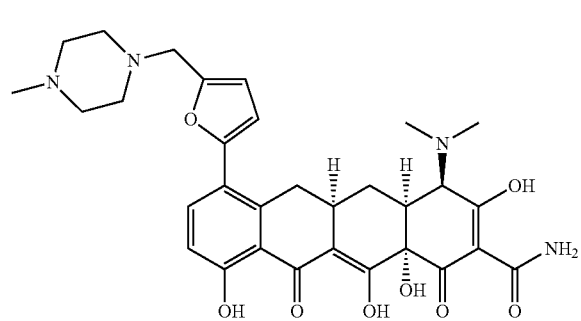 | 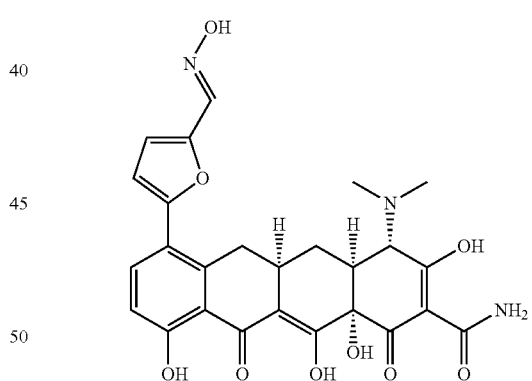 |
| 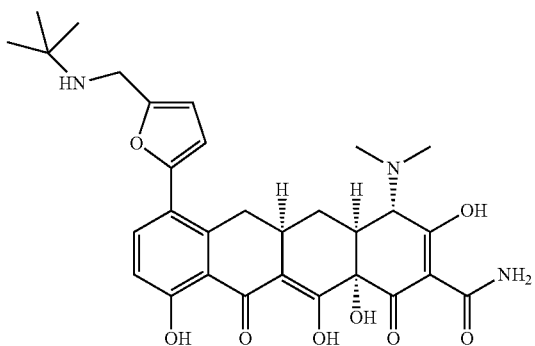 | 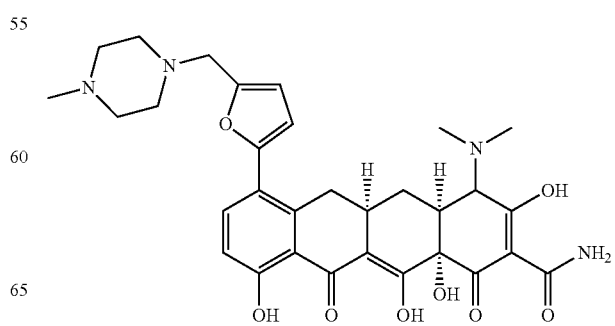 |

1061
-continued

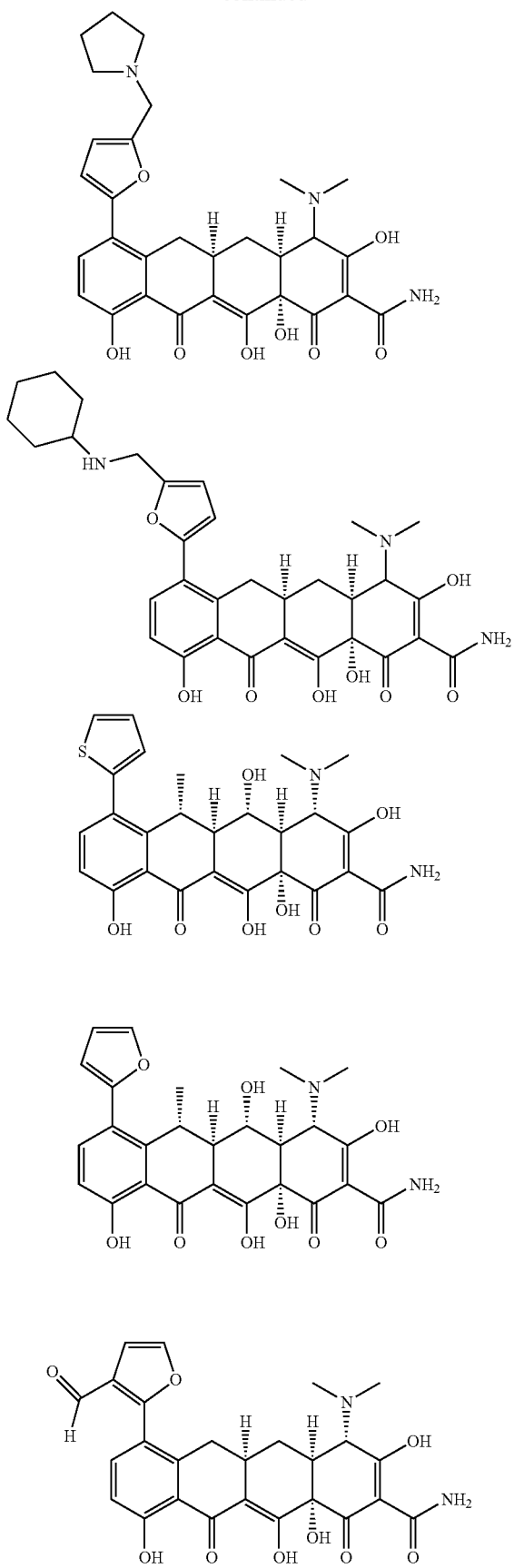

1062
-continued

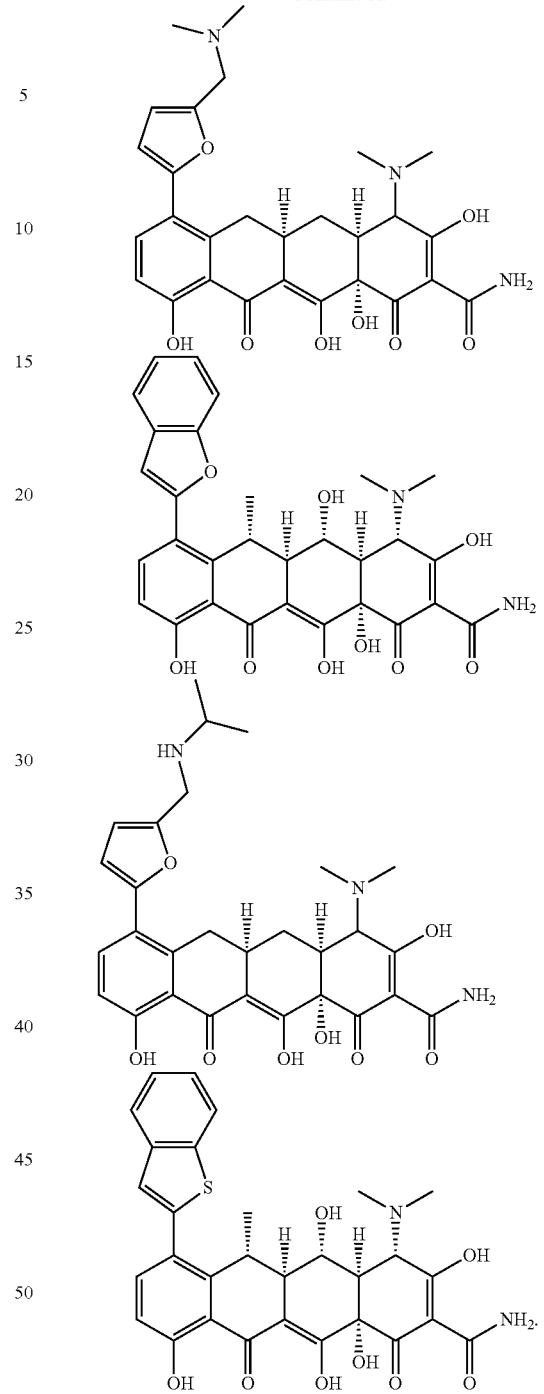

33. The method of claim 30, wherein said substituted tetracycline compound is non-antibacterial.

34. The method of claim 30, wherein said substituted tetracycline compound has anti-gram positive microbial activity.

35. The method of claim 34, wherein said anti-gram positive microbial activity is greater than about 0.05 µg/ml.

36. The method of claim 35, wherein said anti-gram positive microbial activity is greater than about 5 µg/ml.

37. The method of claim 36, wherein said substituted tetracycline compound has a cytotoxicity of 25 µg/ml or greater.

38. The method of claim 30, wherein said substituted tetracycline compound has a MIC of 150 nM or less.

39. The method of claim 38, wherein said substituted tetracycline compound has a MIC of 50 nM or less.

40. The method of claim 39, wherein said substituted tetracycline compound has a MIC of 10 nM or less.

41. The method of claim 40, wherein said substituted tetracycline compound has a MIC of 5 nM or less.

42. A pharmaceutical composition comprising an effective amount of a substituted tetracycline compound to treat malaria in a mammal and a pharmaceutically acceptable carrier, wherein said tetracycline compound is of formula I or a pharmaceutically acceptable salt thereof:

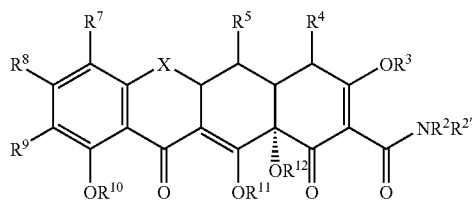

wherein:
X is $CR^{6'}R^6$;
$R^2$ and $R^{2'}$ are each hydrogen;
$R^{4'}$ and $R^{4''}$ are each alkyl;
$R^4$ is $NR^{4'}R^{4''}$;
$R^3$, $R^{11}$ and $R^{12}$ are each hydrogen;
$R^{10}$ is hydrogen;
$R^5$ is hydroxyl, hydrogen or thiol;
$R^6$ and $R^{6'}$ are independently hydrogen, hydroxyl, thiol or alkyl;
$R^7$ is substituted or unsubstituted furanyl, substituted or unsubstituted benzofuranyl, substituted or unsubstituted thienyl or substituted or unsubstituted benzothienyl;
$R^9$ is hydrogen; and
$R^8$ is hydrogen.

43. The pharmaceutical composition of claim 42, wherein said substituted tetracycline compound is selected from the group consisting of:

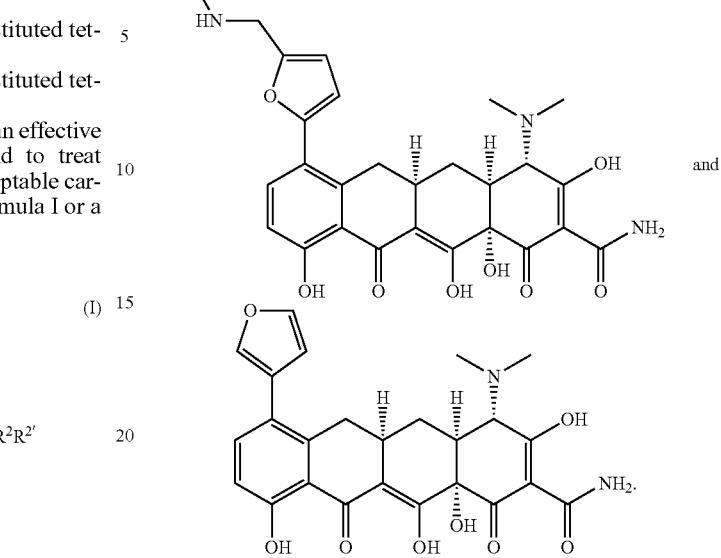

44. The pharmaceutical composition of claim 42, further comprising an anti-malarial compound.

45. The pharmaceutical composition of claim 44, wherein the anti-malarial compound is selected from the group consisting of proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, 1,16-hexadecamethylenebis(N-methylpyrrolidinium)dibromide and pyronaridine.

* * * * *